US008945567B2

(12) United States Patent
Depla et al.

(10) Patent No.: US 8,945,567 B2
(45) Date of Patent: Feb. 3, 2015

(54) MONOVALENT, BIVALENT AND TRIVALENT ANTI HUMAN RESPIRATORY SYNCYTIAL VIRUS (HRSV) NANOBODY CONSTRUCTS FOR THE PREVENTION AND/OR TREATMENT OF RESPIRATORY TRACT INFECTIONS

(75) Inventors: Erik Depla, Destelberg

(56) References Cited

OTHER PUBLICATIONS

Holliger and Hudson; "Engineered antibody fragments and the rise of single domains"; Nature Biotechnology; (2005); 23(9): 1126-1136.
Monegal, et al.; "Immunological applications of single-domain llama recombinant antibodies isolated from a naïve library"; Protein Engineering, Design & Selection: (2009); 22(4): 273-280.
Morton, et al.; "Structural characterization of respiratory syncytial virus fusion inhibitor escape mutants: homology model of the F protein and a syncytium formation assay"; Virology; (2003); 311: 275-288.
Murphy, et al.; "Current approaches to the development of vaccines effective against parainfluenza and respiratory syncytial viruses"; Virus Research; (1988); 11: 1-15.
Ogra; "Respiratory syncytial virus: The virus, the disease and the immune response"; Paediatric Resp. Reviews; (2004); 5(Suppl A): S119-S126.
Souriau and Hudson; "Recombinant antibodies for cancer diagnosis and therapy"; Expert Opin. Biol. Ther.; (2003); 3(2): 305-318.
Wu, et al.; "Development of Motavizumab, an Ultra-potent Antibody for the Prevention of Respiratory Syuncytial Virus Infection in the Upper and Lower Respiratory Tract"; J. Mol. Biol.; (2007); 368: 652-665.
Wu, et al.; "Immunoprophylaxis of RSV Infection: Advancing from RSV-IGIV to Palivizumab and Motavizumab"; Curr. Topics in Microbiology and Immunology; (2008); 317: 103-123.
[No Author Listed] ALEXION Pharmaceuticals#Antibody Therapy Shown Effective in Model for Severe Allergic Asthma. Last accessed at http://www.alxn.com/news/article.aspx?relid=216307 on Aug. 14, 2012.
[No Author Listed], Rabies Antibody Combination. Crucell. http://www.crucell.com/R_and_D-Clinical_Development-Rabies_Antibody_Product. Last accessed on Dec. 16, 2010. 2 pages.
[No Author Listed], Rabies Monoclonal Antibody Cocktail. Crucell. http://www.crucell.com/R_and_D-Clinical_Development-Rabies_Antibody_Product. Last accessed on Oct. 30, 2008. 2 pages.
[No Author Listed], Rabies. WHO Fact Sheet No. 99. World Heath Organization. Sep. 2006. http://www.who.int/mediacentre/factsheets/fs099/en/print.html. Last accessed on Oct. 30, 2008. 3 pages.
[No Author Listed], Rabies. WHO Fact Sheet No. 99. World Heath Organization. Updated Sep. 2010. http://www.who.int/mediacentre/factsheets/fs099/en/index.html. Last accessed on Dec. 16, 2010. 4 pages.
Awasthi et al., Imaging findings in rabies encephalitis. AJNR Am J Neuroradiol. Apr. 2001;22(4):677-80.
Cardoso et al., Nanobodies® with in vitro neutralizing activity protect mice against H5N1 influenza virus infection. Antivirals Congress, Amsterdam, The Netherlands. Nov. 7-9, 2010. Meeting Abstract. 2 pages.
Corral et al., High level expression of soluble glycoproteins in the allantoic fluid of embryonated chicken eggs using a Sendai virus minigenome system. BMC Biotechnol. Apr. 5, 2007;7:17. 9 pages.
De Haard et al., Llama antibodies against a lactococcal protein located at the tip of the phage tail prevent phage infection. J. Bacteriol. Jul. 2005;187(3):4531-41.
Delagrave et al., Effects of humanization by variable domain resurfacing on the antiviral activity of a single-chain antibody against respiratory syncytial virus. Protein Eng. Apr. 1999;12(4):357-62.
Depla et al., Generation and characterization of ultra-potent RSV neutralising Nanobodies. 7th International Respiratory Syncytial Virus Symposium. Rotterdam. The Netherlands. Dec. 2-5, 2010. Presentation Abstract. 2 pages. Final Programme p. 162.
Depla et al., Prophylactic and therapeutic efficacy of anti-RSV Nanobody in a cotton rat challenge model. 7th International Respiratory Syncytial Virus Symposium. Rotterdam, The Netherlands, Dec. 2-5, 2010. Poster Abstract. 2 pages. Final Programme p. 169.
Detalle et al., Assessment of in vivo and in vitro efficacy of an anti-RSV Nanobody®: superior potency over palivizumab and prophylactic effect after pulmonary administration. 1st Symposium on Single Domain Antibodies. Ghent, Belgium. Oct. 14-15, 2010. Meeting Abstract P12.
Dietzschold et al., Differences in cell-to-cell spread of pathogenic and apathogenic rabies virus in vivo and in vitro. J Virol. Oct. 1985;56(1):12-8.
Dimitrov, Cell biology of virus entry. Cell. Jun. 23, 2000;101(7):697-702.
Harmsen et al., Passive immunization of pigs with bispecific llama single-domain antibody fragments against foot-and-mouth disease and porcine immunoglobulin. Vet Microbiol. Nov. 25, 2008;132(1-2):56-64. doi: 10.1016/j.vetmic.2008.04.030. Epub Apr. 30, 2008.
Hultberg et al., Lactobacillli expressing llama VHH fragments neutralise Lactococcus phages. BMC Biotechnol. Sep. 17, 2007;7:58.
Hultberg et al., Llama-derived immunoglobulin single variable domains to build multivalent superpotent and broadened neutralizing anti-viral molecules. XIV International Conference on Negative Stand Viruses. Brugge, Belgium. Jun. 20-25, 2010. Abstract No. 345.
Hultberg et al., Llama-derived single domain antibodies to build multivalent, superpotent and broadened neutralizing anti-viral molecules. PLoS One. Apr. 1, 2011;6(4):e17665. doi: 10.1371/journal.pone.0017665.
Ibanez et al., Nanobodies® with in vitro neutralizing activity protect mice against H5N1 influenza virus infection. XIV International Conference on Negative Strand Viruses. Brugge, Belgium. Jun. 20-25, 2010. Abstract 307.
Ibanez et al., Single domain antibodies with in vitro and in vivo neutralizing activity protect mice against H5N1influenza virus infection. 1st Symposium on Single Domain Antibodies. Ghent, Belgium. Oct. 14-15, 2010. Meeting Abstract P19.
Ibanez et al., Single-domain antibodies with in vitro and in vivo neutralizing activity protect mice against H5N1 influenza virus infection. Options for the Control of Influenza VII. Abstract Book. Hong Kong SAR, China. Sep. 3-7, 2010. Abstract P-174.
Jain et al., Engineering antibodies for clinical applications. Trends Biotechnol. Jul. 2007;25(7):307-16.
Kielian et al., Virus membrane-fusion proteins: more than one way to make a hairpin. Nat Rev Microbiol. Jan. 2006;4(1):67-76.
Kielian, Class II virus membrane fusion proteins. Virology. Jan. 5, 2006;344(1):38-47.
Kodama et al., Specific and effective targeting cancer immunotherapy with a combination of three bispecific antibodies. Immunol Lett. Apr. 22, 2002;81(2):99-106.
Ledeboer et al., Preventing phage lysis of *Lactococcus lactis* in cheese production using a neutralizing heavy-chain antibody fragment from llama. J Dairy Sci. Jun. 2002;85(6):1376-82.
Montano-Hirose et al., Protective activity of a murine monoclonal antibody against European bat lyssavirus 1 (EBL1) infection in mice. Vaccine. Sep. 1993;11(12):1259-66.
Nguyen et al., Efficient generation of respiratory syncytial virus (RSV)-neutralizing human MoAbs via human peripheral blood lymphocyte (hu-PBL)-SCID mice and scFv phage display libraries. Clin Exp Immunol. Oct. 2000;122(1):85-93.
Okuno et al., A common neutralizing epitope conserved between the hemagglutinins of influenza A virus H1 and H2 strains. J Virol. May 1993;67(5):2552-8.
Rosseels et al., Prophylactic treatment with anti-rabies Nanobodies® can protect mice from lethal rabies virus challenge. XIV International Conference on Negative Strand Viruses. Brugge, Belgium. Jun. 20-25, 2010. Abstract 301.
Rosseels et al., VHH selected against the viral spike protein can protect mice against lethal rabies virus challenge. Annual Scientific Meeting of the Institute Pasteur International Network. Hong Kong. Nov. 22-23, 2010. Abstract P025.
Rosseels et al., VHH-based Nanobodies® selected against the viral spike protein can protect mice against lethal rabies virus challenge. WIV-ISP Scientific Report. 2008-2009. pp. 92-95.
Schepens et al., Nanobodies® protect mice against human respiratory syncytial virus infection by inhibiting viral fusion. 1st Symposium on Single Domain Antibodies. Ghent, Belgium. Oct. 14-15, 2010. Meeting Abstract. P30.

(56) References Cited

OTHER PUBLICATIONS

Schepens et al., Nanobodies® protect mice against human respiratory syncytial virus infection by inhibiting viral fusion.7*th* International Respiratory Syncytial Virus Symposium. Rotterdam, The Netherlands. Dec. 2-5, 2010. Presentation Abstract. Final Programme p. 178.
Schepens et al., Nanobodies® protect mice against human respiratory syncytial virus infection. XIV International Conference on Negative Strand Viruses. Brugge, Belgium. Jun. 20-25, 2010. Abstract 318.
Schumacher et al., Inhibition of immune responses against rabies virus by monoclonal antibodies directed against rabies virus antigens. Vaccine. 1992;10(11):754-60.
Spinelli et al., Lactococcal bacteriophage p2 receptor-binding protein structure suggests a common ancestor gene with bacterial and mammalian viruses. Nat Struct Mol Biol. Jan. 2006;13(1):85-9.
Spinelli et al., The crystal structure of a llama heavy chain variable domain. Nat Struct Biol. Sep. 1996;3(9):752-7.
Subbarao et al., Scientific barriers to developing vaccines against avian influenza viruses. Nat Rev Immunol. Apr. 2007;7(4):267-78.
Tremblay et al., Receptor-binding protein of *Lactococcus lactis* phages: identification and characterization of the saccharide receptor-binding site. J Bacteriol. Apr. 2006;188(7):2400-10.
Verschueren, Design of experiments in the framework of a cell based potency assay. BEBPA's 3*rd* Annual biological Assay Conference. Pre-Conference Workshop: Practical Tools for the Bioassay Scientist. Barcelona, Spain. Sep. 29-Oct. 1, 2010. 9:30am-10:15am. Abstract.
Weissenhorn et al., Virus membrane fusion. FEBS Lett. May 22, 2007;581(11):2150-5. Epub Feb. 16, 2007.
Woldehiwet, Rabies: recent developments. Res Vet Sci. Aug. 2002;73(1):17-25.
Wright et al., The efficacy of current rabies vaccines and novel Nanobody®—based antivirals against highly pathogenic phylogroup-1 and -2 members of the *Lyssavirus* genus. XXI International meeting on Rabies in the Americas (RITA XXI). Guadalajara, Jal. Oct. 17-22, 2010.
Wright et al., The efficacy of current vaccines and novel nanobody-based antivirals against highly pathogenic rabies and *Lyssaviruses*. SGM Spring 2010 Meeting. Edinburgh International Conference Centre. Edinburgh, UK. Mar. 29-Apr. 1, 2010. Abstract. p. 81-82.
Baker et al., Structural basis for paramyxovirus-mediated membrane fusion. Mol Cell. Mar. 1999;3(3):309-19.
Barbas et al., Human monoclonal Fab fragments derived from a combinatorial library bind to respiratory syncytial virus F glycoprotein and neutralize infectivity. Proc Natl Acad Sci U S A. Nov. 1, 1992;89(21):10164-8.
Burioni et al., Recombinant human Fab to glycoprotein D neutralizes infectivity and prevents cell-to-cell transmission of herpes simplex viruses 1 and 2 in vitro. Proc Natl Acad Sci U S A. Jan. 4, 1994;91(1):355-9.
Chen et al., N- and C-terminal residues combine in the fusion-pH influenza hemagglutinin HA(2) subunit to form an N cap that terminates the triple-stranded coiled coil. Proc Natl Acad Sci U S A. Aug. 3, 1999;96(16):8967-72.
Crowe et al., Recombinant human respiratory syncytial virus (RSV) monoclonal antibody Fab is effective therapeutically when introduced directly into the lungs of RSV-infected mice. Proc Natl Acad Sci U S A. Feb. 15, 1994;91(4):1386-90.
Dekker et al., Intracellularly expressed single-domain antibody against p15 matrix protein prevents the production of porcine retroviruses. J Virol. Nov. 2003;77(22):12132-9.
Deschacht et al., A novel promiscuous class of camelid single-domain antibody contributes to the antigen-binding repertoire. J Immunol. May 15, 2010;184(10):5696-704. doi:10.4049/jimmunol. 0903722. Epub Apr. 19, 2010.
Earp et al., The many mechanisms of viral membrane fusion proteins. Curr Top Microbiol Immunol. 2004;285:25-66.
Fiers et al., A "universal" human influenza A vaccine. Virus Res. Jul. 2004;103(1-2):173-6.

Forsman et al., Neutralising llama antibody fragments as HIV-1 entry Inhibitors. Eu-WHO Neut workshop. Italy. Mar. 2007. Abstract.
Fujinami et al., Antiviral antibody reacting on the plasma membrane alters measles virus expression inside the cell. Nature. Jun. 7, 1979;279(5713):529-30.
Gerhard, The role of the antibody response in influenza virus infection. Curr Top Microbiol Immunol. 2001;260:171-90.
Goldman et al., Facile generation of heat-stable antiviral and antitoxin single domain antibodies from a semisynthetic llama library. Anal Chem. Dec. 15, 2006;78(24):8245-55.
Greenspan et al., Defining epitopes: It's not as easy as it seems, Nat Biotechnol. Oct. 1999;17(10):936-7.
Hanson et al., Passive immunoprophylaxis and therapy with humanized monoclonal antibody specific for influenza A H5 hemagglutinin in mice. Respir Res. Oct. 14, 2006;7:126.
Harmsen et al., Passive immunization of guinea pigs with llama single-domain antibody fragments against foot-and-mouth disease. Vet Microbiol. Mar. 10, 2007;120(3-4):193-206. Epub Oct. 28, 2006.
Haynes, Progress and challenges in RSV prophylaxis and vaccine development. J Infect Dis. Dec. 15, 2013;208 Suppl 3:S177-83. doi: 10.1093/infdis/jit512.
Heldwein et al., Crystal structure of glycoprotein B from herpes simplex virus 1. Science. Jul. 14, 2006;313(5784):217-20.
Helenius et al., On the entry of Semliki forest virus into BHK-21 cells. J Cell Biol. Feb. 1980;84(2):404-20.
Ibañez et al., Nanobodies with in vitro neutralizing activity protect mice against H5N1 influenza virus infection. J Infect Dis. Apr. 15, 2011;203(8):1063-72.
Kashmiri et al., SDR grafting—a new approach to antibody humanization. Methods. May 2005;36(1):25-34.
Kim et al., Respiratory syncytial virus disease in infants despite prior administration of antigenic inactivated vaccine. Am J Epidemiol. Apr. 1969;89(4):422-34.
Lamarre et al., Protection from lethal coronavirus infection by immunoglobulin fragments. J Immunol. Apr. 15, 1995;154(8):3975-84.
Lescar et al., The fusion glycoprotein shell of Semliki Forest virus: an icosahedral assembly primed for fusogenic activation at endosomal pH. Cell. Apr. 6, 2001;105(1):137-48.
Levine et al., Antibody-mediated clearance of alphavirus infection from neurons. Science. Nov. 8, 1991;254(5033):856-60.
Lu et al., Passive immunotherapy for influenza A H5N1 virus infection with equine hyperimmune globulin F(ab')2 in mice. Respir Res. Mar. 23, 2006;7:43.
Mason et al., Cloning and expression of a single-chain antibody fragment specific for foot-and-mouth disease virus. Virology. Oct. 15, 1996;224(2):548-54.
Modis et al., A ligand-binding pocket in the dengue virus envelope glycoprotein. Proc Natl Acad Sci U S A. Jun. 10, 2003;100(12):6986-91. Epub May 20, 2003.
Moore et al., The entry of entry inhibitors: a fusion of science and medicine. Proc Natl Acad Sci U S A. Sep. 16, 2003;100(19):10598-602. Epub Sep. 5, 2003.
Palladino et al., Virus-neutralizing antibodies of immunoglobulin G (IgG) but not of IgM or IgA isotypes can cure influenza virus pneumonia in SCID mice. J Virol. Apr. 1995;69(4):2075-81.
Pantaleo et al., Effect of anti-V3 antibodies on cell-free and cell-to-cell human immunodeficiency virus transmission. Eur J Immunol. Jan. 1995;25(1):226-31.
Prince et al., Mechanism of antibody-mediated viral clearance in immunotherapy of respiratory syncytial virus infection of cotton rats. J Virol Jun. 1990;64(6):3091-2.
Renegar et al., Role of IgA versus IgG in the control of influenza viral infection in the murine respiratory tract. J Immunol. Aug. 1, 2004;173(3):1978-86.
Rey et al., The envelope glycoprotein from tick-borne encephalitis virus at 2 A resolution. Nature. May 25, 1995;375(6529):291-8.
Roche et al., Crystal structure of the low-pH form of the vesicular stomatitis virus glycoprotein G. Science. Jul. 14, 2006;313(5784):187-91. Erratum in: Science. Sep. 8, 2006;313(5792):1389.
Rudikoff et al., Single amino acid substitution altering antigen-binding specificity. Proc Natl Acad Sci U S A. Mar. 1982;79(6):1979-83.

(56) References Cited

OTHER PUBLICATIONS

Sawyer, Antibodies for the prevention and treatment of viral diseases. Antiviral Res. Aug. 2000;47(2):57-77.

Schofield et al., Variations in the neutralizing and haemagglutination-inhibiting activities of five influenza A virus-specific IgGs and their antibody fragments. J Gen Virol. Oct. 1997;78 (Pt 10):2431-9.

Serruys, In vitro inhibition of HbsAg secretion by single-domain intrabodies. 12th International Symposium on Viral Hepatitis and Liver Disease. 2006. Abstract P.026. p. S69.

Serruys et al., In vitro inhibition of HbsAg secretion by single-domain intrabodies, 12th International Symposium on Viral Hepatitis and Liver Disease, Jul. 1-5, 2006, Paris (Poster).

Serruys et al., HBsAg-specific single-domain intrabodies reduce the secretion of Hepatitis B virus and HBsAg in vivo, Novel Compounds and Strategies to Combat Pathogenic Microorganisms (Symposium Belgian Society for Microbiology), Nov. 24, 2006, Brussels (Poster).

Serruys et al., Generation, characterization and in vitro study of Hepatitis B surface antigen specific single-domain intrabodies, International Meeting on the Molecular Biology of Hepatitis B Viruses, Sep. 16-20, 2007, Rome (Poster).

Serruys et al., Single-domain intrabodies inhibit Hepatitis B Virus replication in mice, International Meeting on the Molecular Biology of Hepatitis B Viruses, Sep. 16-20, 2007, Rome (Poster).

Serruys, Single domain-intrabodies against the Hepatitis B virus (HBV) New Insights in HBV Diversity, Pathogenesis, Diagnosis and Treatment, Dec. 12-14, 2007, Ghent (Oral Presentation).

Serruys et al., Single-Domain Intrabodies Inhibit Hepatitis B Virus (HBV) Replication in Mice (NBC-12), Mar. 13-14, 2008, Ede (Oral Presentation).

Sherwood et al., Rapid assembly of sensitive antigen-capture assays for Marburg virus, using in vitro selection of llama single-domain antibodies, at biosafety level 4. J Infect Dis. Nov. 15, 2007;196 Suppl 2:S213-9.

Sieczkarski et al., Viral entry. Curr Top Microbiol Immunol. 2005;285:1-23.

Skehel et al., Coiled coils in both intracellular vesicle and viral membrane fusion. Cell. Dec. 23, 1998;95(7):871-4.

Smirnov et al., Prevention and treatment of bronchopneumonia in mice caused by mouse-adapted variant of avian H5N2 influenza A virus using monoclonal antibody against conserved epitope in the HA stem region. Arch Virol. 2000;145(8):1733-41.

Smith et al., How viruses enter animal cells. Science. Apr. 9, 2004;304(5668):237-42.

Tamura et al., Structural correlates of an anticarcinoma antibody: identification of specificity-determining residues (SDRs) and development of a minimally immunogenic antibody variant by retention of SDRs only. J Immunol. Feb. 1, 2000;164(3):1432-41.

Thullier et al., A recombinant Fab neutralizes dengue virus in vitro. J Biotechnol. Apr. 15, 1999;69(2-3):183-90.

Vincke et al., General strategy to humanize a camelid single-domain antibody and identification of a universal humanized nanobody scaffold. J Biol Chem. Jan. 30, 2009;284(5):3273-84. doi: 10.1074/jbc.M806889200. Epub Nov. 14, 2008.

Wilson et al., Structure of the haemagglutinin membrane glycoprotein of influenza virus at 3 A resolution. Nature. Jan. 29, 1981;289(5796):366-73.

Wu et al., Ultra-potent antibodies against respiratory syncytial virus: effects of binding kinetics and binding valence on viral neutralization. J Mol Biol. Jul. 1, 2005;350(1):126-44.

Yin et al., Structure of the uncleaved ectodomain of the paramyxovirus (hPIV3) fusion protein. Proc Natl Acad Sci U S A. Jun. 28, 2005;102(26):9288-93. Epub Jun. 17, 2005.

Domain antibodies. http://www.domantis.com/domain.htm. Accessed on Oct. 28, 2009.

Gómez-Sebastián et al., Rotavirus A-specific single-domain antibodies produced in baculovirus-infected insect larvae are protective in vivo. BMC Biotechnol. Sep. 7, 2012;12:59.

Houdebine, Production of pharmaceutical proteins by transgenic animals. Comp Immunol Microbiol Infect Dis. Mar. 2009;32(2):107-21. doi: 10.1016/j.cimid.2007.11.005. Epub Feb. 19, 2008.

Hudson et al., High avidity scFv multimers; diabodies and triabodies. J Immunol Methods. Dec. 10, 1999;231(1-2):177-89.

Ko et al., Production of antibodies in plants: approaches and perspectives. Curr Top Microbiol Immunol. 2009;332:55-78. doi: 10.1007/978-3-540-70868-1_4.

Pakula et al., Genetic analysis of protein stability and function. Annu Rev Genet. 1989;23:289-310.

Stech et al., A continuous-exchange cell-free protein synthesis system based on extracts from cultured insect cells. PLoS One. May 7, 2014;9(5):e96635. doi: 10.1371/journal.pone.0096635.eCollection 2014.

Zhao et al., In vivo selection of respiratory syncytial viruses resistant to palivizumab. J Virol. Apr. 2005;79(7):3962-8.

Mikulecký et al., Increasing affinity of interferon-γ receptor 1 to interferon-γ by computer-aided design. Biomed Res Int. 2013;2013:752514. 12 pages. doi: 10.1155/2013/752514. Epub Oct. 2, 2013.

Sikora et al., SMR proteins SugE and EmrE bind ligand with similar affinity and stoichiometry. Biochem Biophys Res Commun Sep. 16, 2005;335(1):105-11.

Walsh et al., The high- and low-affinity receptor binding sites of growth hormone are allosterically coupled. Proc Natl Acad Sci U S A. Dec. 7, 2004;101(49):17078-83. Epub Nov. 2004 24.

Wang et al., All human Na(+)-K(+)-ATPase alpha-subunit isoforms have a similar affinity for cardiac glycosides. Am J Physiol Cell Physiol. Oct. 2001;281(4):C1336-43.

* cited by examiner

Figure 3A
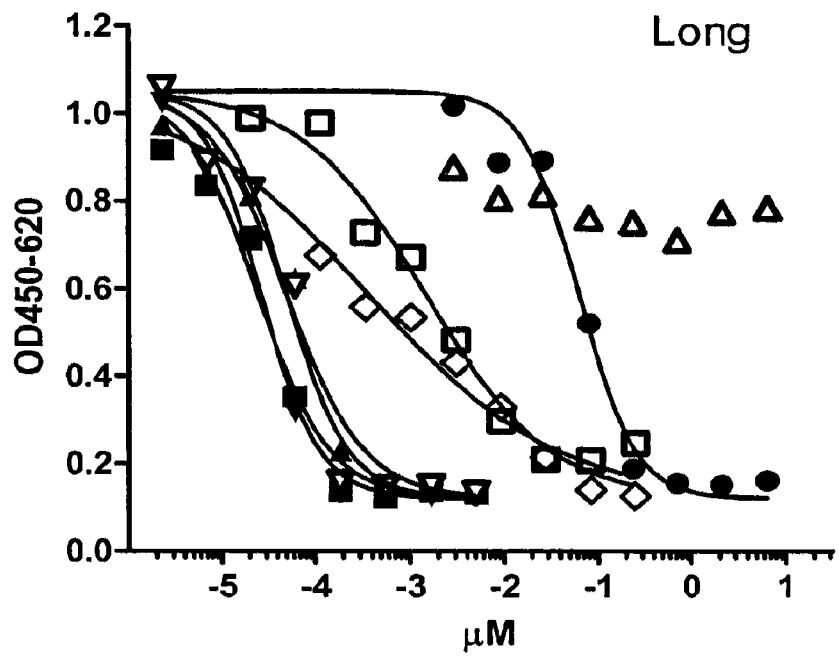
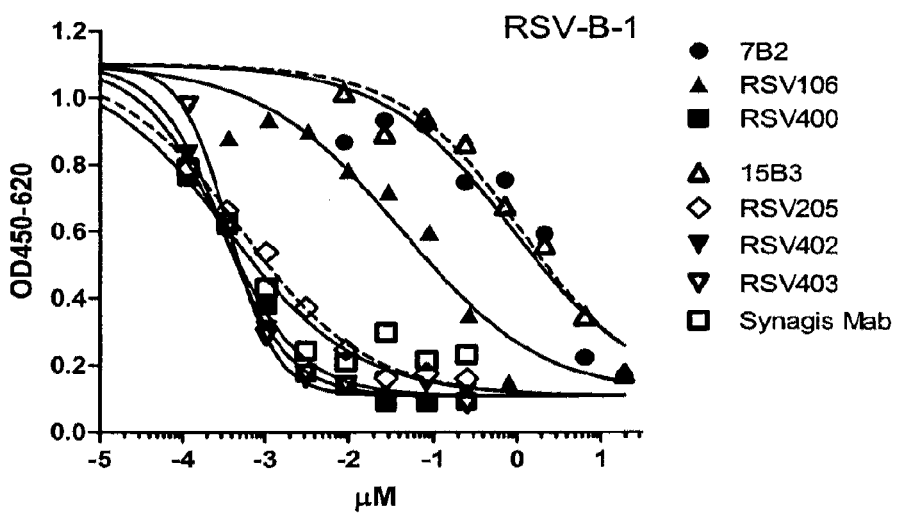

Figure 3B
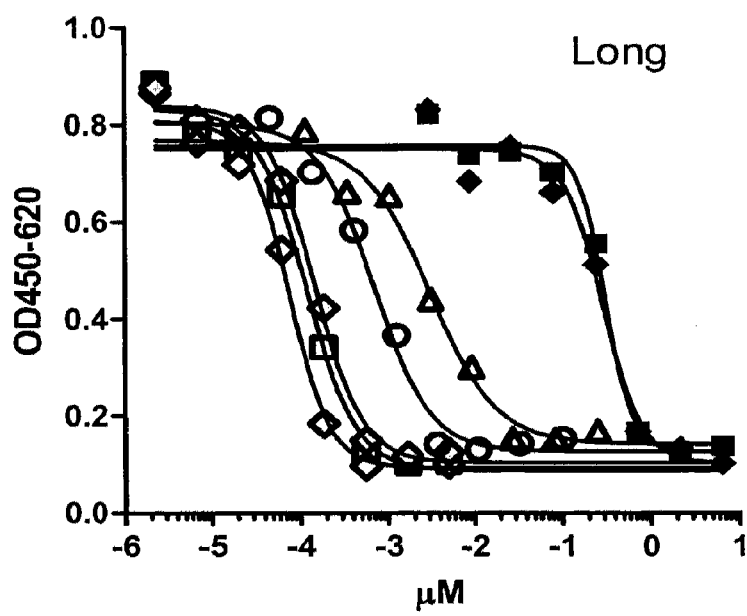
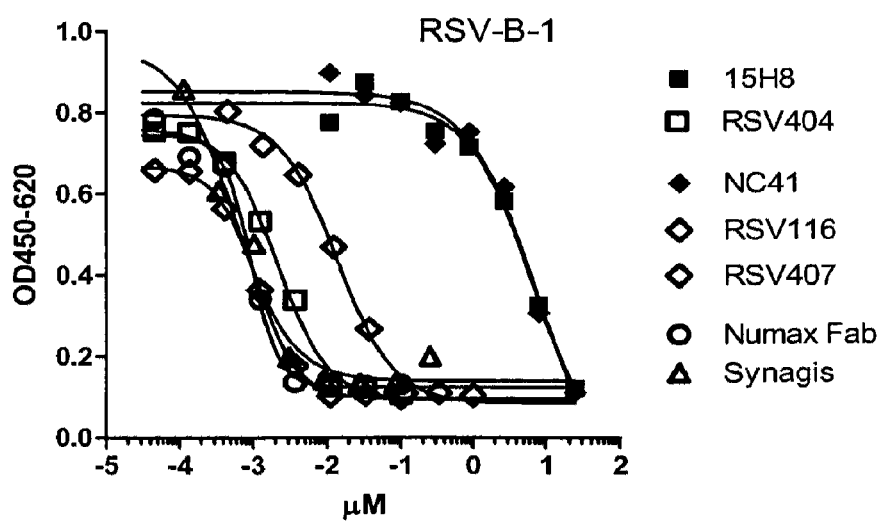

Figure 4G

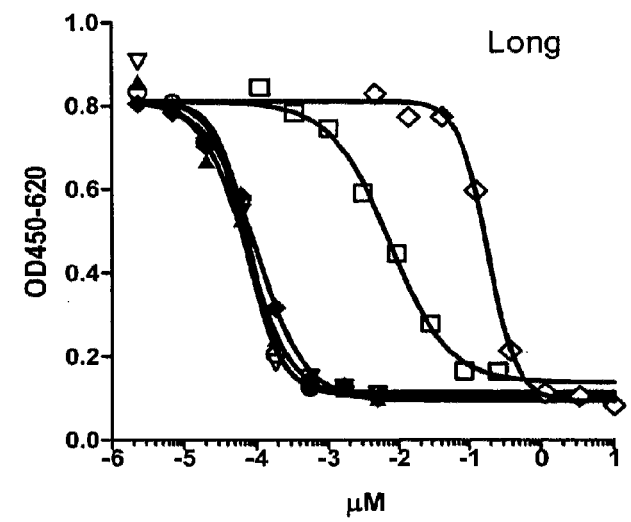
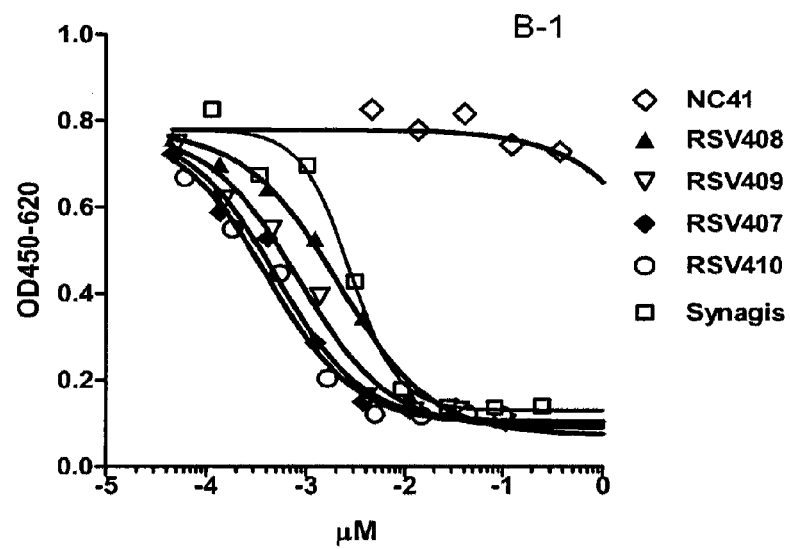
Figure 5

Figure 6

| | V5L | A14P | S19R | I20L | E44G | G54D | A74S | G78L | A83R | D85E | R105Q | Q108L | # mutations |
|---|---|---|---|---|---|---|---|---|---|---|---|---|---|
| NC41v01 | l | p | r | l | g | . | . | l | . | e | q | l | 9 |
| NC41v02 | l | p | r | . | g | . | s | l | . | e | q | l | 9 |
| NC41v03 | l | p | r | . | g | . | s | l | r | e | q | l | 10 |
| NC41v04 | l | p | . | . | g | . | s | l | r | . | q | l | 8 |
| NC41v05 | l | p | . | . | g | . | s | l | . | e | q | l | 8 |
| NC41v06 | l | p | r | l | g | d | . | l | r | e | q | l | 11 |
| NC41v07 | l | p | . | . | g | . | . | l | . | . | q | l | 6 |
| NC41v08 | l | p | . | . | g | . | . | . | r | e | q | l | 7 |
| NC41v09 | l | p | . | . | g | . | s | . | r | . | q | l | 7 |
| NC41v10 | l | p | . | . | g | . | . | . | . | . | q | l | 5 |
| NC41v11 | l | . | . | . | g | . | . | . | . | . | q | l | 4 |
| NC41v12 | l | p | . | . | . | . | . | . | . | . | q | l | 4 |
| NC41v13 | l | p | r | l | g | . | . | . | . | e | q | l | 8 |
| NC41v14 | l | p | r | l | g | . | s | l | . | e | q | l | 10 |
| NC41v15 | l | . | r | l | g | . | . | l | . | e | q | l | 8 |
| NC41v16 | l | p | r | l | . | . | . | l | . | e | q | l | 8 |
| NC41v17 | l | p | r | l | g | . | s | l | r | e | q | l | 11 |
| NC41v18 | l | p | r | l | g | d | s | l | r | e | q | l | 12 |

Figure 7

| | FR1 | CDR1 | FR2 | CDR2 |
|---|---|---|---|---|
| NC41 | evqlvesggglvqaggslslscaasggsls | NYVLG | wfrqapgkerefva | AINWRGDITIGPPNVEG |
| NC41v01 | evqllesggglvqpggslrlscaasggsls | NYVLG | wfrqapgkgrefva | AINWRGDITIGPPNVEG |
| NC41v02 | evqllesggglvqpggslrlscaasggsls | NYVLG | wfrqapgkgrefva | AINWRGDITIGPPNVEG |
| NC41v03 | evqllesggglvqpggslrlscaasggsls | NYVLG | wfrqapgkgrefva | AINWRGDITIGPPNVEG |
| NC41v04 | evqllesggglvqpggslslscaasggsls | NYVLG | wfrqapgkgrefva | AINWRGDITIGPPNVEG |
| NC41v05 | evqllesggglvqpggslrlscaasggsls | NYVLG | wfrqapgkgrefva | AINWRGDITIGPPNVEG |
| NC41v06 | evqllesggglvqpggslslscaasggsls | NYVLG | wfrqapgkgrefva | AINWRGDITIGPPNVEG |
| NC41v07 | evqllesggglvqpggslslscaasggsls | NYVLG | wfrqapgkgrefva | AINWRGDITIGPPNVEG |
| NC41v08 | evqllesggglvqpggslslscaasggsls | NYVLG | wfrqapgkgrefva | AINWRGDITIGPPNVEG |
| NC41v09 | evqllesggglvqpggslrlscaasggsls | NYVLG | wfrqapgkgrefva | AINWRGDITIGPPNVEG |
| NC41v10 | evqllesggglvqaggslslscaasggsls | NYVLG | wfrqapgkgrefva | AINWRGDITIGPPNVEG |
| NC41v11 | evqllesggglvqpggslslscaasggsls | NYVLG | wfrqapgkgrefva | AINWRGDITIGPPNVEG |
| NC41v12 | evqllesggglvqpggslslscaasggsls | NYVLG | wfrqapgkerefva | AINWRGDITIGPPNVEG |
| NC41v13 | evqllesggglvqpggslrlscaasggsls | NYVLG | wfrqapgkgrefva | AINWRGDITIGPPNVEG |
| NC41v14 | evqllesggglvqpggslrlscaasggsls | NYVLG | wfrqapgkgrefva | AINWRGDITIGPPNVEG |
| NC41v15 | evqllesggglvqpggslrlscaasggsls | NYVLG | wfrqapgkgrefva | AINWRGDITIGPPNVEG |
| NC41v17 | evqllesggglvqpggslrlscaasggsls | NYVLG | wfrqapgkgrefva | AINWRDDITIGPPNVEG |
| NC41v18 | evqllesggglvqpggslrlscaasggsls | NYVLG | wfrqapgkgrefva | AINWRDDITIGPPNVEG |

Figure 7: Continued

| | FR3 | CDR3 | FR4 |
|---|---|---|---|
| NC41 | rftisrdnakntgylqmnslapddtavyycga | GTPLNPGAYIYDWSYDY | wgrgtqvtvss |
| NC41v01 | rftisrdnakntlylqmnslapedtavyycga | GTPLNPGAYIYDWSYDY | wgqgtlvtvss |
| NC41v02 | rftisrdnsknntlylqmnslapedtavyycga | GTPLNPGAYIYDWSYDY | wgqgtlvtvss |
| NC41v03 | rftisrdnskntlylqmnslrpedtavyycga | GTPLNPGAYIYDWSYDY | wgqgtlvtvss |
| NC41v04 | rftisrdnskntlylqmnslrpddtavyycga | GTPLNPGAYIYDWSYDY | wgqgtlvtvss |
| NC41v05 | rftisrdnskntlylqmnslapedtavyycga | GTPLNPGAYIYDWSYDY | wgqgtlvtvss |
| NC41v06 | rftisrdnakntlylqmnslrpedtavyycga | GTPLNPGAYIYDWSYDY | wgqgtlvtvss |
| NC41v07 | rftisrdnakntlylqmnslapddtavyycga | GTPLNPGAYIYDWSYDY | wgqgtlvtvss |
| NC41v08 | rftisrdnakntlylqmnslrpedtavyycga | GTPLNPGAYIYDWSYDY | wgqgtlvtvss |
| NC41v09 | rftisrdnsknntlylqmnslrpddtavyycga | GTPLNPGAYIYDWSYDY | wgqgtlvtvss |
| NC41v10 | rftisrdnakntgylqmnslapddtavyycga | GTPLNPGAYIYDWSYDY | wgqgtlvtvss |
| NC41v11 | rftisrdnakntgylqmnslapddtavyycga | GTPLNPGAYIYDWSYDY | wgqgtlvtvss |
| NC41v12 | rftisrdnakntgylqmnslapddtavyycga | GTPLNPGAYIYDWSYDY | wgqgtlvtvss |
| NC41v13 | rftisrdnakntgylqmnslapedtavyycga | GTPLNPGAYIYDWSYDY | wgqgtlvtvss |
| NC41v14 | rftisrdnskntlylqmnslapedtavyycga | GTPLNPGAYIYDWSYDY | wgqgtlvtvss |
| NC41v15 | rftisrdnakntlylqmnslapedtavyycga | GTPLNPGAYIYDWSYDY | wgqgtlvtvss |
| NC41v17 | rftisrdnskntlylqmnslrpedtavyycga | GTPLNPGAYIYDWSYDY | wgqgtlvtvss |
| NC41v18 | rftisrdnskntlylqmnslrpedtavyycga | GTPLNPGAYIYDWSYDY | wgqgtlvtvss |

Figure 8A
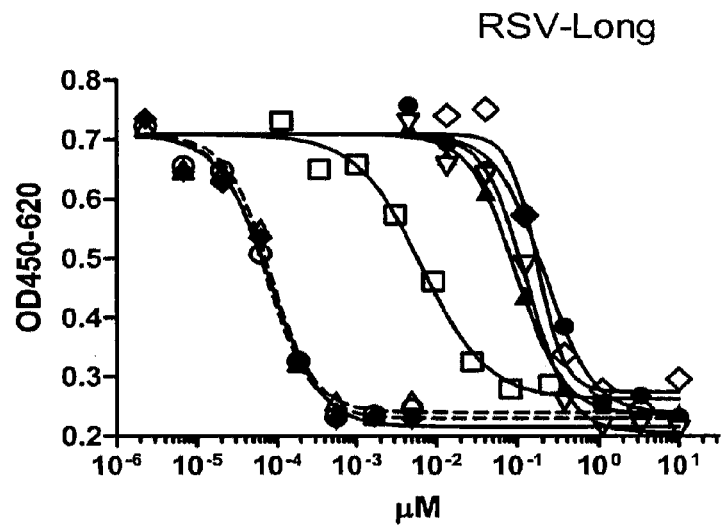
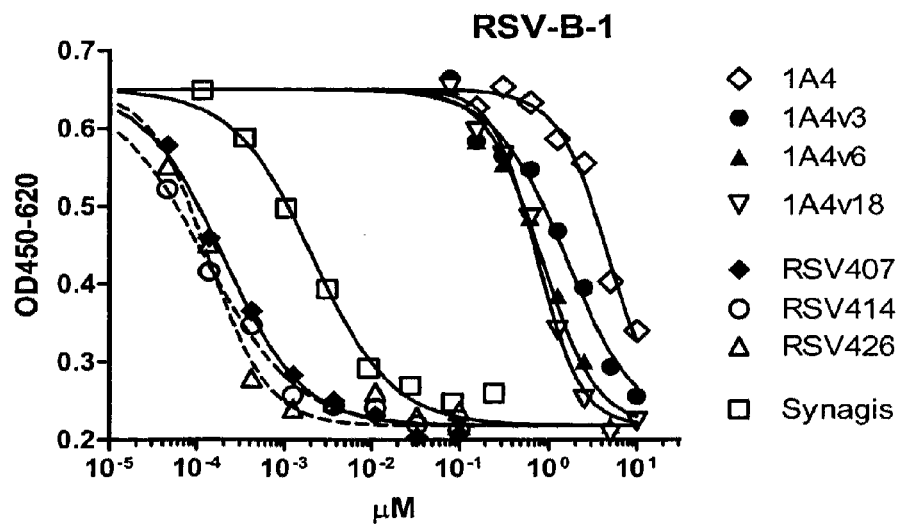

Figure 8B
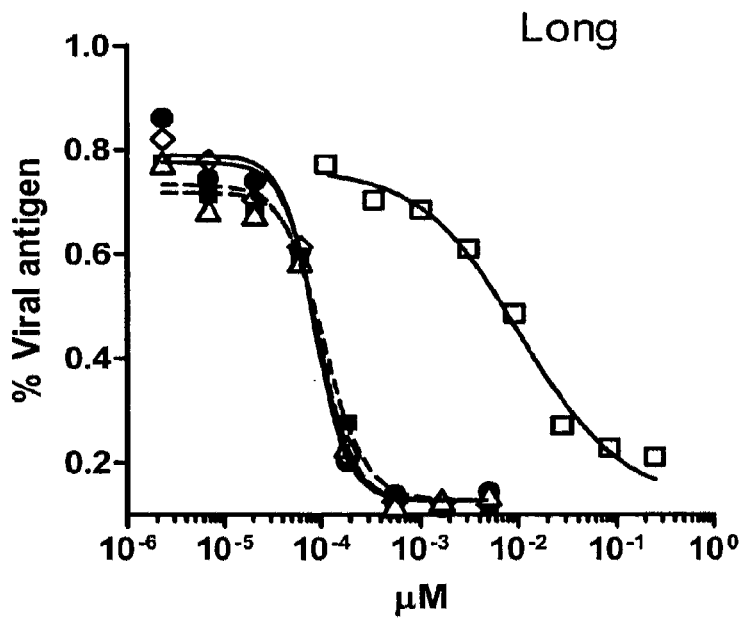
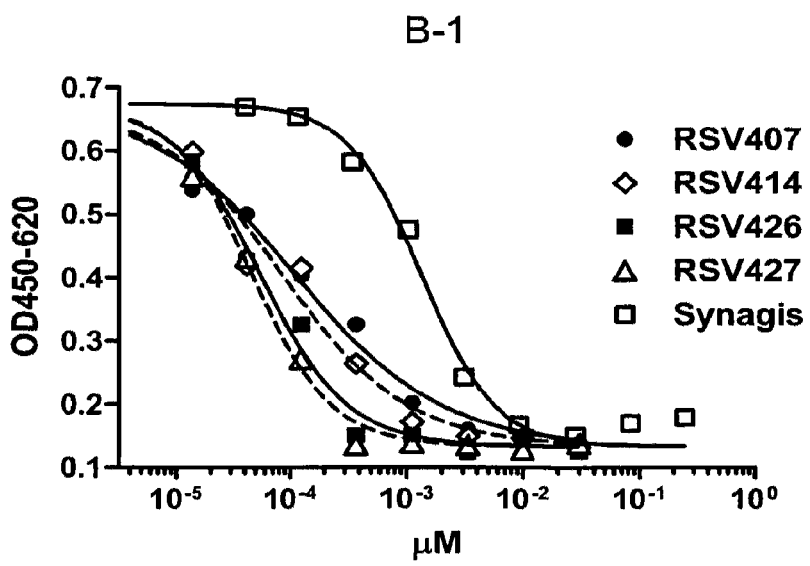

US 8,945,567 B2

MONOVALENT, BIVALENT AND TRIVALENT ANTI HUMAN RESPIRATORY SYNCYTIAL VIRUS (HRSV) NANOBODY CONSTRUCTS FOR THE PREVENTION AND/OR TREATMENT OF RESPIRATORY TRACT INFECTIONS

RELATED APPLICATIONS

This application is a national stage filing under 35 U.S.C. §371 of international application PCT/EP2010/057921, filed Jun. 7, 2010, which was published under PCT Article 21(2) in English, and claims the benefit under 35 U.S.C. §119(e) of U.S. provisional application Ser. No. 61/184,396, filed Jun. 5, 2009, and U.S. provisional application Ser. No. 61/265,014, filed Nov. 30, 2009, the disclosures of which are incorporated by reference herein in their entireties.

FIELD OF THE INVENTION

The present invention relates to amino acid sequences that are directed against/and or that can specifically bind (as defined herein) protein F of hRSV, as well as to compounds or constructs, and in particular proteins and polypeptides, that comprise or essentially consist of one or more such amino acid sequences (also referred to herein as "amino acid sequence(s) of the invention", "compound(s) of the invention", "construct(s) of the invention" and "polypeptide(s) of the invention", respectively).

The invention also relates to nucleic acids encoding such amino acid sequences and polypeptides (also referred to herein as "nucleic acid(s) of the invention" or "nucleotide sequence(s) of the invention"); to methods for preparing such amino acid sequences and polypeptides; to host cells expressing or capable of expressing such amino acid sequences or polypeptides; to compositions, and in particular to pharmaceutical compositions, that comprise such amino acid sequences, polypeptides, compounds or constructs, nucleic acids and/or host cells; and to uses of such amino acid sequences, polypeptides, compounds or constructs, nucleic acids, host cells and/or compositions, in particular for prophylactic and/or therapeutic purposes, such as the prophylactic and/or therapeutic purposes mentioned herein.

Other aspects, embodiments, advantages and applications of the invention will become clear from the further description herein.

BACKGROUND ART

Human respiratory syncytial virus (hRSV) is a member of the Paramyxoviridae family and is an enveloped virus with two main surface glycoproteins that make the spikes of the virus particle. One of these glycoproteins (protein G) is the attachment protein that mediates binding of the virus to the cell surface. The other glycoprotein (protein F or fusion) mediates fusion of the viral and cell membranes, allowing the entry of the viral nucleocapsid into the cell cytoplasm. Inhibition of the steps mediated by either G or F glycoproteins blocks the initial stages of the infectious cycle and neutralizes virus infectivity. Therefore, antibodies directed against either G or F, and which inhibit their respective activities, may neutralize virus infectivity and may protect against a hRSV infection. The F protein is highly conserved and forms trimeric spikes that undergo conformational changes upon activation.

hRSV is the leading cause of severe lower respiratory tract infections (bronchiolitis and pneumonia) in infants and very young children and causes annual epidemics during the winter months. The virus also causes a substantial disease burden among the elderly and adults with underlying cardiopulmonary disorders and/or immunosuppressive conditions are also at risk of severe hRSV disease. The immune response does not prevent re-infections.

There is no vaccine available to prevent hRSV infections. The only drug product available in the market is a humanized monoclonal antibody (Synagis®) directed against one of the viral glycoproteins (protein F) which is used prophylactically in children that are at a very high risk of suffering a severe hRSV infection. The restricted use of Synagis® is due, at least in part, to the high cost of this product. There is clearly a need for improved and/or cheaper prophylactic and/or therapeutic agents for the prevention and or treatment of infections by hRSV.

SUMMARY OF THE INVENTION

The present invention provides amino acid sequences (also referred to as "amino acid sequence(s) of the invention"), polypeptides (also referred to as "polypeptide(s) of the invention") and therapeutic compounds and compositions that are directed against protein F of hRSV and that have improved prophylactic, therapeutic and/or pharmacological properties, in addition to other advantageous properties (such as, for example, improved ease of preparation and/or reduced costs of goods), compared to the prior art amino acid sequences and antibodies. These improved and advantageous properties will become clear from the further description herein. Without being limiting, the amino acid sequences, polypeptides and therapeutic compounds and compositions provided by the invention may show an improved stability, less immunogenicity, improved binding to protein F of hRSV, improved affinity and/or avidity for protein F of hRSV, improved efficacy and/or potency for neutralizing hRSV (as defined herein), an increased selectivity for protein F of hRSV and/or they may be capable of partially or preferably totally blocking the interaction of protein F of hRSV with the target host cell and/or its membrane. They may be capable of neutralizing hRSV by modulating, inhibiting and/or preventing hRSV infectivity, by modulating, inhibiting and/or preventing hRSV fusion with (the cell membrane of) the target host cell, and/or by modulating, inhibiting and/or prevent hRSV entry in the target host cell (as defined herein). They may be cross reactive with and/or capable of neutralizing different strains of hRSV and/or different hRSV escape mutants.

In a first aspect, the present invention provides a number of stretches of amino acid residues (as defined herein) that are particularly suited for binding to a specific epitope on protein F of hRSV. These stretches of amino acid residues may be present in, and/or may be incorporated into, an amino acid sequence of the invention, in particular in such a way that they form (part of) the antigen binding site of the amino acid sequence of the invention. The resulting amino acid sequences will be capable of binding a specific epitope on protein F of hRSV that lies in, forms part of, or overlaps with (i.e. in the primary or tertiary structure) or is in close proximity to (i.e. in the primary or tertiary structure) antigenic site II on protein F of hRSV (i.e. amino acid residues 250-275 of protein F of hRSV).

Accordingly, in one aspect, the present invention provides amino acid sequences that comprise at least a stretch of amino acid residues chosen from the following:

a) SEQ ID NO: 102;
b) a stretch of amino acid residues that has no more than 3, preferably no more than 2, more preferably no more than 1 amino acid difference with SEQ ID NO: 102, provided that:
   i) said stretch of amino acid residues has an Aspartic acid (Asp, D) at position 6 (position 54 determined according to Kabat numbering); and
   ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In a preferred aspect, the present invention provides amino acid sequences that comprise two or more stretches of amino acid residues in which one stretch is chosen from the following:
a) SEQ ID NO: 102;
b) a stretch of amino acid residues that has no more than 3, preferably no more than 2, more preferably no more than 1 amino acid difference with SEQ ID NO: 102, provided that:
   i) said stretch of amino acid residues has an Aspartic acid (Asp, D) at position 6 (position 54 determined according to Kabat numbering); and
   ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and at least one stretch is chosen from:
c) SEQ ID NO: 98;
d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
e) SEQ ID NO: 121; and
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

such that the stretch of amino acid residues that corresponds to one of a), and b) should always be present in the amino acid sequence of the invention and such that the second stretch of amino acid residues is chosen from one of c), d), e) and f).

Even more preferably, the amino acid sequences of the invention comprise three or more stretches of amino acid residues, in which the first stretch of amino acid residues is chosen from the group consisting of:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference; or the second stretch of amino acid residues is chosen from the group consisting of:
c) SEQ ID NO: 102;
d) a stretch of amino acid residues that has no more than 3, preferably no more than 2, more preferably no more than 1 amino acid difference with SEQ ID NO: 102, provided that:
   i) said stretch of amino acid residues has an Aspartic acid (Asp, D) at position 6 (position 54 determined according to Kabat numbering); and
   ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and the third stretch of amino acid residues is chosen from the group consisting of:
e) SEQ ID NO: 121;
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Amino acid sequences comprising one or more of these specific stretches of amino acid residues have shown improved properties such as e.g. improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for protein F of hRSV and/or improved efficacy and/or potency for neutralizing hRSV.

The amino acid sequence of the invention may in particular be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody® (as defined herein, and including but not limited to a $V_{HH}$ sequence); other single variable domains, or any suitable fragment of any one thereof.

In this respect, the amino acid sequences of the invention may essentially consist of 4 framework regions (FR1 to FR4, respectively) and 3 complementarity determining regions (CDR1 to CDR3, respectively), in which CDR2 is chosen from:

a) SEQ ID NO: 102;
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

These preferred complementarity determining regions (CDR2 sequences) are also referred to as "CDR2(s) of the invention".

Preferably, the amino acid sequences of the invention may essentially consist of 4 framework regions (FR1 to FR4, respectively) and 3 complementarity determining regions (CDR1 to CDR3, respectively), in which CDR2 is chosen from the group consisting of:

a) SEQ ID NO: 102; or
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and at least one of CDR1 or CDR3 is chosen from:
  CDR1 chosen from the group consisting of:
c) SEQ ID NO: 98;
d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference; or and/or CDR3 chosen from the group consisting of:
e) SEQ ID NO: 121; or
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Even more preferably, the amino acid sequences of the invention may essentially consist of 4 framework regions (FR1 to FR4, respectively) and 3 complementarity determining regions (CDR1 to CDR3, respectively), in which:

CDR1 is chosen from the group consisting of:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and

CDR2 is chosen from the group consisting of:
c) SEQ ID NO: 102; or
d) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and

CDR3 is chosen from the group consisting of:
e) SEQ ID NO: 121;
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In a specific aspect, the amino acid sequence or Nanobody® of the invention comprises at least SEQ ID NO: 102. Preferably, the amino acid sequence or Nanobody® of the invention comprises SEQ ID NO: 98, SEQ ID NO: 102 and SEQ ID NO: 121.

The present invention also provides a number humanized amino acid sequences that are particularly suited for binding protein F of hRSV. The amino acid sequences of the present invention show reduced immunogenicity upon administration to a human subject. In addition, the amino acid sequences of the present invention show other improved properties such as e.g. improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) for protein F of hRSV, improved affinity and/or improved avidity for protein F of hRSV and/or improved efficacy and/or potency for neutralizing hRSV compared to their corresponding wild type amino acid sequences (as described in PCT application PCT/EP2009/056975 entitled "Amino acid sequences directed against envelope proteins of a virus and polypeptides comprising the same for the treatment of viral diseases" filed by Ablynx N. V on 5 Jun. 2009).

Accordingly, in another aspect, the present invention provides amino acid sequences chosen from the following:
a) SEQ ID NO's: 60-76;
b) amino acid sequences that have no more than 3, preferably no more than 2, more preferably no more than 1 amino acid difference with one of SEQ ID NO's: 60-76, provided that:
i) the amino acid sequence has a Glutamine (Gln, Q) at position 105 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence of the invention comprises or essentially consists of SEQ ID NO: 60-76.

In another aspect, the present invention provides amino acid sequences chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
i) the amino acid sequence has a Glutamine (Gln, Q) at position 105, a Leucine (Leu, L) at position 78 and/or an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences of the invention comprise or essentially consists of one of SEQ ID NO's: 62, 65, 67, 68, 75 and 76.

In yet another aspect, the present invention provides amino acid sequences chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence of the invention comprises or essentially consists of SEQ ID NO: 65. In another preferred aspect, the amino acid sequence of the invention comprises or essentially consists of SEQ ID NO: 76.

In another aspect, the present invention provides amino acid sequences chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
i) the amino acid sequence has a Proline (Pro, P) at position 14, Arginine (Arg, R) at position 19, Leucine (Leu, L) at position 20 and Leucine (Leu, L) at position 108 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence of the invention comprises or essentially consists of SEQ ID NO: 146-153.

In another aspect, the present invention provides amino acid sequences chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:

SEQ ID NO: 146, the amino acid sequence preferably has Glutamine (Gln, Q) at position 105;

SEQ ID NO: 147, the amino acid sequence preferably has Arginine (Arg, R) at position 83 and Glutamine (Gln, Q) at position 105;

SEQ ID NO: 148, the amino acid sequence preferably has Glutamic acid (Glu, E) at position 85 and Glutamine (Gln, Q) at position 105;

SEQ ID NO: 149, the amino acid sequence preferably has Arginine (Arg, R) at position 83, Glutamic acid (Glu, E) at position 85 and Glutamine (Gln, Q) at position 105;

SEQ ID NO: 151, the amino acid sequence preferably has Arginine (Arg, R) at position 83;

SEQ ID NO: 152, the amino acid sequence preferably has Glutamic acid (Glu, E) at position 85;

SEQ ID NO: 153, the amino acid sequence preferably has Arginine (Arg, R) at position 83 and Glutamic acid (Glu, E) at position 85;

(said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences of the invention comprise or essentially consist of one of SEQ ID NO's: 146-149 and 151-153.

The present invention provides a number of sequence optimized amino acid sequences and/or Nanobodies® that show increased stability upon storage during stability studies and that are particularly suited for binding protein F of hRSV. The amino acid sequences of the present invention show reduced pyroglutamate post-translational modification of the N-terminus and hence have increased product stability. In addition, the amino acid sequences of the present invention show other improved properties such as e.g. less immunogenicity, improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) for protein F of hRSV, improved affinity and/or improved avidity for protein F of hRSV and/or improved efficacy and/or potency for neutralizing hRSV compared to their corresponding parental amino acid sequences (as described in PCT application PCT/EP2009/056975 entitled "Amino acid sequences directed against envelope proteins of a virus and polypeptides comprising the same for the treatment of viral diseases" filed by Ablynx N. V on 5 Jun. 2009).

Accordingly, in one aspect of the present invention, amino acid sequences and/or Nanobodies® are provided chosen from the following:

a) SEQ ID NO's: 138-141 and 154-157;

b) amino acid sequences that have no more than 3, preferably no more than 2, more preferably no more than 1 amino acid difference with one of SEQ ID NO's: 138-141 and 154-157, provided that:

i) the amino acid sequence has a Aspartic acid (Asp, D) at position 1 (said position determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence and/or Nanobody® of the invention comprises or essentially consists of one of SEQ ID NO's: 138-141 and 154-157.

The amino acid sequences and Nanobodies® provided by the invention are preferably in essentially isolated form (as defined herein), or form part of a protein or polypeptide of the invention (also referred to as "polypeptide of the invention" or "protein of the invention"), which may comprise or essentially consist of one or more amino acid sequences or Nanobodies® of the invention and which may optionally further comprise one or more further amino acid sequences or Nanobodies® (all optionally linked via one or more suitable linkers).

Accordingly, in another aspect, the invention also relates to a protein or polypeptide (also referred to herein as a "polypeptide of the invention", respectively) that comprises or essentially consists of one or more amino acid sequences and/or Nanobodies® of the invention (or suitable fragments thereof)

For example, and without limitation, the one or more amino acid sequences and/or Nanobodies® of the invention may be used as a binding unit in such a protein or polypeptide, so as to provide a monovalent, multivalent or multiparatopic polypeptide of the invention, respectively, all as described herein. The present invention thus also relates to a polypeptide which is a monovalent construct comprising or essentially consisting of an amino acid sequence or a Nanobody® of the invention. The present invention thus also relates to a polypeptide which is a multivalent polypeptide, such as e.g. a bivalent or trivalent polypeptide. The present invention also relates to a polypeptide which is a multiparatopic polypeptide, such as e.g. a bisparatopic or triparatopic polypeptide.

In a preferred aspect, the invention provides a multivalent, preferably a bivalent or trivalent polypeptide comprising or essentially consisting of at least two amino acid sequences and/or Nanobodies® of the invention (as described above).

In one aspect, the invention provides a multivalent, preferably a bivalent or trivalent polypeptide comprising or essentially consisting of at least two (preferably identical) or at least three (preferably identical) amino acid sequences or Nanobodies® chosen from amino acid sequences that comprise at least a stretch of amino acid residues chosen from the following:

a) SEQ ID NO: 102;

b) a stretch of amino acid residues that has no more than 3, preferably no more than 2, more preferably no more than 1 amino acid difference with SEQ ID NO: 102, provided that:

i) said stretch of amino acid residues has an Aspartic acid (Asp, D) at position 6 (position 54 determined according to Kabat numbering); and ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In another aspect, the invention provides a multivalent, preferably a bivalent or trivalent polypeptide comprising or essentially consisting of at least two (preferably identical) or at least three (preferably identical) amino acid sequences or Nanobodies® chosen from amino acid sequences that comprise two or more stretches of amino acid residues in which one stretch is chosen from the following:
  a) SEQ ID NO: 102;
  b) a stretch of amino acid residues that has no more than 3, preferably no more than 2, more preferably no more than 1 amino acid difference with SEQ ID NO: 102, provided that:
    i) said stretch of amino acid residues has an Aspartic acid (Asp, D) at position 6 (position 54 determined according to Kabat numbering); and
    ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino add sequence comprising said stretch of amino add residues without the 3, 2 or 1 amino acid difference;
  and at least one stretch is chosen from:
  c) SEQ ID NO: 98;
  d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
  e) SEQ ID NO: 121; and
  f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.
  such that the stretch of amino acid residues that corresponds to one of a), and b) should always be present in the amino acid sequence that forms part of the multivalent polypeptide and such that the second stretch of amino acid residues is chosen from one of c), d), e) and f).

Preferred multivalent (such as bivalent or trivalent) polypeptides may comprise or essentially consist of at least two (preferably identical) or at least three (preferably identical) amino acid sequences or Nanobodies® chosen from amino acid sequences that comprise three or more stretches of amino acid residues, in which the first stretch of amino acid residues is chosen from the group consisting of:
  a) SEQ ID NO: 98;
  b) a stretch of amino add residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference; or
the second stretch of amino acid residues is chosen from the group consisting of:
  c) SEQ ID NO: 102;
  d) a stretch of amino acid residues that has no more than 3, preferably no more than 2, more preferably no more than 1 amino acid difference with SEQ ID NO: 102, provided that:
    i) said stretch of amino acid residues has an Aspartic acid (Asp, D) at position 6 (position 54 determined according to Kabat numbering); and
    ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and the third stretch of amino acid residues is chosen from the group consisting of:
  e) SEQ ID NO: 121;
  f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Multivalent (such as bivalent or trivalent) polypeptides may comprise or essentially consist of at least two (preferably identical) or at least three (preferably identical) amino acid sequences or Nanobodies® that essentially consist of 4 framework regions (FR1 to FR4, respectively) and 3 complementarity determining regions (CDR1 to CDR3, respectively), in which CDR2 is chosen from:
  a) SEQ ID NO: 102;
  b) a stretch of amino acid residues that has no more than 3, preferably no more than 2, more preferably no more than 1 amino acid difference with SEQ ID NO: 102, provided that:
    i) said stretch of amino acid residues has an Aspartic acid (Asp, D) at position 6 (position 54 determined according to Kabat numbering); and
    ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Multivalent (such as bivalent or trivalent) polypeptides may comprise or essentially consist of at least two (preferably identical) or at least three (preferably identical) amino acid sequences or Nanobodies® that essentially consist of 4 framework regions (FR1 to FR4, respectively) and 3 complementarity determining regions (CDR1 to CDR3, respectively), in which CDR2 is chosen from the group consisting of:

a) SEQ ID NO: 102; or
b) a stretch of amino acid residues that has no more than 3, preferably no more than 2, more preferably no more than 1 amino acid difference with SEQ ID NO: 102, provided that:
 i) said stretch of amino acid residues has an Aspartic acid (Asp, D) at position 6 (position 54 determined according to Kabat numbering); and
 ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and at least one of CDR1 or CDR3 is chosen from:
 CDR1 chosen from the group consisting of:
c) SEQ ID NO: 98;
d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference; or
 and/or
 CDR3 chosen from the group consisting of:
e) SEQ ID NO: 121; or
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Preferably, multivalent (such as bivalent or trivalent) polypeptides may comprise or essentially consist of at least two (preferably identical) or at least three (preferably identical) amino acid sequences or Nanobodies® that essentially consist of 4 framework regions (FR1 to FR4, respectively) and 3 complementarity determining regions (CDR1 to CDR3, respectively), in which:
 CDR1 is chosen from the group consisting of:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and
 CDR2 is chosen from the group consisting of:
c) SEQ ID NO: 102; or
d) a stretch of amino acid residues that has no more than 3, preferably no more than 2, more preferably no more than 1 amino acid difference with SEQ ID NO: 102, provided that:
 i) said stretch of amino acid residues has an Aspartic acid (Asp, D) at position 6 (position 54 determined according to Kabat numbering); and
 ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and
 CDR3 is chosen from the group consisting of:
e) SEQ ID NO: 121;
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In a specific aspect, the multivalent (such as bivalent or trivalent) polypeptides may comprise or essentially consist of at least two (preferably identical) or at least three (preferably identical) amino acid sequences or Nanobodies® that comprise at least SEQ ID NO: 102, preferably that comprise SEQ ID NO: 98, SEQ ID NO: 102 and SEQ ID NO: 121.

In another aspect, the invention provides a multivalent, preferably a bivalent or trivalent polypeptide comprising or essentially consisting of at least two (preferably identical) amino acid sequences or Nanobodies® chosen from the following:
 a) SEQ ID NO's: 60-76;
 b) amino acid sequences that have no more than 3, preferably no more than 2, more preferably no more than 1 amino acid difference with one of SEQ ID NO's: 60-76, provided that:
  i) the amino acid sequence has a Glutamine (Gln, Q) at position 105 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two identical amino acid sequences or Nanobodies® chosen from the group consisting of SEQ ID NO's: 60-76.

In another aspect, the invention provides a multivalent, preferably a bivalent or trivalent polypeptide comprising or essentially consisting of at least two (preferably identical) amino acid sequences or Nanobodies® chosen from the following:
 a) SEQ ID NO's: 62, 65, 67, 68, 75 and 76;
 b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two identical amino acid sequences or Nanobodies® chosen from the group consisting of SEQ ID NO's: 62, 65, 67, 68, 75 and 76.

In another preferred aspect, the invention provides a multivalent, preferably a bivalent or trivalent polypeptide comprising or essentially consisting of at least two (preferably identical) amino acid sequences or Nanobodies® chosen from the following:
 a) SEQ ID NO's: 65 and 76;
 b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two identical amino acid sequences or Nanobodies® chosen from the group consisting of SEQ ID NO's: 65 and 76.

In another preferred aspect, the invention provides a multivalent, preferably a trivalent polypeptide comprising or essentially consisting of at least three (preferably identical) amino acid sequences or Nanobodies® chosen from the following:
 a) SEQ ID NO's: 60-76;
 b) amino acid sequences that have no more than 3, preferably no more than 2, more preferably no more than 1 amino acid difference with one of SEQ ID NO's: 60-76, provided that:
  i) the amino acid sequence has a Glutamine (Gln, Q) at position 105 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three identical amino acid sequences or Nanobodies® chosen from the group consisting of SEQ ID NO's: 60-76.

In another preferred aspect, the invention provides a multivalent, preferably a trivalent polypeptide comprising or essentially consisting of at least three (preferably identical) amino acid sequences or Nanobodies® chosen from the following:
 a) SEQ ID NO's: 62, 65, 67, 68, 75 and 76;
 b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three identical amino acid sequences or Nanobodies® chosen from the group consisting of SEQ ID NO's: 62, 65, 67, 68, 75 and 76.

In another preferred aspect, the invention provides a multivalent, preferably a trivalent polypeptide comprising or essentially consisting of at least three (preferably identical) amino acid sequences or Nanobodies® chosen from the following:
 a) SEQ ID NO's: 65 and 76;
 b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three identical amino acid sequences or Nanobodies® chosen from the group consisting of SEQ ID NO's: 65 and 76.

A preferred multivalent polypeptide of the invention comprises or essentially consists of three amino acid sequences or Nanobodies® with SEQ ID NO: 62. Another preferred multivalent polypeptide of the invention comprises or essentially consists of three amino acid sequences or Nanobodies® with SEQ ID NO: 65. Another preferred multivalent polypeptide of the invention comprises or essentially consists of three amino acid sequences or Nanobodies® with SEQ ID NO: 76.

In another aspect, the invention provides a multivalent, preferably a bivalent or trivalent polypeptide comprising or essentially consisting of at least two (preferably identical) amino acid sequences or Nanobodies® chosen from the following:

a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Proline (Pro, P) at position 14, Arginine (Arg, R) at position 19, Leucine (Leu, L) at position 20 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two identical amino acid sequences or Nanobodies® chosen from the group consisting of SEQ ID NO's: 146-153.

In another aspect, the invention provides a multivalent, preferably a bivalent or trivalent polypeptide comprising or essentially consisting of at least two (preferably identical) amino acid sequences or Nanobodies® chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two identical amino acid sequences or Nanobodies® chosen from the group consisting of SEQ ID NO's: 146-149 and 151-153.

In another preferred aspect, the invention provides a multivalent, preferably a trivalent polypeptide comprising or essentially consisting of at least three (preferably identical) amino acid sequences or Nanobodies® chosen from the following:

a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Proline (Pro, P) at position 14, Arginine (Arg, R) at position 19, Leucine (Leu, L) at position 20 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three identical amino acid sequences or Nanobodies® chosen from the group consisting of SEQ ID NO's: 146-153.

In another preferred aspect, the invention provides a multivalent, preferably a trivalent polypeptide comprising or essentially consisting of at least three (preferably identical) amino acid sequences or Nanobodies® chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
SEQ ID NO: 146, the amino acid sequence preferably has Glutamine (Gln, Q) at position 105;
SEQ ID NO: 147, the amino acid sequence preferably has Arginine (Arg, R) at position 83 and Glutamine (Gln, Q) at position 105;
SEQ ID NO: 148, the amino acid sequence preferably has Glutamic acid (Glu, E) at position 85 and Glutamine (Gln, Q) at position 105;
SEQ ID NO: 149, the amino acid sequence preferably has Arginine (Arg, R) at position 83, Glutamic add (Glu, E) at position 85 and Glutamine (Gln, Q) at position 105;
SEQ ID NO: 151, the amino acid sequence preferably has Arginine (Arg, R) at position 83;
SEQ ID NO: 152, the amino acid sequence preferably has Glutamic add (Glu, E) at position 85;
SEQ ID NO: 153, the amino acid sequence preferably has Arginine (Arg, R) at position 83 and Glutamic acid (Glu, E) at position 85;
(said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three identical amino acid sequences or Nanobodies® chosen from the group consisting of SEQ ID NO's: 146-149 and 151-153.

In another aspect, the invention provides a multivalent, preferably a bivalent or trivalent polypeptide comprising or essentially consisting of at least one amino acid sequence or Nanobody® chosen from the following:
a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
i) the amino acid sequence has a Aspartic acid (Asp, D) at position 1 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody® chosen from the group consisting of SEQ ID NO's: 138-141 and 154-157.

In another preferred aspect, the invention provides a multivalent, preferably a trivalent polypeptide comprising or essentially consisting of at least one amino acid sequence or Nanobody® chosen from the following:
a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
i) the amino acid sequence has a Aspartic acid (Asp, D) at position 1 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a trivalent polypeptide that comprises or essentially consists of at least one amino acid sequence or Nanobody chosen from the group consisting of SEQ ID NO's: 138-141 and 154-157.

In another preferred aspect, the invention provides a trivalent polypeptide chosen from the following polypeptides:
a) SEQ ID NO's: 77-79 and 158;
b) polypeptides that have no more than 3, preferably no more than 2, more preferably no more than 1 amino acid difference with one of SEQ ID NO's: 77-79 and 158, provided that:
i) the amino acid sequence or Nanobody® encompassed in said polypeptide has a Glutamine (Gln, Q) at position 105, a Leucine (Leu, L) at position 78, an Arginine (Arg, R) at position 83 and/or a Glutamic acid (Glu, E) at position 85 (said positions determined according to Kabat numbering); and
ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of one of SEQ ID NO's: 77-79 and 158.

In another preferred aspect, the invention provides a trivalent polypeptide chosen from the following polypeptides:
a) SEQ ID NO's: 78 and 79;
b) polypeptides that have no more than 3, preferably no more than 2, more preferably no more than 1 amino acid difference with one of SEQ ID NO's: 78 and 79, provided that:
i) the amino acid sequence or Nanobody® encompassed in said polypeptide has an Aspartic acid (Asp, D) at position 54, a Glutamine (Gln, Q) at position 105, a Leucine (Leu, L) at position 78, an Arginine (Arg, R) at position 83 and/or a Glutamic acid (Glu, E) at position 85 (said positions determined according to Kabat numbering); and
ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of SEQ ID NO: 78 or 79.

In another specific aspect, the polypeptide of the invention essentially consists of the amino acid sequence of SEQ ID NO: 77. In another specific aspect, the polypeptide of the invention essentially consists of the amino acid sequence of SEQ ID NO: 78. In another specific aspect, the polypeptide of the invention essentially consists of the amino acid sequence of SEQ ID NO: 79. In another specific aspect, the polypeptide of the invention essentially consists of the amino acid sequence of SEQ ID NO: 158.

In another preferred aspect, the invention provides a trivalent polypeptide chosen from the following polypeptides:
a) SEQ ID NO's: 159-161;
b) polypeptides that have no more than 3, preferably no more than 2, more preferably no more than 1 amino acid difference with one of SEQ ID NO's: 159-161, provided that:
  i) the amino acid sequence or Nanobody® encompassed in said polypeptide has a Proline (Pro, P) at position 14, Arginine (Arg, R) at position 19, Leucine (Leu, L) at position 20 and Leucine (Leu, L) at position 108 (said positions determined according to Kabat numbering); and
  iii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

Preferred trivalent polypeptides of the invention comprise or essentially consist of one of SEQ ID NO's: 159-161.

In another preferred aspect, the invention provides a trivalent polypeptide chosen from the following polypeptides:
a) SEQ ID NO's: 159-161;
b) polypeptides that have no more than 3, preferably no more than 2, more preferably no more than 1 amino acid difference with one of SEQ ID NO's: 159-161, provided that:
  i) the amino acid sequence or Nanobody® encompassed in said polypeptide has a Praline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the polypeptide has no more than 3, preferably no more than 2, more preferably no more than 1 amino acid difference with:
    SEQ ID NO: 159, the amino acid sequence or Nanobody® encompassed in said polypeptide preferably has Arginine (Arg, R) at position 83 and Glutamine (Gln, Q) at position 105;
    SEQ ID NO: 160, the amino acid sequence or Nanobody® encompassed in said polypeptide preferably has Arginine (Arg, R) at position 83, Glutamic acid (Glu, E) at position 85 and Glutamine (Gln, Q) at position 105;
    SEQ ID NO: 161, the amino acid sequence or Nanobody® encompassed in said polypeptide preferably has Arginine (Arg, R) at position 83 and Glutamic acid (Glu, E) at position 85;
    (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

Preferred trivalent polypeptides of the invention comprise or essentially consist of SEQ ID NO: 159-161.

In another preferred aspect, the invention provides a trivalent polypeptide chosen from the following polypeptides:
a) SEQ ID NO's: 142-145 and 162-165;
b) polypeptides that have no more than 3, preferably no more than 2, more preferably no more than 1 amino acid difference with one of SEQ ID NQ's: 142-145 and 162-165, provided that:
  i) the first amino acid sequence or Nanobody® encompassed in said polypeptide has an Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred trivalent polypeptides of the invention comprise or essentially consist of one of SEQ ID NO's: 142-145 and 162-165.

Polypeptides with these sequences show advantageous properties for use as prophylactic, therapeutic and/or pharmacologically active agents such as e.g. improved stability, less immunogenicity, improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for protein F of hRSV and/or improved efficacy and/or potency for neutralizing hRSV.

The invention further relates to compounds or constructs, and in particular proteins or polypeptides (also referred to herein as a "compound(s) of the invention") that comprise or essentially consist of one or more amino acid sequences, Nanobodies® and/or polypeptides of the invention (or suitable fragments thereof), and optionally further comprise one or more other groups, residues, moieties or binding units. As will become clear to the skilled person from the further disclosure herein, such further groups, residues, moieties, binding units or amino acid sequences may or may not provide further functionality to the amino acid sequence, Nanobody® or polypeptide of the invention (and/or to the compound or construct in which it is present) and may or may not modify the properties of the amino acid sequence, Nanobody® and/or polypeptide of the invention.

It is also within the scope of the invention to use parts, fragments, analogs, mutants, variants, alleles and/or derivatives of the amino acid sequences and/or polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against antigenic site II on protein F of hRSV; and more preferably will be capable of specific binding to antigenic site II on protein F of hRSV, and even more preferably capable of binding to antigenic site II on protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Such parts, fragments, analogs, mutants, variants, alleles and/or derivatives will usually also have a hRSV neutralization efficacy and/or potency as defined herein. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

The invention also relates to nucleic acids or nucleotide sequences that encode an amino acid sequence of the invention, a Nanobody® of the invention and/or a polypeptide of the invention (or a suitable fragment thereof). Such a nucleic acid will also be referred to herein as "nucleic acid(s) of the invention" and may for example be in the form of a genetic construct, as further described herein. Accordingly, the present invention also relates to a nucleic acid or nucleotide sequence that is in the form of a genetic construct.

The invention further relates to a host or host cell that expresses (or that under suitable circumstances is capable of expressing) an amino acid sequence of the invention, a Nanobody® of the invention, a polypeptide of the invention and/or a compound or construct of the invention; and/or that contains a nucleic acid of the invention. Some preferred but non-limiting examples of such hosts or host cells will become clear from the further description herein.

The invention further relates to a product or composition containing or comprising at least one amino acid sequence of the invention (or a suitable fragment thereof), at least one Nanobody® of the invention, at least one polypeptide of the invention, at least one compound or construct of the invention, at least one monovalent construct of the invention and/or at least one nucleic acid of the invention, and optionally one or more further components of such compositions known per se, i.e. depending on the intended use of the composition. Such a product or composition may for example be a pharmaceutical composition (as described herein) or a veterinary composition. Some preferred but non-limiting examples of such products or compositions will become clear from the further description herein.

The invention further relates to methods for preparing the amino acid sequences, Nanobodies®, polypeptides, nucleic acids, host cells, products and compositions described herein.

The invention further relates to applications and uses of the amino acid sequences, Nanobodies®, polypeptides, compounds, nucleic acids, host cells, products and compositions described herein, as well as to methods for the prevention and/or treatment of respiratory track infection caused by hRSV. Some preferred but non-limiting applications and uses will become clear from the further description herein.

The amino acid sequences, Nanobodies®, polypeptides, compounds and compositions of the present invention can generally be used to block the interaction of protein F of hRSV with the target host cell and/or its membrane, to neutralize hRSV (different hRSV strains and/or escape mutants), to modulate, inhibit and/or prevent hRSV infectivity (of different hRSV strains and/or escape mutants), to modulate, inhibit and/or prevent fusion (of different hRSV strains and/or escape mutants) with (the cell membrane of) the target host cell and/or to modulate, inhibit and/or prevent hRSV entry in the target host cell (of different hRSV strains and/or escape mutants).

As such, the amino acid sequences, Nanobodies®, polypeptides, compounds and compositions of the present invention can be used for the prevention and/or treatment of diseases and disorders associated with hRSV infection. Examples of such diseases and disorders associated with hRSV infection will be clear to the skilled person based on the disclosure herein, and for example include the following diseases and disorders: respiratory illness, upper respiratory tract infection, lower respiratory tract infection, bronchiolitis (inflammation of the small airways in the lung), pneumonia, dyspnea, cough, (recurrent) wheezing and asthma.

Accordingly, the present invention also relates to a method for the prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma caused by hRSV, said method comprising administering, to a subject in need thereof, a pharmaceutically active amount of at least one amino acid sequence of the invention, Nanobody® of the invention, polypeptide of the invention, compound or construct of the invention or monovalent construct of the invention, or a composition of the invention.

The invention also relates to the use of an amino acid sequence of the invention, a Nanobody® of the invention, a polypeptide of the invention, a compound or construct of the invention or a monovalent construct of the invention in the preparation of a pharmaceutical composition for the prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma; and/or for use in one or more of the methods described herein.

The invention also relates to an amino acid sequence of the invention, a Nanobody® of the invention, a polypeptide of the invention, a compound or construct of the invention or monovalent construct of the invention for prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma.

Other applications and uses of the amino acid sequences, Nanobodies®, polypeptides and compounds and compositions of the invention will become clear to the skilled person from the further disclosure herein.

BRIEF DESCRIPTION OF THE DRAWINGS

FIGS. 3A and B: Potency (RSV neutralization) of monovalent, bivalent and trivalent constructs to neutralize Long and B-1 RSV strains as described in Example 11.

FIG. 5: Neutralization of RSV Long and RSV B-1 strains by trivalent NC41 Nanobody® with different linker lengths as described in Example 15.

FIG. 6: Schematic overview of the humanized residues introduced in selected NC41 variants. Dots indicate the presence of the wildtype residue; letters correspond to the humanized residue. Numbering is according to Kabat.

FIG. 7: Alignment of preferred humanized Nanobody® sequences of the invention.

FIG. 8: Neutralization of hRSV Long strain and B-1 strain by monovalent and trivalent humanized NC41 variants. In FIG. 8A, neutralization by two of the trivalent humanized NC41 variants (RSV414 and RSV426) is compared with their corresponding monovalent Nanobodies®. FIG. 8B shows the neutralization by the trivalent NC41 variants (RSV414, RSV426 and RSV427).

DETAILED DESCRIPTION OF THE INVENTION

Figure 1:
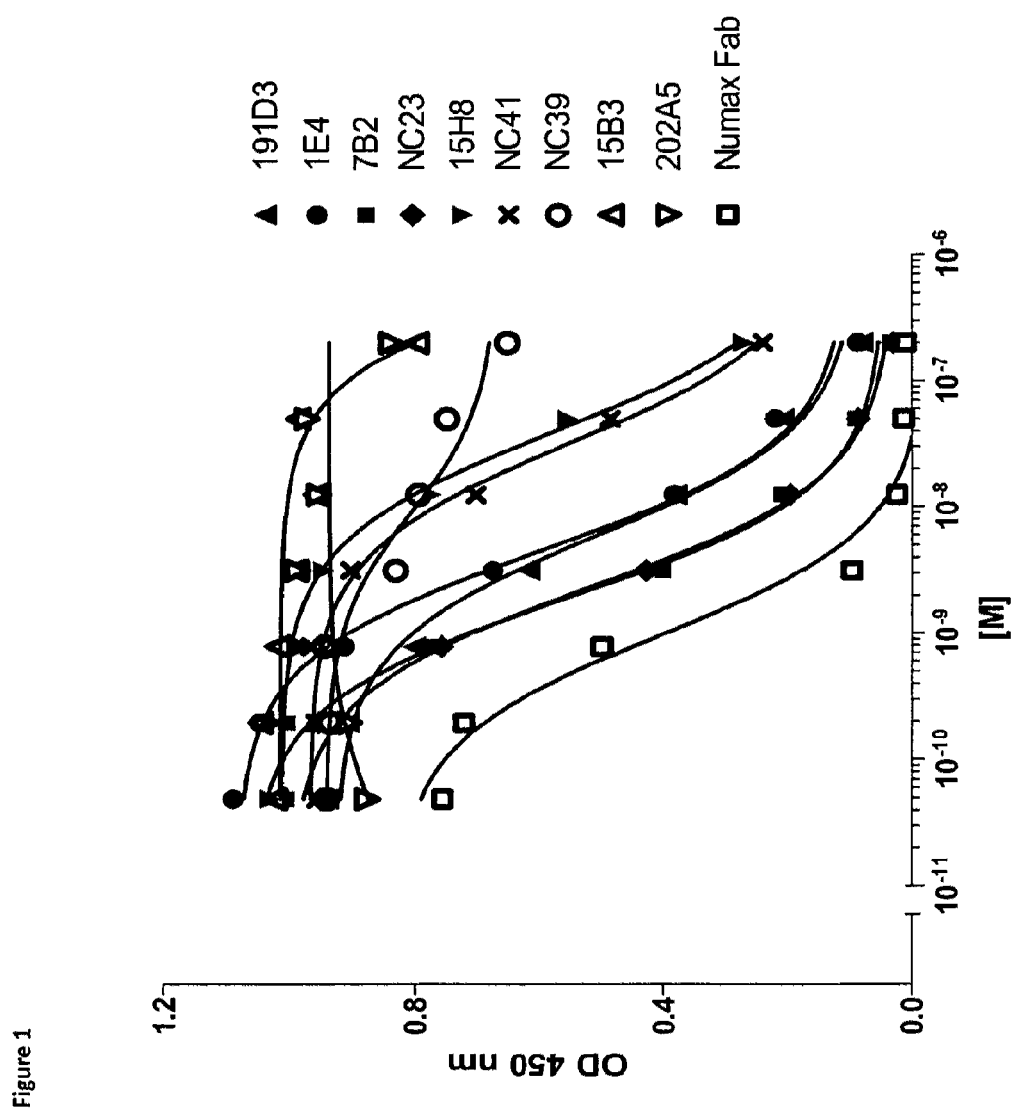
FIG. 1: Competition ELISA: Synagis® Fab competes with purified RSV binding Nanobodies® and Numax Fab for binding to $F_{TM}$-protein as described in Example 8. Nanobody® 202A5 is an irrelevant Nanobody® binding HA of influenza.

In the present description, examples and claims:
a) Unless indicated or defined otherwise, all terms used have their usual meaning in the art, which will be clear to the skilled person. Reference is for example made to the standard handbooks mentioned in paragraph a) on page 46 of WO 08/020,079.
b) Unless indicated otherwise, the terms "immunoglobulin sequence", "sequence", "nucleotide sequence" and "nucleic acid" are as described in paragraph b) on page 46 of WO 08/020,079.
c) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.
d) Amino acid residues will be indicated according to the standard three-letter or one-letter amino acid code. Reference is made to Table R-2 on page 48 of WO 08/020,079.
e) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020,079.
f) The term "in essentially isolated form" has the meaning given to it in paragraph j) on pages 52 and 53 of WO 08/020,079.
g) The terms "domain" and "binding domain" have the meanings given to it in paragraph k) on page 53 of WO 08/020,079.
h) The terms "antigenic determinant" and "epitope", which may also be used interchangeably herein, have the meanings given to it in paragraph 1) on page 53 of WO 08/020,079.
i) As further described in paragraph m) on page 53 of WO 08/020,079, an amino acid sequence (such as a Nanobody®, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.
j) The term "specificity" has the meaning given to it in paragraph n) on pages 53-56 of WO 08/020,079; and as mentioned therein refers to the number of different types of antigens or antigenic determinants to which a particular antigen-binding molecule or antigen-binding protein (such as a Nanobody® or a polypeptide of the invention) molecule can bind. The specificity of an antigen-binding protein can be determined based on affinity and/or avidity, as described on pages 53-56 of WO 08/020,079 (incorporated herein by reference), which also describes some preferred techniques for measuring binding between an antigen-binding molecule (such as a Nanobody® or polypeptide of the invention) and the pertinent antigen. Typically, antigen-binding proteins (such as the amino acid sequences, Nanobodies® and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4 \text{M}^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as e.g. between 10 and 5 nM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020,079, the dissociation constant may be the actual or apparent dissociation constant. Methods for determining the dissociation constant will be clear to the skilled person, and for example include the techniques mentioned on pages 53-56 of WO 08/020,079.
k) The half-life of an amino acid sequence, compound or polypeptide of the invention can generally be defined as described in paragraph o) on page 57 of WO 08/020,079 and as mentioned therein refers to the time taken for the serum concentration of the amino acid sequence, compound or polypeptide to be reduced by 50%, in vivo, for example due to degradation of the amino acid sequence, compound or polypeptide and/or clearance or sequestration of the amino acid sequence, compound or polypeptide by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020,079. As also mentioned in paragraph o) on page 57 of WO 08/020,079, the half-life can be expressed using parameters such as the t1/2-alpha, t1/2-beta and the area under the curve (AUC). Reference is for example made to the Experimental Part below, as well as to the standard handbooks, such as Kenneth, A et al: Chemical Stability of Pharmaceuticals: A Handbook for Pharmacists and Peters et al, Pharmacokinetic analysis: A Practical Approach (1996). Reference is also made to "Pharmacokinetics", M Gibaldi & D Perron, published by Marcel Dekker, 2nd Rev. edition (1982). The terms "increase in half-life" or "increased half-life" as also as defined in paragraph o) on page 57 of WO 08/020,079 and in particular refer to an increase in the t1/2-beta, either with or without an increase in the t1/2-alpha and/or the AUC or both.

l) In respect of a target or antigen, the term "interaction site" on the target or antigen means a site, epitope, antigenic determinant, part, domain or stretch of amino acid residues on the target or antigen that is a site for binding to a receptor or other binding partner, a catalytic site, a cleavage site, a site for allosteric interaction, a site involved in multimerization (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, biological mechanism or biological effect in which the target or antigen is involved) is modulated (as defined herein).

m) An amino add sequence or polypeptide is said to be "specific for" a first target or antigen compared to a second target or antigen when is binds to the first antigen with an affinity (as described above, and suitably expressed as a $K_D$ value, $K_A$ value, $K_{off}$ rate and/or $k_{on}$ rate) that is at least 10 times, such as at least 100 times, and preferably at least 1000 times, and up to 10000 times or more better than the affinity with which said amino acid sequence or polypeptide binds to the second target or antigen. For example, amino acid sequence or polypeptide may bind to the first target or antigen with a $K_D$ value that is at least 10 times less, such as at least 100 times less, and preferably at least 1000 times less, such as 10.000 times less or even less than that, than the $K_D$ with which said amino acid sequence or polypeptide binds to the second target or antigen. Preferably, when an amino acid sequence or polypeptide is "specific for" a first target or antigen compared to a second target or antigen, it is directed against (as defined herein) said first target or antigen, but not directed against said second target or antigen.

n) The terms "(cross)-block", "(cross)-blocked" and "(cross)-blocking" are used interchangeably herein to mean the ability of an amino acid sequence or other binding agent (such as a polypeptide of the invention) to interfere with the binding of other amino acid sequences or binding agents of the invention to a given target. The extend to which an amino acid sequence or other binding agents of the invention is able to interfere with the binding of another to the target, and therefore whether it can be said to cross-block according to the invention, can be determined using competition binding assays. One particularly suitable quantitative cross-blocking assay uses a Biacore machine which can measure the extent of interactions using surface plasmon resonance technology. Another suitable quantitative cross-blocking assay uses an ELISA-based approach to measure competition between amino acid sequences or other binding agents in terms of their binding to the target. The following generally describes a suitable Biacore assay for determining whether an amino acid sequence or other binding agent cross-blocks or is capable of cross-blocking according to the invention. It will be appreciated that the assay can be used with any of the amino acid sequences or other binding agents described herein. The Biacore machine (for example the Biacore 3000) is operated in line with the manufacturer's recommendations. Thus in one cross-blocking assay, the target protein is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test amino add sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the Biacore chip. The amino acid sequences in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound amino acid sequences without damaging the chip-bound target. Typically this is done by treating the chip with 30 mM HCl for 60 seconds. The solution of A* alone is then passed over the target-coated surface and the amount of binding recorded. The chip is again treated to remove all of the bound amino acid sequences without damaging the chip-bound target. The solution of B* alone is then passed over the target-coated surface and the amount of binding recorded. The maximum theoretical binding of the mixture of A* and B* is next calculated, and is the sum of the binding of each amino acid sequence when passed over the target surface alone. If the actual recorded binding of the mixture is less than this theoretical maximum then the two amino acid sequences are cross-blocking each other. Thus, in general, a cross-blocking amino acid sequence or other binding agent according to the invention is one which will bind to the target in the above Biacore cross-blocking assay such that during the assay and in the presence of a second amino acid sequence or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or binding agents in combination. The Biacore assay described above is a primary assay used to determine if amino acid sequences or other binding agents cross-block each other according to the invention. On rare occasions particular amino acid sequences or other binding agents may not bind to a target coupled via amine chemistry to a CM5 Biacore chip (this usually occurs when the relevant binding site on the target is masked or destroyed by the coupling to the chip). In such cases cross-blocking can be determined using a tagged version of the target, for example a N-terminal His-tagged version. In this particular format, an anti-His amino acid sequence would be coupled to the Biacore chip and then the His-tagged target would be passed over the surface of the chip and captured by the anti-His amino acid sequence. The cross blocking analysis would be carried out essentially as described above, except that after each chip regeneration cycle, new His-tagged target would be loaded back onto the anti-His amino acid sequence coated surface. In addition to the example given using N-terminal His-tagged target, C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

Figure 2:
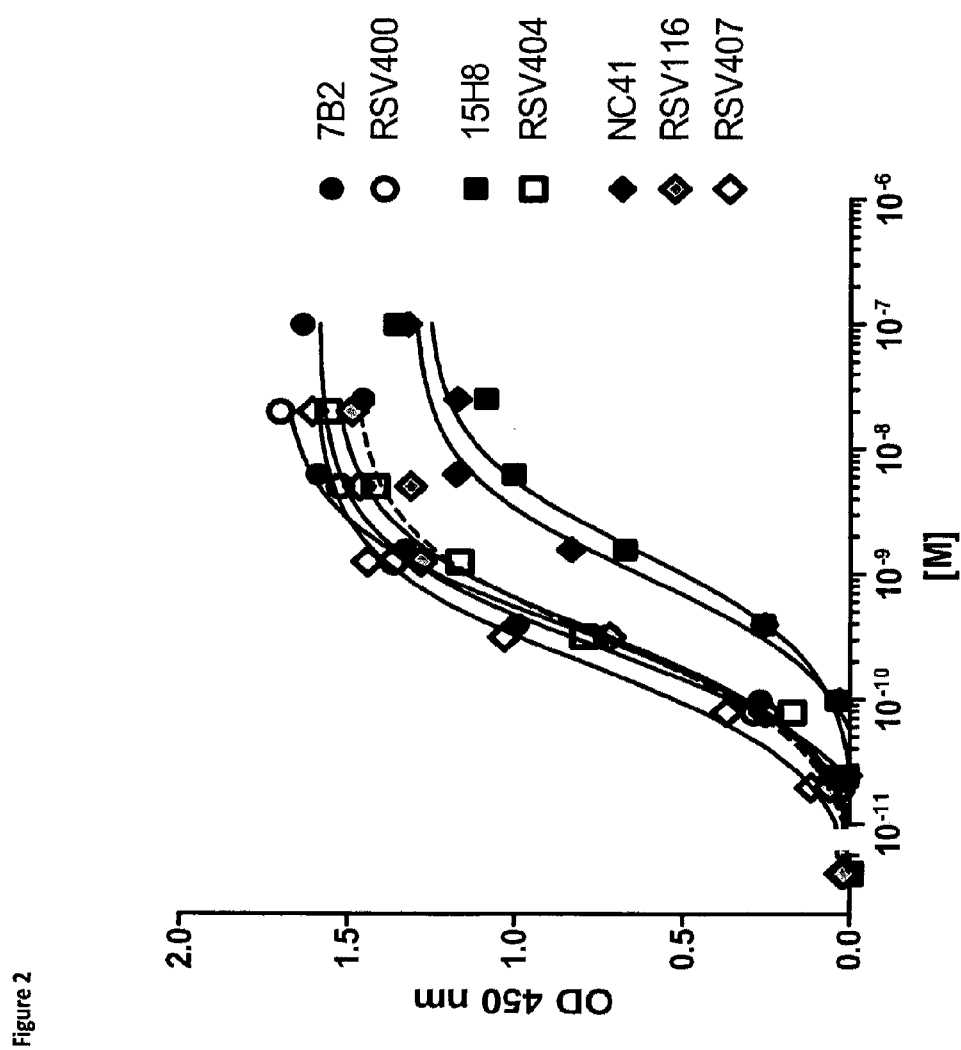
FIG. 2: Binding of monovalent, bivalent and trivalent Nanobodies® to $F_{TM}$-protein as described in Example 10.

The following generally describes an ELISA assay for determining whether an amino acid sequence or other binding agent directed against a target cross-blocks or is capable of cross-blocking as defined herein. It will be appreciated that the assay can be used with any of the amino acid sequences (or other binding agents such as polypeptides of the invention) described herein. The general principal of the assay is to have an amino acid sequence or binding agent that is directed against the target coated onto the wells of an ELISA plate. An excess amount of a second, potentially cross-blocking, anti-target amino acid sequence is added in solution (i.e. not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence. In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti-target amino acid sequence (in this case Ab-X). The background signal for the assay is defined as the signal obtained in wells with the coated amino acid sequence (in this case Ab-X), second solution phase amino acid sequence (in this case Ab-Y), target buffer only (i.e. without target) and target detection reagents. The positive control signal for the assay is defined as the signal obtained in wells with the coated amino acid sequence (in this case Ab-X), second solution phase amino acid sequence buffer only (i.e. without second solution phase amino acid sequence), target and target detection reagents. The ELISA assay may be run in such a manner so as to have the positive control signal be at least 6 times the background signal. To avoid any artifacts (e.g. significantly different affinities between Ab-X and Ab-Y for the target) resulting from the choice of which amino acid sequence to use as the coating amino acid sequence and which to use as the second (competitor) amino acid sequence, the cross-blocking assay may to be run in two formats: 1) format 1 is where Ab-X is the amino acid sequence that is coated onto the ELISA plate and Ab-Y is the competitor amino acid sequence that is in solution and 2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino acid sequence is able to cause a reduction of between 60% and 100%, specifically between 70% and 100%, and more specifically between 80% and 100%, of the target detection signal {i.e. the amount of target bound by the coated amino acid sequence) as compared to the target detection signal obtained in the absence of the solution phase anti-target amino acid sequence (i.e. the positive control wells).

o) An amino acid sequence is said to be "cross-reactive" for two different antigens or antigenic determinants (such as e.g. serum albumin from two different species of mammal, such as e.g. human serum albumin and cyno serum albumin, such as e.g. protein F of different strains of hRSV, such as e.g. protein F of different escape mutants of hRSV) if it is specific for (as defined herein) both these different antigens or antigenic determinants.

p) As further described herein, the total number of amino acid residues in a Nanobody® can be in the region of 110-120, is preferably 112-115, and is most preferably 113. It should however be noted that parts, fragments, analogs or derivatives (as further described herein) of a Nanobody® are not particularly limited as to their length and/or size, as long as such parts, fragments, analogs or derivatives meet the further requirements outlined herein and are also preferably suitable for the purposes described herein.

q) As further described in paragraph q) on pages 58 and 59 of WO 08/020,079 (incorporated herein by reference), the amino acid residues of a Nanobody® are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication), and accordingly FR1 of a Nanobody® comprises the amino acid residues at positions 1-30, CDR1 of a Nanobody® comprises the amino acid residues at positions 31-35, FR2 of a Nanobody® comprises the amino acids at positions 36-49, CDR2 of a Nanobody® comprises the amino acid residues at positions 50-65, FR3 of a Nanobody® comprises the amino acid residues at positions 66-94, CDR3 of a Nanobody® comprises the amino acid residues at positions 95-102, and FR4 of a Nanobody® comprises the amino acid residues at positions 103-113.

r) In the context of the present invention "target host cell (of a virus)" generally refers to a particular cell, which is or is derived from a living subject and which is susceptible to infection by said virus.

s) The term "infectivity of a virus", as used herein, refers to the proportion of living subjects that, when exposed to said virus, actually become infected by said virus.

t) The term "neutralization of a virus", as used herein, refers to the modulation and/or reduction and/or prevention and/or inhibition of the infectivity (as defined herein) of a virus by binding of a neutralizing compound to the virion, as measured using a suitable in vitro, cellular or in vivo assay (such as e.g. the microneutralization assay described by Anderson et al. 1985 (J. Clin. Microbiol. 22: 1050-1052) and 1988 (J. Virol. 62: 4232-4238), modifications of these assays such as e.g. described in Example 6; a plaque reduction assay as for example described by Johnson et al. 1997 (J. Inf. Dis. 176: 1215-1224), and modifications thereof and those mentioned herein). In particular, "neutralizing (a virus)" or "to neutralize (a virus)" may mean either modulating, reducing, preventing or inhibiting the infectivity (as defined herein) of a virus as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to normal (i.e. naturally occurring) infectivity (as defined herein) of a virus, in the same assay under the same conditions but without the presence of the amino acid sequence, Nanobody® or polypeptide of the invention.

u) The term "potency of an amino acid sequence of the invention", "potency of a Nanobody® of the invention", "potency of a polypeptide of the invention", and/or "potency of compound or construct of the invention", as used herein, refers to the capacity of said amino acid sequence of the invention, Nanobody® of the invention, polypeptide of the invention, and/or compound or construct of the invention to neutralize a particular virus (such as e.g. hRSV), to modulate, inhibit and/or prevent infectivity of a virus, to modulate, inhibit and/or prevent fusion of a virus with (the cell membrane of) the target host cell, and/or to modulate, inhibit and/or prevent entry of a virus into the target host cell (as defined herein). The potency may be measured by any suitable assay known in the art or described herein, such as e.g. the micro-neutralization assays as described in the Example section and/or the assays mentioned in point t) above.

v) The term "virus attachment", as used herein, is attachment of a virus (e.g. hRSV) to a target host cell directly (for example by interacting with a viral receptor) or indirectly (for example by mediating the interaction of one or more other proteins or molecules to a viral receptor), w) The term "virus fusion", as used herein, is fusion of a virus (e.g. hRSV) to a target host cell directly (for example by interacting with membrane compounds of the target host cell) or indirectly (for example by mediating the interaction of one or more other proteins or molecules with membrane compounds of the target host cell).

x) The term "viral entry" used herein encompasses any viral-mediated biological pathway that is needed to accomplish virion attachment to a target host cell and/or viral fusion with a target host cell.

y) A "stretch of amino acid residues" means two or more amino acid residues that are adjacent to each other or in close proximity to each other, i.e. in the primary or tertiary structure of the amino acid sequence. In the context of the present invention, the "stretch of amino acid residues" will be (at least partially) responsible for the binding of the amino acid sequence, Nanobody®, polypeptide, compound or construct of the invention to antigenic site II on protein F of hRSV.

z) When comparing two stretches of amino acid residues (or two CDR sequences), the term "amino acid difference" refers to an insertion, deletion or substitution of a single amino acid residue on a position of the stretch of amino acid residues (or CDR sequence) specified in b), d) or f), compared to the stretch of amino acid residues (or CDR sequence) of respectively a), c) or e); it being understood that the stretch of amino acid residues (or CDR sequence) of b), d) and f) can contain one, two or maximal three such amino acid differences compared to the stretch of amino acid residues of respectively a), c) or e).

The "amino acid difference" can be any one, two or maximal three substitutions, deletions and/or insertions, or any combination thereof, that either improve the properties of the amino acid sequence of the invention or that at least do not detract too much from the desired properties or from the balance or combination of desired properties of the amino acid sequence of the invention. In this respect, the resulting amino acid sequence of the invention should at least bind protein F of hRSV with the same, about the same, or a higher affinity compared to the amino acid sequence comprising the one or more stretches of amino acid residues without the one, two or maximal three substitutions, deletions and/or insertions, said affinity as measured by surface plasmon resonance; and/or the resulting amino acid sequence of the invention should at least have a potency that is the same, about the same or higher compared to the amino acid sequence comprising the one or more stretches of amino acid residues without the one, two or maximal three substitutions, deletions and/or insertions. The skilled person will generally be able to determine and select suitable substitutions, deletions and/or insertions, or suitable combinations thereof, based on the disclosure herein and optionally after a limited degree of routine experimentation, which may for example involve introducing a limited number of possible substitutions, deletions or insertions and determining their influence on the properties of the amino acid sequences thus obtained.

For example, and depending on the host organism used to express the amino acid sequence of the invention, such deletions and/or substitutions may be designed in such a way that one or more sites for post-translational modification (such as one or more glycosylation sites) are removed, as will be within the ability of the person skilled in the art.

In a preferred aspect of the invention, the "amino acid difference" is an amino acid substitution. The amino acid substitution may be any one, two or maximal three substitutions that either improve the properties of the amino acid sequence of the invention or that at least do not detract too much from the desired properties or from the balance or combination of desired properties of the amino acid sequence of the invention. In this respect, the resulting amino acid sequence of the invention should at least bind protein F of hRSV with the same, about the same, or a higher affinity compared to the amino acid sequence comprising the one or more stretches of amino acid residues without the one, two or maximal three substitutions, said affinity as measured by surface plasmon resonance; and/or the resulting amino acid sequence of the invention should at least have a potency that is the same, about the same or higher compared to the amino acid sequence comprising the one or more stretches of amino acid residues without the one, two or maximal three substitutions, deletions and/or insertions. The skilled person will generally be able to determine and select suitable substitutions, based on the disclosure herein and optionally after a limited degree of routine experimentation, which may for example involve introducing a limited number of possible substitutions and determining their influence on the properties of the Nanobodies® thus obtained.

The amino acid substitution in the one or more stretches of amino acid residues may be a conservative amino acid substitution. "Conservative" amino acid substitutions are generally amino acid substitutions in which an amino acid residue is replaced with another amino acid residue of similar chemical structure and which has little or essentially no influence on the function, activity or other biological properties of the resulting amino acid sequence. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. The amino acid substitution in the one or more stretches of amino acid residues may provide the amino acid sequence with increased affinity for binding to protein F of hRSV. This may be done by techniques such as random or site-directed mutagenesis and/or other techniques for affinity maturation known per se, such as e.g. described in WO 09/004,065, WO 05/003345, WO 06/023144, EP527809, EP397834.

Without being limiting, rules (partly or fully followed) for substitutions of amino acid residues in the CDRs may be as follows (i.e. substitution with amino acids with similar side chain chemistries):
K is substituted by R;
R is substituted by K;
A is substituted by S or T;
S is substituted by A or T;
T is substituted by A or 5;
I is substituted by L or V;
L is substituted by I or V;
V is substituted by I or L;
F is substituted by Y;
Y is substituted by F;
N is substituted by D;
D is substituted by N;
Q is substituted by E;
E is substituted by Q;
G is substituted by A;
M is substituted by L;
H, C, W and P are kept constant.

Furthermore, and also without being limiting, the rules (partly or fully followed) for substitutions of amino acid residues in the CDRs may be alternatively as follows for substitutions at positions 27 to 35 and positions 50 to 58 (using Kabat numbering system), wherein for positions 27 to 35:
Original amino acid residue in position 27 (Kabat numbering used) is substituted by F; G; R; S; 2 out of F, G, R, S; 3 out of F, G, R, S; or all of them, preferably all of them;
Original amino acid residue in position 28 (Kabat numbering used) is substituted by A; I; S; T; 2 out of A, I, S, T; 3 out of A, I, S, T; or all of them, preferably all of them;
Original amino acid residue in position 29 (Kabat numbering used) is substituted by F; G; L; S; 2 out of F, G, L, 5; 3 out of F, G, L, 5; or all of them, preferably all of them;
Original amino acid residue in position 30 (Kabat numbering used) is substituted by D; G; S; T; 2 out of D, G, S, T; 3 out of D, G, S, T; or all of them, preferably all of them;
Original amino acid residue in position 31 (Kabat numbering used) is substituted by D; I; N; S; T; 2 out of D, I, N, S, T; 3 out of D, I, N, S, T; or all of them, preferably all of them;
Original amino acid residue in position 32 (Kabat numbering used) is substituted by D; N; Y; 2 out of D, N, Y; or all of them, preferably all of them;
Original amino acid residue in position 33 (Kabat numbering used) is substituted by A; G; T; V; 2 out of A, G, T, V; 3 out of A, G, T, V; or all of them, preferably all of them;
Original amino acid residue in position 34 (Kabat numbering used) is substituted by I; M; or all of them, preferably all of them;
Original amino acid residue in position 35 (Kabat numbering used) is substituted by A; G; S; 2 out of A, G, S; or all of them, preferably all of them;
and positions 50 to 58 if original amino acid sequence has an amino acid sequence in position 52a (Kabat numbering used),
Original amino acid residue in position 50 (Kabat numbering used) is substituted by A; C; G; S; T; 2 out of A, C, G, S, T; 3 out of A, C, G, S, T; 4 out of A, C, G, S, T; or all of them, preferably all of them;

Original amino acid residue in position 51 (Kabat numbering used) is substituted by I;

Original amino acid residue in position 52 (Kabat numbering used) is substituted by N; R; S; T; 2 out of N, R, S, T; 3 out of N, R, S, T; or all of them, preferably all of them;

Original amino acid residue in position 52a (Kabat numbering used) is substituted by R; 5; T; W; 2 out of R, S, T, W; 3 out of R, S, T, W; or all of them, preferably all of them;

Original amino acid residue in position 53 (Kabat numbering used) is substituted by D; G; N; S; T; 2 out of D, G, N, S, T; 3 out of D, G, N, S, T; 4 out of D, G, N, S, T; or all of them, preferably all of them;

Original amino acid residue in position 54 (Kabat numbering used) is substituted by D; or all of them, preferably all of them;

Original amino acid residue in position 55 (Kabat numbering used) is substituted by D; G; S; 2 out of D, G, 5; or all of them, preferably all of them;

Original amino acid residue in position 56 (Kabat numbering used) is substituted by I; N; R; S; T; 2 out of I, N, R, S, T; 3 out of I, N, R, S, T; 4 out of I, N, R, S, T; or all of them, preferably all of them;

Original amino acid residue in position 57 (Kabat numbering used) is substituted by T;

Original amino acid residue in position 58 (Kabat numbering used) is substituted by D; H; N; S; Y; 2 out of D, H, N, S, Y; 3 out of 0, H, N, S, Y; 4 out of 0, H, N, S, Y; or all of them, preferably all of them;

and wherein for positions 50 to 58 if original amino acid sequence has not an amino acid sequence in position 52a (Kabat numbering used), Original amino acid residue in position 50 (Kabat numbering used) is substituted by A; C; R; S; T; 2 out of A, G, R, S, T; 3 out of A, G, R, S, T; 4 out of A, G, R, S, T; or all of them, preferably all of them;

Original amino acid residue in position 51 (Kabat numbering used) is substituted by I;

Original amino acid residue in position 52 (Kabat numbering used) is substituted by N; S; T; 2 out of N, S, T; or all of them, preferably all of them;

Original amino acid residue in position 53 (Kabat numbering used) is substituted by N; R; S; T; Y; 2 out of N, R, S, T, Y; 3 out of N, R, S, T, Y; 4 out of N, R, S, T, Y; or all of them, preferably all of them;

Original amino acid residue in position 54 (Kabat numbering used) is substituted by D; G; R; S; 2 out of D, G, R, S; 3 out of D, G, R, S; or all of them, preferably all of them;

Original amino acid residue in position 55 (Kabat numbering used) is substituted by G;

Original amino acid residue in position 56 (Kabat numbering used) is substituted by G; N; R; S; T; 2 out of D, N, R, S, T; 3 out of D, N, R, S, T; 4 out of D, N, R, S, T; or all of them, preferably all of them;

Original amino acid residue in position 57 (Kabat numbering used) is substituted by T;

Original amino acid residue in position 58 (Kabat numbering used) is substituted by D; N; T; Y; 2 out of D, N, T, Y; 3 out of D, N, T, Y; or all of them, preferably all of them.

after which one or more of the potentially useful substitutions (or combinations thereof) thus determined can be introduced into said CDR sequence (in any manner known per se, as further described herein) and the resulting amino acid sequence(s) can be tested for affinity for protein F of hRSV, and/or for other desired properties such as e.g. improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for protein F of hRSV and/or improved efficacy and/or potency for neutralizing hRSV. In this way, by means of a limited degree of trial and error, other suitable substitutions in the CDRs (or suitable combinations thereof) can be determined by the skilled person based on the disclosure herein. The amino acid sequences comprising a stretch of amino acid residues that has one, two or maximal three substitutions, insertions or deletions, and nucleic acid sequences encoding the same, can be provided in any manner known per se, for example using one or more of the techniques mentioned on pages 103 and 104 of WO 08/020,079.

The resulting amino acid sequences of the invention should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein.

aa) When comparing two amino acid sequences, the term "amino acid difference" refers to an insertion, deletion or substitution of a single amino acid residue on a position of the first amino acid sequence, compared to the second amino acid sequence; it being understood that two amino acid sequences can contain one, two or maximal three such amino acid differences. The "amino acid difference" can be any one, any two or maximal any three substitutions, deletions or insertions in the amino acid sequence, i.e. in one or more of the framework regions or in one or more of the CDRs (which may be in a CDR of the invention (i.e. in CDR2) or in another CDR (i.e. in CDR1, CDR2 or CDR3)), or any combination thereof, that either improve the properties of the amino acid sequence of the invention or that at least do not detract too much from the desired properties or from the balance or combination of desired properties of the amino acid sequence of the invention. In this respect, the resulting amino acid sequence of the invention should at least bind protein F of hRSV with the same, about the same, or a higher affinity compared to the amino acid sequence without the one, two or maximal three substitutions, deletions or insertions, said affinity as measured by surface plasmon resonance; and/or the resulting amino acid sequence of the invention should at least have a potency that is the same, about the same or higher compared to the amino acid sequence without the one, two or maximal three substitutions, deletions and/or insertions. The skilled person will generally be able to determine and select suitable substitutions, deletions or insertions, or suitable combinations thereof, based on the disclosure herein and optionally after a limited degree of routine experimentation, which may for example involve introducing a limited number of possible substitutions, deletions or insertions and determining their influence on the properties of the amino acid sequence thus obtained.

In one aspect of the invention, the "amino acid difference" is an amino acid substitution. The amino acid substitution may be any one, two or maximal three substitutions in one or more of the framework regions or in one or more of the CDRs (which may be in a CDR of the invention (i.e. in CDR2) or in another CDR (i.e. in CDR1, CDR2 or CDR3)), or any combination thereof, that either improve the properties of the amino acid sequence of the invention or that at least do not detract too much from the desired properties or from the balance or combination of desired properties of the amino acid sequence of the invention. In this respect, the resulting amino acid sequence of the invention should at least bind protein F of hRSV with the same, about the same, or a higher affinity compared to the amino acid sequence without the one, two or maximal three substitutions, said affinity as measured by surface plasmon resonance; and/or the resulting amino acid sequence of the invention should at least have a potency that is the same, about the same or higher compared to the amino acid sequence without the one, two or maximal three substitutions. The skilled person will generally be able to determine and select suitable substitutions, based on the disclosure herein and optionally after a limited degree of routine experimentation, which may for example involve introducing a limited number of possible substitutions and determining their influence on the properties of the amino acid sequences thus obtained.

As indicated above, the substitutions, insertions or deletions can be in one or more of the framework regions and/or in one or more of the CDR's. As discussed above (see point z) above), the amino acid substitution in one or more of the CDRs can be any substitution such as a "conservative substitution" (as defined herein), it may be driven by certain rules (as defined herein), and/or it may induce improved properties to the resulting amino acid sequences. When such substitutions, insertions or deletions are made in one or more of the framework regions, they may be made at one or more of the Hallmark residues (as e.g. defined in WO 08/020,079; Tables A-3 to A-8) and/or at one or more of the other positions in the framework residues, although substitutions, insertions or deletions at the Hallmark residues are generally less preferred (unless these are suitable humanizing substitutions as described herein). By means of non-limiting examples, a substitution may for example be a conservative substitution (as described herein) and/or an amino acid residue may be replaced by another amino acid residue that naturally occurs at the same position in another $V_{HH}$ domain (see WO 08/020,079, Tables A-5 to A-8), although the invention is generally not limited thereto.

Substitutions, insertions or deletions made (preferably) in one or more of the framework regions may be humanizing substitution (i.e. replacing one or more amino acid residues in the amino acid sequence of a naturally occurring $V_{HH}$ sequence (and in particular in the framework sequences) by one or more of the amino acid residues that occur at the corresponding position(s) in a $V_H$ domain from a conventional 4-chain antibody from a human being). Some preferred, but non-limiting humanizing substitutions (and suitable combinations thereof) will become clear to the skilled person based on the disclosure herein. Potentially useful humanizing substitutions can be ascertained by comparing the sequence of the framework regions of one of the amino acid sequence of the invention defined in a) with the corresponding framework sequence of one or more closely related human $V_H$ sequences, after which one or more of the potentially useful humanizing substitutions (or combinations thereof) thus determined can be introduced into said amino acid sequence of the invention defined in a) (in any manner known per se, as further described herein) and the resulting humanized amino acid sequence can be tested for affinity for protein F of hRSV, for stability, for ease and level of expression, and/or for other desired properties defined herein. In this way, by means of a limited degree of trial and error, other suitable humanizing substitutions (or suitable combinations thereof) can be determined by the skilled person based on the disclosure herein.

The humanizing substitutions should be chosen such that the resulting humanized amino acid sequence and/or Nanobody® still retains the favourable properties of Nanobodies® as defined herein. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies® thus obtained. Generally, as a result of humanization, the amino acid sequence and/or Nanobody® of the invention may become more "human-like", while still retaining the favorable properties of the Nanobodies® of the invention as described herein. As a result, such humanized amino acid sequence and/or Nanobody® may have several advantages, such as a reduced immunogenicity, compared to the corresponding naturally occurring $V_{HH}$ domain. Again, based on the disclosure herein and optionally after a limited degree of routine experimentation, the skilled person will be able to select humanizing substitutions or suitable combinations of humanizing substitutions which optimize or achieve a desired or suitable balance between the favourable properties provided by the humanizing substitutions on the one hand and the favourable properties of naturally occurring $V_{HH}$ domains on the other hand.

The amino acid sequences and/or Nanobodies® of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies® of the "P,R,S-103 group" or the "KERE group" (as defined in WO 08/020,079) is Q108 into L108.

Depending on the host organism used to express the amino acid sequence, Nanobody® or polypeptide of the invention, such deletions and/or substitutions may also be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables A-5-A-8 of WO 08/020,079, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions. Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 198 1, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

The amino acid sequences and/or Nanobodies® with one, two or maximal three substitutions, insertions or deletions, and nucleic acid sequences encoding the same, can be provided in any manner known per se, for example using one or more of the techniques mentioned on pages 103 and 104 of WO 08/020,079.

The resulting amino acid sequences and/or Nanobodies® of the invention should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein.

bb) When comparing two polypeptides, the term "amino acid difference" refers to an insertion, deletion or substitution of a single amino acid residue on a position of the first polypeptide, compared to the second polypeptide; it being understood that two polypeptides can contain one, two or maximal three such amino acid differences.

The "amino acid difference" can be any one, any two or maximal three substitutions, deletions or insertions in the polypeptide, i.e. in one or more of the framework regions or in one or more of the CDRs (which may be in a CDR of the invention (i.e. in CDR2) or in another CDR (i.e. in CDR1, CDR2 or CDR3)), or any combination thereof, that either improve the properties of the polypeptide of the invention or that at least do not detract too much from the desired properties or from the balance or combination of desired properties of the polypeptide of the invention. In this respect, the resulting polypeptide of the invention should at least bind protein F of hRSV with the same, about the same, or a higher affinity compared to the polypeptide without the one, two or maximal three substitutions, deletions or insertions, said affinity as measured by surface plasmon resonance; and/or the resulting polypeptide of the invention should at least have a potency that is the same, about the same or higher compared to the polypeptide without the one, two or maximal three substitutions, deletions and/or insertions. The resulting polypeptide should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein. The skilled person will generally be able to determine and select suitable substitutions, deletions or insertions, or suitable combinations thereof, based on the disclosure herein and optionally after a limited degree of routine experimentation, which may for example involve introducing a limited number of possible substitutions, deletions or insertions and determining their influence on the properties of the polypeptide thus obtained.

In one aspect of the invention, the "amino acid difference" is an amino acid substitution. The amino acid substitution may be any one, any two or maximal any three substitutions in the framework regions or in one or more of the CDRs (which may be in a CDR of the invention (i.e. present in CDR2) or in another CDR (i.e. in CDR1, CDR2 or CDR3)), or any combination thereof, that either improve the properties of the polypeptide of the invention or that at least do not detract too much from the desired properties or from the balance or combination of desired properties of the polypeptide of the invention. In this respect, the resulting polypeptide of the invention should at least bind protein F of hRSV with the same, about the same, or a higher affinity compared to the polypeptide without the one, two or maximal three substitutions, deletions or insertions, said affinity as measured by surface plasmon resonance; and/or the resulting polypeptide of the invention should at least have a potency that is the same, about the same or higher compared to the polypeptide without the one, two or maximal three substitutions, deletions and/or insertions. The resulting polypeptide should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein. The skilled person will generally be able to determine and select suitable substitutions, based on the disclosure herein and optionally after a limited degree of routine experimentation, which may for example involve introducing a limited number of possible substitutions and determining their influence on the properties of polypeptides thus obtained.

As indicated above, the substitutions, insertions or deletions can be in one or more of the framework regions and/or in one or more of the CDR's. As discussed above (see point z)), the substitutions, insertions or deletions in the CDR's may be any possible substitutions, insertions or deletions such as "conservative substitution" (as defined herein), it may be driven by certain rules (as defined herein), and/or it may induce improved properties to the resulting polypeptides.

When such substitutions, insertions or deletions are made in one or more of the framework regions, they may be made at one or more of the Hallmark residues (as e.g. defined in WO 08/020,079; Tables A-3 to A-8) and/or at one or more of the other positions in the framework residues, although substitutions, insertions or deletions at the Hallmark residues are generally less preferred (unless these are suitable humanizing substitutions as described herein). By means of non-limiting examples, a substitution may for example be a conservative substitution (as described herein) and/or an amino acid residue may be replaced by another amino acid residue that naturally occurs at the same position in another $V_{HH}$ domain (see WO 08/020,079, Tables A-5 to A-8), although the invention is generally not limited thereto.

Substitutions, insertions or deletions made (preferably) in one or more of the framework regions may be humanizing substitution. Some preferred, but non-limiting humanizing substitutions (and suitable combinations thereof) will become clear to the skilled person based on the disclosure herein. Potentially useful humanizing substitutions can be ascertained by comparing the sequence of the framework regions of one of the amino acid sequences encompassed in the polypeptide of the invention defined in a) with the corresponding framework sequence of one or more closely related human $V_H$ sequences, after which one or more of the potentially useful humanizing substitutions (or combinations thereof) thus determined can be introduced into said polypeptide of the invention defined in a) (in any manner known per se, as further described herein) and the resulting polypeptide sequence can be tested for affinity for protein F of hRSV, for stability, for ease and level of expression, and/or for other desired properties defined herein. In this way, by means of a limited degree of trial and error, other suitable humanizing substitutions (or suitable combinations thereof) can be determined by the skilled person based on the disclosure herein.

The humanizing substitutions should be chosen such that the resulting humanized polypeptide sequences still retain the favourable properties of Nanobodies® encompassed in the polypeptide as defined herein. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies® encompassed in the polypeptide thus obtained.

Generally, as a result of humanization, the polypeptide of the invention may become more "human-like", while still retaining the favorable properties of the Nanobodies® of the invention encompassed in the polypeptide as described herein. As a result, such humanized polypeptides may have several advantages, such as a reduced immunogenicity, compared to the polypeptides that encompass corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favourable properties provided by the humanizing substitutions on the one hand and the favourable properties of naturally occurring $V_{HH}$ domains on the other hand.

Polypeptides of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies® of the "P,R,S-103 group" or the "KERE group" is Q108 into L108.

Depending on the host organism used to express the polypeptide of the invention, such deletions and/or substitutions may also be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein). As can be seen from the data on the $V_{HH}$ entropy and $V_{HH}$ variability given in Tables A-5-A-8 of WO 08/020,079, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions. Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 198 1, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

The polypeptides with one, two or maximal three substitutions, insertions or deletions, and nucleic acid sequences encoding the same, can be provided in any manner known per se, for example using one or more of the techniques mentioned on pages 103 and 104 of WO 08/020,079.

The resulting polypeptides of the invention should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein.

cc) The figures, sequence listing and the experimental part/examples are only given to further illustrate the invention and should not be interpreted or construed as limiting the scope of the invention and/or of the appended claims in any way, unless explicitly indicated otherwise herein.

For binding to its epitope on protein F of hRSV, an amino acid sequence will usually contain within its amino acid sequence one or more amino acid residues or one or more stretches of amino acid residues (as defined herein; i.e. with each "stretch" comprising two or more amino acid residues that are adjacent to each other or in close proximity to each other, i.e. in the primary or tertiary structure of the amino acid sequence) via which the amino acid sequence of the invention can bind to its epitope on protein F of hRSV. These amino acid residues or stretches of amino acid residues thus form the "site" for binding to the epitope on protein F of hRSV (also referred to herein as the "antigen binding site"; as further defined herein).

The present invention provides a number of stretches of amino acid residues (as defined herein) that are particularly suited for binding to antigenic site II on protein F of hRSV (for a description of antigenic sites in the hRSV F protein reference is made to Lopez et al. 1998, J. virol. 72: 6922-6928). These stretches of amino acid residues may be present in, and/or may be incorporated into, an amino acid sequence of the invention, in particular in such a way that they form (part of) the antigen binding site of the amino acid sequence of the invention. The resulting amino acid sequences will bind a specific epitope on protein F of hRSV that lies in, forms part of, or overlaps with (i.e. in the primary or tertiary structure) or is in close proximity to (i.e. in the primary or tertiary structure) antigenic site II on protein F of hRSV. Also, the resulting amino acid sequences of the invention will preferably be such that they can compete with Synagis® for binding to protein F of hRSV; and/or such that they can bind to the same epitope or binding site on protein F of hRSV as Synagis®, or to an epitope close to said binding site and/or overlapping with said binding site.

The present invention provides a stretch of amino acid residues (SEQ ID NO: 102) that is particularly suited for binding to protein F of hRSV. This stretch of amino acid residues (or variants of SEQ ID NO: 102 as defined herein) may be present in, and/or may be incorporated into, an amino acid sequence of the invention, in particular in such a way that they form (part of) the antigen binding site of the amino acid sequence of the invention. The stretch of amino acid residues has been generated as CDR2 sequence of a heavy chain antibody or $V_{HH}$ sequence (NC41; SEQ ID NO: 5) that was raised against protein F of hRSV and that was further modified in a library approach to generate humanized NC41 Nanobodies® (as described in the Example section). More in particular, the glycine (Gly, G) residue at position 6 of the CDR2 of NC41 was substituted into an Aspartic acid (Asp, D) residue. Surprisingly, improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for protein F of hRSV and/or improved efficacy and/or potency for neutralizing hRSV have been observed for amino acid sequences that comprise this stretch of amino acid residues (SEQ ID NO: 102). This stretch of amino acid residues (or variants of SEQ ID NO: 102, as defined herein) are also referred to herein as "CDR2 sequences of the invention".

Accordingly, in one aspect, the present invention provides amino acid sequences that comprise at least a stretch of amino acid residues chosen from the following:
  a) SEQ ID NO: 102;
  b) a stretch of amino acid residues that has no more than 3, preferably no more than 2, more preferably no more than 1 amino acid difference with SEQ ID NO: 102, provided that:
    i) said stretch of amino acid residues has an Aspartic acid (Asp, D) at position 6 (position 54 determined according to Kabat numbering); and
    ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In a preferred aspect, the present invention provides amino acid sequences that comprise two or more stretches of amino acid residues in which one stretch is chosen from the following:
  a) SEQ ID NO: 102;
  b) a stretch of amino acid residues that has no more than 3, preferably no more than 2, more preferably no more than 1 amino acid difference with SEQ ID NO: 102, provided that:
    i) said stretch of amino acid residues has an Aspartic acid (Asp, D) at position 6 (position 54 determined according to Kabat numbering); and
    ii) the amino acid sequence comprising said stretch of amino acid residues binds protein of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and at least one stretch is chosen from:
  c) SEQ ID NO: 98;
  d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
  e) SEQ ID NO: 121; and
  f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.
  such that the stretch of amino acid residues that corresponds to one of a) and b) should always be present in the amino acid sequence of the invention and such that the second stretch of amino acid residues is chosen from one of c), d), e) and f).

Even more preferably, the amino acid sequences of the invention comprise three or more stretches of amino acid residues, in which the first stretch of amino acid residues is chosen from the group consisting of:
 a) SEQ ID NO: 98;
 b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
the second stretch of amino acid residues is chosen from the group consisting of:
 c) SEQ ID NO: 102;
 d) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and the third stretch of amino acid residues is chosen from the group consisting of:
 e) SEQ ID NO: 121;
 f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Amino acid sequences comprising one or more of the above specified stretches of amino acid residues show improved properties such as e.g. improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for protein F of hRSV and/or improved efficacy and/or potency for neutralizing hRSV.

More in particular, the amino acid sequences of the invention comprising one or more of the above specified stretches of amino acid residues can bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, further described herein) preferably such that they:

bind to protein F of hRSV with a dissociation constant ($K_D$) of 1000 nM to 1 nM or less, preferably 100 nM to 1 nM or less, more preferably 15 nM to 1 nM or even 10 nM to 1 nM or less;

and/or such that they:
 bind to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more;

and/or such that they:
 bind to protein F of hRSV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-2}$, or lower;

Some preferred IC50 values for binding of the amino acid sequences of the invention to protein F of hRSV will become clear from the further description and examples herein.

Assays to determine the IC50 include competition assays such as competition ELISA (e.g. competition with Synagis® or its Fab fragment) or more preferably neutralization assays such as the microneutralization assay described by Anderson et al. (1985, J. Clin. Microbiol. 22: 1050-1052; 1988, J. Virol. 62: 4232-4238), modifications of this assay such as e.g. described in Example 6, or a plaque reduction assay as for example described by Johnson et al. (1997, J. Inf. Dis. 176: 1215-4224), and modifications thereof.

For example, in a competition assay with the Fab fragment of Synagis®, the amino acid sequences of the invention may have IC50 values between 1 nM and 100 nM, preferably between 10 nM and 50 nM, or less.

For example, in a microneutralization assay on hRSV Long (such as e.g. described in Example 6) the amino acid sequences of the invention may have IC50 values between 100 nM and 1000 nM, preferably between 100 nM and 500 nM, or less.

It should be noted that the invention is not limited as to the origin of the amino acid sequence of the invention (or of the nucleotide sequence of the invention used to express it), nor as to the way that the amino acid sequence or nucleotide sequence of the invention is (or has been) generated or obtained. Thus, the amino acid sequences of the invention may be naturally occurring amino acid sequences (from any suitable species) or synthetic or semi-synthetic amino acid sequences.

It should be noted that the invention in its broadest sense is not limited to a specific structural role or function that these stretches of amino acid residues may have in the amino acid sequence of the invention, as long as these stretches of amino acid residues allow the amino acid sequence of the invention to bind to antigenic site II on protein F of hRSV with a certain affinity and/or potency (as defined herein). Thus, generally, the invention in its broadest sense comprises any amino acid sequence that is capable of binding to antigenic site II on protein F of hRSV and that comprises one or more stretches of amino acid residues as defined herein (and in particular a suitable combination of two or more such stretches of amino acid residues) that are suitably linked to each other via one or more further amino acid sequences, such that the entire amino acid sequence forms a binding domain and/or binding unit that is capable of binding to antigenic site II on protein F of hRSV.

Such an amino acid sequence may, for example, be a suitable "protein scaffold" that comprises at least one stretch of amino acid residues as defined herein (i.e. as part of its antigen binding site). Suitable scaffolds for presenting amino acid sequences will be clear to the skilled person, and for example comprise, without limitation, to binding scaffolds based on or derived from immunoglobulins, protein scaffolds derived from protein A domains (such as Affibodies™), tendamistat, fibronectin, lipocalin, CTLA-4, T-cell receptors, designed ankyrin repeats, avimers and PDZ domains (Binz et al. 2005, Nat. Biotech. 23: 1257), and binding moieties based on DNA or RNA including but not limited to DNA or RNA aptamers (Ulrich et al. 2006, Comb. Chem. High Throughput Screen 9(8): 619-32).

Again, any amino acid sequence of the invention that comprises one or more of the stretches of amino acid sequences as defined herein for the amino acid sequences of the invention is preferably such that it can specifically bind (as defined herein) to protein F of hRSV, and more in particular such that it can bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), that is as defined herein. Any amino acid sequence of the invention that comprises one or more of the stretches of amino acid residues as defined herein for the amino acid sequences of the invention is preferably such that it can neutralize hRSV with a potency (as measured in a suitable assay as defined herein) that is as defined herein.

Furthermore, it will also be clear to the skilled person that it may be possible to "graft" one or more of the CDR's defined herein for the amino acid sequences of the invention onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0 605 522, EP 0 460 167, U.S. Pat. No. 7,054,297, Nicaise et al., Protein Science (2004), 13:1882-1891; Ewert et al., Methods, 2004 October; 34(2):184-199; Kettleborough et al., Protein Eng. 1991 October; 4(7): 773-783; O'Brien and Jones, Methods Mol. Biol. 2003: 207: 81-100; and Skerra, J. Mat. Recognit. 2000: 13: 167-187, and Saerens et al., J. Mol. Biol. 2005 Sep. 23; 352(3):597-607, and the further references cited therein. For example, techniques known per se for grafting mouse or rat CDR's onto human frameworks and scaffolds can be used in an analogous manner to provide chimeric proteins comprising one or more of the CDR sequences defined herein for the amino acid sequences of the invention and one or more human framework regions or sequences.

In one specific, but non-limiting aspect, the amino acid sequence of the invention may be an amino acid sequence that comprises an immunoglobulin fold or an amino acid sequence that, under suitable conditions (such as physiological conditions) is capable of forming an immunoglobulin fold (i.e. by folding). Reference is inter alia made to the review by Halaby et al. (1999, J. Protein Eng. 12: 563-71). Preferably, when properly folded so as to form an immunoglobulin fold, the stretches of amino acid residues may be capable of properly forming the antigen binding site for binding the specific antigenic site II on protein F of hRSV; and more preferably capable of binding to antigenic site lion protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In another specific, but non-limiting aspect, the amino acid sequences of the invention are immunoglobulin sequences. In particular, but without limitation, the amino acid sequences of the invention may be amino acid sequences that essentially consist of 4 framework regions (FR1 to FR4 respectively) and 3 complementarity determining regions (CDR1 to CDR3 respectively); or any suitable fragment of such an amino acid sequence that still binds antigenic site II on protein F of hRSV.

In such an amino acid sequence of the invention, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence). When the amino acid sequence of the invention is a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

For a general description of heavy chain antibodies and the variable domains thereof, reference is inter alia made to the prior art cited herein, as well as to the prior art mentioned on page 59 of WO 08/020,079 and to the list of references mentioned on pages 41-43 of the international application WO 06/040153, which prior art and references are incorporated herein by reference.

The framework sequences may preferably be such that the amino acid sequence of the invention is a domain antibody (or an amino acid sequence that is suitable for use as a domain antibody); is a single domain antibody (or an amino acid sequence that is suitable for use as a single domain antibody); is a "dAb" (or an amino acid sequence that is suitable for use as a dAb); or is a Nanobody® (including but not limited to $V_{HH}$ sequence). Again, suitable framework sequences will be clear to the skilled person, for example on the basis the standard handbooks and the further disclosure and prior art mentioned herein.

In particular, the framework sequences present in the amino acid sequences of the invention may contain one or more of Hallmark residues (as defined in WO 08/020,079 (Tables A-3 to A-8)), such that the amino acid sequence of the invention is a Nanobody®. Some preferred, but non-limiting examples of (suitable combinations of) such framework sequences will become clear from the further disclosure herein (see e.g. Table A-6). Generally, Nanobodies® (in particular $V_{HH}$ sequences and partially humanized Nanobodies®) can in particular be characterized by the presence of one or more "Hallmark residues" in one or more of the framework sequences (as e.g. further described in WO 08/020,079, page 61, line 24 to page 98, line 3).

As already described herein, the amino acid sequence and structure of a Nanobody® can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. Some preferred framework sequences and CDR's (and combinations thereof) that are present in the Nanobodies® of the invention are as described herein.

Thus, generally, a Nanobody® can be defined as an amino acid sequence with the (general) structure

FR1-CDR1-FR2-CDR2-FR3-CDR3-FR4 in which FR1 to FR4 refer to framework regions 1 to 4, respectively, and in which CDR2 to CDR3 refer to the complementarity determining regions 1 to 3, respectively, and in which one or more of the Hallmark residues are as further defined herein.

In this respect, the amino acid sequences of the invention may essentially consist of 4 framework regions (FR1 to FR4, respectively) and 3 complementarity determining regions (CDR1 to CDR3, respectively), in which CDR2 is chosen from:

a) SEQ ID NO: 102;
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

These preferred complementarity determining regions (CDR2 sequences) are also referred to as "CDR2(s) of the invention".

Preferably, the amino acid sequences of the invention may essentially consist of 4 framework regions (FR1 to FR4, respectively) and 3 complementarity determining regions (CDR1 to CDR3, respectively), in which CDR2 is chosen from the group consisting of:

a) SEQ ID NO: 102;
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino add sequence comprising said stretch of amino acid residues has the same, about the same, or a higher potency (as defined herein) compared to the amino acid sequence comprising said stretch of amino acid residues without the 3, 2 or 1 amino acid difference;

and at least one of CDR1 or CDR3 is chosen from:
  CDR1 chosen from the group consisting of:
  c) SEQ ID NO: 98;
  d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and/or
  CDR3 chosen from the group consisting of:
  e) SEQ ID NO: 121;
  f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Even more preferably, the amino acid sequences of the invention may essentially consist of 4 framework regions (FR1 to FR4, respectively) and 3 complementarity determining regions (CDR1 to CDR3, respectively), in which:

CDR1 is chosen from the group consisting of:
a) SEQ ID NO: 98;
b) a stretch of amino acid residues that has no more than 3, preferably no more than 2, more preferably no more than 1 amino acid difference with SEQ ID NO: 98, provided that the ammo acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference; or
and
CDR2 is chosen from the group consisting of:
c) SEQ ID NO: 102;
d) a stretch of amino acid residues that has no more than 3, preferably no more than 2, more preferably no more than 1 amino acid difference with SEQ ID NO: 102, provided that:
  i) said stretch of amino add residues has an Aspartic add (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and

CDR3 is chosen from the group consisting of:
e) SEQ ID NO: 121;
f) a stretch of amino acid residues that has no more than 3, preferably no more than 2, more preferably no more than 1 amino acid difference with SEQ ID NO: 121, provided that the amino acid sequence comprising said stretch of amino acid residues binds protein P of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In a specific aspect, the amino acid sequence or Nanobody® of the invention comprises at least SEQ ID NO: 102.

In another specific aspect, the amino acid sequence or Nanobody® of the invention comprises at least SEQ ID NO: 102 and at least one stretch of amino acid residues (CDR sequence) chosen from:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
c) SEQ ID NO: 121;
d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Preferably, the amino acid sequence or Nanobody® of the invention comprises at least SEQ ID NO: 102 and at least two stretches of amino acid residues (CDR sequences) in which one stretch is chosen from the group consisting of the stretches of amino acid residues defined in a) and b) and in which the other stretch is chosen from the group consisting of the stretches of amino acid residues defined in c) and d).

In another specific aspect, the amino acid sequence or Nanobody® of the invention comprises at least SEQ ID NO: 102 and at least one stretch of amino acid residues (CDR sequence) chosen from SEQ ID NO: 98 and SEQ ID NO: 121.

Preferably, the amino acid sequence or Nanobody® of the invention comprises SEQ ID NO: 98, SEQ ID NO: 102 and SEQ ID NO: 121.

Preferred combinations of CDR1, CDR2, and CDR3 sequences are also shown in Table A-6.

The amino acid sequences of the invention may essentially consists of a heavy chain variable domain sequence that is derived from a conventional four-chain antibody or may essentially consist of a heavy chain variable domain sequence that is derived from heavy chain antibody. The amino acid sequences of the invention may essentially consists of a domain antibody (or an amino acid sequence that is suitable for use as a domain antibody), of a single domain antibody (or an amino acid sequence that is suitable for use as a single domain antibody), of a "dAb" (or an amino acid sequence that is suitable for use as a dAb) or of a Nanobody®.

For a general description of (single) domain antibodies, reference is also made to the prior art cited above, as well as to EP 0 368 684. For the term "dAb's", reference is for example made to Ward et al. (1989, Nature 341: 544-6), to Holt et al., 2003, Trends Biotechnol. 21: 484-490; as well as to for example WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may essentially consist of or may be a Nanobody® (as defined herein) or a suitable fragment thereof. [Note: Nanobody®, Nanobodies® and Nanoclone® are registered trademarks of Ablynx N. V.]

A Nanobody® can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as defined in WO 08/020,079 (Tables A-3 to A-8).

More in particular, a Nanobody® can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and which:

i) have at least 80% amino acid identity with at least one of the amino acid sequences of SEQ ID NO's: 60-76, 138-141 and 146-157 (see Table A-4), in which for the purposes of determining the degree of amino acid identity, the amino acid residues that form the CDR sequences are disregarded. In this respect, reference is also made to Table A-6, which lists the framework 1 sequences (SEQ ID NO's: 81-97 and 166), framework 2 sequences (SEQ ID NO's: 99-100), framework 3 sequences (SEQ ID NO's: 103-120 and 167-168) and framework 4 sequences (SEQ ID NO's: 123 and 169) of the Nanobodies® of SEQ ID NO's: 60-76, 138-141 and 146-157 (see Table A-4);

and in which:

ii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020,079.

For a further general description of Nanobodies®, reference is made to the prior art cited herein, such as e.g. described in WO 08/020,079 (page 16).

Such Nanobodies® may be derived in any suitable manner and from any suitable source, and may for example be naturally occurring $V_{HH}$ sequences (i.e. from a suitable species of Camelid) or synthetic or semi-synthetic amino acid sequences.

Again, such Nanobodies® may be derived in any suitable manner and from any suitable source, and may for example be naturally occurring $V_{HH}$ sequences (i.e. from a suitable species of Camelid) or synthetic or semi-synthetic amino acid sequences, including but not limited to "humanized" (as defined herein) Nanobodies®, "camelized" (as defined herein) immunoglobulin sequences (and in particular camelized heavy chain variable domain sequences), as well as Nanobodies® that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when a Nanobody® comprises a $V_{HH}$ sequence, said Nanobody® may be suitably humanized, as further described herein, so as to provide one or more further (partially or fully) humanized Nanobodies® of the invention. Similarly, when a Nanobody® comprises a synthetic or semi-synthetic sequence (such as a partially humanized sequence), said Nanobody® may optionally be further suitably humanized, again as described herein, again so as to provide one or more further (partially or fully) humanized Nanobodies® of the invention.

In particular, humanized Nanobodies® may be amino acid sequences that are as generally defined for Nanobodies® in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody® may be partially humanized or fully humanized.

In this respect, some preferred Nanobodies® of the invention are Nanobodies® which specifically bind (as further defined herein) protein F of hRSV and which:
i) are a humanized variant of the amino acid sequence with SEQ ID NO: 5 (see Table A-1); and/or
ii) have at least 80% amino acid identity with at least one of the amino acid sequences of SEQ ID NO: 5 (see Table A-1) and/or at least one of the amino acid sequences of SEQ ID NO's: 60-76, 138-141 and 146-157 (see Table A-4), in which for the purposes of determining the degree of amino acid identity, the amino acid residues that form the CDR sequences are disregarded;

and in which:
iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020,079.

The present invention provides a number of humanized and/or sequence optimized amino acid sequences and/or Nanobodies® that are particularly suited for binding protein F of hRSV. Therefore, in one aspect of the present invention, amino acid sequences and/or Nanobodies® are provided chosen from the following:
a) SEQ ID NO's: 60-76;
b) amino acid sequences that have no more than 3, preferably no more than 2, more preferably no more than 1 amino acid difference with one of SEQ ID NO's: 60-76, provided that:
  i) the amino acid sequence has a Glutamine (Gln, Q) at position 105 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence and/or Nanobody® of the invention comprises or essentially consists of one of SEQ ID NO's: 60-76.

In another aspect, the present invention provides amino acid sequences and/or Nanobodies® chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequences and/or Nanobodies® are chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences and/or Nanobodies® of the invention comprise or essentially consist of one of SEQ ID NO's: 62, 65, 67, 68, 75 and 76.

In yet another aspect, the present invention provides amino acid sequences and/or Nanobodies® chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequences and/or Nanobodies® are chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferably, the amino acid sequence and/or Nanobody® of the invention comprises or essentially consists of SEQ ID NO: 65. In another preferred aspect, the amino acid sequence and/or Nanobody® of the invention comprises or essentially consists of SEQ ID NO: 76. In another preferred aspect, the amino acid sequence and/or Nanobody® of the invention comprises or essentially consists of SEQ ID NO: 76.

The present invention also provides a number of humanized and/or sequence optimized amino acid sequences and/or Nanobodies® that are chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Proline (Pro, P) at position 14, Arginine (Arg, R) at position 19, Leucine (Leu, L) at position 20 and/or Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence and/or Nanobody® of the invention comprises or essentially consists of one of SEQ ID NO's: 146-153.

In another aspect, the present invention provides amino acid sequences and/or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and/or Leucine (Leu, L) at position 108; and in addition Arginine (Arg, R) at position 83, Glutamic acid (Glu, E) at position 85 and/or Glutamine (Gln, Q) at position 105;
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequences and/or Nanobodies® are chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Praline (Pro, P) at position 14, Arginine (Arg, R) at position 19, Leucine (Leu, L) at position 20 and/or Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences and/or Nanobodies® of the invention comprise or essentially consist of one of SEQ ID NO's: 146-149 and 151-153.

The amino acid sequences and/or Nanobodies® of the present invention show reduced immunogenicity upon administration to a human subject. In addition, the amino acid sequences and/or Nanobodies® of the present invention show improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) for protein F of hRSV compared to their corresponding parental amino acid sequences (as described in PCT application PCT/EP2009/056975 entitled "Amino acid sequences directed against envelope proteins of a virus and polypeptides comprising the same for the treatment of viral diseases" filed by Ablynx N. V on 5 Jun. 2009).

During the production of the Nanobodies of the invention, a high level of pyro glutamate (pGlu) on the amino terminus was detected by RP-HPLC. Levels of more than 15% pGlu were detected following fermentation and the level of pGlu were steadily increasing upon storage during stability studies. Such a modification leads to heterogeneity of the final product and needs to be avoided. The control/prevention of pGlu formation is therefore critical to keep therapeutic proteins within their set specifications. Specific liquid formulations and/or storage conditions are needed for proteins with an N-terminal Glutamic acid thus minimizing the formation of pyro-Glutamic acid.

In the present invention, the possibility of pGlu post-translational modification of the N-terminus was eliminated by changing the N-terminal Glutamic acid (E) [HOOC—(CH2)2—protein] into an Aspartic acid (D) [HOOC—CH2—protein] which lead to increased product stability. Accordingly, the present invention also relates to amino acid sequences and Nanobodies as described above wherein the Glutamic acid at position 1 (said position determined according to Kabat numbering) is changed into an Aspartic acid.

The present invention provides a number of sequence optimized amino acid sequences and/or Nanobodies® that show increased stability upon storage during stability studies. Therefore, in one aspect of the present invention, amino acid sequences and/or Nanobodies® are provided chosen from the following:

a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
  i) the amino acid sequence has a Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence and/or Nanobody® of the invention comprises or essentially consists of one of SEQ ID NO's: 138-141 and 154-157.

In another aspect, the amino acid sequences and/or Nanobodies® of the invention comprise or essentially consist of SEQ ID NO: 5, wherein position 1 (Glu) has been changed into Asp.

In another aspect, the amino acid sequences and/or Nanobodies® of the invention comprise or essentially consist of SEQ ID NO: 62, wherein position 1 (Glu) has been changed into Asp.

In another aspect, the amino acid sequences and/or Nanobodies® of the invention comprise or essentially consist of SEQ ID NO: 65, wherein position 1 (Glu) has been changed into Asp.

In another aspect, the amino add sequences and/or Nanobodies® of the invention comprise or essentially consist of SEQ ID NO: 76, wherein position 1 (Glu) has been changed into Asp.

In another aspect, the amino acid sequences and/or Nanobodies® of the invention comprise or essentially consist of one of SEQ ID NO's: 146-153, wherein position 1 (Glu) has been changed into Asp.

Preferably, the amino acid sequence and/or Nanobody® of the invention comprises or essentially consists of SEQ ID NO: 138. In another preferred aspect, the amino acid sequence and/or Nanobody® of the invention comprises or essentially consists of SEQ ID NO: 139. In another preferred aspect, the amino acid sequence and/or Nanobody® of the invention comprises or essentially consists of SEQ ID NO: 140. In another preferred aspect, the amino acid sequence and/or Nanobody® of the invention comprises or essentially consists of SEQ ID NO: 141. In another preferred aspect, the amino acid sequence and/or Nanobody® of the invention comprises or essentially consists of one of SEQ ID NO's: 154-157.

In another aspect, the amino acid sequences and/or Nanobodies® of the invention comprise or essentially consist of SEQ ID NO: 5, wherein one or more (such as two, three, four, five, six, seven, eight, nine, ten, eleven or twelve) amino acid residues have been mutated selected from the following: Val5Leu, Ala14Pro, Ser19Arg, Ile20Leu, Glu44Gly, Ala74Ser, Gly78Leu, Ala83Arg, Asp85Glu, Arg105Gln, Gln108Leu and Gly54Asp.

In another aspect, the amino acid sequences and/or Nanobodies® of the invention comprise or essentially consist of SEQ ID NO: 5, wherein one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp.

In another aspect, the amino acid sequences and/or Nanobodies® of the invention comprise or essentially consist of SEQ ID NO: 5, wherein one or more (such as two, three or four) amino acid residues have been mutated selected from the following: Ala14Pro, Ser19Arg, Ile20Leu and Gln108Leu.

In another aspect, the amino acid sequences and/or Nanobodies® of the invention comprise or essentially consist of SEQ ID NO: 5, wherein one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

In another aspect, the amino acid sequences and/or Nanobodies® of the invention comprise or essentially consist of SEQ ID NO: 5, wherein one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein position 1 (Glu) has been changed into Asp.

In another aspect, the amino acid sequences and/or Nanobodies® of the invention comprise or essentially consist of SEQ ID NO: 5, wherein one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, and wherein position 1 (Glu) has been changed into Asp.

In another aspect, the amino acid sequences and/or Nanobodies® of the invention comprise or essentially consist of SEQ ID NO: 5, wherein one or more (such as two, three or four) amino acid residues have been mutated selected from the following: Ala14Pro, Ser19Arg, Ile20Leu and Gln108Leu, and wherein position 1 (Glu) has been changed into Asp.

In another aspect, the amino acid sequences and/or Nanobodies® of the invention comprise or essentially consist of SEQ ID NO: 5, wherein one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein position 1 (Glu) has been changed into Asp.

Preferably, the amino acid sequence and/or Nanobody® of the invention comprises or essentially consist of SEQ ID NO: 5, wherein following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Glu;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln;
Ala14Pro, Ser19Arg, Ile20Leu, Gln108Leu, Ala83Arg, Asp85Glu and Arg105Gln;
Glu1Asp;
Glu1Asp, Val5Leu, Ala14Pro, Glu44Gly, Gly78Leu, Ala83Arg, Asp85Glu, Arg105Gln and Gln108Leu;
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln.

The amino acid sequences and/or Nanobodies® of the present invention show improved properties such as e.g. improved stability, less immunogenicity, improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for protein F of hRSV and/or improved efficacy and/or potency for neutralizing hRSV compared to their corresponding wild type amino acid sequences (as described in PCT application PCT/EP2009/056975 entitled "Amino acid sequences directed against envelope proteins of a virus and polypeptides comprising the same for the treatment of viral diseases" filed by Ablynx N. V on 5 Jun. 2009).

More in particular, the amino acid sequences and/or Nanobodies® of the invention can bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) preferably such that they:
bind to protein F of hRSV with a dissociation constant ($K_D$) of 1000 nM to 1 nM or less, preferably 100 nM to 1 nM or less, more preferably 15 nM to 1 nM or even 10 nM to 1 nM or less;
and/or such that they:
bind to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more;
and/or such that they:
bind to protein F of hRSV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower;

Some preferred IC50 values for binding of the amino acid sequences of the invention to protein F of hRSV will become clear from the further description and examples herein.

Assays to determine the IC50 include competition assays such as competition ELISA (e.g. competition with Synagis® or its Fab fragment) or more preferably neutralization assays such as the microneutralization assay described by Anderson et al. (1985, J. Olin. Microbiol. 22: 1050-1052; 1988, J. Virol. 62: 4232-4238), modifications of this assay such as e.g. described in Example 6, or a plaque reduction assay as for example described by Johnson et al. (1997, J. Inf. Dis. 176: 1215-1224), and modifications thereof.

For example, in a competition assay with the Fab fragment of Synagis®, the amino acid sequences of the invention may have IC50 values between 1 nM and 100 nM, preferably between 10 nM and 50 nM, or less.

For example, in a microneutralization assay on hRSV Long (such as e.g. described in Example 6) the amino acid sequences of the invention may have IC50 values between 100 nM and 1000 nM, preferably between 100 nM and 500 nM, or less.

The amino acid sequences and Nanobodies® provided by the invention are preferably in essentially isolated form (as defined herein), or form part of a polypeptide of the invention (also referred to as "polypeptide of the invention" or "construct of the invention"; both are used interchangeably), which may comprise or essentially consist of one or more amino acid sequences or Nanobodies® of the invention and which may optionally further comprise one or more further amino acid sequences or Nanobodies® (all optionally linked via one or more suitable linkers).

Accordingly, in another aspect, the invention relates to a polypeptide (also referred to herein as a "polypeptide of the invention") that comprises or essentially consists of one or more amino acid sequences or Nanobodies® of the invention (or suitable fragments thereof).

The process of designing/selecting and/or preparing a polypeptide of the invention, starting from an amino acid sequence or Nanobody® of the invention, is also referred to herein as "formatting" said amino acid sequence or Nanobody® of the invention; and an amino acid sequence or Nanobody® of the invention that is made part of a polypeptide of the invention is said to be "formatted" or to be "in the format of" said polypeptide of the invention. Examples of ways in which an amino acid sequence or Nanobody® of the invention can be formatted and examples of such formats will be clear to the skilled person based on the disclosure herein; and such formatted amino acid sequences or Nanobodies® form a further aspect of the invention.

For example, and without limitation, the one or more amino acid sequences or Nanobodies® of the invention may be used as a binding unit in such a polypeptide, which may optionally contain one or more further amino add sequences that can serve as a binding unit (i.e. against the same or another epitope on protein F of hRSV and/or against one or more other antigens, proteins or targets than protein F of hRSV), so as to provide a monovalent, multivalent, multiparatopic or multispecific polypeptide of the invention, respectively, all as described herein. The present invention thus also relates to a polypeptide which is a monovalent polypeptide or construct comprising or essentially consisting of an amino acid sequence or Nanobody® of the invention. The present invention thus also relates to a polypeptide which is a multivalent polypeptide or construct, such as e.g. a bivalent or trivalent polypeptide or construct. The present invention also relates to a polypeptide which is a multispecific polypeptide or construct, such as e.g. a bispecific or trispecific polypeptide or construct. The present invention also relates to a polypeptide which is a multiparatopic polypeptide or construct, such as e.g. a bisparatopic or triparatopic polypeptide or construct.

Accordingly, in a preferred, but non-limiting aspect, the amino acid sequence or Nanobody® of the invention comprises at least one further amino acid sequence or Nanobody®, so as to provide a polypeptide of the invention that comprises at least two, such as two, three, four, five or more amino acid sequences or Nanobodies®, in which said amino acid sequences or Nanobodies® may optionally be linked via one or more linker sequences (as defined herein). Polypeptides of the invention that comprise two or more amino acid sequences or Nanobodies®, of which at least one, and preferably all, is/are an amino acid sequence or Nanobody® of the invention, will also be referred to herein as "multivalent" polypeptides of the invention, and the amino acid sequences or Nanobodies® present in such polypeptides will also be referred to herein as being in a "multivalent format". For example a "bivalent" polypeptide of the invention comprises two amino acid sequences and/or Nanobodies®, optionally linked via a linker sequence, whereas a "trivalent" polypeptide of the invention comprises three amino acid sequences and/or Nanobodies®, optionally linked via two linker sequences; etc.; in which at least one of the amino acid sequences and/or Nanobodies® present in the polypeptide, and up to all of the amino acid sequences and/or Nanobodies® present in the polypeptide, is/are a amino acid sequences and/or Nanobodies® of the invention.

In a multivalent polypeptide of the invention, the two or more amino acid sequences or Nanobodies® may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical amino acid sequences or Nanobodies®; (b) a first amino acid sequence or Nanobody® directed against a first antigenic determinant of a protein or antigen and a second amino acid sequence or Nanobody® directed against the same antigenic determinant of said protein or antigen which is different from the first amino acid sequence or Nanobody®; (c) a first amino acid sequence or Nanobody® directed against a first antigenic determinant of a protein or antigen and a second amino acid sequence or Nanobody® directed against another antigenic determinant of said protein or antigen; or (d) a first amino acid sequence or Nanobody® directed against a first protein or antigen and a second amino acid sequence or Nanobody® directed against a second protein or antigen (i.e. different from said first antigen). Similarly, a trivalent polypeptide of the invention may, for example and without being limited thereto, comprise (a) three identical amino acid sequences or Nanobodies®; (b) two identical amino acid sequences or Nanobody® against a first antigenic determinant of an antigen and a third amino acid sequence or Nanobody® directed against a different antigenic determinant of the same antigen; (c) two identical amino acid sequences or Nanobodies® against a first antigenic determinant of an antigen and a third amino acid sequence or Nanobody® directed against a second antigen different from said first antigen; (d) a first amino acid sequence or Nanobody® directed against a first antigenic determinant of a first antigen, a second amino acid sequence or Nanobody® directed against a second antigenic determinant of said first antigen and a third amino acid sequence or Nanobody® directed against a second antigen different from said first antigen; or (e) a first amino acid sequence or Nanobody® directed against a first antigen, a second amino acid sequence or Nanobody® directed against a second antigen different from said first antigen, and a third amino acid sequence or Nanobody® directed against a third antigen different from said first and second antigen.

In a preferred aspect, the invention provides a multivalent, preferably a bivalent or trivalent polypeptide comprising or essentially consisting of at least two (preferably identical) amino acid sequences or Nanobodies® of the invention (as described above).

In one aspect, the invention provides a multivalent, preferably a bivalent or trivalent polypeptide comprising or essentially consisting of at least two (preferably identical) or at least three (preferably identical) amino acid sequences or Nanobodies® chosen from amino acid sequences that comprise at least a stretch of amino acid residues chosen from the following:
- a) SEQ ID NO: 102;
- b) a stretch of amino acid residues that has no more than 3, preferably no more than 2, more preferably no more than 1 amino acid difference with SEQ ID NO: 102, provided that:
  - i) said stretch of amino acid residues has an Aspartic acid (Asp, D) at position 6 (position 54 determined according to Kabat numbering); and
  - ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In another aspect, the invention provides a multivalent, preferably a bivalent or trivalent polypeptide comprising or essentially consisting of at least two (preferably identical) or at least three (preferably identical) amino acid sequences or Nanobodies® chosen from amino acid sequences that comprise two or more stretches of amino acid residues in which one stretch is chosen from the following:
- a) SEQ ID NO: 102;
- b) a stretch of amino acid residues that has no more than 3, preferably no more than 2, more preferably no more than 1 amino acid difference with SEQ ID NO: 102, provided that:
  - i) said stretch of amino acid residues has an Aspartic acid (Asp, D) at position 6 (position 54 determined according to Kabat numbering); and
  - ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and at least one stretch is chosen from:
- c) SEQ ID NO: 98;
- d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
- e) SEQ ID NO: 121; and
- f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

such that the stretch of amino acid residues that corresponds to one of a), and b) should always be present in the amino acid sequence that forms part of the multivalent polypeptide and such that the second stretch of amino acid residues is chosen from one of c), d), e) and f).

Preferred multivalent (such as bivalent or trivalent) polypeptides may comprise or essentially consist of at least two (preferably identical) or at least three (preferably identical) amino acid sequences or Nanobodies® chosen from amino acid sequences that comprise three or more stretches of amino acid residues, in which the first stretch of amino acid residues is chosen from the group consisting of:
- a) SEQ ID NO: 98;
- b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

the second stretch of amino acid residues is chosen from the group consisting of:
- c) SEQ ID NO: 102;
- d) a stretch of amino acid residues that has no more than 3, preferably no more than 2, more preferably no more than 1 amino acid difference with SEQ ID NO: 102, provided that:
  - i) said stretch of amino acid residues has an Aspartic acid (Asp, D) at position 6 (position 54 determined according to Kabat numbering); and
  - ii) the amino acid sequence comprising said stretch of amino acid residues binds protein of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and the third stretch of amino acid residues is chosen from the group consisting of:
- e) SEQ ID NO: 121;
- f) a stretch of amino add residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In yet another aspect, the invention provides a multivalent, preferably a bivalent or trivalent polypeptide comprising or essentially consisting of at least two (preferably identical) or at least three (preferably identical) amino acid sequences or Nanobodies® that essentially consist of 4 framework regions (FR1 to FR4, respectively) and 3 complementarity determining regions (CDR1 to CDR3, respectively), in which CDR2 is chosen from:
  a) SEQ ID NO: 102;
  b) a stretch of amino acid residues that has no more than 3, preferably no more than 2, more preferably no more than 1 amino acid difference with SEQ ID NO: 102, provided that:
    i) said stretch of amino acid residues has an Aspartic acid (Asp, D) at position 6 (position 54 determined according to Kabat numbering); and
    ii) the amino acid sequence comprising said stretch of amino acid residues binds protein of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In yet another aspect, the invention provides a multivalent, preferably a bivalent or trivalent polypeptide comprising or essentially consisting of at least two (preferably identical) or at least three (preferably identical) amino acid sequences or Nanobodies® that essentially consist of 4 framework regions (FR1 to FR4, respectively) and 3 complementarity determining regions (CDR1 to CDR3, respectively), in which CDR2 is chosen from the group consisting of:
  a) SEQ ID NO: 102; or
  b) a stretch of amino acid residues that has no more than 3, preferably no more than 2, more preferably no more than 1 amino acid difference with SEQ ID NO: 102, provided that:
    i) said stretch of amino acid residues has an Aspartic acid (Asp, D) at position 6 (position 54 determined according to Kabat numbering); and
    ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and at least one of CDR1 or CDR3 is chosen from:
  CDR1 chosen from the group consisting of:
  c) SEQ ID NO: 98;
  d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
  CDR3 chosen from the group consisting of:
  e) SEQ ID NO: 121; or
  f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Preferably, multivalent (such as bivalent or trivalent) polypeptides may comprise or essentially consist of at least two (preferably identical) or at least three (preferably identical) amino acid sequences or Nanobodies® that essentially consist of 4 framework regions (FR1 to FR4, respectively) and 3 complementarity determining regions (CDR1 to CDR3, respectively), in which:
  CDR1 is chosen from the group consisting of:
  a) SEQ ID NO: 98;
  b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and
  CDR2 is chosen from the group consisting of:
  c) SEQ ID NO: 102; or
  d) a stretch of amino acid residues that has no more than 3, preferably no more than 2, more preferably no more than 1 amino acid difference with SEQ ID NO: 102, provided that:
    i) said stretch of amino acid residues has an Aspartic acid (Asp, D) at position 6 (position 54 determined according to Kabat numbering); and
    ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference; and
  CDR3 is chosen from the group consisting of:
  e) SEQ ID NO: 121;
  f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

In a specific aspect, the multivalent (such as bivalent or trivalent) polypeptides may comprise or essentially consist of at least two (preferably identical) or at least three (preferably identical) amino acid sequences or Nanobodies® that comprise at least SEQ ID NO: 102.

In another specific aspect, the multivalent (such as bivalent or trivalent) polypeptides may comprise or essentially consist of at least two (preferably identical) or at least three (preferably identical) amino acid sequences or Nanobodies® that comprise at least SEQ ID NO: 102 and at least one stretch of amino acid residues (CDR sequence) chosen from:
  c) SEQ ID NO: 98;
  d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
  e) SEQ ID NO: 121;
  f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Preferred multivalent (such as bivalent or trivalent) polypeptides may comprise or essentially consist of at least two (preferably identical) or at least three (preferably identical) amino acid sequences or Nanobodies® that comprise at least SEQ ID NO: 102 and at least two stretches of amino acid residues (CDR sequences) in which one stretch is chosen from the group consisting of the stretches of amino acid residues defined in c) and d) and in which the other stretch is chosen from the group consisting of the stretches of amino acid residues defined in e) and f).

In a specific aspect, the multivalent (such as bivalent or trivalent) polypeptides may comprise or essentially consist of at least two (preferably identical) or at least three (preferably identical) amino acid sequences or Nanobodies® that comprise at least SEQ ID NO: 102 and at least one stretch of amino acid residues (CDR sequence) chosen from SEQ ID NO: 98 and SEQ ID NO: 121; or amino acid sequences or Nanobodies® that comprise at least SEQ ID NO: 98, SEQ ID NO: 102 and SEQ ID NO: 121.

In another preferred aspect, the invention provides a multivalent, preferably a trivalent polypeptide comprising or essentially consisting of at least three (preferably identical) amino acid sequences or Nanobodies® of the invention (as described above). In another preferred aspect, the invention provides a bivalent polypeptide comprising or essentially consisting of two (preferably identical) amino acid sequences or Nanobodies® of the invention (as described above). In another preferred aspect, the invention provides a trivalent polypeptide comprising or essentially consisting of three (preferably identical) amino acid sequences or Nanobodies® of the invention (as described above).

The invention also provides a multivalent, preferably a bivalent or trivalent polypeptide comprising or essentially consisting of at least two (preferably identical) amino acid sequences or Nanobodies® chosen from the following:
  a) SEQ ID NO's: 60-76;
  b) amino acid sequences that have no more than 3, preferably no more than 2, more preferably no more than 1 amino acid difference with one of SEQ ID NO's: 60-76, provided that:
    i) the amino acid sequence has a Glutamine (Gln, Q) at position 105 (said position determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two identical amino acid sequences or Nanobodies® chosen from one of SEQ ID NO's: 60-76.

In another preferred aspect, the invention provides a multivalent, preferably a bivalent or trivalent polypeptide comprising or essentially consisting of at least two (preferably identical) amino acid sequences or Nanobodies® chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and/or an Arginine (Arg, R) at position 83 (said positions determined according to Kabat numbering); and
    ii) the amino add sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a multivalent, preferably a bivalent or trivalent polypeptide comprising or essentially consisting of at least two (preferably identical) amino acid sequences or Nanobodies® chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two identical amino acid sequences or Nanobodies® chosen from one of SEQ ID NO's: 62, 65, 67, 68, 75 and 76.

In another preferred aspect, the invention provides a multivalent, preferably a bivalent or trivalent polypeptide comprising or essentially consisting of at least two (preferably identical) amino acid sequences or Nanobodies® chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a multivalent, preferably a bivalent or trivalent polypeptide comprising or essentially consisting of at least two (preferably identical) amino acid sequences or Nanobodies® chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two identical amino acid sequences or Nanobodies® chosen from SEQ ID NO's: 65 and 76.

The invention also provides a multivalent, preferably a bivalent or trivalent polypeptide comprising or essentially consisting of at least two (preferably identical) amino acid sequences or Nanobodies® chosen from the following:
  a) SEQ ID NO's: 146-153;
  b) amino acid sequences that have no more than 3, preferably no more than 2, more preferably no more than 1 amino acid difference with one of SEQ ID NO's: 146-153, provided that:
    i) the amino acid sequence has a Proline (Pro, P) at position 14, Arginine (Arg, R) at position 19, Leucine (Leu, L) at position 20 and/or Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two identical amino acid sequences or Nanobodies® chosen from one of SEQ ID NO's: 146-153.

In another preferred aspect, the invention provides a multivalent, preferably a bivalent or trivalent polypeptide comprising or essentially consisting of at least two (preferably identical) amino acid sequences or Nanobodies® chosen from the following:
  a) SEQ ID NO's: 146-149 and 151-153;
  b) amino acid sequences that have no more than 3, preferably no more than 2, more preferably no more than 1 amino acid difference with one of SEQ ID NO's: 146-149 and 151-153, provided that:
    i) the amino acid sequence has a Proline (Pro, P) at position 14, Arginine (Arg, R) at position 19, Leucine (Leu, L) at position 20 and/or Leucine (Leu, L) at position 108; and in addition Arginine (Arg, R) at position 83, Glutamic acid (Glu, E) at position 85 and/or Glutamine (Gln, Q) at position 105;
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a multivalent, preferably a bivalent or trivalent polypeptide comprising or essentially consisting of at least two (preferably identical) amino acid sequences or Nanobodies® chosen from the following:
  a) SEQ ID NO's: 146-149 and 151-153;
  b) amino acid sequences that have no more than 3, preferably no more than 2, more preferably no more than 1 amino acid difference with one of SEQ ID NO's: 146-149 and 151-153, provided that:
    i) the amino acid sequence has a Proline (Pro, P) at position 14, Arginine (Arg, R) at position 19, Leucine (Leu, L) at position 20 and/or Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
      SEQ ID NO: 146, the amino acid sequence preferably has Glutamine (Gln, Q) at position 105;
      SEQ ID NO: 147, the amino acid sequence preferably has Arginine (Arg, R) at position 83 and Glutamine (Gln, Q) at position 105;
      SEQ ID NO: 148, the amino acid sequence preferably has Glutamic acid (Glu, E) at position 85 and Glutamine (Gln, Q) at position 105;

SEQ ID NO: 149, the amino acid sequence preferably has Arginine (Arg, R) at position 83, Glutamic acid (Glu, E) at position 85 and Glutamine (Gln, Q) at position 105;
SEQ ID NO: 151, the amino acid sequence preferably has Arginine (Arg, R) at position 83;
SEQ ID NO: 152, the amino acid sequence preferably has Glutamic acid (Glu, E) at position 85;
SEQ ID NO: 153, the amino acid sequence preferably has Arginine (Arg, R) at position 83 and Glutamic acid (Glu, E) at position 85;
(said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred polypeptides of the invention comprises or essentially consists of at least two identical amino acid sequences or Nanobodies® chosen from SEQ ID NO's: 146-149 and 151-153.

In another preferred aspect, the invention provides a multivalent, preferably a bivalent or trivalent polypeptide comprising or essentially consisting of at least two (preferably identical) amino acid sequences or Nanobodies® that comprise or essentially consist of SEQ ID NO: 5, in which one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

In another preferred aspect, the invention provides a multivalent, preferably a bivalent or trivalent polypeptide comprising or essentially consisting of at least two (preferably identical) amino acid sequences or Nanobodies® that comprise or essentially consist of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp.

In another preferred aspect, the invention provides a multivalent, preferably a bivalent or trivalent polypeptide comprising or essentially consisting of at least two (preferably identical) amino acid sequences or Nanobodies® that comprise or essentially consist of SEQ ID NO: 5, in which one or more (such as two, three or four) amino acid residues have been mutated selected from the following: Ala14Pro, Ser19Arg, Ile20Leu and Gln108Leu.

In another preferred aspect, the invention provides a multivalent, preferably a bivalent or trivalent polypeptide comprising or essentially consisting of at least two (preferably identical) amino acid sequences or Nanobodies® that comprise or essentially consist of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

In another preferred aspect, the invention provides a multivalent, preferably a bivalent or trivalent polypeptide comprising or essentially consisting of at least two (preferably identical) amino acid sequences or Nanobodies® that comprise or essentially consist of SEQ ID NO: 5, in which following amino acid residues have been mutated:

Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or
Ala14Pro, Ser19Arg, Ile20Leu, Gln108Leu, Ala83Arg, Asp85Glu and Arg105Gln.

In another preferred aspect, the invention provides a multivalent, preferably a trivalent polypeptide comprising or essentially consisting of at least three (preferably identical) amino acid sequences or Nanobodies® chosen from the following:
a) SEQ ID NO's: 50-76;
b) amino acid sequences that have no more than 3, preferably no more than 2, more preferably no more than 1 amino acid difference with one of SEQ ID NO's: 60-76, provided that:
i) the amino acid sequence has a Glutamine (Gln, Q) at position 105 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three identical amino acid sequences or Nanobodies® chosen from one of SEQ ID NO's: 60-76.

In another preferred aspect, the invention provides a multivalent, preferably a trivalent polypeptide comprising or essentially consisting of at least three (preferably identical) amino acid sequences or Nanobodies® chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
i) the amino acid sequence has a Glutamine (Gln, Q) at position 105, a Leucine (Leu, L) at position 78 and/or an Arginine (Arg, R) at position 83 (said positions determined according to Kabat numbering); and
ii) the amino acid sequence binds protein F of hRSV with the same, about the same, or a higher affinity (said affinity as measured by surface plasmon resonance)

and/or the amino acid sequence has the same, about the same, or a higher potency (as defined herein) compared to the amino acid sequence without the 3, 2 or 1 amino acid difference.

In another preferred aspect, the invention provides a multivalent, preferably a trivalent polypeptide comprising or essentially consisting of at least three (preferably identical) amino acid sequences or Nanobodies® chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three identical amino acid sequences or Nanobodies® chosen from one of SEQ ID NO's: 62, 65, 67, 68, 75 and 76.

In another preferred aspect, the invention provides a multivalent, preferably a trivalent polypeptide comprising or essentially consisting of at least three (preferably identical) amino acid sequences or Nanobodies® chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a multivalent, preferably a trivalent polypeptide comprising or essentially consisting of at least three (preferably identical) amino acid sequences or Nanobodies® chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three identical amino acid sequences or Nanobodies® chosen from one of SEQ ID NO's: 65 and 76.

The invention also provides a multivalent, preferably a trivalent polypeptide comprising or essentially consisting of at least three (preferably identical) amino acid sequences or Nanobodies® chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Proline (Pro, P) at position 14, Arginine (Arg, R) at position 19, Leucine (Leu, L) at position 20 and/or Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three identical amino acid sequences or Nanobodies® chosen from one of SEQ ID NO's: 146-153.

In another preferred aspect, the invention provides a multivalent, preferably a trivalent polypeptide comprising or essentially consisting of at least three (preferably identical) amino acid sequences or Nanobodies® chosen from the following:
a) SEQ ID NO's: 146-149 and 151-153;
b) amino acid sequences that have no more than 3, preferably no more than 2, more preferably no more than 1 amino add difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and/or Leucine (Leu, L) at position 108; and in addition Arginine (Arg, R) at position 83, Glutamic acid (Glu, E) at position 85 and/or Glutamine (Gln, Q) at position 105;
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a multivalent, preferably a trivalent polypeptide comprising or essentially consisting of at least three (preferably identical) amino acid sequences or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and/or Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred polypeptides of the invention comprises or essentially consists of at least three identical amino acid sequences or Nanobodies® chosen from SEQ ID NO's: 146-149 and 151-153.

In another preferred aspect, the invention provides a multivalent, preferably a trivalent polypeptide comprising or essentially consisting of at least three (preferably identical) amino acid sequences or Nanobodies® that comprise or essentially consist of SEQ ID NO: 5, in which one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

In another preferred aspect, the invention provides a multivalent, preferably a trivalent polypeptide comprising or essentially consisting of at least three (preferably identical) amino acid sequences or Nanobodies® that comprise or essentially consist of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp.

In another preferred aspect, the invention provides a multivalent, preferably a trivalent polypeptide comprising or essentially consisting of at least three (preferably identical) amino acid sequences or Nanobodies® that comprise or essentially consist of SEQ ID NO: 5, in which one or more (such as two, three or four) amino acid residues have been mutated selected from the following: Ala14Pro, Ser19Arg, Ile20Leu and Gln108Leu.

In another preferred aspect, the invention provides a multivalent, preferably a trivalent polypeptide comprising or essentially consisting of at least three (preferably identical) amino acid sequences or Nanobodies® that comprise or essentially consist of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

In another preferred aspect, the invention provides a multivalent, preferably a trivalent polypeptide comprising or essentially consisting of at least three (preferably identical) amino acid sequences or Nanobodies® that comprise or essentially consist of SEQ ID NO: 5, in which following amino acid residues have been mutated:
  Val5Leu, Ala14Pro, Glu44Gly, Gly78Leu, Ala83Arg, Asp85Glu, Arg105Gln and Gln108Leu;
  Ala83Arg, Asp85Glu, Arg105Gln and Gln108Leu;
  Gly78Leu, Ala83Arg, Asp85Glu and Arg105Gln;
  Val5Leu, Ala14Pro, Glu44Gly, Gly78Leu, Ala83Arg, Asp85Glu, Arg105Gln, Gln108Leu and Gly54Asp;
  Ala83Arg, Asp85Glu, Arg105Gln, Gln108Leu and Gly54Asp;
  Gly78Leu, Ala83Arg, Asp85Glu, Arg105Gln and Gly54Asp;
  Gly54Asp;
  Ala14Pro, Ser19Arg, Ile20Leu and Gln108Leu;
  Ala14Pro, Ser19Arg, Ile20Leu, Gln108Leu and Ala83Arg;
  Ala14Pro, Ser19Arg, Ile20Leu, Gln108Leu and Asp85Glu;
  Ala14Pro, Ser19Arg, Ile20Leu, Gln108Leu and Arg105Gln;
  Ala14Pro, Ser19Arg, Ile20Leu, Gln108Leu, Ala83Arg and Asp85Glu;
  Ala14Pro, Ser19Arg, Ile20Leu, Gln108Leu, Ala83Arg and Arg105Gln;
  Ala14Pro, Ser19Arg, Ile20Leu, Gln108Leu, Asp85Glu and Arg105Gln; or
  Ala14Pro, Ser19Arg, Ile20Leu, Gln108Leu, Ala83Arg, Asp85Glu and Arg105Gln.

The invention also provides a multivalent, preferably a bivalent or trivalent polypeptide as described above in which the Glutamic acid at position 1 has been changed into an Aspartic acid.

In this respect, the invention provides a multivalent, preferably a bivalent or trivalent polypeptide comprising or essentially consisting of at least one amino acid sequence or Nanobody® chosen from the following:
  a) SEQ ID NO's: 138-141 and 154-157;
  b) amino acid sequences that have no more than 3, preferably no more than 2, more preferably no more than 1 amino acid difference with one of SEQ ID NO's: 138-141 and 154-157, provided that:
    i) the amino acid sequence has an Aspartic acid (Asp, D) at position 1 (said position determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino add sequence without the 3, 2 or 1 amino acid difference.

In another preferred aspect, the polypeptide of the invention comprises or essentially consists of at least one amino acid sequence or Nanobody® chosen from one of SEQ ID NO's: 138-141 and 154-157.

In another preferred aspect, the invention provides a multivalent, preferably a bivalent or trivalent polypeptide comprising or essentially consisting of at least one amino acid sequence or Nanobody® that comprises or essentially consists of SEQ ID NO: 5, in which the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 62, in which the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 65, in which the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 76, in which the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 75, in which the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 147, in which the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 149, in which the Glutamic acid at position 1 has been changed into Aspartic acid.

In another preferred aspect, the invention provides a multivalent, preferably a bivalent or trivalent polypeptide comprising or essentially consisting of at least one amino acid sequence or that comprises or essentially consists of SEQ ID NO: 153, in which the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 5, in which one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, and wherein the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 5, in which one or more (such as two, three or four) amino acid residues have been mutated selected from the following: Ala14Pro, Ser19Arg, Ile20Leu and Gln108Leu, and wherein the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein the Glutamic acid at position 1 has been changed into Aspartic acid.

In another preferred aspect, the invention provides a multivalent, preferably a bivalent or trivalent polypeptide comprising or essentially consisting of at least one amino acid sequence or Nanobody® that comprises or essentially consists of SEQ ID NO: 5, in which following amino acid residues have been mutated:

Glu1Asp;

Glu1Asp, Val5Leu, Ala14Pro, Glu44Gly, Gly78Leu, Ala83Arg, Asp85Glu, Arg105Gln and Gln108Leu;

Glu1Asp, Ala83Arg, Asp85Glu, Arg105Gln and Gln108Leu;

Glu1Asp, Gly78Leu, Ala83Arg, Asp85Glu and Arg105Gln;

Glu1Asp, Val5Leu, Ala14Pro, Glu44Gly, Gly78Leu, Ala83Arg, Asp85Glu, Arg105Gln, Gln108Leu and Gly54Asp;

Glu1Asp, Ala83Arg, Asp85Glu, Arg105Gln, Gln108Leu and Gly54Asp;

Glu1Asp, Gly78Leu, Ala83Arg, Asp85Glu, Arg105Gln and Gly54Asp;

Glu1Asp and Gly54Asp;

Glu1Asp, Ala14Pro, Ser19Arg, Ile20Leu and Gln108Leu;

Glu1Asp, Ala14Pro, Ser19Arg, Ile20Leu, Gln108Leu and Ala83Arg;

Glu1Asp, Ala14Pro, Ser19Arg, Ile20Leu, Gln108Leu and Asp85Glu;

Glu1Asp, Ala14Pro, Ser19Arg, Ile20Leu, Gln108Leu and Arg105Gln;

Glu1Asp, Ala14Pro, Ser19Arg, Ile20Leu, Gln108Leu, Ala83Arg and Asp85Glu;

Glu1Asp, Ala14Pro, Ser19Arg, Ile20Leu, Gln108Leu, Ala83Arg and Arg105Gln;

Glu1Asp, Ala14Pro, Ser19Arg, Ile20Leu, Gln108Leu, Asp85Glu and Arg105Gln; or

Glu1Asp, Ala14Pro, Ser19Arg, Ile20Leu, Gln108Leu, Ala83Arg, Asp85Glu and Arg105Gln.

In another preferred aspect, the invention provides a bivalent polypeptide comprising or essentially consisting of two (preferably identical) amino acid sequences or Nanobodies® chosen from the following:

a) SEQ ID NO's: 60-76;
b) amino acid sequences that have no more than 3, preferably no more than 2, more preferably no more than 1 amino acid difference with one of SEQ ID NO's: 60-76, provided that:
  i) the amino acid sequence has a Glutamine (Gln, Q) at position 105 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a bivalent polypeptide and comprises or essentially consists of two identical amino acid sequences or Nanobodies® chosen from one of SEQ ID NO's: 60-76.

In another preferred aspect, the invention provides a bivalent polypeptide comprising or essentially consisting of two (preferably identical) amino acid sequences or Nanobodies® chosen from the following:

a) SEQ ID NO's: 62, 65, 67, 68, 75 and 76;

b) amino acid sequences that have no more than 3, preferably no more than 2, more preferably no more than 1 amino acid difference with one of SEQ ID NO's: 62, 65, 67, 68, 75 and 76, provided that:

i) the amino acid sequence has a Glutamine (Gln, Q) at position 105, a Leucine (Leu, L) at position 78 and/or an Arginine (Arg, R) at position 83 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a bivalent polypeptide comprising or essentially consisting of two (preferably identical) amino acid sequences or Nanobodies® chosen from the following:

a) SEQ ID NO's: 62, 65, 67, 68, 75 and 76;

b) amino acid sequences that have no more than 3, preferably no more than 2, more preferably no more than 1 amino acid difference with one of SEQ ID NO's: 62, 65, 67, 68, 75 and 76, provided that:

i) the amino acid sequence has a Glutamine (Gln, Q) at position 105, a Leucine (Leu, L) at position 78 and an Arginine (Arg, R) at position 83 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a bivalent polypeptide and comprises or essentially consists of two identical amino acid sequences or Nanobodies® chosen from one of SEQ ID NO's: 62, 65, 67, 68, 75 and 76.

In another preferred aspect, the invention provides a bivalent polypeptide comprising or essentially consisting of two (preferably identical) amino acid sequences or Nanobodies® chosen from the following:

a) SEQ ID NO's: 65 and 76;

b) amino acid sequences that have no more than 3, preferably no more than 2, more preferably no more than 1 amino acid difference with one of SEQ ID NO's: 65 and 76, provided that:

i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a bivalent polypeptide comprising or essentially consisting of two (preferably identical) amino acid sequences or Nanobodies® chosen from the following:

a) SEQ ID NO's: 65 and 76;

b) amino acid sequences that have no more than 3, preferably no more than 2, more preferably no more than 1 amino acid difference with one of SEQ ID NO's: 65 and 76, provided that:

i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a bivalent polypeptide and comprises or essentially consists of two identical amino acid sequences or Nanobodies® chosen from SEQ ID NO's: 65 and 76.

The invention also provides a bivalent polypeptide comprising or essentially consisting of two (preferably identical) amino acid sequences or Nanobodies® chosen from the following:

a) SEQ ID NO's: 146-153;

b) amino acid sequences that have no more than 3, preferably no more than 2, more preferably no more than 1 amino acid difference with one of SEQ ID NO's: 146-153, provided that:

i) the amino acid sequence has a Praline (Pro, P) at position 14, Arginine (Arg, R) at position 19, Leucine (Leu, L) at position 20 and/or Leucine (Leu, 14 at position 108 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a bivalent polypeptide and comprises or essentially consists of two identical amino acid sequences or Nanobodies® chosen from one of SEQ ID NO's: 146-153.

In another preferred aspect, the invention provides a bivalent polypeptide comprising or essentially consisting of two (preferably identical) amino acid sequences or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
   i) the amino acid sequence has a Proline (Pro, P) at position 14, Arginine (Arg, R) at position 19, Leucine (Leu, L) at position 20 and/or Leucine (Leu, L) at position 108; and in addition Arginine (Arg, R) at position 83, Glutamic acid (Glu, E) at position 85 and/or Glutamine (Gln, Q) at position 105;
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention a bivalent polypeptide comprising or essentially consisting of two (preferably identical) amino acid sequences or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
   i) the amino acid sequence has a Proline (Pro, P) at position 14, Arginine (Arg, R) at position 19, Leucine (Leu, L) at position 20 and/or Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
   SEQ ID NO: 146, the amino acid sequence preferably has Glutamine (Gln, Q) at position 105;
   SEQ ID NO: 147, the amino acid sequence preferably has Arginine (Arg, R) at position 83 and Glutamine (Gln, Q) at position 105;
   SEQ ID NO: 148, the amino acid sequence preferably has Glutamic acid (Glu, E) at position 85 and Glutamine (Gln, Q) at position 105;
   SEQ ID NO: 149, the amino acid sequence preferably has Arginine (Arg, R) at position 83, Glutamic acid (Glu, E) at position 85 and Glutamine (Gln, Q) at position 105;
   SEQ ID NO: 151, the amino acid sequence preferably has Arginine (Arg, R) at position 83;
   SEQ ID NO: 152, the amino acid sequence preferably has Glutamic acid (Glu, E) at position 85;
   SEQ ID NO: 153, the amino acid sequence preferably has Arginine (Arg, R) at position 83 and Glutamic acid (Glu, E) at position 85;
   (said positions determined according to Kabat numbering; and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred polypeptides of the invention comprises or essentially consists of two amino acid sequences or Nanobodies® chosen from SEQ ID NO's: 146-149 and 151-153.

In another preferred aspect, the invention provides a bivalent polypeptide comprising or essentially consisting of two (preferably identical) amino acid sequences or Nanobodies® that comprise or essentially consist of SEQ ID NO: 5, in which one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

In another preferred aspect, the invention provides a bivalent polypeptide comprising or essentially consisting of two (preferably identical) amino acid sequences or Nanobodies® that comprise or essentially consist of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp.

In another preferred aspect, the invention provides a bivalent polypeptide comprising or essentially consisting of two (preferably identical) amino acid sequences or Nanobodies® that comprise or essentially consist of SEQ ID NO: 5, in which one or more (such as two, three or four) amino acid residues have been mutated selected from the following: Ala14Pro, Ser19Arg, Ile20Leu and Gln108Leu.

In another preferred aspect, the invention provides a bivalent polypeptide comprising or essentially consisting of two (preferably identical) amino acid sequences or Nanobodies® that comprise or essentially consist of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

In another preferred aspect, the invention provides a bivalent polypeptide comprising or essentially consisting of two (preferably identical) amino acid sequences or Nanobodies® that comprise or essentially consist of SEQ ID NO: 5, in which following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;

Ala14Pro, Ser19Arg, Ile20Leu, Gln108Leu, Ala83Arg and Arg105Gln;

Ala14Pro, Ser19Arg, Ile20Leu, Gln108Leu, Asp85Glu and Arg105Gln; or

Ala14Pro, Ser19Arg, Ile20Leu, Gln108Leu, Ala83Arg, Asp85Glu and Arg105Gln.

The invention also provides a bivalent polypeptide as described above in which the Glutamic acid at position 1 has been changed into an Aspartic acid.

In this respect, the invention also provides a bivalent polypeptide comprising or essentially consisting of at least one amino acid sequence or Nanobody® chosen from the following:

a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
  i) the amino acid sequence has a Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody® chosen from one of SEQ ID NO's: 138-141 and 154-157.

In another preferred aspect, the invention provides a bivalent polypeptide comprising or essentially consisting of at least one amino acid sequence or Nanobody® that comprises or essentially consists of SEQ ID NO: 5, in which the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 62, in which the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 65, in which the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 76, in which the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 75, in which the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 147, in which the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 149, in which the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 153, in which the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 5, in which one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, and wherein the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 5, in which one or more (such as two, three or four) amino acid residues have been mutated selected from the following: Ala14Pro, Ser19Arg, Ile20Leu and Gln108Leu, and wherein the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein the Glutamic acid at position 1 has been changed into Aspartic acid.

In another preferred aspect, the invention provides a bivalent polypeptide comprising or essentially consisting of at least one amino acid sequence or Nanobody® that comprises or essentially consists of SEQ ID NO: 5, in which following amino acid residues have been mutated:

Glu1Asp;

Glu1Asp, Val5Leu, Ala14Pro, Glu44Gly, Gly78Leu, Ala83Arg, Asp85Glu, Arg105Gln and Gln108Leu;

Glu1Asp, Ala83Arg, Asp85Glu, Arg105Gln and Gln108Leu;

Glu1Asp, Gly78Leu, Ala83Arg, Asp85Glu and Arg105Gln;

Glu1Asp, Val5Leu, Ala14Pro, Glu44Gly, Gly78Leu, Ala83Arg, Asp85Glu, Arg105Gln, Gln108Leu and Gly54Asp;

Glu1Asp, Ala83Arg, Asp85Glu, Arg105Gln, Gln108Leu and Gly54Asp;

Glu1Asp, Gly78Leu, Ala83Arg, Asp85Glu, Arg105Gln and Gly54Asp;

Glu1Asp and Gly54Asp;

Glu1Asp, Ala14Pro, Ser19Arg, Ile20Leu and Gln108Leu;

Glu1Asp, Ala14Pro, Ser19Arg, Ile20Leu, Gln108Leu and Ala83Arg;

Glu1Asp, Ala14Pro, Ser19Arg, Ile20Leu, Gln108Leu and Asp85Glu;

Glu1Asp, Ala14Pro, Ser19Arg, Ile20Leu, Gln108Leu and Arg105Gln;

Glu1Asp, Ala14Pro, Ser19Arg, Ile20Leu, Gln108Leu, Ala83Arg and Asp85Glu;

Glu1Asp, Ala14Pro, Ser19Arg, Ile20Leu, Gln108Leu, Ala83Arg and Arg105Gln;

Glu1Asp, Ala14Pro, Ser19Arg, Ile20Leu, Gln108Leu, Asp85Glu and Arg105Gln; or

Glu1Asp, Ala14Pro, Ser19Arg, Ile20Leu, Gln108Leu, Ala83Arg, Asp85Glu and Arg105Gln.

In another preferred aspect, the invention provides a trivalent polypeptide comprising or essentially consisting of three (preferably identical) amino acid sequences or Nanobodies® chosen from the following:
  a) SEQ ID NO's: 60-76;
  b) amino acid sequences that have no more than 3, preferably no more than 2, more preferably no more than 1 amino acid difference with one of SEQ ID NO's: 60-76, provided that:
    i) the amino acid sequence has a Glutamine (Gln, Q) at position 105 (said position determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a trivalent polypeptide and comprises or essentially consists of three identical amino acid sequences or Nanobodies® chosen from one of SEQ ID NO's: 60-76.

In another preferred aspect, the invention provides a trivalent polypeptide comprising or essentially consisting of three (preferably identical) amino acid sequences or Nanobodies® chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a trivalent polypeptide comprising or essentially consisting of three (preferably identical) amino acid sequences or Nanobodies® chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a trivalent polypeptide and comprises or essentially consists of three identical amino acid sequences or Nanobodies® chosen from one of SEQ ID NO's: 62, 65, 67, 68, 75 and 76.

In another preferred aspect, the invention provides a trivalent polypeptide comprising or essentially consisting of three (preferably identical) amino acid sequences or Nanobodies® chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a trivalent polypeptide comprising or essentially consisting of three (preferably identical) amino acid sequences or Nanobodies® chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a trivalent polypeptide and comprises or essentially consists of three identical amino acid sequences or Nanobodies® chosen from one of SEQ ID NO's: 65 and 76.

The invention also provides a trivalent polypeptide comprising or essentially consisting of three (preferably identical) amino acid sequences or Nanobodies® chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Proline (Pro, P) at position 14, Arginine (Arg, R) at position 19, Leucine (Leu, L) at position 20 and/or Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a trivalent polypeptide and comprises or essentially consists of three identical amino acid sequences or Nanobodies® chosen from one of SEQ ID NO's: 146-153.

In another preferred aspect, the invention provides a trivalent polypeptide comprising or essentially consisting of three (preferably identical) amino acid sequences or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and/or Leucine (Leu, L) at position 108; and in addition Arginine (Arg, R) at position 83, Glutamic acid (Glu, E) at position 85 and/or Glutamine (Gln, Q) at position 105;
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention a trivalent polypeptide comprising or essentially consisting of three (preferably identical) amino acid sequences or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and/or Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino add sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred polypeptides of the invention comprises or essentially consists of three amino acid sequences or Nanobodies® chosen from SEQ ID NO's: 146-149 and 151-153.

In another preferred aspect, the invention provides a trivalent polypeptide comprising or essentially consisting of three (preferably identical) amino acid sequences or Nanobodies® that comprise or essentially consist of SEQ ID NO: 5, in which one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

In another preferred aspect, the invention provides a trivalent polypeptide comprising or essentially consisting of three (preferably identical) amino acid sequences or Nanobodies® that comprise or essentially consist of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp.

In another preferred aspect, the invention provides a trivalent polypeptide comprising or essentially consisting of three (preferably identical) amino acid sequences or Nanobodies® that comprise or essentially consist of SEQ ID NO: 5, in which one or more (such as two, three or four) amino acid residues have been mutated selected from the following: Ala14Pro, Ser19Arg, Ile20Leu and Gln108Leu.

In another preferred aspect, the invention provides a trivalent polypeptide comprising or essentially consisting of three (preferably identical) amino acid sequences or Nanobodies® that comprise or essentially consist of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

In another preferred aspect, the invention provides a trivalent polypeptide comprising or essentially consisting of three (preferably identical) amino acid sequences or Nanobodies® that comprise or essentially consist of SEQ ID NO: 5, in which following amino acid residues have been mutated:

Val5Leu, Ala14Pro, Glu44Gly, Gly78Leu, Ala83Arg, Asp85Glu, Arg105Gln and Gln108Leu;

Ala83Arg, Asp85Glu, Arg105Gln and Gln108Leu; Gly78Leu, Ala83Arg, Asp85Glu and Arg105Gln;

Val5Leu, Ala14Pro, Glu44Gly, Gly78Leu, Ala83Arg, Asp85Glu, Arg105Gln, Gln108Leu and Gly54Asp;

Ala83Arg, Asp85Glu, Arg105Gln, Gln108Leu and Gly54Asp;

Gly78Leu, Ala83Arg, Asp85Glu, Arg105Gln and Gly54Asp;

Gly54Asp;

Ala14Pro, Ser19Arg, Ile20Leu and Gln108Leu;

Ala14Pro, Ser19Arg, Ile20Leu, Gln108Leu and Ala83Arg;

Ala14Pro, Ser19Arg, Ile20Leu, Gln108Leu and Asp85Glu;

Ala14Pro, Ser19Arg, Ile20Leu, Gln108Leu and Arg105Gln;

Ala14Pro, Ser19Arg, Ile20Leu, Gln108Leu, Ala83Arg and Asp85Glu;

Ala14Pro, Ser19Arg, Ile20Leu, Gln108Leu, Ala83Arg and Arg105Gln;

Ala14Pro, Ser19Arg, Ile20Leu, Gln108Leu, Asp85Glu and Arg105Gln; or

Ala14Pro, Ser19Arg, Ile20Leu, Gln108Leu, Ala83Arg, Asp85Glu and Arg105Gln.

A preferred multivalent polypeptide of the invention comprises or essentially consists of three amino add sequences or Nanobodies® with SEQ ID NO: 62. Another preferred multivalent polypeptide of the invention comprises or essentially consists of three amino acid sequences or Nanobodies® with SEQ ID NO: 65. Another preferred multivalent polypeptide of the invention comprises or essentially consists of three amino acid sequences or Nanobodies® with SEQ ID NO: 76. Another preferred multivalent polypeptide of the invention comprises or essentially consists of three amino acid sequences or Nanobodies® with SEQ ID NO: 75. Another preferred multivalent polypeptide of the invention comprises or essentially consists of three amino acid sequences or Nanobodies® with SEQ ID NO: 147. Another preferred multivalent polypeptide of the invention comprises or essentially consists of three amino acid sequences or Nanobodies® with SEQ ID NO: 149. Another preferred multivalent polypeptide of the invention comprises or essentially consists of three amino acid sequences or Nanobodies® with SEQ ID NO: 153.

The invention also provides a trivalent polypeptide as described above in which the Glutamic acid at position 1 has been changed into an Aspartic acid.

In this respect, the invention also provides a trivalent polypeptide comprising or essentially consisting of at least one amino acid sequence or Nanobody® chosen from the following:

a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
   i) the amino acid sequence has a Aspartic acid (Asp, D) at position 1 (said position determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody® chosen from one of SEQ ID NO's: 138-141 and 154-157.

In another preferred aspect, the invention provides a trivalent polypeptide comprising or essentially consisting of at least one amino acid sequence or Nanobody® that comprises or essentially consists of SEQ ID NO: 5, in which the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 62, in which the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 65, in which the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 76, in which the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 75, in which the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 147, in which the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 149, in which the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 153, in which the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 5, in which one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, and wherein the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 5, in which one or more (such as two, three or four) amino acid residues have been mutated selected from the following: Ala14Pro, Ser19Arg, Ile20Leu and Gln108Leu, and wherein the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein the Glutamic acid at position 1 has been changed into Aspartic acid.

In another preferred aspect, the invention provides a trivalent polypeptide comprising or essentially consisting of at least one amino acid sequence or Nanobody® that comprises or essentially consists of SEQ ID NO: 5, in which following amino acid residues have been mutated:
Glu1Asp;
Glu1Asp, Val5Leu, Ala14Pro, Glu44Gly, Gly78Leu, Ala83Arg, Asp85Glu, Arg105Gln and
Gln108Leu;
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln.

In another preferred aspect, the invention provides a trivalent polypeptide chosen from the following polypeptides:
a) SEQ ID NO's: 77-79 and 158;
b) polypeptides that have no more than 3, preferably no more than 2, more preferably no more than 1 amino acid difference with one of SEQ ID NO's: 77-79 and 158, provided that:
i) the amino acid sequences or Nanobodies® encompassed in said polypeptide have a Glutamine (Gln, Q) at position 105, a Leucine (Leu, L) at position 78, an Arginine (Arg, R) at position 83 and/or a Glutamic acid (Glu, E) at position 85 (said positions determined according to Kabat numbering); and
ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

In a preferred aspect, the invention provides a trivalent polypeptide chosen from the following polypeptides:
a) SEQ ID NO is: 77-79 and 158;
b) polypeptides that have no more than 3, preferably no more than 2, more preferably no more than 1 amino acid difference with one of SEQ ID NO's: 77-79 and 158, provided that:
i) the amino acid sequence or Nanobody® encompassed in said polypeptide has a Glutamine (Gln, Q) at position 105, a Leucine (Leu, L) at position 78, an Arginine (Arg, R) at position 83 and a Glutamic acid (Glu, E) at position 85 (said positions determined according to Kabat numbering); and
ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of one of SEQ ID NO's: 77-79 and 158.

In another preferred aspect, the invention provides a trivalent polypeptide chosen from the following polypeptides:
a) SEQ ID NO: 78 and 79;
b) polypeptides that have no more than 3, preferably no more than 2, more preferably no more than 1 amino acid difference with one of SEQ ID NO's: 78 and 79, provided that:
i) the amino acid sequence or Nanobody® encompassed in said polypeptide has an Aspartic acid (Asp, D) at position 54, a Glutamine (Gln, Q) at position 105, a Leucine (Leu, L) at position 78, an Arginine (Arg, R) at position 83 and/or a Glutamic acid (Glu, E) at position 85 (said positions determined according to Kabat numbering); and
ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

In a preferred aspect, the invention provides a trivalent polypeptide chosen from the following polypeptides:

a) SEQ ID NO: 78 and 79; or
b) polypeptides that have no more than 3, preferably no more than 2, more preferably no more than 1 amino acid difference with one of SEQ ID NO's: 78 and 79, provided that:
   i) the amino acid sequence or Nanobody® encompassed in said polypeptide has an Aspartic acid (Asp, D) at position 54, a Glutamine (Gln, Q) at position 105, a Leucine (Leu, L) at position 78, an Arginine (Arg, R) at position 83 and a Glutamic acid (Glu, E) at position 85 (said positions determined according to Kabat numbering); and
   ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

A preferred trivalent polypeptide of the invention comprises or essentially consists of SEQ ID NO: 78. Another preferred trivalent polypeptide of the invention comprises or essentially consists of SEQ ID NO: 79.

In another preferred aspect, the invention provides a trivalent polypeptide chosen from the following polypeptides:
a) SEQ ID NO's: 159-161;
b) polypeptides that have no more than 3, preferably no more than 2, more preferably no more than 1 amino acid difference with one of SEQ ID NO's: 159-161, provided that:
   i) the amino acid sequence or Nanobody® encompassed in said polypeptide has a Proline (Pro, P) at position 14, Arginine (Arg, R) at position 19, Leucine (Leu, L) at position 20 and/or Leucine (Leu, L) at position 108 (said positions determined according to Kabat numbering); and
   ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of one of SEQ ID NO's: 159-161.

In another preferred aspect, the invention provides a trivalent polypeptide chosen from the following polypeptides:
a) SEQ ID NO's: 159-161;
b) polypeptides that have no more than 3, preferably no more than 2, more preferably no more than 1 amino acid difference with one of SEQ ID NO's: 159-161, provided that:
   i) the amino acid sequence or Nanobody® encompassed in said polypeptide has a Praline (Pro, P) at position 14, Arginine (Arg, R) at position 19, Leucine (Leu, L) at position 20 and/or Leucine (Leu, L) at position 108; and in addition Arginine (Arg, R) at position 83, Glutamic acid (Glu, E) at position 85 and/or Glutamine (Gln, Q) at position 105 (said positions determined according to Kabat numbering); and
   ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

In another preferred aspect, the invention provides a trivalent polypeptide chosen from the following polypeptides:
a) SEQ ID NO's: 159-161;
b) polypeptides that have no more than 3, preferably no more than 2, more preferably no more than 1 amino acid difference with one of SEQ ID NO's: 159-161, provided that:
   i) the amino acid sequence or Nanobody® encompassed in said polypeptide has a Proline (Pro, P) at position 14, Arginine (Arg, R) at position 19, Leucine (Leu, L) at position 20 and/or Leucine (Leu, L) at position 108 and in addition Arginine (Arg, R) at position 83, Glutamic acid (Glu, E) at position 85 and/or Glutamine (Gln, Q) at position 105 so that when the polypeptide has no more than 3, preferably no more than 2, more preferably no more than 1 amino acid difference with:
   SEQ ID NO: 159, the amino acid sequence or Nanobody® encompassed in said polypeptide preferably has Arginine (Arg, R) at position 83 and Glutamine (Gln, Q) at position 105;
   SEQ ID NO: 160, the amino acid sequence or Nanobody® encompassed in said polypeptide preferably has Arginine (Arg, R) at position 83, Glutamic add (Glu, E) at position 85 and Glutamine (Gln, Q) at position 105;
   SEQ ID NO: 161, the amino acid sequence or Nanobody® encompassed in said polypeptide preferably has Arginine (Arg, R) at position 83 and Glutamic acid (Glu, E) at position 85;
   (said positions determined according to Kabat numbering); and
   ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of one of SEQ ID NO's: 159-161.

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp.

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three or four) amino acid residues have been mutated selected from the following: Ala14Pro, Ser19Arg, Ile20Leu and Gln108Leu.

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six or seven) amino acid residues have been mutated selected from the following: Ala14Pro, Ser19Arg, Ile20Leu, Ala83Arg, Asp85Glu, Arg105Gln and Gln108Le.

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, following amino acid residues have been mutated:

Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or
Ala14Pro, Ser19Arg, Ile20Leu, Gln108Leu, Ala83Arg, Asp85Glu and Arg105Gln.

In another preferred aspect, the polypeptide of the invention essentially consists of the amino add sequence of SEQ ID NO: 77. In another preferred aspect, the polypeptide of the invention essentially consists of the amino acid sequence of SEQ ID NO: 78. In another preferred aspect, the polypeptide of the invention essentially consists of the amino acid sequence of SEQ ID NO: 79. In another preferred aspect, the polypeptide of the invention essentially consists of one of SEQ ID NO's: 158-161.

During the production of the polypeptides of the invention, a high level of pyro glutamate (pGlu) on the amino terminus was detected by RP-HPLC. Levels of more than 15% pGlu were detected following fermentation and the levels of pGlu were steadily increasing upon storage during stability studies. Such a modification leads to heterogeneity of the final product and needs to be avoided. The control/prevention of pGlu formation is therefore critical to keep therapeutic proteins within their set specifications. Specific liquid formulations and/or storage conditions are needed for proteins with an N-terminal Glutamic acid thus minimizing the formation of pyro-Glutamic acid.

In the present invention, the possibility of pGlu post-translational modification of the N-terminus was eliminated by changing the N-terminal Glutamic acid (E) [HOOC—(CH2) 2—protein] into an Aspartic acid (D) [HOOC—CH2—protein] which lead to increased product stability. Accordingly, the present invention also relates to polypeptides as described above wherein the Glutamic acid at position 1 is changed into an Aspartic acid.

The present invention provides a number of sequence optimized polypeptides that show increased stability upon storage during stability studies. Accordingly, the invention provides a trivalent polypeptide as described above, wherein the first amino acid (Glutamic acid) has been changed into Aspartic acid.

In one aspect, the invention provides a trivalent polypeptide chosen from the following polypeptides:
a) SEQ ID NO's: 142-145 and 162-165;
b) polypeptides that have no more than 3, preferably no more than 2, more preferably no more than 1 amino acid difference with one of SEQ ID NO's: 142-145 and 162-165, provided that:
   i) the first amino acid sequence or Nanobody® encompassed in said polypeptide has an Aspartic acid (Asp, D) at position 1; and
   ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

A preferred trivalent polypeptide of the invention comprises or essentially consists of SEQ ID NO: 142. Another preferred trivalent polypeptide of the invention comprises or essentially consists of SEQ ID NO: 143. Another preferred trivalent polypeptide of the invention comprises or essentially consists of SEQ ID NO: 144. Another preferred trivalent polypeptide of the invention comprises or essentially consists of SEQ ID NO: 145. Another preferred trivalent polypeptide of the invention comprises or essentially consists of one of SEQ ID NO's: 162-165.

In another preferred aspect, the invention provides a trivalent polypeptide comprising or essentially consisting of SEQ ID NO: 53, in which the Glutamic acid at position 1 has been changed into Aspartic acid (Glu1Asp).

In another preferred aspect, the invention provides a trivalent polypeptide comprising or essentially consisting of SEQ ID NO: 77, in which the Glutamic acid at position 1 has been changed into Aspartic acid (Glu1Asp).

In another preferred aspect, the invention provides a trivalent polypeptide comprising or essentially consisting of SEQ ID NO: 78, in which the Glutamic acid at position 1 has been changed into Aspartic acid (Glu1Asp).

In another preferred aspect, the invention provides a trivalent polypeptide comprising or essentially consisting of SEQ ID NO: 79, in which the Glutamic acid at position 1 has been changed into Aspartic acid (Glu1Asp).

In another preferred aspect, the invention provides a trivalent polypeptide comprising or essentially consisting of SEQ ID NO: 158, in which the Glutamic acid at position 1 has been changed into Aspartic acid (Glu1Asp).

In another preferred aspect, the invention provides a trivalent polypeptide comprising or essentially consisting of SEQ ID NO: 159, in which the Glutamic acid at position 1 has been changed into Aspartic acid (Glu1Asp).

In another preferred aspect, the invention provides a trivalent polypeptide comprising or essentially consisting of SEQ ID NO: 160, in which the Glutamic acid at position 1 has been changed into Aspartic acid (Glu1Asp).

In another preferred aspect, the invention provides a trivalent polypeptide comprising or essentially consisting of SEQ ID NO: 161, in which the Glutamic acid at position 1 has been changed into Aspartic acid (Glu1Asp).

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six, seven, eight, nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the Glutamic acid at position 1 has been changed into Aspartic acid (Glu1Asp).

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, and wherein the Glutamic acid at position 1 has been changed into Aspartic acid (Glu1Asp).

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three or four) amino acid residues have been mutated selected from the following: Ala14Pro, Ser19Arg, Ile20Leu and Gln108Leu, and wherein the Glutamic acid at position 1 has been changed into Aspartic acid (Glu1Asp).

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein the Glutamic acid at position 1 has been changed into Aspartic acid (Glu1Asp).

In another preferred aspect, the invention provides a trivalent polypeptide comprising or essentially consisting of SEQ ID NO: 53, in which in at least one (preferably in two, more preferably in all three) Nanobody®/Nanobodies® that form(s) part of SEQ ID NO: 53, following amino acid residues have been mutated:

Glu1Asp
Glu1Asp, Val5Leu, Ala14Pro, Glu44Gly, Gly78Leu, Ala83Arg, Asp85Glu, Arg105Gln and Gln108Leu;
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln.

In another preferred aspect, the polypeptide of the invention essentially consists of the amino acid sequence of SEQ ID NO: 142. In another preferred aspect, the polypeptide of the invention essentially consists of the amino acid sequence of SEQ ID NO: 143. In another preferred aspect, the polypeptide of the invention essentially consists of the amino acid sequence of SEQ ID NO: 144. In another preferred aspect, the polypeptide of the invention essentially consists of the amino acid sequence of SEQ ID NO: 145. In another preferred aspect, the polypeptide of the invention essentially consists of one of SEQ ID NO's: 162-165.

Polypeptides with the amino acid sequences and polypeptide sequences as described above have shown advantageous properties for use as prophylactic, therapeutic and/or pharmacologically active agents such as e.g. improved stability, less immunogenicity, improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for protein F of hRSV and/or improved efficacy and/or potency for neutralizing hRSV.

More in particular, these polypeptides and compounds of the invention can bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) preferably such that they:

bind to protein F of hRSV with a dissociation constant ($K_D$) of 100 nM to 0.1 nM or less, preferably 10 nM to 0.1 nM or less, more preferably 1 nM to 0.1 nM or less;

and/or such that they:

bind to protein F of hRSV with a $k_{on}$-rate of between $10^4$ $M^{-1} S^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more;

and/or such that they:

bind to protein F of hRSV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, more preferably between $5 \times 10^{-3}$ $s^{-1}$ and $10^{-4}$ $s^{-1}$, or lower;

Some preferred IC50 values for binding of the polypeptides of the invention to protein F of hRSV will become clear from the further description and examples herein.

Assays to determine the IC50 include competition assays such as competition ELISA (e.g. competition with Synagis® or its Fab fragment) or more preferably neutralization assays such as the microneutralization assay described by Anderson et al. (1985, J. Clin. Microbiol. 22: 1050-1052), modification of this assay as described in example 6, or a plaque reduction assay as described by Johnson et al. (1997, J. Inf. Dis. 176: 1215-1224), and modifications thereof.

For example, in a competition assay with Synagis®, the polypeptides of the invention may have IC50 values between 1 nM and 100 nM, preferably between 10 nM and 50 nM, or less.

For example, in a microneutralization assay of RSV strain Long (such as e.g. described in Example 6) the polypeptides of the invention may have IC50 values between 10 pM and 1000 pM, preferably between 10 pM and 250 pM, more preferably between 50 pM and 200 pM or less. In a microneutralization assay, the polypeptides of the invention may have IC50 values that are at least the same and preferably better, at least ten times better, preferably twenty times better, more preferably fifty times better, even more preferably sixty, seventy, eighty or more times better compared to the IC50 value obtained with Synagis®.

The invention also relates to a monovalent polypeptide or construct (also referred to as "monovalent polypeptide of the invention" or "monovalent construct of the invention"), comprising or essentially consisting of one amino acid sequence or Nanobody® of the invention. Preferred monovalent constructs of the invention comprise or essentially consist of one of SEQ ID NO's: 60-76, such as one of SEQ ID NO's: 62, 65, 67, 68, 75 and 76, such as e.g. SEQ ID NO's: 65 or 75; one of SEQ ID NO's: 138-141; one of SEQ ID NO's: 146-153; or one of SEQ ID NO's: 154-157. Such a monovalent constructs, as well as the amino acid sequences and Nanobodies® of the invention can be used for the preparation of a polypeptide of the invention, such as e.g. the multivalent polypeptides of the invention described above.

The polypeptides of the invention can generally be prepared by a method which comprises at least the step of suitably linking the amino acid sequence, Nanobody® or monovalent construct of the invention to one or more further amino acid sequences, Nanobodies® or monovalent constructs of the invention, optionally via the one or more suitable linkers, so as to provide the polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent, multiparatopic and/or multispecific amino acids or polypeptides of the invention may comprise at least the steps of linking two or more monovalent amino acid sequences or monovalent constructs of the invention and for example one or more linkers together in a suitable manner. The monovalent constructs (and linkers) can be coupled by any method known in the art and as further described herein. Preferred techniques include the linking of the nucleic acid sequences that encode the monovalent constructs (and linkers) to prepare a genetic construct that expresses the multivalent, multiparatopic and/or multispecific amino acid sequence or polypeptide. Techniques for linking amino acid sequences or nucleic acid sequences will be clear to the skilled person, and reference is again made to the standard handbooks, such as Sambrook et al. and Ausubel et al., mentioned above, as well as the Examples below.

Accordingly, the present invention also relates to the use of an amino acid sequence, a Nanobody® or a monovalent construct of the invention in preparing a multivalent polypeptide of the invention. The method for the preparation of a multivalent polypeptide will comprise the linking of an amino acid sequence, a Nanobody® or a monovalent construct of the invention to at least one further amino acid sequence, Nanobody® or monovalent construct of the invention, optionally via one or more linkers. The amino acid sequence, Nanobody® or monovalent construct is then used as a binding domain or binding unit in providing and/or preparing the multivalent polypeptide comprising two (e.g. in a bivalent polypeptide), three (e.g. in a trivalent polypeptide) or more (e.g. in a multivalent polypeptide) binding units. In this respect, the amino acid sequence, Nanobody® and monovalent construct may be used as a binding domain or binding unit in providing and/or preparing a multivalent and preferably bivalent or trivalent polypeptide of the invention comprising two, three or more binding units. Preferably, the binding domains or binding units are linked via a linker such that the multivalent polypeptide preferably exhibits intramolecular binding compared to intermolecular binding. Also preferably the multivalent polypeptide can simultaneously bind both or all three binding sites on the F protein of RSV.

Accordingly, the present invention also relates to the use of an amino acid sequence or a Nanobody® of the invention (as described above) in preparing a multivalent polypeptide. The method for the preparation of the multivalent polypeptide will comprise the linking of the amino acid sequence or Nanobody® of the invention to at least one further amino acid sequences or Nanobody® of the invention, optionally via one or more linkers.

In a preferred aspect, the present invention relates to the use of an amino acid sequence chosen from the following:
a) SEQ ID NO's: 60-76;
b) amino acid sequences that have no more than 3, preferably no more than 2, more preferably no more than 1 amino acid difference with one of SEQ ID NO's: 60-76, provided that:
  i) the amino acid sequence has a Glutamine (Gln, Q) at position 105 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of one of SEQ ID NO's: 60-76.

In another preferred aspect, the present invention relates to the use of an amino acid sequence chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and/or a Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide. The method for the preparation of the multivalent polypeptide will comprise the linking of said amino acid sequence to at least one further amino acid sequences, optionally via one or more linkers.

In another preferred aspect, the present invention relates to the use of an amino acid sequence chosen from the following:
a) SEQ ID NO's: 62, 65, 67, 68, 75 and 76; or
b) amino acid sequences that have no more than 3, preferably no more than 2, more preferably no more than 1 amino add difference with one of SEQ ID NO's: 62, 65, 67, 68, 75 and 76, provided that:
    i) the amino acid sequence has a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of one of SEQ ID NO: 62, 65, 67, 68, 75 and 76.

In another preferred aspect, the present invention relates to the use of an amino acid sequence chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide. The method for the preparation of the multivalent polypeptide will comprise the linking of said amino acid sequence to at least one further amino acid sequences, optionally via one or more linkers.

In another preferred aspect, the present invention relates to the use of an amino acid sequence chosen from the following:
a) SEQ ID NO's: 65 and 76;
b) amino acid sequences that have no more than 3, preferably no more than 2, more preferably no more than 1 amino add difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of SEQ ID NO: 65. In another preferred aspect, the amino acid sequence used in preparing a multivalent polypeptide comprises or essentially consists of SEQ ID NO: 76.

In a preferred aspect, the present invention relates to the use of an amino acid sequence chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
    i) the amino acid sequence has a Proline (Pro, P) at position 14, Arginine (Arg, R) at position 19, Leucine (Leu, L) at position 20 and/or Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.
in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of one of SEQ ID NO's: 146-153.

In another preferred aspect, the present invention relates to the use of an amino acid sequence chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
    i) the amino acid sequence has a Praline (Pro, P) at position 14, Arginine (Arg, R) at position 19, Leucine (Leu, L) at position 20 and/or Leucine (Leu, L) at position 108; and in addition Arginine (Arg, R) at position 83, Glutamic acid (Glu, E) at position 85 and/or Glutamine (Gln, Q) at position 105 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide. The method for the preparation of the multivalent polypeptide will comprise the linking of said amino acid sequence to at least one further amino acid sequences, optionally via one or more linkers.

In another preferred aspect, the present invention relates to the use of an amino acid sequence chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
   i) the amino acid sequence has a Proline (Pro, P) at position 14, Arginine (Arg, R) at position 19, Leucine (Leu, L) at position 20 and/or Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
      SEQ ID NO: 146, the amino acid sequence preferably has Glutamine (Gln, Q) at position 105;
      SEQ ID NO: 147, the amino acid sequence preferably has Arginine (Arg, R) at position 83 and Glutamine (Gln, Q) at position 105;
      SEQ ID NO: 148, the amino acid sequence preferably has Glutamic acid (Glu, E) at position 85 and Glutamine (Gln, Q) at position 105;
      SEQ ID NO: 149, the amino acid sequence preferably has Arginine (Arg, R) at position 83, Glutamic acid (Glu, E) at position 85 and Glutamine (Gln, Q) at position 105;
      SEQ ID NO: 151, the amino acid sequence preferably has Arginine (Arg, R) at position 83;
      SEQ ID NO: 152, the amino acid sequence preferably has Glutamic acid (Glu, E) at position 85;
      SEQ ID NO: 153, the amino acid sequence preferably has Arginine (Arg, R) at position 83 and Glutamic acid (Glu, E) at position 85;
      (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of one of SEQ ID NO's: 146-149 and 151-153.

In another preferred aspect, the present invention relates to the use of an amino acid sequence that comprises or essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, in preparing a multivalent polypeptide.

In another preferred aspect, the present invention relates to the use of an amino acid sequence that comprises or essentially consists of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, in preparing a multivalent polypeptide.

In another preferred aspect, the present invention relates to the use of an amino acid sequence that comprises or essentially consists of SEQ ID NO: 5, in which one or more (such as two, three or four) amino acid residues have been mutated selected from the following: Ala14Pro, Ser19Arg, Ile20Leu and Gln108Leu, in preparing a multivalent polypeptide.

In another preferred aspect, the present invention relates to the use of an amino acid sequence that comprises or essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, in preparing a multivalent polypeptide.

In another preferred aspect, the present invention relates to the use of an amino acid sequence that comprises or essentially consists of SEQ ID NO: 5, in which following amino acid residues have been mutated:
   Val5Leu, Ala14Pro, Glu44Gly, Gly78Leu, Ala83Arg, Asp85Glu, Arg105Gln and Gln108Leu;
   Ala83Arg, Asp85Glu, Arg105Gln and Gln108Leu;
   Gly78Leu, Ala83Arg, Asp85Glu and Arg105Gln;
   Val5Leu, Ala14Pro, Glu44Gly, Gly78Leu, Ala83Arg, Asp85Glu, Arg105Gln, Gln108Leu and Gly54Asp;
   Ala83Arg, Asp85Glu, Arg105Gln, Gln108Leu and Gly54Asp;
   Gly78Leu, Ala83Arg, Asp85Glu, Arg105Gln and Gly54Asp;
   Gly54Asp;
   Ala14Pro, Ser19Arg, Ile20Leu and Gln108Leu;
   Ala14Pro, Ser19Arg, Ile20Leu, Gln108Leu and Ala83Arg;
   Ala14Pro, Ser19Arg, Ile20Leu, Gln108Leu and Asp85Glu;
   Ala14Pro, Ser19Arg, Ile20Leu, Gln108Leu and Arg105Gln;
   Ala14Pro, Ser19Arg, Ile20Leu, Gln108Leu, Ala83Arg and Asp85Glu;
   Ala14Pro, Ser19Arg, Ile20Leu, Gln108Leu, Ala83Arg and Arg105Gln;
   Ala14Pro, Ser19Arg, Ile20Leu, Gln108Leu, Asp85Glu and Arg105Gln; or
   Ala14Pro, Ser19Arg, Ile20Leu, Gln108Leu, Ala83Arg, Asp85Glu and Arg105Gln,
in preparing a multivalent polypeptide.

In another preferred aspect, the present invention relates to the use of an amino acid sequence chosen from the above wherein the amino acid (Glutamic acid) at position I has been changed into Aspartic acid, in preparing a multivalent polypeptide.

In this respect, the present invention relates to the use of an amino acid sequence chosen from the following:
a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
   i) the amino acid sequence has a Aspartic acid (Asp, D) at position 1 (said position determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of SEQ ID NO: 138. In another preferred aspect, the amino acid sequence used in preparing a multivalent polypeptide comprises or essentially consists of SEQ ID NO: 139. In another preferred aspect, the amino acid sequence used in preparing a multivalent polypeptide comprises or essentially consists of SEQ ID NO: 140. In another preferred aspect, the amino acid sequence used in preparing a multivalent polypeptide comprises or essentially consists of SEQ ID NO: 141. In another preferred aspect, the amino acid sequence used in preparing a multivalent polypeptide comprises or essentially consists of one of SEQ ID NO's: 154-157.

In another preferred aspect, the present invention relates to the use of an amino acid sequence that comprises or essentially consists of SEQ ID NO: 5, in which Glutamic acid at position 1 has been changed into Aspartic acid, in preparing a multivalent polypeptide.

In another preferred aspect, the present invention relates to the use of an amino acid sequence that comprises or essentially consists of SEQ ID NO: 62, in which Glutamic acid at position 1 has been changed into Aspartic acid, in preparing a multivalent polypeptide.

In another preferred aspect, the present invention relates to the use of an amino acid sequence that comprises or essentially consists of SEQ ID NO: 65, in which Glutamic acid at position 1 has been changed into Aspartic acid, in preparing a multivalent polypeptide.

In another preferred aspect, the present invention relates to the use of an amino acid sequence that comprises or essentially consists of SEQ ID NO: 76, in which Glutamic acid at position 1 has been changed into Aspartic acid, in preparing a multivalent polypeptide.

In another preferred aspect, the present invention relates to the use of an amino acid sequence that comprises or essentially consists of SEQ ID NO: 75, in which Glutamic acid at position 1 has been changed into Aspartic acid, in preparing a multivalent polypeptide.

In another preferred aspect, the present invention relates to the use of an amino acid sequence that comprises or essentially consists of SEQ ID NO: 147, in which Glutamic acid at position 1 has been changed into Aspartic acid, in preparing a multivalent polypeptide.

In another preferred aspect, the present invention relates to the use of an amino acid sequence that comprises or essentially consists of SEQ ID NO: 149, in which Glutamic acid at position 1 has been changed into Aspartic acid, in preparing a multivalent polypeptide.

In another preferred aspect, the present invention relates to the use of an amino acid sequence that comprises or essentially consists of SEQ ID NO: 153, in which Glutamic acid at position 1 has been changed into Aspartic acid, in preparing a multivalent polypeptide.

In another preferred aspect, the present invention relates to the use of an amino acid sequence that comprises or essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein Glutamic acid at position 1 has been changed into Aspartic acid, in preparing a multivalent polypeptide.

In another preferred aspect, the present invention relates to the use of an amino acid sequence that comprises or essentially consists of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, and wherein Glutamic acid at position 1 has been changed into Aspartic acid, in preparing a multivalent polypeptide.

In another preferred aspect, the present invention relates to the use of an amino acid sequence that comprises or essentially consists of SEQ ID NO: 5, in which one or more (such as two, three or four) amino acid residues have been mutated selected from the following: Ala14Pro, Ser19Arg, Ile20Leu and Gln108Leu, and wherein Glutamic acid at position 1 has been changed into Aspartic acid, in preparing a multivalent polypeptide.

In another preferred aspect, the present invention relates to the use of an amino acid sequence that comprises or essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein Glutamic acid at position 1 has been changed into Aspartic acid, in preparing a multivalent polypeptide.

In another preferred aspect, the present invention relates to the use of an amino acid sequence that comprises or essentially consists of SEQ ID NO: 5, in which following amino acid residues have been mutated:

Glu1Asp;
Glu1Asp, Val5Leu, Ala14Pro, Glu44Gly, Gly78Leu, Ala83Arg, Asp85Glu, Arg105Gln and Gln108Leu;
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln, in preparing a multivalent polypeptide.

The present invention also relates to the use of two amino acid sequences and/or Nanobodies® of the invention (as described above) in preparing a bivalent polypeptide. The method for the preparation of the bivalent polypeptide will comprise the linking of the amino acid sequences and/or Nanobodies® of the invention, optionally via a linker.

Accordingly, in a preferred aspect, the present invention relates to the use of two (preferably identical) amino acid sequences chosen from the following:
  a) SEQ ID NO's: 60-76;
  b) amino acid sequences that have no more than 3, preferably no more than 2, more preferably no more than 1 amino acid difference with one of SEQ ID NO's: 60-76, provided that:
    i) the amino acid sequence has a Glutamine (Gln, Q) at position 105 (said position determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide. The method for the preparation of the bivalent polypeptide will comprise the linking of said amino acid sequences to each other, optionally via a linker.

In a preferred aspect, the two amino acid sequences used in preparing the bivalent polypeptide comprise or essentially consist of one of SEQ ID NO's: 60-76.

In another preferred aspect, the present invention relates to the use of two (preferably identical) amino acid sequences chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and/or a Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide. The method for the preparation of the bivalent polypeptide will comprise the linking of said amino acid sequences to each other, optionally via a linker.

In another preferred aspect, the present invention relates to the use of two (preferably identical) amino acid sequences chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide. The method for the preparation of the bivalent polypeptide will comprise the linking of said amino acid sequences to each other, optionally via a linker.

In a preferred aspect, the two amino acid sequences used in preparing a bivalent polypeptide comprise or essentially consist of one of SEQ ID NO's: 62, 65, 67, 68, 75 and 76.

In another preferred aspect, the present invention relates to the use of two (preferably identical) amino acid sequences chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide. The method for the preparation of the bivalent polypeptide will comprise the linking of said amino acid sequences to each other, optionally via a linker.

In another preferred aspect, the present invention relates to the use of two (preferably identical) amino acid sequences chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide. The method for the preparation of the bivalent polypeptide will comprise the linking of said amino acid sequences to each other, optionally via a linker.

In another preferred aspect, the present invention relates to the use of two (preferably identical) amino acid sequences chosen from the following:
  a) SEQ ID NO's: 146-153;
  b) amino acid sequences that have no more than 3, preferably no more than 2, more preferably no more than 1 amino acid difference with one of SEQ ID NO's: 146-153, provided that:
    i) the amino acid sequence has a Proline (Pro, P) at position 14, Arginine (Arg, R) at position 19, Leucine (Leu, L) at position 20 and/or Leucine (Leu, L) at position 108 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

in preparing a bivalent polypeptide. The method for the preparation of the bivalent polypeptide will comprise the linking of said amino acid sequence to at least one further amino acid sequence, optionally via one or more linkers.

In a preferred aspect, the amino acid sequences used in preparing a bivalent polypeptide comprises or essentially consists of one of SEQ ID NO's: 146-153.

In another preferred aspect, the present invention relates to the use of two (preferably identical) amino acid sequences chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Praline (Pro, P) at position 14, Arginine (Arg, R) at position 19, Leucine (Leu, L) at position 20 and/or Leucine (Leu, L) at position 108; and in addition Arginine (Arg, R) at position 83, Glutamic acid (Glu, E) at position 85 and/or Glutamine (Girt, Q) at position 105 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a bivalent polypeptide. The method for the preparation of the bivalent polypeptide will comprise the linking of said amino add sequence to at least one further amino acid sequence, optionally via one or more linkers.

In another preferred aspect, the present invention relates to the use of two (preferably identical) amino acid sequences chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and/or Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

in preparing a bivalent polypeptide. The method for the preparation of the bivalent polypeptide will comprise the linking of said amino acid sequence to at least one further amino acid sequences, optionally via one or more linkers.

In a preferred aspect, the amino acid sequences used in preparing a bivalent polypeptide comprises or essentially consists of one of SEQ ID NO's: 146-149 and 151-153.

In another preferred aspect, the present invention relates to the use of two (preferably identical) amino acid sequences that comprises or essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, in preparing a bivalent polypeptide.

In another preferred aspect, the present invention relates to the use of two (preferably identical) amino acid sequences that comprises or essentially consists of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, in preparing a bivalent polypeptide.

In another preferred aspect, the present invention relates to the use of two (preferably identical) amino acid sequences that comprises or essentially consists of SEQ ID NO: 5, in which one or more (such as two, three or four) amino acid residues have been mutated selected from the following: Ala14Pro, Ser19Arg, Ile20Leu and Gln108Leu, in preparing a bivalent polypeptide.

In another preferred aspect, the present invention relates to the use of two (preferably identical) amino acid sequences that comprises or essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, in preparing a bivalent polypeptide.

In another preferred aspect, the present invention relates to the use of two (preferably identical) amino acid sequences that comprises or essentially consists of SEQ ID NO: 5, in which following amino acid residues have been mutated:

Val5Leu, Ala14Pro, Glu44Gly, Gly78Leu, Ala83Arg, Asp85Glu, Arg105Gln and Gln108Leu;

Ala83Arg, Asp85Glu, Arg105Gln and Gln108Leu;

Gly78Leu, Ala83Arg, Asp85Glu and Arg105Gln;

Val5Leu, Ala14Pro, Glu44Gly, Gly78Leu, Ala83Arg, Asp85Glu, Arg105Gln, Gln108Leu and Gly54Asp;

Ala83Arg, Asp85Glu, Arg105Gln, Gln108Leu and Gly54Asp;

Gly78Leu, Ala83Arg, Asp85Glu, Arg105Gln and Gly54Asp; or

Gly54Asp;

Ala14Pro, Ser19Arg, Ile20Leu and Gln108Leu;

Ala14Pro, Ser19Arg, Ile20Leu, Gln108Leu and Ala83Arg;

Ala14Pro, Ser19Arg, Ile20Leu, Gln108Leu and Asp85Glu;

Ala14Pro, Ser19Arg, Ile20Leu, Gln108Leu and Arg105Gln;

Ala14Pro, Ser19Arg, Ile20Leu, Gln108Leu, Ala83Arg and Asp85Glu;

Ala14Pro, Ser19Arg, Ile20Leu, Gln108Leu, Ala83Arg and Arg105Gln;

Ala14Pro, Ser19Arg, Ile20Leu, Gln108Leu, Asp85Glu and Arg105Gln; or

Ala14Pro, Ser19Arg, Ile20Leu, Gln108Leu, Ala83Arg, Asp85Glu and Arg105Gln, in preparing a bivalent polypeptide.

In another preferred aspect, the present invention relates to the use of an amino acid sequence chosen from the above wherein the amino acid (Glutamic acid) at position 1 has been changed into Aspartic acid, in preparing a bivalent polypeptide.

In this respect, the present invention relates to the use of an amino acid sequence chosen from the following:

a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
   i) the amino acid sequence has a Aspartic acid (Asp, D) at position 1 (said position determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a bivalent polypeptide. The method for the preparation of the bivalent polypeptide will comprise the linking of said amino acid sequence to at least one further amino acid sequences, optionally via one or more linkers.

In a preferred aspect, the amino acid sequence used in preparing a bivalent polypeptide comprises or essentially consists of SEQ ID NO: 138. In another preferred aspect, the amino acid sequence used in preparing a bivalent polypeptide comprises or essentially consists of SEQ ID NO: 139. In another preferred aspect, the amino acid sequence used in preparing a bivalent polypeptide comprises or essentially consists of SEQ ID NO: 140. In another preferred aspect, the amino acid sequence used in preparing a bivalent polypeptide comprises or essentially consists of SEQ ID NO: 141. In another preferred aspect, the amino acid sequence used in preparing a bivalent polypeptide comprises or essentially consists of SEQ ID NO: 154-157.

In another preferred aspect, the present invention relates to the use of an amino acid sequence that comprises or essentially consists of SEQ ID NO: 5, in which Glutamic acid at position I has been changed into Aspartic acid, in preparing a bivalent polypeptide.

In another preferred aspect, the present invention relates to the use of an amino acid sequence that comprises or essentially consists of SEQ ID NO: 62, in which Glutamic acid at position 1 has been changed into Aspartic acid, in preparing a bivalent polypeptide.

In another preferred aspect, the present invention relates to the use of an amino acid sequence that comprises or essentially consists of SEQ ID NO: 65, in which Glutamic acid at position 1 has been changed into Aspartic acid, in preparing a bivalent polypeptide.

In another preferred aspect, the present invention relates to the use of an amino acid sequence that comprises or essentially consists of SEQ ID NO: 76, in which Glutamic acid at position 1 has been changed into Aspartic acid, in preparing a bivalent polypeptide.

In another preferred aspect, the present invention relates to the use of an amino acid sequence that comprises or essentially consists of SEQ ID NO: 75, in which Glutamic acid at position 1 has been changed into Aspartic acid, in preparing a bivalent polypeptide.

In another preferred aspect, the present invention relates to the use of an amino acid sequence that comprises or essentially consists of SEQ ID NO: 147, in which Glutamic acid at position 1 has been changed into Aspartic acid, in preparing a bivalent polypeptide.

In another preferred aspect, the present invention relates to the use of an amino acid sequence that comprises or essentially consists of SEQ ID NO: 149, in which Glutamic acid at position 1 has been changed into Aspartic acid, in preparing a bivalent polypeptide.

In another preferred aspect, the present invention relates to the use of an amino acid sequence that comprises or essentially consists of SEQ ID NO: 153, in which Glutamic acid at position 1 has been changed into Aspartic acid, in preparing a bivalent polypeptide.

In another preferred aspect, the present invention relates to the use of an amino acid sequence that comprises or essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein Glutamic add at position 1 has been changed into Aspartic acid, in preparing a bivalent polypeptide.

In another preferred aspect, the present invention relates to the use of an amino acid sequence that comprises or essentially consists of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Gln, Gln108Leu and Gly54Asp, and wherein Glutamic acid at position 1 has been changed into Aspartic acid, in preparing a bivalent polypeptide.

In another preferred aspect, the present invention relates to the use of an amino acid sequence that comprises or essentially consists of SEQ ID NO: 5, in which one or more (such as two, three or four) amino acid residues have been mutated selected from the following: Ala14Pro, Ser19Arg, Ile20Leu and Gln108Leu, and wherein Glutamic acid at position 1 has been changed into Aspartic acid, in preparing a bivalent polypeptide.

In another preferred aspect, the present invention relates to the use of an amino acid sequence that comprises or essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein Glutamic acid at position 1 has been changed into Aspartic acid, in preparing a bivalent polypeptide.

In another preferred aspect, the present invention relates to the use of an amino acid sequence that comprises or essentially consists of SEQ ID NO: 5, in which following amino acid residues have been mutated:
Glu1Asp;
Glu1Asp, Val5Leu, Ala14Pro, Glu44Gly, Gly78Leu, Ala83Arg, Asp85Glu, Arg105Gln and Gln108Leu;
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln,
in preparing a bivalent polypeptide.

The present invention also relates to the use of three amino acid sequences and/or Nanobodies® of the invention (as described above) in preparing a trivalent polypeptide. The method for the preparation of the trivalent polypeptide will comprise the linking of the amino acid sequences and/or Nanobodies® of the invention, optionally via one or two linkers.

In a preferred aspect, the present invention relates to the use of three (preferably identical) amino acid sequences chosen from the following:
a) SEQ ID NO's: 50-76;
b) amino acid sequences that have no more than 3, preferably no more than 2, more preferably no more than 1 amino acid difference with one of SEQ ID NO's: 60-76, provided that:
i) the amino acid sequence has a Glutamine (Gln, Q) at position 105 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide. The method for the preparation of the trivalent polypeptide will comprise the linking of said amino acid sequences to each other, optionally via one or two linkers.

In a preferred aspect, the three amino acid sequences used in preparing the trivalent polypeptide comprise or essentially consist of one of SEQ ID NO's: 60-76.

In another preferred aspect, the present invention relates to the use of three (preferably identical) amino acid sequences chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
i) the amino acid sequence has a Glutamine (Gln, Q) at position 105, a Leucine (Leu, L) at position 78 and/or a Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide. The method for the preparation of the trivalent polypeptide will comprise the linking of said amino acid sequences to each other, optionally via one or two linkers.

In another preferred aspect, the present invention relates to the use of three (preferably identical) amino acid sequences chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID N0's: 62, 65, 67, 68, 75 and 76, provided that:
i) the amino acid sequence has a Glutamine (Gln, Q) at position 105, a Leucine (Leu, L) at position 78 and an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide. The method for the preparation of the trivalent polypeptide will comprise the linking of said amino acid sequence to each other, optionally via one or two linkers.

In a preferred aspect, the three amino acid sequences used in preparing the trivalent polypeptide comprise or essentially consist of one of SEQ ID NO's: 62, 65, 67, 68, 75 and 76.

In another preferred aspect, the present invention relates to the use of three (preferably identical) amino acid sequences chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:

i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide. The method for the preparation of the trivalent polypeptide will comprise the linking of said amino acid sequences to each other, optionally via one or two linkers.

In another preferred aspect, the present invention relates to the use of three (preferably identical) amino acid sequences chosen from the following:

a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide. The method for the preparation of the trivalent polypeptide will comprise the linking of said amino add sequences to each other, optionally via one or two linkers.

In a preferred aspect, the three amino acid sequences used in preparing the trivalent polypeptide comprise or essentially consist of SEQ ID NO: 65. In another preferred aspect, the three amino acid sequences used in preparing the trivalent polypeptide comprise or essentially consist of SEQ ID NO: 76.

In another preferred aspect, the present invention relates to the use of three (preferably identical) amino acid sequences chosen from the following:

a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Praline (Pro, P) at position 14, Arginine (Arg, R) at position 19, Leucine (Leu, L) at position 20 and/or Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

in preparing a trivalent polypeptide. The method for the preparation of the trivalent polypeptide will comprise the linking of said amino acid sequence to at least one further amino acid sequence, optionally via one or two linkers.

In a preferred aspect, the amino acid sequences used in preparing a trivalent polypeptide comprise or essentially consist of one of SEQ ID NO's: 146-153.

In another preferred aspect, the present invention relates to the use of three (preferably identical) amino acid sequences chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and/or Leucine (Leu, L) at position 108; and in addition Arginine (Arg, R) at position 83, Glutamic acid (Glu, E) at position 85 and/or Glutamine (Gln, Q) at position 105 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide. The method for the preparation of the trivalent polypeptide will comprise the linking of said amino acid sequence to at least one further amino acid sequence, optionally via one or two linkers.

In another preferred aspect, the present invention relates to the use of three (preferably identical) amino acid sequences chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and/or Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;

SEQ ID NO: 153, the amino acid sequence preferably has Arginine (Arg, R) at position 83 and Glutamic acid (Glu, E) at position 85;
(said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide. The method for the preparation of the trivalent polypeptide will comprise the linking of said amino acid sequence to at least one further amino acid sequence, optionally via one or two linkers.

In a preferred aspect, the amino acid sequences used in preparing a trivalent polypeptide comprises or essentially consists of one of SEQ ID NO's: 146-149 and 151-153.

In another preferred aspect, the present invention relates to the use of three (preferably identical) amino acid sequences that comprises or essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19Arg, Ile20Leu, Glu44Gly, Ala74Ser, Gly78Leu, Ala83Arg, Asp85Glu, Arg105Gln, Gln108Leu and Gly54Asp, in preparing a trivalent polypeptide.

In another preferred aspect, the present invention relates to the use of three (preferably identical) amino acid sequences that comprises or essentially consists of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, in preparing a trivalent polypeptide.

In another preferred aspect, the present invention relates to the use of three (preferably identical) amino acid sequences that comprises or essentially consists of SEQ ID NO: 5, in which one or more (such as two, three or four) amino acid residues have been mutated selected from the following: Ala14Pro, Ser19Arg, Ile20Leu and Gln108Leu, in preparing a trivalent polypeptide.

In another preferred aspect, the present invention relates to the use of three (preferably identical) amino acid sequences that comprises or essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, in preparing a trivalent polypeptide.

In another preferred aspect, the present invention relates to the use of three (preferably identical) amino acid sequences that comprises or essentially consists of SEQ ID NO: 5, in which following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln;
Ala14Pro, Ser19Arg, Ile20Leu, Gln108Leu, Ala83Arg, Asp85Glu and Arg105Gln,
in preparing a trivalent polypeptide.

In another preferred aspect, the present invention relates to the use of SEQ ID NO: 62 in preparing SEQ ID NO: 77. The method for the preparation of the multivalent polypeptide will comprise the linking of an amino acid sequence with SEQ ID NO: 62 to at least two further amino acid sequences with SEQ ID NO: 62, via a 15GS (SEQ ID NO: 128) linker.

In another preferred aspect, the present invention relates to the use of SEQ ID NO: 65 in preparing SEQ ID NO: 78. The method for the preparation of the multivalent polypeptide will comprise the linking of an amino acid sequence with SEQ ID NO: 65 to at least two further amino acid sequences with SEQ ID NO: 65, via a 15GS (SEQ ID NO: 128) linker.

In another preferred aspect, the present invention relates to the use of SEQ ID NO: 76 in preparing SEQ ID NO: 79. The method for the preparation of the multivalent polypeptide will comprise the linking of an amino acid sequence with SEQ ID NO: 76 to at least two further amino acid sequences with SEQ ID NO: 76, via a 15GS (SEQ ID NO: 128) linker.

In another preferred aspect, the present invention relates to the use of SEQ ID NO: 75 in preparing SEQ ID NO: 158. The method for the preparation of the multivalent polypeptide will comprise the linking of an amino acid sequence with SEQ ID NO: 75 to at least two further amino acid sequences with SEQ ID NO: 75, via a 15GS (SEQ ID NO: 128) linker.

In another preferred aspect, the present invention relates to the use of SEQ ID NO: 147 in preparing SEQ ID NO: 159. The method for the preparation of the multivalent polypeptide will comprise the linking of an amino acid sequence with SEQ ID NO: 147 to at least two further amino acid sequences with SEQ ID NO: 147, via a 15GS (SEQ ID NO: 128) linker.

In another preferred aspect, the present invention relates to the use of SEQ ID NO: 149 in preparing SEQ ID NO: 160. The method for the preparation of the multivalent polypeptide will comprise the linking of an amino acid sequence with SEQ ID NO: 149 to at least two further amino acid sequences with SEQ ID NO: 149, via a 1505 (SEQ ID NO: 128) linker.

In another preferred aspect, the present invention relates to the use of SEQ ID NO: 153 in preparing SEQ ID NO: 161. The method for the preparation of the multivalent polypeptide will comprise the linking of an amino acid sequence with SEQ ID NO: 153 to at least two further amino acid sequences with SEQ ID NO: 153, via a 15GS (SEQ ID NO: 128) linker.

In another preferred aspect, the present invention relates to the use of an amino acid sequence chosen from the above wherein the amino acid (Glutamic acid) at position 1 has been changed into Aspartic acid, in preparing a trivalent polypeptide.

In this respect, the present invention relates to the use of an amino acid sequence chosen from the following:
a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
  i) the amino acid sequence has a Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide. The method for the preparation of the trivalent polypeptide will comprise the linking of said amino acid sequence to at least two further amino acid sequences, optionally via one or more linkers.

In a preferred aspect, the amino acid sequence used in preparing a trivalent polypeptide comprises or essentially consists of SEQ ID NO: 138. In another preferred aspect, the amino acid sequence used in preparing a trivalent polypeptide comprises or essentially consists of SEQ ID NO: 139. In another preferred aspect, the amino acid sequence used in preparing a trivalent polypeptide comprises or essentially consists of SEQ ID NO: 140. In another preferred aspect, the amino acid sequence used in preparing a trivalent polypeptide comprises or essentially consists of SEQ ID NO: 141. In another preferred aspect, the amino acid sequence used in preparing a trivalent polypeptide comprises or essentially consists of one of SEQ ID NO's: 154-157.

In another preferred aspect, the present invention relates to the use of an amino acid sequence that comprises or essentially consists of SEQ ID NO: 5, in which Glutamic acid at position 1 has been changed into Aspartic acid, in preparing a trivalent polypeptide.

In another preferred aspect, the present invention relates to the use of an amino acid sequence that comprises or essentially consists of SEQ ID NO: 62, in which Glutamic acid at position 1 has been changed into Aspartic acid, in preparing a trivalent polypeptide.

In another preferred aspect, the present invention relates to the use of an amino acid sequence that comprises or essentially consists of SEQ ID NO: 65, in which Glutamic acid at position 1 has been changed into Aspartic acid, in preparing a trivalent polypeptide.

In another preferred aspect, the present invention relates to the use of an amino acid sequence that comprises or essentially consists of SEQ ID NO: 76, in which Glutamic acid at position 1 has been changed into Aspartic acid, in preparing a trivalent polypeptide.

In another preferred aspect, the present invention relates to the use of an amino acid sequence that comprises or essentially consists of SEQ ID NO: 75, in which Glutamic acid at position 1 has been changed into Aspartic acid, in preparing a trivalent polypeptide.

In another preferred aspect, the present invention relates to the use of an amino acid sequence that comprises or essentially consists of SEQ ID NO: 147, in which Glutamic acid at position 1 has been changed into Aspartic acid, in preparing a trivalent polypeptide.

In another preferred aspect, the present invention relates to the use of an amino acid sequence that comprises or essentially consists of SEQ ID NO: 149, in which Glutamic acid at position 1 has been changed into Aspartic acid, in preparing a trivalent polypeptide.

In another preferred aspect, the present invention relates to the use of an amino acid sequence that comprises or essentially consists of SEQ ID NO: 153, in which Glutamic acid at position 1 has been changed into Aspartic acid, in preparing a trivalent polypeptide.

In another preferred aspect, the present invention relates to the use of an amino acid sequence that comprises or essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein Glutamic acid at position 1 has been changed into Aspartic acid, in preparing a trivalent polypeptide.

In another preferred aspect, the present invention relates to the use of an amino acid sequence that comprises or essentially consists of SEQ ID NO: 5, in which one or more (such as two, three, four, five, six, seven, eight or nine) amino acid residues have been mutated selected from the following: Val5Leu, Ala14Pro, Glu44Gly, Gly78Leu, Ala83Arg, Asp85Glu, Arg105Gln, Gln108Leu and Gly54Asp, and wherein Glutamic acid at position 1 has been changed into Aspartic acid, in preparing a trivalent polypeptide.

In another preferred aspect, the present invention relates to the use of an amino acid sequence that comprises or essentially consists of SEQ ID NO: 5, in which one or more (such as two, three or four) amino acid residues have been mutated selected from the following: Ala14Pro, Ser19Arg, Ile20Leu and Gln108Leu, and wherein Glutamic acid at position 1 has been changed into Aspartic acid, in preparing a trivalent polypeptide.

In another preferred aspect, the present invention relates to the use of an amino acid sequence that comprises or essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein Glutamic acid at position 1 has been changed into Aspartic acid, in preparing a trivalent polypeptide.

In another preferred aspect, the present invention relates to the use of an amino acid sequence that comprises or essentially consists of SEQ ID NO: 5, in which following amino acid residues have been mutated:
  Glu1Asp;
  Glu1Asp, Val5Leu, Ala14Pro, Glu44Gly, Gly78Leu, Ala83Arg, Asp85Glu, Arg105Gln and Gln108Leu;
  Glu1Asp, Ala83Arg, Asp85Glu, Arg105Gln and Gln108Leu;
  Glu1Asp, Gly78Leu, Ala83Arg, Asp85Glu and Arg105Gln;
  Glu1Asp, Val5Leu, Ala14Pro, Glu44Gly, Gly78Leu, Ala83Arg, Asp85Glu, Arg105Gln, Gln108Leu and Gly54Asp;
  Glu1Asp, Ala83Arg, Asp85Glu, Arg105Gln, Gln108Leu and Gly54Asp;
  Glu1Asp, Gly78Leu, Ala83Arg, Asp85Glu, Arg105Gln and Gly54Asp;
  Glu1Asp and Gly54Asp;
  Glu1Asp, Ala14Pro, Ser19Arg, Ile20Leu and Gln108Leu;
  Glu1Asp, Ala14Pro, Ser19Arg, Ile20Leu, Gln108Leu and Ala83Arg;
  Glu1Asp, Ala14Pro, Ser19Arg, Ile20Leu, Gln108Leu and Asp85Glu;
  Glu1Asp, Ala14Pro, Ser19Arg, Ile20Leu, Gln108Leu and Arg105Gln;
  Glu1Asp, Ala14Pro, Ser19Arg, Ile20Leu, Gln108Leu, Ala83Arg and Asp85Glu;

Glu1Asp, Ala14Pro, Ser19Arg, Ile20Leu, Gln108Leu, Ala83Arg and Arg105Gln;

Glu1Asp, Ala14Pro, Ser19Arg, Ile20Leu, Gln108Leu, Asp85Glu and Arg105Gln; or

Glu1Asp, Ala14Pro, Ser19Arg, Ile20Leu, Gln108Leu, Ala83Arg, Asp85Glu and Arg105Gln, in preparing a trivalent polypeptide.

In another preferred aspect, the present invention relates to the use of SEQ ID NO: 138 in preparing SEQ ID NO: 142. The method for the preparation of the multivalent polypeptide will comprise the linking of an amino acid sequence with SEQ ID NO: 138 to at least two further amino acid sequences (preferably SEQ ID NO: 5), via a 15GS (SEQ ID NO: 128) linker.

In another preferred aspect, the present invention relates to the use of SEQ ID NO: 139 in preparing SEQ ID NO: 143. The method for the preparation of the multivalent polypeptide will comprise the linking of an amino acid sequence with SEQ ID NO: 139 to at least two further amino acid sequences (preferably SEQ ID NO: 62), via a 15GS (SEQ ID NO: 128) linker.

In another preferred aspect, the present invention relates to the use of SEQ ID NO: 140 in preparing SEQ ID NO: 144. The method for the preparation of the multivalent polypeptide will comprise the linking of an amino acid sequence with SEQ ID NO: 140 to at least two further amino acid sequences (preferably SEQ ID NO: 65), via a 15GS (SEQ ID NO: 128) linker.

In another preferred aspect, the present invention relates to the use of SEQ ID NO: 154 in preparing SEQ ID NO: 162. The method for the preparation of the multivalent polypeptide will comprise the linking of an amino acid sequence with SEQ ID NO: 154 to at least two further amino acid sequences (preferably SEQ ID NO: 75), via a 15GS (SEQ ID NO: 128) linker.

In another preferred aspect, the present invention relates to the use of SEQ ID NO: 155 in preparing SEQ ID NO: 163. The method for the preparation of the multivalent polypeptide will comprise the linking of an amino acid sequence with SEQ ID NO: 155 to at least two further amino acid sequences (preferably SEQ ID NO: 147), via a 15GS (SEQ ID NO: 128) linker.

In another preferred aspect, the present invention relates to the use of SEQ ID NO: 156 in preparing SEQ ID NO: 164. The method for the preparation of the multivalent polypeptide will comprise the linking of an amino acid sequence with SEQ ID NO: 156 to at least two further amino acid sequences (preferably SEQ ID NO: 149), via a 15GS (SEQ ID NO: 128) linker.

In another preferred aspect, the present invention relates to the use of SEQ ID NO: 157 in preparing SEQ ID NO: 165. The method for the preparation of the multivalent polypeptide will comprise the linking of an amino acid sequence with SEQ ID NO: 157 to at least two further amino acid sequences (preferably SEQ ID NO: 153), via a 15GS (SEQ ID NO: 128) linker.

Polypeptides of the invention that contain at least two amino acid sequences and/or Nanobodies®, in which at least one amino acid sequence or Nanobody® is directed against a first antigen (i.e. against protein F of hRSV) and at least one amino acid sequence or Nanobody® is directed against a second antigen (i.e. different from protein F of hRSV), will also be referred to as "multispecific" polypeptides of the invention, and the amino acid sequences or Nanobodies® present in such polypeptides will also be referred to herein as being in a "multispecific format". Thus, for example, a "bispecific" polypeptide of the invention is a polypeptide that comprises at least one amino acid sequence or Nanobody® of the invention directed against a first antigen (i.e. protein F of hRSV) and at least one further amino acid sequence or Nanobody® directed against a second antigen (i.e. different from protein F of hRSV), whereas a "trispecific" polypeptide of the invention is a polypeptide that comprises at least one amino acid sequence or Nanobody® of the invention directed against a first antigen (i.e. protein F of hRSV), at least one further amino acid sequence or Nanobody® directed against a second antigen (i.e. different from protein F of hRSV) and at least one further amino acid sequence or Nanobody® directed against a third antigen (i.e. different from both protein F of hRSV and the second antigen); etc.

Accordingly, in its simplest form, a bispecific polypeptide of the invention is a bivalent polypeptide of the invention (as defined herein), comprising a first amino acid sequence or Nanobody® of the invention directed against protein F of hRSV, and a second amino acid sequence or Nanobody® directed against a second antigen, in which said first and second amino acid sequence or Nanobody® may optionally be linked via a linker sequence (as defined herein); whereas a trispecific polypeptide of the invention in its simplest form is a trivalent polypeptide of the invention (as defined herein), comprising a first amino acid sequence or Nanobody® of the invention directed against protein F of hRSV, a second amino acid sequence or Nanobody® directed against a second antigen and a third amino acid sequence or Nanobody® directed against a third antigen, in which said first, second and third amino acid sequence or Nanobody® may optionally be linked via one or more, and in particular two, linker sequences.

In a specific aspect, the polypeptide of the invention is a trivalent, bispecific polypeptide. A trivalent, bispecific polypeptide of the invention in its simplest form may be a trivalent polypeptide of the invention (as defined herein), comprising two identical amino acid sequences or Nanobodies® against protein F of hRSV and a third amino acid sequence or Nanobody® directed against another antigen, in which said first, second and third amino acid sequence or Nanobody® may optionally be linked via one or more, and in particular two, linker sequences.

A preferred, but non-limiting example of a multispecific polypeptide of the invention comprises at least one amino acid sequence or Nanobody® of the invention and at least one Nanobody® that provides for an increased half-life. Some preferred, but non-limiting examples of such Nanobodies® include Nanobodies® directed against serum proteins, such as human serum albumin, thyroxine-binding protein, (human) transferrin, fibrinogen, an immunoglobulin such as IgG, IgE or igM, or one of the other serum proteins listed in WO 04/003019.

For example, for experiments in mice, Nanobodies® against mouse serum albumin (MSA) can be used, whereas for pharmaceutical use, Nanobodies® against human serum albumin can be used.

Another embodiment of the present invention is a polypeptide construct as described above wherein said at least one (human) serum protein is any of (human) serum albumin, (human) serum immunoglobulins, (human) thyroxine-binding protein, (human) transferrin, (human) fibrinogen, etc.

Accordingly, in a specific aspect, the polypeptide of the invention is a bispecific polypeptide comprising a first amino acid sequence or Nanobody® of the invention against protein F of hRSV and a second amino acid sequence or Nanobody® directed against (human) serum albumin, in which said first and second amino acid sequence or Nanobody® may optionally be linked via a linker sequence.

In another specific aspect, the polypeptide of the invention is a trivalent, bispecific polypeptide, comprising two identical amino acid sequences or Nanobodies® of the invention against protein F of hRSV and a third amino acid sequence or Nanobody® directed against (human) serum albumin, in which said first, second and third amino acid sequence or Nanobody® may optionally be linked via one or more, and in particular two, linker sequences.

In another specific aspect, the polypeptide of the invention is a tetravalent, bispecific polypeptide, comprising three identical amino acid sequences or Nanobodies® of the invention against protein F of hRSV and a fourth amino acid sequence or Nanobody® directed against (human) serum albumin, in which said first, second, third and fourth amino acid sequence or Nanobody® may optionally be linked via one or more, and in particular two or three, linker sequences.

According to a specific, but non-limiting aspect of the invention, the polypeptides of the invention contain, besides the one or more amino acid sequences or Nanobodies® of the invention, at least one Nanobody® against human serum albumin. These Nanobodies® against human serum albumin may be as generally described in the applications by Ablynx N. V. cited above (see for example WO 04/062551). Some particularly preferred Nanobodies® that provide for increased half-life and that can be used in the polypeptides of the invention include the Nanobodies® ALB-1 to ALB-10 disclosed in WO 06/122787 (see Tables II and III) of which ALB-8 (SEQ ID NO: 62 in WO 06/122787) is particularly preferred.

In another aspect, the invention relates to a compound or construct, and in particular a protein or polypeptide (also referred to herein as a "compound of the invention") that comprises or essentially consists of one or more amino acid sequences, Nanobodies® and/or polypeptides of the invention (or suitable fragments thereof), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence, Nanobody® or polypeptide of the invention (and/or to the compound. construct or polypeptide in which it is present) and may or may not modify the properties of the amino acid sequence, Nanobody® and/or polypeptide of the invention.

Such groups, residues, moieties or binding units may for example be chemical groups, residues, moieties, which may or may not by themselves be biologically and/or pharmacologically active. For example, and without limitation, such groups may be linked to the one or more amino acid sequences, Nanobodies® and/or polypeptides of the invention so as to provide a "derivative" of an amino acid sequence, Nanobody® and/or polypeptide of the invention, as further described herein.

Also within the scope of the present invention are compounds or constructs that comprise or essentially consist of one or more derivates as described herein, and optionally further comprise one or more other groups, residues, moieties or binding units, optionally linked via one or more linkers. Preferably, said one or more other groups, residues, moieties or binding units are amino acid sequences.

In the compounds, constructs or polypeptides described above, the one or more amino acid sequences, Nanobodies® and/or polypeptides of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound, construct or polypeptide is a fusion (protein) or fusion (polypeptide).

A compound or construct of the invention may comprises an amino acid sequence, Nanobody® or polypeptide of the invention, which is fused at its amino terminal end, at its carboxy terminal end, or both at its amino terminal end and at its carboxy terminal end to at least one further amino acid sequence, i.e. so as to provide a fusion protein comprising said amino acid sequence, Nanobody® or polypeptide of the invention and the one or more further amino acid sequences.

The one or more further amino acid sequence may be any suitable and/or desired amino acid sequences. The further amino acid sequences may or may not change, alter or otherwise influence the (biological) properties of the amino acid sequence, Nanobody® or polypeptide of the invention, and may or may not add further functionality to the amino acid sequence, Nanobody® or the polypeptide of the invention. Preferably, the further amino acid sequence is such that it confers one or more desired properties or functionalities to the amino acid sequence, Nanobody® or the polypeptide of the invention.

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the compounds of the invention, compared to the amino acid sequence, Nanobody® or polypeptide of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

The further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the amino acid sequence or Nanobody® of the invention is directed, or a different protein, polypeptide, antigen, antigenic determinant or epitope). For example, the further amino acid sequence may provide a second binding site that is directed against a serum protein (such as, for example, human serum albumin or another serum protein such as IgG), so as to provide increased half-life in serum. Such amino acid sequences for example include Nanobodies®, as well as the small peptides and binding proteins described in WO 91/01743, WO 01/45746 and WO 02/076489 and the dAb's described in WO 03/002609 and WO 04/003019. Reference is also made to Harmsen et al., Vaccine, 23 (41); 4926-42, 2005, as well as to EP 0 368 684, as well as to WO 08/028,977, WO 08/043,821, WO 08/043,822 by Ablynx N. V. and WO 08/068,280.

Such amino acid sequences may in particular be directed against serum albumin (and more in particular human serum albumin) and/or against IgG (and more in particular human IgG). For example, such amino acid sequences may be amino acid sequences that are directed against (human) serum albumin and amino acid sequences that can bind to amino acid residues on (human) serum albumin that are not involved in binding of serum albumin to FcRn (see for example WO 06/0122787) and/or amino acid sequences that are capable of binding to amino acid residues on serum albumin that do not form part of domain III of serum albumin (see again for example WO 06/0122787); amino acid sequences that have or can provide an increased half-life (see for example WO 08/028,977); amino acid sequences against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*), reference is again made to WO 08/028,977); amino acid sequences that can bind to serum albumin in a pH independent manner (see for example WO 08/043,821) and/or amino acid sequences that are conditional binders (see for example WO 08/043,822).

According to another embodiment, the one or more further amino acid sequences may comprise one or more parts, fragments or domains of conventional 4-chain antibodies (and in particular human antibodies) and/or of heavy chain antibodies. For example, although usually less preferred, an amino acid sequence, Nanobody® or polypeptide of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

Accordingly, in the compound or construct of the invention, said one or more other groups, residues, moieties or binding units may be chosen from the group consisting of domain antibodies, amino acid sequences that are suitable for use as a domain antibody, single domain antibodies, amino acid sequences that are suitable for use as a single domain antibody, "dAb's", amino acid sequences that are suitable for use as a dAb, or Nanobodies®.

In one specific aspect of the invention, the compound, construct or polypeptide of the invention comprising at least one amino acid sequence, Nanobody® or polypeptide of the invention may have an increased half-life, compared to the corresponding amino acid sequence, Nanobody® or polypeptide of the invention. Some preferred, but non-limiting examples of such compounds, constructs and polypeptides will become clear to the skilled person based on the further disclosure herein, and for example comprise amino acid sequences, Nanobodies® or polypeptides of the invention that have been chemically modified to increase the half-life thereof (for example, by means of pegylation); or compounds of the invention that comprise at least one amino acid sequence, Nanobody® or polypeptide of the invention that is linked to at least one moiety (and in particular at least one amino acid sequence) that increases the half-life of the amino acid sequence, Nanobody® or polypeptide of the invention. Examples of compounds of the invention that comprise such half-life extending moieties will become clear to the skilled person based on the further disclosure herein; and for example include, without limitation, compounds in which the one or more amino acid sequences, Nanobodies® or polypeptides of the invention are suitable linked to one or more serum proteins or fragments thereof (such as serum albumin or suitable fragments thereof) or to one or more binding units that can bind to serum proteins (such as, for example, Nanobodies® or (single) domain antibodies that can bind to serum proteins such as serum albumin, serum immunoglobulins such as IgG, or transferrine); compounds in which an amino acid sequence, Nanobody® or polypeptide of the invention is linked to an Fc portion (such as a human Fc) or a suitable part or fragment thereof; or compounds in which the one or more amino acid sequences, Nanobodies® or polypeptides of the invention are suitable linked to one or more small proteins or peptides that can bind to serum proteins (such as, without limitation, the proteins and peptides described in WO 91/01743, WO 01/45746, WO 02/076489).

The at least one amino acid sequence, Nanobody® or polypeptide may also be linked to one or more (preferably human) $C_H1$, $C_H2$ and/or $C_H3$ domains, optionally via a linker sequence. For instance, an amino acid sequence, Nanobody® or polypeptide linked to a suitable $C_H1$ domain could for example be used—together with suitable light chains—to generate antibody fragments/structures analogous to conventional Fab fragments or F(ab')$_2$ fragments, but in which one or (in case of an F(ab')$_2$ fragment) one or both of the conventional $V_H$ domains have been replaced by an amino acid sequence, Nanobody® or polypeptide of the invention. Also, two amino acid sequences or Nanobodies® could be linked to a $C_H3$ domain (optionally via a linker) to provide a construct with increased half-life in vivo.

According to one specific aspect, one or more amino acid sequences, Nanobodies® or polypeptides of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the amino acid sequence, Nanobody® or polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a Nanobody®), in which the Camelidae $C_H2$ and/or $C_H5$ domain have been replaced by human $C_H2$ and $C_H3$ domains, so as to provide an immunoglobulin that consists of 2 heavy chains each comprising a Nanobody® and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the amino acid sequences, Nanobodies® or polypeptides of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to WO 09/068,628. Coupling of an amino acid sequence, Nanobody® or polypeptide of the invention to an Fc portion may also lead to an increased half-life, compared to the corresponding amino acid sequence, Nanobody® or polypeptide of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more amino acid sequences, Nanobodies® or polypeptides and one or more constant domains with increased half-life in vivo will be clear to the skilled person, and may for example comprise amino acid sequences, Nanobodies® or polypeptides linked to a $C_H3$ domain, optionally via a linker sequence. Generally, any fusion protein or derivatives with increased half-life will preferably have a molecular weight of more than 50 kD, the cut-off value for renal absorption.

In another specific, but non-limiting, aspect, in order to form a compound of the invention, one or more amino acid sequences, Nanobodies® or polypeptides of the invention may be linked (optionally via a suitable linker or hinge region) to naturally occurring, synthetic or semisynthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al., J Biol Chem 1996 271 7494, describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

Generally, the amino acid sequences, Nanobodies® or polypeptides of the invention (or compounds, constructs or comprising the same) with increased half-life preferably have a half-life that is at least 1.5 times, preferably at least 2 times, such as at least 5 times, for example at least 10 times or more than 20 times, greater than the half-life of the corresponding amino acid sequence, Nanobody® or polypeptide of the invention per se. For example, the amino acid sequences, Nanobodies®, compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence, Nanobody® or polypeptide of the invention per se.

In a preferred, but non-limiting aspect of the invention, such amino acid sequences, Nanobodies®, compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), at preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

The further amino acid sequences may also form a signal sequence or leader sequence that directs secretion of the amino acid sequence, Nanobody® or the polypeptide of the invention from a host cell upon synthesis (for example to provide a pre-, pro- or prepro-form of the polypeptide of the invention, depending on the host cell used to express the polypeptide of the invention).

The further amino acid sequence may also form a sequence or signal that allows the amino acid sequence, Nanobody® or polypeptide of the invention to be directed towards and/or to penetrate or enter into specific organs, tissues, cells, or parts or compartments of cells, and/or that allows the amino acid sequence, Nanobody® or polypeptide of the invention to penetrate or cross a biological barrier such as a cell membrane, a cell layer such as a layer of epithelial cells. Suitable examples of such amino acid sequences will be clear to the skilled person, and for example include, but are not limited to, the "Peptrans" vectors mentioned above, the sequences described by Cardinale et al. and the amino acid sequences and antibody fragments known per se that can be used to express or produce the Nanobodies® and polypeptides of the invention as so-called "intrabodies", for example as described in WO 94/02610, WO 95/22618, U.S. Pat. No. 7,004,940, WO 03/014960, WO 99/07414; WO 05/01690; EP 1 512 696; and in Cattaneo, A. & Biocca, S. (1997) intracellular Antibodies: Development and Applications. Landes and Springer-Verlag; and in Kontermann, Methods 34, (2004), 163-170, and the further references described therein.

Such a protein, polypeptide, compound or construct may also be in essentially isolated form (as defined herein).

The compounds or polypeptides of the invention can generally be prepared by a method which comprises at least the step of suitably linking the one or more amino acid sequences, Nanobodies®, monovalent constructs and/or polypeptides of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

Suitable spacers or linkers for use in multivalent and/or multispecific polypeptides or constructs will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, its should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each amino acid sequence or Nanobody® by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type (gly$_x$ser$_y$)$_z$, such as (for example (gly$_4$ ser)$_3$ or (gly$_3$ser$_2$)$_3$, as described in WO 99/42077, hinge-like regions such as the hinge regions of naturally occurring heavy chain antibodies or similar sequences (such as described in WO 94/04678).

Some other particularly preferred linkers are poly-alanine (such as AAA), as well as the linkers mentioned in Table A-7, of which GS15 is particularly preferred.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for protein F of hRSV, or for one or more of the other antigens. Based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the amino acid sequences, Nanobodies®, compounds and polypeptides of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for ease of expression and production, a polypeptide of the invention will be a linear polypeptide. However, the invention in its broadest sense is not limited thereto. For example, when a polypeptide of the invention comprises three of more amino acid sequences or Nanobodies®, it is possible to link them by use of a linker with three or more "arms", which each "arm" being linked to an amino acid sequence or Nanobody®, so as to provide a "star-shaped" construct. It is also possible, although usually less preferred, to use circular constructs.

As will also be clear from the disclosure herein, it is also within the scope of the invention to use parts or fragments, or combinations of two or more parts or fragments, of the amino acid sequences, Nanobodies® or polypeptides of the invention as defined herein, and in particular parts or fragments of the amino acid sequences of SEQ ID NO's: 50-76, 138-141 and 146-157 or the polypeptides of SEQ ID N0's: 77-79, 142-145 and 158-165. Thus, according to one embodiment of the invention, the term "amino acid sequence of the invention", "Nanobody® of the invention" and "polypeptide of the invention" in its broadest sense also covers such parts or fragments.

Generally, such parts or fragments of the amino acid sequences, Nanobodies® or polypeptides of the invention (including variants thereof as defined herein) have amino acid sequences in which, compared to the amino acid sequence of the corresponding full length amino acid sequence or Nanobody® of the invention, one or more of the amino acid residues at the N-terminal end, one or more amino acid residues at the &terminal end, one or more contiguous internal amino acid residues, or any combination thereof, have been deleted and/or removed.

The parts or fragments are preferably such that they can bind to antigenic site II on protein F of hRSV, with an affinity (suitably measured and/or expressed as a $K_D$-value (actual or apparent), a $K_A$-value (actual or apparent), a $k_{on}$-rate and/or a $k_{off}$-rate, or alternatively as an IC$_{50}$ value, as further described herein) that is as defined herein.

In particular, amino acid sequences, Nanobodies®, polypeptides and parts or fragments are preferably such that they:

bind to protein F of hRSV with a dissociation constant ($K_D$) of 1000 nM to 1 nM or less, preferably 100 nM to 1 nM or less, more preferably 10 nM to 1 nM or less;

and/or such that they:

bind to protein F of hRSV with a $k_{on}$-rate of between 10$^4$ M$^{-1}$ s$^{-1}$ to about 10$^7$ M$^{-1}$ s$^{-1}$, preferably between 10$^5$ M$^{-1}$ s$^{-1}$ and 10$^7$ M$^{-1}$ s$^{-1}$, more preferably about 10$^6$ M$^{-1}$ s$^{-1}$ or more;

and/or such that they:

bind to protein F of hRSV with a $k_{off}$-rate between 10$^{-2}$ s$^{-1}$ ($t_{1/2}$=0.50 s) and 10$^{-4}$ s$^{-1}$ (providing a near irreversible complex with a $t_{1/2}$ of multiple days), preferably between 10$^{-3}$ s$^{-1}$ and 10$^{-4}$ s$^{-1}$, or lower.

The affinity of the parts or fragments against protein F of hRSV, can be determined in a manner known per se, for example using the assay described herein.

Such parts or fragments will usually also have a hRSV neutralization efficacy and/or potency as defined herein.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length amino acid sequence, Nanobody® or polypeptide of the invention.

Also, any part or fragment is such preferably that it comprises at least one of the CDR's (and preferably at least CDR3 or part thereof) and at least one other CDR (i.e. CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting embodiment, such a part or fragment comprises at least CDR3, such as FR3, CDR3 and FR4 of the corresponding full length Nanobody® of the invention, i.e. as for example described in the International application WO 03/050531 (tasters et al.).

As already mentioned above, it is also possible to combine two or more of such parts or fragments (i.e. from the same or different amino acid sequences or Nanobodies® of the invention), i.e. to provide further parts or fragments (as defined herein) of an amino acid sequence, a Nanobody® or a polypeptide of the invention. It is for example also possible to combine one or more parts or fragments of an amino acid sequence, a Nanobody® or a polypeptide of the invention with one or more parts or fragments of a human $V_H$ domain.

According to one preferred embodiment, the parts or fragments have a degree of sequence identity of at least 50%, preferably at least 60%, more preferably at least 70%, even more preferably at least 80%, such as at least 90%, 95% or 99% or more with one of the amino acid sequences or Nanobodies® of SEQ ID NO's: 60-76, 138-141 and 146-157 or with one of the polypeptides of SEQ ID NO's: 77-79, 142-145 and 158-165.

The parts and fragments, and nucleic acid sequences encoding the same, can be provided and optionally combined in any manner known per se. For example, such parts or fragments can be obtained by inserting a stop codon in a nucleic acid that encodes a full-sized amino acid sequence, Nanobody® or polypeptide of the invention, and then expressing the nucleic acid thus obtained in a manner known per se (e.g. as described herein). Alternatively, nucleic acids encoding such parts or fragments can be obtained by suitably restricting a nucleic acid that encodes a full-sized amino acid sequence, Nanobody® or polypeptide of the invention or by synthesizing such a nucleic acid in a manner known per se. Parts or fragments may also be provided using techniques for peptide synthesis known per se.

The invention in its broadest sense also comprises derivatives of the amino acid sequences, Nanobodies®, compounds or polypeptides of the invention. Such derivatives can generally be obtained by modification, and in particular by chemical and/or biological (e.g. enzymatical) modification, of the amino acid sequences, Nanobodies®, compounds or polypeptides of the invention and/or of one or more of the amino acid residues that form the amino acid sequences, Nanobodies®, compounds or polypeptides of the invention.

Examples of such modifications, as well as examples of amino acid residues within the amino acid sequence, Nanobody® sequence, compound or polypeptide sequences that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the amino acid sequence, Nanobody®, compound or polypeptide of the invention, and in particular of one or more functional groups, residues or moieties that confer one or more desired properties or functionalities to the amino acid sequence, Nanobody®, compound or polypeptide of the invention. Example of such functional groups will be clear to the skilled person.

For example, such modification may comprise the introduction (e.g. by covalent binding or in any other suitable manner) of one or more functional groups that that increase the half-life, the solubility and/or the absorption of the amino acid sequence, Nanobody®, compound or polypeptide of the invention, that reduce the immunogenicity and/or the toxicity of the amino acid sequence, Nanobody®, compound or polypeptide of the invention, that eliminate or attenuate any undesirable side effects of the amino acid sequence, Nanobody®, compound or polypeptide of the invention, and/or that confer other advantageous properties to and/or reduce the undesired properties of the amino acid sequence, Nanobody®, compound or polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to an amino acid sequence, Nanobody®, compound or polypeptide of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in an amino acid sequence, Nanobody®, compound or polypeptide of the invention, an amino acid sequence, Nanobody®, compound or polypeptide of the invention may be modified so as to suitably introduce one or more cysteine residues for attachment of PEG, or an amino acid sequence comprising one or more cysteine residues for attachment of PEG may be fused to the N- and/or C-terminus of an amino acid sequence, Nanobody®, compound or polypeptide of the invention, all using techniques of protein engineering known per se to the skilled person.

Preferably, for the amino acid sequences, Nanobodies®, compounds or polypeptides of the invention of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the amino acid sequence, Nanobody®, compound or polypeptide of the invention.

Yet another modification may comprise the introduction of one or more detectable labels or other signal-generating groups or moieties, depending on the intended use of the labelled amino acid sequence, Nanobody®, compound or polypeptide of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or CFP and its analogs), radio-isotopes (such as $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled amino acid sequences, Nanobodies®, compounds or polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the amino acid sequence, Nanobody®, compound or polypeptide of the invention to another protein, polypeptide or chemical compound that is bound to the other half of the binding pair, i.e. through formation of the binding pair. For example, an amino acid sequence, Nanobody®, compound or polypeptide of the invention may be conjugated to biotin, and linked to another protein, polypeptide, compound or carrier conjugated to avidin or streptavidin. For example, such a conjugated amino acid sequence, Nanobody®, compound or polypeptide of the invention may be used as a reporter, for example in a diagnostic system where a detectable signal-producing agent is conjugated to avidin or streptavidin. Such binding pairs may for example also be used to bind the amino acid sequence, Nanobody®, compound or polypeptide of the invention to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the amino acid sequence, Nanobody®, compound or polypeptide of the invention.

Other potential chemical and enzymatical modifications will be clear to the skilled person. Such modifications may also be introduced for research purposes (e.g. to study function-activity relationships). Reference is for example made to Lundblad and Bradshaw, Biotechnol. Appl. Biochem., 26, 143-151 (1997).

Preferably, the derivatives are such that they bind to protein F of hRSV, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the amino acid sequences, Nanobodies®, polypeptides or compounds per se). Such derivatives will usually also have a hRSV neutralization efficacy and/or potency as defined herein.

As mentioned above, the invention also relates to proteins or polypeptides that essentially consist of or comprise at least one amino acid sequence, Nanobody®, compound or polypeptide of the invention. By "essentially consist of" is meant that the amino acid sequence of the protein or polypeptide of the invention either is exactly the same as the amino acid sequence, Nanobody®, compound or polypeptide of the invention or corresponds to the amino acid sequence, Nanobody®, compound or polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence, Nanobody®, compound or polypeptide.

Said amino acid residues may or may not change, alter or otherwise influence the (biological) properties of the amino acid sequence, Nanobody®, compound or polypeptide of the invention and may or may not add further functionality to the amino acid sequence, Nanobody®, compound or polypeptide. For example, such amino acid residues:

a) can comprise an N-terminal Met residue, for example as result of expression in a heterologous host cell or host organism.
b) may form a signal sequence or leader sequence that directs secretion of the amino acid sequence, Nanobody®, compound or polypeptide from a host cell upon synthesis. Suitable secretory leader peptides will be clear to the skilled person, and may be as further described herein. Usually, such a leader sequence will be linked to the N-terminus of the amino acid sequence, Nanobody®, compound or polypeptide, although the invention in its broadest sense is not limited thereto;
c) may form a sequence or signal that allows the amino acid sequence, Nanobody®, compound or polypeptide to be directed towards and/or to penetrate or enter into specific organs, tissues, cells, or parts or compartments of cells, and/or that allows the amino acid sequence, Nanobody®, compound or polypeptide to penetrate or cross a biological barrier such as a cell membrane, a cell layer such as a layer of epithelial cells, a tumor including solid tumors, or the blood-brain-barrier. Examples of such amino acid sequences will be clear to the skilled person. Some non-limiting examples are the small peptide vectors ("Pep-trans vectors") described in WO 03/026700 and in Temsamani et al., Expert Opin. Biol. Ther., 1, 773 (2001); Temsamani and Vidal, Drug Discov. Today, 9, 1012 (004) and Rousseile, J. Pharmacal. Exp. Ther., 296, 124-131 (2001), and the membrane translocator sequence described by Zhao et al., Apoptosis, 8, 631-637 (2003). C-terminal and N-terminal amino acid sequences for intracellular targeting of antibody fragments are for example described by Cardinale et al., Methods, 34, 171 (2004). Other suitable techniques for intracellular targeting involve the expression and/or use of so-called "intrabodies" comprising a amino acid sequence, Nanobody®, compound or polypeptide of the invention, as mentioned below;
d) may form a "tag", for example an amino acid sequence or residue that allows or facilitates the purification of the amino acid sequence, Nanobody®, compound or polypeptide, for example using affinity techniques directed against said sequence or residue. Thereafter, said sequence or residue may be removed (e.g. by chemical or enzymatical cleavage) to provide the amino acid sequence, Nanobody®, compound or polypeptide (for this purpose, the tag may optionally be linked to the amino acid sequence, Nanobody®, compound or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA (SEQ ID NO: 111);

e) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the amino acid sequences, Nanobodies®, compounds or polypeptides of the invention.

The invention further relates to methods for preparing the amino acid sequences, Nanobodies®, polypeptides, compounds, nucleic acids, host cells, products and compositions described herein.

The amino acid sequences, Nanobodies®, polypeptides, compounds and nucleic acids of the invention can be prepared in a manner known per se, as will be clear to the skilled person from the further description herein. For example, the amino acid sequences, Nanobodies® and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies®, polypeptides and nucleic acids include the methods and techniques described herein.

The method for producing an amino acid sequence of the invention, a Nanobody® of the invention, a polypeptide of the invention, or a monovalent construct of the invention may comprise the following steps:

the expression, in a suitable host cell or host organism (also referred to herein as a "host of the invention") or in another suitable expression system of a nucleic acid that encodes said amino acid sequence, Nanobody® or polypeptide of the invention (also referred to herein as a "nucleic acid of the invention"),
optionally followed by:
a isolating and/or purifying the amino acid sequence, Nanobody® or polypeptide of the invention thus obtained.

In particular, such a method may comprise the steps of:
cultivating and/or maintaining a host of the invention under conditions that are such that said host of the invention expresses and/or produces at least one amino acid sequence, Nanobody® and/or polypeptide of the invention;
optionally followed by:
isolating and/or purifying the amino acid sequence, Nanobody® or polypeptide of the invention thus obtained.

Accordingly, the present invention also relates to a nucleic acid or nucleotide sequence that encodes an amino acid sequence, a Nanobody®, a polypeptide or a monovalent construct of the invention (also referred to as "nucleic acid of the invention" or "nucleotide sequence of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences, Nanobodies® and/or polypeptides of the invention given herein, and/or can be isolated from a suitable natural source. Also, as will be clear to the skilled person, to prepare a nucleic acid of the invention, also several nucleotide sequences, such as at least one nucleotide sequence encoding an amino acid sequence or Nanobody® and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
a) at least one nucleic acid of the invention; operably connected to
b) one or more regulatory elements, such as a promoter and optionally a suitable terminator; and optionally also
c) one or more further elements of genetic constructs known per se;

in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used; the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e. under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence, Nanobody® or polypeptide of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. No. 7,207,410, U.S. Pat. No. 5,693,492 and EP 1 085 089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e. for expression and/or production of the amino acid sequence, Nanobody® or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example:

a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylo-* coccus, for example of *Staphylococcus carnosus*; and of *Lactococcus*, for example of *Lactococcus lactis*;

a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;

a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*;

an amphibian cell or cell line, such as *Xenopus oocytes*;

an insect-derived cell or cell line, such as cells/cell lines derived from *lepidoptera*, including but not limited to *Spodoptera* SF9 and Sf21 cells or cells/cell lines derived from *Drosophila*, such as Schneider and Kc cells;

a plant or plant cell, for example in tobacco plants; and/or a mammalian cell or cell line, for example a cell or cell line derived from a human, a cell or a cell line from mammals including but not limited to CHO-cells, BHK-cells (for example BILK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The amino acid sequences, Nanobodies® and polypeptides of the invention can also be introduced and expressed in one or more cells, tissues or organs of a multicellular organism, for example for prophylactic and/or therapeutic purposes (e.g. as a gene therapy). For this purpose, the nucleotide sequences of the invention may be introduced into the cells or tissues in any suitable way, for example as such (e.g. using liposomes) or after they have been inserted into a suitable gene therapy vector (for example derived from retroviruses such as adenovirus, or parvoviruses such as adeno-associated virus). As will also be clear to the skilled person, such gene therapy may be performed in vivo and/or in situ in the body of a patient by administering a nucleic acid of the invention or a suitable gene therapy vector encoding the same to the patient or to specific cells or a specific tissue or organ of the patient; or suitable cells (often taken from the body of the patient to be treated, such as explanted lymphocytes, bone marrow aspirates or tissue biopsies) may be treated in vitro with a nucleotide sequence of the invention and then be suitably (re-) introduced into the body of the patient. All this can be performed using gene therapy vectors, techniques and delivery systems which are well known to the skilled person, and for example described in Culver, K. W., "Gene Therapy", 1994, p. xii, Mary Ann Liebert, Inc., Publishers, New York, N.Y.); Giordano, Nature F Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 4077-1086; Onodera, Blood 91; (1998), 30-36; Verma, Gene Ther. 5 (1998), 692-699; Nabel, Ann. N.Y. Acad. Sci.: 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. No. 5,580,859; U.S. Pat. No. 5,589,466; or Schaper, Current Opinion in Biotechnology 7 (1996), 635-640. For example, in situ expression of ScFv fragments (Afanasieva et al., Gene Ther., 10, 1850-1859 (2003)) and of diabodies (Blanco et al., J. Immunol, 171, 1070-1077 (2003)) has been described in the art.

For expression of the amino acid sequences, Nanobodies® or polypeptides in a cell, they may also be expressed as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

The amino add sequences, Nanobodies® and polypeptides of the invention can for example also be produced in the milk of transgenic mammals, for example in the milk of rabbits, cows, goats or sheep (see for example U.S. Pat. No. 6,741, 957, U.S. Pat. No. 6,304,489 and U.S. Pat. No. 6,849,992 for general techniques for introducing transgenes into mammals), in plants or parts of plants including but not limited to their leaves, flowers, fruits, seed, roots or turbers (for example in tobacco, maize, soybean or alfalfa) or in for example pupae of the silkworm *Bombix mori*.

Furthermore, the amino acid sequences, Nanobodies® and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies® is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of Nanobodies® or Nanobody®-containing protein therapeutics include strains of *E. coli, Pichia pastoris, S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation.

Again, such expression/production systems are also made available by some of the companies mentioned above.

The choice of the specific expression system would depend in part on the requirement for certain post-translational modifications, more specifically glycosylation. The production of a Nanobody®-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired amino acid sequence, Nanobody® or polypeptide to be obtained.

Thus, according to one non-limiting embodiment of the invention, the amino acid sequence, Nanobody® or polypeptide of the invention is glycosylated. According to another non-limiting embodiment of the invention, the amino acid sequence, Nanobody® or polypeptide of the invention is non-glycosylated.

According to one preferred, but non-limiting embodiment of the invention, the amino acid sequence, Nanobody® or polypeptide of the invention is produced in a bacterial cell, in particular a bacterial cell suitable for large scale pharmaceutical production, such as cells of the strains mentioned above.

According to another preferred, but non-limiting embodiment of the invention, the amino acid sequence, Nanobody® or polypeptide of the invention is produced in a yeast cell, in particular a yeast cell suitable for large scale pharmaceutical production, such as cells of the species mentioned above.

According to yet another preferred, but non-limiting embodiment of the invention, the amino acid sequence, Nanobody® or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the amino acid sequences, Nanobodies® and the polypeptides of the invention, the amino acid sequences, Nanobodies® and polypeptides of the invention can be produced either intracellularly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. When eukaryotic host cells are used, extracellular production is usually preferred since this considerably facilitates the further isolation and downstream processing of the amino acid sequences, Nanobodies®, polypeptides and proteins obtained. Bacterial cells such as the strains of *E. coli* mentioned above normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular an amino acid sequence, Nanobody® or a polypeptide of the invention, can be used.

Thus, according to one non-limiting embodiment of the invention, the amino acid sequence, Nanobody® or polypeptide of the invention is an amino acid sequence, Nanobody® or polypeptide that has been produced intracellularly and that has been isolated from the host cell, and in particular from a bacterial cell or from an inclusion body in a bacterial cell. According to another non-limiting embodiment of the invention, the amino acid sequence, Nanobody® or polypeptide of the invention is an amino acid sequence, Nanobody® or polypeptide that has been produced extracellularly, and that has been isolated from the medium in which the host cell is cultivated.

Some preferred, but non-limiting promoters for use with these host cells include, for expression in *E. coli*: lac promoter (and derivatives thereof such as the lacUV5 promoter); arabinose promoter; left-(PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;

for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1,10,7 (galactose metabolic enzymes), ADH2 (alcohol dehydrogenase 2), PHO5 (acid phosphatase), CUP1 (copper metallothionein); heterologous: CaMV (cauliflower mosaic virus 355 promoter);

for expression in *Pichia pastoris*: the AOX1 promoter (alcohol oxidase I);

for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;

Some preferred, but non-limiting vectors for use with these host cells include:

vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMTneo (342-12) (ATCC 37224), pRSVgpt (ATCC37199), pRSVneo (ATCC37198), pSV2-dhfr (ATCC 37146), pUC-Tag (ATCC 37460) and 1ZD35 (ATCC 37565), as well as viral-based expression systems, such as those based on adenovirus;

vectors for expression in bacterial cells: pET vectors (Novagen) and pQE vectors (Qiagen);

vectors for expression in yeast or other fungal cells: pYES2 (Invitrogen) and *Pichia* expression vectors (Invitrogen);

vectors for expression in insect cells: pBlueBacII (Invitrogen) and other baculovirus vectors vectors for expression in plants or plant cells: for example vectors based on cauliflower mosaic virus or tobacco mosaic virus, suitable strains of *Agrobacterium*, or Ti-plasmid based vectors.

Some preferred, but non-limiting secretory sequences for use with these host cells include:

for use in bacterial cells such as *E. coli*: PelB, BIa, OmpA, OmpC, OmpF, OmpT, SU, PhoA, PhoE, MalE, Lpp, LamB, and the like; TAT signal peptide, hemolysin C-terminal secretion signal;

for use in yeast: α-mating factor prepro-sequence, phosphatase (pho1), invertase (Suc), etc.;

for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) farm further aspects of the present invention.

Preferably, these host cells or host organisms are such that they express, or are (at least) capable of expressing (e.g. under suitable conditions), an amino acid sequence, Nanobody® or polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences, Nanobodies® or polypeptides of the invention, the transformed host cell or transformed host organism may generally be kept, maintained and/or cultured under conditions such that the (desired) amino acid sequence, Nanobody® or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

It will also be clear to the skilled person that the amino acid sequence, Nanobody® or polypeptide of the invention may (first) be generated in an immature form (as mentioned above), which may then be subjected to post-translational modification, depending on the host cell/host organism used. Also, the amino acid sequence, Nanobody® or polypeptide of the invention may be glycosylated, again depending on the host cell/host organism used.

The amino acid sequence, Nanobody® or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, Nanobody® or polypeptide of the invention) and/or preparative immunological techniques (i.e. using antibodies against the amino acid sequence to be isolated).

The invention further relates to a product or composition containing or comprising at least one amino acid sequence of the invention (or a suitable fragment thereof), at least one Nanobody® of the invention, at least one polypeptide of the invention, at least one compound or construct of the invention, at least one monovalent construct of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

Generally, for pharmaceutical use, the amino acid sequences, Nanobodies® and polypeptides of the invention may be formulated as a pharmaceutical preparation or compositions comprising at least one amino acid sequence, Nanobody® or polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one amino acid of the invention, at least one Nanobody® of the invention, at least one compound or construct of the invention or at least one polypeptide of the invention and at least one suitable carrier, diluent or excipient (i.e. suitable for pharmaceutical use), and optionally one or more further active substances.

Generally, the amino acid sequences, Nanobodies®, compounds, constructs and polypeptides of the invention can be formulated and administered in any suitable manner known per se, for which reference is for example made to the general background art cited above (and in particular to WO 04/041862, WO 04/041863, WO 04/041865, WO 04/041867 and WO 08/020,079) as well as to the standard handbooks, such as Remington's Pharmaceutical Sciences, 18$^{th}$ Ed., Mack Publishing Company, USA (1990), Remington, the Science and Practice of Pharmacy, 21 st Edition, Lippincott Williams and Wilkins (2005); or the Handbook of Therapeutic Antibodies (S. Dubel, Ed.), Wiley, Weinheim, 2007 (see for example pages 252-255).

For example, the amino acid sequences, Nanobodies®, compounds, constructs and polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020,079. Usually, aqueous solutions or suspensions will be preferred.

The amino acid sequences, Nanobodies®, compounds, constructs and polypeptides of the invention can also be administered using gene therapy methods of delivery. See, e.g., U.S. Pat. No. 5,399,346, which is incorporated by reference in its entirety. Using a gene therapy method of delivery, primary cells transfected with the gene encoding an amino acid sequence, Nanobody® or polypeptide of the invention can additionally be transfected with tissue specific promoters to target specific organs, tissue, grafts, tumors, or cells and can additionally be transfected with signal and stabilization sequences for subcelluiarly localized expression.

Thus, the amino acid sequences, Nanobodies®, compounds, constructs and polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the amino acid sequences, Nanobodies®, compounds, constructs and polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the amino acid sequence, Nanobody®, compound, construct or polypeptide of the invention. Their percentage in the compositions and preparations may, of course, be varied and may conveniently be between about 2 to about 60% of the weight of a given unit dosage form. The amount of the amino acid sequence, Nanobody®, compound, construct or polypeptide of the invention in such therapeutically useful compositions is such that an effective dosage level will be obtained.

The tablets, troches, pilis, capsules, and the like may also contain binders, excipients, disintegrating agents, lubricants and sweetening or flavouring agents, for example those mentioned on pages 143-144 of WO 08/020,079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the amino acid sequences, Nanobodies®, compounds, constructs and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the amino acid sequences, Nanobodies®, compounds, constructs and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The amino acid sequences, Nanobodies®, compounds, constructs and polypeptides of the invention may also be administered intravenously or intraperitoneally by infusion or injection, as further described on pages 144 and 145 of WO 08/020,079.

For topical administration, the amino acid sequences, Nanobodies®, compounds, constructs and polypeptides of the invention may be applied in pure form, i.e., when they are liquids. However, it will generally be desirable to administer them to the skin as compositions or formulations, in combination with a dermatologically acceptable carrier, which may be a solid or a liquid, as further described on page 145 of WO 08/020,079.

Generally, the concentration of the amino acid sequences, Nanobodies®, compounds, constructs and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

In a preferred aspect, the amino acid sequences, Nanobodies®, compounds, constructs and/or polypeptides of the invention and/or compositions comprising the same are administered to the pulmonary tissue. In the context of the present invention, "pulmonary tissue" is for the purposes of this invention equivalent with lung tissue or lung. The lung comprises 2 distinct zones: a conducting and a respiratory zone, within which the airway and vascular compartments lie (see e.g. "Pulmonary Drug Delivery", Edited by Karoline Bechtold-Peters and Henrik Luessen, 2007, ISBN 978-3-87193-322-6 pages 16-28).

For pulmonary delivery, the amino acid sequences, Nanobodies®, compounds, constructs and polypeptides of the invention may be applied in pure form, i.e., when they are liquids or a dry powder. However, it will be preferred to administer them to the pulmonary tissue as composition or formulation comprising an amino acid sequence, Nanobody®, compound, construct and/or polypeptide of the invention and a carrier suitable for pulmonary delivery. Accordingly the present invention also relates to a pharmaceutical composition comprising the amino acid sequence, Nanobody®, compound, construct and/or polypeptide of the invention and a carrier suitable for pulmonary delivery. Carriers suitable for pulmonary delivery are known in the art.

The amino acid sequences, Nanobodies®, compounds, constructs and/or polypeptides of the invention may also be administered as micro- or nanoparticles of pure drugs with particle sizes and distributions favorable for pulmonary delivery.

Accordingly the present invention also relates to a pharmaceutical device suitable for the pulmonary delivery of the amino acid sequences, Nanobodies®, compounds, constructs and/or polypeptides of the invention and suitable in the use of a composition comprising the same. This device may be an inhaler for liquids (e.g. a suspension of fine solid particles or droplets) comprising the amino acid sequence, Nanobody®, compound, constructs and/or polypeptide of the invention. Preferably this device is an aerosol comprising the amino acid sequence, Nanobody®, compound, construct and/or polypeptide of the invention. The device may also be a dry powder inhaler comprising the amino acid sequence, Nanobody®, compound, construct and/or polypeptide of the invention in the form of a dry powder.

In a preferred method, the administration to the pulmonary tissue is performed by inhaling the amino acid sequences, Nanobodies®, compounds, constructs and/or polypeptides of the invention and/or the composition comprising the same in an aerosol cloud. According to the invention, inhaling of the aerosol cloud can be performed by an inhaler device. The device should generate from a formulation comprising the amino acid sequences, Nanobodies®, compounds, constructs and/or polypeptides of the invention (and/or composition comprising the same) an aerosol cloud of the desired particle size (distribution) at the appropriate moment of the mammal's inhalation cycle, containing the right dose of the amino acid sequences, Nanobodies®, compounds, constructs and/or polypeptides of the invention ("Pulmonary drug delivery", Bechtold-Peters and Luessen, eds., ISBN 978-3-87193-322-6, page 125).

In the context of the present invention, "aerosol" denotes a suspension of fine solid particles or liquid droplets (or combination thereof) in a gas wherein for the purposes of this invention the particles and/or droplets comprise the amino acid sequences, Nanobodies®, compounds, constructs and/or polypeptides of the invention.

The device should generate from the formulation an aerosol cloud of the desired particle size (distribution) at the appropriate moment of the mammal's inhalation cycle, containing the right dose of amino acid sequences, Nanobodies®, compounds, constructs and/or polypeptides of the invention. The following 4 requirements (formulation, particle size, time and dose) should be considered ("Pulmonary Drug Delivery", Bechtold-Peters and Luessen, eds., supra, pages 125 and 126):

- The formulations that are used in the devices may vary from aqueous solutions or suspensions used in nebulizers to the propellant-based solutions or suspensions used in metered dose inhaler or even specially engineered powder mixtures for the dry powder inhalers. All these different formulations require different principles for aerosol generation, which emphasizes the mutual dependency of device and formulation;
- Since the site of deposition of aerosol particles depends on their (aerodynamic) size and velocity, the desired particle size of the aerosol cloud varies depending on the desired site of deposition in the lung, which is related to the therapeutic goal of the administration;
- As the aerosol cloud can be tuned to be released at different moments during the inhalation cycle generated by the mammal, it is preferred that for the agents of the invention (to be deposited in the peripheral parts of the lung) the aerosol is released at the start of the inhalation cycle;
- Doses may vary considerably and may e.g. vary e.g. for a human from a few microgram to several hundreds of microgram or even milligrams, e.g. about up to about 10 to 100 milligrams.

Various inhalation systems are e.g. described on pages 129 to 148 in the review ("Pulmonary Drug Delivery", Bechtold-Peters and Luessen, eds., supra) and include, but are not limited to, nebulizers, metered dose inhalers, metered dose liquid inhalers, and dry powder inhalers. Devices taking into account optimized and individualized breathing pattern for controlled inhalation maneuvers may also be used (see AKITA® technology on page 157 of "Pulmonary Drug Delivery", Bechtold-Peters and Luessen, eds., supra).

However, not only the device is important to pulmonary delivery of the amino acid sequences, Nanobodies®, compounds, constructs and/or polypeptides of the invention but also the right formulation is critical to achieve an effective delivery. This can be in principle achieved by using one of the following approaches:

- Administration of aqueous solutions or suspensions comprising the amino acid sequences, Nanobodies®, compounds, constructs and/or polypeptides of the invention (e.g. nasal drops) into the nasal cavities;
- Nebulisation of aqueous solutions or suspensions comprising the amino acid sequences, Nanobodies®, compounds, constructs and/or polypeptides of the invention;
- Atomization by means of liquefied propellants; and
- Dispersion of dry powders.

Hence formulations of the amino acid sequences, Nanobodies®, compounds, constructs and/or polypeptides of the invention have to be adopted and adjusted to the chosen inhalation device. Appropriate formulations, i.e. the excipients in addition to the amino acid sequences, Nanobodies®, compounds, constructs and/or polypeptides of the invention, are e.g. described in chapter IV of "Pulmonary Drug Delivery", Bechtold-Peters and Luessen, eds., supra. In this respect, reference is also made to U.S. provisional application No. 61/303,447 entitled "Methods and compositions for the preparation of aerosols" filed by Ablynx N. V. on 12 Feb. 2010.

The amount of the amino acid sequences, Nanobodies®, compounds, constructs and polypeptides of the invention required for use in treatment will vary not only with the particular amino acid sequence, Nanobody®, compounds, constructs or polypeptide selected but also with the route of administration, the nature of the condition being treated and the age and condition of the patient and will be ultimately at the discretion of the attendant physician or clinician. Also the dosage of the amino acid sequences, Nanobodies®, compounds, constructs and polypeptides of the invention varies depending on the target host cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

The invention further relates to applications and uses of the amino acid sequences, Nanobodies®, polypeptides, compounds, nucleic acids, host cells, products and compositions described herein, as well as to methods for the prevention and/or treatment respiratory track infection caused by hRSV. Some preferred but non-limiting applications and uses will become clear from the further description herein.

The amino acid sequences, Nanobodies®, polypeptides, compounds and compositions of the present invention can generally be used to block the interaction of protein F of hRSV with the target host cell and/or its membrane, to neutralize hRSV (different hRSV strains and/or escape mutants), to modulate, inhibit and/or prevent hRSV infectivity (of different hRSV strains and/or escape mutants), to modulate, inhibit and/or prevent fusion (of different hRSV strains and/or escape mutants) with (the cell membrane of) the target host cell and/or to modulate, inhibit and/or prevent hRSV entry in the target host cell (of different hRSV strains and/or escape mutants).

In one aspect, the amino acid sequences, Nanobodies®, polypeptides, compounds and compositions of the present invention can block the interaction of protein F of hRSV with the target host cell and/or its membrane by at least 1%, preferably at least 5%, such as at least 10% or at least 25%, for example by at least 50%, at least 60%, at least 70%, at least 80%, or 90% or more, compared to the interaction of protein F of hRSV with the target host cell and/or its membrane under the same conditions but without the presence of the amino acid sequence, Nanobody® or polypeptide of the invention, measured in any suitable manner known per se, for example using one of the assays described herein.

In another aspect, the amino acid sequences, Nanobodies®, polypeptides, compounds and compositions of the present invention neutralize hRSV infectivity by at least 1%, preferably at least 5%, such as at least 10% or at least 25%, for example by at least 50%, at least 60%, at least 70%, at least 80%, or 90% or more, compared to, the neutralization of hRSV under the same conditions but without the presence of the amino acid sequence, Nanobody® or polypeptide of the invention, measured in any suitable manner known per se, for example using one of the assays described herein.

In the context of the present invention, "modulating" or "to modulate" generally means either reducing, preventing or inhibiting viral infectivity, fusion and/or viral entry and/or reducing, preventing or inhibiting the biological pathways that are mediated by protein F of hRSV, as measured using a suitable in vitro, cellular or in vivo assay (such as those mentioned herein). In particular, "modulating" or "to modulate" may mean either reducing, preventing or inhibiting viral infectivity, fusion and/or viral entry and/or reducing, preventing or inhibiting the biological pathways that are mediated by protein F of hRSV as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to normal (i.e. naturally occurring) viral infectivity, fusion and/or viral entry and/or normal (i.e. naturally occurring) the biological pathways that are mediated by protein F of hRSV in the same assay under the same conditions but without the presence of the amino acid sequence, Nanobody® or polypeptide of the invention.

In one aspect, the amino acid sequences, Nanobodies®, polypeptides, compounds and compositions of the present invention may modulate, inhibit and/or prevent hRSV infectivity by at least 1%, preferably at least 5%, such as at least 10% or at least 25%, for example by at least 50%, at least 60%, at least 70%, at least 80%, or 90% or more, compared to the infectivity under the same conditions but without the presence of the amino acid sequence, Nanobody® or polypeptide of the invention, measured in any suitable manner known per se, for example using one of the assays described herein.

The term "viral entry" used herein encompasses any viral-mediated biological pathway that is needed to accomplish virion attachment to a target host cell and/or viral fusion with a target host cell. It is encompassed in the present invention that viral entry, which may be any viral-mediated biological pathway that is needed to accomplish virion attachment to a target host cell and/or viral fusion with a target host cell, can be modulated and/or reduced and/or prevented and/or inhibited by specific binding of the amino acid sequences, Nanobodies®, polypeptides and/or compounds of the invention, as measured using a suitable in vitro, cellular or in vivo assay (such as those mentioned herein). In particular, viral entry, which can be mediated by protein F of hRSV, can be modulated, reduced, prevented or inhibited by specific binding of the amino acid sequences, Nanobodies®, polypeptides and/or compounds of the invention to protein F of hRSV, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to normal (i.e. naturally occurring) viral entry (as defined herein), which can be mediated by protein F of hRSV, in the same assay under the same conditions but without the presence of the amino acid sequence, Nanobody®, polypeptide and/or compound of the invention. Thus, it is also encompassed that that viral attachment and/or viral fusion can be modulated and/or reduced and/or prevented and/or inhibited by specific binding of the amino acid sequences, Nanobodies®, polypeptides and/or compounds of the invention to protein F of hRSV, as measured using a suitable in vitro, cellular or in vivo assay (such as those mentioned herein). In particular, viral attachment and/or viral fusion, which can be mediated by protein F of hRSV, can be modulated, reduced, prevented or inhibited by specific binding of the amino acid sequences, Nanobodies®, polypeptides and/or compounds of the invention to protein F of hRSV, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to normal (i.e. naturally occurring) viral attachment and/or viral fusion, which can be mediated by protein F of hRSV in the same assay under the same conditions but without the presence of the amino acid sequence, Nanobody®, polypeptide and/or compound of the invention.

In this respect, the amino acid sequences, Nanobodies®, polypeptides, compounds and compositions of the present invention may modulate, inhibit and/or prevent hRSV entry in the target host cell by at least 1%, preferably at least 5%, such as at least 10% or at least 25%, for example by at least 50%, at least 60%, at least 70%, at least 80%, or 90% or more, compared to the entry in the target host cell under the same conditions but without the presence of the amino acid sequence, Nanobody® or polypeptide of the invention, for example using one of the assays described herein.

The amino acid sequences, Nanobodies®, polypeptides, compounds and compositions of the present invention may also modulate, inhibit and/or prevent fusion of hRSV with (the cell membrane of) the target host cell by at least 1%, preferably at least 5%, such as at least 10% or at least 25%, for example by at least 50%, at least 60%, at least 70%, at least 80%, or 90% or more, compared to fusion of hRSV with (the cell membrane of) the target host cell under the same conditions but without the presence of the amino acid sequence, Nanobody® or polypeptide of the invention, measured in any suitable manner known per se, for example using one of the assays described herein.

The multivalent (such as bivalent or trivalent) polypeptides of the invention have shown improved affinity and/or improved cross-reactivity for different genotypes, subtypes, viral escape mutants and/or strains of hRSV compared to the monovalent amino acid sequence or Nanobody®. In one aspect, the multivalent (such as bivalent or trivalent) polypeptides of the invention may bind different strains of RSV (such as e.g. Long, A-2 and/or B-1). In yet another aspect, the multivalent (such as bivalent or trivalent) polypeptides of the invention may bind different escape mutants of hRSV (such as e.g. described in Lopez et al. 1998, J. Virol. 72: 6922-6928) and/or escape mutants specific for antigen site II, antigen site IV-VI or the combination of both antigenic sites.

Accordingly, the invention also relates to the use of a multivalent (e.g. trivalent, bivalent) polypeptide of the invention, and/or of a pharmaceutical composition comprising the same for binding and/or neutralization of different strains of a hRSV. In a preferred aspect, a bivalent humanized and/or sequence optimized NC41 Nanobody® (such as e.g. a bivalent polypeptide comprising two Nanobodies® selected from SEQ ID NO's: 60-76, 138-141 and 146-157) is used. In another preferred aspect, a trivalent humanized and/or sequence optimized NC41 Nanobody® (such as e.g. a trivalent polypeptide comprising three Nanobodies® selected from SEQ ID NO's: 60-76, 138-141 and 146-157) is used. In another preferred aspect, one of SEQ ID NO's: 77-79, 142-145 and 158-165 is used.

The invention also relates to the use of a multivalent (e.g. trivalent, bivalent) polypeptide of the invention, and/or of a pharmaceutical composition comprising the same for binding and/or neutralization of one or more escape mutants of a hRSV. In a preferred aspect, a bivalent humanized NC41 Nanobody® (such as e.g. a bivalent polypeptide comprising two Nanobodies® selected from SEQ ID NO's: 60-76, 138-141 and 146-157) is used. In another preferred aspect, a trivalent humanized NC41 Nanobody® (such as e.g. a trivalent polypeptide comprising three Nanobodies® selected from SEQ ID NO's: 60-76, 138-141 and 146-157) is used. In another preferred aspect, one of SEQ ID NO's: 77-79, 142-145 and 158-165 is used.

The invention also relates to a method for the prevention and/or treatment of at least one viral disease, said method comprising administering, to a subject in need thereof, a pharmaceutically active amount of an amino acid sequence of the invention, of a Nanobody® of the invention, of a polypeptide of the invention, of a compound or construct of the invention and/or of a pharmaceutical composition comprising the same.

As such, the amino acid sequences, Nanobodies®, polypeptides, compounds and compositions of the present invention can be used for the prevention and/or treatment of diseases and disorders associated with hRSV infection. Examples of such diseases and disorders associated with hRSV infection will be clear to the skilled person based on the disclosure herein, and for example include the following diseases and disorders: respiratory illness, upper respiratory tract infection, lower respiratory tract infection, bronchiolitis (inflammation of the small airways in the lung), pneumonia, dyspnea, cough, (recurrent) wheezing and asthma.

Accordingly, the present invention also relates to a method for the prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma caused by hRSV, said method comprising administering, to a subject in need thereof, a pharmaceutically active amount of at least one amino acid sequence of the invention, Nanobody® of the invention, polypeptide of the invention, compound or construct of the invention or monovalent construct of the invention, or a composition of the invention.

The invention also relates to the use of an amino acid sequence of the invention, a Nanobody® of the invention, a polypeptide of the invention, a compound or construct of the invention or monovalent construct of the invention in the preparation of a pharmaceutical composition for prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma; and/or for use in one or more of the methods described herein.

The invention also relates to an amino acid sequence of the invention, a Nanobody® of the invention, a polypeptide of the invention, a compound or construct of the invention or monovalent construct of the invention for prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

More in particular, the present invention may relate to a method for the prevention and/or treatment of infection by hRSV, said method comprising administering, to a subject in need thereof, a pharmaceutically active amount of a multivalent (e.g. trivalent or bivalent) polypeptide or compound of the invention, and/or of a pharmaceutical composition comprising the same. More in particular, the present invention may relate to a method for the prevention and/or treatment of infection by hRSV, said method comprising administering, to a subject in need thereof, a pharmaceutically active amount of a bivalent compound or polypeptide of the invention. More in particular, the present invention may relate to a method for the prevention and/or treatment of infection by hRSV, said method comprising administering, to a subject in need thereof, a pharmaceutically active amount of a bivalent humanized and/or sequence optimized NC41 Nanobody® (such as e.g. a bivalent polypeptide comprising two Nanobodies® selected from SEQ ID NO's: 60-76, 138-141 and 146-157). More in particular, the present invention may relate to a method for the prevention and/or treatment of infection by hRSV, said method comprising administering, to a subject in need thereof, a pharmaceutically active amount of a trivalent compound or polypeptide of the invention. More in particular, the present invention may relate to a method for the prevention and/or treatment of infection by hRSV, said method comprising administering, to a subject in need thereof, a pharmaceutically active amount of a trivalent humanized NC41 Nanobody® (such as e.g. a trivalent polypeptide comprising three Nanobodies® selected from SEQ ID NO's: 60-76, 138-141 and 146-157). More in particular, the present invention may relate to a method for the prevention and/or treatment of infection by hRSV, said method comprising administering, to a subject in need thereof, a pharmaceutically active amount of one of SEQ ID NO's: 77-79, 142-145 and 158-165.

More in particular, the present invention may relate to a method for the prevention and/or treatment of infection by hRSV said method comprising administering to the pulmonary tissue of a subject in need thereof, a pharmaceutically active amount of an amino acid sequence of the invention, of a Nanobody® of the invention, of a polypeptide of the invention, and/or of a pharmaceutical composition comprising the same.

In another aspect, the invention relates to a method for immunotherapy, and in particular for passive immunotherapy, which method comprises administering, to a subject suffering from or at risk of the diseases and disorders mentioned herein, a pharmaceutically active amount of an amino acid sequence of the invention, of a Nanobody® of the invention, of a polypeptide of the invention, of a compound or construct of the invention and/or of a pharmaceutical composition comprising the same.

In the above methods, the amino acid sequences, Nanobodies®, compounds or constructs and/or polypeptides of the invention and/or the compositions comprising the same can be administered in any suitable manner, depending on the specific pharmaceutical formulation or composition to be used. Thus, the amino acid sequences, Nanobodies® and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

Thus, in general, the amino acid sequences, Nanobodies®, compounds or constructs and polypeptides according to the invention and/or the compositions comprising the same can be administered in any suitable manner; for example but not limited thereto, the amino acid sequences, Nanobodies®, compounds or constructs and polypeptides according to the invention and compositions comprising the same can be administered intranasally and/or by inhalation and/or by any other suitable form of pulmonary delivery; methods for pulmonary delivery and/or intranasal delivery and/or delivery by inhalation of a Nanobody®, amino acid sequence, compound or construct and/or polypeptide of the invention will be known to the skilled person and are e.g. described in the handbook "Drug Delivery: Principles and Applications" (2005) by Binghe Wang, Teruna Siahaan and Richard Soltero (Eds, Wiley Interscience (John Wiley & Sons)); in the International application WO 08/049,897 of Ablynx N. V. entitled "Intranasal delivery of polypeptides and proteins"; in "Pharmacology PreTest™ Self-Assessment and Review" (11$^{th}$ Edition) by Rosenfeld G. C., Loose-Mitchell D. S.; and in "Pharmacology" (3$^{rd}$ Edition) by Lippincott Williams & Wilkins, New York; Shlafer M. McGraw-Hill Medical Publishing Division, New York; Yang K. Y., Graff L. R., Caughey A. B. Blueprints Pharmacology, Blackwell Publishing.

Accordingly, the present invention also relates to a method for administering an effective amount of a amino acid sequence, Nanobody®, compound or construct and/or polypeptide of the invention and/or a composition comprising the same, wherein said method comprises the step of administering the amino acid sequence, Nanobody®, compound or construct and/or polypeptide and/or composition comprising the same to the pulmonary tissue. In such method, the amino acid sequence, Nanobody®, compound or construct and/or polypeptide and/or a composition comprising the same can be administered by any method know in the art for pulmonary delivery such as e.g. by use of an inhaler or intranasal delivery device or aerosol.

In a preferred aspect of the invention, the amino acid sequence, Nanobody®, compound or construct and/or polypeptide will bind and/or neutralize virus present in the pulmonary tissue. Preferably in such method for pulmonary delivery at least 5%, preferably at least 10%, 20%, 30%, 40%, more preferably at least 50%, 60%, 70%, and even more preferably at least 80% or more of the amino acid sequence, Nanobody®, compound or construct and/or polypeptide of the invention is stable in the pulmonary tissue for at least 24 hours, preferably at least 48 hours more preferably at least 72 hours.

It has been surprisingly found that the amino acid sequences, Nanobodies®, compounds or constructs and/or polypeptides of the invention have a long lasting stability in the pulmonary tissue. E.g. it has been found that a Nanobody® directed against hRSV remains functional in the lung for at least 48 hours (see PCT/EP2009/056975 entitled Amino acid sequences directed against envelope proteins of a virus and polypeptides comprising the same for the treatment of viral diseases filed by Ablynx N. V. on 5 Jun. 2009). Thus, embodiments of the invention with treatment intervals such as once a day, once every 2$^{nd}$, 3$^{rd}$, 4$^{th}$, 5$^{th}$, 6$^{th}$ or once every week are thought to be possible taken the estimated long lasting stability of the amino acid sequences, Nanobodies®, compounds or constructs and/or polypeptides of the invention.

Accordingly, the invention relates to a method for delivering an amino acid sequence, Nanobody®, compound or construct and/or polypeptide of the invention to the pulmonary tissue of a subject without being inactivated, said method comprising the step of pulmonary administering said amino acid sequence, Nanobody®, compound or construct and/or polypeptide of the invention to said subject.

The invention also relates to a method for the prevention and/or treatment of hRSV infection, said method comprising administering to the pulmonary tissue of a subject in need thereof, a pharmaceutically active amount of an amino acid sequence of the invention, of a Nanobody® of the invention, of a polypeptide of the invention, of a compound or construct of the invention and/or of a pharmaceutical composition comprising the same.

More in particular, the invention relates to a method for the prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma, said method comprising administering, to the pulmonary tissue of a subject in need thereof, a pharmaceutically active amount of an amino acid sequence of the invention, of a Nanobody® of the invention, of a polypeptide of the invention, of a compound or construct of the invention and/or of a pharmaceutical composition comprising the same.

More in particular, the present invention may relate to a method for the prevention and/or treatment of infection by hRSV, said method comprising administering, to the pulmonary tissue of a subject in need thereof, a pharmaceutically active amount of a multivalent (e.g. trivalent, bivalent) polypeptide or compound of the invention, and/or of a pharmaceutical composition comprising the same. More in particular, the present invention may relate to a method for the prevention and/or treatment of infection by hRSV, said method comprising administering, to the pulmonary tissue of a subject in need thereof, a pharmaceutically active amount of a bivalent compound or polypeptide of the invention. More in particular, the present invention may relate to a method for the prevention and/or treatment of infection by hRSV, said method comprising administering, to the pulmonary tissue of a subject in need thereof, a pharmaceutically active amount of a bivalent humanized NC41 Nanobody® (such as e.g. a bivalent polypeptide comprising two Nanobodies® selected from SEQ ID NO's: 60-76, 138-141 and 146-157). More in particular, the present invention may relate to a method for the prevention and/or treatment of infection by hRSV, said method comprising administering, to the pulmonary tissue of a subject in need thereof, a pharmaceutically active amount of a trivalent compound or polypeptide of the invention. More in particular, the present invention may relate to a method for the prevention and/or treatment of infection by hRSV, said method comprising administering, to the pulmonary tissue of a subject in need thereof, a pharmaceutically active amount of a trivalent humanized NC41 Nanobody® (such as e.g. a trivalent polypeptide comprising three Nanobodies® selected from SEQ ID NO's: 60-76, 138-141 and 146-157). More in particular, the present invention may relate to a method for the prevention and/or treatment of infection by hRSV, said method comprising administering, to the pulmonary tissue of a subject in need thereof, a pharmaceutically active amount of one of SEQ ID NO's: 77-79, 142-145 and 158-165.

Also for example but not limited thereto, the amino acid sequences, Nanobodies®, compounds or constructs, and polypeptides according to the invention and compositions comprising the same, can be administered intramuscularly and/or by any suitable form of delivery to the brain, such as any suitable form of delivery which allows said amino acid sequences, Nanobodies®, polypeptides, compounds or constructs and compositions comprising the same to be transported across the blood-brain-barrier. Such methods for intramuscular delivery and/or any suitable form of delivery to the brain of a Nanobody®, amino acid sequence and/or polypeptide of the invention will be known to the skilled person and are e.g. described in the handbook "Drug Delivery: Principles and Applications" (2005) by Binghe Wang, Teruna Siahaan and Richard Soltero (Eds. Wiley Interscience (John Wiley & Sons)); in "Pharmacology PreTest™ Self-Assessment and Review" ($11^{th}$ Edition) by Rosenfeld G. C., Loose-Mitchell D. S.; and in "Pharmacology" ($3^{rd}$ Edition) by Lippincott Williams & Wilkins, New York; Shlafer M. McGraw-Hill Medical Publishing Division, New York; Yang K. Y., Graff L. R., Caughey A. B. Blueprints Pharmacology, Blackwell Publishing.

The amino acid sequences, Nanobodies®, compounds or constructs and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, Nanobody®, compound or construct or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, Nanobodies®, compounds or constructs and/or polypeptides of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency of the specific amino acid sequence, Nanobody®, compound or construct and polypeptide of the invention to be used, the specific route of administration and the specific pharmaceutical formulation or composition used, the amino acid sequences, Nanobodies®, compounds or constructs and polypeptides of the invention will generally be administered in an amount between 1 gram and 1 microgram per kg body weight per day, preferably between 0.1 gram and 10 microgram per kg body weight per day, most preferably between 0.01 gram and 100 microgram per kg body weight per day such as about 0.1, 0.5, 1, 2, 5 or 10 milligram per kg body weight per day, either continuously (e.g. by infusion), as a single daily dose or as multiple divided doses during the day. Amino acid sequences, Nanobodies®, compounds or constructs and polypeptides of the invention that contain a half-life extending moiety may be administered in an amount between 1 milligram and 100 milligram per kg body weight, preferably between 1 milligram and 50 milligram per kg body weight, such as about 10, 15, 20 or 30 milligram per kg body weight once or twice a month. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, and similar factors well known to the skilled person.

When the amino acid sequence, Nanobody®, compound or construct and/or polypeptide and/or a composition comprising the same is administered to the pulmonary tissue the treatment regime may be once or twice daily, preferably once daily, or once every 2, 3, 4, 5, 6, or 7 days.

Usually, in the above method, a single amino acid sequence, Nanobody®, compound or construct, or polypeptide of the invention will be used. It is however within the scope of the invention to use two or more amino acid sequences, Nanobodies®, compounds or constructs and/or polypeptides of the invention in combination.

The Nanobodies®, amino acid sequences, compounds or constructs and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, Nanobodies®, compounds or constructs, and polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an amino acid sequence, Nanobody®, compound or construct, or polypeptide of the invention in the preparation of a pharmaceutical composition for prevention and/or treatment of at least one viral disease; and/or for use in one or more of the methods of treatment mentioned herein.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention also relates to the use of an amino acid sequence, Nanobody®, compound or construct or polypeptide of the invention in the preparation of a pharmaceutical composition for the prevention and/or treatment of at least one disease or disorder that can be prevented and/or treated by administering an amino acid sequence, Nanobody®, compound or construct or polypeptide of the invention to a patient.

More in particular, the invention relates to the use of an amino acid sequence, Nanobody®, compound or construct or polypeptide of the invention in the preparation of a pharmaceutical composition for the prevention and/or treatment of viral diseases, and in particular for the prevention and treatment of one or more of the diseases and disorders listed herein.

Again, in such a pharmaceutical composition, the one or more amino acid sequences, Nanobodies®, compounds or constructs or polypeptides of the invention may also be suitably combined with one or more other active principles, such as those mentioned herein.

Further uses of the amino acid sequences, Nanobodies®, polypeptides, nucleic acids, genetic constructs and hosts and host cells of the invention will be clear to the skilled person based on the disclosure herein. For example, and without limitation, the amino acid sequences of the invention can be linked to a suitable carrier or solid support so as to provide a medium than can be used in a manner known per se to purify an envelope protein of a virus from compositions and preparations comprising the same. Derivatives of the amino acid sequences of the invention that comprise a suitable detectable label can also be used as markers to determine (qualitatively or quantitatively) the presence of an envelope protein of a virus in a composition or preparation or as a marker to selectively detect the presence of an envelope protein of a virus on the surface of a cell or tissue (for example, in combination with suitable cell sorting techniques).

The invention will now be further described by means of the following non-limiting preferred aspects, examples and figures:

The entire contents of all of the references (including literature references, issued patents, published patent applications, and co-pending patent applications) cited throughout this application are hereby expressly incorporated by reference, in particular for the teaching that is referenced hereinabove.

Aspects

Aspect A-1. Amino acid sequence that is directed against and/or specifically binds protein F of hRSV and that comprises at least a stretch of amino acid residues chosen from the following:
a) SEQ ID NO: 102;
b) a stretch of amino acid residues that has no more than 3, preferably no more than 2, more preferably no more than 1 amino acid difference with SEQ ID NO: 102, provided that:
i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect A-2. Amino acid sequence according to aspect A-1, that comprises two or more stretches of amino acid residues in which one stretch is chosen from the following:
a) SEQ ID NO: 102;
b) a stretch of amino acid residues that has no more than 3, preferably no more than 2, more preferably no more than 1 amino acid difference with SEQ ID NO: 102, provided that:
i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and at least one stretch is chosen from:
c) SEQ ID NO: 98;
d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
e) SEQ ID NO: 121; and
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.
such that the stretch of amino acid residues that corresponds to one of a) and b) should always be present in the amino acid sequence of the invention and such that the second stretch of amino acid residues is chosen from one of c), d), e) and f).

Aspect A-3. Amino acid sequence according to aspect A-1 or A-2, that comprises three or more stretches of amino acid residues, in which the first stretch of amino acid residues is chosen from the group consisting of:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
the second stretch of amino acid residues is chosen from the group consisting of:
c) SEQ ID NO: 102;
d) a stretch of amino acid residues that has no more than 3, preferably no more than 2, more preferably no more than 1 amino acid difference with SEQ ID NO: 102, provided that:
i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and the third stretch of amino acid residues is chosen from the group consisting of:
e) SEQ ID NO: 121;
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect A-4. Amino acid sequence according to any of aspects A-1 to A-3, that specifically binds antigenic site II on protein F of hRSV and/or that competes with Synagis® for binding protein F of hRSV.

Aspect A-5, Amino acid sequence according to any of aspects A-1 to A-4, that is a naturally occurring amino acid sequence (from any suitable species) or a synthetic or semi-synthetic amino acid sequence.

Aspect A-6. Amino acid sequence according to any of aspects A-1 to A-5, that comprises an immunoglobulin fold or that under suitable conditions is capable of forming an immunoglobulin fold.

Aspect A-7. Amino acid sequence according to any of aspects A-1 to A-6, that is an immunoglobulin sequence.

Aspect A-8. Amino acid sequence according to any of aspects A-1 to A-7, that is a naturally occurring immunoglobulin sequence (from any suitable species) or a synthetic or semi-synthetic immunoglobulin sequence.

Aspect A-9. Amino acid sequence according to any of aspects A-1 to A-8, that is a humanized immunoglobulin sequence, a camelized immunoglobulin sequence or an immunoglobulin sequence that has been obtained by techniques such as affinity maturation.

Aspect A-10. Amino acid sequence according to any of aspects A-1 to A-9, that essentially consists of a heavy chain variable domain sequence (e.g. a $V_H$-sequence).

Aspect A-11. Amino acid sequence according to any of aspects A-1 to A-10, that essentially consists of a heavy chain variable domain sequence that is derived from a conventional four-chain antibody or that essentially consist of a heavy chain variable domain sequence that is derived from heavy chain antibody.

Aspect A-12. Amino acid sequence according to any of aspects A-1 to A-11, that essentially consists of a domain antibody (or an amino acid sequence that is suitable for use as a domain antibody), of a single domain antibody (or an amino acid sequence that is suitable for use as a single domain antibody), of a "dAb" (or an amino acid sequence that is suitable for use as a dAb) or of a Nanobody® (including but not limited to a $V_{HH}$ sequence).

Aspect A-13. Amino acid sequence according to any of aspects A-1 to A-12, that essentially consist of 4 framework regions (FR1 to FR4, respectively) and 3 complementarity determining regions (CDR1 to CDR3, respectively), in which CDR2 is chosen from:
a) SEQ ID NO: 102;
b) a stretch of amino acid residues that has no more than 3, preferably no more than 2, more preferably no more than 1 amino acid difference with SEQ ID NO: 102, provided that:
i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect A-14. Amino acid sequence according to aspect A-13, that essentially consists of 4 framework regions (FR1 to FR4, respectively) and 3 complementarity determining regions (CDR1 to CDR3, respectively), in which CDR2 is chosen from the group consisting of:
a) SEQ ID NO: 102; or
b) a stretch of amino acid residues that has no more than 3, preferably no more than 2, more preferably no more than 1 amino acid difference with SEQ ID NO: 102, provided that:
i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and at least one of CDR1 or CDR3 is chosen from:
CDR1 chosen from the group consisting of:
c) SEQ ID NO: 98;
d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and/or
CDR3 chosen from the group consisting of:
e) SEQ ID NO: 121;
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect A-15. Amino acid sequence according to any of aspects A-13 or A-14, that consists of 4 framework regions (FR1 to FR4, respectively) and 3 complementarity determining regions (CDR1 to CDR3, respectively), in which:
CDR1 is chosen from the group consisting of:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and
CDR2 is chosen from the group consisting of:
c) SEQ ID NO: 102;
d) a stretch of amino acid residues that has no more than 3, preferably no more than 2, more preferably no more than 1 amino acid difference with SEQ ID NO: 102, provided that:

i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and
CDR3 is chosen from the group consisting of:
e) SEQ ID NO: 121;
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect A-16. Amino acid sequence according to any of aspects A-1 to A-15, that comprises at least SEQ ID NO: 102.

Aspect A-17. Amino acid sequence according to aspect A-16, that comprises at least SEQ ID NO: 102 and at least one stretch of amino acid residues (CDR sequence) chosen from:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
c) SEQ ID NO: 121; and
d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect A-18, Amino acid sequence according to any of aspects A-16 or A-17, that comprises at least SEQ ID NO: 102 and a CDR1 sequence chosen from:
a) SEQ ID NO: 98; and
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and a CDR3 sequence chosen from:
c) SEQ ID NO: 121; and
d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect A-19. Amino acid sequence according to any of aspects A-16 to A-18, that comprises at least SEQ ID NO: 102 and at least one stretch of amino acid residues (CDR sequence) chosen from SEQ ID NO: 98 and SEQ ID NO: 121.

Aspect A-20. Amino acid sequence according to any of aspects A-16 to A-19, that comprises SEQ ID NO: 98, SEQ ID NO: 102 and SEQ ID NO: 121.

Aspect A-21. Amino acid sequence according to any of aspects A-1 to A-20, that essentially consists of a Nanobody® that:
a) has at least 80% amino acid identity with at least one of the amino acid sequences of SEQ ID NO's: 60-76, 138-141 and 146457, in which for the purposes of determining the degree of amino acid identity, the amino acid residues that form the CDR sequences are disregarded;
and in which:
b) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020,079.

Aspect A-22. Amino acid sequence according to any of aspects A-1 to A-21, that essentially consists of a humanized Nanobody®.

Aspect A-23. Amino acid sequence according to aspect A-22, that essentially consists of a humanized Nanobody® which can bind (as further defined herein) to protein F of hRSV and which:
i) is a humanized variant of the amino acid sequences of SEQ ID NO: 5 (see Table A-1); and/or
ii) has at least 80% amino acid identity with the amino acid sequences of SEQ ID NO: 5 (see Table A-1) and/or at least one of the amino acid sequences of SEQ ID NO's: 60-76, 138-141 and 146-157 (see Table A-4), in which for the purposes of determining the degree of amino acid identity, the amino acid residues that form the CDR sequences are disregarded;
and in which:
iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020,079.

Aspect A-24. Amino acid sequence according to any of aspects A-1 to A-23, that is in essentially isolated form.

Aspect A-25. Amino acid sequence according to any of aspects A-1 to A-24, for administration to a subject, wherein said amino acid sequence does not naturally occur in said subject.

Aspect A-26. Amino acid sequence according to any of aspects A-1 to A-25, that can specifically bind to protein F of hRSV with a dissociation constant ($K_D$) of 1000 nM to 1 nM or less, preferably 100 nM to 1 nM or less, more preferably 10 nM to 1 nM or less.

Aspect A-27. Amino acid sequence according to any of aspects A-1 to A-26, that can specifically bind to protein F of hRSV with a $k_{on}$-rate of between $10^4$ $M^{-1}$ $s^{-1}$ to about $10^7$ $M^{-1}$ $s^{-1}$ preferably between $10^5$ and $10^7$ $M^{-1}$ $s^{-1}$, more preferably about $10^6$ $M^{-1}$ $s^{-1}$ or more.

Aspect A-28. Amino acid sequence according to any of aspects A-1 to A-27, that can specifically bind to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

Aspect A-29. Amino acid sequence according to any of aspects A-1 to A-28, that can neutralize hRSV (for example, as measured in a microneutralization assay on hRSV Long (such as e.g. described in Example 6) with an IC50 value between 100 nM and 1000 nM, preferably between 100 nM and 500 nM, or less.

Aspect B-1. Nanobody® that is directed against and/or that specifically binds protein F of hRSV, in which CDR2 is chosen from:
a) SEQ ID NO: 102;
b) a stretch of amino acid residues that has no more than 3, preferably no more than 2, more preferably no more than 1 amino acid difference with SEQ ID NO: 102, provided that:
i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect B-2. Nanobody® according to aspect B-1, in which CDR2 is chosen from the group consisting of:
a) SEQ ID NO: 102; or
b) a stretch of amino acid residues that has no more than 3, preferably no more than 2, more preferably no more than 1 amino acid difference with SEQ ID NO: 102, provided that:
i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and at least one of CDR1 or CDR3 is chosen from:
CDR1 chosen from the group consisting of:
c) SEQ ID NO: 98;
d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and/or
CDR3 chosen from the group consisting of:
e) SEQ ID NO: 121;
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect B-3. Nanobody® according to any of aspects B-1 or B-2, in which:
CDR1 is chosen from the group consisting of:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and
CDR2 is chosen from the group consisting of:
c) SEQ ID NO: 102;
d) a stretch of amino acid residues that has no more than 3, preferably no more than 2, more preferably no more than 1 amino acid difference with SEQ ID NO: 102, provided that:
i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and

CDR3 is chosen from the group consisting of:

e) SEQ ID NO: 121;

f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect B-4. Nanobody® according to any of aspects B-1 to B-3, that comprises at least SEQ ID NO: 102.

Aspect B-5. Nanobody® according to aspect B-4, that comprises at least SEQ ID NO: 102 and at least one CDR sequence chosen from:

a) SEQ ID NO: 98;

b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

c) SEQ ID NO: 121; and d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect B-6, Nanobody® according to any of aspects B-4 or B-5, that comprises at least SEQ ID NO: 102 and a CDR1 sequence chosen from:

a) SEQ ID NO: 98; and b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and a CDR3 sequence chosen from:

c) SEQ ID NO: 121; and d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect B-7. Nanobody® according to any of aspects B-4 to B-6, that comprises at least SEQ ID NO: 102 and at least one CDR sequence chosen from SEQ ID NO: 98 and SEQ ID NO: 121.

Aspect B-8. Nanobody® according to any of aspects B-4 to B-7, that comprises SEQ ID NO: 98, SEQ ID NO: 102 and SEQ ID NO: 121.

Aspect B-9. Nanobody® according to any of aspects B-1 to B-8, that is in essentially isolated form.

Aspect B-10. Nanobody® according to any of aspects B-1 to B-9, that can specifically bind to protein F of hRSV with a dissociation constant ($K_D$) of 1000 nM to 1 nM or less, preferably 100 nM to 1 nM or less, more preferably 10 nM to 1 nM or less.

Aspect B-11. Nanobody® according to any of aspects B-1 to B-10, that can specifically bind to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect B-12. Nanobody® according to any of aspects B-1 to B-11, that can specifically bind to protein F of hRSV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

Aspect B-13. Nanobody® according to any of aspects B-1 to B-12, that can neutralize hRSV (for example, as measured in a microneutralization assay on hRSV Long (such as e.g. described in Example 6) with an IC50 value between 100 nM and 1000 nM, preferably between 100 nM and 500 nM, or less.

Aspect B-14. Nanobody® according to any of aspects B-1 to B-13, that is a naturally occurring Nanobody® (from any suitable species) or a synthetic or semi-synthetic Nanobody®.

Aspect B-15. Nanobody® according to any of aspects B-1 to B-14, that is a $V_{HH}$ sequence, a partially humanized $V_{HH}$ sequence, a fully humanized $V_{HH}$ sequence, a camelized heavy chain variable domain or a Nanobody® that has been obtained by techniques such as affinity maturation.

Aspect B-16. Nanobody® according to any of aspects B-1 to B-15, which is a partially humanized Nanobody®.

Aspect B-17. Nanobody® according to any of aspects B-1 to B-16, which is a fully humanized Nanobody®.

Aspect B-18. Nanobody® according to any of aspects B-1 to B-17, that essentially consists of a humanized Nanobody® which can bind (as further defined herein) to protein F of hRSV and which:

i) is a humanized variant of the amino acid sequences of SEQ ID NO: 5 (see Table A-1); and/or ii) has at least 80% amino acid identity with the amino acid sequences of SEQ ID NO: 5 (see Table A-1) and/or at least one of the amino acid sequences of SEQ ID NO's: 60-76, 138-141 and 146-157 (see Table A-4), in which for the purposes of determining the degree of amino acid identity, the amino acid residues that form the CDR sequences are disregarded;

and in which:
  iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020,079.

Aspect C-1: Amino acid sequence that is directed against and/or specifically binds protein F of hRSV chosen from the following:
  a) SEQ ID NO's: 60-76;
  b) amino acid sequences that have no more than 3, preferably no more than 2, more preferably no more than 1 amino acid difference with one of SEQ ID NO's: 60-76, provided that:
    i) the amino acid sequence has a Glutamine (Gln, Q) at position 105 (said position determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect C-2: Amino acid sequence according to aspect C-1, that comprises or essentially consists of one of SEQ ID NO's: 60-76.

Aspect C-3: Amino acid sequence that is directed against and/or specifically binds protein F of hRSV chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect C-4: Amino acid sequence according to aspect C-3, that is chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect C-5: Amino acid sequence according to any of aspects C-3 or C-4, that comprises or essentially consists of one of SEQ ID NO's: 62, 65, 67, 68, 75 and 76.

Aspect C-6: Amino acid sequence that is directed against and/or specifically binds protein F of hRSV chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino add sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino add difference.

Aspect C-7: Amino acid sequence according to aspect C-6, that is chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect C-8: Amino acid sequence that is directed against and/or specifically binds protein F of hRSV chosen from the following:
  a) SEQ ID NO's: 146-153;
  b) amino add sequences that have no more than 3, preferably no more than 2, more preferably no more than 1 amino acid difference with one of SEQ ID NO's: 146-153, provided that:
    i) the amino acid sequence has a Praline (Pro, P) at position 14, Arginine (Arg, R) at position 19, Leucine (Leu, L) at position 20 and Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect C-9: Amino acid sequence according to aspect C-8, that comprises or essentially consists of one of SEQ ID NO's: 146-153.

Aspect C-10: Amino acid sequence that is directed against and/or specifically binds protein F of hRSV chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108; and in addition Arginine (Arg, R) at position 83, Glutamic acid (Glu, E) at position 85 and/or Glutamine (Gln, Q) at position 105 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect C-11: Amino acid sequence according to aspect C-10, that is chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino add sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect C-12: Amino acid sequence according to any of aspects C-10 or C-11, that comprises or essentially consists of one of SEQ ID NO's: 146-149 and 151-153.

Aspect C-13: Amino acid sequence comprising or essentially consisting of SEQ ID NO: 5, in which one or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-14: Amino acid sequence according to aspect C-13, comprising or essentially consisting of SEQ ID NO: 5, in which two or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-15: Amino acid sequence according to aspect C-14, comprising or essentially consisting of SEQ ID NO: 5, in which three or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-16: Amino acid sequence according to aspect C-15, comprising or essentially consisting of SEQ ID NO: 5, in which four or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-17: Amino acid sequence according to aspect C-16, comprising or essentially consisting of SEQ ID NO: 5, in which five or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-18: Amino acid sequence according to aspect C-17, comprising or essentially consisting of SEQ ID NO: 5, in which six or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-19: Amino acid sequence according to aspect C-18, comprising or essentially consisting of SEQ ID NO: 5, in which seven or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-20: Amino acid sequence according to aspect C-19, comprising or essentially consisting of SEQ ID NO: 5, in which eight or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-21: Amino acid sequence according to aspect C-20, comprising or essentially consisting of SEQ ID NO: 5, in which nine or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-22: Amino acid sequence according to aspect C-21, comprising or essentially consisting of SEQ ID NO: 5, in which ten or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-23: Amino acid sequence according to aspect C-22, comprising or essentially consisting of SEQ ID NO: 5, in which following amino acid residues have been mutated:

Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect C-24: Amino acid sequence according to aspect C-13, comprising or essentially consisting of SEQ ID NO: 5, in which one or more amino acid residues have been mutated selected from the following: Ser19R, Ile20Leu, Ala74Ser, Gly78Leu, Ala83Arg, Asp85Glu, Arg105Gln and Gly54D.

Aspect C-25: Amino acid sequence according to aspect C-13, comprising or essentially consisting of SEQ ID NO: 5, in which one or more amino acid residues have been mutated selected from the following: Gly78Leu, Ala83Arg, Asp85Glu, Arg105Gln and Gly54D.

Aspect C-26: Amino acid sequence according to aspect C-25, comprising or essentially consisting of SEQ ID NO: 5, in which following amino acid residues have been mutated: Gly78Leu, Ala83Arg, Asp85Glu, Arg105Gln and Gly54D.

Aspect C-27: Amino acid sequence comprising or essentially consisting of SEQ ID NO: 5, in which one or more amino acid residues have been mutated selected from the following: Ala14Pro, Ser19Arg, Ile20Leu and Gln108Leu.

Aspect C-28: Amino acid sequence comprising or essentially consisting of SEQ ID NO: 5, in which one or more amino acid residues have been mutated selected from the following: Ala14Pro, Ser19Arg, Ile20Leu, Ala83Arg, Asp85Glu, Arg105Gln and Gln108Leu.

Aspect C-29: Amino acid sequence according to aspect C-8, comprising or essentially consisting of SEQ ID NO: 5, wherein following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or
Ala14Pro, Ser19Arg, Ile20Leu, Gln108Leu, Ala83Arg, Asp85Glu and Arg105Gln.

Aspect C-30: Amino acid sequence comprising or essentially consisting of SEQ ID NO: 62.

Aspect C-31: Amino acid sequence comprising or essentially consisting of SEQ ID NO: 65.

Aspect C-32: Amino acid sequence comprising or essentially consisting of SEQ ID NO: 76.

Aspect C-33: Amino acid sequence comprising or essentially consisting of any of SEQ ID NO's: 146-153: 76

Aspect C-34: Amino acid sequence according to any of aspects C-1 to C-33, that can specifically bind to protein F of hRSV with a dissociation constant ($K_D$) of 1000 nM to 1 nM or less, preferably 100 nM to 1 nM or less, more preferably 10 nM to 1 nM or less.

Aspect C-35: Amino acid sequence according to any of aspects C-1 to C-34, that can specifically bind to protein F of hRSV with a k-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6 M^{-1}$ $s^{-1}$ or more.

Aspect C-36: Amino acid sequence according to any of aspects C-1 to C-35, that can specifically bind to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

Aspect C-37: Amino acid sequence according to any of aspects C-1 to C-36, that can neutralize hRSV (for example, as measured in a microneutralization assay on hRSV Long (such as e.g. described in Example 6) with an IC50 value between 100 nM and 1000 nM, preferably between 100 nM and 500 nM, or less.

Aspect C-38: Amino acid sequence according to any of aspects C-1 to C-37, that specifically binds antigenic site II on protein F of hRSV and/or that competes with Synagis® for binding protein F of hRSV.

Aspect D-1: Nanobody® that is directed against and/or specifically binds protein F of hRSV, chosen from the following:
a) SEQ ID NO's: 60-76;
b) amino acid sequences that have no more than 3, preferably no more than 2, more preferably no more than 1 amino acid difference with one of SEQ ID NO's: 60-76, provided that:
  i) the amino acid sequence has a Glutamine (Gln, Q) at position 105 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect D-2: Nanobody® according to aspect D-1, that comprises or essentially consists of one of SEQ ID NO's: 60-76.

Aspect D-3: Nanobody® that is directed against and/or specifically binds protein F of hRSV chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect D-4: Nanobody® according to any of aspect D-3, that is chosen from the following:

a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
   i) the amino acid sequence has a Glutamine (Gln, Q) at position 105, a Leucine (Leu, L) at position 78 and an Arginine (Arg, R) at position 83 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect D-5: Nanobody® according to any of aspects D-3 or D-4, that comprises or essentially consists of one of SEQ ID NO's: 62, 65, 67, 68, 75 and 76.

Aspect D-6: Nanobody® that is directed against and/or specifically binds protein r of hRSV chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
   i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect D-7: Nanobody® according to any of aspect D-6, that is chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
   i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
   the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect D-8: Nanobody® that is directed against and/or specifically binds protein F of hRSV chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
   i) the amino acid sequence has a Praline (Pro, P) at position 14, Arginine (Arg, R) at position 19, Leucine (Leu, L) at position 20 and Leucine (Leu, L) at position 108 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect D-9: Nanobody according to aspect D-8, that comprises or essentially consists of one of SEQ ID NO's: 146-153.

Aspect D-10: Nanobody that is directed against and/or specifically binds protein F of hRSV chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
   i) the amino acid sequence has a Proline (Pro, P) at position 14, Arginine (Arg, R) at position 19, Leucine (Leu, L) at position 20 and Leucine (Leu, L) at position 108; and in addition Arginine (Arg, R) at position 83, Glutamic add (Glu, E) at position 85 and/or Glutamine (Gln, Q) at position 105 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect D-11: Nanobody according to aspect D-10, that is chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
   i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
      SEQ ID NO: 146, the amino acid sequence preferably has Glutamine (Gln, Q) at position 105;
      SEQ ID NO: 147, the amino acid sequence preferably has Arginine (Arg, R) at position 83 and Glutamine (Gln, Q) at position 105;
      SEQ ID NO: 148, the amino acid sequence preferably has Glutamic acid (Glu, E) at position 85 and Glutamine (Gln, Q) at position 105;
      SEQ ID NO: 149, the amino acid sequence preferably has Arginine (Arg, R) at position 83, Glutamic acid (Glu, E) at position 85 and Glutamine (Gln, Q) at position 105;
      SEQ ID NO: 151, the amino add sequence preferably has Arginine (Arg, R) at position 83;

SEQ ID NO: 152, the amino acid sequence preferably has Glutamic acid (Glu, E) at position 85;

SEQ ID NO: 153, the amino acid sequence preferably has Arginine (Arg, R) at position 83 and Glutamic acid (Glu, E) at position 85;

(said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect D-12: Nanobody according to any of aspects D-10 or D-11, that comprises or essentially consists of one of SEQ ID NO's: 146-149 and 151-153.

Aspect D-13: Nanobody® comprising or essentially consisting of SEQ ID NO: 5, in which one or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-14: Nanobody® according to aspect D-13, comprising or essentially consisting of SEQ ID NO: 5, in which two or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-15: Nanobody® according to aspect D-14, comprising or essentially consisting of SEQ ID NO: 5, in which three or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-16: Nanobody® according to aspect D-150, comprising or essentially consisting of SEQ ID NO: 5, in which four or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-17: Nanobody® according to aspect D-16, comprising or essentially consisting of SEQ ID NO: 5, in which five or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, an 108Leu and Gly54D.

Aspect D-18: Nanobody® according to aspect D-17, comprising or essentially consisting of SEQ ID NO: 5, in which six or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-19: Nanobody® according to aspect D-18, comprising or essentially consisting of SEQ ID NO: 5, in which seven or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-20: Nanobody® according to aspect D-19, comprising or essentially consisting of SEQ ID NO: 5, in which eight or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-21: Nanobody® according to aspect D-20, comprising or essentially consisting of SEQ ID NO: 5, in which nine or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-22: Nanobody® according to aspect D-21, comprising or essentially consisting of SEQ ID NO: 5, in which ten or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-23: Nanobody® according to aspect D-22, comprising or essentially consisting of SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect D-24: Nanobody® according to aspect D-13, comprising or essentially consisting of SEQ ID NO: 5, in which one or more amino acid residues have been mutated selected from the following: Ser19R, Ile20Leu, Ala74Ser, Gly78Leu, Ala83Arg, Asp85Glu, Arg105Gln and Gly54D.

Aspect D-25: Nanobody® according to aspect D-8, comprising or essentially consisting of SEQ ID NO: 5, in which one or more amino acid residues have been mutated selected from the following: Gly78Leu, Ala83Arg, Asp85Glu, Arg105Gln and Gly54D.

Aspect D-26: Nanobody® according to aspect D-20, comprising or essentially consisting of SEQ ID NO: 5, in which following amino acid residues have been mutated: Gly78Leu, Ala83Arg, Asp85Glu, Arg105Gln and Gly54D.

Aspect D-27: Nanobody® comprising or essentially consisting of SEQ ID NO: 5, in which one or more amino acid residues have been mutated selected from the following: Ala14Pro, Ser19Arg, Ile20Leu and Gln108Leu.

Aspect D-28: Nanobody® comprising or essentially consisting of SEQ ID NO: 5, in which one or more amino acid residues have been mutated selected from the following: Ala14Pro, Ser19Arg, Ile20Leu, Ala83Arg, Asp85Glu, Arg105Gln and Gln108Leu.

Aspect D-29: Nanobody® according to aspect D-13, comprising or essentially consisting of SEQ ID NO: 5, wherein following amino acid residues have been mutated:

Val5Leu, Ala14Pro, Glu44Gly, Gly78Leu, Ala83Arg, Asp85Glu, Arg105Gln and Gln108Leu;

Ala83Arg, Asp85Glu, Arg105Gln and Gln108Leu;

Gly78Leu, Ala83Arg, Asp85Glu and Arg105Gln;

Val5Leu, Ala14Pro, Glu44Gly, Gly78Leu, Ala83Arg, Asp85Glu, Arg105Gln, Gln108Leu and Gly54Asp;

Ala83Arg, Asp85Glu, Arg105Gln, Gln108Leu and Gly54Asp;

Gly78Leu, Ala83Arg, Asp85Glu, Arg105Gln and Gly54Asp;

Gly54Asp;

Ala14Pro, Ser19Arg, Ile20Leu and Gln108Leu;

Ala14Pro, Ser19Arg, Ile20Leu, Gln108Leu and Ala83Arg;

Ala14Pro, Ser19Arg, Ile20Leu, Gln108Leu and Asp85Glu;

Ala14Pro, Ser19Arg, Ile20Leu, Gln108Leu and Arg105Gln;

Ala14Pro, Ser19Arg, Ile20Leu, Gln108Leu, Ala83Arg and Asp85Glu;

Ala14Pro, Ser19Arg, Ile20Leu, Gln108Leu, Ala83Arg and Arg105Gln;

Ala14Pro, Ser19Arg, Ile20Leu, Gln108Leu, Asp85Glu and Arg105Gln; or

Ala14Pro, Ser19Arg, Ile20Leu, Gln108Leu, Ala83Arg, Asp85Glu and Arg105Gln.

Aspect D-30: Nanobody® comprising or essentially consisting of SEQ ID NO: 62.

Aspect D-31: Nanobody® comprising or essentially consisting of SEQ ID NO: 65.

Aspect D-32: Nanobody® comprising or essentially consisting of SEQ ID NO: 76.

Aspect D-33: Nanobody® comprising or essentially consisting of any of SEQ ID NO's: 146-153.

Aspect D-34: Nanobody® according to any of aspects D-1 to D-33, that can specifically bind to protein F of hRSV with a dissociation constant ($K_D$) of 1000 nM to 1 nM or less, preferably 100 nM to 1 nM or less, more preferably 10 nM to 1 nM or less.

Aspect D-35: Nanobody® according to any of aspects D-1 to D-34, that can specifically bind to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect D-36: Nanobody® according to any of aspects D-1 to D-35, that can specifically bind to protein F of hRSV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

Aspect D-37: Nanobody® according to any of aspects D-1 to D-36, that can neutralize hRSV (for example, as measured in a microneutralization assay on hRSV Long (such as e.g. described in Example 6) with an IC50 value between 100 nM and 1000 nM, preferably between 100 nM and 500 nM, or less.

Aspect D-38: Nanobody® according to any of aspects D-1 to D-37, that specifically binds antigenic site II on protein F of hRSV and/or that competes with Synagis® for binding protein F of hRSV.

Aspect W-1: Amino acid sequence according to any of aspects A-1 to A-29 and C-1 to C-38, that is directed against and/or specifically binds protein F of hRSV, wherein the amino acid sequence has Aspartic acid (Asp, D) at position 1 (said position determined according to Kabat numbering).

Aspect W-2: Amino acid sequence that is directed against and/or specifically binds protein F of hRSV chosen from the following:
a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
  i) the amino acid sequence has a Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect W-3: Amino acid sequence according to aspect W-2, that comprises or essentially consists of one of SEQ ID NO's: 138-141 and 154-157.

Aspect W-4: Amino acid sequence comprising or essentially consisting of SEQ ID NO: 5, in which the Glutamic acid at position 1 has been changed into Aspartic acid.

Aspect W-5: Amino acid sequence comprising or essentially consisting of SEQ ID NO: 62, in which the Glutamic acid at position 1 has been changed into Aspartic acid.

Aspect W-6: Amino acid sequence comprising or essentially consisting of SEQ ID NO: 65, in which the Glutamic acid at position 1 has been changed into Aspartic acid.

Aspect W-7: Amino acid sequence comprising or essentially consisting of SEQ ID NO: 76, in which the Glutamic acid at position 1 has been changed into Aspartic acid.

Aspect W-8: Amino acid sequence comprising or essentially consisting of SEQ ID NO: 75, in which the Glutamic acid at position 1 has been changed into Aspartic acid.

Aspect W-9: Amino acid sequence comprising or essentially consisting of SEQ ID NO: 147, in which the Glutamic add at position 1 has been changed into Aspartic acid.

Aspect W-10: Amino acid sequence comprising or essentially consisting of SEQ ID ND: 149, in which the Glutamic acid at position 1 has been changed into Aspartic acid.

Aspect W-11: Amino acid sequence comprising or essentially consisting of SEQ ID NO: 153, in which the Glutamic acid at position 1 has been changed into Aspartic acid.

Aspect W-12: Amino acid sequence comprising or essentially consisting of SEQ ID NO: 5, in which one or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-13: Amino acid sequence according to aspect W-12, comprising or essentially consisting of SEQ ID NO: 5, in which two or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-14: Amino acid sequence according to aspect W-13, comprising or essentially consisting of SEQ ID NO: 5, in which three or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-15: Amino acid sequence according to aspect W-14, comprising or essentially consisting of SEQ ID NO: 5, in which four or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-16: Amino acid sequence according to aspect W-15, comprising or essentially consisting of SEQ ID NO: 5, in which five or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-17: Amino acid sequence according to aspect W-16, comprising or essentially consisting of SEQ ID NO: 5, in which six or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-18: Amino acid sequence according to aspect W-17, comprising or essentially consisting of SEQ ID NO: 5, in which seven or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-19: Amino acid sequence according to aspect W-18, comprising or essentially consisting of SEQ ID NO: 5, in which eight or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-20: Amino acid sequence according to aspect W-19, comprising or essentially consisting of SEQ ID NO: 5, in which nine or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-21: Amino acid sequence according to aspect W-20, comprising or essentially consisting of SEQ ID NO: 5, in which ten or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic add.

Aspect W-22: Amino acid sequence according to aspect W-21, comprising or essentially consisting of SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect W-23: Amino acid sequence according to aspect W-12, comprising or essentially consisting of SEQ ID NO: 5, in which one or more amino acid residues have been mutated selected from the following: Ser19R, Ile20Leu, Ala74Ser, Gly78Leu, Ala83Arg, Asp85Glu, Arg105Gln and Gly54D, and wherein the Glutamic acid at position 1 has been changed into Aspartic acid.

Aspect W-24: Amino acid sequence according to aspect W-12, comprising or essentially consisting of SEQ ID NO: 5, in which one or more amino acid residues have been mutated selected from the following: Gly78Leu, Ala83Arg, Asp85Glu, Arg105Gln and Gly54D, and wherein the glutamic acid at position 1 has been changed into Aspartic acid.

Aspect W-25: Amino acid sequence according to aspect W-24, comprising or essentially consisting of SEQ ID NO: 5, in which following amino acid residues have been mutated: Gly78Leu, Ala83Arg, Asp85Glu, Arg105Gln and Gly54D, and wherein the glutamic acid at position 1 has been changed into Aspartic acid.

Aspect W-26: Amino acid sequence comprising or essentially consisting of SEQ ID NO: 5, in which one or more amino acid residues have been mutated selected from the following: Ala14Pro, Ser19Arg, Ile20Leu and Gln108Leu, and wherein the Glutamic acid at position 1 has been changed into Aspartic acid.

Aspect W-27: Amino acid sequence comprising or essentially consisting of SEQ ID NO: 5, in which one or more amino acid residues have been mutated selected from the following: Ala14Pro, Ser19Arg, Ile20Leu, Ala83Arg, Asp85Glu, Arg105Gln and Gln108Leu, and wherein the Glutamic acid at position 1 has been changed into Aspartic acid.

Aspect W-28: Amino acid sequence according to aspect W-2 or W-3, comprising or essentially consisting of SEQ ID NO: 5, wherein following amino acid residues have been mutated:
- Glu1Asp, Val5Leu, Ala14Pro, Glu44Gly, Gly78Leu, Ala83Arg, Asp85Glu, Arg105Gln and Gln108Leu;
- Glu1Asp, Ala83Arg, Asp85Glu, Arg105Gln and Gln108Leu;
- Glu1Asp, Gly78Leu, Ala83Arg, Asp85Glu and Arg105Gln;
- Glu1Asp, Val5Leu, Ala14Pro, Glu44Gly, Gly78Leu, Ala83Arg, Asp85Glu, Arg105Gln, Gln108Leu and Gly54Asp;
- Glu1Asp, Ala83Arg, Asp85Glu, Arg105Gln, Gln108Leu and Gly54Asp;
- Glu1Asp, Gly78Leu, Ala83Arg, Asp85Glu, Arg105Gln and Gly54Asp;
- Glu1Asp and Gly54Asp;
- Glu1Asp, Ala14Pro, Ser19Arg, Ile20Leu and Gln108Leu;
- Glu1Asp, Ala14Pro, Ser19Arg, Ile20Leu, Gln108Leu and Ala83Arg;
- Glu1Asp, Ala14Pro, Ser19Arg, Ile20Leu, Gln108Leu and Asp85Glu;
- Glu1Asp, Ala14Pro, Ser19Arg, Ile20Leu, Gln108Leu and Arg105Gln;
- Glu1Asp, Ala14Pro, Ser19Arg, Ile20Leu, Gln108Leu, Ala83Arg and Asp85Glu;
- Glu1Asp, Ala14Pro, Ser19Arg, Ile20Leu, Gln108Leu, Ala83Arg and Arg105Gln;
- Glu1Asp, Ala14Pro, Ser19Arg, Ile20Leu, Gln108Leu, Asp85Glu and Arg105Gln; or
- Glu1Asp, Ala14Pro, Ser19Arg, Ile20Leu, Gln108Leu, Ala83Arg, Asp85Glu and Arg105Gln.

Aspect W-29: Amino acid sequence comprising or essentially consisting of SEQ ID NO: 138.

Aspect W-30: Amino acid sequence comprising or essentially consisting of SEQ ID NO: 139.

Aspect W-31: Amino acid sequence comprising or essentially consisting of SEQ ID NO: 140.

Aspect W-32: Amino acid sequence comprising or essentially consisting of SEQ ID NO: 141.

Aspect W-33: Amino acid sequence comprising or essentially consisting of any of SEQ ID NO's: 154-157.

Aspect W-34: Amino acid sequence according to any of aspects W-1 to W-33, that can specifically bind to protein F of hRSV with a dissociation constant ($K_D$) of 1000 nM to 1 nM or less, preferably 100 nM to 1 nM or less, more preferably 10 nM to 1 nM or less.

Aspect W-35: Amino acid sequence according to any of aspects W-1 to W-34, that can specifically bind to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect W-36: Amino acid sequence according to any of aspects W-1 to W-35, that can specifically bind to protein F of hRSV with a $k_{off}$-rate between $10^{-2}$ $s^{-1}$ ($t_{1/2}$=0.69 s) and $10^{-4}$ s$^{-1}$ (providing a near irreversible complex with a t$_{1/2}$ of multiple days), preferably between $10^{-3}$ s$^{-1}$ and $10^{-4}$ s$^{-1}$, or lower.

Aspect W-37: Amino acid sequence according to any of aspects W-1 to W-36, that can neutralize hRSV (for example, as measured in a microneutralization assay on hRSV Long (such as e.g. described in Example 6) with an IC50 value between 100 nM and 1000 nM, preferably between 100 nM and 500 nM, or less.

Aspect W-38: Amino acid sequence according to any of aspects W-1 to W-37, that specifically binds antigenic site II on protein F of hRSV and/or that competes with Synagis® for binding protein F of hRSV.

Aspect X-1: Nanobody® that is directed against and/or specifically binds protein F of hRSV according to any of aspects B-1 to B-18 and D-1 to D-38, wherein the Nanobody has Aspartic acid (Asp, D) at position 1 (said position determined according to Kabat numbering).

Aspect X-2: Nanobody® that is directed against and/or specifically binds protein F of hRSV, chosen from the following:
a) SEQ ID NO's: 138-141 and 154-157;
b) amino add sequences that have no more than 3, preferably no more than 2, more preferably no more than 1 amino acid difference with one of SEQ ID NO's: 138-141 and 154-157, provided that:
i) the amino add sequence has a Aspartic acid (Asp, D) at position 1 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect X-3: Nanobody® according to aspect X-2, that comprises or essentially consists of one of SEQ ID NO's: 138-141 and 154-157.

Aspect X-4: Nanobody® comprising or essentially consisting of SEQ ID NO: 5, in which Glutamic acid at position 1 has been changed into Aspartic acid.

Aspect X-5: Nanobody® comprising or essentially consisting of SEQ ID NO: 62, in which Glutamic acid at position 1 has been changed into Aspartic acid.

Aspect X-6: Nanobody® comprising or essentially consisting of SEQ ID NO: 65, in which Glutamic acid at position 1 has been changed into Aspartic acid.

Aspect X-7: Nanobody® comprising or essentially consisting of SEQ ID NO: 76, in which Glutamic acid at position 1 has been changed into Aspartic acid.

Aspect X-8: Nanobody® comprising or essentially consisting of SEQ ID NO: 75, in which Glutamic acid at position 1 has been changed into Aspartic acid.

Aspect X-9: Nanobody® comprising or essentially consisting of SEQ ID NO: 147, in which Glutamic acid at position 1 has been changed into Aspartic acid.

Aspect X-10: Nanobody® comprising or essentially consisting of SEQ ID NO: 149, in which Glutamic acid at position 1 has been changed into Aspartic acid.

Aspect X-11: Nanobody® comprising or essentially consisting of SEQ ID NO: 153, in which Glutamic acid at position 1 has been changed into Aspartic acid.

Aspect X-12: Nanobody® comprising or essentially consisting of SEQ ID NO: 5, in which one or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-13: Nanobody® according to aspect X-12, comprising or essentially consisting of SEQ ID NO: 5, in which two or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-14: Nanobody® according to aspect X-13, comprising or essentially consisting of SEQ ID NO: 5, in which three or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-15: Nanobody® according to aspect X-14, comprising or essentially consisting of SEQ ID NO: 5, in which four or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-16: Nanobody® according to aspect X-15, comprising or essentially consisting of SEQ ID NO: 5, in which five or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-17: Nanobody® according to aspect X-16, comprising or essentially consisting of SEQ ID NO: 5, in which six or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-18: Nanobody® according to aspect X-17, comprising or essentially consisting of SEQ ID NO: 5, in which seven or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-19: Nanobody® according to aspect X-18, comprising or essentially consisting of SEQ ID NO: 5, in which eight or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-20: Nanobody® according to aspect X-19, comprising or essentially consisting of SEQ ID NO: 5, in which nine or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-21: Nanobody® according to aspect X-20, comprising or essentially consisting of SEQ ID NO: 5, in which ten or more amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-22: Nanobody® according to aspect X-21, comprising or essentially consisting of SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein Glutamic acid at position 1 has been changed into Aspartic acid.

Aspect X-23: Nanobody® according to aspect X-12, comprising or essentially consisting of SEQ ID NO: 5, in which one or more amino acid residues have been mutated selected from the following: Ser19R, Ile20Leu, Ala74Ser, Gly78Leu, Ala83Arg, Asp85Glu, Arg105Gln and Gly54D, and wherein Glutamic acid at position 1 has been changed into Aspartic acid.

Aspect X-24: Nanobody® according to aspect X-12, comprising or essentially consisting of SEQ ID NO: 5, in which one or more amino acid residues have been mutated selected from the following: Gly78Leu, Ala83Arg, Asp85Glu, Arg105Gln and Gly54D, and wherein Glutamic acid at position 1 has been changed into Aspartic acid.

Aspect X-25: Nanobody® according to aspect X-24, comprising or essentially consisting of SEQ ID NO: 5, in which following amino acid residues have been mutated: Gly78Leu, Ala83Arg, Asp85Glu, Arg105Gln and Gly54D, and wherein Glutamic acid at position 1 has been changed into Aspartic acid.

Aspect X-26: Nanobody® comprising or essentially consisting of SEQ ID NO: 5, in which one or more amino acid residues have been mutated selected from the following: Ala14Pro, Ser19Arg, Ile20Leu and Gln108Leu, and wherein Glutamic acid at position 1 has been changed into Aspartic acid.

Aspect X-27: Nanobody® comprising or essentially consisting of SEQ ID NO: 5, in which one or more amino acid residues have been mutated selected from the following: Ala14Pro, Ser19Arg, Ile20Leu, Ala83Arg, Asp85Glu, Arg105Gln and Gln108Leu, and wherein Glutamic acid at position 1 has been changed into Aspartic acid.

Aspect X-28: Nanobody® according to aspect X-2, comprising or essentially consisting of SEQ ID NO: 5, wherein following amino acid residues have been mutated:
Glu1Asp, Val5Leu, Ala14Pro, Glu44Gly, Gly78Leu, Ala83Arg, Asp85Glu, Arg105Gln and Gln108Leu;
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln.

Aspect X-29: Nanobody® comprising or essentially consisting of SEQ ID NO: 138.

Aspect X-30: Nanobody® comprising or essentially consisting of SEQ ID NO: 139.

Aspect X-31: Nanobody® comprising or essentially consisting of SEQ ID NO: 140.

Aspect X-32: Nanobody® comprising or essentially consisting of SEQ ID NO: 141.

Aspect X-33: Nanobody® comprising or essentially consisting of any of SEQ ID NO's: 154-157.

Aspect X-34: Nanobody® according to any of aspects X-1 to X-33, that can specifically bind to protein F of hRSV with a dissociation constant ($K_D$) of 1000 nM to 1 nM or less, preferably 100 nM to 1 nM or less, more preferably 10 nM to 1 nM or less.

Aspect X-35: Nanobody® according to any of aspects X-1 to X-34, that can specifically bind to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect X-36: Nanobody® according to any of aspects X-1 to X-35, that can specifically bind to protein F of hRSV with a $k_{off}$ rate between $10^2$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

Aspect X-37: Nanobody® according to any of aspects X-1 to X-36, that can neutralize hRSV (for example, as measured in a microneutralization assay on hRSV Long (such as e.g. described in Example 6) with an IC50 value between 100 nM and 1000 nM, preferably between 100 nM and 500 nM, or less.

Aspect X-38: Nanobody® according to any of aspects X-1 to X-37, that specifically binds antigenic site II on protein F of hRSV and/or that competes with Synagis® for binding protein F of hRSV.

Aspect E-1: Polypeptide that comprises or essentially consists of one or more amino acid sequences according to any of aspects A-1 to A-29, C-1 to C-38 and W-1 to W-38 and/or one or more Nanobodies® according to any of aspects B-1 to B-18, D-1 to D-38 and X-1 to X-38, and optionally further comprises one or more other amino acid binding units, optionally linked via one or more peptidic linkers.

Aspect E-2: Polypeptide according to aspect E-1, in which said one or more other binding units are immunoglobulin sequences.

Aspect E-3: Polypeptide according to any of aspects E-1 or E-2, in which said one or more other binding units are chosen from the group consisting of domain antibodies, amino acid sequences that are suitable for use as a domain antibody, single domain antibodies, amino acid sequences that are suitable for use as a single domain antibody, "dAb's", amino acid sequences that are suitable for use as a dAb, or Nanobodies®.

Aspect E-4: Polypeptide according to any of aspects E-1 to E-3, in which said one or more amino acid sequences are immunoglobulin sequences.

Aspect E-5: Polypeptide according to any of aspects E-1 to E-4, in which said one or more amino acid sequences are chosen from the group consisting of domain antibodies, amino acid sequences that are suitable for use as a domain antibody, single domain antibodies, amino acid sequences that are suitable for use as a single domain antibody, "dAb's", amino add sequences that are suitable for use as a dAb, or Nanobodies®.

Aspect E-6: Polypeptide according to any of aspects E-1 to E-5, that comprises or essentially consists of one or more Nanobodies® according to any of aspects B-1 to B-18, D-1 to D-8 and X-1 to X-38 and in which said one or more other binding units are Nanobodies®.

Aspect E-7: Polypeptide according to any of aspects E-1 to E-6, which is a multivalent construct.

Aspect E-8: Multivalent polypeptide according to aspect E-7, that comprises or essentially consists of at least two amino acid sequences according to any of aspects A-1 to A-29 and C-1 to C-38 and/or Nanobodies® according to any of aspects B-1 to B-18 and D-1 to D-38 and/or at least one amino acid sequence according to any of aspects W-1 to W-38 and/or at least one Nanobody® according to any of aspects X-1 to X-38.

Aspect E-9: Multivalent polypeptide according to aspect E-8, wherein said at least two amino acid sequences and/or Nanobodies® are identical.

Aspect E-10: Multivalent polypeptide according to any of aspects E-7 to E-9, comprising or essentially consisting of at least two amino acid sequences and/or Nanobodies® that comprise at least a stretch of amino acid residues chosen from the following:
a) SEQ ID NO: 102;
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-11: Multivalent polypeptide according to any of aspects E-7 to E-10, comprising or essentially consisting of at least two amino acid sequences and/or Nanobodies® that comprise at Feast a stretch of amino acid residues chosen from the following:
a) SEQ ID NO: 102;
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or 2 higher potency (as defined herein) compared to the amino acid sequence comprising said stretch of amino acid residues without the 3, 2 or 1 amino acid difference;

and at least one stretch is chosen from:
c) SEQ ID NO: 98;
d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
e) SEQ ID NO: 121; and
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

such that the stretch of amino acid residues that corresponds to one of a) and b) should always be present in the amino acid sequence of the invention and such that the second stretch of amino acid residues is chosen from one of c), d), e) and f).

Aspect E-12: Multivalent polypeptide according to any of aspects E-7 to E-11, comprising or essentially consisting of at least two amino acid sequences and/or Nanobodies® that comprise at least a stretch of amino acid residues chosen from the following:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

a second stretch of amino acid residues chosen from the group consisting of:
c) SEQ ID NO: 102;
d) a stretch of amino acid residues that has no more than 3, preferably no more than 2, more preferably no more than 1 amino acid difference with SEQ ID NO: 102, provided that:

i) said stretch of amino acid residues has an Aspartic acid (Asp, D) at position 6 (position 54 determined according to Kabat numbering); and ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and a third stretch of amino acid residues chosen from the group consisting of:

e) SEQ ID NO: 121;

f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-13: Multivalent polypeptide according to any of aspects E-7 to E-12, comprising or essentially consisting of at least two amino acid sequences and/or Nanobodies® that comprise at least SEQ ID NO: 102.

Aspect E-14: Multivalent polypeptide according to any of aspects E-7 to E-13, comprising or essentially consisting of at least two amino acid sequences and/or Nanobodies® that comprise at least SEQ ID NO: 102 and at least one stretch of amino acid residues (CDR sequence) chosen from:

a) SEQ ID NO: 98;

b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

c) SEQ ID NO: 121; and d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino add sequence comprising said stretch of amino add residues has the same, about the same, or a higher potency (as defined herein) compared to the amino acid sequence comprising said stretch of amino acid residues without the 3, 2 or 1 amino acid difference.

Aspect E-15: Multivalent polypeptide according to any of aspects E-7 to E-14, comprising or essentially consisting of at least two amino acid sequences and/or Nanobodies® that comprise at least SEQ ID NO: 102 and a CDR1 sequence chosen from:

a) SEQ ID NO: 98;

b) a stretch of amino acid residues that has no more than 3, preferably no more than 2, more preferably no more than 1 amino acid difference with SEQ ID NO: 98, provided that the amino add sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and a CDR3 sequence chosen from:

c) SEQ ID NO: 121;

d) a stretch of amino add residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-16: Multivalent polypeptide according to any of aspects E-7 to E-15, comprising or essentially consisting of at least two amino acid sequences and/or Nanobodies® that comprise at least SEQ ID NO: 102 and at least one stretch of amino acid residues (CDR sequence) chosen from SEQ ID NO: 98 and SEQ ID NO: 121.

Aspect E-17: Multivalent polypeptide according to any of aspects E-7 to E-16, comprising or essentially consisting of at least two amino acid sequences and/or Nanobodies® that comprise SEQ ID NO: 98, SEQ ID NO: 102 and SEQ ID NO: 121.

Aspect E-18: Multivalent polypeptide according to any of aspect E-8 to E-17, wherein said at least two amino acid sequences and/or Nanobodies® are identical.

Aspect E-19: Multivalent polypeptide according to any of aspects E-7 to E-9, comprising or essentially consisting of at least two amino acid sequences and/or Nanobodies® chosen from the following:

a) SEQ ID NO's: 60-76;

b) amino acid sequences that have no more than 3, preferably no more than 2, more preferably no more than 1 amino acid difference with one of SEQ ID NO's: 60-76, provided that:

i) the amino acid sequence has a Glutamine (Gln, Q) at position 105 (said position determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-20: Multivalent polypeptide according to aspect E-19, wherein said at least two amino acid sequences and/or Nanobodies® are identical.

Aspect E-21: Multivalent polypeptide according to aspect E-20, that comprises or essentially consists of at least two identical amino acid sequences and/or Nanobodies® chosen from one of SEQ ID NO's: 60-76.

Aspect E-22: Multivalent polypeptide according to any of aspects E-7 to E-9, comprising or essentially consisting of at least two amino acid sequences and/or Nanobodies® chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
i) the amino acid sequence has a Glutamine (Gln, Q) at position 105, a Leucine (Leu, L) at position 78 and/or an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-23: Multivalent polypeptide according to aspect E-22, comprising or essentially consisting of at least two amino acid sequences and/or Nanobodies® chosen from the following:
a) SEQ ID NO's: 62, 65, 67, 58, 75 and 76;
b) amino acid sequences that have no more than 3, preferably no more than 2, more preferably no more than 1 amino acid difference with one of SEQ ID NO's: 62, 65, 67, 68, 75 and 76, provided that:
i) the amino acid sequence has a Glutamine (Gln, Q) at position 105, a Leucine (Leu, L) at position 78 and an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-24: Multivalent polypeptide according to any of aspects E-22 or E-23, wherein said at least two amino acid sequences and/or Nanobodies® are identical.

Aspect E-25: Multivalent polypeptide according to aspect E-24, that comprises or essentially consists of at least two identical amino acid sequences and/or Nanobodies® chosen from one of SEQ ID NO's: 62, 65, 67, 68, 75 and 76.

Aspect E-26: Multivalent polypeptide according to any of aspects E-7 to E-9, comprising or essentially consisting of at least two amino acid sequences and/or Nanobodies® chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-27: Multivalent polypeptide according to aspect E-26, comprising or essentially consisting of at least two amino acid sequences and/or Nanobodies® chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-28: Multivalent polypeptide according to any of aspects E-26 or E-27, wherein said at least two amino acid sequences and/or Nanobodies® are identical.

Aspect E-29: Multivalent polypeptide according to aspect E-28, that comprises or essentially consists of at least two identical amino acid sequences and/or Nanobodies® chosen from SEQ ID NO's: 65 and 76.

Aspect E-30: Multivalent polypeptide according to any of aspects E-7 to E-9, comprising or essentially consisting of at least two amino acid sequences and/or Nanobodies® chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
i) the amino acid sequence has a Praline (Pro, P) at position 14, Arginine (Arg, R) at position 19, Leucine (Leu, L) at position 20 and Leucine (Leu, L) at position 108 (said positions determined according to Kabat numbering); and
ii) the amino add sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-31: Multivalent polypeptide according to aspect E-30, wherein said at least two amino acid sequences and/or Nanobodies® are identical.

Aspect E-32: Multivalent polypeptide according to aspect E-31, that comprises or essentially consists of at least two identical amino acid sequences and/or Nanobodies® chosen from one of SEQ ID NO's: 146-153.

Aspect E-33: Multivalent polypeptide according to any of aspects E-7 to E-9, comprising or essentially consisting of at least two amino acid sequences and/or Nanobodies® chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
   i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-34: Multivalent polypeptide according to aspect E-33, comprising or essentially consisting of at least two amino acid sequences and/or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
   i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
      SEQ ID NO: 146, the amino acid sequence preferably has Glutamine (Gln, Q) at position 105;
      SEQ ID NO: 147, the amino acid sequence preferably has Arginine (Arg, R) at position 83 and Glutamine (Gln, Q) at position 105;
      SEQ ID NO: 148, the amino acid sequence preferably has Glutamic acid (Glu, E) at position 85 and Glutamine (Gln, Q) at position 105;
      SEQ ID NO: 149, the amino acid sequence preferably has Arginine (Arg, R) at position 83, Glutamic acid (Glu, E) at position 85 and Glutamine (Gln, Q) at position 105;
      SEQ ID NO: 151, the amino acid sequence preferably has Arginine (Arg, R) at position 83;
      SEQ ID NO; 152, the amino acid sequence preferably has Glutamic acid (Glu, E) at position 85;
      SEQ ID NO: 153, the amino acid sequence preferably has Arginine (Arg, R) at position 83 and Glutamic acid (Glu, E) at position 85;
      (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-35: Multivalent polypeptide according to any of aspects E-33 or E-34, wherein said at least two amino acid sequences and/or Nanobodies® are identical.

Aspect E-36: Multivalent polypeptide according to aspect E-35, that comprises or essentially consists of at least two identical amino acid sequences and/or Nanobodies® chosen from one of SEQ ID NO's: 62, 65, 67, 68, 75, 76, 147, 149 and 153.

Aspect E-37: Multivalent polypeptide comprising or essentially consisting of at least two amino acid sequences and/or Nanobodies® with SEQ ID NO: 5, in which one or more (such as two, three, four, five, six, seven, eight or nine, ten, eleven, or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

Aspect E-38: Multivalent polypeptide according to aspect E-37, comprising or essentially consisting of at least two amino acid sequences and/or Nanobodies® with SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect E-39: Multivalent polypeptide according to aspect E-37, comprising or essentially consisting of at least two amino acid sequences and/or Nanobodies® with SEQ ID NO: 5, in which one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D.

Aspect E-40: Multivalent polypeptide according to aspect E-37, comprising or essentially consisting of at least two amino acid sequences and/or Nanobodies® with SEQ ID NO: 5, in which one or more (such as two, three, four or five) amino acid residues have been mutated selected from the following: Gly78Leu, Ala83Arg, Asp85Glu, Arg105Gln and Gly54D.

Aspect E-41: Multivalent polypeptide according to aspect E-40, comprising or essentially consisting of at least two amino acid sequences and/or Nanobodies® with SEQ ID NO: 5, in which following amino acid residues have been mutated: Gly78Leu, Ala83Arg, Asp85Glu, Arg105Gln and Gly54D.

Aspect E-42: Multivalent polypeptide comprising or essentially consisting of at least two amino acid sequences and/or Nanobodies® with SEQ ID NO: 5, in which one or more (such as two, three or four) amino acid residues have been mutated selected from the following: Ala14Pro, Ser19Arg, Ile20Leu and Gln108Leu.

Aspect E-43: Multivalent polypeptide comprising or essentially consisting of at least two amino acid sequences and/or Nanobodies® with SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

Aspect E-44: Multivalent polypeptide according to aspect E-37, comprising or essentially consisting of at least two amino acid sequences and/or Nanobodies® with SEQ ID NO: 5, in which following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;

Ala83Arg, Asp85Glu, Arg105Gln, Gln108Leu and Gly54Asp;

Gly78Leu, Ala83Arg, Asp85Glu, Arg105Gln and Gly54Asp;

Gly54Asp;

Ala14Pro, Ser19Arg, Ile20Leu and Gln108Leu;

Ala14Pro, Ser19Arg, Ile20Leu, Gln108Leu and Ala83Arg;

Ala14Pro, Ser19Arg, Ile20Leu, Gln108Leu and Asp85Glu;

Ala14Pro, Ser19Arg, Ile20Leu, Gln108Leu and Arg105Gln;

Ala14Pro, Ser19Arg, Ile20Leu, Gln108Leu, Ala83Arg and Asp85Glu;

Ala14Pro, Ser19Arg, Ile20Leu, Gln108Leu, Ala83Arg and Arg105Gln;

Ala14Pro, Ser19Arg, Ile20Leu, Gln108Leu, Asp85Glu and Arg105Gln; or

Ala14Pro, Ser19Arg, Ile20Leu, Gln108Leu, Ala83Arg, Asp85Glu and Arg105Gln.

Aspect E-45: Multivalent polypeptide according to aspect E-7, that comprises or essentially consists of at least three amino acid sequences according to any of aspects A-1 to A-29, C-1 to C-38 and W-1 to W-38 and/or Nanobodies® according to any of aspects B-1 to B-18, D-1 to D-38 and X-1 to X-38.

Aspect E-46: Multivalent polypeptide according to aspect E-45, wherein said at least three amino acid sequences and/or Nanobodies® are identical.

Aspect E-47: Multivalent polypeptide according to any of aspects E-45 or E-46, comprising or essentially consisting of at least three amino acid sequences and/or Nanobodies® that comprise at least a stretch of amino acid residues chosen from the following:

a) SEQ ID NO: 102;

b) a stretch of amino acid residues that has no more than 3, preferably no more than 2, more preferably no more than 1 amino acid difference with SEQ ID NO: 102, provided that:

i) said stretch of amino acid residues has an Aspartic acid (Asp, D) at position 6 (position 54 determined according to Kabat numbering); and ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-48: Multivalent polypeptide according to any of aspects E-45 or E-46, comprising or essentially consisting of at least three amino acid sequences and/or Nanobodies® that comprise at least a stretch of amino acid residues chosen from the following:

a) SEQ ID NO: 102;

b) a stretch of amino acid residues that has no more than 3, preferably no more than 2, more preferably no more than 1 amino acid difference with SEQ ID NO: 102, provided that:

i) said stretch of amino acid residues has an Aspartic acid (Asp, D) at position 6 (position 54 determined according to Kabat numbering); and ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and at least one stretch is chosen from:

c) SEQ ID NO: 98;

d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

e) SEQ ID NO: 121; and f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

such that the stretch of amino acid residues that corresponds to one of a) and b) should always be present in the amino acid sequence of the invention and such that the second stretch of amino acid residues is chosen from one of c), d), e) and f).

Aspect E-49: Multivalent polypeptide according to any of aspects E-45 or E-46, comprising or essentially consisting of at least three amino acid sequences and/or Nanobodies® that comprise at least a stretch of amino acid residues chosen from the following:

a) SEQ ID NO: 98; and b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

a second stretch of amino acid residues chosen from the group consisting of:

c) SEQ ID NO: 102; and d) a stretch of amino acid residues that has no more than 3, preferably no more than 2, more preferably no more than 1 amino acid difference with SEQ ID NO: 102, provided that:

i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino add difference;

and a third stretch of amino acid residues chosen from the group consisting of:

e) SEQ ID NO: 121; and f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-50: Multivalent polypeptide according to any of aspects E-45 to E-46, comprising or essentially consisting of at least three amino acid sequences and/or Nanobodies® that comprise at least SEQ ID NO: 102.

Aspect E-51: Multivalent polypeptide according to any of aspects E-45 to E-46, comprising or essentially consisting of at least three amino acid sequences and/or Nanobodies® that comprise at least SEQ ID NO: 102 and at least one stretch of amino acid residues (CDR sequence) chosen from:

a) SEQ ID NO: 98;

b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

c) SEQ ID NO: 121; and d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-52: Multivalent polypeptide according to any of aspects E-45 to E-46, comprising or essentially consisting of at least three amino acid sequences and/or Nanobodies® that comprises at least SEQ ID NO: 102 and a CDR1 sequence chosen from:

a) SEQ ID NO: 98; and b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and a CDR3 sequence chosen from:

c) SEQ ID NO: 121; and d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-53: Multivalent polypeptide according to any of aspects E-45 to E-46, comprising or essentially consisting of at least three amino acid sequences and/or Nanobodies® that comprise at least SEQ ID NO: 102 and at least one stretch of amino acid residues (CDR sequence) chosen from SEQ ID NO: 98 and SEQ ID NO: 121.

Aspect E-54: Multivalent polypeptide according to any of aspects E-45 to E-46, comprising or essentially consisting of at least three amino acid sequences and/or Nanobodies® that comprise SEQ ID NO: 98, SEQ ID NO: 102 and SEQ ID NO: 121.

Aspect E-55: Multivalent polypeptide according to any of aspect E-47 to E-53, wherein said at least three amino acid sequences and/or Nanobodies® are identical.

Aspect E-56: Multivalent polypeptide according to any of aspects E-45 or E-46, comprising or essentially consisting of at least three amino acid sequences and/or Nanobodies® chosen from the following:

a) SEQ ID NO's: 60-75;

b) amino acid sequences that have no more than 3, preferably no more than 2, more preferably no more than 1 amino acid difference with one of SEQ ID NO's: 60-76, provided that:

i) the amino acid sequence has a Glutamine (Gln, Q) at position 105 (said position determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-57: Multivalent polypeptide according to aspect E-56, wherein said at least three amino acid sequences and/or Nanobodies® are identical.

Aspect E-58: Multivalent polypeptide according to aspect E-57, that comprises or essentially consists of at least three identical amino acid sequences and/or Nanobodies® chosen from one of SEQ ID NO's: 60-76.

Aspect E-59: Multivalent polypeptide according to any of aspects E-45 or E-46, comprising or essentially consisting of at least three amino acid sequences and/or Nanobodies® chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leo, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-60: Multivalent polypeptide according to aspect E-59, comprising or essentially consisting of at least three amino acid sequences and/or Nanobodies® chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-61: Multivalent polypeptide according to any of aspects E-59 or E-60, wherein said at least three amino acid sequences and/or Nanobodies® are identical.

Aspect E-62: Multivalent polypeptide according to aspect E-61, that comprises or essentially consists of at least three identical amino acid sequences and/or Nanobodies® chosen from one of SEQ ID NO's: 62, 65, 67, 68, 75 and 76.

Aspect E-63: Multivalent polypeptide according to any of aspects E-45 or E-46, comprising or essentially consisting of at least three amino acid sequences and/or Nanobodies® chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-64: Multivalent polypeptide according to aspect E-63, comprising or essentially consisting of at least three amino acid sequences and/or Nanobodies® chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-65: Multivalent polypeptide according to any of aspects E-63 or E-64, wherein said at least three amino acid sequences and/or Nanobodies® are identical.

Aspect E-66: Multivalent polypeptide according to aspect E-65, that comprises or essentially consists of at least three identical amino add sequences and/or Nanobodies® chosen from SEQ ID NO's: 65 and 76.

Aspect E-67: Multivalent polypeptide according to any of aspects E-45 or E-46, comprising or essentially consisting of at least three amino acid sequences and/or Nanobodies® chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Proline (Pro, P) at position 14, Arginine (Arg, R) at position 19, Leucine (Leu, L) at position 20 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-68: Multivalent polypeptide according to aspect E-67, wherein said at least three amino acid sequences and/or Nanobodies® are identical.

Aspect E-69: Multivalent polypeptide according to aspect E-68, that comprises or essentially consists of at least three identical amino acid sequences and/or Nanobodies® chosen from one of SEQ ID NO's: 146-153.

Aspect E-70: Multivalent polypeptide according to any of aspects E-45 or E-46, comprising or essentially consisting of at least three amino acid sequences and/or Nanobodies® chosen from the following:

a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
   i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-71: Multivalent polypeptide according to aspect E-70, comprising or essentially consisting of at least three amino acid sequences and/or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
   i) the amino acid sequence has a Praline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
      SEQ ID NO: 146, the amino acid sequence preferably has Glutamine (Gln, Q) at position 105;
      SEQ ID NO: 147, the amino acid sequence preferably has Arginine (Arg, R) at position 83 and Glutamine (Gln, Q) at position 105;
      SEQ ID NO: 148, the amino acid sequence preferably has Glutamic acid (Glu, E) at position 85 and Glutamine (Gln, Q) at position 105;
      SEQ ID NO: 149, the amino acid sequence preferably has Arginine (Arg, R) at position 83, Glutamic acid (Glu, E) at position 85 and Glutamine (Gln, Q) at position 105;
      SEQ ID NO: 151, the amino acid sequence preferably has Arginine (Arg, R) at position 83;
      SEQ ID NO: 152, the amino acid sequence preferably has Glutamic acid (Glu, E) at position 85;
      SEQ ID NO: 153, the amino acid sequence preferably has Arginine (Arg, R) at position 83 and Glutamic acid (Glu, E) at position 85;
      (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-72: Multivalent polypeptide according to any of aspects E-70 or E-71, wherein said at least three amino acid sequences and/or Nanobodies® are identical.

Aspect E-73: Multivalent polypeptide according to aspect E-72, that comprises or essentially consists of at least three identical amino acid sequences and/or Nanobodies® chosen from one of SEQ ID NO's: 62, 65, 67, 68, 75, 76, 147, 149 and 153.

Aspect E-74: Multivalent polypeptide comprising or essentially consisting of at least three amino acid sequences and/or Nanobodies® with SEQ ID NO: 5, in which one or more (such as two, three, four, five, six, seven, eight or nine, ten, eleven, or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

Aspect E-75: Multivalent polypeptide according to aspect E-74, comprising or essentially consisting of at least three amino acid sequences and/or Nanobodies® with SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect E-76: Multivalent polypeptide according to aspect E-74, comprising or essentially consisting of at least three amino acid sequences and/or Nanobodies® with SEQ ID NO: 5, in which one or more (such as two, three, four, five, six, seven or eight amino acid residues have been mutated selected from the following: Ser19R, Ile20Leu, Ala74Ser, Gly78Leu, Ala83Arg, Asp85Glu, Arg105Gln and Gly54D.

Aspect E-77: Multivalent polypeptide according to aspect E-74, comprising or essentially consisting of at least three amino acid sequences and/or Nanobodies® with SEQ ID NO: 5, in which one or more (such as two, three, four or five) amino acid residues have been mutated selected from the following: Gly78Leu, Ala83Arg, Asp85Glu, Arg105Gln and Gly54D.

Aspect E-78: Multivalent polypeptide according to aspect E-77, comprising or essentially consisting of at least three amino acid sequences and/or Nanobodies® with SEQ ID NO: 5, in which following amino acid residues have been mutated: Gly78Leu, Ala83Arg, Asp85Glu, Arg105Gln and Gly54D.

Aspect E-79: Multivalent polypeptide comprising or essentially consisting of at least three amino acid sequences and/or Nanobodies® with SEQ ID NO: 5, in which one or more (such as two, three or four) amino acid residues have been mutated selected from the following: Ala14Pro, Ser19Arg, Ile20Leu and Gln108Leu.

Aspect E-80: Multivalent polypeptide comprising or essentially consisting of at least three amino acid sequences and/or Nanobodies® with SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

Aspect E-81: Multivalent polypeptide according to aspect E-74, comprising or essentially consisting of at least three amino acid sequences and/or Nanobodies® with SEQ ID NO: 5, in which following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;

Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or
Ala14Pro, Ser19Arg, Ile20Leu, Gln108Leu, Ala83Arg, Asp85Glu and Arg105Gln, Aspect E-82: Multivalent polypeptide according to any of aspects E-7 to E-9, comprising or essentially consisting of at least one amino add sequence and/or Nanobody® chosen from the following:
  a) SEQ ID NO's: 138-141 and 154-157;
  b) amino acid sequences that have no more than 3, preferably no more than 2, more preferably no more than 1 amino acid difference with one of SEQ ID NO's: 138-141, provided that:
    i) the amino acid sequence has a Aspartic acid (Asp, D) at position 1 (said position determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-83: Multivalent polypeptide according to aspect E-82, that comprises or essentially consists of at least one amino acid sequence and/or Nanobody® chosen from one of SEQ ID NO's: 138-141 and 154-157.

Aspect E-84: Multivalent polypeptide comprising or essentially consisting of at least one amino acid sequence and/or Nanobody® with SEQ ID NO: 5, in which the Glutamic acid at position 1 has been changed into Aspartic acid.

Aspect E-85: Multivalent polypeptide comprising or essentially consisting of at least one amino acid sequence and/or Nanobody® with SEQ ID NO: 62, in which the Glutamic acid at position 1 has been changed into Aspartic acid.

Aspect E-86: Multivalent polypeptide comprising or essentially consisting of at least one amino acid sequence and/or Nanobody® with SEQ ID NO: 65, in which the Glutamic acid at position 1 has been changed into Aspartic acid.

Aspect E-87: Multivalent polypeptide comprising or essentially consisting of at least one amino acid sequence and/or Nanobody® with SEQ ID NO: 76, in which the Glutamic acid at position 1 has been changed into Aspartic acid.

Aspect E-88: Multivalent polypeptide comprising or essentially consisting of at least one amino acid sequence and/or Nanobody® with SEQ ID NO: 75, in which the Glutamic acid at position 1 has been changed into Aspartic acid.

Aspect E-89: Multivalent polypeptide comprising or essentially consisting of at least one amino acid sequence and/or Nanobody® with SEQ ID NO: 147, in which the Glutamic acid at position 1 has been changed into Aspartic acid.

Aspect E-90: Multivalent polypeptide comprising or essentially consisting of at least one amino acid sequence and/or Nanobody® with SEQ ID NO: 149, in which the Glutamic acid at position 1 has been changed into Aspartic acid.

Aspect E-91: Multivalent polypeptide comprising or essentially consisting of at least one amino acid sequence and/or Nanobody® with SEQ ID NO: 153, in which the Glutamic acid at position 1 has been changed into Aspartic acid.

Aspect E-92: Multivalent polypeptide comprising or essentially consisting of at least one amino acid sequence and/or Nanobody® with SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the Glutamic acid at position 1 has been changed into Aspartic acid.

Aspect E-93: Multivalent polypeptide according to aspect E-92, comprising or essentially consisting of at least one amino acid sequence and/or Nanobody® with SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid.

Aspect E-94: Multivalent polypeptide according to aspect E-92, comprising or essentially consisting of at least one amino acid sequence and/or Nanobody® with SEQ ID NO: 5, in which one or more (such as two three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, and wherein the Glutamic acid at position 1 has been changed into Aspartic acid.

Aspect E-95: Multivalent polypeptide according to aspect E-92, comprising or essentially consisting of at least one amino acid sequence and/or Nanobody® with SEQ ID NO: 5, in which one or more (such as two, three, four or five) amino acid residues have been mutated selected from the following: Gly78Leu, Ala83Arg, Asp85Glu, Arg105Gln and Gly54D, and wherein the Glutamic acid at position 1 has been changed into Aspartic acid.

Aspect E-96: Multivalent polypeptide according to aspect E-95, comprising or essentially consisting of at least one amino acid sequence and/or Nanobody® with SEQ ID NO: 5, in which following amino acid residues have been mutated: Gly78Leu, Ala83Arg, Asp85Glu, Arg105Gln and Gly54D, and wherein the Glutamic acid at position 1 has been changed into Aspartic acid.

Aspect E-97: Multivalent polypeptide comprising or essentially consisting of at least one amino acid sequence and/or Nanobody® with SEQ ID NO: 5, in which one or more (such as two, three or four) amino acid residues have been mutated selected from the following: Ala14Pro, Ser19Arg, Ile20Leu and Gln108Leu, and wherein the Glutamic acid at position 1 has been changed into Aspartic acid.

Aspect E-98: Multivalent polypeptide comprising or essentially consisting of at least one amino acid sequence and/or Nanobody® with SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein the Glutamic acid at position 1 has been changed into Aspartic acid.

Aspect E-99: Multivalent polypeptide according to aspect E-92, comprising or essentially consisting of at least one amino acid sequence and/or Nanobody® with SEQ ID NO: 5, in which following amino acid residues have been mutated:

Glu1Asp;
Glu1Asp, Val5Leu, Ala14Pro, Glu44Gly, Gly78Leu, Ala83Arg, Asp85Glu, Arg105Gln and Gln108Leu;
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg, Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln.

Aspect E-100: Bivalent polypeptide according to aspect E-7, that comprises or essentially consists of two amino acid sequences according to any of aspects A-1 to A-29, C-1 to C-38 and W-1 to W-38 and/or Nanobodies® according to any of aspects B-1 to B-18, D-1 to D-38 and X-1 to X-38.

Aspect E-101: Bivalent polypeptide according to aspect E-100, wherein said two amino acid sequences and/or Nanobodies® are identical.

Aspect E-102: Bivalent polypeptide according to any of aspects E-100 or E-101, comprising or essentially consisting of two amino acid sequences and/or Nanobodies® that comprise at least a stretch of amino acid residues chosen from the following:
a) SEQ ID NO: 102;
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-103: Bivalent polypeptide according to any of aspects E-100 or E-101, comprising or essentially consisting of two amino acid sequences and/or Nanobodies® that comprise at least a stretch of amino acid residues chosen from the following:
a) SEQ ID NO: 102;
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino add sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and at least one stretch is chosen from:
c) SEQ ID NO: 98;
d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
e) SEQ ID NO: 121; and
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.
such that the stretch of amino acid residues that corresponds to one of a) and b) should always be present in the amino acid sequence of the invention and such that the second stretch of amino acid residues is chosen from one of c), d), e) and f).

Aspect E-104: Bivalent polypeptide according to any of aspects E-100 or E-101, comprising or essentially consisting of two amino acid sequences and/or Nanobodies® that comprise at least a stretch of amino acid residues chosen from the following:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

a second stretch of amino acid residues chosen from the group consisting of:

c) SEQ ID NO: 102;

d) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

and a third stretch of amino acid residues chosen from the group consisting of:

e) SEQ ID NO: 121;

f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-105: Bivalent polypeptide according to any of aspects E-100 or E-101, comprising or essentially consisting of two amino acid sequences and/or Nanobodies® that comprise at least SEQ ID NO: 102.

Aspect E-106: Bivalent polypeptide according to any of aspects E-100 or E-101, comprising or essentially consisting of two amino acid sequences and/or Nanobodies® that comprise at least SEQ ID NO: 102 and at least one stretch of amino acid residues (CDR sequence) chosen from:

a) SEQ ID NO: 98;

b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;

c) SEQ ID NO: 121; and d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-107: Bivalent polypeptide according to any of aspects E-100 or E-101, comprising or essentially consisting of two amino acid sequences and/or Nanobodies® that comprise at least SEQ ID NO: 102 and a CDR1 sequence chosen from:

a) SEQ ID NO: 98; and b) a stretch of amino add residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino add residues without the 3, 2 or 1 amino acid difference;

and a CDR3 sequence chosen from:

c) SEQ ID NO: 121; and d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-108: Bivalent polypeptide according to any of aspects E-100 or E-101, comprising or essentially consisting of two amino acid sequences and/or Nanobodies® that comprise at least SEQ ID NO: 102 and at least one stretch of amino acid residues (CDR sequence) chosen from SEQ ID NO: 98 and SEQ ID NO: 121.

Aspect E-109: Bivalent polypeptide according to any of aspects E-100 or E-101, comprising or essentially consisting of two amino acid sequences and/or Nanobodies® that comprise SEQ ID NO: 98, SEQ ID NO: 102 and SEQ ID NO: 121.

Aspect E-110: Bivalent polypeptide according to any of aspect E-102 to E-109, wherein said at least two amino acid sequences and/or Nanobodies® are identical.

Aspect E-111: Bivalent polypeptide according to any of aspects E-100 or E-101, comprising or essentially consisting of two amino acid sequences and/or Nanobodies® chosen from the following:

a) SEQ ID NO's: 60-76;
b) amino acid sequences that have no more than 3, preferably no more than 2, more preferably no more than 1 amino add difference with one of SEQ ID NO's: 60-76, provided that:
  i) the amino acid sequence has a Glutamine (Gln, Q) at position 105 (said position determined according to Kabat numbering); and
  ii) the amino add sequence hinds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-112: Bivalent polypeptide according to aspect E-111, wherein said two amino acid sequences and/or Nanobodies® are identical.

Aspect E-113: Bivalent polypeptide according to aspect E-112, that comprises or essentially consists of two identical amino acid sequences and/or Nanobodies® chosen from one of SEQ ID NO's: 60-76.

Aspect E-114: Bivalent polypeptide according to any of aspects E-100 or E-101, comprising or essentially consisting of two amino acid sequences and/or Nanobodies® chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-115: Bivalent polypeptide according to aspect E-114, comprising or essentially consisting of two amino acid sequences and/or Nanobodies® chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-116: Bivalent polypeptide according to any of aspects E-114 or E-415, wherein said two amino acid sequences and/or Nanobodies® are identical.

Aspect E-117: Bivalent polypeptide according to aspect E-116, that comprises or essentially consists of two identical amino acid sequences and/or Nanobodies® chosen from one of SEQ ID NO's: 62, 65, 67, 68, 75 and 76.

Aspect E-118: Bivalent polypeptide according to any of aspects E-100 or E-101, comprising or essentially consisting of two amino acid sequences and/or Nanobodies® chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-119: Bivalent polypeptide according to aspect E-118, comprising or essentially consisting of two amino acid sequences and/or Nanobodies® chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-120: Bivalent polypeptide according to any of aspects E-118 or E-119, wherein said two amino acid sequences and/or Nanobodies® are identical.

Aspect E-121: Bivalent polypeptide according to aspect E-120, that comprises or essentially consists of two identical amino acid sequences and/or Nanobodies® chosen from SEQ ID NO's: 65 and 76.

Aspect E-122: Bivalent polypeptide according to any of aspects E-100 or E-101, comprising or essentially consisting of two amino acid sequences and/or Nanobodies® chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Proline (Pro, P) at position 14, Arginine (Arg, R) at position 19, Leucine (Leu, L) at position 20 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino add sequence has the same, about the same, or a higher potency (as defined herein) compared to the amino acid sequence without the 3, 2 or 1 amino acid difference.

Aspect E-123: Bivalent polypeptide according to aspect E-122, wherein said two amino acid sequences and/or Nanobodies® are identical.

Aspect E-124: Bivalent polypeptide according to aspect E-123, that comprises or essentially consists of two identical amino acid sequences and/or Nanobodies® chosen from one of SEQ ID NO's: 146-153.

Aspect E-125: Bivalent polypeptide according to any of aspects E-100 or E-101, comprising or essentially consisting of two amino acid sequences and/or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-126: Bivalent polypeptide according to aspect E-125, comprising or essentially consisting of two amino acid sequences and/or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-127: Bivalent polypeptide according to any of aspects E-125 or E-126, wherein said two amino acid sequences and/or Nanobodies® are identical.

Aspect E-128: Bivalent polypeptide according to aspect E-127, that comprises or essentially consists of two identical amino acid sequences and/or Nanobodies® chosen from one of SEQ ID NO's: 62, 65, 67, 68, 75, 76, 147, 149 and 153.

Aspect E-129: Bivalent polypeptide comprising or essentially consisting of two amino acid sequences and/or Nanobodies® with SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

Aspect E-130: Bivalent polypeptide according to aspect E-129, comprising or essentially consisting of two amino acid sequences and/or Nanobodies® with SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect E-131: Bivalent polypeptide according to aspect E-129, comprising or essentially consisting of two amino acid sequences and/or Nanobodies® with SEQ ID NO: 5, in which one or more (two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D.

Aspect E-132: Bivalent polypeptide according to aspect E-129, comprising or essentially consisting of two amino acid sequences and/or Nanobodies® with SEQ ID NO: 5, in which one or more (such as two, three, four or five) amino acid residues have been mutated selected from the following: Gly78Leu, Ala83Arg, Asp85Glu, Arg105Gln and Gly54D.

Aspect E-133: Bivalent polypeptide according to aspect E-132, comprising or essentially consisting of two amino acid sequences and/or Nanobodies® with SEQ ID NO: 5, in which following amino acid residues have been mutated: Gly78Leu, Ala83Arg, Asp85Glu, Arg105Gln and Gly54D.

Aspect E-134: Bivalent polypeptide comprising or essentially consisting of two amino acid sequences and/or Nanobodies® with SEQ ID NO: 5, in which one or more (such as two, three or four) amino acid residues have been mutated selected from the following: Ala14Pro, Ser19Arg, Ile20Leu and Gln108Leu.

Aspect E-135: Bivalent polypeptide comprising or essentially consisting of two amino acid sequences and/or Nanobodies® with SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

Aspect E-136: Bivalent polypeptide according to aspect E-129, comprising or essentially consisting of two amino acid sequences and/or Nanobodies® with SEQ ID NO: 5, in which following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or
Ala14Pro, Ser19Arg, Ile20Leu, Gln108Leu, Ala83Arg, Asp85Glu and Arg105Gln.

Aspect E-137: Bivalent polypeptide according to any of aspects E-100 or E-101, comprising or essentially consisting of at least one amino acid sequence and/or Nanobody® chosen from the following:
a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
i) the amino acid sequence has a Aspartic acid (Asp, D) at position 1 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-138: Bivalent polypeptide according to aspect E-137, that comprises or essentially consists of at least one amino acid sequence and/or Nanobody® chosen from one of SEQ ID NO's: 138-141 and 154-157.

Aspect E-139: Bivalent polypeptide comprising or essentially consisting of at least one amino acid sequence and/or Nanobody® with SEQ ID NO: 5, in which the Glutamic acid at position 1 is changed into Aspartic acid.

Aspect E-140: Bivalent polypeptide comprising or essentially consisting of at least one amino acid sequence and/or Nanobody® with SEQ ID NO: 62, in which the Glutamic acid at position 1 is changed into Aspartic acid.

Aspect E-141: Bivalent polypeptide comprising or essentially consisting of at least one amino acid sequence and/or Nanobody® with SEQ ID NO: 65, in which the Glutamic acid at position 1 is changed into Aspartic acid.

Aspect E-142: Bivalent polypeptide comprising or essentially consisting of at least one amino acid sequence and/or Nanobody® with SEQ ID NO: 76, in which the Glutamic acid at position 1 is changed into Aspartic acid.

Aspect E-143: Bivalent polypeptide comprising or essentially consisting of at least one amino acid sequence and/or Nanobody® with SEQ ID NO: 75, in which the Glutamic acid at position 1 is changed into Aspartic acid.

Aspect E-144: Bivalent polypeptide comprising or essentially consisting of at least one amino acid sequence and/or Nanobody® with SEQ ID NO: 147, in which the Glutamic acid at position 1 is changed into Aspartic acid.

Aspect E-145: Bivalent polypeptide comprising or essentially consisting of at least one amino acid sequence and/or Nanobody® with SEQ ID NO: 149, in which the Glutamic acid at position 1 is changed into Aspartic acid.

Aspect E-146: Bivalent polypeptide comprising or essentially consisting of at least one amino acid sequence and/or Nanobody® with SEQ ID NO: 153, in which the Glutamic acid at position 1 is changed into Aspartic acid.

Aspect E-147: Bivalent polypeptide comprising or essentially consisting of at least one amino acid sequence and/or Nanobody® with SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, wherein the Glutamic acid at position 1 is changed into Aspartic acid.

Aspect E-148: Bivalent polypeptide according to aspect E-147, comprising or essentially consisting of at least one amino acid sequence and/or Nanobody® with SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, wherein the Glutamic acid at position 1 is changed into Aspartic acid.

Aspect E-149: Bivalent polypeptide according to aspect E-147, comprising or essentially consisting of at least one amino acid sequence and/or Nanobody® with SEQ ID NO: 5, in which one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, wherein the Glutamic acid at position 1 is changed into Aspartic acid.

Aspect E-150: Bivalent polypeptide according to aspect E-147, comprising or essentially consisting of at least one amino acid sequence and/or Nanobody® with SEQ ID NO: 5, in which one or more (such as two, three, four or five) amino acid residues have been mutated selected from the following: Gly78Leu, Ala83Arg, Asp85Glu, Arg105Gln and Gly54D, wherein the Glutamic acid at position 1 is changed into Aspartic acid.

Aspect E-151: Bivalent polypeptide according to aspect E-150, comprising or essentially consisting of at least one amino acid sequence and/or Nanobody® with SEQ ID NO: 5, in which following amino acid residues have been mutated: Gly78Leu, Ala83Arg, Asp85Glu, Arg105Gln and Gly54D, wherein the Glutamic acid at position 1 is changed into Aspartic acid.

Aspect E-152: Bivalent polypeptide comprising or essentially consisting of at least one amino acid sequence and/or Nanobody® with SEQ ID NO: 5, in which one or more (such as two, three or four) amino acid residues have been mutated selected from the following: Ala14Pro, Ser19Arg, Ile20Leu and Gln108Leu, wherein the Glutamic acid at position 1 is changed into Aspartic acid.

Aspect E-153: Bivalent polypeptide comprising or essentially consisting of at least one amino acid sequence and/or Nanobody® with SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, wherein the Glutamic acid at position 1 is changed into Aspartic acid.

Aspect E-154: Bivalent polypeptide according to aspect E-147, comprising or essentially consisting of at least one amino acid sequence and/or Nanobody® with SEQ ID NO: 5, in which following amino acid residues have been mutated:
Glu1Asp;
Glu1Asp, Val5Leu, Ala14Pro, Glu44Gly, Gly78Leu, Ala83Arg, Asp85Glu, Arg105Gln and Gln108Leu
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser1.9Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln.

Aspect E-155: Trivalent polypeptide according to aspect E-7, that comprises or essentially consists of three amino acid sequences according to any of aspects A-1 to A-29, C-1 to C-38 and W-1 to W-38 and/or Nanobodies® according to any of aspects B-1 to B-18, D-1 to D-38 and X-1 to X-38.

Aspect E-156: Trivalent polypeptide according to aspect E-155, wherein said three amino acid sequences and/or Nanobodies® are identical.

Aspect E-157: Trivalent polypeptide according to any of aspects E-155 or E-156, comprising or essentially consisting of three amino acid sequences and/or Nanobodies® that comprise at least a stretch of amino acid residues chosen from the following:
a) SEQ ID NO: 102;
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-158: Trivalent polypeptide according to any of aspects E-155 or E-156, comprising or essentially consisting of three amino acid sequences and/or Nanobodies® that comprise at least a stretch of amino acid residues chosen from the following:
a) SEQ ID NO: 102;
b) a stretch of amino acid residues that has no more than 3, preferably no more than 2, more preferably no more than 1 amino acid difference with SEQ ID NO: 102, provided that:
  i) said stretch of amino acid residues has an Aspartic acid (Asp, D) at position 6 (position 54 determined according to Kabat numbering); and
  ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and at least one stretch is chosen from:
c) SEQ ID NO: 98;
d) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
e) SEQ ID NO: 121; and
f) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.
such that the stretch of amino acid residues that corresponds to one of a) and b) should always be present in the amino acid sequence of the invention and such that the second stretch of amino acid residues is chosen from one of c), d), e) and f).

Aspect E-159: Trivalent polypeptide according to any of aspects E-155 or E-156, comprising or essentially consisting of three amino acid sequences and/or Nanobodies® that comprise at least a stretch of amino acid residues chosen from the following:
a) SEQ ID NO: 98; and
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
a second stretch of amino acid residues chosen from the group consisting of:
c) SEQ ID NO: 102; and
d) a stretch of amino acid residues that has no more than 3, preferably no more than 2, more preferably no more than 1 amino acid difference with SEQ ID NO: 102, provided that:
i) said stretch of amino acid residues has an Aspartic acid (Asp, D) at position 6 (position 54 determined according to Kabat numbering); and
ii) the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino add sequence comprising said stretch of amino acid residues without the 3, 2 or 1 amino acid difference;
and a third stretch of amino acid residues chosen from the group consisting of:
e) SEQ ID NO: 121; and
f) a stretch of amino acid residues that has no more than 3, preferably no more than 2, more preferably no more than 1 amino acid difference with SEQ ID NO: 121, provided that the amino acid sequence comprising said stretch of amino add residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-160: Trivalent polypeptide according to any of aspects E-155 or E-156, comprising or essentially consisting of three amino acid sequences and/or Nanobodies® that comprise at least SEQ ID NO: 102.

Aspect E-161: Trivalent polypeptide according to any of aspects E-155 or E-156, comprising or essentially consisting of three amino acid sequences and/or Nanobodies® that comprise at least SEQ ID NO: 102 and at least one stretch of amino acid residues (CDR sequence) chosen from:
a) SEQ ID NO: 98;
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
c) SEQ ID NO: 121; and
d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-162: Trivalent polypeptide according to any of aspects E-155 or E-156, comprising or essentially consisting of three amino acid sequences and/or Nanobodies® that comprises at least SEQ ID NO: 102 and a CDR1 sequence chosen from:
a) SEQ ID NO: 98; and
b) a stretch of amino acid residues that has no more than 3, preferably no more than 2, more preferably no more than 1 amino acid difference with SEQ ID NO: 98, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference;
and a CDR3 sequence chosen from:
c) SEQ ID NO: 121; and
d) a stretch of amino acid residues that has no more than 3, preferably no more than 2, more preferably no more than 1 amino acid difference with SEQ ID NO: 121, provided that the amino acid sequence comprising said stretch of amino acid residues binds protein F of hRSV with the same, about the same, or a higher affinity (said affinity as measured by surface plasmon resonance) and/or the amino acid sequence comprising said stretch of amino acid residues has the same, about the same, or a higher potency (as defined herein) compared to the amino acid sequence comprising said stretch of amino acid residues without the 3, 2 or 1 amino acid difference.

Aspect E-163: Trivalent polypeptide according to any of aspects E-155 or E-156, comprising or essentially consisting of three amino acid sequences and/or Nanobodies® that comprise at least SEQ ID NO: 102 and at least one stretch of amino acid residues (CDR sequence) chosen from SEQ ID NO: 98 and SEQ ID NO: 121.

Aspect E-164: Trivalent polypeptide according to any of aspects E-155 or E-156, comprising or essentially consisting of three amino acid sequences and/or Nanobodies® that comprise SEQ ID NO: 98, SEQ ID NO: 102 and SEQ ID NO: 121.

Aspect E-165: Trivalent polypeptide according to any of aspect E-157 to E-164, wherein said at least three amino acid sequences and/or Nanobodies® are identical.

Aspect E-166: Trivalent polypeptide according to any of aspects E-155 or E-156, comprising or essentially consisting of three amino acid sequences and/or Nanobodies® chosen from the following:
  a) SEQ ID NO's: 60-76;
  b) amino acid sequences that have no more than 3, preferably no more than 2, more preferably no more than 1 amino acid difference with one of SEQ ID NO's: 60-76, provided that:
    i) the amino acid sequence has a Glutamine (Gln, Q) at position 105 (said position determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-167: Trivalent polypeptide according to aspect E-166, wherein said three amino acid sequences and/or Nanobodies® are identical.

Aspect E-168: Trivalent polypeptide according to aspect E-167, that comprises or essentially consists of three identical amino acid sequences and/or Nanobodies® chosen from one of SEQ ID NO's: 60-76.

Aspect E-169: Trivalent polypeptide according to any of aspects E-155 or E-156, comprising or essentially consisting of three amino acid sequences and/or Nanobodies® chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-170: Trivalent polypeptide according to aspect E-169, comprising or essentially consisting of three amino acid sequences and/or Nanobodies® chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-171: Trivalent polypeptide according to any of aspects B-169 or E-170, wherein said three amino acid sequences and/or Nanobodies® are identical.

Aspect E-172: Trivalent polypeptide according to aspect S-171, that comprises or essentially consists of three identical amino acid sequences and/or Nanobodies® chosen from one of SEQ ID NO's: 62, 65, 67, 68, 75 and 76.

Aspect E-173: Trivalent polypeptide according to any of aspects E-155 or E-156, comprising or essentially consisting of three amino acid sequences and/or Nanobodies® chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-174: Trivalent polypeptide according to aspect E-173, comprising or essentially consisting of three amino acid sequences and/or Nanobodies® chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-175: Trivalent polypeptide according to any of aspects E-173 or E-174, wherein said three amino acid sequences and/or Nanobodies® are identical.

Aspect E-176: Trivalent polypeptide according to aspect E-175, that comprises or essentially consists of three identical amino acid sequences and/or Nanobodies® chosen from SEQ ID NO's: 65 and 76.

Aspect E-177: Trivalent polypeptide according to any of aspects E-155 or E-156, comprising or essentially consisting of three amino acid sequences and/or Nanobodies® chosen from the following:

a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Proline (Pro, P) at position 14, Arginine (Arg, R) at position 19, Leucine (Leu, L) at position 20 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-178: Trivalent polypeptide according to aspect E-177, wherein said three amino acid sequences and/or Nanobodies® are identical.

Aspect E-179: Trivalent polypeptide according to aspect E-178, that comprises or essentially consists of three identical amino acid sequences and/or Nanobodies® chosen from one of SEQ ID NO's: 146-153.

Aspect E-180: Trivalent polypeptide according to any of aspects E-155 or E-156, comprising or essentially consisting of three acid sequences and/or Nanobodies® chosen from the following:
a) SEQ ID NO's: 146-149 and 151-153;
b) amino add sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-181: Trivalent polypeptide according to aspect E-180, comprising or essentially consisting of three amino acid sequences and/or Nanobodies® chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-182: Trivalent polypeptide according to any of aspects E-180 or E-181, wherein said three amino acid sequences and/or Nanobodies® are identical.

Aspect E-183: Trivalent polypeptide according to aspect E-182, that comprises or essentially consists of three identical amino acid sequences and/or Nanobodies® chosen from one of SEQ ID NO's: 62, 65, 67, 68, 75, 76, 147, 149 and 153.

Aspect E-184: Trivalent polypeptide comprising or essentially consisting of three amino acid sequences and/or Nanobodies® with SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

Aspect E-185: Trivalent polypeptide according to aspect E-184, comprising or essentially consisting of three amino acid sequences and/or Nanobodies® with SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect E-186: Trivalent polypeptide according to aspect E-184, comprising or essentially consisting of three amino acid sequences and/or Nanobodies® with SEQ ID NO: 5, in which one or more (such as two, three, four, five, six, seven or eight) amino add residues have been mutated selected from the following: Ser19R, Ile20Leu, Ala74Ser, Gly78Leu, Ala83Arg, Asp85Glu, Arg105Gln and Gly54D.

Aspect E-187: Trivalent polypeptide according to aspect E-184, comprising or essentially consisting of three amino acid sequences and/or Nanobodies® with SEQ ID NO: 5, in which one or more (such as two, three, four or five) amino acid residues have been mutated selected from the following: Gly78Leu, Ala83Arg, Asp85Glu, Arg105Gln and Gly54D.

Aspect E-188: Trivalent polypeptide according to aspect E-187, comprising or essentially consisting of three amino acid sequences and/or Nanobodies® with SEQ ID NO: 5, in which following amino acid residues have been mutated: Gly78Leu, Ala83Arg, Asp85Glu, Arg105Gln and Gly54D.

Aspect E-189: Trivalent polypeptide comprising or essentially consisting of three amino acid sequences and/or Nanobodies® with SEQ ID NO: 5, in which one or more (such as two, three or four) amino acid residues have been mutated selected from the following: Ala14Pro, Ser19Arg, Ile20Leu and Gln108Leu.

Aspect E-190: Trivalent polypeptide comprising or essentially consisting of three amino acid sequences and/or Nanobodies® with SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

Aspect E-191: Trivalent polypeptide according to aspect E-184, comprising or essentially consisting of three amino acid sequences and/or Nanobodies® with SEQ ID NO: 5, in which following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or
Ala14Pro, Ser19Arg, Ile20Leu, Gln108Leu, Ala83Arg, Asp85Glu and Arg105Gln.

Aspect E-192: Trivalent polypeptide comprising or essentially consisting of three amino acid sequences and/or Nanobodies® with SEQ ID NO: 62.

Aspect E-193: Trivalent polypeptide comprising or essentially consisting of three amino acid sequences and/or Nanobodies® with SEQ ID NO: 65.

Aspect E-194: Trivalent polypeptide comprising or essentially consisting of three amino acid sequences and/or Nanobodies® with SEQ ID NO: 76.

Aspect E-195: Trivalent polypeptide comprising or essentially consisting of three amino acid sequences and/or Nanobodies® with SEQ ID NO: 75.

Aspect E-196: Trivalent polypeptide comprising or essentially consisting of three amino acid sequences and/or Nanobodies® with SEQ ID NO: 147.

Aspect E-197: Trivalent polypeptide comprising or essentially consisting of three amino acid sequences and/or Nanobodies® with SEQ ID NO: 149.

Aspect E-198: Trivalent polypeptide comprising or essentially consisting of three amino acid sequences and/or Nanobodies® with SEQ ID NO: 153.

Aspect E-199: Trivalent polypeptide according to any of aspects E-155 or E-156, comprising or essentially consisting of at least one amino acid sequence and/or Nanobody® chosen from the following:
a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
i) the amino acid sequence has a Aspartic acid (Asp, D) at position 1 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-200: Trivalent polypeptide according to aspect E-199, that comprises or essentially consists of at least one amino acid sequence and/or Nanobody® chosen from one of SEQ ID NO's: 138-141 and 154-157.

Aspect E-201: Trivalent polypeptide comprising or essentially consisting of at least one amino acid sequence and/or Nanobody® with SEQ ID NO: 5, in which the Glutamic acid at position 1 as been changed into Aspartic acid.

Aspect E-202: Trivalent polypeptide comprising or essentially consisting of at least one amino acid sequence and/or Nanobody® with SEQ ID NO: 62, in which the Glutamic acid at position 1 as been changed into Aspartic acid.

Aspect E-203: Trivalent polypeptide comprising or essentially consisting of at least one amino acid sequence and/or Nanobody® with SEQ ID NO: 65, in which the Glutamic acid at position 1 as been changed into Aspartic acid.

Aspect E-204: Trivalent polypeptide comprising or essentially consisting of at least one amino acid sequence and/or Nanobody® with SEQ ID NO: 76, in which the Glutamic acid at position 1 as been changed into Aspartic acid.

Aspect E-205: Trivalent polypeptide comprising or essentially consisting of at least one amino acid sequence and/or Nanobody® with SEQ ID NO: 75, in which the Glutamic acid at position 1 as been changed into Aspartic acid.

Aspect E-206: Trivalent polypeptide comprising or essentially consisting of at least one amino acid sequence and/or Nanobody® with SEQ ID NO: 147, in which the Glutamic acid at position 1 as been changed into Aspartic acid.

Aspect E-207: Trivalent polypeptide comprising or essentially consisting of at least one amino acid sequence and/or Nanobody® with SEQ ID NO: 149, in which the Glutamic acid at position 1 as been changed into Aspartic acid.

Aspect E-208: Trivalent polypeptide comprising or essentially consisting of at least one amino acid sequence and/or Nanobody® with SEQ ID NO: 153, in which the Glutamic acid at position 1 as been changed into Aspartic acid.

Aspect E-209: Trivalent polypeptide comprising or essentially consisting of at least one amino acid sequence and/or Nanobody® with SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the Glutamic acid at position 1 as been changed into Aspartic acid.

Aspect E-210: Trivalent polypeptide according to aspect E-209, comprising or essentially consisting of at least one amino acid sequence and/or Nanobody® with SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 as been changed into Aspartic acid.

Aspect E-211: Trivalent polypeptide according to aspect E-209, comprising or essentially consisting of at least one amino acid sequence and/or Nanobody® with SEQ ID NO: 5, in which one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, and wherein the Glutamic acid at position 1 as been changed into Aspartic acid.

Aspect E-212: Trivalent polypeptide according to aspect E-209, comprising or essentially consisting of at least one amino acid sequence and/or Nanobody® with SEQ ID NO: 5, in which one or more (such as two, three, four or five) amino acid residues have been mutated selected from the following: Gly78Leu, Ala83Arg, Asp85Glu, Arg105Gln and Gly54D, and wherein the Glutamic acid at position 1 as been changed into Aspartic acid.

Aspect E-213: Trivalent polypeptide according to aspect E-212, comprising or essentially consisting of at least one amino acid sequence and/or Nanobody® with SEQ ID NO: 5, in which following amino acid residues have been mutated: Gly78Leu, Ala83Arg, Asp85Glu, Arg105Gln and Gly54D, and wherein the Glutamic acid at position 1 as been changed into Aspartic acid.

Aspect E-214: Trivalent polypeptide according to aspect E-209, comprising or essentially consisting of at least one amino acid sequence and/or Nanobody® with SEQ ID NO: 5, in which following amino acid residues have been mutated:

Glu1Asp;
Glu1Asp, Val5Leu, Ala14Pro, Glu44Gly, Gly78Leu, Ala83Arg, Asp85Glu, Arg105Gln and Gln108Leu;
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln.

Aspect E-215: Trivalent polypeptide that is directed against and/or specifically binds protein F of hRSV, chosen from the following polypeptides:
a) SEQ ID NO's: 77-79 and 158;
b) polypeptides that have no more than 3, preferably no more than 2, more preferably no more than 1 amino acid difference with one of SEQ ID NO's: 77-79 and 158, provided that:
  i) the amino acid sequences or Nanobodies® encompassed in said polypeptide have a Glutamine (Gln, Q) at position 105, a Leucine (Leu, L) at position 78, an Arginine (Arg, R) at position 83 and/or a Glutamic acid (Glu, E) at position 85 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-215: Trivalent polypeptide according to aspect E-215, chosen from the following polypeptides:
a) SEQ ID NO's: 77-79 and 158;
b) polypeptides that have no more than 3, preferably no more than 2, more preferably no more than 1 amino acid difference with one of SEQ ID NO's: 77-79 and 158, provided that:
  i) the amino acid sequence or Nanobody® encompassed in said polypeptide has a Glutamine (Gln, Q) at position 105, a Leucine (Leu, L) at position 78, an Arginine (Arg, R) at position 83 and a Glutamic acid (Glu, E) at position 85 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-217: Trivalent polypeptide that is directed against and/or specifically binds protein F of hRSV, chosen from the following polypeptides:
a) SEQ ID NO: 78 and 79;
b) polypeptides that have no more than 3, preferably no more than 2, more preferably no more than 1 amino acid difference with one of SEQ ID NO's: 78 and 79, provided that:
  i) the amino acid sequence or Nanobody® encompassed in said polypeptide has an Aspartic acid (Asp, D) at position 54, a Glutamine (Gln, Q) at position 105, a Leucine (Leu, L) at position 78, an Arginine (Arg, R) at position 83 and/or a Glutamic acid (Glu, E) at position 85 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-218: Trivalent polypeptide according to aspect E-217, chosen from the following polypeptides:

a) SEQ ID NO: 78 and 79; or
b) polypeptides that have no more than 3, preferably no more than 2, more preferably no more than 1 amino acid difference with one of SEQ ID NO's: 78 and 79, provided that:
  i) the amino acid sequence or Nanobody® encompassed in said polypeptide has an Aspartic acid (Asp, D) at position 54, a Glutamine (Gln, Q) at position 105, a Leucine (Leu, L) at position 78, an Arginine (Arg, R) at position 83 and a Glutamic add (Glu, E) at position 85 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-219: Trivalent polypeptide that is directed against and/or specifically binds protein F of hRSV, chosen from the following polypeptides:
a) SEQ ID NO's: 159-161;
b) polypeptides that have no more than 3, preferably no more than 2, more preferably no more than 1 amino acid difference with one of SEQ ID NO's: 159-161, provided that:
  i) the amino acid sequence or Nanobody® encompassed in said polypeptide has a Praline (Pro, P) at position 14, Arginine (Arg, R) at position 19, Leucine (Leu, L) at position 20 and Leucine (Leu, L) at position 108 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-220: Trivalent polypeptide according to aspect E-219, chosen from the following polypeptides:
a) SEQ ID NO's: 159-161;
b) polypeptides that have no more than 3, preferably no more than 2, more preferably no more than 1 amino acid difference with one of SEQ ID NO's: 159-161, provided that:
  i) the amino acid sequence or Nanobody® encompassed in said polypeptide has a Proline (Pro, P) at position 14, Arginine (Arg, R) at position 19, Leucine (Leu, L) at position 20 and Leucine (Leu, L) at position 108; and in addition Arginine (Arg, R) at position 83, Glutamic acid (Glu, E) at position 85 and/or Glutamine (Gln, Q) at position 105 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-221: Trivalent polypeptide according to any of aspects E-219 or E-220, chosen from the following polypeptides:

a) SEQ ID NO's: 159-161;
b) polypeptides that have no more than 3, preferably no more than 2, more preferably no more than 1 amino acid difference with one of SEQ ID NO's: 159-161, provided that:
  i) the amino acid sequence or Nanobody® encompassed in said polypeptide has a Proline (Pro, P) at position 14, Arginine (Arg, R) at position 19, Leucine (Leu, L) at position 20 and Leucine (Leu, L) at position 108; and in addition Arginine (Arg, R) at position 83, Glutamic acid (Glu, E) at position 85 and/or Glutamine (Gln, 4) at position 105 so that when the polypeptide has no more than 3, preferably no more than 2, more preferably no more than 1 amino acid difference with:
    SEQ ID NO: 159, the amino acid sequence or Nanobody® encompassed in said polypeptide preferably has Arginine (Arg, R) at position 83 and Glutamine (Gln, 4) at position 105;
    SEQ ID NO: 160, the amino acid sequence or Nanobody® encompassed in said polypeptide preferably has Arginine (Arg, R) at position 83, Glutamic acid (Glu, E) at position 85 and Glutamine (Gln, Q) at position 105;
    SEQ ID NO: 161, the amino acid sequence or Nanobody® encompassed in said polypeptide preferably has Arginine (Arg, R) at position 83 and Glutamic acid (Glu, E) at position 85;
    (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-222: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp.

Aspect E-223: Trivalent polypeptide comprising or essentially consisting of SEQ ID NO: 53, in which in at least one (preferably in two, more preferably in all three) Nanobody®/Nanobodies® that form(s) part of SEQ ID NO: 53, following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D.

Aspect E-224: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D.

Aspect E-225: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four or five) amino acid residues have been mutated selected from the following: Gly78Leu, Ala83Arg, Asp85Glu, Arg105Gln and Gly54D.

Aspect E-226: Trivalent polypeptide comprising or essentially consisting of SEQ ID NO: 53, in which in at least one (preferably in two, more preferably in all three) Nanobody®/Nanobodies® that form(s) part of SEQ ID NO: 53, following amino acid residues have been mutated: Gly78Leu, Ala83Arg, Asp85Glu, Arg105Gln and Gly54D.

Aspect E-227: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three or four) amino acid residues have been mutated selected from the following: Ala14Pro, Ser19Arg, Ile20Leu and Gln108Leu.

Aspect E-228: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu.

Aspect E-229: Trivalent polypeptide comprising or essentially consisting of SEQ ID NO: 53, in which in at least one (preferably in two, more preferably in all three) Nanobody®/Nanobodies® that form(s) part of SEQ ID NO: 53, following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or
Ala14Pro, Ser19Arg, Ile20Leu, Gln108Leu, Ala83Arg, Asp85Glu and Arg105Gln.

Aspect E-230: Trivalent polypeptide comprising or essentially consist of SEQ ID ND: 77.

Aspect E-231: Trivalent polypeptide comprising or essentially consist of SEQ ID NO: 78.

Aspect E-232: Trivalent polypeptide comprising or essentially consist of SEQ ID ND: 79.

Aspect E-233: Trivalent polypeptide comprising or essentially consist of one of SEQ ID NO's: 159-161.

Aspect E-234: Trivalent polypeptide that is directed against and/or specifically binds protein F of hRSV, chosen from the following polypeptides:

a) SEQ ID NO's: 142-145 and 162-165;
b) polypeptides that have no more than 3, preferably no more than 2, more preferably no more than 1 amino acid difference with one of SEQ ID NO's: 142-145 and 162-165, provided that:
  i) the first amino add sequence or Nanobody® encompassed in said polypeptide has an Aspartic acid (Asp, D) at position 1; and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-235: Trivalent polypeptide comprising or essentially consisting of SEQ ID NO: 53, in which the first Glutamic acid has been changed into Aspartic acid.

Aspect E-236: Trivalent polypeptide comprising or essentially consisting of SEQ ID NO: 77, in which the first Glutamic acid has been changed into Aspartic acid.

Aspect E-237: Trivalent polypeptide comprising or essentially consisting of SEQ ID NO: 78, in which the first Glutamic acid has been changed into Aspartic acid.

Aspect E-238: Trivalent polypeptide comprising or essentially consisting of SEQ ID NO: 79, in which the first Glutamic acid has been changed into Aspartic acid.

Aspect E-239: Trivalent polypeptide comprising or essentially consisting of SEQ ID NO: 158, in which the first Glutamic acid has been changed into Aspartic acid.

Aspect E-240: Trivalent polypeptide comprising or essentially consisting of SEQ ID NO: 159, in which the first Glutamic acid has been changed into Aspartic acid.

Aspect E-241: Trivalent polypeptide comprising or essentially consisting of SEQ ID NO: 160, in which the first Glutamic acid has been changed into Aspartic acid.

Aspect E-242: Trivalent polypeptide comprising or essentially consisting of SEQ ID NO: 161, in which the first Glutamic acid has been changed into Aspartic acid.

Aspect E-243: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the first Glutamic acid has been changed into Aspartic acid.

Aspect E-244: Trivalent polypeptide comprising or essentially consisting of SEQ ID NO: 53, in which in at least one (preferably in two, more preferably in all three) Nanobody®/Nanobodies® that form(s) part of SEQ ID NO: 53, following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the first Glutamic acid has been changed into Aspartic acid.

Aspect E-245: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, and wherein the first Glutamic acid has been changed into Aspartic acid.

Aspect E-246: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four or five) amino acid residues have been mutated selected from the following: Gly78Leu, Ala83Arg, Asp85Glu, Arg105Gln and Gly54D, and wherein the first Glutamic acid has been changed into Aspartic acid.

Aspect E-247: Trivalent polypeptide comprising or essentially consisting of SEQ ID NO: 53, in which in at least one (preferably in two, more preferably in all three) Nanobody®/Nanobodies® that form(s) part of SEQ ID NO: 53, following amino acid residues have been mutated: Gly78Leu, Ala83Arg, Asp85Glu, Arg105Gln and Gly54D, and wherein the first Glutamic acid has been changed into Aspartic acid.

Aspect E-248: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three or four) amino acid residues have been mutated selected from the following: Ala14Pro, Ser19Arg, Ile20Leu and Gln108Leu, and wherein the first Glutamic acid has been changed into Aspartic acid.

Aspect E-249: Trivalent polypeptide comprising or essentially consisting of SEQ ID NO: 53, in which in at least one (preferably in two, more preferably in all three) Nanobody®/Nanobodies® that form(s) part of SEQ ID NO: 53, one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein the first Glutamic acid has been changed into Aspartic acid.

Aspect E-250: Trivalent polypeptide comprising or essentially consisting of SEQ ID NO: 53, in which in at least one (preferably in two, more preferably in all three) Nanobody®/Nanobodies® that form(s) part of SEQ ID NO: 53, following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu, Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or
Ala14Pro, Ser19Arg, Ile20Leu, Gln108Leu, Ala83Arg, Asp85Glu and Arg105Gln,
and wherein the first Glutamic acid has been changed into Aspartic acid.

Aspect E-251: Trivalent polypeptide comprising or essentially consist of SEQ ID NO: 142.
Aspect E-252: Trivalent polypeptide comprising or essentially consist of SEQ ID NO: 143.
Aspect E-253: Trivalent polypeptide comprising or essentially consist of SEQ ID NO: 144.
Aspect E-254: Trivalent polypeptide comprising or essentially consist of SEQ ID NO: 145.
Aspect E-255: Trivalent polypeptide comprising or essentially consist of one of SEQ ID NO's: 162-165
Aspect E-256: Polypeptide according to any of aspects E-1 to E-255, that can specifically bind to protein F of hRSV with a dissociation constant ($K_D$) of 100 nM to 0.1 nM or less, preferably 10 nM to 0.1 nM or less, more preferably 1 nM to 0.1 nM or less.
Aspect E-257: Polypeptide according to any of aspects E-1 to E-256, that can specifically bind to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.
Aspect E-258: Polypeptide according to any of aspects E-1 to E-257, that can specifically bind to protein F of hRSV with a $k_{off}$ rate between $10^{-2}$ $s^{-1}$ ($t_{1/2}2=0.69$ s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, more preferably between $5 \times 10^{-3}$ $s^{-1}$ and $10^{-4}$ $s^{-1}$, or lower.
Aspect E-259: Polypeptide y according to any of aspects E-1 to E-258, that can neutralize hRSV (for example, as measured in a microneutralization assay on hRSV Long (such as e.g. described in Example 6) with an IC50 value between 10 pM and 1000 pM, preferably between 10 pM and 250 pM, more preferably between 50 pM and 200 pM or less.
Aspect E-260: Polypeptide according to any of aspects E-1 to E-259, that can neutralize hRSV (for example, as measured in a microneutralization assay on hRSV Long (such as e.g. described in Example 6) with an IC50 value that is at least the same and preferably better, at least ten times better, preferably twenty times better, more preferably fifty times better, even more preferably sixty, seventy, eighty or more times better compared to the IC50 value obtained with Synagis®.
Aspect E-261: Polypeptide according to any of aspects E-1 to E-260, which is a multispecific construct.
Aspect F-1: Monovalent construct, comprising or essentially consisting of one amino acid sequence according to any of aspects A-1 to A-29, C-1 to C-38 and W-1 to W-38 and/or one Nanobody® according to any of aspects B-1 to B-18, D-1 to D-38 and X-1 to X-38.
Aspect F-2: Monovalent construct according to aspect F-1, in which said amino acid sequence is chosen from the group consisting of domain antibodies, amino acid sequences that are suitable for use as a domain antibody, single domain antibodies, amino acid sequences that are suitable for use as a single domain antibody, "dAb's", amino acid sequences that are suitable for use as a dAb, or Nanobodies®.
Aspect F-3: Monovalent construct, comprising or essentially consisting of one Nanobody® according to any of aspects B-1 to B-18, D-1 to D-38 and X-1 to X-38.
Aspect F-4: Monovalent construct, that is chosen from the group consisting of SEQ ID NO's: 76, SEQ ID NO's: 138-141 and SEQ ID NO's: 146-157.
Aspect F-5: Use of a monovalent construct according to any of aspects F-1 to F-4, in preparing a multivalent polypeptide according to any of aspects E-1 to E-261.

Aspect F-6: Use of a monovalent construct according to aspect F-5, wherein the monovalent construct is used as a binding domain or binding unit in preparing a multivalent construct comprising two or more binding units.

Aspect F-7: Use of a monovalent construct according to any of aspects F-5 or F-6, in preparing a multivalent polypeptide that preferably exhibits intramolecular binding compared to intermolecular binding.

Aspect F-8: Use of a monovalent construct according to any of aspects F-5 to F-7, as a binding domain or binding unit in preparing a multivalent construct, wherein the binding domains or binding units are linked via a linker such that the multivalent polypeptide preferably exhibits intramolecular binding compared to intermolecular binding and/or the multivalent polypeptide can simultaneously bind all binding site on protein F of hRSV.

Aspect F-9: Use of a monovalent construct according to any of aspects F-5 to F-8, wherein the monovalent construct is chosen from the following:
  a) SEQ ID NO's: 60-76;
  b) amino acid sequences that have no more than 3, preferably no more than 2, more preferably no more than 1 amino acid difference with one of SEQ ID NO's: 60-76, provided that:
    i) the amino acid sequence has a Glutamine (Gln, Q) at position 105 (said position determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
  in preparing a multivalent polypeptide.

Aspect F-10: Use of a monovalent construct according to aspect F-9, wherein the monovalent construct essentially consists of one of SEQ ID NO's: 60-76.

Aspect F-11: Use of a monovalent construct according to any of aspects F-5 to F-8, wherein the monovalent construct is chosen from the following:
  a) SEQ ID NO's: 62, 65, 67, 68, 75 and 76;
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and/or a Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
  in preparing a multivalent polypeptide.

Aspect F-12: Use of a monovalent construct according to aspect F-11, wherein the monovalent construct is chosen from the following:
  a) SEQ ID NO's: 62, 65, 67, 68, 75 and 76; or
  b) amino acid sequences that have no more than 3, preferably no more than 2, more preferably no more than 1 amino acid difference with one of SEQ ID NO's: 62, 65, 67, 68, 75 and 76, provided that:
    i) the amino acid sequence has a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
  in preparing a multivalent polypeptide.

Aspect F-13: Use of a monovalent construct according to aspect F-11 or F-12, wherein the monovalent essentially consists of one of SEQ ID NO: 62, 65, 67, 68, 75 and 76.

Aspect F-14: Use of a monovalent construct according to any of aspects F-5 to F-8, wherein the monovalent construct is chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic add (Asp, D) at position 54, a Glutamine (Gln, Q) at position 105, a Leucine (Leu, L) at position 78 and/or an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide.

Aspect F-15: Use of a monovalent construct according aspect F-14, wherein the monovalent construct is chosen from the following:
  a) SEQ ID NO's: 65 and 76;
  b) amino acid sequences that have no more than 3, preferably no more than 2, more preferably no more than 1 amino acid difference with one of SEQ ID NO's: 65 and 76, provided that:
    i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
  in preparing a multivalent polypeptide.

Aspect F-16: Use of a monovalent construct essentially consisting of SEQ ID NO: 62 in preparing a multivalent polypeptide.

Aspect F-17: Use of a monovalent construct essentially consisting of SEQ ID NO: 65 in preparing a multivalent polypeptide.

Aspect F-18: Use of a monovalent construct essentially consisting of SEQ ID NO: 76 in preparing a multivalent polypeptide.

Aspect F-19: Use of a monovalent construct according to any of aspects F-5 to F-8, wherein the monovalent construct is chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Proline (Pro, P) at position 14, Arginine (Arg, R) at position 19, Leucine (Leu, L) at position 20 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide.

Aspect F-20: Use of a monovalent construct according to aspect F-19, wherein the monovalent construct essentially consists of one of SEQ ID NO's: 146-153.

Aspect F-21: Use of a monovalent construct according to any of aspects F-5 to F-8, wherein the monovalent construct is chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108; and in addition Arginine (Arg, R) at position 83, Glutamic acid (Glu, E) at position 85 and/or Glutamine (Gln, Q) at position 105 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide.

Aspect F-22: Use of a monovalent construct according to aspect F-21, wherein the monovalent construct is chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide.

Aspect F-23: Use of a monovalent construct according to aspect F-21 or F-22, wherein the monovalent essentially consists of one of SEQ ID NO: 146-149 and 151-153.

Aspect F-24: Use of a monovalent construct according to any of aspects F-5 to F-8, wherein the monovalent construct essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, in preparing a multivalent polypeptide.

Aspect F-25: Use of a monovalent construct according to aspects F-24, wherein the monovalent construct essentially consists of SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, in preparing a multivalent polypeptide.

Aspect F-26: Use of a monovalent construct according to aspects F-24, wherein the monovalent construct essentially consists of SEQ ID NO: 5, in which one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, in preparing a multivalent polypeptide.

Aspect F-27: Use of a monovalent construct according to aspects F-24, wherein the monovalent construct essentially consists of SEQ ID NO: 5, in which one or more (such as two, three, four or five) amino acid residues have been mutated selected from the following: Gly78Leu, Ala83Arg, Asp85Glu, Arg105Gln and Gly54D, in preparing a multivalent polypeptide.

Aspect F-28: Use of a monovalent construct according to aspects F-27, wherein the monovalent construct essentially consists of SEQ ID NO: 5, in which following amino acid residues have been mutated: Gly78Leu, Ala83Arg, Asp85Glu, Arg105Gln and Gly54D, in preparing a multivalent polypeptide.

Aspect F-29: Use of a monovalent construct according to any of aspects F-5 to F-8, wherein the monovalent construct essentially consists of SEQ ID NO: 5, in which one or more (such as two, three or four) amino acid residues have been mutated selected from the following: Ala14Pro, Ser19Arg, Ile20Leu and Gln108Leu, in preparing a multivalent polypeptide.

Aspect F-30: Use of a monovalent construct according to any of aspects F-5 to F-8, wherein the monovalent construct essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, in preparing a multivalent polypeptide.

Aspect F-31: Use of a monovalent construct according to aspects F-24, wherein the monovalent construct essentially consists of SEQ ID NO: 5, in which following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or
Ala14Pro, Ser19Arg, Ile20Leu, Gln108Leu, Ala83Arg, Asp85Glu and Arg105Gln,
in preparing a multivalent polypeptide.

Aspect F-32: Use of a monovalent construct according to any of aspects F-5 to F-8, wherein the monovalent construct is chosen from the following:
a) SEQ ID NO's; 138-141 and 154-157;
b) amino acid sequences that have no more than 3, preferably no more than 2, more preferably no more than 1 amino acid difference with one of SEQ ID NO's: 138-141 and 154-157, provided that:
i) the amino acid sequence has a Aspartic acid (Gln, Q) at position 1 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide.

Aspect F-33: Use of a monovalent construct according to aspect F-32, wherein the monovalent construct essentially consists of one of SEQ ID NO's: 138-141 and 154-157.

Aspect F-34: Use of a monovalent construct according to any of aspects F-5 to F-8, wherein the monovalent construct essentially consists of SEQ ID NO: 5, in which the Glutamic acid at position 1 has been changed into Aspartic acid, in preparing a multivalent polypeptide.

Aspect F-35: Use of a monovalent construct according to any of aspects F-5 to F-8, wherein the monovalent construct essentially consists of SEQ ID NO: 62, in which the Glutamic acid at position 1 has been changed into Aspartic acid, in preparing a multivalent polypeptide.

Aspect F-36: Use of a monovalent construct according to any of aspects F-5 to F-8, wherein the monovalent construct essentially consists of SEQ ID NO: 65, in which the Glutamic acid at position 1 has been changed into Aspartic acid, in preparing a multivalent polypeptide.

Aspect F-37: Use of a monovalent construct according to any of aspects F-5 to F-8, wherein the monovalent construct essentially consists of SEQ ID NO: 76, in which the Glutamic acid at position 1 has been changed into Aspartic acid, in preparing a multivalent polypeptide.

Aspect F-38: Use of a monovalent construct according to any of aspects F-5 to F-8, wherein the monovalent construct essentially consists of SEQ ID NO: 75, in which the Glutamic acid at position 1 has been changed into Aspartic acid, in preparing a multivalent polypeptide.

Aspect F-39: Use of a monovalent construct according to any of aspects F-5 to F-8, wherein the monovalent construct essentially consists of SEQ ID NO: 147, in which the Glutamic acid at position 1 has been changed into Aspartic acid, in preparing a multivalent polypeptide.

Aspect F-40: Use of a monovalent construct according to any of aspects F-5 to F-8, wherein the monovalent construct essentially consists of SEQ ID NO: 149, in which the Glutamic acid at position 1 has been changed into Aspartic acid, in preparing a multivalent polypeptide.

Aspect F-41: Use of a monovalent construct according to any of aspects F-5 to F-8, wherein the monovalent construct essentially consists of SEQ ID NO: 153, in which the Glutamic acid at position 1 has been changed into Aspartic acid, in preparing a multivalent polypeptide.

Aspect F-42: Use of a monovalent construct according to any of aspects F-5 to F-8, wherein the monovalent construct essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the Glutamic acid at position 1 has been changed into Aspartic acid, in preparing a multivalent polypeptide.

Aspect F-43: Use of a monovalent construct according to aspects F-42, wherein the monovalent construct essentially consists of SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid, in preparing a multivalent polypeptide.

Aspect F-44: Use of a monovalent construct according to aspects F-42, wherein the monovalent construct essentially consists of SEQ ID NO: 5, in which one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, and wherein the Glutamic acid at position 1 has been changed into Aspartic acid, in preparing a multivalent polypeptide.

Aspect F-45: Use of a monovalent construct according to aspects F-42, wherein the monovalent construct essentially consists of SEQ ID NO: 5, in which one or more (such as two, three, four, or five) amino acid residues have been mutated selected from the following: Gly78Leu, Ala83Arg, Asp85Glu, Arg105Gln and Gly54D, and wherein the Glutamic acid at position 1 has been changed into Aspartic acid, in preparing a multivalent polypeptide.

Aspect F-46: Use of a monovalent construct according to aspects F-42, wherein the monovalent construct essentially consists of SEQ ID NO: 5, in which following amino acid residues have been mutated: Gly78Leu, Ala83Arg, Asp85Glu, Arg105Gln and Gly54D, and wherein the Glutamic acid at position 1 has been changed into Aspartic acid, in preparing a multivalent polypeptide.

Aspect F-47: Use of a monovalent construct according to any of aspects F-5 to F-8, wherein the monovalent construct essentially consists of SEQ ID NO: 5, in which one or more (such as two, three or four) amino acid residues have been mutated selected from the following: Ala14Pro, Ser19Arg, Ile20Leu and Gln108Leu, and wherein the Glutamic acid at position 1 has been changed into Aspartic acid, in preparing a multivalent polypeptide.

Aspect F-48: Use of a monovalent construct according to any of aspects F-5 to F-8, wherein the monovalent construct essentially consists of SEQ ID NO: 5, in which one or more (such as two, three, four, five, six, seven, eight or nine, ten, eleven or twelve) amino acid residues have been mutated selected from the following: Ala14Pro, Ser19Arg, Ile20Leu, Ala83Arg, Asp85Glu, Arg105Gln and Gln108Leu, and wherein the Glutamic acid at position 1 has been changed into Aspartic acid, in preparing a multivalent polypeptide.

Aspect F-49: Use of a monovalent construct according to aspects F-42, wherein the monovalent construct essentially consists of SEQ ID NO: 5, in which following amino acid residues have been mutated:

Glu1Asp;
Glu1Asp, Val5Leu, Ala14Pro, Glu44Gly, Gly78Leu, Ala83Arg, Asp85Glu, Arg105Gln and Gln108Leu;
Glu1Asp, Ala83Arg, Asp85Glu, Arg105Gln and Gln108Leu;
Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu and Arg105Gln; or
Glu1Asp, Ala14Pro, Ser19Arg, Ile20Leu, Gln108Leu, Ala83Arg, Asp85Glu and Arg105Gln,
in preparing a multivalent construct.

Aspect F-50: Use of two monovalent constructs according to any of aspects F-1 to F-4 in preparing a bivalent polypeptide.

Aspect F-51: Use of two monovalent constructs according to aspect F-50, in preparing a bivalent construct that preferably exhibits intramolecular binding compared to intermolecular binding.

Aspect F-52: Use of two monovalent constructs according to any of aspects F-50 to F-51, as a binding domain or binding unit in preparing a bivalent polypeptide, wherein the binding domains, or binding units are linked via a linker such that the bivalent polypeptide preferably exhibits intramolecular binding compared to intermolecular binding and/or the bivalent polypeptide can simultaneously bind both binding site on protein F of hRSV.

Aspect F-53: Use of two monovalent constructs according to any of aspects F-50 to F-52, wherein the monovalent constructs are chosen from the following:
a) SEQ ID NO's: 60-76;
b) amino acid sequences that have no more than 3, preferably no more than 2, more preferably no more than 1 amino acid difference with one of SEQ ID NO's: 60-76, provided that:
  i) the amino acid sequence has a Glutamine (Gln, Q) at position 105 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide.

Aspect F-54: Use of two monovalent constructs according to aspect F-53, wherein the two monovalent constructs are identical.

Aspect F-55: Use of two monovalent constructs according to aspects F-53 or F-54, wherein the two monovalent constructs essentially consist of one of SEQ ID NO's: 60-76.

Aspect F-56: Use of two monovalent constructs according to any of aspects F-50 to F-52, wherein the monovalent constructs are chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and/or a Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide.

Aspect F-57: Use of two monovalent constructs according to aspect F-56, wherein the monovalent constructs are chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
i) the amino add sequence has a Glutamine (Gln, Q) at position 105, a Leucine (Leu, L) at position 78 and an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide.

Aspect F-58: Use of two monovalent constructs according to aspects F-56 or F-57, wherein the two monovalent constructs are identical.

Aspect F-59: Use of two monovalent constructs according to aspect F-58, wherein the two monovalent constructs essentially consist of one of SEQ ID NO's: 62, 65, 67, 68, 75 and 76.

Aspect F-60: Use of two monovalent constructs according to any of aspects F-50 to F-52, wherein the monovalent constructs are chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide.

Aspect F-61: Use of two monovalent constructs according to aspect F-60, wherein the monovalent constructs are chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide.

Aspect F-62: Use of two monovalent constructs according to aspects F-60 or F-61, wherein the two monovalent constructs are identical.

Aspect F-63: Use of two monovalent constructs essentially consisting of SEQ ID NO: 62 in preparing a bivalent polypeptide.

Aspect F-64: Use of two monovalent constructs essentially consisting of SEQ ID NO: 65 in preparing a bivalent polypeptide.

Aspect F-65: Use of two monovalent constructs essentially consisting of SEQ ID NO: 76 in preparing a bivalent polypeptide.

Aspect F-66: Use of two monovalent constructs according to any of aspects F-50 to F-52, wherein the monovalent constructs are chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
i) the amino acid sequence has a Proline (Pro, P) at position 14, Arginine (Arg, R) at position 19, Leucine (Leu, 1) at position 20 and Leucine (Leu, L) at position 108 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide.

Aspect F-67: Use of two monovalent constructs according to aspect F-66, wherein the two monovalent constructs are identical.

Aspect F-68: Use of two monovalent constructs according to aspects F-66 or F-67, wherein the two monovalent constructs essentially consist of one of SEQ ID NO's: 146-153.

Aspect F-69: Use of two monovalent constructs according to any of aspects F-50 to F-52, wherein the monovalent constructs are chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide.

Aspect F-70: Use of two monovalent constructs according to aspect F-69, wherein the monovalent constructs are chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
    SEQ ID NO: 146, the amino acid sequence preferably has Glutamine (Gln, Q) at position 105;
    SEQ ID NO: 147, the amino acid sequence preferably has Arginine (Arg, R) at position 83 and Glutamine (Gln, Q) at position 105;
    SEQ ID NO: 148, the amino acid sequence preferably has Glutamic acid (Glu, E) at position 85 and Glutamine (Gln, Q) at position 105;
    SEQ ID NO: 149, the amino acid sequence preferably has Arginine (Arg, R) at position 83, Glutamic acid (Glu, E) at position 85 and Glutamine (Gln, Q) at position 105;
    SEQ ID NO: 151, the amino acid sequence preferably has Arginine (Arg, R) at position 83;
    SEQ ID NO: 152, the amino acid sequence preferably has Glutamic acid (Glu, E) at position 85;
    SEQ ID NO: 153, the amino acid sequence preferably has Arginine (Arg, R) at position 83 and Glutamic acid (Glu, E) at position 85;
    (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide.

Aspect F-71: Use of two monovalent constructs according to aspects F-69 or F-70, wherein the two monovalent constructs are identical.

Aspect F-72: Use of two monovalent constructs according to aspect F-71, wherein the two monovalent constructs essentially consist of one of SEQ ID NO's: 146-149 and 151-153.

Aspect F-73: Use of two monovalent constructs according to any of aspects F-50 to F-52, wherein the monovalent construct essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, in preparing a bivalent polypeptide.

Aspect F-74: Use of two monovalent constructs according to aspects F-73, wherein the monovalent construct essentially consists of SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, in preparing a bivalent polypeptide.

Aspect F-75: Use of two monovalent constructs according to aspects F-73, wherein the monovalent construct essentially consists of SEQ ID NO: 5, in which one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, in preparing a bivalent polypeptide.

Aspect F-76: Use of two monovalent constructs according to aspects F-73, wherein the monovalent construct essentially consists of SEQ ID NO: 5, in which one or more (such as two, three, four or five) amino acid residues have been mutated selected from the following: Gly78Leu, Ala83Arg, Asp85Glu, Arg105Gln and Gly54D, in preparing a bivalent polypeptide.

Aspect F-77: Use of two monovalent constructs according to aspects F-76, wherein the monovalent construct essentially consists of SEQ ID NO: 5, in which following amino add residues have been mutated: Gly78Leu, Ala83Arg, Asp85Glu, Arg105Gln and Gly54D, in preparing a bivalent polypeptide.

Aspect F-78: Use of two monovalent constructs according to any of aspects F-50 to F-52, wherein the monovalent construct essentially consists of SEQ ID NO: 5, in which one or more (such as two, three or four) amino acid residues have been mutated selected from the following: Ala14Pro, Ser19Arg, Ile20Leu and Gln108Leu, in preparing a bivalent polypeptide.

Aspect F-79: Use of two monovalent constructs according to any of aspects F-50 to F-52, wherein the monovalent construct essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, in preparing a bivalent polypeptide.

Aspect F-80: Use of two monovalent constructs according to aspects F-73, wherein the monovalent construct essentially consists of SEQ ID NO: 5, in which following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln; or Ala14Pro, Ser19Arg, Ile20Leu, Gln108Leu, Ala83Arg, Asp85Glu and Arg105Gln,
in preparing a bivalent polypeptide.

Aspect F-81: Use of a monovalent constructs according to any of aspects F-50 to F-52, wherein the monovalent construct is chosen from the following:
a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:
i) the amino acid sequence has a Aspartic acid (Asp, D) at position 1 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide.

Aspect F-82: Use of a monovalent constructs according to aspect F-81, wherein the monovalent construct essentially consist of one of SEQ ID NO's: 138-141 and 154-157.

Aspect F-83: Use of a monovalent constructs according to any of aspects F-50 to F-52, wherein the monovalent construct essentially consists of SEQ ID NO: 5, in which the Glutamic acid at position 1 has been changed into Aspartic acid, in preparing a bivalent polypeptide.

Aspect F-84: Use of a monovalent constructs according to any of aspects F-50 to F-52, wherein the monovalent construct essentially consists of SEQ ID NO: 62, in which the Glutamic acid at position 1 has been changed into Aspartic acid, in preparing a bivalent polypeptide.

Aspect F-85: Use of a monovalent constructs according to any of aspects F-50 to F-52, wherein the monovalent construct essentially consists of SEQ ID NO: 65, in which the Glutamic acid at position 1 has been changed into Aspartic acid, in preparing a bivalent polypeptide.

Aspect F-86: Use of a monovalent constructs according to any of aspects F-50 to F-52, wherein the monovalent construct essentially consists of SEQ ID NO: 76, in which the Glutamic acid at position 1 has been changed into Aspartic acid, in preparing a bivalent polypeptide.

Aspect F-87: Use of a monovalent constructs according to any of aspects F-50 to F-52, wherein the monovalent construct essentially consists of SEQ ID NO: 75, in which the Glutamic acid at position 1 has been changed into Aspartic acid, in preparing a bivalent polypeptide.

Aspect F-88: Use of a monovalent constructs according to any of aspects F-50 to F-52, wherein the monovalent construct essentially consists of SEQ ID NO: 147, in which the Glutamic acid at position 1 has been changed into Aspartic acid, in preparing a bivalent polypeptide.

Aspect F-89: Use of a monovalent constructs according to any of aspects F-50 to F-52, wherein the monovalent construct essentially consists of SEQ ID NO: 149, in which the Glutamic acid at position 1 has been changed into Aspartic acid, in preparing a bivalent polypeptide.

Aspect F-90: Use of a monovalent constructs according to any of aspects F-50 to F-52, wherein the monovalent construct essentially consists of SEQ ID NO: 153, in which the Glutamic acid at position 1 has been changed into Aspartic acid, in preparing a bivalent polypeptide.

Aspect F-91: Use of a monovalent constructs according to any of aspects F-50 to F-52, wherein the monovalent construct essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the Glutamic acid at position 1 has been changed into Aspartic acid, in preparing a bivalent polypeptide.

Aspect F-92: Use of a monovalent constructs according to aspects F-91, wherein the monovalent construct essentially consists of SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 has been changed into Aspartic acid, in preparing a bivalent polypeptide.

Aspect F-93: Use of a monovalent constructs according to aspects F-91, wherein the monovalent construct essentially consists of SEQ ID NO: 5, in which one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, and wherein the Glutamic acid at position 1 has been changed into Aspartic acid, in preparing a bivalent polypeptide.

Aspect F-94: Use of a monovalent constructs according to aspects F-91, wherein the monovalent construct essentially consists of SEQ ID NO: 5, in which one or more (such as two, three, four or five) amino acid residues have been mutated selected from the following: Gly78Leu, Ala83Arg, Asp85Glu, Arg105Gln and Gly54D, and wherein the Glutamic acid at position 1 has been changed into Aspartic acid, in preparing a bivalent polypeptide.

Aspect F-95: Use of a monovalent constructs according to aspects F-94, wherein the monovalent construct essentially consists of SEQ ID NO: 5, in which following amino acid residues have been mutated: Gly78Leu, Ala83Arg, Asp85Glu, Arg105Gln and Gly54D, and wherein the Glutamic acid at position 1 has been changed into Aspartic acid, in preparing a bivalent polypeptide.

Aspect F-96: Use of a monovalent constructs according to any of aspects F-50 to F-52, wherein the monovalent construct essentially consists of SEQ ID NO: 5, in which one or more (such as two, three or four) amino acid residues have been mutated selected from the following: Ala14Pro, Ser19Arg, Ile20Leu and Gln108Leu, and wherein the Glutamic acid at position 1 has been changed into Aspartic acid, in preparing a bivalent polypeptide.

Aspect F-97: Use of a monovalent constructs according to any of aspects F-50 to F-52, wherein the monovalent construct essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein the Glutamic acid at position 1 has been changed into Aspartic acid, in preparing a bivalent polypeptide.

Aspect F-98: Use of a monovalent constructs according to aspects F-91, wherein the monovalent construct essentially consists of SEQ ID NO: 5, in which following amino acid residues have been mutated:
Glu1Asp;
Glu1Asp, Val5Leu, Ala14Pro, Glu44Gly, Gly78Leu, Ala83Arg, Asp85Glu, Arg105Gln and Gln108Leu;
Glu1Asp, Ala83Arg, Asp85Glu, Arg105Gln and Gln108Leu;

Glu1Asp, Gly78Leu, Ala83Arg, Asp85Glu and Arg105Gln;
Glu1Asp, Val5Leu, Ala14Pro, Glu44Gly, Gly78Leu, Ala83Arg, Asp85Glu, Arg105Gln, Gln108Leu and Gly54Asp;
Glu1Asp, Ala83Arg, Asp85Glu, Arg105Gln, Gln108Leu and Gly54Asp;
Glu1Asp, Gly78Leu, Ala83Arg, Asp85Glu, Arg105Gln and Gly54Asp;
Glu1Asp and Gly54Asp;
Glu1Asp, Ala14Pro, Ser19Arg, Ile20Leu and Gln108Leu;
Glu1Asp, Ala14Pro, Ser19Arg, Ile20Leu, Gln108Leu and Ala83Arg;
Glu1Asp, Ala14Pro, Ser19Arg, Ile20Leu, Gln108Leu and Asp85Glu;
Glu1Asp, Ala14Pro, Ser19Arg, Ile20Leu, Gln108Leu and Arg105Gln;
Glu1Asp, Ala14Pro, Ser19Arg, Ile20Leu, Gln108Leu, Ala83Arg and Asp85Glu;
Glu1Asp, Ala14Pro, Ser19Arg, Ile20Leu, Gln108Leu, Ala83Arg and Arg105Gln;
Glu1Asp, Ala14Pro, Ser19Arg, Ile20Leu, Gln108Leu, Asp85Glu, Arg105Gln; or
Glu1Asp, Ala14Pro, Ser19Arg, Ile20Leu, Gln108Leu, Ala83Arg, Asp85Glu and Arg105Gln,
in preparing a bivalent polypeptide.

Aspect F-99: Use of three monovalent constructs according to any of aspects F-1 to F-4 in preparing a trivalent polypeptide.

Aspect F-100: Use of three monovalent constructs according to aspect F-99, in preparing a trivalent construct that preferably exhibits intramolecular binding compared to intermolecular binding.

Aspect F-101: Use of three monovalent construct according to any of aspects F-99 to F-100, as a binding domain or binding unit in preparing a trivalent polypeptide, wherein the binding domains or binding units are linked via a linker such that the trivalent polypeptide preferably exhibits intramolecular binding compared to intermolecular binding and/or the trivalent polypeptide can simultaneously bind all three binding site on protein F of hRSV.

Aspect F-102: Use of three monovalent constructs according to any of aspects F-99 to F-101, wherein the monovalent constructs are chosen from the following:
a) SEQ ID NO's: 60-76;
b) amino acid sequences that have no more than 3, preferably no more than 2, more preferably no more than 1 amino acid difference with one of SEQ ID NO's: 60-76, provided that:
  i) the amino acid sequence has a Glutamine (Gln, Q) at position 105 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide.

Aspect F-103: Use of three monovalent constructs according to aspect F-102, wherein the three monovalent constructs are identical.

Aspect F-104: Use of three monovalent constructs according to aspects F-102 or F-103, wherein the three monovalent constructs essentially consist of one of SEQ ID NO's: 60-76.

Aspect F-105: Use of three monovalent constructs according to any of aspects F-99 to F-101, wherein the monovalent constructs are chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and/or a Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide.

Aspect F-106: Use of three monovalent constructs according to aspect F-105, wherein the monovalent constructs are chosen from the following:
a) SEQ ID NO's: 62, 65, 67, 68, 75 and 76;
b) amino acid sequences that have no more than 3, preferably no more than 2, more preferably no more than 1 amino acid difference with one of SEQ ID NO's: 62, 65, 67, 68, 75 and 76, provided that:
  i) the amino acid sequence has a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide.

Aspect F-107: Use of three monovalent constructs according to aspects F-105 or F-106, wherein the three monovalent constructs are identical.

Aspect F-108: Use of three monovalent constructs according to aspect F-107, wherein the three monovalent constructs essentially consist of one of SEQ ID NO's: 62, 65, 67, 68, 75 and 76.

Aspect F-109: Use of three monovalent constructs according to any of aspects F-99 to F-101, wherein the monovalent constructs are chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and/or an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide.

Aspect F-110: Use of three monovalent constructs according to aspect F-109, wherein the monovalent constructs are chosen from the following:
a) SEQ ID NO's: 65 and 76;
b) amino acid sequences that have no more than 3, preferably no more than 2, more preferably no more than 1 amino acid difference with one of SEQ ID NO's: 65 and 76, provided that:
  i) the amino acid sequence has an Aspartic acid (Asp, D) at position 54, a Glutamine (Gln, Q) at position 105, a Leucine (Leu, L) at position 78 and an Arginine (Arg, R) at position 83 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide.

Aspect F-111: Use of three monovalent constructs according to aspects F-109 or F-110, wherein the three monovalent constructs are identical.

Aspect F-112: Use of three monovalent constructs essentially consisting of SEQ ID NO: 62 in preparing a trivalent polypeptide.

Aspect F-113: Use of three monovalent constructs essentially consisting of SEQ ID NO: 65 in preparing a trivalent polypeptide.

Aspect F-114: Use of three monovalent constructs essentially consisting of SEQ ID NO: 76 in preparing a trivalent polypeptide.

Aspect F-115: Use of three monovalent constructs according to any of aspects F-99 to F-101, wherein the monovalent constructs are chosen from the following:
a) SEQ ID NO's: 146-153;
b) amino acid sequences that have no more than 3, preferably no more than 2, more preferably no more than 1 amino acid difference with one of SEQ ID NO's: 146-153, provided that:
  i) the amino acid sequence has a Praline (Pro, P) at position 14, Arginine (Arg, R) at position 19, Leucine (Leu, L) at position 20 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide.

Aspect F-116: Use of three monovalent constructs according to aspect F-115, wherein the three monovalent constructs are identical.

Aspect F-117: Use of three monovalent constructs according to aspects F-115 or F-116, wherein the three monovalent constructs essentially consist of one of SEQ ID NO's: 146-153.

Aspect F-118: Use of three monovalent constructs according to any of aspects F-99 to F-101, wherein the monovalent constructs are chosen from the following:
a) SEQ ID NO's: 146-14.9 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Proline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide.

Aspect F-119: Use of three monovalent constructs according to aspect F-118, wherein the monovalent constructs are chosen from the following:
a) SEQ ID NO's: 146-149 and 151-153;
b) amino acid sequences that have no more than 3, preferably no more than 2, more preferably no more than 1 amino acid difference with one of SEQ ID NO's: 146-149 and 151-153, provided that:
  i) the amino acid sequence has a Praline (Pro, P) at position 14, Arginine (Arg, R) at position 19, Leucine (Leu, L) at position 20 and Leucine (Leu, L) at position 108 and in addition Arginine (Arg, R) at position 83, Glutamic acid (Glu, E) at position 85 and/or Glutamine (Gln, Q) at position 105 so that when the amino acid sequence has no more than 3, preferably no more than 2, more preferably no more than 1 amino acid difference with:
   SEQ ID NO: 146, the amino acid sequence preferably has Glutamine (Gln, Q) at position 105;
   SEQ ID NO: 147, the amino acid sequence preferably has Arginine (Arg, R) at position 83 and Glutamine (Gln, Q) at position 105;
   SEQ ID NO: 148, the amino add sequence preferably has Glutamic acid (Glu, E) at position 85 and Glutamine (Gln, Q) at position 105;
   SEQ ID NO: 149, the amino acid sequence preferably has Arginine (Arg, R) at position 83, Glutamic acid (Glu, E) at position 85 and Glutamine (Gln, Q) at position 105;
   SEQ ID NO: 151, the amino acid sequence preferably has Arginine (Arg, R) at position 83;
   SEQ ID NO: 152, the amino acid sequence preferably has Glutamic acid (Glu, E) at position 85;
   SEQ ID NO: 153, the amino acid sequence preferably has Arginine (Arg, R) at position 83 and Glutamic acid (Glu, E) at position 85;
   (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide.

Aspect F-120: Use of three monovalent constructs according to aspects F-118 or F-119, wherein the three monovalent constructs are identical.

Aspect F-121: Use of three monovalent constructs according to aspect F-120, wherein the three monovalent constructs essentially consist of one of SEQ ID NO's: 146-149 and 151-153.

Aspect F-122: Use of three monovalent constructs according to any of aspects F-99 to F-101, wherein the monovalent construct essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, in preparing a trivalent polypeptide.

Aspect F-123: Use of three monovalent constructs according to aspects F-122, wherein the monovalent construct essentially consists of SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, in preparing a trivalent polypeptide.

Aspect F-124: Use of three monovalent constructs according to aspects F-122, wherein the monovalent construct essentially consists of SEQ ID NO: 5, in which one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, in preparing a trivalent polypeptide.

Aspect F-125: Use of three monovalent constructs according to aspects F-122, wherein the monovalent construct essentially consists of SEQ ID NO: 5, in which one or more (such as two, three, four or five) amino acid residues have been mutated selected from the following: Gly78Leu, Ala83Arg, Asp85Glu, Arg105Gln and Gly54D, in preparing a trivalent polypeptide.

Aspect F-126: Use of three monovalent constructs according to aspects F-125, wherein the monovalent construct essentially consists of SEQ ID NO: 5, in which following amino acid residues have been mutated: Gly78Leu, Ala83Arg, Asp85Glu, Arg105Gln and Gly54D, in preparing a trivalent polypeptide.

Aspect F-127: Use of three monovalent constructs according to any of aspects F-99 to F-101, wherein the monovalent construct essentially consists of SEQ ID NO: 5, in which one or more (such as two, three or four) amino acid residues have been mutated selected from the following: Ala14Pro, Ser19Arg, Ile20Leu and Gln108Leu, in preparing a trivalent polypeptide.

Aspect F-128: Use of three monovalent constructs according to any of aspects F-99 to F-101, wherein the monovalent construct essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, in preparing a trivalent polypeptide.

Aspect F-129: Use of three monovalent constructs according to aspects F-122, wherein the monovalent construct essentially consists of SEQ ID NO: 5, in which following amino acid residues have been mutated:
Val5Leu, Ala14Pro, Glu44Gly, Gly78Leu, Ala83Arg, Asp85Glu, Arg105Gln and Gln108Leu;
Ala83Arg, Asp85Glu, Arg105Gln and Gln108Leu;
Gly78Leu, Ala83Arg, Asp85Glu and Arg105Gln;
Val5Leu, Ala14Pro, Glu44Gly, Gly78Leu, Ala83Arg, Asp85Glu, Arg105Gln, Gln108Leu and Gly54Asp;
Ala83Arg, Asp85Glu, Arg105Gln, Gln108Leu and Gly54Asp;
Gly78Leu, Ala83Arg, Asp85Glu, Arg105Gln and Gly54Asp;
Gly54Asp;
Ala14Pro, Ser19Arg, Ile20Leu and Gln108Leu;
Ala14Pro, Ser19Arg, Ile20Leu, Gln108Leu and Ala83Arg;
Ala14Pro, Ser19Arg, Ile20Leu, Gln108Leu and Asp85Glu;
Ala14Pro, Ser19Arg, Ile20Leu, Gln108Leu and Arg105Gln;
Ala14Pro, Ser19Arg, Ile20Leu, Gln108Leu, Ala83Arg and Asp85Glu;
Ala14Pro, Ser19Arg, Ile20Leu, Gln108Leu, Ala83Arg and Arg105Gln;
Ala14Pro, Ser19Arg, Ile20Leu, Gln108Leu, Asp85Glu and Arg105Gln;
Ala14Pro, Ser19Arg, Ile20Leu, Gln108Leu, Ala83Arg, Asp85Glu and Arg105Gln,
in preparing a trivalent polypeptide.

Aspect F-130: Use of an amino acid sequence with SEQ ID NO: 62 in preparing a trivalent polypeptide with SEQ ID NO: 77, wherein an amino acid sequence with SEQ ID NO: 62 is linked to at least two further amino acid sequences with SEQ ID NO: 62, via a 15GS linker.

Aspect F-131: Use of an amino acid sequence with SEQ ID NO: 65 in preparing a trivalent polypeptide with SEQ ID NO: 78, wherein an amino acid sequence with SEQ ID NO: 65 is linked to at least two further amino acid sequences with SEQ ID NO: 65, via a 15GS linker.

Aspect F-132: Use of an amino acid sequence with SEQ ID NO: 76 in preparing a trivalent polypeptide with SEQ ID NO: 79, wherein an amino acid sequence with SEQ ID NO: 76 is linked to at least two further amino acid sequences with SEQ ID NO: 76, via a 15GS linker.

Aspect F-133: Use of an amino acid sequence with SEQ ID NO: 75 in preparing a trivalent polypeptide with SEQ ID NO: 158, wherein an amino acid sequence with SEQ ID NO: 75 is linked to at least two further amino acid sequences with SEQ ID NO: 75, via a 15GS linker.

Aspect F-134: Use of an amino acid sequence with SEQ ID NO: 147 in preparing a trivalent polypeptide with SEQ ID NO: 159, wherein an amino acid sequence with SEQ ID NO: 147 is linked to at least two further amino acid sequences with SEQ ID NO: 147, via a 15GS linker.

Aspect F-135: Use of an amino acid sequence with SEQ ID NO: 149 in preparing a trivalent polypeptide with SEQ ID NO: 160, wherein an amino acid sequence with SEQ ID NO: 149 is linked to at least two further amino acid sequences with SEQ ID NO: 149, via a 15GS linker.

Aspect F-136: Use of an amino acid sequence with SEQ ID NO: 153 in preparing a trivalent polypeptide with SEQ ID NO: 161, wherein an amino acid sequence with SEQ ID NO: 153 is linked to at least two further amino acid sequences with SEQ ID NO: 153, via a 15GS linker.

Aspect F-137: Use of a monovalent constructs according to any of aspects F-99 to F-101, wherein the monovalent constructs are chosen from the following:
a) SEQ ID NO's: 138-141 and 154-157;
b) amino acid sequences that have no more than 3, preferably no more than 2, more preferably no more than 1 amino acid difference with one of SEQ ID NO's: 138-141 and 154-157, provided that:

i) the amino acid sequence has a Aspartic acid (Asp, D) at position 1 (said position determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide.

Aspect F-138: Use of a monovalent constructs according to aspect F-137, wherein the monovalent construct essentially consist of one of SEQ ID NO's: 138-141 and 154-157.

Aspect F-139: Use of a monovalent construct according to any of aspects F-99 to F-101, wherein the monovalent construct essentially consists of SEQ ID NO: 5, in which the Glutamic acid at position 1 is changed into Aspartic acid, in preparing a trivalent polypeptide.

Aspect F-140: Use of a monovalent construct according to any of aspects F-99 to F-101, wherein the monovalent construct essentially consists of SEQ ID NO: 62, in which the Glutamic acid at position 1 is changed into Aspartic acid, in preparing a trivalent polypeptide.

Aspect F-141: Use of a monovalent construct according to any of aspects F-99 to F-101, wherein the monovalent construct essentially consists of SEQ ID NO: 65, in which the Glutamic acid at position 1 is changed into Aspartic acid, in preparing a trivalent polypeptide.

Aspect F-142: Use of a monovalent construct according to any of aspects F-99 to F-101, wherein the monovalent construct essentially consists of SEQ ID NO: 76, in which the Glutamic acid at position 1 is changed into Aspartic acid, in preparing a trivalent polypeptide.

Aspect F-143: Use of a monovalent construct according to any of aspects F-99 to F-101, wherein the monovalent construct essentially consists of SEQ ID NO: 75, in which the Glutamic acid at position 1 is changed into Aspartic acid, in preparing a trivalent polypeptide.

Aspect F-144: Use of a monovalent construct according to any of aspects F-99 to F-101, wherein the monovalent construct essentially consists of SEQ ID NO: 147, in which the Glutamic acid at position 1 is changed into Aspartic acid, in preparing a trivalent polypeptide.

Aspect F-145: Use of a monovalent construct according to any of aspects F-99 to F-101, wherein the monovalent construct essentially consists of SEQ ID NO: 149, in which the Glutamic acid at position 1 is changed into Aspartic acid, in preparing a trivalent polypeptide.

Aspect F-146: Use of a monovalent construct according to any of aspects F-99 to F-101, wherein the monovalent construct essentially consists of SEQ ID NO: 153, in which the Glutamic acid at position 1 is changed into Aspartic acid, in preparing a trivalent polypeptide.

Aspect F-147: Use of a monovalent construct according to any of aspects F-99 to F-101, wherein the monovalent construct essentially consists of SEQ ID NO: 5, in which one or more (such as two, three, four, five, six, seven, eight or nine, ten, eleven or twelve) amino acid residues have been mutated selected from the following: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54Asp, and wherein the Glutamic acid at position 1 is changed into Aspartic acid, in preparing a trivalent polypeptide.

Aspect F-248: Use of a monovalent construct according to aspects F-147, wherein the monovalent construct essentially consists of SEQ ID NO: 5, in which following amino acid residues have been mutated: Val5Leu, Ala14Pro, Ser19R, Ile20Leu, Glu44Gly, Ala74Ser, Gly78Leu, Ala83Arg, Asp85Glu, Arg105Gln, Gln108Leu and Gly54D, and wherein the Glutamic acid at position 1 is changed into Aspartic acid, in preparing a trivalent construct.

Aspect F-149: Use of a monovalent construct according to aspects F-147, wherein the monovalent construct essentially consists of SEQ ID NO: 5, in which one or more (such as two, three, four, five, six, seven or eight) amino acid residues have been mutated selected from the following: Ser19R, Ile20Leu, Ala74Ser, Gly78Leu, Ala83Arg, Asp85Glu, Arg105Gln and Gly54D, and wherein the Glutamic acid at position 1 is changed into Aspartic acid, in preparing a trivalent polypeptide.

Aspect F-150: Use of a monovalent construct according to aspects F-147, wherein the monovalent construct essentially consists of SEQ ID NO: 5, in which one or more (such as two, three, four or five) amino acid residues have been mutated selected from the following: Gly78Leu, Ala83Arg, Asp85Glu, Arg105Gln and Gly54D, and wherein the Glutamic acid at position 1 is changed into Aspartic acid, in preparing a trivalent polypeptide.

Aspect F-151: Use of a monovalent construct according to aspects F-150, wherein the monovalent construct essentially consists of SEQ ID NO: 5, in which following amino acid residues have been mutated: Gly78Leu, Ala83Arg, Asp85Glu, Arg105Gln and Gly54D, and wherein the Glutamic acid at position 1 is changed into Aspartic acid, in preparing a trivalent polypeptide.

Aspect F-152: Use of a monovalent construct according to any of aspects F-99 to F-101, wherein the monovalent construct essentially consists of SEQ ID NO: 5, in which one or more (such as two, three or four) amino acid residues have been mutated selected from the following: Ala14Pro, Ser19Arg, Ile20Leu and Gln108Leu, and wherein the Glutamic acid at position 1 is changed into Aspartic acid, in preparing a trivalent polypeptide.

Aspect F-153: Use of a monovalent construct according to any of aspects F-99 to F-101, wherein the monovalent construct essentially consists of SEQ ID NO: 5, in which one or more (such as two, three, four, five, six or seven) amino acid residues have been mutated selected from the following: Ala14Pro, Ser19Arg, Ile20Leu, Ala83Arg, Asp85Glu, Arg105Gln and Gln108Leu, and wherein the Glutamic acid at position 1 is changed into Aspartic acid, in preparing a trivalent polypeptide.

Aspect F-154: Use of a monovalent construct according to aspects F-147, wherein the monovalent construct essentially consists of SEQ ID NO: 5, in which following amino acid residues have been mutated:

Glu1Asp;

Glu1Asp, Val5Leu, Ala14Pro, Glu44Gly, Gly78Leu, Ala83Arg, Asp85Glu, Arg105Gln and Gln108Leu;

Glu1Asp, Ala83Arg, Asp85Glu, Arg105Gln and Gln108Leu;

Glu1Asp, Gly78Leu, Ala83Arg, Asp85Glu and Arg105Gln;

Glu1Asp, Val5Leu, Ala14Pro, Glu44Gly, Gly78Leu, Ala83Arg, Asp85Glu, Arg105Gln, Gln108Leu and Gly54Asp;

Glu1Asp, Ala83Arg, Asp85Glu, Arg105Gln, Gln108Leu and Gly54Asp;

Glu1Asp, Gly78Leu, Ala83Arg, Asp85Glu, Arg105Gln and Gly54Asp;

Glu1Asp and Gly54Asp;

Glu1Asp, Ala14Pro, Ser19Arg, Ile20Leu and Gln108Leu;

Glu1Asp, Ala14Pro, Ser19Arg, Ile20Leu, Gln108Leu and Ala83Arg;

Glu1Asp, Ala14Pro, Ser19Arg, Ile20Leu, Gln108Leu and Asp85Glu;

Glu1Asp, Ala14Pro, Ser19Arg, Ile20Leu, Gln108Leu and Arg105Gln;

Glu1Asp, Ala14Pro, Ser19Arg, Ile20Leu, Gln108Leu, Ala83Arg and Asp85Glu;

Glu1Asp, Ala14Pro, Ser19Arg, Ile20Leu, Gln108Leu, Ala83Arg and Arg105Gln;

Glu1Asp, Ala14Pro, Ser19Arg, Ile20Leu, Gln108Leu, Asp85Glu and Arg105Gln; or

Glu1Asp, Ala14Pro, Ser19Arg, Ile20Leu, Gln108Leu, Ala83Arg, Asp85Glu and Arg105Gln, in preparing a trivalent construct.

Aspect F-155: Use of an amino acid sequence with SEQ ID NO: 138 in preparing a trivalent polypeptide with SEQ ID NO: 142, wherein an amino acid sequence with SEQ ID NO: 138 is linked to at least two further amino acid sequences with SEQ ID NO: 5, via a 15GS linker.

Aspect F-156: Use of an amino acid sequence with SEQ ID NO: 139 in preparing a trivalent polypeptide with SEQ ID NO: 143, wherein an amino acid sequence with SEQ ID NO: 139 is linked to at least two further amino acid sequences with SEQ ID NO: 62, via a 15GS linker.

Aspect F-157: Use of an amino acid sequence with SEQ ID NO: 140 in preparing a trivalent polypeptide with SEQ ID NO: 144, wherein an amino acid sequence with SEQ ID NO: 140 is linked to at least two further amino acid sequences with SEQ ID NO: 65, via a 15GS linker.

Aspect F-158: Use of an amino acid sequence with SEQ ID NO: 141 in preparing a trivalent polypeptide with SEQ ID NO: 145, wherein an amino acid sequence with SEQ ID NO: 141 is linked to at least two further amino acid sequences with SEQ ID NO: 76, via a 15GS linker.

Aspect F-159: Use of an amino acid sequence with SEQ ID NO: 154 in preparing a trivalent polypeptide with SEQ ID NO: 162, wherein an amino acid sequence with SEQ ID NO: 154 is linked to at least two further amino acid sequences with SEQ ID NO: 75, via a 15GS linker.

Aspect F-160: Use of an amino acid sequence with SEQ ID NO: 155 in preparing a trivalent polypeptide with SEQ ID NO: 163, wherein an amino acid sequence with SEQ ID NO: 155 is linked to at least two further amino acid sequences with SEQ ID NO: 147, via a 15GS linker.

Aspect F-161: Use of an amino acid sequence with SEQ ID NO: 156 in preparing a trivalent polypeptide with SEQ ID NO: 164, wherein an amino acid sequence with SEQ ID NO: 156 is linked to at least two further amino acid sequences with SEQ ID NO: 149, via a 15GS linker.

Aspect F-162: Use of an amino acid sequence with SEQ ID NO: 157 in preparing a trivalent polypeptide with SEQ ID NO: 165, wherein an amino acid sequence with SEQ ID NO: 157 is linked to at least two further amino acid sequences with SEQ ID NO: 153, via a 15GS linker.

Aspect E-262: Polypeptide according to any of aspects E-1 to E-261, which has an increased half-life, compared to the corresponding amino acid sequence according to any of aspects A-1 to A-29, C-1 to C-38 and W-1 to W-38 per se or Nanobody® according to any of aspects B-1 to B-18, D-1 to D-38 and X-1 to X-38 per se, respectively.

Aspect E-263: Polypeptide according to aspects E-262, in which one or more other binding units provide the polypeptide with increased half-life, compared to the corresponding amino acid sequence according to any of aspects A-1 to A-29, C-1 to C-38 and W-1 to W-38 per se or Nanobody® according to any of aspects B-1 to B-18, D-1 to D-38 and X-1 to X-38 per se, respectively.

Aspect E-264: Polypeptide according to aspects E-262 or E-263, in which said one or more other binding units that provide the polypeptide with increased half-life is chosen from the group consisting of serum proteins or fragments thereof, binding units that can bind to serum proteins, an Fc portion, and small proteins or peptides that can bind to serum proteins.

Aspect E-265: Polypeptide according to any of aspects E-262 to E-264, in which said one or more other binding units that provide the polypeptide with increased half-life is chosen from the group consisting of human serum albumin or fragments thereof.

Aspect E-266: Polypeptide according to any of aspects E-262 to E-265, in which said one or more other binding units that provides the polypeptide with increased half-life are chosen from the group consisting of binding units that can bind to serum albumin (such as human serum albumin) or a serum immunoglobulin (such as IgG).

Aspect E-267: Polypeptide according to any of aspects E-262 to E-266, in which said one or more other binding units that provides the polypeptide with increased half-life are chosen from the group consisting of domain antibodies, amino acid sequences that are suitable for use as a domain antibody, single domain antibodies, amino acid sequences that are suitable for use as a single domain antibody, "dAb's", amino acid sequences that are suitable for use as a dAb, or Nanobodies® that can bind to serum albumin (such as human serum albumin) or a serum immunoglobulin (such as IgG).

Aspect E-268: Polypeptide according to any of aspects E-262 to E-267, in which said one or more other binding units that provides the polypeptide with increased half-life is a Nanobody® that can bind to serum albumin (such as human serum albumin) or a serum immunoglobulin (such as IgG).

Aspect E-269: Polypeptide according to any of aspects E-262 to E-268, that has a serum half-life that is at least 1.5 times, preferably at least 2 times, such as at least 5 times, for example at least 10 times or more than 20 times, greater than the half-life of the corresponding amino acid sequence according to any of aspects A-1 to A-29, C-1 to C-38 and W-1 to W-38 per se or Nanobody® according to any of aspects B-1 to B-18, D-1 to D-38 and X-1 to X-38 per se, respectively.

Aspect E-270: Polypeptide according to any of aspects E-262 to E-269, that has a serum half-life that is increased with more than 1 hours, preferably more than 2 hours, more preferably more than 6 hours, such as more than 12 hours, or even more than 24, 48 or 72 hours, compared to the corresponding amino acid sequence according to any of aspects A-1 to A-29, C-1 to C-38 and W-1 to W-38 per se or Nanobody® according to any of aspects B-1 to B-18, D-1 to D-38 and X-1 to X-38 per se, respectively.

Aspect E-271: Polypeptide according to any of aspects E-262 to E-270, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect G-1: Compound or construct, that comprises or essentially consists of one or more amino acid sequences according to any of aspects A-1 to A-29, C-1 to C-38 and W-1 to W-38 and/or one or more Nanobodies® according to any of aspects B-1 to B-18, D-1 to D-38 and X-1 to X-38 and/or one or more polypeptides according to any of aspects E-1 to E-271, and optionally further comprises one or more other groups, residues, moieties or binding units, optionally linked via one or more linkers.

Aspect G-2: Compound or construct according to aspect 0-1, in which said one or more other groups, residues, moieties or binding units are amino acid sequences.

Aspect G-3: Compound or construct according to any of aspects G-1 or G-2, in which said one or more linkers, if present, are one or more amino acid sequences.

Aspect G-4: Compound or construct according to any of aspects G-1 to G-3, in which said one or more other groups, residues, moieties or binding units are immunoglobulin sequences.

Aspect G-5: Compound or construct according to any of aspects G-1 to G-4, in which said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb's", amino acid sequences that are suitable for use as a dAb, or Nanobodies®.

Aspect G-6: Compound or construct according to any of aspects G-1 to G-5, in which said one or more amino acid sequences of the invention are immunoglobulin sequences.

Aspect G-7: Compound or construct according to any of aspects G-1 to G-6, in which said one or more amino acid sequences of the invention are chosen from the group consisting of domain antibodies, amino acid sequences that are suitable for use as a domain antibody, single domain antibodies, amino acid sequences that are suitable for use as a single domain antibody, "dAb's", amino acid sequences that are suitable for use as a dAb, or Nanobodies®.

Aspect G-8: Compound or construct according to any of aspects G-1 to G-7, that comprises or essentially consists of one or more Nanobodies® according to any of aspects B-1 to B-18, D-1 to D-38 and X-1 to X-38, and in which said one or more other groups, residues, moieties or binding units are Nanobodies®.

Aspect G-9: Compound or construct according to any of aspects G-1 to G-8, which is a multivalent construct.

Aspect G-10: Compound or construct according to any of aspects G-1 to G-9, which is a multispecific construct.

Aspect G-11: Compound or construct according to any of aspects G-1 to G-10, which has an increased half-life, compared to the corresponding amino acid sequence according to any of aspects A-1 to A-29, C-1 to C-38 and W-1 to W-38 per se or Nanobody® according to any of aspects B-1 to B-18, D-1 to D-38 and X-1 to X-38 per se, or polypeptide according to any of aspects E-1 to E-271 per se, respectively.

Aspect G-12: Compound or construct according to any of aspects G-1 to G-11, in which said one or more other groups, residues, moieties or binding units provide the compound or construct with increased half-life, compared to the corresponding amino acid sequence according to any of aspects A-1 to A-29, C-1 to C-38 and W-1 to W-38 per se or Nanobody® according to any of aspects B-1 to B-18, D-1 to D-38 and X-1 to X-38 per se, or polypeptide according to any of aspects E-1 to E-271 per se, respectively.

Aspect G-13: Compound or construct according to aspect G-12, in which said one or more other groups, residues, moieties or binding units that provide the compound or construct with increased half-life is chosen from the group consisting of serum proteins or fragments thereof, binding units that can bind to serum proteins, an Fc portion, and small proteins or peptides that can bind to serum proteins.

Aspect G-14: Compound or construct according to any of aspects G-12 or G-13, in which said one or more other groups, residues, moieties or binding units that provide the compound or construct with increased half-life is chosen from the group consisting of human serum albumin or fragments thereof.

Aspect G-15: Compound or construct according to any of aspects G-12 to G-14, in which said one or more other groups, residues, moieties or binding units that provide the compound or construct with increased half-life are chosen from the group consisting of binding units that can bind to serum albumin (such as human serum albumin) or a serum immunoglobulin (such as IgG).

Aspect G-16: Compound or construct according to any of aspects G-12 to G-15, in which said one or more other groups, residues, moieties or binding units that provides the compound or construct with increased half-life are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies® that can bind to serum albumin (such as human serum albumin) or a serum immunoglobulin (such as IgG).

Aspect G-17: Compound or construct according to any of aspects G-12 to G-16, in which said one or more other groups, residues, moieties or binding units that provides the compound or construct with increased half-life is a Nanobody® that can bind to serum albumin (such as human serum albumin) or a serum immunoglobulin (such as IgG).

Aspect G-18: Compound or construct according to any of aspects G-11 to G-17, that has a serum half-life that is at least 1.5 times, preferably at least 2 times, such as at least 5 times, for example at least 10 times or more than 20 times, greater than the half-life of the corresponding amino acid sequence according to any of aspects A-1 to A-29, C-1 to C-38 and W-1 to W-38 per se or Nanobody® according to any of aspects B-1 to B-18, D-1 to D-30 and X-1 to X-38 per se, or polypeptide according to any of aspects E-1 to E-271 per se, respectively.

Aspect G-19: Compound or construct according to any of aspects G-11 to G-18, that has a serum half-life that is increased with more than 1 hours, preferably more than 2 hours, more preferably more than 6 hours, such as more than 12 hours, or even more than 24, 48 or 72 hours, compared to the corresponding amino acid sequence according to any of aspects A-1 to A-29, C-1 to C-38 and W-1 to W-38 per se or Nanobody® according to any of aspects B-1 to B-18, D-1 to D-38 and X-1 to X-38 per se, or polypeptide according to any of aspects E-1 to E-271 per se, respectively.

Aspect G-20: Compound or construct according to any of aspects G-11 to G-19, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect M-1: Nucleic acid or nucleotide sequence, that encodes an amino acid sequence according to any of aspects A-1 to A-29, C-1 to C-30 and W-1 to W-38, a Nanobody® according to any of aspects B-1 to B-18, D-1 to D-30 and X-1 to X-38, a polypeptide according to any of aspects E-1 to E-271, a compound or construct according to any of aspects G-1 to G-20, that is such that it can be obtained by expression of a nucleic acid or nucleotide sequence encoding the same, or a monovalent construct according to any of aspects F-1 to F-4.

Aspect M-2: Nucleic acid or nucleotide sequence according to aspect M-1, that is in the form of a genetic construct.

Aspect M-3: Use of a nucleic acid or nucleotide sequence according to aspect M-1, that encodes a monovalent construct according to any of aspects F-1 to F-4, for the preparation of a genetic construct that encodes a multivalent polypeptide according to any of aspects E-1 to E-271.

Aspect M-4: Use of a nucleic acid or nucleotide sequence according to aspect M-2, wherein the genetic construct encodes a multivalent (such as a bivalent) construct.

Aspect N-1: Host or host cell that expresses, or that under suitable circumstances is capable of expressing, an amino acid sequence according to any of aspects A-1 to A-29, C-1 to C-38 and W-1 to W-38, a Nanobody® according to any of aspects B-1 to B-18, D-1 to D-38 and X-1 to X-38, a polypeptide according to any of aspects E-1 to E-271, a compound or construct according to any of aspects G-1 to G-20, that is such that it can be obtained by expression of a nucleic acid or nucleotide sequence encoding the same, or a monovalent construct according to any of aspects F-1 to F-4; and/or that comprises a nucleic acid or nucleotide sequence according to aspects M-1 or M-2.

Aspect O-1: Composition, comprising at least one amino acid sequence according to any of aspects A-1 to A-29, C-1 to C-38 and W-1 to W-38, Nanobody® according to any of aspects B-1 to B-18, D-1 to D-38 and X-1 to X-38, polypeptide according to any of aspects E-1 to E-271, compound or construct according to any of aspects G-1 to G-20, monovalent construct according to any of aspects F-1 to F-4, or nucleic acid or nucleotide sequence according to aspects M-1 or M-2.

Aspect O-2: Composition according to aspect O-1, which is a pharmaceutical composition.

Aspect O-3: Composition according to aspects O-1 or O-2, which is a pharmaceutical composition, that further comprises at least one pharmaceutically acceptable carrier, diluent or excipient and/or adjuvant, and that optionally comprises one or more further pharmaceutically active polypeptides and/or compounds.

Aspect P-1: Method for producing an amino acid sequence according to any of aspects A-1 to A-29, C-1 to C-38 and W-1 to W-38, a Nanobody® according to any of aspects B-1 to B-18, D-1 to D-38 and X-1 to X-38, a polypeptide according to any of aspects E-1 to E-271, a compound or construct according to any of aspects G-1 to G-20, that is such that it can be obtained by expression of a nucleic acid or nucleotide sequence encoding the same, or a monovalent construct according to any of aspects F-1 to F-4, or a composition according to any of aspects O-1 to O-3, said method at least comprising the steps of:
a) expressing, in a suitable host cell or host organism or in another suitable expression system, a nucleic acid or nucleotide sequence according to aspects M-1 or M-2, optionally followed by:
b) isolating and/or purifying the amino acid sequence according to any of aspects A-1 to A-29, C-1 to C-38 and W-1 to W-38, the Nanobody® according to any of aspects B-1 to B-18, D-1 to D-38 and X-1 to X-38, the polypeptide according to any of aspects E-1 to E-271, the compound or construct according to any of aspects G-1 to G-20, that is such that it can be obtained by expression of a nucleic acid or nucleotide sequence encoding the same, or the monovalent construct according to any of aspects F-1 to F-4, thus obtained.

Aspect P-2: Method for producing an amino acid sequence according to any of aspects A-1 to A-29, C-1 to C-38 and W-1 to W-38, a Nanobody® according to any of aspects B-1 to B-18, D-1 to D-38 and X-1 to X-38, a polypeptide according to any of aspects E-1 to K-271, a compound or construct according to any of aspects G-1 to G-20, that is such that it can be obtained by expression of a nucleic acid or nucleotide sequence encoding the same, or a monovalent construct according to any of aspects F-1 to F-4, or a composition according to any of aspects O-1 to O-3, said method at least comprising the steps of:
a) cultivating and/or maintaining a host or host cell according to aspect N-1 under conditions that are such that said host or host cell expresses and/or produces at least one amino acid sequence according to any of aspects A-1 to A-29, C-1 to C-38 and W-1 to W-38, Nanobody® according to any of aspects B-1 to B-18, D-1 to D-38 and X-1 to X-38, a polypeptide according to any of aspects E-1 to E-271, compound or construct according to any of aspects G-1 to G-20, that is such that it can be obtained by expression of a nucleic acid or nucleotide sequence encoding the same, or monovalent construct according to any of aspects F-1 to F-4, or composition according to any of aspects O-1 to O-3,
optionally followed by:
b) isolating and/or purifying the amino acid sequence according to any of aspects A-1 to A-29, C-1 to C-38 and W-1 to W-38, the Nanobody® according to any of aspects B-1 to B-18, D-1 to D-38 and X-1 to X-38, the polypeptide according to any of aspects E-1 to E-271, the compound or construct according to any of aspects G-1 to G-20, that is such that it can be obtained by expression of a nucleic acid or nucleotide sequence encoding the same, or the monovalent construct according to any of aspects F-1 to F-4, or the composition according to aspects O-1 to O-3, thus obtained.

Aspect P-3: Method for preparing a bivalent or trivalent polypeptide according to any of aspects E-7 to E-261, said method comprising at least the steps of linking two or more monovalent amino acid sequences or monovalent construct according to any of aspects F-1 to F-4 and for example one or more linkers.

Aspect P-4: Method according to aspect P-3, comprising the steps of:
a) linking two or more nucleic acid sequences according to aspect M-1, encoding a monovalent construct according to any of aspects F-1 to F-4 (and also for example nucleic acids encoding one or more linkers and further one or more further elements of genetic constructs known per se) to obtain a genetic construct according to aspect M-2;

b) expressing, in a suitable host cell or host organism or in another suitable expression system, the genetic construct obtained in a) optionally followed by:
c) isolating and/or purifying the bivalent or trivalent polypeptide according to any of aspects E-7 to E-261, thus obtained.

Aspect Q-1: Method for screening amino acid sequences directed against protein F of hRSV, said method comprising at least the steps of:
a. providing a set, collection or library of nucleic acid sequences encoding amino acid sequences;
b. screening said set, collection or library of nucleic acid sequences for nucleic acid sequences that encode an amino acid sequence that can bind to and/or has affinity for an envelope protein of a virus and that is cross-blocked or is cross blocking a Nanobody® of the invention, e.g. one of SEQ ID NO's: 60-76, 138-141 and 146-157 (Table A-4), or a polypeptide or construct comprising at least one Nanobody® of the invention, e.g. a polypeptide or construct comprising at least one of SEQ ID NO: 77-99, 142-145 and 158-165 (see Table A-5); and
c. isolating said nucleic acid sequence, followed by expressing said amino acid sequence.

Aspect R-1: Method for the prevention and/or treatment of hRSV infection, said method comprising administering, to a subject in need thereof, a pharmaceutically active amount of at least one amino acid sequence according to any of aspects A-1 to A-29, C-1 to C-30 and W-1 to W-38, Nanobody® according to any of aspects B-1 to B-18, D-1 to D-38 and X-1 to X-38, polypeptide according to any of aspects E-1 to E-271, compound or construct according to any of aspects G-1 to G-20, monovalent construct according to any of aspects F-1 to F-4 and/or composition according to aspects O-1 to O-3.

Aspect R-2: Method for the prevention and/or treatment of at least one of respiratory illness, upper respiratory tract infection, lower respiratory tract infection, bronchiolitis (inflammation of the small airways in the lung), pneumonia, dyspnea, cough, (recurrent) wheezing and asthma, said method comprising administering, to a subject in need thereof, a pharmaceutically active amount of at least one amino acid sequence according to any of aspects A-1 to A-29, C-1 to C-38 and W-1 to W-38, Nanobody® according to any of aspects B-1 to B-18, D-1 to D-38 and X-1 to X-38, polypeptide according to any of aspects E-1 to E-271, compound or construct according to any of aspects G-1 to G-20, monovalent construct according to any of aspects F-1 to F-4 and/or composition according to aspects O-1 to O-3.

Aspect R-3: Method for the prevention and/or treatment of at least one disease or disorder that can be prevented and/or treated by administering, to a subject in need thereof, an amino acid sequence according to any of aspects A-1 to A-29, C-1 to C-38 and W-1 to W-38, a Nanobody® according to any of aspects B-1 to B-18, D-1 to D-38 and X-1 to X-38, a polypeptide according to any of aspects E-1 to E-271, a compound or construct according to any of aspects G-1 to G-20, a monovalent construct according to any of aspects F-1 to F-4 and/or a composition according to aspects O-1 to O-3, said method comprising administering, to a subject in need thereof, a pharmaceutically active amount of at least one amino acid sequence according to any of aspects A-1 to A-29, C-1 to C-38 and W-1 to W-38, Nanobody® according to any of aspects B-1 to B-18, D-1 to F-38 and X-1 to X-38, polypeptide according to any of aspects E-1 to E-271, compound or construct according to any of aspects G-1 to G-20, monovalent construct according to any of aspects F-1 to F-4 and/or composition according to aspects O-1 to O-3.

Aspect R-4: Method for immunotherapy, said method comprising administering, to a subject in need thereof, a pharmaceutically active amount of at least one amino acid sequence according to any of aspects A-1 to A-29, C-1 to C-38 and W-1 to W-38, Nanobody® according to any of aspects B-1 to B-18, D-1 to D-38 and X-1 to X-38, polypeptide according to any of aspects E-1 to E-271, compound or construct according to any of aspects G-1 to G-20, monovalent construct according to any of aspects F-1 to F-4 and/or composition according to aspects O-1 to O-3.

Aspect R-5: Use of an amino acid sequence according to any of aspects A-1 to A-29, C-1 to C-38 and W-1 to W-38, a Nanobody® according to any of aspects B-1 to B-18, D-1 to D-38 and X-1 to X-38, a polypeptide according to any of aspects E-1 to E-271, a compound or construct according to any of aspects G-1 to G-20, a monovalent construct according to any of aspects F-1 to F-4 and/or composition according to aspects O-1 to O-3 in the preparation of a pharmaceutical composition for prevention and/or treatment of hRSV infection; and/or for use in one or more of the methods according to aspects R-1 to R-4.

Aspect R-6: Amino acid sequence according to any of aspects A-1 to A-29, C-1 to C-38 and W-1 to W-38, Nanobody® according to any of aspects B-1 to B-18, D-1 to D-38 and X-1 to X-38, polypeptide according to any of aspects E-1 to E-271, compound or construct according to any of aspects G-1 to G-20, monovalent construct according to any of aspects F-1 to F-4 and/or composition according to aspects O-1 to O-3 for prevention and/or treatment of at least one of respiratory illness, upper respiratory tract infection, lower respiratory tract infection, bronchiolitis (inflammation of the small airways in the lung), pneumonia, dyspnea, cough, (recurrent) wheezing and asthma.

Aspect S-1: Part or fragment of an amino acid sequence according to any of aspects A-1 to A-29, C-1 to C-38 and W-1 to W-38, a Nanobody® according to any of aspects B-1 to B-18, D-1 to D-38 and X-1 to X-38, and/or a polypeptide according to any of aspects E-1 to E-271.

Aspect S-2: Part or fragment according to aspect S-1, that can specifically bind to antigenic II on protein F of hRSV and/or competes with Synagis® for binding protein F of hRSV.

Aspect S-3: Part of fragment according to any of aspects S-1 to S-2, that can specifically bind to protein F of hRSV with a dissociation constant ($K_D$) of 1000 nM to 1 nM or less, preferably 100 nM to 1 nM or less, more preferably 10 nM to 1 nM or less.

Aspect S-4: Part or fragment according to any of aspects S-2 to S-3, that can specifically bind to protein F of hRSV with a $k_{on}$-rate of between $10^4 M^{-1} s^{-1}$ to about $10^7 M^{-1} s^{-1}$, preferably between $10^5 M^{-1} s^{-1}$ and $10^7 M^{-1} s^{-1}$, more preferably about $10^6 M^{-1} s^{-1}$ or more.

Aspect S-5: Part or fragment according to any of aspects S-2 to S-4 that can specifically bind to protein F of hRSV with a $k_{off}$ rate between $10^{-2} s^{-1}$ ($t_{1/2}$=0.69 s) and $10^{-4} s^{-1}$ (providing a near irreversible complex with a $t_{1/2}$ of multiple days, preferably between $10^{-3} s^{-1}$ and $10^{-4} s^{-1}$, or lower.

Aspect S-6: Compound or construct, that comprises or essentially consists of one or more parts or fragments according to any of aspects S-1 to S-5, and optionally further comprises one or more other groups, residues, moieties or binding units, optionally linked via one or more linkers.

Aspect S-7: Compound or construct according to aspect S-6, in which said one or more other groups, residues, moieties or binding units are amino acid sequences.

Aspect S-8: Compound or construct according to aspects S-6 or S-7, in which said one or more linkers, if present, are one or more amino acid sequences.

Aspect S-9: Nucleic acid or nucleotide sequence, that encodes a part or fragment according to any of aspects S-1 to S-5 or a compound or construct according to any of aspects S-6 to S-8.

Aspect S-10: Composition, comprising at least one part or fragment according to any of aspects S-1 to S-5, compound or construct according to any of aspects S-6 to S-8, or nucleic acid or nucleotide sequence according to aspect S-9.

Aspect T-1: Derivative of an amino acid sequence according to any of aspects A-1 to A-29, C-1 to C-38 and W-1 to W-38 or of a Nanobody® according to any of aspects B-1 to B-18, D-1 to D-38 and X-1 to X-38.

Aspect T-2: Derivative according to aspect T-1, that can specifically bind to antigenic site II on protein F of hRSV and/or compete with Synagis® for binding protein F of hRSV.

Aspect T-3: Derivative according to any of aspects T-1 to T-2, that can specifically bind to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect T-4: Derivative according to any of aspects T-2 to T-3, that can specifically bind to protein F of hRSV with a $k_{off}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect T-5: Derivative according to any of aspects T-2 to T-4, that can specifically bind to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^1$ and $10^{-4}$ $s^{-1}$, or lower.

Aspect T-6: Derivative of a compound or construct according to any of aspects G-1 to G-20 or a polypeptide according to any of aspects E-1 to E-271.

Aspect T-7: Derivative according to aspect T-6, that can specifically bind to antigenic site II on protein F of hRSV and/or compete with Synagis® for binding protein F of hRSV.

Aspect T-8: Derivative according to any of aspects T-6 to T-7, that can specifically bind to protein F of hRSV with a dissociation constant ($K_D$) of 100 nM to 0.1 nM or less, preferably 10 nM to 0.1 nM or less, more preferably 1 nM to 0.1 nM or less.

Aspect T-9: Derivative according to any of aspects T-6 to T-8, that can specifically bind to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect T-10: Derivative according to any of aspects T-6 to T-9, that can specifically bind to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, more preferably between $5\times10^{-3}$ $s^{-1}$ and $10^{-4}$ $s^{-1}$, or lower.

Aspect T-11: Derivative according to any of aspects T-6 to T-10, that can neutralize hRSV, e.g. in a microneutralization assay of RSV strain Long (such as e.g. described in Example 6), with an IC50 value between 10 pM and 1000 pM, preferably between 10 pM and 250 pM, more preferably between 50 pM and 200 pM or less.

Aspect T-12: Derivative according to any of aspects T-6 to T-11, that can neutralize hRSV, e.g. in a microneutralization assay of RSV strain Long (such as e.g. described in Example 6), with an IC50 value that is at least the same and preferably better, at least ten times better, preferably twenty times better, more preferably fifty times better, even more preferably sixty, seventy, eighty or more times better compared to the IC50 value obtained with Synagis®.

Aspect T-13: Derivative according to any of aspects T-1 to T-12, that has a serum half-life that is at least 1.5 times, preferably at least 2 times, such as at least 5 times, for example at least 10 times or more than 20 times, greater than the half-life of the corresponding amino acid sequence according to any of aspects A-1 to A-29, C-1 to C-38 and W-1 to W-38 per se, Nanobody® according to any of aspects B-1 to B-18, D-1 to D-38 and X-1 to X-38 per se, polypeptide according to any of aspects E-1 to E-261, compound or construct according to any of aspects G-1 to G-20 per se, or monovalent construct according to any of aspects F-1 to F-4 per se, respectively.

Aspect T-14: Derivative according to any of aspects T-1 to T-13, that has a serum half-life that is increased with more than 1 hours, preferably more than 2 hours, more preferably more than 6 hours, such as more than 12 hours, or even more than 24, 48 or 72 hours, compared to the corresponding amino acid sequence according to any of aspects A-1 to A-29, C-1 to C-38 and W-1 to W-38 per se, Nanobody® according to any of aspects B-1 to B-18, D-1 to D-38 and X-1 to X-38 per se, polypeptide according to any of aspects E-1 to E-261, compound or construct according to any of aspects G-1 to G-20 per se, or monovalent construct according to any of aspects F-1 to F-4 per se, respectively.

Aspect T-15: Derivative according to any of aspects T-1 to T-14, that has a serum half-life in human of at least about 12 hours, preferably at least 24 hours, more preferably at least 48 hours, even more preferably at least 72 hours or more; for example, at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect T-16: Derivative according to any of aspects T-1 to T-15, that is a pegylated derivative.

Aspect T-17: Compound or construct, that comprises or essentially consists of one or more derivatives according to any of aspects T-1 to T-16, and optionally further comprises one or more other groups, residues, moieties or binding units, optionally linked via one or more linkers.

Aspect T-18: Compound or construct according to aspect T-17, in which said one or more other groups, residues, moieties or binding units are amino acid sequences.

Aspect T-19: Compound or construct according to aspects T-17 or T-18, in which said one or more linkers, if present, are one or more amino acid sequences.

Aspect T-20: Nucleic acid or nucleotide sequence, that encodes a derivative according to any of aspects T-1 to T-16 or a compound or construct according to any of aspects T-17 to T-19.

Aspect T-21: Composition, comprising at least one derivative according to any of aspects T-1 to T-16, compound or construct according to any of aspects T-17 to T-19, or nucleic acid or nucleotide sequence according to aspect T-20.

Aspect U-1: A method for administering an effective amount of an amino acid sequence according to any of claims A-1 to A-29, C-1 to C-38 and W-1 to W-38, a Nanobody® according to any of claims B-1 to B-18, D-1 to D-38 and X-1 to X-38, a polypeptide according to any of claims E-1 to E-271, a compound or construct according to any of claims G-1 to G-20 and/or a monovalent construct according to any of claims F-1 to F-4, and/or a composition comprising the same, wherein said method comprises the step of administering the amino acid sequence according to any of claims A-1 to A-29, C-1 to C-38 and W-1 to W-38, the Nanobody® according to any of claims B-1 to B-18, D-1 to D-38 and X-1 to X-38, the polypeptide according to any of claims E-1 to E-271, the compound or construct according to any of claims G-1 to G-20 and/or the monovalent construct according to any of claims F-1 to F-4, and/or a composition comprising the same to the pulmonary tissue.

Aspect U-2: The method according to aspect U-1, wherein the amino acid sequence according to any of claims A-1 to A-29, C-1 to C-38 and W-1 to W-38, the Nanobody® according to any of claims B-1 to B-18, D-1 to D-38 and X-1 to X-38, the polypeptide according to any of claims E-1 to E-271, the compound or construct according to any of claims G-1 to G-20 and/or the monovalent construct according to any of claims F-1 to F-4, and/or a composition comprising the same is administered by use of an inhaler, intranasal delivery device or aerosol.

Aspect U-3: Method according to any of aspects U-1 or U-2, wherein at least 5%, preferably at least 10%, 20%, 30%, 40%, more preferably at least 50%, 60%, 70%, and even more preferably at least 80% or more of the amino acid sequence according to any of claims A-1 to A-29, C-1 to C-38 and W-1 to W-38, the Nanobody® according to any of claims B-1 to B-18, D-1 to D-38 and X-1 to X-38, the polypeptide according to any of claims E-1 to E-271, the compound or construct according to any of claims G-1 to G-20 and/or the monovalent construct according to any of claims F-1 to F-4, and/or a composition comprising the same is stable in the pulmonary tissue for at least 24 hours, preferably at least 48 hours more preferably at least 72 hours.

Aspect U-4: Method according to any of aspects U-1 to U-3, wherein the amino acid sequence according to any of claims A-1 to A-29, C-1 to C-38 and W-1 to W-38, the Nanobody® according to any of claims B-1 to B-18, D-1 to D-38 and X-1 to X-38, the polypeptide according to any of claims E-1 to E-271, the compound or construct according to any of claims G-1 to G-20 and/or the monovalent construct according to any of claims F-1 to F-4, and/or a composition comprising the same are applied in pure form, i.e., when they are liquids or a dry powder.

Aspect U-5: Method according to any of aspects U-1 to U-3, wherein the amino acid sequence according to any of claims A-1 to A-29, C-1 to C-38 and W-1 to W-38, the Nanobody® according to any of claims B-1 to B-18, D-1 to D-38 and X-1 to X-38, the polypeptide according to any of claims E-1 to E-271, the compound or construct according to any of claims G-1 to G-20 and/or the monovalent construct according to any of claims F-1 to F-4, and/or a composition comprising the same are administered to the pulmonary tissue as composition or formulation comprising an amino acid sequence according to any of claims A-1 to A-29, C-1 to C-38 and W-1 to W-38, a Nanobody® according to any of claims B-1 to B-18, D-1 to D-38 and X-1 to X-38, a polypeptide according to any of claims E-1 to E-271, a compound or construct according to any of claims G-1 to G-20 and/or a monovalent construct according to any of claims F-1 to F-4, and a carrier suitable for pulmonary delivery.

Aspect U-6; Pharmaceutical composition comprising an amino add sequence according to any of claims A-1 to A-29, C-1 to C-38 and W-1 to W-38, a Nanobody® according to any of claims B-1 to B-18, D-1 to D-38 and X-1 to X-38, a polypeptide according to any of claims E-1 to E-271, a compound or construct according to any of claims G-1 to G-20 and/or a monovalent construct according to any of claims F-1 to F-4, and a carrier suitable for pulmonary delivery.

Aspect U-7: Pharmaceutical device suitable for the pulmonary delivery of an amino acid sequence according to any of claims A-1 to A-29, C-1 to C-38 and W-1 to W-38, a Nanobody® according to any of claims B-1 to B-18, D-1 to D-38 and X-1 to X-38, a polypeptide according to any of claims E-1 to E-271, a compound or construct according to any of claims G-1 to G-20 and/or a monovalent construct according to any of claims F-1 to F-4 and/or suitable in the use of a composition comprising the same.

Aspect U-8: Pharmaceutical device according to aspect U-7 that is an inhaler for liquids (e.g. a suspension of fine solid particles or droplets) comprising an amino acid sequence according to any of claims A-1 to A-29, C-1 to C-38 and W-1 to W-38, a Nanobody® according to any of claims B-1 to B-18, D-1 to D-38 and X-1 to X-38, a polypeptide according to any of claims E-1 to E-271, a compound or construct according to any of claims G-1 to G-20 and/or a monovalent construct according to any of claims F-1 to F-4.

Aspect U-9: Pharmaceutical device according to aspect U-7 that is an aerosol comprising an amino acid sequence according to any of claims A-1 to A-29, C-1 to C-38 and W-1 to W-38, a Nanobody® according to any of claims B-1 to B-18, D-1 to D-38 and X-1 to X-38, a polypeptide according to any of claims E-1 to E-271, a compound or construct according to any of claims G-1 to G-20 and/or a monovalent construct according to any of claims F-1 to F-4.

Aspect U-10: Pharmaceutical device according to aspect U-7 that is a dry powder inhaler comprising an amino acid sequence according to any of claims A-1 to A-29, C-1 to C-38 and W-1 to W-38, a Nanobody® according to any of claims B-1 to B-18, D-1 to D-38 and X-1 to X-38, a polypeptide according to any of claims E-1 to E-271, a compound or construct according to any of claims G-1 to G-20 and/or a monovalent construct according to any of claims F-1 to F-4 in the form of a dry powder.

Aspect U-11: Method for the prevention and/or treatment of hRSV infection, said method comprising administering to the pulmonary tissue of a subject in need thereof, a pharmaceutically active amount of an amino acid sequence according to any of claims A-1 to A-29, C-1 to C-38 and W-1 to W-38, a Nanobody® according to any of claims B-1 to B-18, D-1 to D-38 and X-1 to X-38, a polypeptide according to any of claims E-1 to E-271, a compound or construct according to any of claims G-1 to G-20 and/or a monovalent construct according to any of claims F-1 to F-4 and/or of a pharmaceutical composition comprising the same.

Aspect U-12: Method for the prevention and/or treatment of respiratory illness, upper respiratory tract infection, lower respiratory tract infection, bronchiolitis (inflammation of the small airways in the lung), pneumonia, dyspnea, cough, (recurrent) wheezing and asthma, said method comprising administering to the pulmonary tissue of a subject in need thereof, a pharmaceutically active amount of an amino acid sequence according to any of claims A-1 to A-29, C-1 to C-38 and W-1 to W-38, a Nanobody® according to any of claims B-1 to B-18, D-1 to D-38 and X-1 to X-38, a polypeptide according to any of claims E-1 to E-271, a compound or construct according to any of claims G-1 to G-20 and/or a monovalent construct according to any of claims F-1 to F-4, and/or of a pharmaceutical composition comprising the same.

Aspect V-1: Method for the prevention and/or treatment of hRSV infection, said method comprising administering, to a subject in need thereof, a pharmaceutically active amount of a multivalent polypeptide according to any of aspects E-7 to E-261, and/or of a pharmaceutical composition comprising the same.

Aspect V-2: Use of a multivalent polypeptide according to any of aspects E-7 to E-261, and/or of a pharmaceutical composition comprising the same for binding and/or neutralization of hRSV.

Aspect V-3: Use of a multivalent polypeptide according to any of aspects E-7 to E-261, and/or of a pharmaceutical composition comprising the same for binding and/or neutralization of different strains of hRSV.

Aspect V-4: Use of a multivalent polypeptide according to any of aspects E-7 to E-261, and/or of a pharmaceutical composition comprising the same for binding and/or neutralization of one or more escape mutants of a virus.

Aspect V-5: Method or use according to any of aspects V-1 to V-4, wherein the multivalent polypeptide is bivalent.

Aspect V-6: Method or use according to any of aspects V-1 to V-4, wherein the multivalent polypeptide is trivalent.

Aspect V-7: Method or use according to any of aspects V-1 to V-6, wherein said multivalent polypeptide is administered according to any of the methods of claims U-1 to U-5 and/or U-11 to U-12.

Aspect V-8: Method for the prevention and/or treatment of infection by hRSV virus, said method comprising administering, to a subject in need thereof, a pharmaceutically active amount of a multivalent polypeptide according to any of aspects E-7 to E-261 and/or of a pharmaceutical composition comprising the same.

Aspect V-9: Method according to aspect V-8 wherein the multivalent compound or construct is selected from Table A-5 (SEQ ID NO's: 77-99, 138-141 and 146-157).

Aspect V-10: Method according to any of aspects V-8 or V-9, wherein infection by one or more RSV escape mutants is treated.

Aspect V-11: Method according to aspect V-10, wherein the escape mutant is an escape mutant specific for antigenic site II.

Aspect V-12: Use of a multivalent compound or construct according to any of aspects E-7 to E-261, and/or of a pharmaceutical composition comprising the same for binding and/or neutralization one or more different escape mutants of RSV.

Aspect V-13: Use according to claim V-12 wherein the escape mutant is an escape mutant specific for antigenic site Aspect V-14: Method according to any of aspects V-8 or V-9, wherein infection by one or more strains of hRSV is treated.

Aspect V-15: Method according to aspect V-14, wherein the RSV strain is Long.

Aspect V-16: Method according to aspect V-14, wherein the RSV strain is A-2.

Aspect V-17: Method according to aspect V-14, wherein the RSV strain is B-1.

Aspect V-18: Method according to aspect V-14, wherein the multivalent polypeptide binds and/or neutralizes RSV strain Long and A-2.

Aspect V-19: Method according to aspect V-14, wherein the multivalent polypeptide binds and/or neutralizes RSV strain Long and B-1.

Aspect V-20: Method according to aspect V-14, wherein the multivalent polypeptide binds and/or neutralizes RSV strain B-1 and A-2.

Aspect V-21: Method according to aspect V-14, wherein the multivalent polypeptide binds and/or neutralizes RSV strain Long, A-2 and B-1.

Aspect V-22: Use of a multivalent compound or construct according to any of aspects E-7 to E-261, and/or of a pharmaceutical composition comprising the same for binding and/or neutralization different strains of hRSV.

Aspect V-23: Use according to aspect V-22, wherein the strains of RSV are Long and A-2.

Aspect V-24: Use according to aspect V-22, wherein the strains of RSV are Long and B-1.

Aspect V-25: Use according to aspect V-22, wherein the strains of RSV are A-1 and B-1. Aspect V-26: Use according to aspect V-22, wherein the strains of RSV are Long, A-2 and B-1.

EXAMPLES

Example 1

Immunizations

Two llamas (156 and 157) were immunized according to standard protocols with 6 boosts of hRSV $F_{TM}$-(membrane anchorless form of the fusion protein, 70 kDa; Corrall T. et al. 2007, BMC Biotechnol. 7: 17). Blood was collected from these animals 7 days after boost 6 and 10 days after boost 6.

Two llamas (212 and 213) were immunized intramuscularly in the neck with 1 mg of RNA-inactivated RSV strain long A (Hytest, Turku Finland; #8RSV79), followed by 4 boosts of 0.5 mg RSV in a biweekly regimen. Two llamas (206 and 207) were immunized intramuscularly with 1 mg of RNA-inactivated RSV strain long A, boosted with 0.25 mg of RSV after 2 weeks, followed by 3 boosts with 50 μg of recombinant hRSV $F_{TM}$-NN (membrane anchorless form of the fusion protein, 70 kDa: Corral et al. 2007; BMC Biotechnol. 7: 17) in a biweekly regimen. For all immunizations the antigens were prepared as oil-PBS emulsions with Stimune as adjuvant. Blood was collected from these animals 4 days and 10 days after the fourth immunization, while also a Lymph node biopsy was taken 4 days after the fourth immunization. For the Nanoclone procedure, 100 mL blood was collected 11 days after the final boost from llamas 206 and 207.

Example 2

Library Construction

Peripheral blood mononuclear cells were prepared from blood samples using Ficoll-Hypaque according to the manufacturer's instructions. Next, total RNA was extracted from these cells as well as from the lymph node bow cells and used as starting material for RT-PCR to amplify Nanobody® encoding gene fragments. These fragments were cloned into phagemid vector derived from pUC119 which contains the LacZ promoter, a coliphage pIII protein coding sequence, a resistance gene for ampicillin or carbenicillin, a multicloning site and the gen3 leader sequence. In frame with the Nano-

269 body® coding sequence, the vector codes for a C-terminal c-myc tag and a (His)6 tag. Phage was prepared according to standard methods and stored at 4° C. for further use, making phage libraries 156, 157, 206, 207, 212 and 213.

Example 3

Nanobody® Selection with the F-Protein of hRSV

To identify Nanobodies® recognizing the fusion protein of RSV, libraries 156, 157, 206, 207, 212 and 213 were used for selection on $F_{TM}$-NN (membrane anchorless form of the Long fusion protein, 70 kDa; Corral T. et al. 2007, BMC Biotechnol. 7: 17). The $F_{TM}$-protein (25 ng/well) was immobilized on Nunc Maxisorp ELISA plates. A control was included with 0 µg/ml $F_{TM}$-. Bound phages were eluted from the $F_{TM}$-using trypsin and Synagis® (Palivizumab, MedImmune, humanized monoclonal antibody, described in Zhao and Sullender 2005, J. Virol. 79: 3962) in the first and second round of selections. Remicade (Infliximab, anti-TNF; Centocor) was used as a control for Synagis®. A 100 molar excess of Synagis® was used in order to identify Nanobodies® binding specifically at the Synagis® binding site on RSV. Outputs from the first round selections, eluted with Synagis® were used for second round selections.

In addition, selections were done using inactivated hRSV strain Long (Hytest #8RSV79). The $F_{TM}$-NN protein (25 ng/well) or RSV (5 to 50 µg/well) was immobilized on Nunc Maxisorp ELISA plates, next to a control with 0 µg/ml antigen. Bound phages were eluted from the $F_{TM}$-NN using trypsin, Synagis® (Palivizumab, humanized monoclonal antibody, described in Zhao and Sullender 2005, J. Virol. 79: 396), or 101F Fab (WO 06/050280, humanized monoclonal antibody) in the first round of selection. Outputs from the first round selections eluted with Synagis® or 101F Fab were used for second round selections, using either Numax Fab (Motavizumab or MEDI-524, a third-generation humanized monoclonal antibody product evolved from palivizumab; WO 06/050166), Synagis® or 101F Fab for elution. Remicade (Infliximab, anti-TNF, see also WO 09/068,625) was used as a control for Synagis®, while Omnitarg Fab (anti-Herz; in-house produced) served as control for Numax Fab and 101F Fab. A 100 molar excess of Synagis®, Numax Fab or 101F Fab was used in order to identify Nanobodies® binding specifically to antigenic sites II or IV-VI epitopes on the RSV F-protein. To obtain Nanobodies® specific for the antigenic site IV-VI, second round selections were performed using two biotinylated peptides: at first, a peptide comprising residues 422-436 of the F-protein (Long) (Abgent, San Diego, Calif.) encompassing the 101E binding epitope (Wu et al. 2007, J. Gen. Virol. 88: 2719-2723), secondly, a peptide mimic of the epitope of Mab19 (HWSISKPQ-PEG4-K-biotin)(Chargelegue et al. 1998, J. Virol. 72: 2040-2056).

Outputs of both rounds of selections were analyzed for enrichment factor (phage present in eluate relative to controls). Based on these parameters the best selections were chosen for further analysis. Individual colonies were picked and grown in 96 deep well plates (1 mL volume) and induced by adding IPTG for Nanobody® expression. Periplasmic extracts (volume: ~80 µl) were prepared according to standard methods.

For testing of selected clones in RSV neutralization assays, periplasmatic extracts from 10 ml cultures were partially purified by using IMAC PhyTips (Phynexus Inc, San Jose, Calif.). In here 800 µl of periplasmic extracts was loaded onto PhyTips 200+ columns prepacked with immobilized metal affinity chromatography resin, followed by elution of

270

His-tagged Nanobodies® in 30 µl of 0.1M glycine-HCl/ 0.15M NaCl (pH3), after which eluates were neutralized with 5 µl of 0.5 M Tris-HCl pH8.5.

Example 4

Nanobody® Selection with $F_{TM}$-NN of RSV Using Nanoclone Technology

Peripheral blood mononuclear cells (PBMCs) were prepared from blood samples using Ficoll-Hypaque according to the manufacturer's instructions. Antigen specific B-cells expressing heavy chain antibodies on their surface were isolated from the PBMCs via FACS sorting (for a description of the Nanoclone technology reference is made to WO 06/079372). Thereto, $F_{TM}$-NN protein was labeled with Alexa Fluor 488 dye (Invitrogen, Carlsbad, Calif.; cat. nr. A20000) and subsequently desalted to remove residual non-conjugated Alexa Fluor 488 dye according to the manufacturer's instructions.

Pre-immune (background control) and immune PBMC of a llama were stained with fluorescent dye conjugated IgG1 (conventional heavy+light chain immunoglobulins), IgG2- and IgG3 (heavy chain immunoglobulin classes) specific mouse monoclonal antibodies, fluorescently labeled DH59B antibody (CD172a) (VMRD, Inc. Pullman, W A; Cat No. DH59B; Davis et al. 1987, Vet. Immunol. Immunopathol. 15: 337-376) and Alexa 488 labeled antigen. TOPRO3 was included as a live/dead cell discriminator dye. IgG1+ B-lymphocytes, monocytes, neutrophils and dead cells were gated out and therefore rejected from sorting. Antigen-specific (A488+) IgG2- or IgG3 positive B cells were single cell sorted individually into separate PCR plate wells containing RT-PCR buffer.

For llama 206, 1.9% antigen positive cells of the total amount of IgG2/IgG3 positive living cells was obtained (1.0% in pre-immune reference sample), for llama 207 4.2% positive cells were obtained (0.7% in pre-immune reference sample). Heavy chain variable region genes were amplified directly from these B-cells by single-cell RT-PCR and nested PCR. PCR products were subsequently cloned into a TOPO-adapted expression vector derived from pUC119 which contained the LacZ promoter, a resistance gene for ampicillin or carbenicillin, a multicloning site and the gen3 leader sequence. In frame with the Nanobody® coding sequence, the vector coded for a C-terminal c-myc tag and a (His)6 tag. The cloned constructs were transformed in TOP10 *Escherichia coli* cells via high throughput electroporation. Single clones were grown in 96 deep well plates (1 ml volume) and induced by adding IPTG for Nanobody® expression. Periplasmic extracts (volume: ~80 µl) were prepared via osmotic shock and analyzed for binding to $F_{TM}$-in a binding ELISA.

In short, 2 µg/ml of $F_{TM}$-was immobilized directly on Maxisorp microtiter plates (Nunc). Free binding sites were blocked using 4% Marvel in PBS. Next, 10 µl of periplasmic extract containing Nanobody® of the different clones in 100 µl 2% Marvel PBST were allowed to bind to the immobilized antigen. After incubation and a wash step, Nanobody® binding was revealed using a rabbit-anti-VHH secondary antibody (for the periplasmic fractions). After a wash step the Nanobodies® in the periplasmic fractions were detected with a HRP-conjugated goat-anti-rabbit antibody. Binding specificity was determined based on OD values compared to controls having received no Nanobody®.

In total, 8 positive $F_{TM}$-NN binders (4 from llama 206, 4 from llama 207) were obtained out of 52 cloned VHHs.

Example 5

Screening for Nanobodies® that Bind to Antigenic Site II or IV-VI

Periplasmic extracts containing single Nanobodies® were analyzed for binding to the antigen site II or IV-VI, using an Alphascreen® assay (Perkin Elmer; Waltham, Mass.)(Garcia-Barreno at al. 1989, J. Virol. 63: 925-932; Lopeze at al. 1998, J. Virol. 72: 6922-6928). In this setup $F_{TM}$-NN is bound simultaneously by Fabs of Synagis® and 101F, allowing detection of Nanobodies® that interfere with binding of each of the respective antigenic sites II and IV-VI. In here, periplasmic extracts were added to $F_{TM}$-NN protein (0.3 nM) and incubated for 15 minutes. Subsequently biotinylated Fab Synagis® (0.3 nM) and Fab 101F conjugated acceptor beads (10 µg/ml) were added and this mixture was incubated for 1 hour. Finally streptavidin-coated donor beads (10 µg/ml) were added and after 1 hour incubation the plate was read on the Envision microplate reader. Periplasmic extracts were diluted 25-fold which corresponds roughly to a final concentration of 40 nM. The assay was validated by titration of the known competitors of Synagis®, mabs 18B2 (Argene, Varilhes, France; 18042 N1902) and 2F7 (Abcam, Cambridge, UK; ab43812). Also Synagis® Fab, Numax Fab, and 101F Fab were analyzed, with Numax Fab having the lowest IC50 value (8.6 E-11 M) followed by Synagis® Fab (5.97 E-10 M) and 101F Fab (1.12 E-9 M). For the screening of periplasmatic extracts (at 1/25 dilution) both Numax Fab (40 nM) and 101F Fab (40 nM) were used as positive controls, while irrelevant periplasmatic extracts served as negative controls. Clones that interfered with binding to $F_{TM}$-NN protein in the Alphascreen® more than 75% relative to the negative controls were identified as hit. In total 341 hits were identified out of 1856 clones, derived from all 6 llamas but the majority coming from llamas 206 and 207. In addition, out of 8 clones obtained from Nanoclone selections 3 clones showed competition.

The correct antigen site (II or IV-VI) of the competitors was deconvoluted by means of a competition ELISA with biotinylated Synagis® Fab (2 nM) or biotinylated 101F Fab (3 nM) for binding to $F_{TM}$-NN protein (1 µg/ml). In short, the $F_{TM}$-NN protein was immobilized on Maxisorp microtiter plates (Nunc) and free binding sites were blocked using 4% Marvel in PBS. Periplasmatic extracts were diluted ⅒ and mixed with the biotinylated Fab prior to binding to the immobilized $F_{TM}$-NN protein. Control periplasmic fractions selected against other viral coat proteins were included. The competing antibody was allowed to bind to the immobilized antigen with or without Nanobody®. After incubation and a wash step, detection occurred via Extravidin-HRP conjugated secondary antibodies (Sigma-Aldrich, St. Louis, Mo.; Cat. No. E2886). Binding specificity was determined based on OD values compared to controls having received no Nanobody®.

All hits were subjected to sequence analysis and classified into families according to their CDR3 sequences (see Table C-4 and A-1 in PCT application PCT/EP2009/056975 entitled "Amino acid sequences directed against envelope proteins of a virus and polypeptides comprising the same for the treatment of viral diseases" filed by Ablynx N.V on 5 Jun. 2009).

Example 6

Screening for RSV Neutralizing Nanobodies®

From all six hRSV libraries 163 unique sequences (160 identified from phage libraries, 3 derived from Nanoclone) were analyzed for RSV Long neutralizing capacity in a micro-neutralization assay as partially purified proteins. Hep2 cells were seeded at a concentration of $1.5 \times 10^4$ cells/well into 96-well plates in DMEM medium containing 10% fetal calf serum (FCS) supplemented with Penicillin and Streptomycin (100 U/ml and 100 µg/ml, respectively) and incubated for 24 hours at 37° C. in a 5% $CO_2$ atmosphere. The virus stock used is referred to as hRSV strain long, Long LM-2 and Long M2 (used interchangeably) and is a virus stock derived from ATCC VR-26 of which the sequence of the F protein corresponds to P12568 or M22643. The virus stock has been passaged several times from the ATCC stock. The sequence of the F-protein was confirmed to be identical to P12568 (see example 9). A standard quantity of hRSV strain Long LM-2 was pre-incubated with serial dilutions of a fixed volume of Phytips purified Nanobodies® (20 µl) in a total volume of 50 µl for 30 minutes at 37° C. The medium of the Hep2 cells was replaced with the premix to allow infection for 2 hours, after which 0.1 ml of assay medium was added. The assay was performed in DMEM medium supplemented with 2.5% fetal calf serum and Penicillin and Streptomycin (100 U/ml and 100 µg/ml, respectively). Cells were incubated for an additional 72 hours at 37° C. in a 5% CO2 atmosphere, after which cells were washed twice with 0.05% Tween-20 in PBS and once with PBS alone, after which the cells were fixed with 80% cold acetone (Sigma-Aldrich, St. Louis, Mo.) in PBS (100 µl/well) for 20 minutes at 4° C. and left to dry completely. Next the presence of the F-protein on the cell surface was detected in an ELISA type assay. Thereto, fixed Hep2 cells were blocked with 2% Bovine Serum Albumin (BSA) solution in PBS for 1 hour at room temperature, than incubated for 1 hour with Synagis® (2 µg/ml). For detection goat Anti-Human IgG, Fcγ fragment specific-HRP (Jackson ImmunoResearch, West Grove, Pa.) was used, after which the ELISA was developed according to standard procedures.

In addition to the previously identified RSV neutralizing Nanobodies® 191D3 (SEQ ID NO: 9) and 192C4 (SEQ ID NO: 11), which were included as positive controls in the screening, 5 antigenic site II clones showed strong RSV Long neutralizing activity: 1E4 (also referred to as 207D1; SEQ ID NO: 1), 7B2 (SEQ ID NO: 2), NC23 (SEQ ID NO: 3), and two members of the same family 15H8 (SEQ ID NO: 4) and NC41 (SEQ ID NO: 5) (Table A-1). None of the antigenic site IV-VI specific Nanobodies® showed more than very weak neutralizing activity for hRSV Long LM-2 strain.

Example 7

Production of hRSV Nanobodies®

In addition to the previously identified RSV neutralizing Nanobodies® 191D3 (SEQ ID NO: 9) and 191E4 (SEQ ID NO: 10), which were included as positive controls in the screening, five new neutralizing Nanobodies® selected from the screening described above (1E4, 7B2, 15H8, NC23 and NC41) as well as 1 antigenic site IV-VI Nanobodies® (15B3; SEQ ID ND: 7) were expressed, purified and further characterised. Thereto the encoding sequences were recloned in an expression vector derived from pUC119 which contained the LacZ promoter, a resistance gene for kanamycin, a multicloning site and the OmpA signal peptide sequence. In frame with the Nanobody® coding sequence, the vector coded for a C-terminal c-myc tag and a (His)6 tag.

Expression occurred in *E. coli* TG-1 cells as c-myc, His6-tagged proteins in a culture volume of 1 L. Expression was induced by addition of 1 mM IPTG and allowed to continue for 3 hours at 37° C. After spinning the cell cultures, periplasmic extracts were prepared by freeze-thawing the pellets and resuspension in dPBS. These extracts were used as starting material for immobilized metal affinity chromatography (IMAC) using Histrap FF crude columns (GE healthcare, Uppsala, Sweden). Nanobodies® were eluted from the column with 250 mM imidazole and subsequently desalted towards dPBS.

Example 8

Characterization of hRSV Nanobodies®

Binding to F-Protein in ELISA

All purified Nanobodies® were shown to bind to the F-protein in a binding ELISA to $F_{TM}$-NN protein and to hRSV. Results for hRSV binding are shown in Table B-1. In short, 1 µg/ml of $F_{TM}$-NN or 5 µg/ml hRSV (Hytest Turku, Finland) were immobilized directly on Maxisorp microtiter plates. Free binding sites were blocked with 1% casein. Serial dilutions of purified Nanobodies® were allowed to bind the antigen for 1 hour. Nanobody® binding was revealed using a rabbit-anti-VEIN secondary antibody, and final detection with a HRP-conjugated goat-anti-rabbit antibody. Binding specificity was determined based on OD values compared to irrelevant Nanobody® controls.

Binding to F-Protein in Biacore

To determine the precise binding affinities of the purified Nanobodies®, a kinetic analysis was performed using Surface Plasmon resonance analysis on the $F_{TM}$-NN protein. For preincubation of the Sensorchip CM5, 10 µg/ml hRSV $F_{TM}$-protein was left on for 120 seconds. For immobilization by amine coupling, EDC/NHS was used for activation and ethanolamine HCl for deactivation (Biacore, amine coupling kit). 100 nM Synagis® was added and then 100 nM of the Nanobodies®. Evaluation of the off-rates was performed by fitting a 1:1 interaction model (Langmuir binding model) by Biacore T100 software v1.1. The off-rates and affinity constants are shown in Table B-1.

Competition with Synagis®

The ability of purified Nanobodies® to compete with Synagis® Mab or biotinylated Synagis® Fab for binding to $F_{TM}$-NN was determined in competition ELISA following the procedure as essentially described in example 5. FIG. 1 shows a representative example of a competition ELISA wherein purified Nanobodies® compete with biotinylated Synagis® Fab for binding to $F_{TM}$-NN. EC50 values are summarized in Table B-1.

Example 9

In Vitro Micro Neutralization of Distinct hRSV Strains

The potency of purified Nanobodies® in neutralization of different type A and B RSV strains was tested by the in vitro micro neutralization assay (see Example 6). Viral stocks of RSV Long LM-2 (Accession No. P12568; ATCC VR-26), RSV A-2 (ATCC VR-1540; lot nr. 3199840) and RSV B-1 (ATCC VR-1580; lot nr. 5271356) were prepared into Hep2 cells and subsequently titrated to determine the optimal infectious dose for use in the micro neutralization assay. Results of neutralization potencies of the different purified Nanobodies® are shown in Table B-1. While all six Nanobodies® that recognize the Synagis® epitope could efficiently neutralize type A strains Long and A-2, they failed to neutralize infection with the B-1 strain or did so at concentrations >1 µM. The 101F competitors 15B3 and 191E4 showed very weak neutralization potency on the B-1 strain only when administrated at µM concentrations.

The sequences of the respective F-proteins of the different RSV strains were verified by means of reverse-transcriptase PCR and subsequent sequence analysis. Briefly, total RNA was isolated from RSV-infected Hep2 cells using RNeasy mini kit (Qiagen, Venlo, Netherlands), after which complementary DNA was prepared using Superscript III reverse transcriptase kit (Invitrogen, Carlsbad, Calif.). The F-protein of RSV A strains was amplified and sequenced using the primers described in Kimura et al. 2004 (Antiviral Research 61: 165-171). For amplification of the RSV B-1 strain F-protein the following primers were used: FB1_outer_for: cttagcagaaaaccgtga (SEQ ID NO: 13); FB1_outer_rev: tgggttgatttgggattg (SEQ ID NO: 14); FB1_seq_1123-for: ggactgatagaggatggta (SEQ ID NO: 15); FB1_seq_1526-rev: gctgacttcacttggtaa (SEQ ID NO: 16). The sequence of RSV B-1 strain corresponded to Accession nr P13843, with an additional point mutation Ser540Leu. The sequence for the RSV Long M2 strain corresponded completely to the reported sequence (Accession nr M22643). The sequence for the strain RSV A-2 corresponded to Accession M11486. See also Table A-2.

Example 10

Construction, Production and Characterization of Multivalent hRSV Nanobodies®

Multivalent Nanobody® constructs connected by Gly-Ser linkers of different lengths and composition were generated by means of separate PCR reactions (1 for the N-terminal, 1 for the middle (in case of trivalent) and 1 for the C-terminal Nanobody® subunit) using different sets of primers encompassing specific restriction sites. Similarly, multivalent constructs connected by Ala-Ala-Ala linker were generated. All constructs were cloned into an expression vector derived from pUC119 which contained the LacZ promoter, a resistance gene for kanamycin, a multicloning site and the OmpA signal peptide sequence. In frame with the Nanobody® coding sequence, the vector coded for a C-terminal c-myc tag and a (His)6 tag. In case a 35 Gly-Ser-linker was present in the multivalent construct, an expression vector was used derived from pUC119 which contained the LacZ promoter, a resistance gene for kanamycin and the OmpA signal peptide sequence. Directly downstream of the signal peptide a multiple cloning site was present for Nanobody® insertion, followed by a 35Gly-Ser linker encoding DNA sequence and a second multiple cloning site for cloning of a second Nanobody® sequence. In frame with the resulting Nanobody®-35Gly-Ser-Nanobody® coding sequence, the vector coded for a C-terminal c-myc tag and a (His)6 tag. Table B-2 lists the multivalent constructs generated with RSV-specific Nanobodies®. The sequences of the multivalent constructs are shown in Table A-3.

Multivalent RSV Nanobody® constructs were expressed, purified and further characterized. Production was done in *E. coli* TG1 cells, followed by purification from the periplasmic fraction via the His-tag by IMAC and desalting, essentially as described in Example 7. For certain trivalent constructs (e.g. RSV401, RSV404, RSV406) production was done in *P. pas-*

*toris* followed by purification from the medium fraction. All trivalent Nanobodies® were subjected to gel filtration as a final step to remove possible bivalent and monovalent degradation products.

Binding of purified multivalent Nanobodies® to the hRSV F-protein was confirmed in ELISA on both $F_{TM}$-protein and on hRSV (see Example 8). For the majority of Nanobodies® the formatting into bivalent and trivalent constructs resulted in a clear but limited (up to 10-fold increase) avidity effect, with the exception of multivalents of 7B2 and NC23 which showed similar EC50 values as their monovalent counterparts (as shown for 7B2 in FIG. 2).

Example 11

Potency of Bi- and Trivalent Constructs to Neutralize hRSV

The potency of the Nanobody® constructs was evaluated in the RSV neutralization assay on different RSV strains (see examples 6 and 9). Bivalent Nanobodies® binding antigenic site II showed marked increases in potencies of 100- to 1000-fold (i.e. much higher than the increase in affinity) in neutralization of Long relative to their monovalent counterparts, with IC50 values ranging from 50-380 pM, being better or similar to Numax Fab. On the RSV B-1 strains however, the potency increase was much less strong, and none of the dimeric constructs was more potent than Synagis®. Surprisingly, this could be overcome by the generation of trivalent constructs, as shown in FIG. 3. Trivalent constructs with three Nanobodies® binding antigenic site II were at least 1000-fold more potent neutralizers on RSV B-1 strains than their monovalent counterparts.

Example 12

Reactivity of Monovalent Nanobodies® with Escape Mutants of the Long Strain

A number of escape mutants, described in Lopez et al. 1998 (J. Virol. 72: 6922-6928), and specific for antigenic site II (R47F/4, R47F/7, RAK13/4, R7C2/11, R7C2/1) or IV-VI (R7.936/1, R7.936/4, R7.936/6, R7.432/1) or the combination of both (RRA3), were selected for testing their reactivity with 10 monovalent Nanobodies®, including Nanobody® 19107 (SEQ ID NO: 8) previously identified as not binding to antigenic sites II or IV-VI.

This assay was performed according to Lopez et al. 1998 (J. Virol. 72: 6922-6928). In brief, each Nanobody® was tested at 0.2 µg/ml in ELISA using antigen extracts of HEp-2 cells infected with the different escape mutants. Absorbance results were normalized for reactivity on the reference virus strain (Long wild type) strain as well as on the control Nanobody® 191C7. Results are shown in Table B-3.

A reactivity of >75% is indicated as a filled black square, dark hatched squares correspond to a reactivity between 75 and 50%, light hatched squares correspond to a reactivity of 25-50% and less than 25% reactivity is indicated by a blank square. In general Nanobodies® already identified as antigenic site II binders previously (192C4, 191D3, 191F2, NC23, 15H8, 7B2 and NC41) were found to be sensitive to typical mutations in antigenic site II, while the other Nanobodies® already identified as antigenic site IV-VI binders were indeed sensitive for mutations in these sites.

Example 13

Reactivity of Multivalent Nanobodies® with Escape Mutants of the Long Strain

Subsequently a number of multivalent constructs was analyzed on a limited panel of escape viruses to assess binding. This assay was performed according to Lopez et al. 1998 (J. Virol. 72: 6922-6928). In brief, each Nanobody® was tested at 0.1 µg/ml for monovalent Nanobodies® and at 0.05 µg/ml for bi- and trivalent Nanobodies® in ELISA using antigen extracts of HEp-2 cells infected with the different escape mutants. Absorbance results were normalized for reactivity on the reference virus strain (Long wild type) strain as well as on the control Nanobody® (191E4; SEQ ID NO: 10, in this particular assay). Results are shown in Table B-4.

A reactivity of >75% is indicated as a filled black square, dark hatched squares correspond to a reactivity between 75 and 50%, light hatched squares correspond to a reactivity of 25-50% and less than 25% reactivity is indicated by a blank square. Remarkably, multivalent constructs showed improved binding compared to their monovalent counterpart, to the mutant virus R7C2/11. In addition the biparatopic construct RSV403 was not sensitive to any of the mutants.

Example 14

Neutralization of Escape Mutants of the Long Strain by Multivalent Nanobodies®

In examples 12 and 13, the binding of monovalent Nanobodies® to typical antigenic site it and/or IV-VI RSV escape mutants has been described. Binding of Nanobodies® specifically recognizing these antigenic sites was almost lost or significantly reduced. Formatting of these Nanobodies® into bi- or trivalent constructs partially restored binding activity but not for all three escape mutant viruses. Binding to the escape mutant R7C2/1 (mutation K272E in antigenic site II) remained below the level of 25% for any bi- or trivalent construct consisting solely of antigenic site II binding Nanobodies®. The Nanobodies® 15B3 and 191E4, which are binding to antigenic site IV-VI, were the only Nanobodies® (as such or in biparatopic constructs) able to bind this mutant at a level of 75% or more.

More detailed analysis of the data indicated that binding towards R7C2/1 slightly increased when the valency of the Nanobody® was increased. The binding of 7B2 constructs was 0, 4.4 and 13% respectively for the monovalent, bivalent (RSV106) and trivalent (RSV400) formats. Such a low level of residual binding is expected to result in very high loss of potency to neutralize RSV.

The neutralizing potency of Nanobodies® was assessed on the same selected set of escape mutants as described in example 13. For this purpose the monovalent Nanobodies® 7B2, 15H8 and NC41 were compared to their respective trivalent counterparts, RSV400, RSV 404 and RSV 407. Of note, in example 13 only RSV400 was assessed for binding these escape mutants. In addition also the biparatopic trivalent molecule RSV403 (7B2-15B3-7B2) was analyzed for its neutralizing capacity.

The hRSV micro neutralization assay was essentially performed as described in example 6. In brief, Hep2 cells were seeded at a concentration of $1.5 \times 10^4$ cells/well into 96-well plates in DMEM medium containing 10% fetal calf serum (FCS) supplemented with Penicillin and Streptomycin (100 U/ml and 100 µg/ml, respectively) and incubated for 24 hours at 37° C. in a 5% $CO_2$ atmosphere. Viral stocks of different viruses were prepared into Hep2 cells and subsequently titrated to determine the optimal infectious dose for use in the micro neutralization assay. A standard quantity of the specific hRSV strain was pre-incubated with serial dilutions of purified Nanobodies® in a total volume of 50 µl for 30 minutes at 37° C. The medium of the Hep2 cells was replaced with the premix to allow infection for 2 hours, after which 0.1 ml of assay medium was added. The assay was performed in DMEM medium supplemented with 2.5% fetal calf serum and Penicillin and Streptomycin (100 U/ml and 100 µg/ml, respectively). Cells were incubated for an additional 72 hours at 37° C. in a 5% CO2 atmosphere, after which cells were washed twice with 0.05% Tween-20 in PBS and once with PBS alone, after which the cells were fixed with 80% cold acetone (Sigma-Aldrich, St. Louis, Mo.) in PBS (100 µl/well) for 20 minutes at 4° C. and left to dry completely. Next the presence of the F-protein on the cell surface was detected in an ELISA type assay. Thereto, fixed Hep2 cells were blocked with 5% Porcine Serum Albumin solution in PBS for 1 hour at room temperature, than incubated for 1 hour with anti-F-protein polyclonal rabbit serum (Corral et al. 2007, BMC Biotechnol, 7: 17) or Synagis® (2 µg/ml). For detection goat Anti-rabbit-HRP conjugated antibodies or goat Anti-Human IgG, Fcγ fragment specific-HRP (Jackson ImmunoResearch, West Grove, Pa.) was used, after which the ELISA was developed according to standard procedures.

Figure 4A:
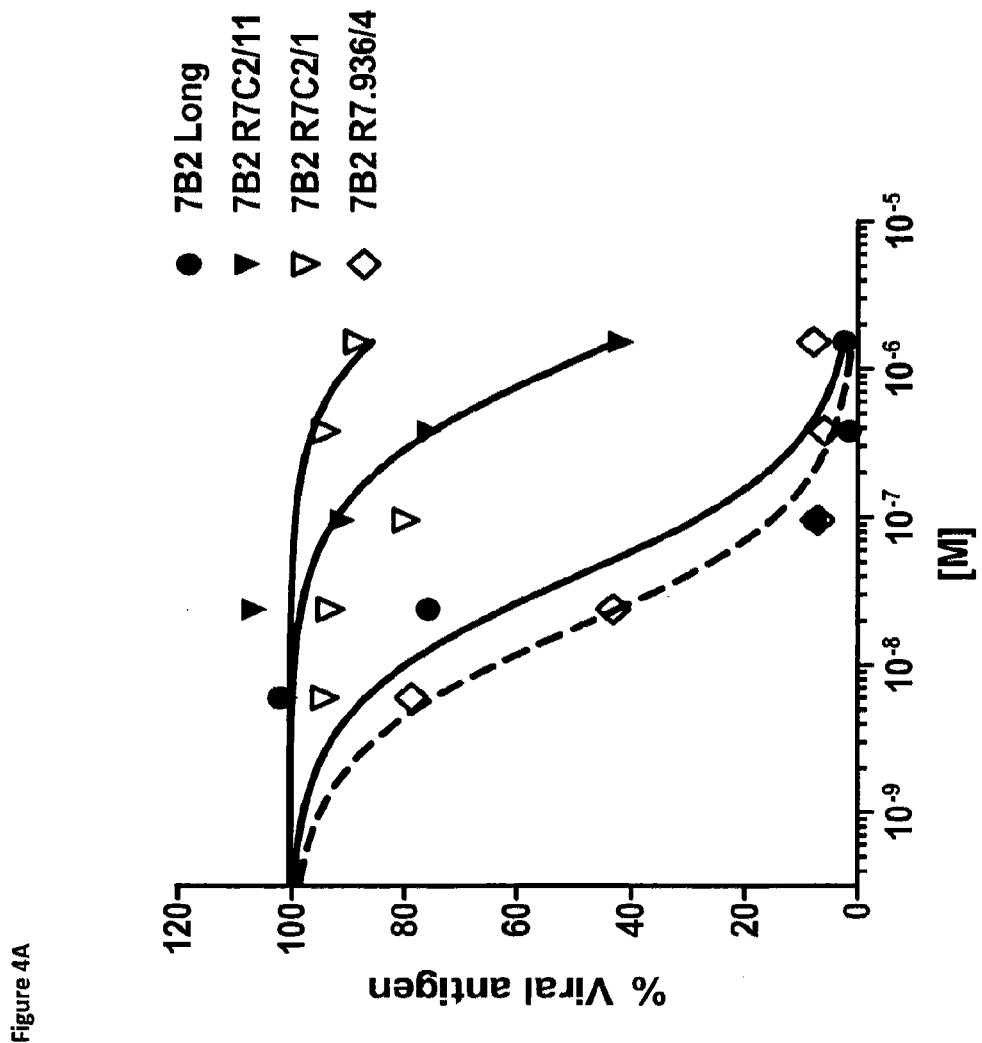
FIG. 4: Neutralization assay of RSV Long and the escape mutants R7C2/1; R7C2/11 and R7.936/4 by the monovalent Nanobodies® 7B2 (A), 15H8, (B) NC41 (C) at a concentration range from about 2 µM to 6 nM and the trivalent Nanobodies® RSV 400 (D), RSV 404 (E), RSV 407 (F) and RSV 403 (G) at a concentration range of about 20 nM to 100 pM. Curve fitting was only done for data of monovalent Nanobodies®.
Figure 4B:
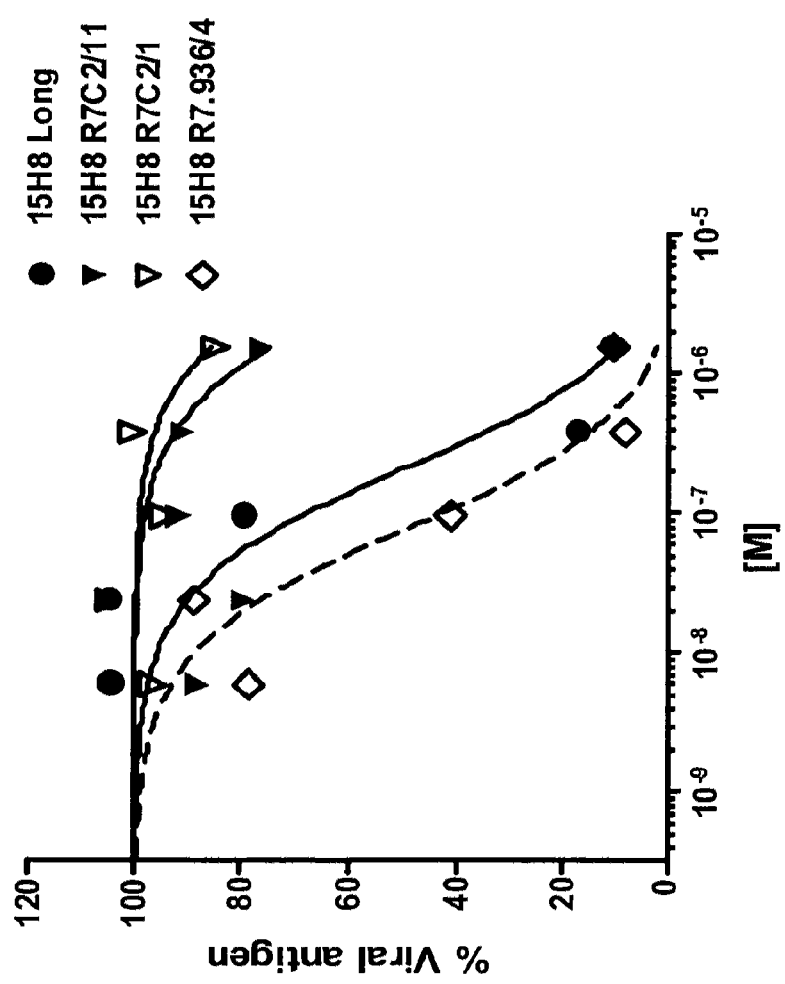
Figure 4C:
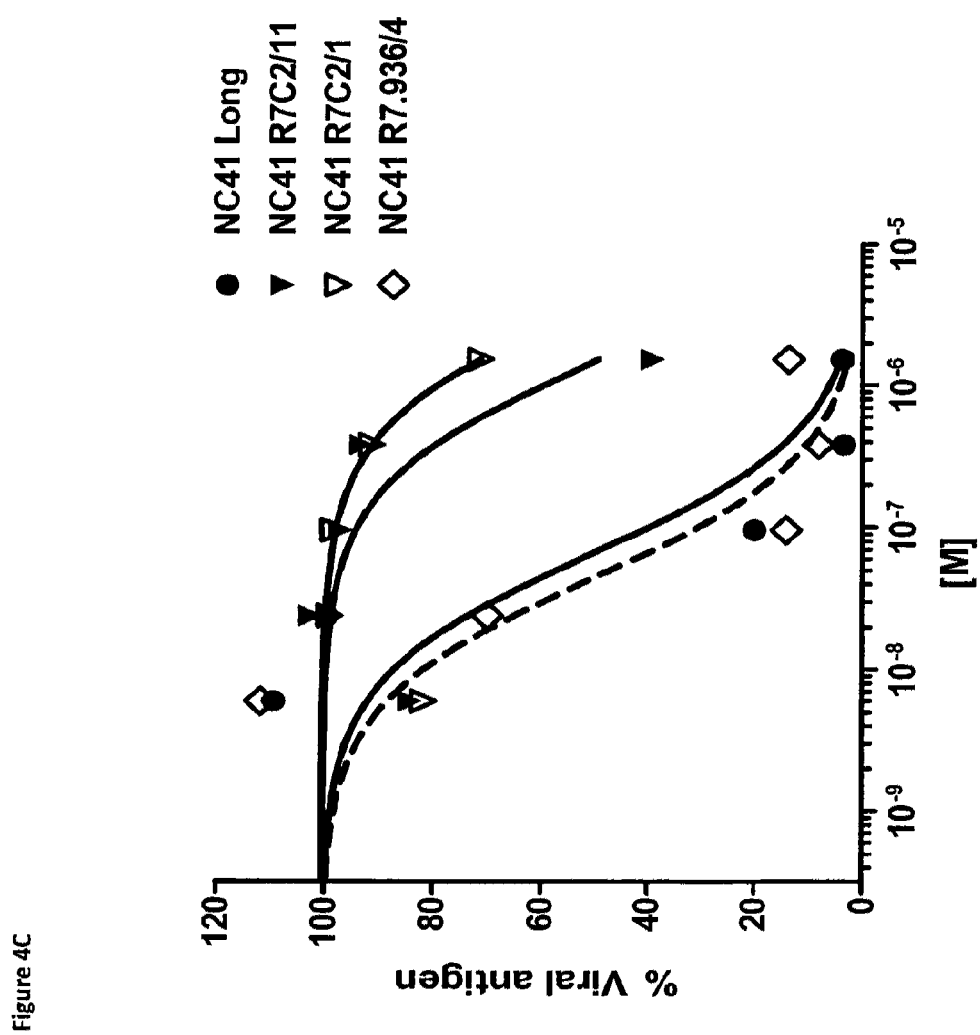
Figure 4D:
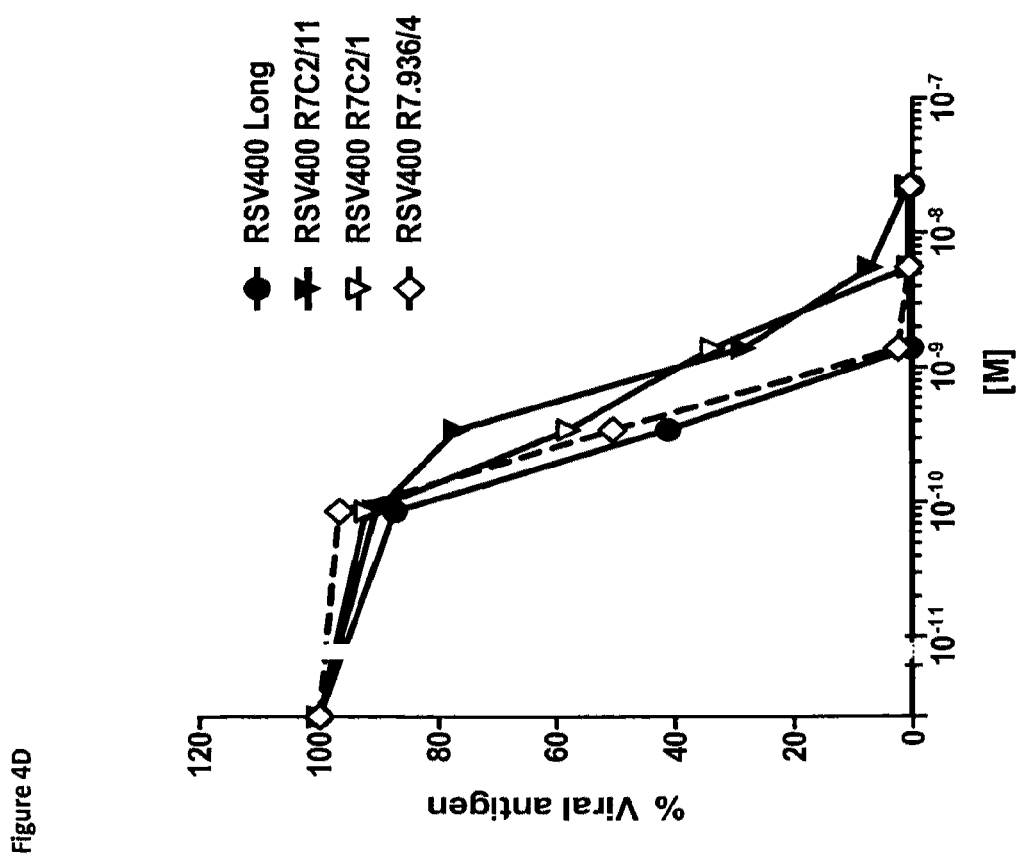
Figure 4E:
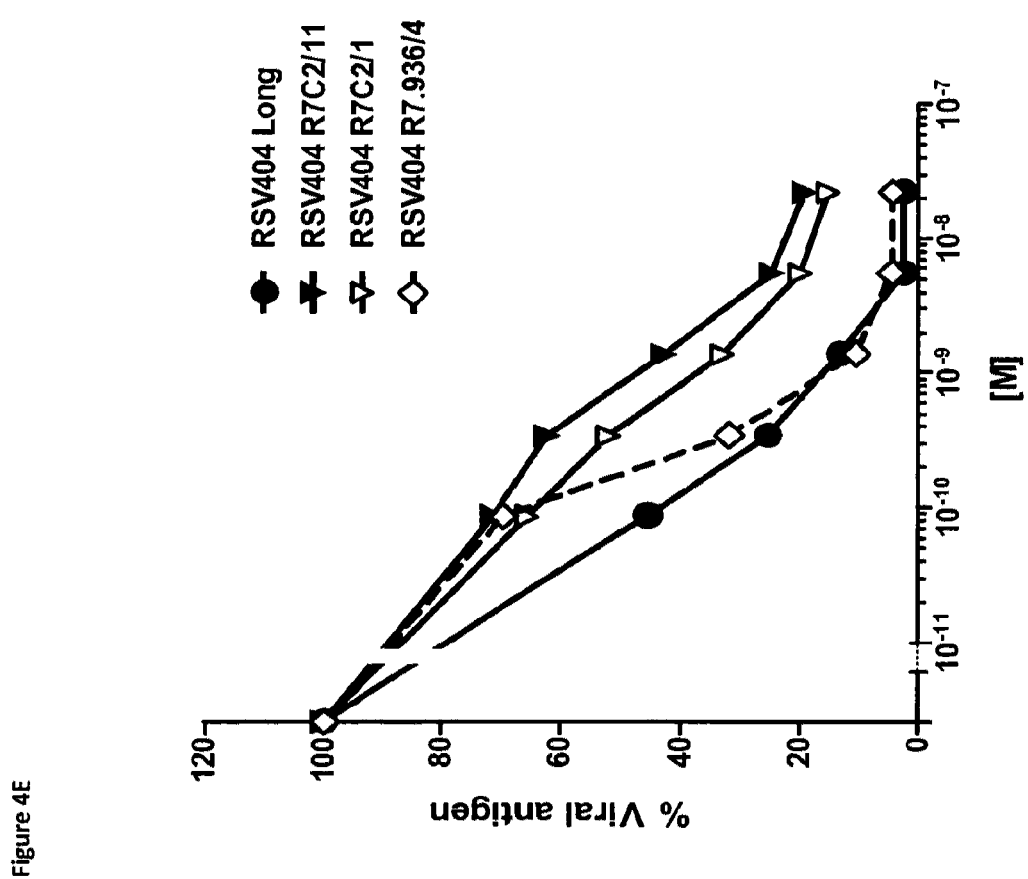
Figure 4F:
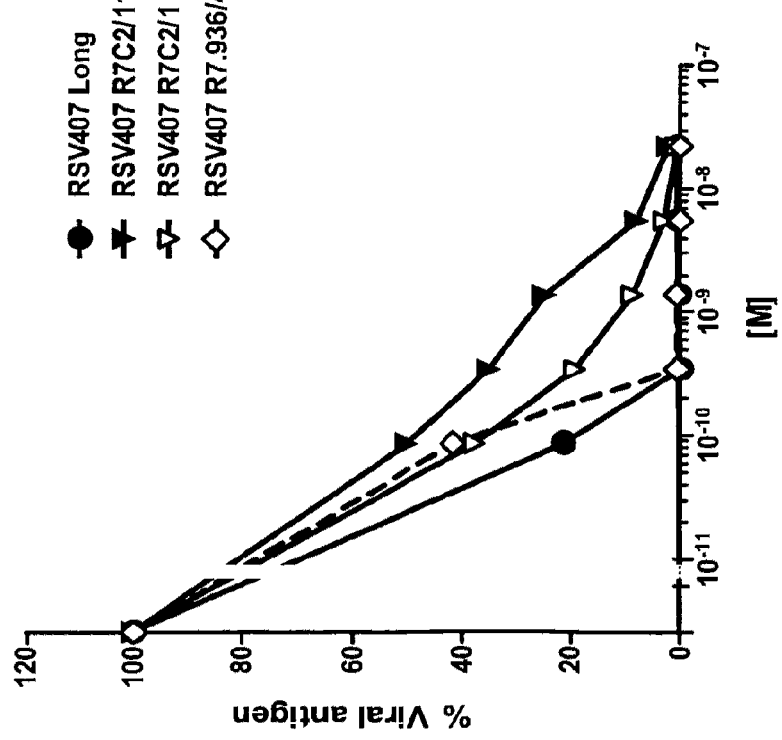
Figure 4G:
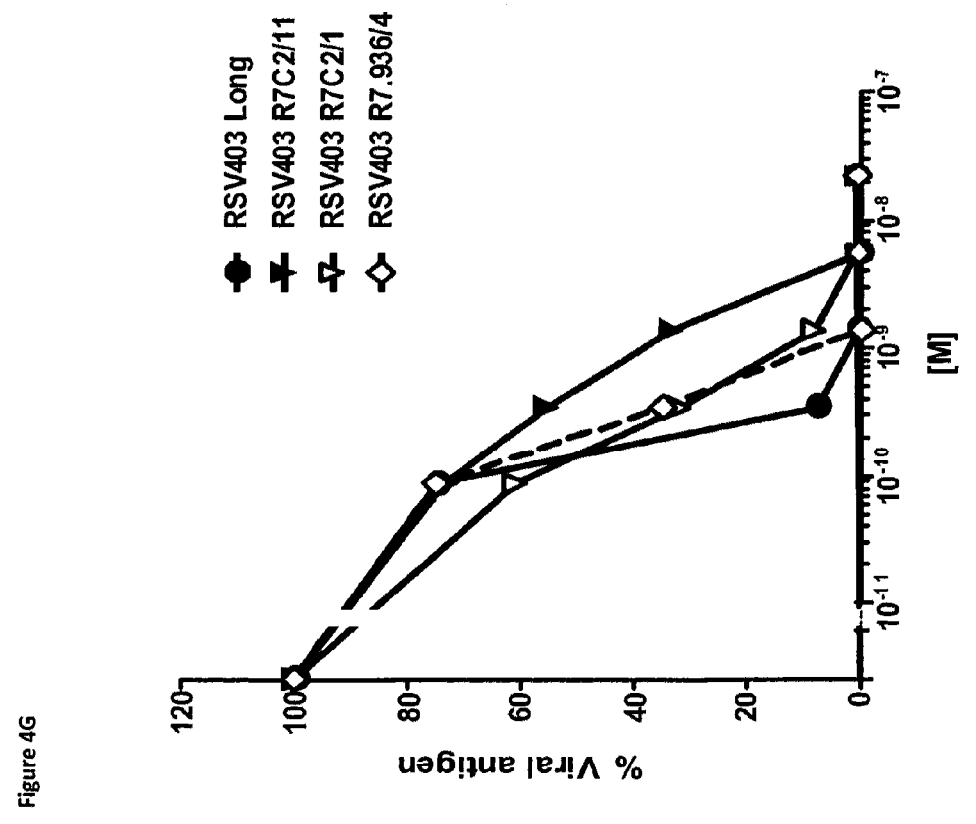

As shown in FIGS. 4A-C, the monovalent Nanobodies® had almost no neutralizing potential towards the antigenic site II escape mutant viruses R7C2/11 and R7C2/1. The potency to neutralize the R7.936/4 antigenic site IV-VI variant was comparable to the potency to neutralize the wild type Long strain. These data are in line with the binding data of example 12 and the epitope mapping as described for these Nanobodies® in example 5.

The trivalent Nanobody® constructs however, were potently neutralizing all 3 escape mutants (FIGS. 4D-G). Maximal inhibition was observed at concentrations as low as about 20 nM while this level of inhibition was not observed for the monovalent Nanobodies® at concentrations up to 2 µM. The potent neutralization of R7C2/1, almost equivalent to the neutralization of R7C2/11, is most surprising since example 13 showed a very significant loss of binding activity for the trivalent molecule RSV400 which was expected to result in a very high loss of neutralization potency. The bivalent IgG Synagis® Palivizumab, also recognizing antigenic site II was not able to block replication of R7C2/1 or R7C2/11 significantly at concentrations of about 0.2 µM. At this concentration an IC50 was not reached while R7.936/4 and wild type Long virus were neutralized with an IC50 of a few nM (data not shown).

Example 15

Analysis of Impact of Linker Length on Potency of NC41 Trivalents

To determine the impact of the linker length of trivalents of NC41, different constructs with linkers ranging from 3Ala, 9GS, 15GS, to 20GS linkers (RSV408, RSV409, RSV407 and RSV410 resp.) were generated. All four NC41 trivalents were able to completely neutralize both RSV B-1 and Long strains (FIG. 5). No effect of linker length was observed in neutralization of RSV Long, as all constructs were equally potent. By contrast, the constructs with 9GS and 3Ala linkers had increased IC50 values on the B-1 strain, indicating that a minimal linker length of 15GS is required for maximal potency. This may be explained by the observation that bivalent NC41 constructs already are very potent neutralizers on Long, while on the B-1 strain the potency difference between bivalent and trivalent NC41 is much larger (see Example 11). In RSV408 and RSV409 the accessibility of the middle Nanobody® may be less optimal.

Example 16

Humanization of Nanobody® NC41

The sequence of Nanobody® NC41 was aligned to the human germline VH3-23 to allow selection of residues suitable for further humanization of the Nanobody® sequence. In addition, in silico analysis was done to identify residues that are potentially prone to post-translational modifications, such as Asp isomerisation, and to identify mutations that might improve the chemical stability. The CDR regions and the so-called Hallmark residues, which are known to be essential for the stability and potency of Nanobodies® were excluded for modification.

For NC41 in total 11 positions were selected for mutation to the corresponding human residue: Four mutations were simultaneously introduced (Val5Leu, Ala14Pro, Glu44Gly, Gln108Leu), as these residues were not expected to dramatically affect the Nanobody® function (based on data from other Nanobodies®). In this basic variant, seven residues of which it was unknown whether mutation to the human counterpart was allowed (Ser19Arg, Ile20leu, Ala74Ser, Gly78Leu, Ala83Arg, Asp85Glu, Arg105Gln) were mutated using a library approach, allowing either the wildtype or the corresponding human amino acid at each position. The resulting library, with a theoretical diversity of 128, was generated by gene assembly using overlapping oligonucleotide sequences containing degenerated codon use, and subsequently cloned into an expression vector derived from pUC119 which contained the LacZ promoter, a resistance gene for kanamycin, a multicloning site and the OmpA leader sequence. In frame with the Nanobody® coding sequence, the vector coded for a C-terminal c-myc tag and a (His)6 tag. Nanobodies® were produced in the periplasm of *E. coli* (see Example 7). Library diversity was confirmed by sequence analysis.

Periplasmic extracts from 368 individual NC41 variants and wildtype NC41 were generated and subjected to a functional screening cascade to identify the best humanized NC41 variant, in terms of both potency and stability. In a first step, RSV binding of humanized NC41 variants to RSV Long was determined in ELISA (Hytest, Turku Finland; #8RSV79)(see Example 8).

Moreover, the positive binders were analyzed for binding to Hep2 cells infected with RSV B-1 strain. In here, Hep2 cells were seeded into 96-wells plates and infected with RSV B-1 strain, essentially following the procedure described for the neutralization assay (see Example 6). Three days later cells were fixed with ice-cold acetone and plates were used in an ELISA assay using periplasmic extracts at different dilutions. Nanobody® binding to Hep2-B1 infected cells was detected using anti-VHH rabbit polyclonal antibody, followed by goat Anti-rabbit-HRP conjugated antibodies, after which the ELISA was developed according to standard procedures.

Additionally, in order to verify if the introduced mutations affected the temperature stability, periplasmatic extracts of all binders were heated to 74° C. for 2 hours, which is 5° C. above the melting temperature of wildtype NC41. The binding to RSV long before and after heating was analyzed in ELISA, and the ratio of binding signal after vs. before heating was taken as measure for temperature stability.

Finally, the kinetic off-rates of the variants were determined in Biacore assay on the $F_{tm}$-NN protein, as described in Example 8.

All binders were sequenced and ranked according to their capacity to bind the F-protein of RSV. When analyzing the sequences of the strongest binders, a clear preference for Gln105 (human residue) was observed in all cases. Whereas the Ile20Leu mutation appeared underrepresented, for all other positions there was no clear preference for either the wild type or the human sequence, with variants containing up to 10 mutations compared to wildtype NC41. Notably, in one variant an additional pointmutation (Gly54Asp) within the CDR2 region was observed. This variant, NC41 variant 6, showed the lowest off-rate of all variants and wildtype NC41, resulting in affinity increase.

Based on the sequence and functional data, 18 variants (Table A-4) were selected for further characterization as purified proteins (FIGS. 6 and 7). All variants were produced and purified, and potencies for neutralization of RSV Long and B-1 were determined in the micro neutralizations assay. While most variants showed very similar activity to wildtype NC41, several variants showed increased potency on both Long (2-fold) and B-1 (6-fold), with the strongest neutralizers being NC41 variants 6, 8, 9 17, and 18. Notably, variant 18 was maximally humanized at all 11 positions, with the additional introduction of Asp54 in the CDR2 region. Variant 10 and 11 were more potent in neutralizing B-1 strain than NC41, but not on Long strain.

For a select panel of NC41 variants the kinetic binding parameters were determined in Biacore on $F_{tm}$. NN protein (Table B-5) as described in Example 8. No significant differences in the calculated data were observed for NC41 and the humanized NC41 variants 6, 8 and 17. It should be noted that the on-rates of all NC41 variants were at the detection limit of the instrument, but the off-rates could be ranked as v06<v17<NC41<v08. The impact of the Gly to Asp mutation in CDR2 (position 54) could be clearly demonstrated when comparing v17 and v18 as this is the only difference in these maximally humanized variants. Neutralization was tested for both the Long strain and the B-1 strain in two independent assays in comparison to the NC41 wild type as shown in table B-5. In both assays NC41v18 was more potent than NC41 on both viruses and in both assays NC41v18 was more potent than NC41v17 on the Long strain. The improved neutralization of NC41v18 was also observed for the B-1 strain in the second assay.

All NC41 variants were subjected to heat-induced unfolding to assess the effect of the introduced mutations on the stability of the protein. Thereto the melting temperature (Tm) was determined by stepwise increase in temperature in presence of Sypro Orange, a dye that binds to Trp residues that become exposed upon unfolding of the protein. All variants showed to have increased Tm relative to wildtype NC41 (69° C.), up to 9° C. for variant 18.

Example 17

Further Sequence Optimization of NC41 for Expression

The sequence of Nanobody® NC41 was further analyzed with the aim to optimise expression in *Pichia pastoris*. NC41 variants 19-26 were designed by combining humanized positions that were shown to be permitted without loss in potency in the micro-neutralization assay (Example 16). Four mutations were simultaneous introduced (Ala14Pro, Ser19Arg, Ile20Leu, Gln108Leu), while three mutations were both individually and in each possible combination examined (Ala83Arg, Asp85Glu, Arg105Gln)(see Table A-4). All constructs were cloned into an expression vector and introduced into the *Pichia pastoris* strain XL-33, after which the number of incorporations in the *Pichia* genome was assessed by quantitative real-time PCR. From each construct one clone with 1-2 copies and one with four or more copies were selected for small scale productions, and expression yield of NC41 variants relative to wild type was estimated by gel electrophoresis on SDS-PAGE gels. NC41 variants 20, 22, 24, 25 and 26 showed the highest expression, with similar expression levels as wild type NC41 already at low copy number.

NC41 variants 22 and 26 were recloned in an expression vector for *E. coli* for production and purification of Myc-Histagged Nanobodies (see example 7). The potency of both variants for neutralization of RSV Long was tested in the micro neutralization assay, as described in example 6. Both variants were equally potent as wild type NC41 (IC50 of 126 and 310 nM for v22 and v26, respectively).

Example 18

Sequence Optimization of RSV407 for Chemical Stability

During the production of the Nanobodies and polypeptides of the invention, pyro glutamate (pGlu) on the amino terminus was observed (via RP-HPLC). Levels of more than 15% pGlu were detected following fermentation and the level of pGlu was steadily increasing upon storage during stability studies. Therefore, the N-terminal Glutamate (E) was changed into an Aspartate (D). This would eliminate the possibility of pGlu post-translational modification of the N-terminus and hence lead to increased product stability.

The amino acid sequence of the sequence optimized Nanobody® variant is given in Table A-5 (RSV434; SEQ ID NO: 142) respectively. For the production of this Nanobody® a *Pichia* expression system was developed based on the commercially available system from Invitrogen using X-33 as a host strain. The system makes use of the AOX1 promoter to drive the production of the Nanobody® and uses the alpha mating secretion peptide for secretion of the Nanobody® into the medium.

The sequence optimized RSV434 was analyzed for expression levels, via RP-HPLC, SE-HPLC and compared to the parental molecule (RSV407) with respect to RSV neutralization.

There was no significant difference in expression level compared to RSV407 and both the low and high copy number clones were producing more than 1 g/L clarified medium (cell free).

One ml samples were captured on a 1 ml MEP Hypercel column, eluted and analyzed via SE-HPLC and RP-HPLC. SE-HPLC analysis showed monomeric material, whereas RP-HPLC analysis, as expected, clearly showed the absence of the pGlu post peak.

RSV434 was further purified from the medium, captured on MEP HyperCell and polished via anion exchange chromatography.

Figure 9A:
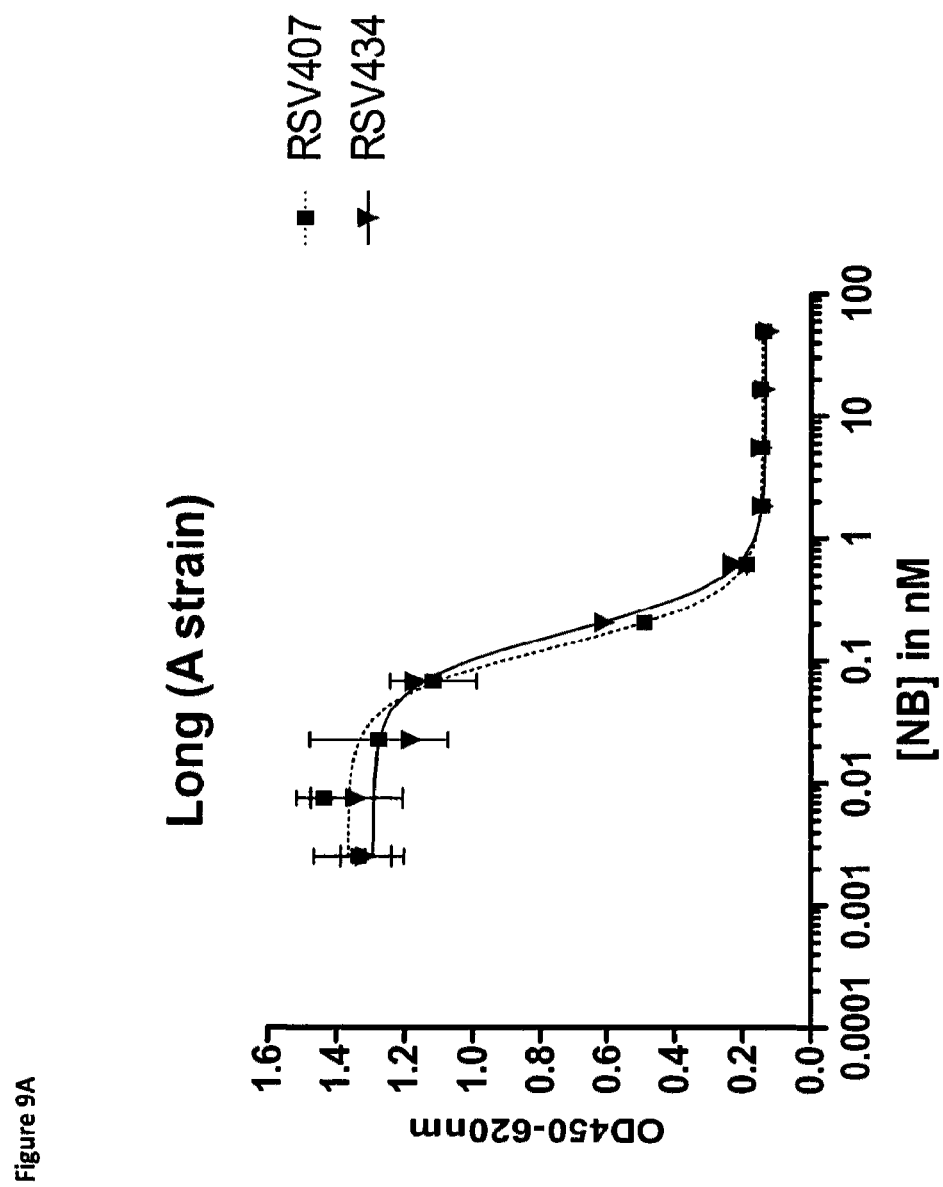
FIG. 9: Neutralization of hRSV Long (A) and B-1 (B) strains by RSV407 and RSV434.
Figure 9B:
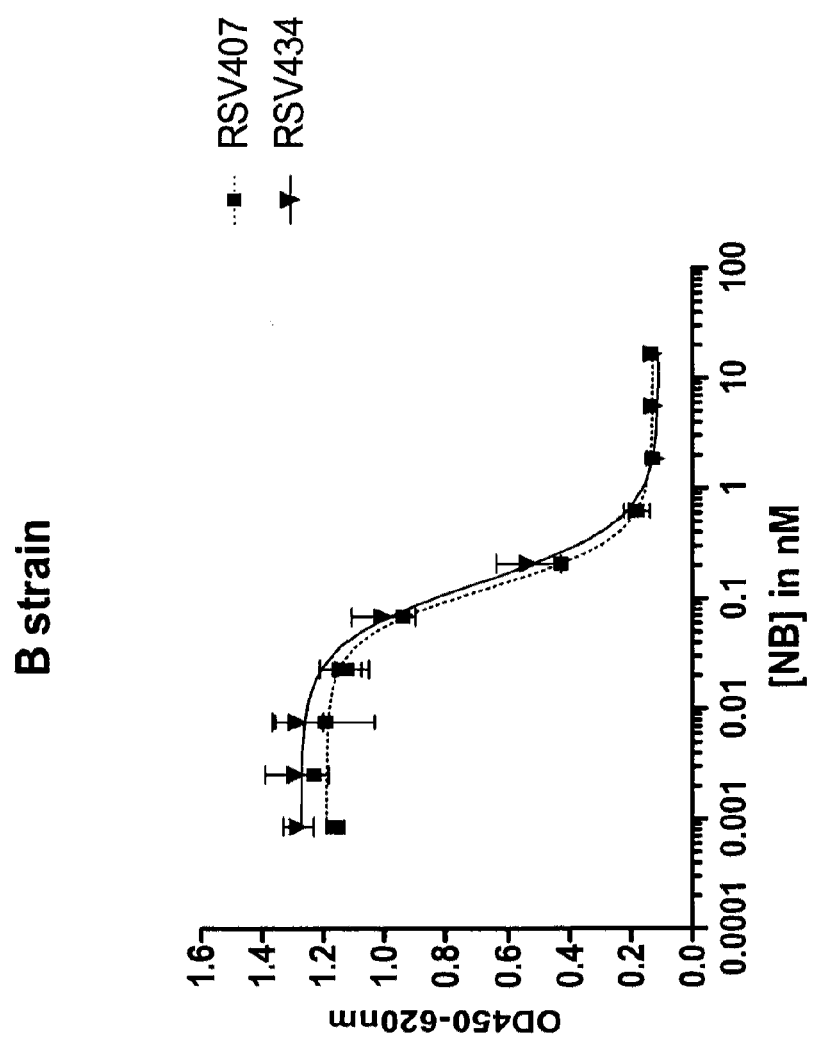

Rn hRSV micro neutralization assay was essentially performed as described in example 6. FIG. 9 shows the neutralization on both RSV Long and B-1 strains by both RSV407 and its sequence optimized variant RSV434.

Example 19

Preparation of Multivalent Constructs of Humanized and/or Sequence Optimized NC41 Nanobody®

NC41 humanized variants of Example 16 were formatted as trivalent constructs using 15GS linkers (sequences are shown in Table A-5). The trivalents were produced and purified as described in Example 10. FIG. 8A shows the neutralization on both RSV Long and B-1 strains of two of the trivalent humanized NC41 variants with their corresponding monovalent Nanobodies®. FIG. 8B shows the neutralization on both RSV Long and B-1 strains of the trivalent NC41 variants. IC50 values for neutralization of RSV Long and B-1 strains by the trivalent NC41 variants are shown in Table B-7. Similar as to parental NC41 trivalent (RSV407), trivalents of the humanized NC41 variants were around 60 times more potent neutralizers of Long than Synagis®. On the B-1 strain trivalents were more potent neutralizers than Synagis, but here also slightly enhanced compared to the trivalent of parental NC41 RSV407 in following order RSV427>RSV426>RSV414. The increased potency of monovalent variants for B-1 thus appeared to have resulted in slightly improved trivalents.

Based on further sequence optimization shown in Examples 17 and 18, a number of additional trivalent constructs (Table B-6) were generated. All constructs were cloned in a *Pichia pastoris* expression vector, transformed into *Pichia* and subjected to fermentation to test expression levels, stability and potency. Both in small scale shake flask expressions and fermentation RSV440 (variant 26) and RSV441 (variant 22) showed high expression levels.

Example 20

In Vitro Efficacy of the Multivalent Constructs

The neutralizing capacity of Nanobody RSV434 and Synagis was evaluated in a plaque reduction assay against 31 RSV/A and 30 RSV/B clinical isolates. Both anti-RSV compounds as well as Synagis were tested at a single concentration of 40 µg/ml.

Synagis and RSV434 both performed efficiently with respectively 87% and 97% of the strains being reduced in virus titers by at least 100-fold compared to PBS control (Table B-8). In addition, RSV434 showed greater neutralizing capacity compared to Synagis. The majority of the RSV strains (84%) were completely inhibited by RSV434 while significantly fewer strains (20%) were completely inhibited by Synagis (Table B-8).

Example 21

In Vivo Efficacy of the Multivalent Constructs

Figure 10A:
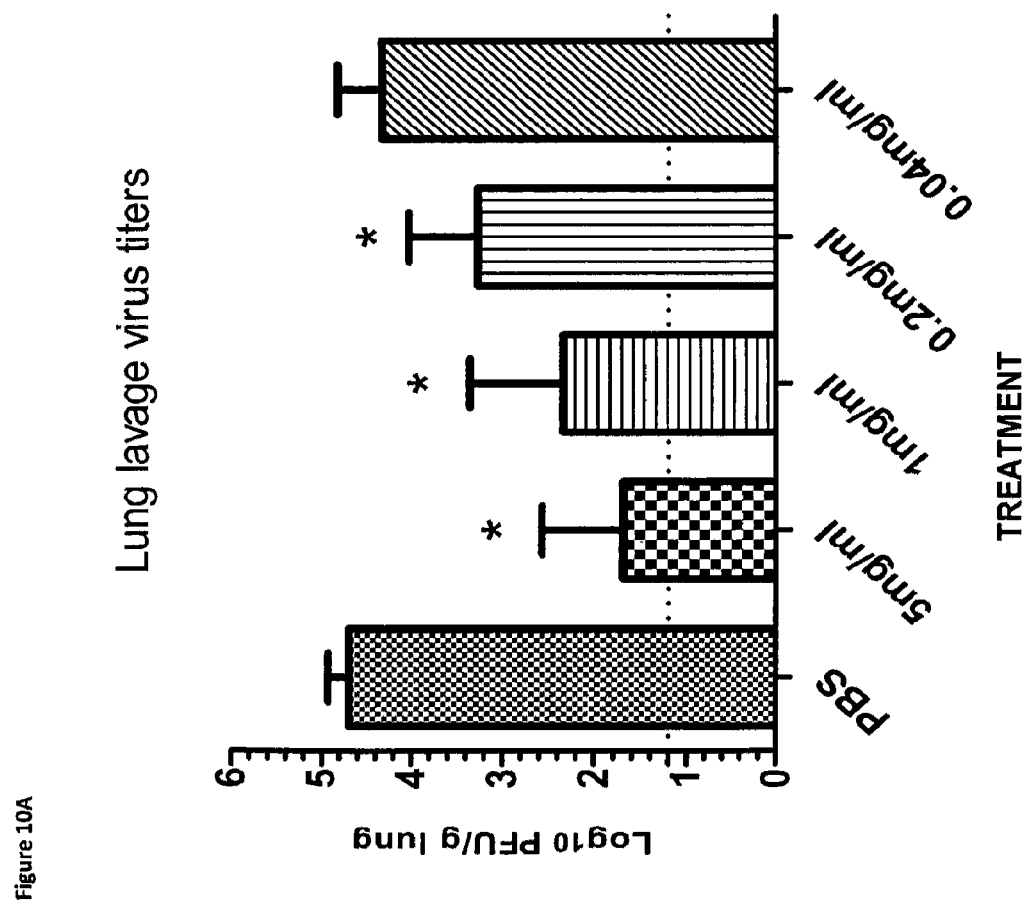
FIG. 10: Efficacy testing (prophylactic) of RSV407 in cotton rat model as described in Example 21. Rats were intranasally administered with various concentrations of RSV407 (day −1) 24 hours prior to RSV infection (day 0). The virus titer (left, mean±sem, n=6) and viral RNA level (right) was determined in lung lavages at the peak level of viremia, being day 4 after infection (*=P<0.05 in two tailed student's t-test versus untreated).
Figure 10B:
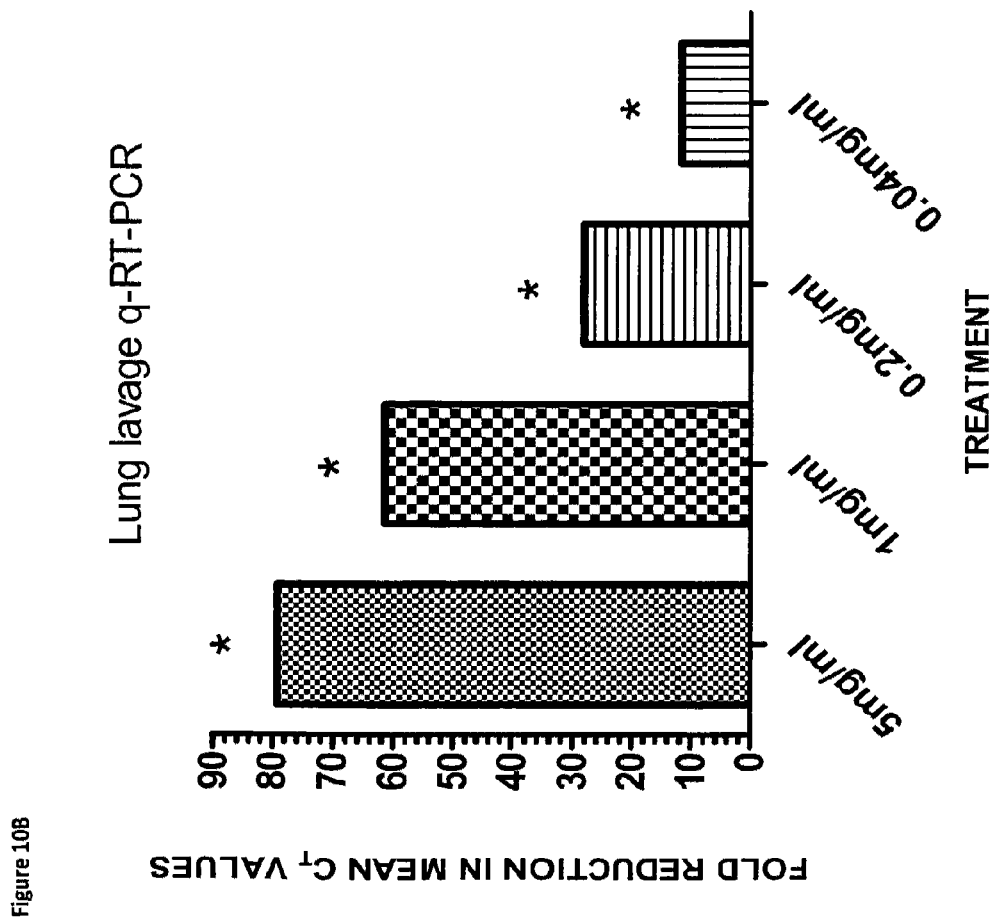

The cotton rat model is the golden standard model for RSV. In this model, the cotton rats are infected with the RSV/Tracy strain (day 0) and 4 days after infection, viral titers and viral RNA are assessed in lung lavages and nasal washes. In a prophylactic set-up, a significant and dose-dependent decrease in viral load was observed upon intranasal administration of RSV407, 24 hours before RSV infection (FIG. 10).

Figure 11A:
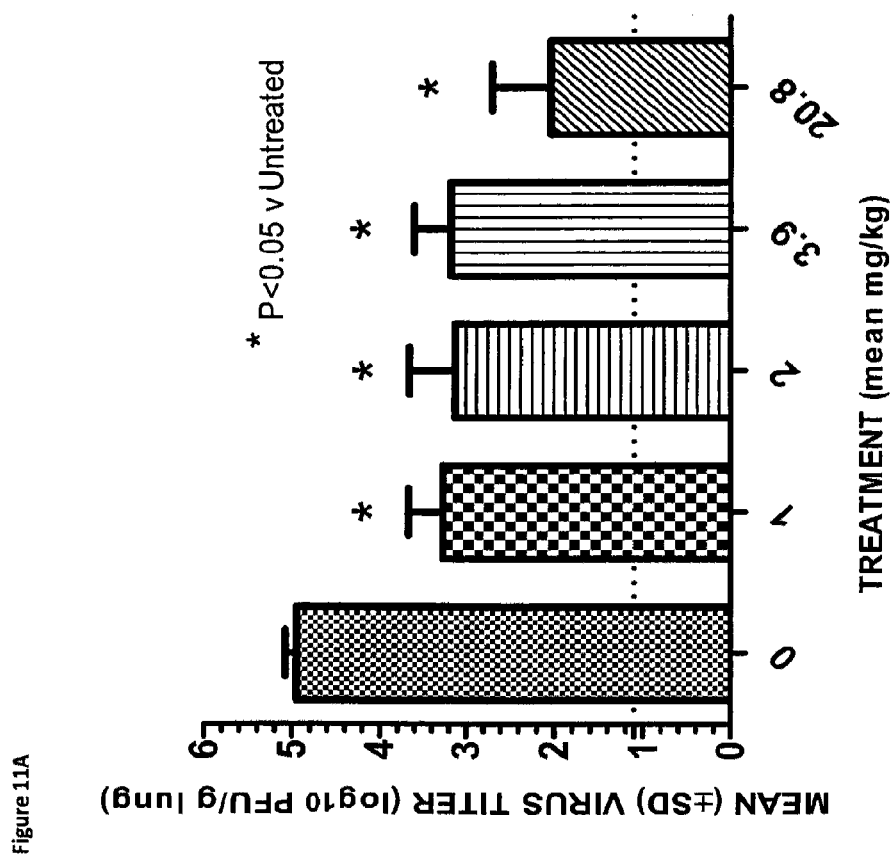
FIG. 11: Efficacy testing (therapeutic) of RSV434 in cotton rat model as described in Example 21. Rats were infected with RSV on day 0 and treated with 0, 1, 2, 4 or 20 mg/kg of RSV434 at day 2 and 3 by intranasal instillation (n=6). The virus titer in nasal (A) and lung lavages (B) was determined at the peak level of viremia (day 4 after infection). The horizontal lines show the detection limits.
Figure 11B:
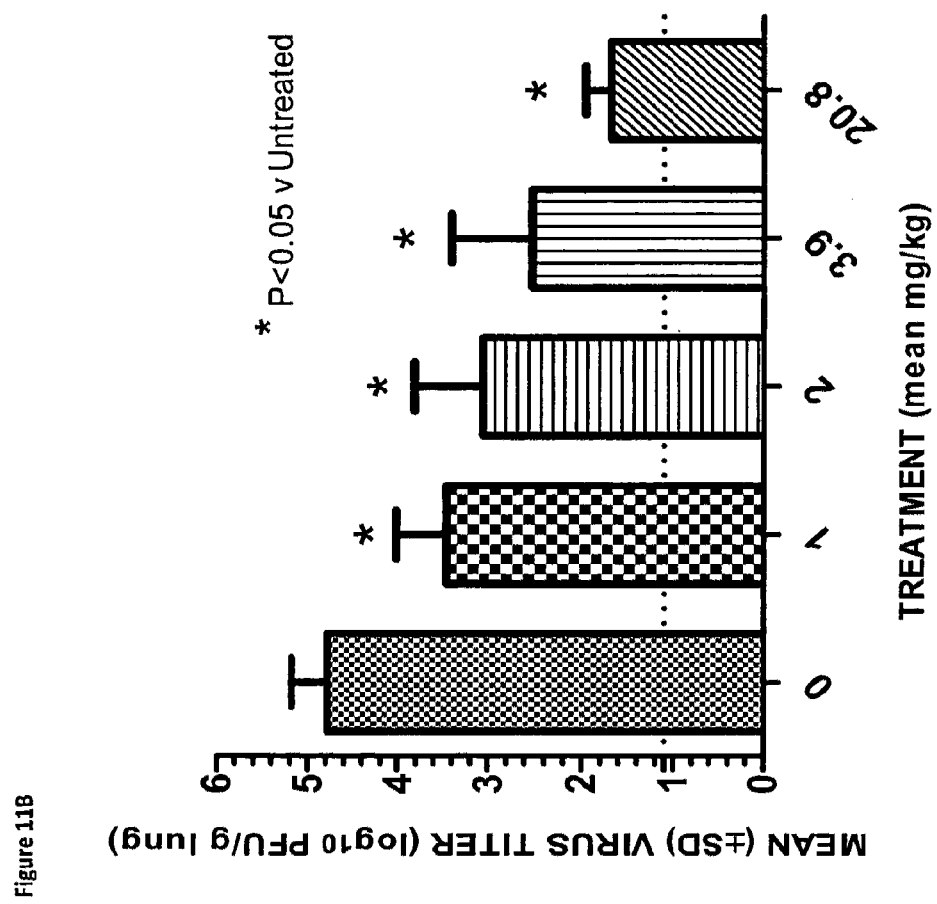

In addition, a therapeutic approach was explored in which infected cotton rats were treated with the Nanobodies, including RSV434, after 24 h or 48 h of infection thereby mimicking the situation of RSV infected humans, in both cases significant inhibition of viral replication was observed (Table B-9 and FIG. 11).

In all studies performed to date, the Nanobody was delivered intranasally as a mimic for pulmonary delivery. Using this route of administration 9-41% of Nanobody was available in the lungs as assessed by ELISA on bronchial lavage taken shortly after administration.

In an attempt to overcome the possible interference of residual Nanobody in the lung lavages, the viral detection was delayed to day 7 post inoculation. A separate pharmacokinetic study performed in Sprague Dawley rats allowed to estimate the half life of the Nanobody in the lung to be about 10.8. At day 7 which is 5-6 days after the last administration, the Nanobody is sufficiently cleared from the lung to no longer interfere in the assay. The viral load of positive control animals dropped from 10E5 to 10E2 pfu/ml. Nevertheless it was still possible to show a reduction of about 0.6 log by treatment with RSV407 (Table B-9).

As an alternative approach a quantitative PCR was developed to detect viral RNA. Both in prophylactic and therapeutic experiments a significant reduction in RSV RNA was observed (Table B-9).

Example 22

Generation of RSV Escape Mutants

In order to identify the critical contact residues with the F-protein, the generation of RSV Long escape mutants was analyzed after culturing RSV Long in presence of Nanobodies at about their respective IC90 concentrations. Both monovalent NC41 (at 5 µg/ml) and its trivalent RSV407 (at 2.5 ng/ml) were used, as well as the bispecific trivalent RSV413 (NC41-15B3-NC41) to verify if a construct that recognizes two different epitopes would affect the time frame of viral escape onset. After 12 passages of successive incubation of Long on Hep2 cells in presence of Nanobodies, viral out growth was observed for the conditions with monovalent NC41 but surprisingly not with the trivalent Nanobodies. Single virus stocks were purified from plaques for repetitive rounds, after which the sequence of the F-protein of the potential escape variant could be determined. Two distinct escape variants were identified for NC41, NC41/13 with the mutation of N262Y, and NC41/17 containing mutation N276Y.

Tables

TABLE A-1

Sequences of monovalent Nanobodies ® that bind RSV F protein

| Nanobody ® | SEQ ID NO: | Sequence |
| --- | --- | --- |
| 1E4 207D1 | 1 | EVQLVESGGGLVQAGGSLRLSCEASGRTFSSYGMGWERQAPGKEREF VAAVSRLSGPRTVYADSVKGRFTISRDNAENTVYLQMNSLKPEDTAV YTCAAELTNRNPGAYYYTWAYDYWGQGTQVTVSS |
| 7B2 | 2 | EVQLVESGGGLVQAGDSLRLSCAASGRTFSSYAMGWFRQAPGKEREF VAAISWSDGSTYYADSVKGRFTISRDNAKNTVYLQMNSLKPEDTAVY YCAADLTSTNPGSYIYIWAYDYWGQGTQVTVSS |

TABLE A-1-continued

Sequences of monovalent Nanobodies ® that bind RSV F protein

| Nanobody ® | SEQ ID NO: | Sequence |
|---|---|---|
| NC23 | 3 | EVQLVESGGGLVQPGGSLRLSCAASGRTFSSIAMGWFRQAPGKEREF VAAISWSRGRTFYADSVKGRFIISRDDAANTAYLQMNSLKPEDTAVY YCAVDTASWNSGSFIYDWAYDHWGQGTQVTVSS |
| 15H8 19C4 | 4 | EVQLVESGGGLVQAGGSLRLSCAASGRSFSNYVLGWERQAPGKEREF VAAISFRGDSAIGAPSVEGRFTISRDNAKNTGYLQMNSLVPDDTAVY YCGAGTPLNPGAYIYDWSYDYWGRGTQVTVSS |
| NC41 | 5 | EVQLVESGGGLVSISCAASGGSLSNYVLGWFRQAPGKEREF VAAINWRGDITIGPPNVEGRFTISRDNAKNTGYLQMNSLAPDDTAVY YCGAGTPLNPGAYIYDWSYDYWGRGTQVTVSS |
| NC39 | 6 | EVQLVESGGGWVQAGGSLRLSCAASGRAFSSYAMGWIRQAPGKEREF VAGIDQSGESTAYGASASGRFIISRDNAKNTVHLLMNSLQSDDTAVY YCVADGVLATTLNWDYWGQGTQVTVSS |
| 15B3 | 7 | EVQLVESGGGLVQPGGSLRLSCAASGLTLDYYALGWFRQAPGKEREG VSCISSSDHSTTYTDSVKGRFTISWDNAKNTLYLQMNSLKPGDTAVY YCAADPALGCYSGSYYPRYDYWGQGTQVTVSS |
| 191C7 | 8 | EVQLVESGGGLVQAGGSLRLSCAASGSSGVINAMAWHRQAPGKEREL VAHISSGGSTYYGDFVKGRFTISRDNAKDTVYLQMNSLKPEDTAVYY CHVPWMDYNRRDYWGQGTQVTVSS |
| 191D3 1G3 | 9 | EVQLVESGGGLVQAGGSLRLSCEASGRTYSRYGMGWFRQAPGKEREF VAAVSRLSGPRTVYADSVKGRFTISRDNAENTVYLQMNSLKPEDTAV YTCAAELTNRNSGAYYYAWAYDYWGQGTQVTVSS |
| 191E4 1B2 | 10 | EVQLVESGGGLVQAGGSLRLSCAASGPTFSADTMGWFRQAPGKEREF VATIPWSGGIAYYSDSVKGRFTMSRDNAKNTVDLQMNSLKPEDTALY YCAGSSRIYIYSDSLSERSYDYWGQGTQVTVSS |
| 192C4 | 11 | EVQLVESGGGLVQAGGSLRLSCEASGRTFSSYAMVGWFRQAPGKERE FVAAVTRWSGARTVYADSVKGRFTISRDNAENTVYLQMNSLKPEDTA VYTCAADSTNRNSGAVYYSWAYDYWGQGTQVTVSS |
| 192F2 | 12 | EVQLVESGGGLVQAGGSLRLSCEASGRTFSPIAMGWFRQAPGKEREF VAVVTRWSGARTVYADSVKGRFTISRDNAENTVYLQMNSLKPEDTAV YTCAADSTNRNSGAIYYTWAYDYWGQGTQVTVSS |

TABLE A-2

F-protein sequences

| F-protein | SEQ ID NO: | Sequence |
|---|---|---|
| RSV LONG M-2 | 17 | MELPILKANAITTILAAVTFCFASSQNITEEFYQSTCSAVSKG YLSALRIGWYTSVITIELSNIKENKCNGTDAKVKLIKQELDKY KNAVTFLQLLMQSTFAANNRARRELPRFMNYTLNNTKKTNVTL SKKRKRRFLGFLLGVGSATASGTAVSKVLHLEGEVNKIKSALL SINKAVVSLSNGVSVLTSKVLDLKNYIDKQLLPIVNKQSCRIS NIETVIEFQQKNNRLLEITREFSVNAGVTTPVSTYMLTNSELL SLINDMPITNDQKKLMSNNVQIVRQQSYSIMSIIKEEVLAYVV QLPLYGVIDTPCWKLHTSPLCTTNTKEGSNICLTRTDRGWYCD NAGSVSFFPQAETCKVQSNRVFCDTMNSLTLPSEVNLCNVDIF NPKYDCHIMTSKTDVSSSVITSLGAIVSCYGKTKCTASNKNRG IIKTFSNGCDYVSNKGVDTVSVGNTLYYVNKQEGKSZYVKGEP IINFYDPLVFPSDEFDASISQVNEKINQSLAFIRKSDELLHHV NAGKSTTNIMITTIIIVIIVILLSLIAVGLLLYCKARSTPVTL SKDQLSGINNIAFSN |
| RSV A-2 | 118 | MELLILKANAITTILTAVTFCFASGQNITEEFYQSICSAVSKG YLSALRTGWYTSVITIELSNIKHNKONGTDAKVKLIKQELDKY KNAVTELTLLMQSTQATNNRARRELPRFMNYTLNNAKKTNVIL SNKRKRRFLGFLLGVGSATASGVAVSKVLHLEGEVNKIKSALL STNKAVVSLSNGVSVLTSKVLDLKNYIDKQLLPIVNKQSCSIS NIETVIEFQQKNNRLLEITREFSVNAGVITPVSTYMLINSELL SLINDMPITNDQKKLMSNNVQIVRQQSYSTMSIIKEEVLAYVV QLPLYGVIDTPOWKLHISPLOTTNTKEGSNICLTRIDRGWYCD NAGSVSFFPQAETCKVQSNRVFCDTMNSLTLPSEVNLQNVDIF NPKYDCKIMISKTDVSSSVITSLGAIVSCYGKTKCIASNKNRG |

TABLE A-2-continued

F-protein sequences

| F-protein | SEQ ID NO: | Sequence |
|---|---|---|
| | | IIKTFSNGCDYVSNKGVDTVSVGNTLYYVNKQEGKSLYVKGEP<br>IINFYDPLVFPSDEFDASISQVNEKINQSLAFIRKSDELLHNV<br>NAGKSTTNIMITTIIVIIVILLSLTAVGLLLYCKARSTPVTL<br>SKDQLSGINNIAFSN |
| RSV B-1 | 19 | MELLIHRSSAIFLTLAVNALYLISSQNITEEFYQSTCSAVSRGY<br>FSALRIGWYTSVITIELSNIKETKCNGTDTKVKLIKQELDKYKN<br>AVIELQLLMQNTPAANNRARREAPQYMNYTINTYKNLNVSISKK<br>RKRRFLGFLLGVGSAILSGIAVSKVLHLEGEVNKTKNALLSTNK<br>AVVSLSNGVSVLTSKVLDLKNYINNALLPIVNQQSCRISNIETV<br>IEFQQMNSRLLEITREFSVNAGVTTPLSTYMLTNSELLSLINDM<br>PITNDQKKLMSSNVQIVRQQSYSIMSIIKEEVLAYVVQLPIYGV<br>IDTPCWKLHISPLCTTNIKEGSNICLIRTDRGWYCDNAGSVFF<br>PQADTCKVQSNRVFCDTMNSLILPSEVSLQNTDIFNSKYDCKIM<br>TSKTDISSSVITSLGAIVSCYGKIKCIASNKNRGIIKTFSNGCD<br>YVSKKGVDTVSVGNTLYYVNKLEGKNLYVKGEPIINYYDPLVEP<br>SDEFDASISQVNEKINQSLAFIRRSDELLHNVNTGKSTINTMIT<br>TIIIVIIVVLLLLIAIGLLLYCKAKNTPVTLSNDQLSGINNTAF<br>SK |

TABLE A-3

Amino acid sequences of multivalent constructs that bind hRSV

| Construct | SEQ ID NO: | Sequence |
|---|---|---|
| RSV101 | 20 | EVQLVESGGGLVQAGGSLRLSCEASGRTYSRYGMGWFRQAPGKEREFVAA<br>VSRLSGPRTVYADSVKGRFTISRDNAENTVYLQMNSLKPEDTAVYTCAAE<br>LTNRNSGAYYYAWAYDYWGQGTQVTVSSGGGGSGGGGSGGGGSEVQLVES<br>GGGLVQAGGSLRLSCEASGRTYSRYGMGWFRQAPGKEREFVAAVSRLSGP<br>RTVYADSVKGRFTISRDNAENTVYLQMNSLKPEDTAVYTCAAELTNRNSG<br>AYYYAWAYDYWGQGTQVTVSS |
| RSV102 | 21 | EVQLVESGGGLVQAGGSLRLSCEASGRTYSRYGMGWFRQAPGKEREFVAA<br>VSRLSGPRTVYADSVKGRFTISRDNAENTVYLQMNSLKPEDTAVYTCAAE<br>LTNRNSGAYYYAWAYDYWGQGTQVTVSSGGGGSGGGGSGGGGSGGGGSGG<br>GGSEVQLVESGGGLVQAGGSLRLSCEASGRTYSRYGMGWFRQAPGKEREF<br>VAAVSRLSGPRTVYADSVKGRFTISRDNAENTVYLQMNSLKPEDTAVYTC<br>AAELTNRNSGAYYYAWAYDYWGQGTQVTVSS |
| RSV103 | 22 | EVQLVESGGGLVQAGGSLRLSCEASGRTYSRYGMGWFRQAPGKEREFVAA<br>VSRLSGPRTVYADSVKGRFTISRDNAENTVYLQMNSLKPEDTAVYTCAAE<br>LTNRNSGAYYYAWAYDYWGQGTQVTVSSGGGGSGGGGSGGGGSGGGGSGG<br>GGSGGGGSGGGGSEVQLVESGGGLVQAGGSLRLSCEASGRTYSRYGMSWF<br>RQAPGKEREFVAAVSRLSGPRTVYADSVKGRFTISRDNAENTVTLQMNSL<br>KPEDTAVYTCAAELTNRNSGAYYYRWAYDYWGQGTQVTVSS |
| RSV104 | 23 | EVQLVESGGGLVQAGGSLRLSCEASGRTYSRYGMGWFRQAPGKEREFVAA<br>VSRLSGPRTVYADSVKGRFTISRDNAENTVYLQMNSLKPEDTAVYTCAAE<br>LTNRNSGAYYYAWAYDYWGQGTQVTVSSGGGGSGGGSEVQLVESGGGLVQ<br>AGGSLRLSCEASGRTYSRYGMGWFRQAPGKEREFVAAVSRLSGPRTVYAD<br>SVKGRFTISRDNAENTVYLQMNSLKPEDTAVYTCAAELTNRNSGAYYYAW<br>AYDYWGQCTQVTVSS |
| RSV105 | 24 | EVQLVESGGGLVQAGDSLRLSCAASGRTFSSYAMGWFRQAPGKEREFVAA<br>ISWSDGSTYYADSVKGRFTISRDNAKNTVYLQMNSLKPEDTAVYYCAADL<br>TSTNPGSYIYIWAYDYWGQGTQVTVSSGGGGSGGGSEVQLVESGGGLVQA<br>GDSLRLSCAASGRTFSSYAMGWFRQAPGKEREFVAAISWSDGSTYYADSV<br>KGRFTISRDNAKNTVYLQMNSLKPEDTAVYYCAADLTSTNPGSYIYIWAY<br>DYWGQGTQVTVSS |
| RSV106 | 25 | EVQLVESGGGLVQAGDSLRLSCAASGRTFSSYAMGWFRQAPGKEREFVAA<br>ISWSDGSTYYADSVKGRFTISRDNAKNTVYLQMNSLKPEDTAVYYCAADL<br>TSTNPGSYIYIWAYDYWGQGTQVTVSSGGGGSGGGGSGGGGSEVQLVESG<br>GGLVQAGDSLRLSCAASGRTFSSYAMGWFRQAPGKEREFVAAISWSDGST<br>YYADSVKGRFTISRDNAKNTVYLQMNSLKPEDTAVYYCAADLTSTNPGSY<br>IYIWAYDYWGQGTQVTVSS |
| RSV107 | 26 | EVQLVESGGGLVQAGGSLRLSCAASGRSFSNYVLGWFRQAPGKEREFVAA<br>ISFRGDSAIGAPSVEGRFTISRDNAKNTGYLQMNSLVPDDTAVYYCGAGT<br>PLNPGAYIYDWSYDYWGRGTQVTVSSGGGGSGGGSEVQLVESGGGLVQAG |

TABLE A-3-continued

Amino acid sequences of multivalent constructs that bind hRSV

| Construct | SEQ ID NO: | Sequence |
|---|---|---|
| | | GSLRLSCAASGRSFSNYVLGWFRQAPGKEREFVAAISFRGDSAIGAPSVE GRFTISRDNAKNTGYLQMNSLVPDDTAVYYCGAGTPLNPGAYIYDWSYDY WGRGTQVTVSS |
| RSV108 | 27 | EVQLVESGGGLVQAGGSLRLSCAASGRSFSNYVLGWFRQAPGKEREFVAA ISFRGDSAIGAPSVEGRFTISRDNAKNTGYLQMNSLVPDDTAVYYCGAGT PLNPGAYIYDWSYDYWGRGTQVTVSSGGGGSGGGGSGGGGSEVQLVESGG GLVQAGGSLRLSCAASGRSFSNYVLGWFRQAPGKEREFVAAISFRGDSAI GAPSVEGRFTISRDNAKNTGYLQMNSLVPDDTAVYYCGAGTPLNPGAYIY DWSYDYWGRGTQVTVSS |
| RSV109 | 28 | EVQLVESGGGLVQPGGSLRLSCAASGRTFSSIAMGWFRQAPGKEREFVAA ISWSRGRTFYADSVKGRFIISRDDAANTAYLQMNSLKPEDTAVYYCAVDT ASWNSGSFIYDWAYDHWGQGTQVTVSSGGGGSGGGGSEVQLVESGGGLVQP GGSLRLSCAASGRTFSSIAMGWFRQAPGKEREFVAAISWSRGRTFYADSV KGRFIISRDDAANTAYLQMNSLKPEDTAVYYCAVDTASWNSGSFIYDWAY DHWGQGTQVTVSS |
| RSV110 | 29 | EVQLVESGGGLVQPGGSLRLSCAASGRTFSSIAMGWFRQAPGKEREFVAA ISWSRGRTFYADSVKGRFIISRDDAANTAYLQMNSLKPEDTAVYYCAVDT ASWNSGSFIYDWAYDHWGQGTQVTVSSGGGGSGGGGSGGGGSEVQLVESG GGLVQPGGSLRLSCAASGRTFSSIAMGWFRQAPGKEREFVAAISWSRGRT FYADSVKGRFIISRDDAANTAYLQMNSLKPEDTAVYYCAVDTASWNSGSF IYDWAYDHWGQGTQVTVSS |
| RSV113 | 30 | EVQLVESGGGLVQPGGSLRLSCAASGLTLDYYALGWFRQAPGKEREGVSC ISSSDHSTTYTDSVKGRFTISWDNAKNTLYLQMNSLKPGDTAVYYCAADP ALGCYSGSYYPRYDYWGQGTQVTVSSGGGGSGGGGSGGGGSEVQLVESGG GLVQPGGSLRLSCAASGLTLDYYALGWFRQAPGKEREGVSCISSSDHSTT YTDSVKGRFTISWDNAKNTLYLQMNSLKPGDTAVYYCAADPALGCYSGSY YPRYDYWGQGTQVTVSS |
| RSV114 | 31 | EVQLVESGGGWVQAGGSLRLSCAASGRAFSSYAMGWIRQAPGKEREFVAG IDQSGESTAYGASASGRFIISRDNAKNTVHLLMNSLQSDDTAVYYCVADG VLATTLNWDYWGQGTQVTVSSGGGGSGGGGSGGGGSGGGGSEVQLVESGG GWVQAGGSLRLSCAASGRAFSSYAMGWIRQAPGKEREFVAGIDQSGESTA YGASASGRFIISRDNAKNTVHLLMNSLQSDDTAVYYCVADGVLATTLNWD YWGQGTQVTVSS |
| RSV115 | 32 | EVQLVESGGGLVQAGGSLRLSCAASGPTFSADTMGWFRQAPGKEREFVAT IPWSGGIAYYSDSVKGRFTMSRDNAKNTVDLQMNSLKPEDTALYYCAGSS RIYIYSDSLSERSYDYWGQGTQVTVSSGGGGSGGGGSGGGGGSEVQLV ESGGGLVQAGGSLRLSCAASGPTFSADTMGWFRQAPGKEREFVATIPWSG GIAYYSDSVKGRFTMSRDNAKNTVDLQMNSLKPEDTALYYCAGSSRIYIY SDSLSERSYDYWGQGTQVTVSS |
| RSV116 | 33 | EVQLVESGGGLVQAGGSLSISCAASGGSLSNYVLGWFRQAPGKEREFVAA INWRGDITIGPPNVEGRFTISRDNAKNTGYLQMNSLAPDDTAVYYCGAGT PLNPGAYIYDWSYDYWGRGTQVTVSSGGGGSGGGGSGGGGSEVQLVESCG GLVQAGGSLSISCAASGGSLSNYVLGWFRQAPGKEREFVAAINWRGDITI GPPNVEGRFTISRDNAKNTGYLQMNSLAPDDTAVYYCGAGTPLNPGAYIY DWSYDYWGRGTQVTVSS |
| RSV201 | 34 | EVQLVESGGGLVQAGGSLRLSCEASGRTYSRYGMGWFRQAPGKEREFVAA VSRLSGPRTVYADSVKGRFTISRDNAENTVYLQMNSLKPEDTAVYTCAAE LTNRNSGAYYYAWAYDYWGQGTQVTVSSGGGGSGGGGSEVQLVESGGGLVQ AGGSLRLSCAASGPTFSADTMGWFRQAPGKEREFVATIPWSGGIAYYSDS VKGRFTMSRDNAKNTVDLQMNSLKPEDTALYYCAGSSRIYIYSDSLSERS YDYWGQGTQVTVSS |
| RSV202 | 35 | EVQLVESGGGLVQAGGSLRLSCEASGRTYSRYGMGWFRQAPGKEREFVAA VSRLSGPRTVYADSVKGRFTISRDNAENTVYLQMNSLKPEDTAVYTCAAE LTNRNSGAYYYAWAYDYWGQGTQVTVSSGGGGSGGGGSGGGGSEVQLVES GGGLVQAGGSLRLSCAASGPTFSADTMGWFRQAPGKEREFVATIPWSGGI AYYSDSVKGRFTMSRDNAKNTVDLQMNSLKPEDTALYYCAGSSRIYIYSD SLSERSYDYWGQGTQVTVSS |
| RSV203 | 36 | EVQLVESGGGLVQAGGSLRLSCEASGRTYSRYGMGWERQAPGKEREFVAA VSRLSGPRTVYADSVKGRFTISRDNAENTVYLQMNSLKPEDTAVYTCAAE LTNRNSGAYYYAWAYDYWGQGTQVTVSSGGGGSGGGGSGGGGSGGGGSGG GGSEVQLVESGGGLVQAGGSLRLSCAASGPTFSADTMGWFRQAPGKEREF VATIPWSGGIAYYSDSVKGRFTMSRDNAKNTVDLQMNSLKPEDTALYYCA GSSRIYIYSDSLSERSYDYWGQGTQVTVSS |

TABLE A-3-continued

Amino acid sequences of multivalent constructs that bind hRSV

| Construct | SEQ ID NO: | Sequence |
|---|---|---|
| RSV204 | 37 | EVQLVESGGGLVQAGDSLRLSCAASGRTFSSYAMGWFRQAPGREREFVAA<br>ISWSDGSTYYRDSVKGRFTISRDNAKNTVYLQMNSLKPEDTAVYYCAADL<br>TSTNPGSYIYIWAYDYWGQGTQVTVSSGGGGSGGGGSGGGGSEVQLVESG<br>GGLVQRGGSLRLSCAASGRSFSNYVLGWFRQAPGKEREFVAAISFRGDSA<br>IGAPSVEGRFTISRDNAENTGYLQMNSLVPDDTAVYYCGAGTPLNPGAYI<br>YDWSYDYWGRGTQVTVSS |
| RSV205 | 38 | EVQLVESGGGLVQAGDSLRLSCAASGRTFSSYAMGWFRQAPGKEREF<br>VAAISWSDGSTYYADSVKGRFTISRDNAKNTVYLQMNSLKPEDTAVY<br>YCAADLTSTNPGSYIYIWAYDYWGQGTQVTVSSGGGGSGGGGSGGGG<br>SEVQLVESGGGLVQPGGSLRLSCAASGLTLDYYALGWFRQAPGKERE<br>GVSCISSSDHSTTYTDSVKGRFTISWDNAKNTLYLQMNSLKPGDTAV<br>YYCAADPALGCYSGSYYPRYDYWGQGTQVTVSS |
| RSV206 | 39 | EVQLVESGGGLVQAGGSLRLSCAASGRSFSNYVLGWFRQAPGKEREF<br>VAAISFRGDSAIGAPSVEGRFTISRDNAKNTGYLQMNSLVPDDTAVY<br>YCGAGTPLNPGAYIYDWSYDYWGRGTQVTVSSGGGGSGGGGSGGGGS<br>EVQLVESGGGLVQAGDSLRLSCAASGRTFSSYAMGWFRQAPGKEREF<br>VAAISWSDGSTYYADSVKGRFTISRDNAKNTVYLQMNSLKPEDTAVY<br>YCAADLTSTNPGSYIYIWAYDYWGQGTQVTVSS |
| RSV207 | 40 | EVQLVESGGGLVQAGGSLRLSCAASGRSFSNYVLGWFRQAPGKEREF<br>VAAISFRGDSAIGAPSVEGRFTISRDNAKNTGYLQMNSLVPDDTAVY<br>YCGAGTPLNPGAYIYDWSYDYWGRGTQVTVSSGGGGSGGGGSGGGGS<br>EVQLVESGGGLVQAGDSLRLSCAASGRTFSSYAMGWFRQAPGKEREF<br>VAAISWSDGSTYYADSVKGRFTISRDNAKNTVYLQMNSLKPEDTAVY<br>YCAADLTSINPGSYIYIWAYDYWGQGTQVTVSS |
| RSV301 | 41 | EVQLVESGGGINQAGGSLRLSCAASGPTFSADTMGWFRQAPGKEREF<br>VATIPWSGGIAYYSDSVKGRFTMSRDNAKNTVDLQMNSLKPEDTALY<br>YCAGSSRIYIYSDSLSERSYDYWGQGTQVTVSSGGGGSGGGSEVQLV<br>ESGGGLVQAGGSLRLSCEASGRTYSRYGMGWFRQAPGKEREFVAAVS<br>RLSGPRTVYADSVKGRFTISRDNAENTVYLQMNSLKPEDTAVYTCAA<br>ELTNRNSGAYYYAWAYDYWGQGTQVTVSS |
| RSV302 | 42 | EVQLVESGGGLVQAGGSLRLSCAASGPTFSADTMGWFRQAPGKEREF<br>VATIPWSGGIAYYSDSVKGRFTMSRDNAKNTVDLQMNSLKPEDTALY<br>YCAGSSRIYIYSDSLSERSYDYWGQGTQVTVSSGGGGSGGGGSGGGG<br>SEVQLVESGGGLVQAGGSLRLSCEASGRTYSRYGMGWFRQAPGKERE<br>FVAAVSRLSGPRTVYADSVKGRFTISRDNAENTVYLQMNSLKPEDTA<br>VYTCAAELTNRNSGAYYYAWAYDYWGQGTQVTVSS |
| RSV303 | 43 | EVQLVESGGGLVQAGGSLRLSCAASGPTFSADTMGWFRQAPGKEREF<br>VATIPWSGGIAYYSDSVKGRFTMSRDNAKNTVDLQMNSLKPEDTALY<br>YCAGSSRIYIYSDSLSERSYDYWGQGTQVTVSSGGGGSGGGGSGGGG<br>SGGGGSGGGGSEVQLVESGGGLVQAGGSLRLSCEASGRTYSRYGMGW<br>FRQAPGKEREFVAAVSRLSGPRTVYADSVKGRFTISRDNAENTVYLQ<br>MNSLKPEDTAVYTCAAELTNRNSGAYYYAWAYDYWGQGTQVTVSS |
| RSV305 | 44 | EVQLVESGGGLVQPGGSLRLSCAASGLTLDYYALGWFRQAPGKEREG<br>VSCISSSDHSTTYTDSVKGRFTISWDNAKNTLYLQMNSLKPGDTAVY<br>YCAADPALGCYSGSYYPRYDYWGQGTQVTVSSGGGCSGGGGSGGGGS<br>EVQLVESGGGLVQAGDSLRLSCAASGRTFSSYAMGWFRQAPGKEREF<br>VAAISWSDGSTYYADSVKGRFTISRDNAKNTVYLQMNSLKPEDTAVY<br>YCAADLTSTNPGSYIYIWAYDYWGQGTQVIVSS |
| RSV306 | 45 | EVQLVESGGGLVQPGGSLRLSCAASGLTLDYYALGWFRQAPGKEREG<br>VSCISSSDHSTTYTDSVKGRFTISWDNAKNTLYLQMNSLKPGDTAVY<br>YCAADPALGCYSGSYYPRYDYWGQGTQVTVSSGGGGSGGGGSGGGGS<br>EVQLVESGGGLVQAGGSLRLSCAASGRSFSNYVLGWFRQAPGKEREF<br>VAAISFRGDSAIGAPSVEGRFTISRDNAKNTGYLQMNSLVPDDTAVY<br>YCGAGTPLNPGAYIYDWSYDYWGRGTQVTVSS |
| RSV400 | 46 | EVQLVESGGGLVQAGDSLRLSCAASGRTFSSYAMGWFRQAPGKEREFV<br>AAISWSDGSTYYADSVKGRFTISRDNAKNTVYLQMNSLKPEDTAVYYC<br>AADLTSTNPGSYIYIWAYDYWGQGTQVTVSSGGGGSGGGGSGGGGSEV<br>QLVESGGGLVQAGQSLRLSCAASGETESSYANGWFRQAPGKEREFVAA<br>SWSDGSTYILDSVKGRFTISRDNPLKNTVYLQMNSLKPEDTAVYYCAA<br>DLTSTNPGSYIYIWAYDYWGQGTQVTVSSGGGGSGGGGSGGGGSEVQL<br>VESGGGLVQAGDSLRLSCAASGRTESSYAMGWFRQAPGKEREFVAATS<br>WSDGSTYYADSVKGRFTISRDNAKNTVYLQMNSLKPEDTAVYYCAADL<br>TSTNPGSYIYIWAYDYWGQGTQVTVSS |

TABLE A-3-continued

Amino add sequences of multivalent constructs that bind hRSV

| Construct | SEQ ID NO: | Sequence |
|---|---|---|
| RSV401 | 47 | EVQLVESGGGLVQAGDSLRLSCAASGRTFSSYAMGWFRQAPGKEREFV<br>AAISWSDGSTYYADSVKGRFTISRDNAKNTVYLQMNSLKPEDTAVYYC<br>AADLTSTNPGSYIYIWAYDYWGQGTQVTVSSGGGGSGGGGSGGGGSE<br>QLVESGGGLVQAGDSLRLSCAASGRTFSSYAMGWFRQAPGKEREFVAA<br>ISWSDGSTYYADSVKGRFTISRDNAKNTVYLQMNSLKPEDTAVYYCAA<br>DLTSTNPGSYIYIWAYDYWGQGTQVTVSSGGGGSGGGGSGGGGSEVQL<br>VESGGGLVQPGGSLRLSCAASGLTLDYYALGWFRQAPGKEREGVSCIS<br>SSDHSTTYTDSVKGRFTISWDNAKNTLYLQMNSLKPGETAVYYCAADP<br>ALGCYSGSYYPRYDYWGQGTQVTVSS |
| RSV402 | 48 | EVQLVESGGGLVQPGGSLRLSCAASGLTLDYYALGWFRQAPGKEREGV<br>SCISSSDHSTTYTDSVKGRFTISWDNAKNTLYLQMNSLKPGDTAVYYC<br>AADPALGCYSGSYYPRYDYWGQGTQVTVSSGGGGSGGGGSGGGGSEVQ<br>LVESGGGLVQAGDSLRLSCAASGRTFSSYAMGWFRQAPGKEREFVAAI<br>SWSDGSTYYADSVKGRFTISRDNAKNTVYLQMNSLKPEDTAVYYCAAD<br>LTSTNPGSYIYIWAYDYWGQGTQVTVSSGGGGSGGGGSGGGGSEVQLV<br>ESGGGLVQAGDSLRLSCAASGRTFSSYAMGWFRQAPGKEREFVAAISW<br>SDGSTYYADSVKGRFTISRDNAKNTVYLQMNSLKPEDTAVYYCAADLT<br>STNPGSYIYIWAYDYWGQGTQVTVSS |
| RSV403 | 49 | EVQLVESGGGLVQAGDSLRLSCAASGRTFSSYAMGWFRQAPGKEREFV<br>AAISWSDGSTYYADSVKGRFTISRDNAKNTVYLQMNSLKPEDTAVYYC<br>AADLTSTNPGSYIYIWAYDYWGQGTQVTVSSGGGGSGGGGSGGGGSEV<br>QLVESGGGLVQPGGSLRLSCAASGLTLDYYALGWERQAPGKEREGVSC<br>ISSSDHSTTYTDSVKGRFTISWDNAKNTLYLQMNSLKPGDTAVYYCAA<br>DPALGQYSGSYYPRYDYWGQGTQVTVSSGGGGSGGGGSGGGGSEVQLV<br>ESGGGLVQAGDSLRLSCAASGRTESSYAMGWERQAPGKEREFVAAISW<br>SDGSTYYADSVKGRFTISRDNAKNTVYLQMNSLKPEDTAVYYCAADLT<br>STNPGSYIYIWAYDYWGQGTQVTVSS |
| RSV404 | 50 | EVQLVESGGGLVQAGGSLRLSCAASGRSFSNYVLGWFRQAPGKEREFV<br>AAISFRGDSAIGAPSVEGRFTISRDNAKNTGYLQMNSLVPDDTAVYYC<br>GAGTPLNPGAYIYDWSYDYWGRGTQVTVSSGGGGSGGGGSGGGCSEVQ<br>LVESGGGLVQAGGSLRLSCAASGRSFSNYVLGWFRQAPGKEREFVAAI<br>SFRGDSAIGAPSVEGRFTISRDNAKNTGYLQMNSLVPDDTAVYYCGAG<br>TPLNPGAYIYDWSYDYWGRGTQVTVSSGGGGSGGGGSGGGGSEVQLVE<br>SGGGLVQAGGSLRLSCAASGRSFSNYVLGWFRQAPGKEREFVAAISFR<br>GDSAIGAPSVEGRFTISRDNAKNTGYLQMNSLVPDDTAVYYCGAGTPL<br>NPGAYIYDWSYDYWGRGTQVTVSS |
| RSV405 | 51 | EVQLVESGGGLVQAGGSLRISCEASGRTYSRYGMGWFRQAPGKEREFV<br>AAVSRLSGPRTVYADSVKGRFTISRDNAENTVYLQMNSLKPEDTAVYT<br>CAAELTNRNSGAYYYAWAYDYWGQGTQVTVSSGGGGSGGGGSGGGGSE<br>VQLVESGGGLVQAGGSLRLSCEASGRTYSRYGMGWFRQAPGKEREFVA<br>AVSRLSGPRTVYADSVKGRFTISRDNAENTVYLQMNSLKPEDTAVYTC<br>AAELTNRNSGAYYYAWAYDYWGQGTQVTVSSGGGGSGGGGSGGGGSEV<br>QLVESGGGLVQAGGSLRLSCEASGRTYSRYGMGWFRQAPGKEREFVAA<br>VSRLSGPRTVYADSVKGRFTISRDNAENTVYLQMNSLKPEDTAVYTCA<br>AELTNRNSGAYYYAWAYDYWGQGTQVTVSS |
| RSV406 | 52 | EVQLVESGGGLVQPGGSLRLSCAASGRTFSSIAMGWFRQAPGKEREFV<br>AAISWSRGRTFYADSVKGRFIISRDDAANTAYLQMNSLKPEDTAVYYC<br>AVDTASWNSGSFIYDWAYDHWGQGTQVTVSSGGGGSGGGGSGGGGSEV<br>QLVESGGGLVQPGGSLRLSCAASGRTFSSIAMGWFRQAPGKEREFVAA<br>ISWSRGRTFYADSVKGRFIISRDDAANTAYLQMNSLKPEDTAVYYCAV<br>DTASWNSGSFIYDWAYDHWGQGTQVTVSSGGGGSGGGGSGGGGSEVQL<br>VESGGGLVQPGGSLRLSCARSGRTFSSIAMGWERQAPGKEREFVAAIS<br>WSRGRTFYADSVKGRFIISRDDAANTAYLQMNSLKPFDTAVYYCAVDT<br>ASWNSGSFIYDWAYDHWGQGTQVTVSS |
| RSV407 | 53 | EVQLVESGGGLVQAGGSLSISCAASGGSLSNYVLGWFRQAPGKEREFV<br>AAINWRGDITIGPPNVEGRFTISRDNAKNTGYLQMNSLAPDDTAVYYC<br>GAGTPFLNPGAYIYDWSYDYWCRGTQVTVSSGGGSGSGGGGSGGGGSEVQ<br>LVESGGGLVQAGGSLSISCAASGGSLSNYVLGWFRQAPGKEREFVAAI<br>NWRGDITIGPPNVEGRFTISRDNAKNTGYLQMNSLAFDDTAVYYCGAG<br>TPLNPGAYIYDWSYDYWGRGTQVTVSSGGCGSGGGGSGGGGSFVQLVE<br>SGGGLVQAGGSLSISCAASGGSLSNYVLGWFRQAPGKEREFVAAINWR<br>GDITIGPPNVEGRFTISRDNAKNTGYLQMNSLAPDDTAVYYCGAGTPL<br>NPGAYIYDWSYDYWGRGTQVTVSS |
| RSV408 | 54 | EVQLVESGGGLVQAGGSLSISCAASGGSLSNYVLGWFRQAPGKEREFV<br>AAINWRGDITIGPPNVEGRFTISRDNAKNTGYLQMNSLAPDDTAVYYC<br>GAGTPLNPGAYIYDWSYDYWGRGTQVTVSSGGGGSGGGGSGGGGSEVQ<br>GSLSISCAASGGSLSNYVLGWFRQAPGKEREFVAAINWRGDITIGPPN<br>VEGRFTISRDNAKNTGYLQMNSLAPDDTAVYYCGAGTPLNPGAYIYDW |

TABLE A-3-continued

Amino acid sequences of multivalent constructs that bind hRSV

| Construct | SEQ ID NO: | Sequence |
|---|---|---|
| | | SYDYWGRGTQVTVSSAAAEVQLVESGGGLVQAGGSLSISCAASGGSLS NYVLGWFRQAPGKEREFVAAINWRGDITIGPPNVEGRFTISRDNAKNT GYLQMNSLAPDDTAVYYCGAGTPLNPGAYIYDWSYDYWGRGTQVTVSS |
| RSV409 | 55 | EVQLVESGGGLVQAGGSLSISCAASGGSLSNYVEGWFRQAPGKEREFV AAINWRGDITIGPPNVEGRFTISRDNAKNTGYLQMNSLAPDDTAVYYC GAGTPLNPGAYIYDWSYDYWGRGTQVTVSSGGGGSGGGGSEVQLVESGG GLVQAGGSLSISCAASGGSLSNYVLGWFRQAPGKEREFVAAINWRGDI TIGPPNVEGRFTISRDNAKNTGYLQMNSLAPDDTAVYYCGAGTPLNPG AYIYDWSYDYWGRGTQVTVSSGGGGSGGGGSEVQLVESGGGLVQAGGSL SISCAASGGSLSNYVLGWFRQAPGKEREFVRAINWRGDITIGPPNVEG RFTISRDNAKNTGYLQMNSLAPDDTAVYYCGAGTPLNPGAYTYDWSYD YWGRGTQVTVSS |
| RSV410 | 56 | EVQLVESGGGIVQAGGSLSISCAASGGSLSNYVLGWFRQAPGKEREFV AAINWRGDITIGPPNVEGRFTISRDNAKNTGYLQMNSLAPDDTAVYYC GAGTPLNPGAYIYDWSYDYWGRGTQVTVSSGGGGSGGGGSGGGGSGGG GSEVQLVESGGGLVQAGGSLSISCAASGGSLSNYVLCWFRQAPGKERE FVAAINWRCDITIGPPNVEGRFTISRDNAKNTGYLQMNSLAPDDTAVY YCGAGTPLNPGAYIYDWSYDYWGRGTQVTVSSGGGGSGGGGSGGGGSG GGGSEVQLVESGGGLVQAGGSLSISCAASGGSLSNYVLGWFRQAPGKE REFVAAINWRGDITIGPPNVEGRETISRDNAKNTGYLQMNSLAPDDTA VYYCGAGTPLNPGAYIYDWSYDYWGRGTQVTVSS |
| RSV411 | 57 | EVQLVESGGGLVQAGGSLSISCAASGGSLSNYVLGWFRQAPGKEREFVAA INWRGDITIGPPNVEGRFTISRDNAKNTGYLQMNSLAPDDTAVYYCGAGT PLNPGAYTYDWSYDYWGRGTQVTVSSGGGGSGGGGSGOGGSEVQLVESGG GLVQAGGSLSISCAASGGSLSNYVLGWFRQAPGKEREFVAAINWRGDITI GPPNVEGRFTISRDNAKNTGYLQMNSLAPDDTAVYYCGAGTPLNPGAYTI DWSYDYWGRGTQVTVSSGGGGSGSGGSGGGGSEVQLVESGGCLVQPGGSL RLSCAASGLTLDYYALGWFRQAPGKEREGVSCISSSDHSTTYTDSVKGRF TISWDNAKNTLYLQMNSLKPGDTAVYYCAADPALGCYSGSYYPRYDYWGQ GTQVTVSS |
| RSV412 | 58 | EVQLVESGGGLVQPGGSLRLSCAASGLTLDYYALGWFRQAPGKEREGVSC ISSSDHSTTYTDSVKGRFTISWDNAKNTLYLQMNSLKPGDTAVYYCAADP ALGCYSGSYYPRYDYWGQGTQVTVSSGGGGSGGGGSGGGGSEVQLVESGG GLVQAGGSLSISCAASGGSLSNYVLGWFRQAPGKEREFVAAINWRGDITI GPPNVEGRFTISRDNAKNTGYLQMNSLAPDDTAVYYCGAGTPLNPGAYIY DWSYDYWGRGTQVTVSSGGGCSGGGGSGGGGSEVQLVESSGGLVQAGGSL SISCAASGGSLSNYVLGWFRQAPGKEREFVAAINWRGDITIGPPNVEGRF TISRDNAKNTGYLQMNSLAPDDTAVYYCGAGTPLNPGAYIYDWSYDYWGR GTQVTVSS |
| RSV413 | 59 | EVQLVESGGGLVQAGGSLSISCAASGGSLSNYVLGWFRQAPGKEREFVAA INWRGDITIGPPNVEGRFTISRDNAKNTGYLQMNSLAPDDTAVYYCGAGT PLNPGAYIYDWSYDYWGRGTQVTVSSGGGGSGGGGSGGGGSEVQLVESGG GLVQPGGSLRLSCAASGLTLDYYALGWFRQAPGKEREGVSCISSSDHSTT YTDSVKGRFTISWDNAKNTLYLQMNSLKPGDTAVYYCAALPALGCYSGSY YPRYDYWGQGTQVTVSSGGGGSGGGGSGGGGSEVQLVESGGGLVQAGGSL SISCAASGGSLSNYVLGWFRQAPGKEREFVAAINWRGDITIGPPNVEGRF TISRDNAKNTGYLQMNSLAPDDTAVYYCGAGTPLNPGAYIYDWSYDYWGR GTQVTVSS |

TABLE A-4

Sequences of humanized and/or sequence optimized NC41 variants

| Nanobody ® | SEQ ID | Sequence |
|---|---|---|
| NC41v01 | 60 | EVQLLESGGGLVQPGGSLRLSCAASGGSLSNYVLGWFRQAPGKGREFVA AINWRGDITIGPPNVEGRFTISRDNAKNTLYLQMNSLAPEDTAVYYCG TABLE A-4-continued Sequences of humanized and/or sequence optimized NC41 variants

| Nanobody ® | SEQ ID | Sequence |
|---|---|---|
| NC41v04 | 63 | EVQLLESGGGLVQPGGSLSISCAASGGSLSNYVLGWFRQAPGKGREFVA<br>AINWRGDITIGPPNVEGRFTISRDNSKNTLYLQMNSLRPDDTAVYYCGA<br>GTPLNPGAYTYDWSYDYNGQGTLVTVSS |
| NC41v05 | 64 | EVQLLESGGGLVQPGGSLSISCAASGGSLSNYVLGWFRQAPGKGREFVA<br>AINWRGDITIGPPNVEGRFTISRDNSKNTLYLQMNSLAPEDTAVYYCGA<br>GTPLNPGAYIYDWSYDYWGQCTLVTVSS |
| NC41v06 | 65 | EVQLLESGGGLVQPGGSLRLSCAASGGSLSNYVLGWFRQAPGKGREFVA<br>AINWRDDITIGPPNVEGRFTISRDNAKNTLYLQMNSLRPEDTLVYYGGA<br>GTPLNPGAYIYDWSYDYNGQGTLVTVSS |
| NC41v07 | 66 | EVQLLESGGGLVQPGGSLSISCAASGGSLSNYVLGWFRQAPGKGREFVA<br>AINWRGDITIGPPNVEGRFTISRDNAKNTLYLQMNSLAPDDTAVYYCGA<br>GTPLNPGAYIYDWSYDYWCQGTLVTVSS |
| NC41v08 | 67 | EVQLLESGGGLVQPGGSLSISCAASGGSLSNYVLGWFRQAPGKGREFVA<br>AINWRGDITIGPPNVEGRFTISRDNAKNTLYLQMNSLRPEDTAVYYCGA<br>GTPLNPGAYIYDWSYDYWGQGTLVTVSS |
| NC41v09 | 68 | EVQLLESGGGLVQPGGSLSISCAASGGSLSNYVLGWFRQAPGKGREFVA<br>AINWRCDITIGPPNVEGRFTISRDNSKNTLYLQMNSLRPDDTAVYYCGA<br>GTPLNPGAYIYDWSYDYWGQGTLVTVSS |
| NC41v10 | 69 | EVQLLESGGGLVQPGGSLSISCAASGGSLSNYVLGWFRQAPGKGREFVA<br>AINWRGDITIGFPNVEGRFTISRDNAKNTGYLQMNSLAPDDTAVYYCGA<br>GTPLNPGAYIYDWSYDYWGQGTLVTVSS |
| NC47v11 | 70 | EVQLLESGGCLVQAGGSLSISCAASGGSLSNYVLGWFRQAPGKGREFVA<br>AINWRGDITIGPPNVEGRFTISRDNAKNTGYLQMNSLAPDDTAVYYCGA<br>GTPLNPGAYIYDWSYDYWGQGTINTVSS |
| NC41v17 | 71 | EVQLLESGGGLVQPGGSLSISCAASGGSLSNYVLGWFRQAPGKEREFVA<br>AINWRGDITIGPPNVEGRFTISRDNAKNTGYLQMNSLAPDDTAVYYCGA<br>GTPLNPGAYIYDWSYDYWGQGTLVTVSS |
| NC41v13 | 72 | EVQLLESGGGLVQPGGSLRLSCAASGGSLSNYVLGWFRQAPGKGREFVA<br>AINWRGDITIGPPNVEGRFTISRDNAKNTGYLQMNSLAPEDTAVYYCGA<br>GTPLNPCAYIYDWSYDYWGQGTLVTVSS |
| NC41v14 | 73 | EVQLLESGGGLVQPGGSLRLSCAASGGSLSNYVLGWFRQAPGKGREFVA<br>AINWRGDITIGPPNVEGRFTISRDNSKNTLYLQMNSLAPEDTAVYYCGA<br>GTPLNPGAYIYDWSYDYWGQGTLVTVSS |
| NC41v15 | 74 | EVQLLESGGGLVQPGGSLRLSCAASGGSLSNYVLGWFRQAPGKGREFVA<br>AINWRGDITIGPPNVEGRFTISRDNAKNTLYLQMNSLAPEDTAVYYCGA<br>GTPLNPGAYIYDWSYDYWGQGTLVTVSS |
| NC41v17 | 75 | EVQLLESGGGLVQPGGSLRLSCAASGGSLSNYVLGWFRQAPGKGREFVA<br>AINWRGDITIGPPNVEGRFTISRDNSKNTLYLQMNSLRPEDTAVYYCGA<br>GTPLNPGAYIYDWSYDYWGQGTLVTVSS |
| NC41v16 | 76 | EVQLLESGGGLVQPGGSLRLSCAASGGSLSNYVLGWFRQAPGKGREFVA<br>AINWRDDITIGPPNVEGRFTISRDNSKNTLYLQMNSLRPEDTAVYYCGA<br>GTPLNPGAYIYDWSYDYWGQGTLVTVSS |
| NC41v19 | 146 | EVQLVESGGGLVQPGGSLRLSCAASGGSLSNYVLGWFRQAPGKEREFVA<br>AINWRGDITIGPPNVEGRFTISRDNAKNTGYLQMNSLAPDDTAVYYCGA<br>GTPLNPGAYIYDWSYDYWCQGTLVTVSS |
| NC41v20 | 147 | EVQLVESGGGLVQPGGSLRLSCAASGGSLSNYVLGWFRQAPGKEREFVA<br>AINWRGDITIGFPNVEGRFTISRDNAKNTGYLQMNSLRPDDTAVYYCGA<br>GTPLNPGAYIYDWSYDYWCQGTLVTVSS |
| NC41v21 | 148 | EVQLVESGGGLVQPGGSLRLSCAASGGSLSNYVLGWFRQAPGKEREFVA<br>AINWRGDITIGPPNVEGRFTISRDNAKNTGYLQMNSLAPEDTAVYYCGA<br>GTPLNPGAYIYDWSYDYWGQGTLVTVSS |
| NC41v22 | 149 | EVQLVESGGGLVQPGGSLRLSCAASGGSLSNYVLGWFRQAPGKEREFVA<br>AINWRGDITIGPPNVEGRFTISRDNAKNTGYLQMNSLRPEDTAVYYCGA<br>GTPLNPGAYIYDWSYDYWGQGTLVTVSS |
| NC41v23 | 150 | EVQLVESGGGLVQPGGSLRLSCAASGGSLSNYVLGWFRQAPGKEREFVA<br>AINWRGDITIGPPNVEGRFTISRDNAKNTGYLQMNSLRPEDTAVYYCGA<br>GTPLNPGAYIYDWSYDYWGRGTINTVSS |

TABLE A-4-continued

Sequences of humanized and/or sequence optimized NC41 variants

| Nanobody® | SEQ ID | Sequence |
|---|---|---|
| NC41v24 | 151 | EVQLVESGGGLVQPGGSLRLSCAASGGSLSNYVLGWFRQAPGKEREFVA<br>AINWRGDITIGPPNVEGRFTISRDNAKNTGYLQMNSLRPDDTAVYYCGA<br>GTPLNPGAYIYDWSYDYWGRGTLVTVSS |
| NC41v25 | 152 | EVQLVESGGGLVQPGGSLRLSCAASGGSLSNYVLGWFRQAPGKEREFVA<br>AINWRGDITIGPPNVEGRFTISRDNAKNTGYLQMNSLAPEDTAVYYCGA<br>GTPLNPGAYIYDWSYDYWGRGTLVTVSS |
| NC41v26 | 153 | EVQLVESGGGLVQPGGSLRLSCAASGGSLSNYVLGWFRQAPGKEREFVA<br>AINWRGDITIGPPNVEGRFTISRDNAKNTCYLQMNSLRPEDTAVYYCGA<br>GTPLNPGAYIYDWSYDYWGRGTLVTVSS |
| NC41 E1D | 138 | DVQLVESGGGLVQAGGSLSISCAASGGSLSNYVLGWFRQAPGKEREFVL<br>AINWRGDITIGPPNVEGRFTISRDNAKNTGYLQMNSLAPDDTAVYYCGA<br>GTPLNPGAYIYDWSYDYWGRGTQVTVSS |
| NC41v03 E1D | 139 | DVQLLESGGGLVQPGGSLRLSCAASGGSLSNYVLGWFRQAPGKGREFVAA<br>INWRGDITIGPPNVEGRFTISRDNSKNTLYLQMNSLRPEDTAVYYCGAGT<br>PLNPGAYIYDWSYDYWGQGTLVTVSS |
| NC41v06 315 | 140 | DVQLLESGGGLVUGGSLRLSCAASGGSLSNYVLGWFRQAPGKGRETFAAI<br>NWRDDITIGPPNVEGRFTISRDNAKNTLYLQMNSLRPEDTAVYYCGAGTP<br>LNPGAYIYDWSYDYWGQGTLVTVSS |
| NC41v18 315 | 141 | DVQLLESGGGLVQGGSLRLSCAASGGSLSNYVLGWFRQAPGKGREFVAA<br>INWRDDITIGPPNVEGRFTISRDNSKNTLYLWNSLRPEDTAVYYCGAGT<br>PLNPGAYIYDWSYDYWGQGTLVTVSS |
| NC41v17 E1D | 154 | DVQLLESGGGLVQPGGSLRLSCAASGGSLSNYVLGWFRQAPGKGREFVA<br>AINWRGDITIGPPNVEGRETISRDNSKNTLYLQMNSLRPEDTAVYYCGA<br>GTPLNPGAYIYDWSYDYWGQGTLVTVSS |
| NC41v21 E1D | 155 | DVQLVESGGGLVQPGGSLRLSCAASGGSLSNYVLGWFRQAPGKEREFVA<br>AINWRGDITIGFPNVEGRFTISRDNAKNTGYLQMNSLAPEDTAVYYCGA<br>GTPLNPGAYIYDWSYDYTGQGTLVTVSS |
| NC41v22 E1D | 156 | DVQLVESGGGLVQPGGSLRLSCAASGGSLSNYVLGWFRQAPGKEREFVA<br>AINWRGDITIGPPNVEGRFTISRDNAKNTGYLQMNSLRPEDTAVYYCGA<br>GTPLNPGAYIYDWSYDYWGQGTLVTVSS |
| NC41v26 315 | 157 | DVQLVESGGGLVQPGGSLRLSCAASGGSLSNYVLGWFRQAPGKEREFVA<br>AINWRGDITIGPPNVEGRFTISRDNAKNTGYLQMNSLRPEDTAVYYCGA<br>GTPLNPGATIYDWSYDYWGRGIIVTVSS |

TABLE A-5

Amino acid sequence of multivalent humanized and/or sequence optimized constructs that bind hRSV

| Nanobody® | SEQ ID NO | Sequence |
|---|---|---|
| RSV414 | 77 | EVQLLESGGGLVQPGGSLRISCAASGGSLSNYVLGWFRQPPGNGREFVAAI<br>NWRGDITIGPPNVEGRFTISRDNSKNTLYLQMNSLRPEDTAVYYCGAGTPL<br>NPGAYIYDWSYDYWGQGTLVTVSSGGGGSGSGGSGGGSEVQLLESGGGLV<br>QPGGSLRISCAASGGSLSNYVLSWFRQAPGKGREFVAAINWRGDITIGPPN<br>VEGRFTISRDNSKNTLYLQMNSLRPEDTAVYYCGAGTPLNPGAYIYDWSYD<br>YWGQGTLVTVSSGGGGSGGGGSGGGCSEVQLLESGGGLVQPGGSLRISCAA<br>SGGSLSNYVLGWFRQAPGKGREFVAAINWRGDITIGPPNVEGRFTISRDNS<br>KNTLYLQMNSLRPEDTAVYYCGAGTPLNPGAYIYDWSYDYWGQGTLVTVSS |
| RSV426 | 78 | EVQLLESGGGLVQPGGSLRLSCAASGGSLSNYVLGWFRQAPGKGREFVAAI<br>NWRDDITIGPPNVEGRFTISRDNAKNTLYLQMNSLRPEDTAVYYCGAGTPL<br>NPGAYTYDWSYDYWGQGTLVTVSSGGGGSGGGGSGGGSGEVTLLESGGGLV<br>QPGGSLRLSQRRSSCSLSNYVLGWFRQAPGKGREFVAAINWRDDITIGPPN<br>VEGRFTISRDNAKNTLYLQMNSLRPEDTAVYYCGAGTPLNPGAYIYDWSYD<br>YWGQGTLVTVSSGGGGSGGGGSGGGSEVQLLESGGGLVQPGGSLRLSCAA<br>SGGSLSNYVLGWFRQAPGKGREFVAAINWRDDITIGPPNVEGRFTISRDNA<br>KNTLYLQMNSLRPEDTAVYYCGAGTPLNPGAYIYDWSYDYWGQGTLVTVSS |
| RSV427 | 79 | EVQLLESGGGLVQPGGSLRLSCAASGGSLSNYVLGWFRQAPGKGREFVAAI<br>NWRDDITIGPPNVEGRFTISRDNSKNTLYLQMNSLRPEDTAVYYCGAGTPL |

TABLE A-5-continued

Amino acid sequence of multivalent humanized and/or sequence optimized constructs that bind hRSV

| Nanobody ® | SEQ ID NO | Sequence |
|---|---|---|
| | | NPGAYIYDWSYDYWGQGTLVTVSSGGGGSGGGGSGGGGSEVQLLESGGGLV<br>QPGGSLRLSCAASGGSLSNYVLGWFRQAPGKGREFVAAINWRDDITIGPPN<br>VEGRFTISRDNSKNTLYLQMNSLRPEDTAVYYCGAGTPLNPGAYIYDWSYD<br>YWGQGTLVTVSSGGGGSSGGGGSGGGGSEVQLLESGGGLVQPGGSLRLSCAA<br>SGGSLSNYVLSWFRQAPGKGREFVAAINWRDDITIGPPNVEGRFTISRDNS<br>KNTLYLQMNSLRPEDTAVYYCGAGTPLNPGAYIYDWSYDYWGQGTLVTVSS |
| RSV442 | 158 | EVQLLESGGGLVQPGGSLRLSCARSGGSLSNYVLGWFRQAPGKGREFVAAI<br>NWRGDITIGPPNVEGRFTISRDNSKNTLYLQMNSLRFEDTAVYYCGACTPL<br>NPGAYTYDWSYDYWGQGTLVTVSSGGGGSGGGGSGGGGSEVQLLESGGGLV<br>QPGGSLRLSCAASGGSLSNYVLGWFRQAPGKGREFVAAINWRGDITIGPPN<br>VEGRFTISRDNSKNTLYLWINSLRPEDTAVYYCGAGTPLNPGAYIYDWSYD<br>YWGQGTLVTVSSGGGGSGGGGSGGGGSZVQLLESGGGLVQPGGSLRLSCAA<br>SGGSLSNYVLSWFRQAPGKREEVAAINWRGDITIGPPNVEGRFTISRDNS<br>KNTLYLQMNSLRPEDTAVYYCGASTPLNPGAYIYDWSYDYWGQGTLVTVSS |
| RSV436 | 159 | EVQLVESGGGLVQPGGSLRLSCAASGGSLSNYVLGWFRQAPGKEREFVAAI<br>NWRGDITIGPPNVEGRFTISRDNAKNTGYLQMNSLRPDDTAVYYCGAGTPL<br>NPGAYIYDWSYDYWGQGTLVTVSSSGGCSGGGGSGGGGSEVQLVESGGGLV<br>QPGGSLRLSCAASGGSLSNYVLGWFRQAPGKGREFVAAINWRGDITIGPPN<br>VEGRFTISRDNAKNTGYLQMNSLRPDDTAVYYCGAGTPLNPGAYIYDWSYD<br>YWGQGTLVTVSSGGGGSGGGGSGGGGSEVQLLESGGGLVQPGGSLRLSCAA<br>SGGSLSNYVLGWFRQAPGKEREFVAAINWRGDITIGPPNVEGRFTISRDNA<br>KNTGYLQMNSLRPDDTAVYYCGAGTPLNPGAYIYDWSYDYWGQGTLVTVSS |
| RSV438 | 160 | EVQLVESGSGLVQPGGSLRLSCAASGGSLSNYVLGWFRQAPGKEREFVAAI<br>NWRGDITIGPPNVEGRFTISRDNAKNTGYLQMNSLRPEDTAVYYCGAGTPL<br>NPGAYIYDWSYDYWGQGTLVTVSSGGGGSGGGGSGGGGSEVQLVESGGGLV<br>QPGGSLRLSCAASGGSLSNYVLGWFRQAPGKEREFVAAINWRGDITIGPPN<br>VEGRFTISRDNAKNTGYLQMNSLRPEDTAVYYCGAGTYDWSYD<br>YWGQGTLVTVSSGGGGSGGGGSGGGGSEVQLVESGGGLVQPGGSLRLSCAA<br>SGGSLSNYVLGWFRQAPGKERETVAAINWRGDITIGPPNVEGRFTISRDNA<br>KNTGYLQMNSLRPEDTAVYYCGAGTPLNPGAYIYDWSYDYWGQGTLVTVSS |
| RSV439 | 161 | EVQLVESGGGLVQPGGSLRLSCAASGGSLSNYVLGWFRQAPGKEREFVAAINW<br>RGDITIGPPNVEGRFTISRDNSKNTLYLQMNSLRPEDTAVYYCGAGTPLNPGA<br>YIYDWSYDYWGRGTLVTVSSGGGGSGGGGSGGGGSEVQLVESGGGINQPGGSL<br>RLSCAASGGSLSNYVLGWFRQAPGKEREFVAAINWRGDITIGPPNVEGRFTIS<br>RDNAKNTGYLQMNSLRPEDTAVYYCGAGTPLNPGAYIYDWSYDYWGRGTLVTV<br>SSGGGGSGGGGSGGGGSEVQLVESGGGLVQPGGSLRLSCAASGGSLSNYVLGW<br>FRQAPGKEREFVAAINWRGDITIGPPNVEGRFTISRDNAHNTGYLQMNSLRPE<br>DTAVYYCGAGTPLNPGAYIYDWSYDYWGRGTLVTVSS |
| RSV434 | 142 | DVQLVESGGCLVQAGGSLSISCAASGGSLSNYVLGWFRQAPGKEREFVAAINW<br>RGDTTIGFPNVEGRFTISRDNAKNTGYLQMNSLAEDDTAVYYCGAGTPLNPGA<br>YIYDWSYDYWGRCTQVTVSSGGGGSGGGGSOGGCSEVQLVESGGGLVQAGGSL<br>SISCAASGGSLSNYVLGWFRQAPGHEREFVAAINWRGDITIGPPNVEGRFTIS<br>RDNAKNTGYLWINSLAPDDTAVYYCGAGTPLNPGAYIYDWSYDYWORGTQVTV<br>SSGGGGSGGGGSGGGGSEVQLVESGGGLVQAGGSLSISCAASGGSLSNYVLGW<br>FRQAPGKEREFVAAINWRGDITIGPPNVEGRFTISRDNAKNTGYLQMNSLAPD<br>DTAVYYCGAGTPLNPGLYIYDWSYDYWGRGTQVTVSS |
| RSV443 | 143 | DVQLLESGGGLVQPGGSLRISCAASGGSLSNYVLGWFRQAPGKGREFVAAINW<br>RGDITIGPPNVEGRFTISRDNSKNTLYLQMNSLRPEDTAVYYCGAGTPLNPGA<br>YIYDWSYDYWGQGTLVTVSSGGGGSGGGGSGGGGSEVQLLESGGGLVQPGGSL<br>RISCAASGGSLSNYVLGWFRQAPGKGREFVAAINWRGDITIGPPNVEGRFTIS<br>RDNSKNTLYLQMNSLRPEDTLVYYCGAGTPLNPGAYTYDWSYDYWGQGTLVTV<br>SSGGGGSGGGGSGGGGSEVQLLESGGGLVQPGGSLRISCAASGGSLSNYVLGW<br>FRQAPGKGREFVAAINWRGDITIGPPNVEGRFTISRDNSKNTLYLQMNSLRPE<br>DTAVYYCGAGTPLNPGAYIYDWSYDYWGQTTNTVSS |
| RSV444 | 144 | DVQLLESGGGLVQPGGSLRLSCAASGGSLSNYVLGWFRQAPGKGREFVAAINW<br>RDDITIGPPNVEGRFTISRDNAKNTLYLQMNSLRPEDTAVYYCGAGTPLNPGA<br>YIYDWSYDYWGQGTLVTVSSGGGGSGGGGSGGGCSEVQLLESGGGLVQPGGSL<br>RLSCAASGGSLSNYVLGWFRQAPGKGREFVRAINWRDDITIGPPNVEGRFTIS<br>RDNAKNTLYLQMNSLRPEDTAVYYCGAGTPLNPGAYTYDWSYDYWGQGTLVTV<br>SSGGGGSGGGGSGGGGSEVQLLESGGGLVQPGGSLRLSCAASGGSLSNYVLGW<br>FRQAPGKGREFVAAINWRDDITIGPPNVEGRFTISRDNAKNTLYLQMNSLRPE<br>DTAVYYCGAGTPLNPGAYIYDWSYDYWGQGTLVTVSS |
| RSV445 | 145 | DVQLLESGGGLVQPGGSLRLSCAASGGSLSNYVLGWFRQAPGKGREFVAAINW<br>RDDITIGPPNVEGRFTTSRDNSKNTLYLQMNSLRPEDTAVYYCGAGTPLNPGA<br>YIYDWSYDYWGQGTLVTVSSGGGCSGGGGSGGGGSEVQLLESGGGLVQPGGSL<br>RLSCAASGGSLSNYVLGWFRQAPGKGREFVAAINWRDDITIGPPNVEGRFTIS |

TABLE A-5-continued

Amino acid sequence of multivalent humanized and/or sequence optimized constructs that bind hRSV

| Nanobody® | SEQ ID NO | Sequence |
|---|---|---|
| | | RDNSKNTLYLQMNSLRPEDTAVYYCGAGTPLNPGA TABLE A-6-continued Preferred combinations of CDR sequences

| Nanobody | SEQ ID | FR1 | SEQ ID | CDR1 | SEQ ID | FR2 | SEQ ID | CDR2 |
|---|---|---|---|---|---|---|---|---|
| NC41v08 | 67 | evqllesggglvqpggslsiscaasggsls | 88 | NYVLG | 98 | wfrqapgkgrefva | 100 | AINWRGDITIGPPNVEG |
| NC41v09 | 68 | evqllesggglvqpggslsiscaasggsls | 89 | NYVLG | 98 | wfrqapgkgrefva | 100 | AINWRGDITIGPPNVEG |
| WC41v10 | 69 | evqllesgqglvqpggslsiscaasggsls | 90 | NYVLG | 98 | wfrqapgkgrefva | 100 | AINWRGDITIGPPNVEG |
| NC41v11 | 70 | evqllesqggavgaggslsiscaasggsls | 91 | NYVLG | 98 | wfrqapgkgrefva | 100 | AINWRGDITTGPPNVEG |
| NC41v12 | 71 | evqllesggglvqpggslsiscaasggsls | 92 | NYVLG | 98 | wfrqapgkgrefva | 99 | AINWRGDITTGPPNVEG |
| NC41v13 | 72 | evqllesggglvqpggslrlscaasggsls | 93 | NYVLG | 98 | wfrqapgkgrefva | 100 | AINWRGDIT1GPPNVEG |
| NC41v14 | 73 | evqllesggglvqpggslrlscaasggsls | 94 | NYVLG | 98 | wfrqapgkgrefva | 100 | AINWRGDITTGPPNVEG |
| NC41v15 | 74 | evqllesgqglvgaggslrlscaasggsls | 95 | NYVLG | 98 | wfrqapgkgrefva | 100 | AINWRGDITTGPPNVEG |
| NC41v17 | 75 | evqllesggglvqpggslrlscaasggsls | 96 | NYVLG | 98 | wfrqapgkgrefva | 100 | AINWRGDITTGPPNVEG |
| NC41v18 | 76 | evqllesggglvqpggslrlscaasggsls | 97 | NYVLG | 98 | wfrqapgkgrefva | 100 | AINWRDDITIGPPNVEG |
| NC41v19 | 146 | EVQLVESGGGLVQPGGSLRLSCAASGGSLS | 166 | NYVLG | 98 | WFRQAPGKEREFVA | 99 | AINWRGDITIGPPNVEG |
| NC41v20 | 147 | EVQINESGGGLVQPGGSLRLSCAASGGSLS | 166 | NYVLG | 98 | WFRQAPGKEREFVA | 99 | AINWRGDITIGPPNVEG |
| NC41v21 | 148 | EVQLVESGGGLVQPGGSLRLSCAASGGSLS | 166 | NYVLG | 98 | WFPQAPGNEREDIA | 99 | AINWRGDITIGPPNVEG |
| NC41v22 | 149 | EVQLVESGGGLVQPGGSLRLSCAASCGSLS | 166 | NYVLG | 98 | WFRQAPGKEREFVA | 99 | AINWRGDITIGPPNVEG |
| NC41v23 | 150 | EVQLVESGGGLVQPGGSLRLSCAASGGSLS | 166 | NYVLG | 98 | WFRQAPGKEREFVA | 99 | AINPRGDITIGPPNVEG |
| NC41v24 | 151 | EVQLVESGGGLVQPGGSLRLSCAASGGSLS | 166 | NYVLG | 98 | WFRQAPGNEREFVA | 99 | AINWRGDITIGPPNVEG |
| NC41v25 | 152 | EVQLVESGGGLVQPGGSLRLSCAASGGSLS | 166 | NYVLG | 98 | WFRQAPGNEREEVA | 99 | AINWRGDITIGPPNVEG |
| NC41v26 | 153 | EVQLVESGGGLVQPGGSLRLSCAASGGSLS | 166 | NYVLG | 98 | WFRQAPGKEREFVA | 99 | AINWRGDITIGPPNVEG |

| Nanobody ® | SEQ ID | FR3 | SEQ ID | CDR 3 | SEQ ID | FR4 | SEQ ID |
|---|---|---|---|---|---|---|---|
| NC41 | 101 | RFTISRDNAKNTGYLQMNSLAPDDTAVYYCGA | 103 | GTPLNPGAYIYDWSYDY | 121 | WGRGTDVTVSS | 122 |
| NC41v01 | 101 | rftisrdnakntlylqmnslapedtavyycga | 104 | GTPLNPGAYIYDWSYDY | 121 | wgggtlvtvss | 123 |
| NC41v02 | 101 | rftisrdnskntlylqmnslapedtavyycga | 105 | GTPLNPGAYIYDWSYDY | 121 | wgqgtlvtvss | 123 |
| NC41v03 | 101 | rftisrdnskntlyiqmpslrpedtavyycga | 106 | GTPLNPGAYIYDWSYDY | 121 | wgqgtlvtvss | 123 |
| NC41v04 | 101 | rftisrdnskntlylqmnslrpddtavyycga | 107 | GTPLNPGAYIYDWSYDY | 121 | wgqgtlvtvss | 123 |
| NC41v05 | 101 | rftisrdnskntlylqmnslapedtavyycga | 108 | GTPLNPGAYIYDWSYDY | 121 | wgqgtlvtvss | 123 |
| NC41v06 | 102 | rftisrdnakntlylqmnsirpedtavyycga | 109 | GTPLNPGAYIYDWSYDY | 121 | wgqgtlvtvss | 123 |

TABLE A-6-continued

Preferred combinations of CDR sequences

| | | | | | | | |
|---|---|---|---|---|---|---|---|
| NC41v07 | 101 | rftisrdnakntlylq mnslapddtavyycga | 110 | GTPLNPGAYI YDWSYDY | 121 | wgggtlvtvss | 123 |
| NC41v08 | 101 | rftisrdnakntlylq mnslrpedtavyycga | 111 | GTPLNPGAYI YDWSYDY | 121 | wgqgtlvtvss | 123 |
| NC41v09 | 10 | rftisrdnskntlylq mnslrpddtavyycga | 112 | GTPLNPGAYI YDWSYDY | 121 | wgqgtlvtvss | 123 |
| WC41v10 | 101 | rftisrdnakntgylq mnslapddtavyycga | 113 | GTPLNPGAYI YDWSYDY | 121 | wgqgtlvtvss | 123 |
| NC41v11 | 101 | rftisrdnakntgylq mnslapddtavyycga | 114 | GTPLNPGAYI YDWSYDY | 121 | wgqgtlvtvss | 123 |
| NC41v12 | 101 | rftisrdnakntgylq mnslapddtavyycga | 115 | GTPLPPGAYT YDWSYDY | 121 | wgqgtlvtvss | 123 |
| NC41v13 | 101 | rftisrdnakntgylq mnslapedtavyycga | 116 | GTPLNPGAYI YDWSYDY | 121 | wgqgtlvtvss | 123 |
| 8C41v14 | 101 | rftisrdnskntlylq mnslapedtavyycga | 117 | GTPENPGAYI YDWSYDY | 121 | wgqgtlvtvss | 123 |
| NC41v15 | 101 | rftisrdnakntlylq mnslapedtavyycga | 118 | GTPLNPGAYI YDWSYDY | 121 | wgggtlvtvss | 123 |
| NC41v17 | 101 | rftisrdnskntlylq mnslrpedtavyycga | 119 | GTPLNPGAYI YDWSYDY | 121 | wgggtlvtvss | 123 |
| NC41v18 | 102 | rftisrdnskntlylq mnslrpedtavyycga | 120 | GTPLNPGAYI YDWSYDY | 121 | wgqgtlvtvss | 123 |
| NC41v19 | 101 | RFTISPDNAKETGYLQ MNSLAPDDTAVYYCGA | 103 | GTPLNPGAYI YDWSYDY | 121 | WGQGTLVTVSS | 123 |
| NC41v20 | 101 | RFTISRDNAKNTGYLQ MNSLRPDDTAVYYCGA | 167 | GTPIMPGAYI YDWSYDY | 121 | WGQGTLVTVSS | 123 |
| NC41v21 | 101 | RFTISRDNAKNTGYLQ MNSLAPEDTAVYYCGA | 116 | GTPLNPGAYI YDWSYDY | 121 | WGQGTLVTVSS | 123 |
| NC41v22 | 101 | RFTISPDNAKNTGYLQ MNSLRPEDTAVYYCGA | 166 | GTPLNPGAYI YDWSYDY | 121 | WGQGTLVTVSS | 123 |
| NC41v23 | 101 | RFTISPDNAKNTGYLQ MNSLAPDDTAVYYCGA | 103 | GTPLNPGAYI YDWSYDY | 121 | WGRGTLVTVSS | 169 |
| NC41v24 | 101 | RFTISRDNAKNTGYLQ MNSLPPDDTAVYYCGA | 167 | GTPLNPGAYI YDWSYDY | 121 | WGRGTLVTVSS | 169 |
| NC41v25 | 101 | RFTISRDNAKNTGYLQ MNSLAPEDTAVYYCGA | 116 | GTPLNPGAYI YDWSYDY | 121 | WGRGTLVTVSS | 169 |
| NC41v26 | 101 | RFTISPDNAKNTGYLQ MNSLRPEDTAVYYCGA | 168 | GTPLNPGAYI YDWSYDY | 121 | WGRGTLVTVSS | 169 |

TABLE A-7

Linker sequences

| Linker | SEQ ID NO: | Sequences |
|---|---|---|
| SGS | 124 | GGGGS |
| 7GS | 125 | SGGSGGS |
| 9GS | 126 | GGGGSGGGS |
| 10GS | 127 | GGGGSGGGGS |
| 15GS | 128 | GGGGSGGGGSGGGGS |
| 18GS | 129 | GGGGSGGGGSGGGGGGS |

TABLE A-7-continued

Linker sequences

| Linker | SEQ ID NO | Sequences |
|---|---|---|
| 20GS | 130 | GGGGSGGGGSGGGGSGGGGS |
| 25GS | 131 | GGGGSGGGGSGGGGSGGGGSGGGGS |
| 30GS | 132 | GGGGSGGGGSGGGGSGGGGSGGGGSGGGGS |
| 35GS | 133 | GGGGSGGGGSGGGGSGGGGSGGGGSGGGGSGGGCS |
| G1 hinge | 134 | EPKSCDKTHTCPPCP |
| 9GS-G1 hinge | 135 | GGGGSGGGSEPKSCDKTHTCPPCP |
| G3 hinge | 136 | ELKTPLGDTTHTCPRCPEPKSCDTPPPCPRCPEPKSCDTPPPCPRCP EPKSCDTPPPCPRCP |
| 3Ala | 137 | AAA |

TABLE B-1

Characteristics of Nanobodies ® that bind hRSV F-protein

| Clone | Family | Epitope | Binding hRSV EC50 | Competition Synagis ® Fab EC50 | kinetic analysis | | | RSV neutralization IC50 (nM)(n = 2) | | |
|---|---|---|---|---|---|---|---|---|---|---|
| | | | | | ka (1/Ms) | kd (1/s) | KD | Long | A-2 | B1 |
| 191D3 | LG 3sub2 | II | 1.5E−10 | 5.9E−09 | 1.5E+06 | 2.8E−03 | 1.9E−09 | 253 | 227 | — |
| 1E4 | LG 3sub2 | II | 6.6E−11 | 4.5E−09 | 8.0E+05 | 1.3E−03 | 1.6E−09 | 380 | 298 | ND |
| 7B2 | 16 | II | 9.0E−11 | 1.9E−09 | 5.7E+05 | 6.5E−04 | 1.1E−09 | 91 | 177 | 2690 |
| NC23 | 34 | II | 1.0E−10 | 2.3E−09 | 8.0E+05 | 7.4E−04 | 9.2E−10 | 144 | 109 | — |
| 15H8 | 29 | II | 8.3E−10 | 3.9E−08 | 1.2E+06 | 2.1E−02 | 1.6E−08 | 200 | 218 | 2340 |
| NC41 | 29 | II | 4.1E−10 | 3.2E−08 | 8.2E+05 | 6.7E−03 | 8.1E−09 | 58 | 26 | 4000 |
| 15B3 | 4sub1 | IV-VI | 5.8E−11 | — | 4.1E+05 | 2.7E−04 | 6.7E−10 | — | — | 1274 |
| 191E4 | LG 21 | IV-VI | 8.3E−11 | — | 5.7E+05 | 1.5E−04 | 2.7E−10 | — | — | 4327 |
| Synagis ® | | II | | | 2.8E+05 | 1.8E−04 | 6.4E−10 | 4 | 2.5 | 1.7 |

TABLE B-2

Nomenclature for multivalent Nanobody ® constructs directed against hRSV F-protein

| Type | Name | Construct | SEQ ID NO |
|---|---|---|---|
| Bivalent | RSV101 | 191D3-15GS-191D3 | 20 |
| | RSV102 | 191D3-25GS-191D3 | 21 |
| | RSV103 | 191D3-35GS-191D3 | 22 |
| | RSV104 | 191D3-9GS-191D3 | 23 |
| | RSV105 | 7B2-9GS-7B2 | 24 |
| | RSV106 | 7B2-15GS-7B2 | 25 |
| | RSV107 | 15H8-9GS-15H8 | 26 |
| | RSV108 | 15H8-15GS-15H8 | 27 |
| | RSV109 | NC23-9GS-NC23 | 28 |
| | RSV110 | NC23-15GS-NC23 | 29 |
| | RSV113 | 15B3-15GS-15B3 | 30 |
| | RSV114 | NC39-20GS-NC39 | 31 |
| | RSV115 | 191E4-18GS-191E4 | 32 |
| | RSV116 | NC41-15GS-NC41 | 33 |
| Biparatope | RSV201 | 191D3-9GS-191E4 | 34 |
| | RSV202 | 191D3-15GS-191E4 | 35 |
| | RSV203 | 191D3-25GS-191E4 | 36 |
| | RSV204 | 7B2-15GS-15H8 | 37 |
| | RSV205 | 7B2-15GS-15B3 | 38 |
| | RSV206 | 15H8-15GS-15B3 | 39 |
| | RSV207 | 15H8-15GS-7B2 | 40 |
| | RSV301 | 191E4-9GS-191D3 | 41 |
| | RSV302 | 191E4-15GS-191D3 | 42 |
| | RSV303 | 191E4-25GS-191D3 | 43 |
| | RSV305 | 15B3-15GS-7B2 | 44 |
| | RSV306 | 15B3-15GS-15H8 | 45 |
| Trivalent | RSV400 | 7B2-15GS-7B2-15GS-7B2 | 46 |
| | RSV401 | 7B2-15GS-7B2-15GS-15B3 | 47 |
| | RSV402 | 15B3-15GS-7B2-15GS-7B2 | 48 |
| | RSV403 | 7B2-15GS-15B3-15GS-7B2 | 49 |
| | RSV404 | 15H8-15GS-15H8-15GS-15H8 | 50 |
| | RSV405 | 191D3-15GS-191D3-15GS-191D3 | 51 |
| | RSV406 | NC23-15GS-NC23-15GS-NC23 | 52 |
| | RSV407 | NC41-15GS-NC41-15GS-NC41 | 53 |
| | RSV408 | NC41-AAA-NC41-AAA-NC41 | 54 |
| | RSV409 | NC41-9GS-NC41-9GS-NC41 | 55 |
| | RSV410 | NC41-20GS-NC41-20GS-NC41 | 56 |
| | RSV411 | NC41-15GS-NC41-15GS-15B3 | 57 |
| | RSV412 | 15B3-15GS-NC41-15GS-NC41 | 58 |
| | RSV413 | NC41-15GS-15B3-15GS-NC41 | 59 |

TABLE B-3

Reactivity of monovalent Nanbodies® with antigen extracts of HEp-2 cells infected with different escape mutants of the Long strain

| Nanobody® | R47F/4 | R47F/7 | RAK13/4 | R7C2/11 | R7C2/1 | R7.936/1 | R7.936/4 | R7.936/6 | R9.432/1 | RRA3 |
|---|---|---|---|---|---|---|---|---|---|---|
| 192C4 | | | | | | ■ | ■ | ■ | ■ | |
| 191D3 | | ▨ | | | | ■ | ■ | ■ | ■ | |
| 191E4 | ■ | ■ | ■ | ■ | ■ | ▨ | ▨ | ▨ | ■ | |
| 192F2 | | | | | | ■ | ■ | ■ | ■ | |
| 191C7 | ■ | ■ | ■ | ■ | ■ | ■ | ■ | ■ | ■ | ■ |
| 15B3 | ■ | ■ | ■ | ■ | ■ | ■ | | ▨ | ■ | |
| NC23 | | ■ | | ▨ | | ■ | ■ | ■ | ■ | |
| 15H8 | | | | | | ■ | ■ | ■ | ■ | |
| 7B2 | | ▨ | | | | ■ | ■ | ■ | ■ | |
| NC41 | | ▨ | | | | ■ | ■ | ■ | ■ | |
| aa substitution | N262Y | N268I | N216D/N262Y | K272T | K272E | V447A | K433T | K432T | S436F | N262Y/R429S |

TABLE B-4

Reactivity of monovalent and bivalent Nanobodies® with antigen extracts of HEp-2 cells infected with different escape mutants of the Long strain

| Nanobody® | R7C2/11 | R7C2/1 | R7.936/4 |
|---|---|---|---|
| 7B2 | | | ■ |
| RSV106: 7B2-7B2 | ▨ | | ■ |
| RSV400: 7B2-7B2-7B2 | ■ | | |
| RSV403: 7B2-15B3-7B2 | | | |
| 15B3 | ■ | | |
| RSV113: 15B3-15B3 | ■ | | ▨ |
| 191D3 | | | ■ |
| RSV101: 191D3-191D3 | | | ■ |
| 15H8 | | | ■ |
| RSV108: 15H8-15H8 | ▨ | | ■ |
| NC23 | | | ■ |
| RSV110: NC23-NC23 | ▨ | | ■ |
| 191E4 | ■ | ■ | ■ |
| aa substitution | K272T | K272E | K433T |

TABLE B-5

Neutralization and kinetic binding parameters in Biacore on $F_{tm}$-NN protein for selected NC41 variants

| | Neutralization IC50 (nM) | | | | Biacore ($F_{tm}$-NN) | | |
|---|---|---|---|---|---|---|---|
| Name | Long | B-1 | Long | B-1 | ka (1/Ms) | kd (1/s) | KD (M) |
| NC41 | 202 | 4707 | 122 | 3291 | 1.7E+06 | 6.70E−03 | 4.00E−09 |
| NC41v03 | 255 | 1507 | nd | nd | nd | nd | nd |

TABLE B-5-continued

Neutralization and kinetic binding parameters in Biacore on $F_{tm}$-NN protein for selected NC41 variants

| Name | Neutralization IC50 (nM) | | | | Biacore ($F_{tm}$NN) | | |
|---|---|---|---|---|---|---|---|
| | Long | B-1 | Long | B-1 | ka (1/Ms) | kd (1/s) | KD (M) |
| NC41v06 | 111 | 806 | nd | nd | 2.0E+06 | 4.80E−03 | 2.50E−09 |
| NC41v17 | 249 | 677 | 149 | 346 | 1.9E+06 | 5.90E−03 | 3.20E−09 |
| NC41v18 | 116 | 728 | 98 | 194 | nd | nd | nd |
| Synagis | 7.3 | 2.1 | 6.0 | 2.9 | | | |

TABLE B-6

Trivalent humanized and/or sequence optimized variants of NC41

| Name | Construct | SEQ ID NO |
|---|---|---|
| RSV414 | NC41v03-15GS-NC41v03-15GS-NC41v03 | 77 |
| RSV426 | NC41v06-15GS-NC41v06-15GS-NC41v06 | 78 |
| RSV427 | NC41v18-15GS-NC41v18-15GS-NC41v18 | 79 |
| RSV434 | NC41$^{E1D}$-15GS-NC41-15GS-NC41 | 142 |
| RSV435 | NC41v17$^{E1D}$-15GS-NC41v17-15GS-NC41v17 | 162 |
| RSV436 | NC41v20-15GS-NC41v20-15GS-NC41v20 | 159 |
| RSV437 | NC41v20$^{E1D}$-15GS-NC41v20-15GS-NC41v20 | 163 |
| RSV438 | NC41v22-15GS-NC41v22-15GS-NC41v22 | 160 |
| RSV439 | NC41v26-15GS-NC41v26-15GS-NC41v26 | 161 |
| RSV440 | NC41v26$^{E1D}$-15GS-NC41v26-15GS-NC41v26 | 165 |
| RSV441 | NC41v22$^{E1D}$-15GS-NC41v22-15GS-NC41v22 | 164 |
| RSV442 | NC41v17-15GS-NC41v17-15GS-NC41v17 | 158 |
| RSV443 | NC41v03$^{E1D}$-15GS-NC41v03-15GS-NC41v03 | 143 |
| RSV444 | NC41v06$^{E1D}$-15GS-NC41v06-15GS-NC41v06 | 144 |
| RSV445 | NC41v18$^{E1D}$-15GS-NC41v18-15GS-NC41v18 | 145 |

TABLE B-7

Neutralization of Long and B-1 by trivalent NC41 variants

| ID | Trivalent | Long | | B-1 | |
|---|---|---|---|---|---|
| | | IC50 [M] | Ratio to Synagis | IC50 [M] | Ratio to Synagis |
| Experimental Series 1 | | | | | |
| RSV407 | NC41 | 9.41E−11 | 59 | 6.6E−10 | 3 |
| RSV414 | NC41v03 | 7.81E−11 | 72 | 1.61E−10 | 11 |
| RSV426 | NC41v06 | 8.98E−11 | 63 | 9.32E−11 | 20 |
| RSV427 | NC41v18 | 9.13E−11 | 62 | 4.61E−11 | 40 |
| Experimental Series 2 | | | | | |
| RSV407 | NC41 | 13.06E−11 | 111 | 51E−11 | 11 |
| RSV434 | NC41 (E1D) | 15E−11 | 107 | 56E−11 | 9 |
| RSV441 | NC41v22 (E1D) | 7.94$^E$−11 | 209 | | |

TABLE B-9

Overview table of all cotton rat experiments performed showing both the detection of replication competent virus and viral RNA at day 4 post inoculation (in experiment 3 detection at day 7 was also performed)

| | Nanobody dose | Treatment regimen | Viral load difference versus control ($\log_{10}$ pfu) | Fold reduction viral RNA ($2^{\Delta CT}$) |
|---|---|---|---|---|
| Exp 1 RSV407 | 5 mg/kg | Prophylactic day −1 | −2.59* | 286.7* |
| | | Therapeutic day +1, 2, +3 | −2.88* | 4.4* |
| | | Therapeutic day +2, +3 | −2.83* | 4.6* |
| Exp 2 RSV407 | 5 mg/kg | Prophylactic day −1 | −3.01* | 79.2* |
| | 1 mg/kg | | −2.37* | 61.3* |
| | 0.2 mg/kg | | −1.43* | 28.1* |
| | 0.04 mg/kg | | −0.37 | 11.7* |
| Exp 3 RSV407 | 5 mg/kg | Therapeutic day +1 | −2.04* | 2.9* |
| | | (Read out at day 7) | (0.63*) | (1.8) |
| | | Therapeutic day +1, +2 | −2.47* | 2.5* |
| | | (Read out at day 7) | (0.57) | (4.5*) |
| Exp 4 RVS407 | 0.2 mg/kg | Prophylactic day −1 | −0.75* | 29.8* |
| RSV503 | 1 mg/kg | | −1.27* | 31.4* |
| | 0.2 mg/kg | | −0.71* | 30.4* |
| | 0.04 mg/kg | | −0.22* | 15.5* |
| Exp 5 RSV434 | 20 mg/kg | Therapeutic day +2, +3 | −2.89* | 10.2* |
| | 4 mg/kg | | −1.76* | 1.9 |
| | 2 mg/kg | | −1.81* | 5.5* |
| | 1 mg/kg | | −1.66* | 3.9* |
| Exp 6 RSV434 | 5 mg/ml | Therapeutic day +2, +3 | −3.15* | 10* |
| | 20 mg/ml | | −2.64* | 2.4* |
| | 80 mg/ml | | −3.30* | 4.3* |

*$p < 0.05$

TABLE B-8

Neutralization capacity of RSV434 and Synagis in plaque assay against various clinical isolates

| RSV group | Number with 100-fold reduction or greater (%) | | Comparison between study drugs P value | Number with complete virus inhibition (%) | | Comparison between study drugs P value |
|---|---|---|---|---|---|---|
| | Synagis | RSV434 | | Synagis | RSV434 | |
| RSV/A | 27/31 (87.1%) | 31/31 (100%) | 0.11 | 1/31 (3.2%) | 29/31 (93.5%) | <0.0001 |
| RSV/B | 26/30 (86.7%) | 28/30 (93.3%) | 0.67 | 11/30 (36.7%) | 22/30 (73.3%) | 0.009 |
| Total | 53/61 (86.9%) | 59/61 (96.7%) | 0.09 | 12/61 (19.7) | 51/61 (83.6%) | <0.0001 |

The invention claimed is:

1. A polypeptide consisting of an amino acid sequence comprising or consisting of SEQ ID NO:142.

2. A composition, comprising the polypeptide according to claim 1.

3. The composition according to claim 2, wherein the composition is a pharmaceutical composition.

4. The pharmaceutical composition according to claim 3, wherein the pharmaceutical composition comprises a carrier suitable for pulmonary delivery.

5. A method for the treatment of hRSV infection, said method comprising administering to a subject in need thereof a pharmaceutically effective amount of the polypeptide according to claim 1.

6. The method of claim 5, wherein the hRSV infection is a lower respiratory tract infection.

7. A pharmaceutical device suitable for the pulmonary delivery of a polypeptide, wherein the pharmaceutical device comprises the polypeptide according to claim 1.

8. The pharmaceutical device according to claim 7, wherein the pharmaceutical device is a nebulizer.

* * * * *

SEQUENCE LISTING

<160> NUMBER OF SEQ ID NOS: 169

<210> SEQ ID NO 1
<211> LENGTH: 128
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Phe Ser Ser Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Gly Pro Arg Thr Val Tyr Ala Asp Ser
    50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Pro Gly Ala Tyr Tyr Tyr Thr
            100                 105                 110

Trp Ala Tyr Asp Tyr Trp Gly Gln Gly Thr Gln Val Thr Val Ser Ser
        115                 120                 125

<210> SEQ ID NO 2
<211> LENGTH: 127
<212> TYPE: PRT
<213> ORGANISM: Artificial Sequence
<220> FEATURE:
<223> OTHER INFORMATION: Nanobody sequence

<400> SEQUENCE: 2

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser
        115                 120                 125

<210> SEQ ID NO 3
<211> LENGTH: 127
<212> TYPE: PRT
<213> ORGANISM: Artificial Sequence
<220> FEATURE:
<223> OTHER INFORMATION: Nanobody sequence -continued

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Ala Met Gly Trp Phe Arg Gln Ala Pro Gly Lys Glu Arg Glu Phe Val
        35                  40                  45

Ala Ala Ile Ser Trp Ser Arg Gly Arg Thr Phe Tyr Ala Asp Ser Val
    50                  55                  60

Lys Gly Arg Phe Ile Ile Ser Arg Asp Asp Ala Ala Asn Thr Ala Tyr
65                  70                  75                  80

Leu Gln Met Asn Ser Leu Lys Pro Glu Asp Thr Ala Val Tyr Tyr Cys
                85                  90                  95

Ala Val Asp Thr Ala Ser Trp Asn Ser Gly Ser Phe Ile Tyr Asp Trp
            100                 105                 110

Ala Tyr Asp His Trp Gly Gln Gly Thr Gln Val Thr Val Ser Ser
        115                 120                 125
```

<210> SEQ ID NO 4
<211> LENGTH: 126
<212> TYPE: PRT
<213> ORGANISM: Artificial Sequence
<220> FEATURE:
<223> OTHER INFORMATION: Nanobody sequence

<400> SEQUENCE: 4

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Asn Tyr
            20                  25                  30

Val Leu Gly Trp Phe Arg Gln Ala Pro Gly Lys Glu Arg Glu Phe Val
        35                  40                  45

Ala Ala Ile Ser Phe Arg Gly Asp Ser Ala Ile Gly Ala Pro Ser Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Val Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser
        115                 120                 125
```

<210> SEQ ID NO 5
<211> LENGTH: 126
<212> TYPE: PRT
<213> ORGANISM: Artificial Sequence
<220> FEATURE:
<223> OTHER INFORMATION: Nanobody sequence

<400> SEQUENCE: 5

```
Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45
```

-continued

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Arg Gly Thr Gln Val Thr Val Ser Ser
                115                 120                 125

<210> SEQ ID NO 6
<211> LENGTH: 121
<212> TYPE: PRT
<213> ORGANISM: Artificial Sequence
<220> FEATURE:
<223> OTHER INFORMATION: Nanobody sequence

<400> SEQUENCE: 6

Glu Val Gln Leu Val Glu Ser Gly Gly Gly Trp Val Gln Ala Gly Gly
1               5                   10                  15

Ser Leu Arg Leu Ser Cys Ala Ala Ser Gly Arg Ala Phe Ser Ser Tyr
                20                  25                  30

Ala Met Gly Trp Ile Arg Gln Ala Pro Gly Lys Glu Arg Glu Phe Val
            35                  40                  45

Ala Gly Ile Asp Gln Ser Gly Glu Ser Thr Ala Tyr Gly Ala Ser Ala
        50                  55                  60

Ser Gly Arg Phe Ile Ile Ser Arg Asp Asn Ala Lys Asn Thr Val His
65                  70                  75                  80

Leu Leu Met Asn Ser Leu Gln Ser Asp Asp Thr Ala Val Tyr Tyr Cys
                85                  90                  95

Val Ala Asp Gly Val Leu Ala Thr Thr Leu Asn Trp Asp Tyr Trp Gly
                100                 105                 110

Gln Gly Thr Gln Val Thr Val Ser Ser
            115                 120

<210> SEQ ID NO 7
<211> LENGTH: 126
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Leu Asp Tyr Tyr
                20                  25                  30

Ala Leu Gly Trp Phe Arg Gln Ala Pro Gly Lys Glu Arg Glu Gly Val
            35                  40                  45

Ser Cys Ile Ser Ser Ser Asp His Ser Thr Thr Tyr Thr Asp Ser Val
        50                  55                  60

Lys Gly Arg Phe Thr Ile Ser Trp Asp Asn Ala Lys Asn Thr Leu Tyr
65                  70                  75                  80

Leu Gln Met Asn Ser Leu Lys Pro Gly Asp Thr Ala Val Tyr Tyr Cys
                85                  90                  95

Ala Ala Asp Pro Ala Leu Gly Cys Tyr Ser Gly Ser Tyr Tyr Pro Arg
                100                 105                 110

```
Tyr Asp Tyr Trp Gly Gln Gly Thr Gln Val Thr Val Ser Ser
        115                 120                 125

<210> SEQ ID NO 8
<211> LENGTH: 118
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Gly Val Ile Asn
            20                  25                  30

Ala Met Ala Trp His Arg Gln Ala Pro Gly Lys Glu Arg Glu Leu Val
        35                  40                  45

Ala His Ile Ser Ser Gly Gly Ser Thr Tyr Tyr Gly Asp Phe Val Lys
    50                  55                  60

Gly Arg Phe Thr Ile Ser Arg Asp Asn Ala Lys Asp Thr Val Tyr Leu
65                  70                  75                  80

Gln Met Asn Ser Leu Lys Pro Glu Asp Thr Ala Val Tyr Tyr Cys His
                85                  90                  95

Val Pro Trp Met Asp Tyr Asn Arg Arg Asp Tyr Trp Gly Gln Gly Thr
            100                 105                 110

Gln Val Thr Val Ser Ser
        115

<210> SEQ ID NO 9
<211> LENGTH: 128
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Pro Arg Thr Val Tyr Ala Asp Ser
    50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Ser Gly Ala Tyr Tyr Tyr Ala
            100                 105                 110

Trp Ala Tyr Asp Tyr Trp Gly Gln Gly Thr Gln Val Thr Val Ser Ser
        115                 120                 125

<210> SEQ ID NO 10
<211> LENGTH: 127
<212> TYPE: PRT
<213> ORGANISM: Artificial Sequence
<220> FEATURE:
<223> OTHER INFORMATION: Nanobody sequence
```

<400> SEQUENCE: 10

Glu Val Gln Leu Val Glu Ser Gly Gly Gly Leu Val Gln Ala Gly Gly
1               5                   10                  15

Ser Leu Arg Leu Ser Cys Ala Ala Ser Gly Pro Thr Phe Ser Ala Asp
            20                  25                  30

Thr Met Gly Trp Phe Arg Gln Ala Pro Gly Lys Glu Arg Glu Phe Val
        35                  40                  45

Ala Thr Ile Pro Trp Ser Gly Ile Ala Tyr Tyr Ser Asp Ser Val
    50                  55                  60

Lys Gly Arg Phe Thr Met Ser Arg Asp Asn Ala Lys Asn Thr Val Asp
65                  70                  75                  80

Leu Gln Met Asn Ser Leu Lys Pro Glu Asp Thr Ala Leu Tyr Tyr Cys
                85                  90                  95

Ala Gly Ser Ser Arg Ile Tyr Ile Tyr Ser Asp Ser Leu Ser Glu Arg
            100                 105                 110

Ser Tyr Asp Tyr Trp Gly Gln Gly Thr Gln Val Thr Val Ser Ser
            115                 120                 125

<210> SEQ ID NO 11
<211> LENGTH: 129
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Phe Ser Ser Tyr
            20                  25                  30

Ala Met Val Gly Trp Phe Arg Gln Ala Pro Gly Lys Glu Arg Glu Phe
        35                  40                  45

Val Ala Ala Val Thr Arg Trp Ser Gly Ala Arg Thr Val Tyr Ala Asp
    50                  55                  60

Ser Val Lys Gly Arg Phe Thr Ile Ser Arg Asp Asn Ala Glu Asn Thr
65                  70                  75                  80

Val Tyr Leu Gln Met Asn Ser Leu Lys Pro Glu Asp Thr Ala Val Tyr
                85                  90                  95

Thr Cys Ala Ala Asp Ser Thr Asn Arg Asn Ser Gly Ala Val Tyr Tyr
            100                 105                 110

Ser Trp Ala Tyr Asp Tyr Trp Gly Gln Gly Thr Gln Val Thr Val Ser
            115                 120                 125

Ser

<210> SEQ ID NO 12
<211> LENGTH: 128
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Phe Ser Pro Ile
            20                  25                  30

Ala Met Gly Trp Phe Arg Gln Ala Pro Gly Lys Glu Arg Glu Phe Val
            35                  40                  45

Ala Val Val Thr Arg Trp Ser Gly Ala Arg Thr Val Tyr Ala Asp Ser
    50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
                85                  90                  95

Cys Ala Ala Asp Ser Thr Asn Arg Asn Ser Gly Ala Ile Tyr Tyr Thr
            100                 105                 110

Trp Ala Tyr Asp Tyr Trp Gly Gln Gly Thr Gln Val Thr Val Ser Ser
        115                 120                 125

<210> SEQ ID NO 13
<211> LENGTH: 18
<212> TYPE: DNA
<213> ORGANISM: Artificial Sequence
<220> FEATURE:
<223> OTHER INFORMATION: Primer sequence

<400> SEQUENCE: 13
cttagcagaa aaccgtga                                                    18

<210> SEQ ID NO 14
<211> LENGTH: 18
<212> TYPE: DNA
<213> ORGANISM: Artificial Sequence
<220> FEATURE:
<223> OTHER INFORMATION: Primer sequence

<400> SEQUENCE: 14
tgggttgatt tgggattg                                                    18

<210> SEQ ID NO 15
<211> LENGTH: 19
<212> TYPE: DNA
<213> ORGANISM: Artificial Sequence
<220> FEATURE:
<223> OTHER INFORMATION: Primer sequence

<400> SEQUENCE: 15
ggactgatag aggatggta                                                   19

<210> SEQ ID NO 16
<211> LENGTH: 18
<212> TYPE: DNA
<213> ORGANISM: Artificial Sequence
<220> FEATURE:
<223> OTHER INFORMATION: Primer sequence

<400> SEQUENCE: 16
gctgacttca cttggtaa                                                    18

<210> SEQ ID NO 17
<211> LENGTH: 271
<212> TYPE: PRT
<213> ORGANISM: Artificial Sequence
<220> FEATURE:
<223> OTHER INFORMATION: Nanobody sequence

<400> SEQUENCE: 17

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Gly Pro Arg Thr Val Tyr Ala Asp Ser
 50                  55                  60

Val Lys Gly Arg Phe Thr Ile Ser Arg Asp Asn Ala Glu Asn Thr Val
 65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Ser Gly Ala Tyr Tyr Tyr Ala
            100                 105                 110

Trp Ala Tyr Asp Tyr Trp Gly Gln Gly Thr Gln Val Thr Val Ser Ser
            115                 120                 125

Gly Gly Gly Gly Ser Gly Gly Gly Ser Gly Gly Gly Gly Ser Glu
            130                 135                 140

Val Gln Leu Val Glu Ser Gly Gly Gly Leu Val Gln Ala Gly Gly Ser
145                 150                 155                 160

Leu Arg Leu Ser Cys Glu Ala Ser Gly Arg Thr Tyr Ser Arg Tyr Gly
                165                 170                 175

Met Gly Trp Phe Arg Gln Ala Pro Gly Lys Glu Arg Glu Phe Val Ala
            180                 185                 190

Ala Val Ser Arg Leu Ser Gly Pro Arg Thr Val Tyr Ala Asp Ser Val
            195                 200                 205

Lys Gly Arg Phe Thr Ile Ser Arg Asp Asn Ala Glu Asn Thr Val Tyr
210                 215                 220

Leu Gln Met Asn Ser Leu Lys Pro Glu Asp Thr Ala Val Tyr Thr Cys
225                 230                 235                 240

Ala Ala Glu Leu Thr Asn Arg Asn Ser Gly Ala Tyr Tyr Tyr Ala Trp
            245                 250                 255

Ala Tyr Asp Tyr Trp Gly Gln Gly Thr Gln Val Thr Val Ser Ser
            260                 265                 270

<210> SEQ ID NO 18
<211> LENGTH: 280
<212> TYPE: PRT
<213> ORGANISM: Artificial Sequence
<220> FEATURE:
<223> OTHER INFORMATION: Nanobody sequence

<400> SEQUENCE: 18

Val Gln Leu Val Glu Ser Gly Gly Gly Leu Val Gln Ala Gly Gly Ser
1               5                   10                  15

Leu Arg Leu Ser Cys Glu Ala Ser Gly Arg Thr Tyr Ser Arg Tyr Gly
            20                  25                  30

Met Gly Trp Phe Arg Gln Ala Pro Gly Lys Glu Arg Glu Phe Val Ala
            35                  40                  45

Ala Val Ser Arg Leu Ser Gly Pro Arg Thr Val Tyr Ala Asp Ser Val
            50                  55                  60

Lys Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Ala Val Tyr Thr Cys
                85                  90                  95

Ala Ala Glu Leu Thr Asn Arg Asn Ser Gly Ala Tyr Tyr Tyr Ala Trp
            100                 105                 110

```
Ala Tyr Asp Tyr Trp Gly Gln Gly Thr Gln Val Thr Val Ser Ser Gly
            115                 120                 125
Gly Gly Gly Ser Gly Gly Gly Ser Gly Gly Gly Ser Gly Gly
130                 135                 140
Gly Gly Ser Gly Gly Gly Ser Glu Val Gln Leu Val Glu Ser Gly
145                 150                 155                 160
Gly Gly Leu Val Gln Ala Gly Gly Ser Leu Arg Leu Ser Cys Glu Ala
                165                 170                 175
Ser Gly Arg Thr Tyr Ser Arg Tyr Gly Met Gly Trp Phe Arg Gln Ala
            180                 185                 190
Pro Gly Lys Glu Arg Glu Phe Val Ala Ala Val Ser Arg Leu Ser Gly
        195                 200                 205
Pro Arg Thr Val Tyr Ala Asp Ser Val Lys Gly Arg Phe Thr Ile Ser
    210                 215                 220
Arg Asp Asn Ala Glu Asn Thr Val Tyr Leu Gln Met Asn Ser Leu Lys
225                 230                 235                 240
Pro Glu Asp Thr Ala Val Tyr Thr Cys Ala Ala Glu Leu Thr Asn Arg
                245                 250                 255
Asn Ser Gly Ala Tyr Tyr Tyr Ala Trp Ala Tyr Asp Tyr Trp Gly Gln
            260                 265                 270
Gly Thr Gln Val Thr Val Ser Ser
        275                 280

<210> SEQ ID NO 19
<211> LENGTH: 291
<212> TYPE: PRT
<213> ORGANISM: Artificial Sequence
<220> FEATURE:
<223> OTHER INFORMATION: Nanobody sequence

<400> SEQUENCE: 19

Glu Val Gln Leu Val Glu Ser Gly Gly Gly Leu Val Gln Ala Gly Gly
1               5                   10                  15
Ser Leu Arg Leu Ser Cys Glu Ala Ser Gly Arg Thr Tyr Ser Arg Tyr
            20                  25                  30
Gly Met Gly Trp Phe Arg Gln Ala Pro Gly Lys Glu Arg Glu Phe Val
        35                  40                  45
Ala Ala Val Ser Arg Leu Ser Gly Pro Arg Thr Val Tyr Ala Asp Ser
    50                  55                  60
Val Lys Gly Arg Phe Thr Ile Ser Arg Asp Asn Ala Glu Asn Thr Val
65                  70                  75                  80
Tyr Leu Gln Met Asn Ser Leu Lys Pro Glu Asp Thr Ala Val Tyr Thr
                85                  90                  95
Cys Ala Ala Glu Leu Thr Asn Arg Asn Ser Gly Ala Tyr Tyr Tyr Ala
            100                 105                 110
Trp Ala Tyr Asp Tyr Trp Gly Gln Gly Thr Gln Val Thr Val Ser Ser
        115                 120                 125
Gly Gly Gly Gly Ser Gly Gly Gly Ser Gly Gly Gly Ser Gly
    130                 135                 140
Gly Gly Ser Gly Gly Gly Ser Gly Gly Gly Ser Gly Gly
145                 150                 155                 160
Gly Gly Ser Glu Val Gln Leu Val Glu Ser Gly Gly Gly Leu Val Gln
                165                 170                 175
Ala Gly Gly Ser Leu Arg Leu Ser Cys Glu Ala Ser Gly Arg Thr Tyr
            180                 185                 190
```

```
Ser Arg Tyr Gly Met Gly Trp Phe Arg Gln Ala Pro Gly Lys Glu Arg
        195                 200                 205

Glu Phe Val Ala Ala Val Ser Arg Leu Ser Gly Pro Arg Thr Val Tyr
    210                 215                 220

Ala Asp Ser Val Lys Gly Arg Phe Thr Ile Ser Arg Asp Asn Ala Glu
225                 230                 235                 240

Asn Thr Val Tyr Leu Gln Met Asn Ser Leu Lys Pro Glu Asp Thr Ala
            245                 250                 255

Val Tyr Thr Cys Ala Ala Glu Leu Thr Asn Arg Asn Ser Gly Ala Tyr
                260                 265                 270

Tyr Tyr Ala Trp Ala Tyr Asp Tyr Trp Gly Gln Gly Thr Gln Val Thr
        275                 280                 285

Val Ser Ser
    290

<210> SEQ ID NO 20
<211> LENGTH: 265
<212> TYPE: PRT
<213> ORGANISM: Artificial Sequence
<220> FEATURE:
<223> OTHER INFORMATION: Nanobody sequence

<400> SEQUENCE: 20

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Gly Pro Arg Thr Val Tyr Ala Asp Ser
    50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
            85                  90                  95

Cys Ala Ala Glu Leu Thr Asn Arg Asn Ser Gly Ala Tyr Tyr Tyr Ala
                100                 105                 110

Trp Ala Tyr Asp Tyr Trp Gly Gln Gly Thr Gln Val Thr Val Ser Ser
        115                 120                 125

Gly Gly Gly Gly Ser Gly Gly Gly Ser Glu Val Gln Leu Val Glu Ser
    130                 135                 140

Gly Gly Gly Leu Val Gln Ala Gly Gly Ser Leu Arg Leu Ser Cys Glu
145                 150                 155                 160

Ala Ser Gly Arg Thr Tyr Ser Arg Tyr Gly Met Gly Trp Phe Arg Gln
                165                 170                 175

Ala Pro Gly Lys Glu Arg Glu Phe Val Ala Ala Val Ser Arg Leu Ser
            180                 185                 190

Gly Pro Arg Thr Val Tyr Ala Asp Ser Val Lys Gly Arg Phe Thr Ile
        195                 200                 205

Ser Arg Asp Asn Ala Glu Asn Thr Val Tyr Leu Gln Met Asn Ser Leu
    210                 215                 220

Lys Pro Glu Asp Thr Ala Val Tyr Thr Cys Ala Ala Glu Leu Thr Asn
225                 230                 235                 240

Arg Asn Ser Gly Ala Tyr Tyr Tyr Ala Trp Ala Tyr Asp Tyr Trp Gly
            245                 250                 255
```

-continued

Gln Gly Thr Gln Val Thr Val Ser Ser
        260                 265

<210> SEQ ID NO 21
<211> LENGTH: 263
<212> TYPE: PRT
<213> ORGANISM: Artificial Sequence
<220> FEATURE:
<223> OTHER INFORMATION: Nanobody sequence

<400> SEQUENCE: 21

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Ala Gly Asp Ser Leu Arg Leu Ser Cys Ala Ala
145                 150                 155                 160

Ser Gly Arg Thr Phe Ser Ser Tyr Ala Met Gly Trp Phe Arg Gln Ala
                165                 170                 175

Pro Gly Lys Glu Arg Glu Phe Val Ala Ala Ile Ser Trp Ser Asp Gly
            180                 185                 190

Ser Thr Tyr Tyr Ala Asp Ser Val Lys Gly Arg Phe Thr Ile Ser Arg
        195                 200                 205

Asp Asn Ala Lys Asn Thr Val Tyr Leu Gln Met Asn Ser Leu Lys Pro
    210                 215                 220

Glu Asp Thr Ala Val Tyr Tyr Cys Ala Ala Asp Leu Thr Ser Thr Asn
225                 230                 235                 240

Pro Gly Ser Tyr Ile Tyr Ile Trp Ala Tyr Asp Tyr Trp Gly Gln Gly
                245                 250                 255

Thr Gln Val Thr Val Ser Ser
        260

<210> SEQ ID NO 22
<211> LENGTH: 269
<212> TYPE: PRT
<213> ORGANISM: Artificial Sequence
<220> FEATURE:
<223> OTHER INFORMATION: Nanobody sequence

<400> SEQUENCE: 22

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

```
Ala Met Gly Trp Phe Arg Gln Ala Pro Gly Lys Glu Arg Glu Phe Val
            35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
            115                 120                 125

Gly Gly Gly Ser Gly Gly Gly Ser Gly Gly Gly Ser Glu Val
            130                 135                 140

Gln Leu Val Glu Ser Gly Gly Gly Leu Val Gln Ala Gly Asp Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Asp Gly Ser Thr Tyr Tyr Ala Asp Ser Val Lys Gly
            195                 200                 205

Arg Phe Thr Ile Ser Arg Asp Asn Ala Lys Asn Thr Val Tyr Leu Gln
            210                 215                 220

Met Asn Ser Leu Lys Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Gln Val Thr Val Ser Ser
            260                 265

<210> SEQ ID NO 23
<211> LENGTH: 261
<212> TYPE: PRT
<213> ORGANISM: Artificial Sequence
<220> FEATURE:
<223> OTHER INFORMATION: Nanobody sequence

<400> SEQUENCE: 23

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Asn Tyr
            20                  25                  30

Val Leu Gly Trp Phe Arg Gln Ala Pro Gly Lys Glu Arg Glu Phe Val
            35                  40                  45

Ala Ala Ile Ser Phe Arg Gly Asp Ser Ala Ile Gly Ala Pro Ser Val
    50                  55                  60

Glu Gly Arg Phe Thr Ile Ser Arg Asp Asn Ala Lys Asn Thr Gly Tyr
 65                  70                  75                  80

Leu Gln Met Asn Ser Leu Val Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
            115                 120                 125
```

```
Gly Gly Ser Gly Gly Ser Glu Val Gln Leu Val Glu Ser Gly Gly
        130                 135                 140
Gly Leu Val Gln Ala Gly Gly Ser Leu Arg Leu Ser Cys Ala Ala Ser
145                 150                 155                 160
Gly Arg Ser Phe Ser Asn Tyr Val Leu Gly Trp Phe Arg Gln Ala Pro
                165                 170                 175
Gly Lys Glu Arg Glu Phe Val Ala Ala Ile Ser Phe Arg Gly Asp Ser
            180                 185                 190
Ala Ile Gly Ala Pro Ser Val Glu Gly Arg Phe Thr Ile Ser Arg Asp
        195                 200                 205
Asn Ala Lys Asn Thr Gly Tyr Leu Gln Met Asn Ser Leu Val Pro Asp
    210                 215                 220
Asp Thr Ala Val Tyr Tyr Cys Gly Ala Gly Thr Pro Leu Asn Pro Gly
225                 230                 235                 240
Ala Tyr Ile Tyr Asp Trp Ser Tyr Asp Tyr Trp Gly Arg Gly Thr Gln
                245                 250                 255
Val Thr Val Ser Ser
            260

<210> SEQ ID NO 24
<211> LENGTH: 267
<212> TYPE: PRT
<213> ORGANISM: Artificial Sequence
<220> FEATURE:
<223> OTHER INFORMATION: Nanobody sequence

<400> SEQUENCE: 24

Glu Val Gln Leu Val Glu Ser Gly Gly Gly Leu Val Gln Ala Gly Gly
1               5                   10                  15
Ser Leu Arg Leu Ser Cys Ala Ala Ser Gly Arg Ser Phe Ser Asn Tyr
            20                  25                  30
Val Leu Gly Trp Phe Arg Gln Ala Pro Gly Lys Glu Arg Glu Phe Val
        35                  40                  45
Ala Ala Ile Ser Phe Arg Gly Asp Ser Ala Ile Gly Ala Pro Ser Val
    50                  55                  60
Glu Gly Arg Phe Thr Ile Ser Arg Asp Asn Ala Lys Asn Thr Gly Tyr
65                  70                  75                  80
Leu Gln Met Asn Ser Leu Val Pro Asp Asp Thr Ala Val Tyr Tyr Cys
                85                  90                  95
Gly Ala Gly Thr Pro Leu Asn Pro Gly Ala Tyr Ile Tyr Asp Trp Ser
            100                 105                 110
Tyr Asp Tyr Trp Gly Arg Gly Thr Gln Val Thr Val Ser Ser Gly Gly
        115                 120                 125
Gly Gly Ser Gly Gly Gly Gly Ser Gly Gly Gly Gly Ser Glu Val Gln
    130                 135                 140
Leu Val Glu Ser Gly Gly Gly Leu Val Gln Ala Gly Gly Ser Leu Arg
145                 150                 155                 160
Leu Ser Cys Ala Ala Ser Gly Arg Ser Phe Ser Asn Tyr Val Leu Gly
                165                 170                 175
Trp Phe Arg Gln Ala Pro Gly Lys Glu Arg Glu Phe Val Ala Ala Ile
            180                 185                 190
Ser Phe Arg Gly Asp Ser Ala Ile Gly Ala Pro Ser Val Glu Gly Arg
        195                 200                 205
Phe Thr Ile Ser Arg Asp Asn Ala Lys Asn Thr Gly Tyr Leu Gln Met
    210                 215                 220
```

```
Asn Ser Leu Val Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser
            260                 265

<210> SEQ ID NO 25
<211> LENGTH: 263
<212> TYPE: PRT
<213> ORGANISM: Artificial Sequence
<220> FEATURE:
<223> OTHER INFORMATION: Nanobody sequence

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Ala Met Gly Trp Phe Arg Gln Ala Pro Gly Lys Glu Arg Glu Phe Val
        35                  40                  45

Ala Ala Ile Ser Trp Ser Arg Gly Arg Thr Phe Tyr Ala Asp Ser Val
    50                  55                  60

Lys Gly Arg Phe Ile Ile Ser Arg Asp Asp Ala Ala Asn Thr Ala Tyr
65                  70                  75                  80

Leu Gln Met Asn Ser Leu Lys Pro Glu Asp Thr Ala Val Tyr Tyr Cys
                85                  90                  95

Ala Val Asp Thr Ala Ser Trp Asn Ser Gly Ser Phe Ile Tyr Asp Trp
            100                 105                 110

Ala Tyr Asp His Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Gly Ser Leu Arg Leu Ser Cys Ala Ala
145                 150                 155                 160

Ser Gly Arg Thr Phe Ser Ser Ile Ala Met Gly Trp Phe Arg Gln Ala
                165                 170                 175

Pro Gly Lys Glu Arg Glu Phe Val Ala Ala Ile Ser Trp Ser Arg Gly
            180                 185                 190

Arg Thr Phe Tyr Ala Asp Ser Val Lys Gly Arg Phe Ile Ile Ser Arg
        195                 200                 205

Asp Asp Ala Ala Asn Thr Ala Tyr Leu Gln Met Asn Ser Leu Lys Pro
    210                 215                 220

Glu Asp Thr Ala Val Tyr Tyr Cys Ala Val Asp Thr Ala Ser Trp Asn
225                 230                 235                 240

Ser Gly Ser Phe Ile Tyr Asp Trp Ala Tyr Asp His Trp Gly Gln Gly
                245                 250                 255

Thr Gln Val Thr Val Ser Ser
            260

<210> SEQ ID NO 26
<211> LENGTH: 269
<212> TYPE: PRT
<213> ORGANISM: Artificial Sequence
<220> FEATURE:
<223> OTHER INFORMATION: Nanobody sequence
```

<400> SEQUENCE: 26

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Arg Thr Phe Ser Ser Ile
            20                  25                  30
Ala Met Gly Trp Phe Arg Gln Ala Pro Gly Lys Glu Arg Glu Phe Val
        35                  40                  45
Ala Ala Ile Ser Trp Ser Arg Gly Arg Thr Phe Tyr Ala Asp Ser Val
    50                  55                  60
Lys Gly Arg Phe Ile Ile Ser Arg Asp Asp Ala Ala Asn Thr Ala Tyr
65                  70                  75                  80
Leu Gln Met Asn Ser Leu Lys Pro Glu Asp Thr Ala Val Tyr Tyr Cys
                85                  90                  95
Ala Val Asp Thr Ala Ser Trp Asn Ser Gly Ser Phe Ile Tyr Asp Trp
            100                 105                 110
Ala Tyr Asp His Trp Gly Gln Gly Thr Gln Val Thr Val Ser Ser Gly
        115                 120                 125
Gly Gly Gly Ser Gly Gly Gly Ser Gly Gly Gly Ser Glu Val
    130                 135                 140
Gln Leu Val Glu Ser Gly Gly Gly Leu Val Gln Pro Gly Gly Ser Leu
145                 150                 155                 160
Arg Leu Ser Cys Ala Ala Ser Gly Arg Thr Phe Ser Ser Ile Ala Met
                165                 170                 175
Gly Trp Phe Arg Gln Ala Pro Gly Lys Glu Arg Glu Phe Val Ala Ala
            180                 185                 190
Ile Ser Trp Ser Arg Gly Arg Thr Phe Tyr Ala Asp Ser Val Lys Gly
        195                 200                 205
Arg Phe Ile Ile Ser Arg Asp Asp Ala Ala Asn Thr Ala Tyr Leu Gln
    210                 215                 220
Met Asn Ser Leu Lys Pro Glu Asp Thr Ala Val Tyr Tyr Cys Ala Val
225                 230                 235                 240
Asp Thr Ala Ser Trp Asn Ser Gly Ser Phe Ile Tyr Asp Trp Ala Tyr
                245                 250                 255
Asp His Trp Gly Gln Gly Thr Gln Val Thr Val Ser Ser
            260                 265
```

```
<210> SEQ ID NO 27
<211> LENGTH: 267
<212> TYPE: PRT
<213> ORGANISM: Artificial Sequence
<220> FEATURE:
<223> OTHER INFORMATION: Nanobody sequence
```

<400> SEQUENCE: 27

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Leu Thr Leu Asp Tyr Tyr
            20                  25                  30
Ala Leu Gly Trp Phe Arg Gln Ala Pro Gly Lys Glu Arg Glu Gly Val
        35                  40                  45
Ser Cys Ile Ser Ser Ser Asp His Ser Thr Thr Tyr Thr Asp Ser Val
    50                  55                  60
Lys Gly Arg Phe Thr Ile Ser Trp Asp Asn Ala Lys Asn Thr Leu Tyr
65                  70                  75                  80
Leu Gln Met Asn Ser Leu Lys Pro Gly Asp Thr Ala Val Tyr Tyr Cys
```

```
                85                  90                  95
Ala Ala Asp Pro Ala Leu Gly Cys Tyr Ser Gly Ser Tyr Tyr Pro Arg
            100                 105                 110

Tyr Asp Tyr Trp Gly Gln Gly Thr Gln Val Thr Val Ser Ser Gly Gly
            115                 120                 125

Gly Gly Ser Gly Gly Gly Ser Gly Gly Gly Ser Glu Val Gln
130                 135                 140

Leu Val Glu Ser Gly Gly Leu Val Gln Pro Gly Gly Ser Leu Arg
145                 150                 155                 160

Leu Ser Cys Ala Ala Ser Gly Leu Thr Leu Asp Tyr Tyr Ala Leu Gly
                165                 170                 175

Trp Phe Arg Gln Ala Pro Gly Lys Glu Arg Glu Gly Val Ser Cys Ile
            180                 185                 190

Ser Ser Ser Asp His Ser Thr Thr Tyr Thr Asp Ser Val Lys Gly Arg
            195                 200                 205

Phe Thr Ile Ser Trp Asp Asn Ala Lys Asn Thr Leu Tyr Leu Gln Met
210                 215                 220

Asn Ser Leu Lys Pro Gly Asp Thr Ala Val Tyr Tyr Cys Ala Ala Asp
225                 230                 235                 240

Pro Ala Leu Gly Cys Tyr Ser Gly Ser Tyr Tyr Pro Arg Tyr Asp Tyr
                245                 250                 255

Trp Gly Gln Gly Thr Gln Val Thr Val Ser Ser
            260                 265

<210> SEQ ID NO 28
<211> LENGTH: 262
<212> TYPE: PRT
<213> ORGANISM: Artificial Sequence
<220> FEATURE:
<223> OTHER INFORMATION: Nanobody sequence

<400> SEQUENCE: 28

Glu Val Gln Leu Val Glu Ser Gly Gly Gly Trp Val Gln Ala Gly Gly
1               5                   10                  15

Ser Leu Arg Leu Ser Cys Ala Ala Ser Gly Arg Ala Phe Ser Ser Tyr
            20                  25                  30

Ala Met Gly Trp Ile Arg Gln Ala Pro Gly Lys Glu Arg Glu Phe Val
            35                  40                  45

Ala Gly Ile Asp Gln Ser Gly Glu Ser Thr Ala Tyr Gly Ala Ser Ala
        50                  55                  60

Ser Gly Arg Phe Ile Ile Ser Arg Asp Asn Ala Lys Asn Thr Val His
65                  70                  75                  80

Leu Leu Met Asn Ser Leu Gln Ser Asp Asp Thr Ala Val Tyr Tyr Cys
                85                  90                  95

Val Ala Asp Gly Val Leu Ala Thr Thr Leu Asn Trp Asp Tyr Trp Gly
            100                 105                 110

Gln Gly Thr Gln Val Thr Val Ser Ser Gly Gly Gly Gly Ser Gly Gly
            115                 120                 125

Gly Gly Ser Gly Gly Gly Gly Ser Gly Gly Gly Ser Glu Val Gln
130                 135                 140

Leu Val Glu Ser Gly Gly Gly Trp Val Gln Ala Gly Gly Ser Leu Arg
145                 150                 155                 160

Leu Ser Cys Ala Ala Ser Gly Arg Ala Phe Ser Ser Tyr Ala Met Gly
                165                 170                 175

Trp Ile Arg Gln Ala Pro Gly Lys Glu Arg Glu Phe Val Ala Gly Ile
```

```
                    180                 185                 190

Asp Gln Ser Gly Glu Ser Thr Ala Tyr Gly Ser Ala Ser Gly Arg
            195                 200                 205

Phe Ile Ile Ser Arg Asp Asn Ala Lys Asn Thr Val His Leu Leu Met
        210                 215                 220

Asn Ser Leu Gln Ser Asp Asp Thr Ala Val Tyr Tyr Cys Val Ala Asp
225                 230                 235                 240

Gly Val Leu Ala Thr Thr Leu Asn Trp Asp Tyr Trp Gly Gln Gly Thr
                245                 250                 255

Gln Val Thr Val Ser Ser
            260

<210> SEQ ID NO 29
<211> LENGTH: 272
<212> TYPE: PRT
<213> ORGANISM: Artificial Sequence
<220> FEATURE:
<223> OTHER INFORMATION: Nanobody sequence

<400> SEQUENCE: 29

Glu Val Gln Leu Val Glu Ser Gly Gly Gly Leu Val Gln Ala Gly Gly
1               5                   10                  15

Ser Leu Arg Leu Ser Cys Ala Ala Ser Gly Pro Thr Phe Ser Ala Asp
            20                  25                  30

Thr Met Gly Trp Phe Arg Gln Ala Pro Gly Lys Glu Arg Glu Phe Val
        35                  40                  45

Ala Thr Ile Pro Trp Ser Gly Gly Ile Ala Tyr Tyr Ser Asp Ser Val
    50                  55                  60

Lys Gly Arg Phe Thr Met Ser Arg Asp Asn Ala Lys Asn Thr Val Asp
65                  70                  75                  80

Leu Gln Met Asn Ser Leu Lys Pro Glu Asp Thr Ala Leu Tyr Tyr Cys
            85                  90                  95

Ala Gly Ser Ser Arg Ile Tyr Ile Tyr Ser Asp Ser Leu Ser Glu Arg
        100                 105                 110

Ser Tyr Asp Tyr Trp Gly Gln Gly Thr Gln Val Thr Val Ser Ser Gly
    115                 120                 125

Gly Gly Gly Ser Gly Gly Gly Gly Ser Gly Gly Gly Gly Gly Gly Gly
130                 135                 140

Ser Glu Val Gln Leu Val Glu Ser Gly Gly Gly Leu Val Gln Ala Gly
145                 150                 155                 160

Gly Ser Leu Arg Leu Ser Cys Ala Ala Ser Gly Pro Thr Phe Ser Ala
            165                 170                 175

Asp Thr Met Gly Trp Phe Arg Gln Ala Pro Gly Lys Glu Arg Glu Phe
        180                 185                 190

Val Ala Thr Ile Pro Trp Ser Gly Gly Ile Ala Tyr Tyr Ser Asp Ser
    195                 200                 205

Val Lys Gly Arg Phe Thr Met Ser Arg Asp Asn Ala Lys Asn Thr Val
210                 215                 220

Asp Leu Gln Met Asn Ser Leu Lys Pro Glu Asp Thr Ala Leu Tyr Tyr
225                 230                 235                 240

Cys Ala Gly Ser Ser Arg Ile Tyr Ile Tyr Ser Asp Ser Leu Ser Glu
            245                 250                 255

Arg Ser Tyr Asp Tyr Trp Gly Gln Gly Thr Gln Val Thr Val Ser Ser
        260                 265                 270
```

-continued

```
<210> SEQ ID NO 30
<211> LENGTH: 267
<212> TYPE: PRT
<213> ORGANISM: Artificial Sequence
<220> FEATURE:
<223> OTHER INFORMATION: Nanobody sequence

<400> SEQUENCE: 30

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser
            260                 265

<210> SEQ ID NO 31
<211> LENGTH: 264
<212> TYPE: PRT
<213> ORGANISM: Artificial Sequence
<220> FEATURE:
<223> OTHER INFORMATION: Nanobody sequence

<400> SEQUENCE: 31

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
            20                  25                  30

Gly Met Gly Trp Phe Arg Gln Ala Pro Gly Lys Glu Arg Glu Phe Val
        35                  40                  45
```

```
Ala Ala Val Ser Arg Leu Ser Gly Pro Arg Thr Val Tyr Ala Asp Ser
     50                  55                  60

Val Lys Gly Arg Phe Thr Ile Ser Arg Asp Asn Ala Glu Asn Thr Val
 65                  70                  75                  80

Tyr Leu Gln Met Asn Ser Leu Lys Pro Glu Asp Thr Ala Val Tyr Thr
                 85                  90                  95

Cys Ala Ala Glu Leu Thr Asn Arg Asn Ser Gly Ala Tyr Tyr Tyr Ala
                100                 105                 110

Trp Ala Tyr Asp Tyr Trp Gly Gln Gly Thr Gln Val Thr Val Ser Ser
            115                 120                 125

Gly Gly Gly Gly Ser Gly Gly Ser Glu Val Gln Leu Val Glu Ser
    130                 135                 140

Gly Gly Gly Leu Val Gln Ala Gly Gly Ser Leu Arg Leu Ser Cys Ala
145                 150                 155                 160

Ala Ser Gly Pro Thr Phe Ser Ala Asp Thr Met Gly Trp Phe Arg Gln
                165                 170                 175

Ala Pro Gly Lys Glu Arg Glu Phe Val Ala Thr Ile Pro Trp Ser Gly
            180                 185                 190

Gly Ile Ala Tyr Tyr Ser Asp Ser Val Lys Gly Arg Phe Thr Met Ser
    195                 200                 205

Arg Asp Asn Ala Lys Asn Thr Val Asp Leu Gln Met Asn Ser Leu Lys
210                 215                 220

Pro Glu Asp Thr Ala Leu Tyr Tyr Cys Ala Gly Ser Ser Arg Ile Tyr
225                 230                 235                 240

Ile Tyr Ser Asp Ser Leu Ser Glu Arg Ser Tyr Asp Tyr Trp Gly Gln
                245                 250                 255

Gly Thr Gln Val Thr Val Ser Ser
            260

<210> SEQ ID NO 32
<211> LENGTH: 270
<212> TYPE: PRT
<213> ORGANISM: Artificial Sequence
<220> FEATURE:
<223> OTHER INFORMATION: Nanobody sequence

<400> SEQUENCE: 32

Glu Val Gln Leu Val Glu Ser Gly Gly Gly Leu Val Gln Ala Gly Gly
 1               5                  10                  15

Ser Leu Arg Leu Ser Cys Glu Ala Ser Gly Arg Thr Tyr Ser Arg Tyr
             20                  25                  30

Gly Met Gly Trp Phe Arg Gln Ala Pro Gly Lys Glu Arg Glu Phe Val
         35                  40                  45

Ala Ala Val Ser Arg Leu Ser Gly Pro Arg Thr Val Tyr Ala Asp Ser
     50                  55                  60

Val Lys Gly Arg Phe Thr Ile Ser Arg Asp Asn Ala Glu Asn Thr Val
 65                  70                  75                  80

Tyr Leu Gln Met Asn Ser Leu Lys Pro Glu Asp Thr Ala Val Tyr Thr
                 85                  90                  95

Cys Ala Ala Glu Leu Thr Asn Arg Asn Ser Gly Ala Tyr Tyr Tyr Ala
                100                 105                 110

Trp Ala Tyr Asp Tyr Trp Gly Gln Gly Thr Gln Val Thr Val Ser Ser
            115                 120                 125

Gly Gly Gly Gly Ser Gly Gly Gly Ser Gly Gly Gly Ser Glu
    130                 135                 140
```

-continued

```
Val Gln Leu Val Glu Ser Gly Gly Leu Val Gln Ala Gly Gly Ser
145                 150                 155                 160

Leu Arg Leu Ser Cys Ala Ala Ser Gly Pro Thr Phe Ser Ala Asp Thr
            165                 170                 175

Met Gly Trp Phe Arg Gln Ala Pro Gly Lys Glu Arg Glu Phe Val Ala
            180                 185                 190

Thr Ile Pro Trp Ser Gly Gly Ile Ala Tyr Tyr Ser Asp Ser Val Lys
            195                 200                 205

Gly Arg Phe Thr Met Ser Arg Asp Asn Ala Lys Asn Thr Val Asp Leu
        210                 215                 220

Gln Met Asn Ser Leu Lys Pro Glu Asp Thr Ala Leu Tyr Tyr Cys Ala
225                 230                 235                 240

Gly Ser Ser Arg Ile Tyr Ile Tyr Ser Asp Ser Leu Ser Glu Arg Ser
            245                 250                 255

Tyr Asp Tyr Trp Gly Gln Gly Thr Gln Val Thr Val Ser Ser
            260                 265                 270
```

<210> SEQ ID NO 33
<211> LENGTH: 280
<212> TYPE: PRT
<213> ORGANISM: Artificial Sequence
<220> FEATURE:
<223> OTHER INFORMATION: Nanobody sequence

<400> SEQUENCE: 33

```
Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Gly Pro Arg Thr Val Tyr Ala Asp Ser
    50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Ser Gly Ala Tyr Tyr Tyr Ala
            100                 105                 110

Trp Ala Tyr Asp Tyr Trp Gly Gln Gly Thr Gln Val Thr Val Ser Ser
        115                 120                 125

Gly Gly Gly Gly Ser Gly Gly Gly Gly Ser Gly Gly Gly Gly Ser Gly
        130                 135                 140

Gly Gly Ser Gly Gly Gly Ser Glu Val Gln Leu Val Glu Ser
145                 150                 155                 160

Gly Gly Gly Leu Val Gln Ala Gly Gly Ser Leu Arg Leu Ser Cys Ala
            165                 170                 175

Ala Ser Gly Pro Thr Phe Ser Ala Asp Thr Met Gly Trp Phe Arg Gln
            180                 185                 190

Ala Pro Gly Lys Glu Arg Glu Phe Val Ala Thr Ile Pro Trp Ser Gly
            195                 200                 205

Gly Ile Ala Tyr Tyr Ser Asp Ser Val Lys Gly Arg Phe Thr Met Ser
        210                 215                 220

Arg Asp Asn Ala Lys Asn Thr Val Asp Leu Gln Met Asn Ser Leu Lys
225                 230                 235                 240
```

-continued

```
Pro Glu Asp Thr Ala Leu Tyr Tyr Cys Ala Gly Ser Ser Arg Ile Tyr
                245                 250                 255
Ile Tyr Ser Asp Ser Leu Ser Glu Arg Ser Tyr Asp Tyr Trp Gly Gln
            260                 265                 270
Gly Thr Gln Val Thr Val Ser Ser
        275                 280

<210> SEQ ID NO 34
<211> LENGTH: 268
<212> TYPE: PRT
<213> ORGANISM: Artificial Sequence
<220> FEATURE:
<223> OTHER INFORMATION: Nanobody sequence

<400> SEQUENCE: 34

Glu Val Gln Leu Val Glu Ser Gly Gly Gly Leu Val Gln Ala Gly Asp
1               5                   10                  15
Ser Leu Arg Leu Ser Cys Ala Ala Ser Gly Arg Thr Phe Ser Ser Tyr
            20                  25                  30
Ala Met Gly Trp Phe Arg Gln Ala Pro Gly Lys Glu Arg Glu Phe Val
        35                  40                  45
Ala Ala Ile Ser Trp Ser Asp Gly Ser Thr Tyr Tyr Ala Asp Ser Val
    50                  55                  60
Lys Gly Arg Phe Thr Ile Ser Arg Asp Asn Ala Lys Asn Thr Val Tyr
65                  70                  75                  80
Leu Gln Met Asn Ser Leu Lys Pro Glu Asp Thr Ala Val Tyr Tyr Cys
                85                  90                  95
Ala Ala Asp Leu Thr Ser Thr Asn Pro Gly Ser Tyr Ile Tyr Ile Trp
            100                 105                 110
Ala Tyr Asp Tyr Trp Gly Gln Gly Thr Gln Val Thr Val Ser Ser Gly
        115                 120                 125
Gly Gly Gly Ser Gly Gly Gly Ser Gly Gly Gly Ser Glu Val
    130                 135                 140
Gln Leu Val Glu Ser Gly Gly Leu Val Gln Ala Gly Gly Ser Leu
145                 150                 155                 160
Arg Leu Ser Cys Ala Ala Ser Gly Arg Ser Phe Ser Asn Tyr Val Leu
                165                 170                 175
Gly Trp Phe Arg Gln Ala Pro Gly Lys Glu Arg Glu Phe Val Ala Ala
            180                 185                 190
Ile Ser Phe Arg Gly Asp Ser Ala Ile Gly Ala Pro Ser Val Glu Gly
        195                 200                 205
Arg Phe Thr Ile Ser Arg Asp Asn Ala Lys Asn Thr Gly Tyr Leu Gln
    210                 215                 220
Met Asn Ser Leu Val Pro Asp Asp Thr Ala Val Tyr Tyr Cys Gly Ala
225                 230                 235                 240
Gly Thr Pro Leu Asn Pro Gly Ala Tyr Ile Tyr Asp Trp Ser Tyr Asp
                245                 250                 255
Tyr Trp Gly Arg Gly Thr Gln Val Thr Val Ser Ser
            260                 265

<210> SEQ ID NO 35
<211> LENGTH: 268
<212> TYPE: PRT
<213> ORGANISM: Artificial Sequence
<220> FEATURE:
<223> OTHER INFORMATION: Nanobody sequence

<400> SEQUENCE: 35
```

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Ser Gly Gly Gly Ser Glu Val
130                 135                 140

Gln Leu Val Glu Ser Gly Gly Leu Val Gln Pro Gly Gly Ser Leu
145                 150                 155                 160

Arg Leu Ser Cys Ala Ala Ser Gly Leu Thr Leu Asp Tyr Tyr Ala Leu
            165                 170                 175

Gly Trp Phe Arg Gln Ala Pro Gly Lys Glu Arg Glu Gly Val Ser Cys
        180                 185                 190

Ile Ser Ser Ser Asp His Ser Thr Thr Tyr Thr Asp Ser Val Lys Gly
195                 200                 205

Arg Phe Thr Ile Ser Trp Asp Asn Ala Lys Asn Thr Leu Tyr Leu Gln
210                 215                 220

Met Asn Ser Leu Lys Pro Gly Asp Thr Ala Val Tyr Tyr Cys Ala Ala
225                 230                 235                 240

Asp Pro Ala Leu Gly Cys Tyr Ser Gly Ser Tyr Tyr Pro Arg Tyr Asp
            245                 250                 255

Tyr Trp Gly Gln Gly Thr Gln Val Thr Val Ser Ser
        260                 265

<210> SEQ ID NO 36
<211> LENGTH: 268
<212> TYPE: PRT
<213> ORGANISM: Artificial Sequence
<220> FEATURE:
<223> OTHER INFORMATION: Nanobody sequence

<400> SEQUENCE: 36

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Asn Tyr
            20                  25                  30

Val Leu Gly Trp Phe Arg Gln Ala Pro Gly Lys Glu Arg Glu Phe Val
        35                  40                  45

Ala Ala Ile Ser Phe Arg Gly Asp Ser Ala Ile Gly Ala Pro Ser Val
50                  55                  60

Glu Gly Arg Phe Thr Ile Ser Arg Asp Asn Ala Lys Asn Thr Gly Tyr
65                  70                  75                  80

Leu Gln Met Asn Ser Leu Val Pro Asp Asp Thr Ala Val Tyr Tyr Cys
                85                  90                  95

```
Gly Ala Gly Thr Pro Leu Asn Pro Gly Ala Tyr Ile Tyr Asp Trp Ser
                100                 105                 110

Tyr Asp Tyr Trp Gly Arg Gly Thr Gln Val Thr Val Ser Ser Gly Gly
            115                 120                 125

Gly Gly Ser Gly Gly Gly Ser Gly Gly Gly Ser Glu Val Gln
130                 135                 140

Leu Val Glu Ser Gly Gly Gly Leu Val Gln Ala Gly Asp Ser Leu Arg
145                 150                 155                 160

Leu Ser Cys Ala Ala Ser Gly Arg Thr Phe Ser Ser Tyr Ala Met Gly
                165                 170                 175

Trp Phe Arg Gln Ala Pro Gly Lys Glu Arg Glu Phe Val Ala Ala Ile
            180                 185                 190

Ser Trp Ser Asp Gly Ser Thr Tyr Tyr Ala Asp Ser Val Lys Gly Arg
        195                 200                 205

Phe Thr Ile Ser Arg Asp Asn Ala Lys Asn Thr Val Tyr Leu Gln Met
210                 215                 220

Asn Ser Leu Lys Pro Glu Asp Thr Ala Val Tyr Tyr Cys Ala Ala Asp
225                 230                 235                 240

Leu Thr Ser Thr Asn Pro Gly Ser Tyr Ile Tyr Ile Trp Ala Tyr Asp
                245                 250                 255

Tyr Trp Gly Gln Gly Thr Gln Val Thr Val Ser Ser
            260                 265

<210> SEQ ID NO 37
<211> LENGTH: 268
<212> TYPE: PRT
<213> ORGANISM: Artificial Sequence
<220> FEATURE:
<223> OTHER INFORMATION: Nanobody sequence

<400> SEQUENCE: 37

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Asn Tyr
            20                  25                  30

Val Leu Gly Trp Phe Arg Gln Ala Pro Gly Lys Glu Arg Glu Phe Val
        35                  40                  45

Ala Ala Ile Ser Phe Arg Gly Asp Ser Ala Ile Gly Ala Pro Ser Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Val Pro Asp Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Arg Gly Thr Gln Val Thr Val Ser Ser Gly Gly
            115                 120                 125

Gly Gly Ser Gly Gly Gly Ser Gly Gly Gly Ser Glu Val Gln
130                 135                 140

Leu Val Glu Ser Gly Gly Gly Leu Val Gln Ala Gly Asp Ser Leu Arg
145                 150                 155                 160

Leu Ser Cys Ala Ala Ser Gly Arg Thr Phe Ser Ser Tyr Ala Met Gly
                165                 170                 175

Trp Phe Arg Gln Ala Pro Gly Lys Glu Arg Glu Phe Val Ala Ala Ile
            180                 185                 190
```

```
Ser Trp Ser Asp Gly Ser Thr Tyr Tyr Ala Asp Ser Val Lys Gly Arg
        195                 200                 205

Phe Thr Ile Ser Arg Asp Asn Ala Lys Asn Thr Val Tyr Leu Gln Met
210                 215                 220

Asn Ser Leu Lys Pro Glu Asp Thr Ala Val Tyr Tyr Cys Ala Ala Asp
225                 230                 235                 240

Leu Thr Ser Thr Asn Pro Gly Ser Tyr Ile Tyr Ile Trp Ala Tyr Asp
                245                 250                 255

Tyr Trp Gly Gln Gly Thr Gln Val Thr Val Ser Ser
        260                 265

<210> SEQ ID NO 38
<211> LENGTH: 264
<212> TYPE: PRT
<213> ORGANISM: Artificial Sequence
<220> FEATURE:
<223> OTHER INFORMATION: Nanobody sequence

<400> SEQUENCE: 38

Glu Val Gln Leu Val Glu Ser Gly Gly Gly Leu Val Gln Ala Gly Gly
1               5                   10                  15

Ser Leu Arg Leu Ser Cys Ala Ala Ser Gly Pro Thr Phe Ser Ala Asp
            20                  25                  30

Thr Met Gly Trp Phe Arg Gln Ala Pro Gly Lys Glu Arg Glu Phe Val
        35                  40                  45

Ala Thr Ile Pro Trp Ser Gly Gly Ile Ala Tyr Tyr Ser Asp Ser Val
    50                  55                  60

Lys Gly Arg Phe Thr Met Ser Arg Asp Asn Ala Lys Asn Thr Val Asp
65                  70                  75                  80

Leu Gln Met Asn Ser Leu Lys Pro Glu Asp Thr Ala Leu Tyr Tyr Cys
                85                  90                  95

Ala Gly Ser Ser Arg Ile Tyr Ile Tyr Ser Asp Ser Leu Ser Glu Arg
            100                 105                 110

Ser Tyr Asp Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Ala Gly Gly Ser Leu Arg Leu Ser Cys Glu Ala
145                 150                 155                 160

Ser Gly Arg Thr Tyr Ser Arg Tyr Gly Met Gly Trp Phe Arg Gln Ala
                165                 170                 175

Pro Gly Lys Glu Arg Glu Phe Val Ala Ala Val Ser Arg Leu Ser Gly
            180                 185                 190

Pro Arg Thr Val Tyr Ala Asp Ser Val Lys Gly Arg Phe Thr Ile Ser
        195                 200                 205

Arg Asp Asn Ala Glu Asn Thr Val Tyr Leu Gln Met Asn Ser Leu Lys
210                 215                 220

Pro Glu Asp Thr Ala Val Tyr Thr Cys Ala Ala Glu Leu Thr Asn Arg
225                 230                 235                 240

Asn Ser Gly Ala Tyr Tyr Tyr Ala Trp Ala Tyr Asp Tyr Trp Gly Gln
                245                 250                 255

Gly Thr Gln Val Thr Val Ser Ser
            260

<210> SEQ ID NO 39
```

<211> LENGTH: 270
<212> TYPE: PRT
<213> ORGANISM: Artificial Sequence
<220> FEATURE:
<223> OTHER INFORMATION: Nanobody sequence

<400> SEQUENCE: 39

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Pro Thr Phe Ser Ala Asp
            20                  25                  30

Thr Met Gly Trp Phe Arg Gln Ala Pro Gly Lys Glu Arg Glu Phe Val
        35                  40                  45

Ala Thr Ile Pro Trp Ser Gly Gly Ile Ala Tyr Tyr Ser Asp Ser Val
    50                  55                  60

Lys Gly Arg Phe Thr Met Ser Arg Asp Asn Ala Lys Asn Thr Val Asp
65                  70                  75                  80

Leu Gln Met Asn Ser Leu Lys Pro Glu Asp Thr Ala Leu Tyr Tyr Cys
                85                  90                  95

Ala Gly Ser Ser Arg Ile Tyr Ile Tyr Ser Asp Ser Leu Ser Glu Arg
            100                 105                 110

Ser Tyr Asp Tyr Trp Gly Gln Gly Thr Gln Val Thr Val Ser Ser Gly
        115                 120                 125

Gly Gly Gly Ser Gly Gly Gly Ser Gly Gly Gly Gly Ser Glu Val
    130                 135                 140

Gln Leu Val Glu Ser Gly Gly Gly Leu Val Gln Ala Gly Gly Ser Leu
145                 150                 155                 160

Arg Leu Ser Cys Glu Ala Ser Gly Arg Thr Tyr Ser Arg Tyr Gly Met
                165                 170                 175

Gly Trp Phe Arg Gln Ala Pro Gly Lys Glu Arg Glu Phe Val Ala Ala
            180                 185                 190

Val Ser Arg Leu Ser Gly Pro Arg Thr Val Tyr Ala Asp Ser Val Lys
        195                 200                 205

Gly Arg Phe Thr Ile Ser Arg Asp Asn Ala Glu Asn Thr Val Tyr Leu
    210                 215                 220

Gln Met Asn Ser Leu Lys Pro Glu Asp Thr Ala Val Tyr Thr Cys Ala
225                 230                 235                 240

Ala Glu Leu Thr Asn Arg Asn Ser Gly Ala Tyr Tyr Tyr Ala Trp Ala
                245                 250                 255

Tyr Asp Tyr Trp Gly Gln Gly Thr Gln Val Thr Val Ser Ser
            260                 265                 270
```

<210> SEQ ID NO 40
<211> LENGTH: 280
<212> TYPE: PRT
<213> ORGANISM: Artificial Sequence
<220> FEATURE:
<223> OTHER INFORMATION: Nanobody sequence

<400> SEQUENCE: 40

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Pro Thr Phe Ser Ala Asp
            20                  25                  30

Thr Met Gly Trp Phe Arg Gln Ala Pro Gly Lys Glu Arg Glu Phe Val
        35                  40                  45

Ala Thr Ile Pro Trp Ser Gly Gly Ile Ala Tyr Tyr Ser Asp Ser Val
```

```
                50                  55                  60
Lys Gly Arg Phe Thr Met Ser Arg Asp Asn Ala Lys Asn Thr Val Asp
 65                  70                  75                  80

Leu Gln Met Asn Ser Leu Lys Pro Glu Asp Thr Ala Leu Tyr Tyr Cys
                     85                  90                  95

Ala Gly Ser Ser Arg Ile Tyr Ile Tyr Ser Asp Ser Leu Ser Glu Arg
                100                 105                 110

Ser Tyr Asp Tyr Trp Gly Gln Gly Thr Gln Val Thr Val Ser Ser Gly
            115                 120                 125

Gly Gly Gly Ser Gly Gly Gly Ser Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Ala Gly Gly Ser Leu Arg Leu Ser Cys Glu Ala
                165                 170                 175

Ser Gly Arg Thr Tyr Ser Arg Tyr Gly Met Gly Trp Phe Arg Gln Ala
            180                 185                 190

Pro Gly Lys Glu Arg Glu Phe Val Ala Ala Val Ser Arg Leu Ser Gly
        195                 200                 205

Pro Arg Thr Val Tyr Ala Asp Ser Val Lys Gly Arg Phe Thr Ile Ser
210                 215                 220

Arg Asp Asn Ala Glu Asn Thr Val Tyr Leu Gln Met Asn Ser Leu Lys
225                 230                 235                 240

Pro Glu Asp Thr Ala Val Tyr Thr Cys Ala Ala Glu Leu Thr Asn Arg
                245                 250                 255

Asn Ser Gly Ala Tyr Tyr Tyr Ala Trp Ala Tyr Asp Tyr Trp Gly Gln
            260                 265                 270

Gly Thr Gln Val Thr Val Ser Ser
        275                 280

<210> SEQ ID NO 41
<211> LENGTH: 268
<212> TYPE: PRT
<213> ORGANISM: Artificial Sequence
<220> FEATURE:
<223> OTHER INFORMATION: Nanobody sequence

<400> SEQUENCE: 41

Glu Val Gln Leu Val Glu Ser Gly Gly Gly Leu Val Gln Pro Gly Gly
 1                   5                  10                  15

Ser Leu Arg Leu Ser Cys Ala Ser Gly Leu Thr Leu Asp Tyr Tyr
                20                  25                  30

Ala Leu Gly Trp Phe Arg Gln Ala Pro Gly Lys Glu Arg Glu Gly Val
            35                  40                  45

Ser Cys Ile Ser Ser Ser Asp His Ser Thr Thr Tyr Thr Asp Ser Val
 50                  55                  60

Lys Gly Arg Phe Thr Ile Ser Trp Asp Asn Ala Lys Asn Thr Leu Tyr
 65                  70                  75                  80

Leu Gln Met Asn Ser Leu Lys Pro Gly Asp Thr Ala Val Tyr Tyr Cys
                     85                  90                  95

Ala Ala Asp Pro Ala Leu Gly Cys Tyr Ser Gly Ser Tyr Tyr Pro Arg
                100                 105                 110

Tyr Asp Tyr Trp Gly Gln Gly Thr Gln Val Thr Val Ser Ser Gly Gly
            115                 120                 125

Gly Gly Ser Gly Gly Gly Gly Ser Gly Gly Gly Gly Ser Glu Val Gln
```

```
                    130                 135                 140
Leu Val Glu Ser Gly Gly Gly Leu Val Gln Ala Gly Asp Ser Leu Arg
145                 150                 155                 160

Leu Ser Cys Ala Ala Ser Gly Arg Thr Phe Ser Ser Tyr Ala Met Gly
                    165                 170                 175

Trp Phe Arg Gln Ala Pro Gly Lys Glu Arg Glu Phe Val Ala Ala Ile
                180                 185                 190

Ser Trp Ser Asp Gly Ser Thr Tyr Tyr Ala Asp Ser Val Lys Gly Arg
            195                 200                 205

Phe Thr Ile Ser Arg Asp Asn Ala Lys Asn Thr Val Tyr Leu Gln Met
        210                 215                 220

Asn Ser Leu Lys Pro Glu Asp Thr Ala Val Tyr Tyr Cys Ala Ala Asp
225                 230                 235                 240

Leu Thr Ser Thr Asn Pro Gly Ser Tyr Ile Tyr Ile Trp Ala Tyr Asp
                    245                 250                 255

Tyr Trp Gly Gln Gly Thr Gln Val Thr Val Ser Ser
                260                 265
```

<210> SEQ ID NO 42
<211> LENGTH: 267
<212> TYPE: PRT
<213> ORGANISM: Artificial Sequence
<220> FEATURE:
<223> OTHER INFORMATION: Nanobody sequence

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Leu Asp Tyr Tyr
                20                  25                  30

Ala Leu Gly Trp Phe Arg Gln Ala Pro Gly Lys Glu Arg Glu Gly Val
            35                  40                  45

Ser Cys Ile Ser Ser Ser Asp His Ser Thr Thr Tyr Thr Asp Ser Val
        50                  55                  60

Lys Gly Arg Phe Thr Ile Ser Trp Asp Asn Ala Lys Asn Thr Leu Tyr
65                  70                  75                  80

Leu Gln Met Asn Ser Leu Lys Pro Gly Asp Thr Ala Val Tyr Tyr Cys
                85                  90                  95

Ala Ala Asp Pro Ala Leu Gly Cys Tyr Ser Gly Ser Tyr Tyr Pro Arg
            100                 105                 110

Tyr Asp Tyr Trp Gly Gln Gly Thr Gln Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Ala Gly Gly Ser Leu Arg
145                 150                 155                 160

Leu Ser Cys Ala Ala Ser Gly Arg Ser Phe Ser Asn Tyr Val Leu Gly
                    165                 170                 175

Trp Phe Arg Gln Ala Pro Gly Lys Glu Arg Glu Phe Val Ala Ala Ile
                180                 185                 190

Ser Phe Arg Gly Asp Ser Ala Ile Gly Ala Pro Ser Val Glu Gly Arg
            195                 200                 205

Phe Thr Ile Ser Arg Asp Asn Ala Lys Asn Thr Gly Tyr Leu Gln Met
        210                 215                 220

Asn Ser Leu Val Pro Asp Asp Thr Ala Val Tyr Tyr Cys Gly Ala Gly
```

```
                 225                 230                 235                 240

Thr Pro Leu Asn Pro Gly Ala Tyr Ile Tyr Asp Trp Ser Tyr Asp Tyr
                 245                 250                 255

Trp Gly Arg Gly Thr Gln Val Thr Val Ser Ser
            260                 265

<210> SEQ ID NO 43
<211> LENGTH: 411
<212> TYPE: PRT
<213> ORGANISM: Artificial Sequence
<220> FEATURE:
<223> OTHER INFORMATION: Nanobody sequence

<400> SEQUENCE: 43

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Ser Gly Gly Gly Ser Glu Val
    130                 135                 140

Gln Leu Val Glu Ser Gly Gly Gly Leu Val Gln Ala Gly Asp Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Asp Gly Ser Thr Tyr Tyr Ala Asp Ser Val Lys Gly
        195                 200                 205

Arg Phe Thr Ile Ser Arg Asp Asn Ala Lys Asn Thr Val Tyr Leu Gln
    210                 215                 220

Met Asn Ser Leu Lys Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Gln Val Thr Val Ser Ser Gly Gly Gly
            260                 265                 270

Gly Ser Gly Gly Gly Ser Gly Gly Gly Ser Glu Val Gln Leu
        275                 280                 285

Val Glu Ser Gly Gly Gly Leu Val Gln Ala Gly Asp Ser Leu Arg Leu
    290                 295                 300

Ser Cys Ala Ala Ser Gly Arg Thr Phe Ser Ser Tyr Ala Met Gly Trp
305                 310                 315                 320

Phe Arg Gln Ala Pro Gly Lys Glu Arg Glu Phe Val Ala Ala Ile Ser
```

```
                         325                 330                 335
Trp Ser Asp Gly Ser Thr Tyr Tyr Ala Asp Ser Val Lys Gly Arg Phe
            340                 345                 350

Thr Ile Ser Arg Asp Asn Ala Lys Asn Thr Val Tyr Leu Gln Met Asn
            355                 360                 365

Ser Leu Lys Pro Glu Asp Thr Ala Val Tyr Tyr Cys Ala Ala Asp Leu
370                 375                 380

Thr Ser Thr Asn Pro Gly Ser Tyr Ile Tyr Ile Trp Ala Tyr Asp Tyr
385                 390                 395                 400

Trp Gly Gln Gly Thr Gln Val Thr Val Ser Ser
            405                 410

<210> SEQ ID NO 44
<211> LENGTH: 410
<212> TYPE: PRT
<213> ORGANISM: Artificial Sequence
<220> FEATURE:
<223> OTHER INFORMATION: Nanobody sequence

<400> SEQUENCE: 44

Glu Val Gln Leu Val Glu Ser Gly Gly Gly Leu Val Gln Ala Gly Asp
1               5                  10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Ser Gly Gly Gly Ser Glu Val
    130                 135                 140

Gln Leu Val Glu Ser Gly Gly Gly Leu Val Gln Ala Gly Asp Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Asp Gly Ser Thr Tyr Tyr Ala Asp Ser Val Lys Gly
        195                 200                 205

Arg Phe Thr Ile Ser Arg Asp Asn Ala Lys Asn Thr Val Tyr Leu Gln
    210                 215                 220

Met Asn Ser Leu Lys Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Gln Val Thr Val Ser Ser Gly Gly Gly
            260                 265                 270

Gly Ser Gly Gly Gly Gly Ser Gly Gly Gly Gly Ser Glu Val Gln Leu
```

```
                    275                 280                 285
Val Glu Ser Gly Gly Gly Leu Val Gln Pro Gly Gly Ser Leu Arg Leu
            290                 295                 300

Ser Cys Ala Ala Ser Gly Leu Thr Leu Asp Tyr Tyr Ala Leu Gly Trp
305                 310                 315                 320

Phe Arg Gln Ala Pro Gly Lys Glu Arg Glu Gly Val Ser Cys Ile Ser
                325                 330                 335

Ser Ser Asp His Ser Thr Thr Tyr Thr Asp Ser Val Lys Gly Arg Phe
                340                 345                 350

Thr Ile Ser Trp Asp Asn Ala Lys Asn Thr Leu Tyr Leu Gln Met Asn
            355                 360                 365

Ser Leu Lys Pro Gly Asp Thr Ala Val Tyr Tyr Cys Ala Ala Asp Pro
370                 375                 380

Ala Leu Gly Cys Tyr Ser Gly Ser Tyr Tyr Pro Arg Tyr Asp Tyr Trp
385                 390                 395                 400

Gly Gln Gly Thr Gln Val Thr Val Ser Ser
                405                 410

<210> SEQ ID NO 45
<211> LENGTH: 410
<212> TYPE: PRT
<213> ORGANISM: Artificial Sequence
<220> FEATURE:
<223> OTHER INFORMATION: Nanobody sequence

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Leu Asp Tyr Tyr
            20                  25                  30

Ala Leu Gly Trp Phe Arg Gln Ala Pro Gly Lys Glu Arg Glu Gly Val
        35                  40                  45

Ser Cys Ile Ser Ser Ser Asp His Ser Thr Thr Tyr Thr Asp Ser Val
    50                  55                  60

Lys Gly Arg Phe Thr Ile Ser Trp Asp Asn Ala Lys Asn Thr Leu Tyr
65                  70                  75                  80

Leu Gln Met Asn Ser Leu Lys Pro Gly Asp Thr Ala Val Tyr Tyr Cys
                85                  90                  95

Ala Ala Asp Pro Ala Leu Gly Cys Tyr Ser Gly Ser Tyr Tyr Pro Arg
            100                 105                 110

Tyr Asp Tyr Trp Gly Gln Gly Thr Gln Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Ala Gly Asp Ser Leu Arg
145                 150                 155                 160

Leu Ser Cys Ala Ala Ser Gly Arg Thr Phe Ser Ser Tyr Ala Met Gly
                165                 170                 175

Trp Phe Arg Gln Ala Pro Gly Lys Glu Arg Glu Phe Val Ala Ala Ile
            180                 185                 190

Ser Trp Ser Asp Gly Ser Thr Tyr Tyr Ala Asp Ser Val Lys Gly Arg
        195                 200                 205

Phe Thr Ile Ser Arg Asp Asn Ala Lys Asn Thr Val Tyr Leu Gln Met
    210                 215                 220

Asn Ser Leu Lys Pro Glu Asp Thr Ala Val Tyr Tyr Cys Ala Ala Asp
```

```
            225                 230                 235                 240
Leu Thr Ser Thr Asn Pro Gly Ser Tyr Ile Tyr Ile Trp Ala Tyr Asp
                245                 250                 255

Tyr Trp Gly Gln Gly Thr Gln Val Thr Val Ser Ser Gly Gly Gly
                260                 265                 270

Ser Gly Gly Gly Gly Ser Gly Gly Gly Ser Glu Val Gln Leu Val
                275                 280                 285

Glu Ser Gly Gly Gly Leu Val Gln Ala Gly Asp Ser Leu Arg Leu Ser
    290                 295                 300

Cys Ala Ala Ser Gly Arg Thr Phe Ser Ser Tyr Ala Met Gly Trp Phe
305                 310                 315                 320

Arg Gln Ala Pro Gly Lys Glu Arg Glu Phe Val Ala Ala Ile Ser Trp
                325                 330                 335

Ser Asp Gly Ser Thr Tyr Tyr Ala Asp Ser Val Lys Gly Arg Phe Thr
                340                 345                 350

Ile Ser Arg Asp Asn Ala Lys Asn Thr Val Tyr Leu Gln Met Asn Ser
                355                 360                 365

Leu Lys Pro Glu Asp Thr Ala Val Tyr Tyr Cys Ala Ala Asp Leu Thr
                370                 375                 380

Ser Thr Asn Pro Gly Ser Tyr Ile Tyr Ile Trp Ala Tyr Asp Tyr Trp
385                 390                 395                 400

Gly Gln Gly Thr Gln Val Thr Val Ser Ser
                405                 410

<210> SEQ ID NO 46
<211> LENGTH: 410
<212> TYPE: PRT
<213> ORGANISM: Artificial Sequence
<220> FEATURE:
<223> OTHER INFORMATION: Nanobody sequence

<400> SEQUENCE: 46

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
                35                  40                  45

Ala Ala Ile Ser Trp Ser Asp Gly Ser Thr Tyr Tyr Ala Asp Ser Val
                50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
                100                 105                 110

Ala Tyr Asp Tyr Trp Gly Gln Gly Thr Gln Val Thr Val Ser Ser Gly
                115                 120                 125

Gly Gly Ser Gly Gly Gly Gly Ser Gly Gly Gly Ser Glu Val
                130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Leu Thr Leu Asp Tyr Tyr Ala Leu
                165                 170                 175

Gly Trp Phe Arg Gln Ala Pro Gly Lys Glu Arg Glu Gly Val Ser Cys
```

```
                180                 185                 190
Ile Ser Ser Ser Asp His Ser Thr Thr Tyr Thr Asp Ser Val Lys Gly
            195                 200                 205

Arg Phe Thr Ile Ser Trp Asp Asn Ala Lys Asn Thr Leu Tyr Leu Gln
        210                 215                 220

Met Asn Ser Leu Lys Pro Gly Asp Thr Ala Val Tyr Tyr Cys Ala Ala
225                 230                 235                 240

Asp Pro Ala Leu Gly Cys Tyr Ser Gly Ser Tyr Tyr Pro Arg Tyr Asp
                245                 250                 255

Tyr Trp Gly Gln Gly Thr Gln Val Thr Val Ser Ser Gly Gly Gly Gly
            260                 265                 270

Ser Gly Gly Gly Gly Ser Gly Gly Gly Ser Glu Val Gln Leu Val
        275                 280                 285

Glu Ser Gly Gly Gly Leu Val Gln Ala Gly Asp Ser Leu Arg Leu Ser
290                 295                 300

Cys Ala Ala Ser Gly Arg Thr Phe Ser Ser Tyr Ala Met Gly Trp Phe
305                 310                 315                 320

Arg Gln Ala Pro Gly Lys Glu Arg Glu Phe Val Ala Ala Ile Ser Trp
                325                 330                 335

Ser Asp Gly Ser Thr Tyr Tyr Ala Asp Ser Val Lys Gly Arg Phe Thr
            340                 345                 350

Ile Ser Arg Asp Asn Ala Lys Asn Thr Val Tyr Leu Gln Met Asn Ser
        355                 360                 365

Leu Lys Pro Glu Asp Thr Ala Val Tyr Tyr Cys Ala Ala Asp Leu Thr
370                 375                 380

Ser Thr Asn Pro Gly Ser Tyr Ile Tyr Ile Trp Ala Tyr Asp Tyr Trp
385                 390                 395                 400

Gly Gln Gly Thr Gln Val Thr Val Ser Ser
                405                 410

<210> SEQ ID NO 47
<211> LENGTH: 408
<212> TYPE: PRT
<213> ORGANISM: Artificial Sequence
<220> FEATURE:
<223> OTHER INFORMATION: Nanobody sequence

<400> SEQUENCE: 47

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Asn Tyr
            20                  25                  30

Val Leu Gly Trp Phe Arg Gln Ala Pro Gly Lys Glu Arg Glu Phe Val
        35                  40                  45

Ala Ala Ile Ser Phe Arg Gly Asp Ser Ala Ile Gly Ala Pro Ser Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Val Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Gly Ser Gly Gly Gly Gly Ser Glu Val Gln
```

```
                    130                 135                 140
Leu Val Glu Ser Gly Gly Gly Leu Val Gln Ala Gly Gly Ser Leu Arg
145                 150                 155                 160

Leu Ser Cys Ala Ala Ser Gly Arg Ser Phe Ser Asn Tyr Val Leu Gly
                    165                 170                 175

Trp Phe Arg Gln Ala Pro Gly Lys Glu Arg Glu Phe Val Ala Ala Ile
                    180                 185                 190

Ser Phe Arg Gly Asp Ser Ala Ile Gly Ala Pro Ser Val Glu Gly Arg
                    195                 200                 205

Phe Thr Ile Ser Arg Asp Asn Ala Lys Asn Thr Gly Tyr Leu Gln Met
                210                 215                 220

Asn Ser Leu Val Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                    245                 250                 255

Trp Gly Arg Gly Thr Gln Val Thr Val Ser Ser Gly Gly Gly Gly Ser
                    260                 265                 270

Gly Gly Gly Gly Ser Gly Gly Gly Ser Glu Val Gln Leu Val Glu
                275                 280                 285

Ser Gly Gly Gly Leu Val Gln Ala Gly Gly Ser Leu Arg Leu Ser Cys
290                 295                 300

Ala Ala Ser Gly Arg Ser Phe Ser Asn Tyr Val Leu Gly Trp Phe Arg
305                 310                 315                 320

Gln Ala Pro Gly Lys Glu Arg Glu Phe Val Ala Ala Ile Ser Phe Arg
                    325                 330                 335

Gly Asp Ser Ala Ile Gly Ala Pro Ser Val Glu Gly Arg Phe Thr Ile
                    340                 345                 350

Ser Arg Asp Asn Ala Lys Asn Thr Gly Tyr Leu Gln Met Asn Ser Leu
                355                 360                 365

Val Pro Asp Asp Thr Ala Val Tyr Tyr Cys Gly Ala Gly Thr Pro Leu
                370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405

<210> SEQ ID NO 48
<211> LENGTH: 414
<212> TYPE: PRT
<213> ORGANISM: Artificial Sequence
<220> FEATURE:
<223> OTHER INFORMATION: Nanobody sequence

<400> SEQUENCE: 48

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
                20                  25                  30

Gly Met Gly Trp Phe Arg Gln Ala Pro Gly Lys Glu Arg Glu Phe Val
            35                  40                  45

Ala Ala Val Ser Arg Leu Ser Gly Pro Arg Thr Val Tyr Ala Asp Ser
        50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
```

```
                    85                  90                  95
Cys Ala Ala Glu Leu Thr Asn Arg Asn Ser Gly Ala Tyr Tyr Ala
                100                 105                 110

Trp Ala Tyr Asp Tyr Trp Gly Gln Gly Thr Gln Val Thr Val Ser Ser
                115                 120                 125

Gly Gly Gly Ser Gly Gly Gly Gly Ser Gly Gly Gly Ser Glu
130                 135                 140

Val Gln Leu Val Glu Ser Gly Gly Leu Val Gln Ala Gly Gly Ser
145                 150                 155                 160

Leu Arg Leu Ser Cys Glu Ala Ser Gly Arg Thr Tyr Ser Arg Tyr Gly
                165                 170                 175

Met Gly Trp Phe Arg Gln Ala Pro Gly Lys Glu Arg Glu Phe Val Ala
                180                 185                 190

Ala Val Ser Arg Leu Ser Gly Pro Arg Thr Val Tyr Ala Asp Ser Val
                195                 200                 205

Lys Gly Arg Phe Thr Ile Ser Arg Asp Asn Ala Glu Asn Thr Val Tyr
210                 215                 220

Leu Gln Met Asn Ser Leu Lys Pro Glu Asp Thr Ala Val Tyr Thr Cys
225                 230                 235                 240

Ala Ala Glu Leu Thr Asn Arg Asn Ser Gly Ala Tyr Tyr Ala Trp
                245                 250                 255

Ala Tyr Asp Tyr Trp Gly Gln Gly Thr Gln Val Thr Val Ser Ser Gly
                260                 265                 270

Gly Gly Gly Ser Gly Gly Gly Gly Ser Gly Gly Gly Ser Glu Val
                275                 280                 285

Gln Leu Val Glu Ser Gly Gly Leu Val Gln Ala Gly Gly Ser Leu
290                 295                 300

Arg Leu Ser Cys Glu Ala Ser Gly Arg Thr Tyr Ser Arg Tyr Gly Met
305                 310                 315                 320

Gly Trp Phe Arg Gln Ala Pro Gly Lys Glu Arg Glu Phe Val Ala Ala
                325                 330                 335

Val Ser Arg Leu Ser Gly Pro Arg Thr Val Tyr Ala Asp Ser Val Lys
                340                 345                 350

Gly Arg Phe Thr Ile Ser Arg Asp Asn Ala Glu Asn Thr Val Tyr Leu
                355                 360                 365

Gln Met Asn Ser Leu Lys Pro Glu Asp Thr Ala Val Tyr Thr Cys Ala
                370                 375                 380

Ala Glu Leu Thr Asn Arg Asn Ser Gly Ala Tyr Tyr Ala Trp Ala
385                 390                 395                 400

Tyr Asp Tyr Trp Gly Gln Gly Thr Gln Val Thr Val Ser Ser
                405                 410

<210> SEQ ID NO 49
<211> LENGTH: 411
<212> TYPE: PRT
<213> ORGANISM: Artificial Sequence
<220> FEATURE:
<223> OTHER INFORMATION: Nanobody sequence

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
                20                  25                  30

Ala Met Gly Trp Phe Arg Gln Ala Pro Gly Lys Glu Arg Glu Phe Val
```

```
            35                  40                  45
Ala Ala Ile Ser Trp Ser Arg Gly Arg Thr Phe Tyr Ala Asp Ser Val
 50                  55                  60

Lys Gly Arg Phe Ile Ile Ser Arg Asp Asp Ala Ala Asn Thr Ala Tyr
 65                  70                  75                  80

Leu Gln Met Asn Ser Leu Lys Pro Glu Asp Thr Ala Val Tyr Tyr Cys
                 85                  90                  95

Ala Val Asp Thr Ala Ser Trp Asn Ser Gly Ser Phe Ile Tyr Asp Trp
                100                 105                 110

Ala Tyr Asp His Trp Gly Gln Gly Thr Gln Val Thr Val Ser Ser Gly
                115                 120                 125

Gly Gly Gly Ser Gly Gly Gly Ser Gly Gly Gly Ser Glu Val
 130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Arg Thr Phe Ser Ser Ile Ala Met
                165                 170                 175

Gly Trp Phe Arg Gln Ala Pro Gly Lys Glu Arg Glu Phe Val Ala Ala
                180                 185                 190

Ile Ser Trp Ser Arg Gly Arg Thr Phe Tyr Ala Asp Ser Val Lys Gly
                195                 200                 205

Arg Phe Ile Ile Ser Arg Asp Asp Ala Ala Asn Thr Ala Tyr Leu Gln
                210                 215                 220

Met Asn Ser Leu Lys Pro Glu Asp Thr Ala Val Tyr Tyr Cys Ala Val
225                 230                 235                 240

Asp Thr Ala Ser Trp Asn Ser Gly Ser Phe Ile Tyr Asp Trp Ala Tyr
                245                 250                 255

Asp His Trp Gly Gln Gly Thr Gln Val Thr Val Ser Ser Gly Gly Gly
                260                 265                 270

Gly Ser Gly Gly Gly Ser Gly Gly Gly Ser Glu Val Gln Leu
                275                 280                 285

Val Glu Ser Gly Gly Gly Leu Val Gln Pro Gly Gly Ser Leu Arg Leu
290                 295                 300

Ser Cys Ala Ala Ser Gly Arg Thr Phe Ser Ser Ile Ala Met Gly Trp
305                 310                 315                 320

Phe Arg Gln Ala Pro Gly Lys Glu Arg Glu Phe Val Ala Ala Ile Ser
                325                 330                 335

Trp Ser Arg Gly Arg Thr Phe Tyr Ala Asp Ser Val Lys Gly Arg Phe
                340                 345                 350

Ile Ile Ser Arg Asp Asp Ala Ala Asn Thr Ala Tyr Leu Gln Met Asn
                355                 360                 365

Ser Leu Lys Pro Glu Asp Thr Ala Val Tyr Tyr Cys Ala Val Asp Thr
                370                 375                 380

Ala Ser Trp Asn Ser Gly Ser Phe Ile Tyr Asp Trp Ala Tyr Asp His
385                 390                 395                 400

Trp Gly Gln Gly Thr Gln Val Thr Val Ser Ser
                405                 410

<210> SEQ ID NO 50
<211> LENGTH: 408
<212> TYPE: PRT
<213> ORGANISM: Artificial Sequence
<220> FEATURE:
<223> OTHER INFORMATION: Nanobody sequence
```

<400> SEQUENCE: 50

```
Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
            260                 265                 270

Gly Gly Gly Gly Ser Gly Gly Gly Gly Ser Glu Val Gln Leu Val Glu
        275                 280                 285

Ser Gly Gly Gly Leu Val Gln Ala Gly Gly Ser Leu Ser Ile Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365

Ala Pro Asp Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405
```

```
<210> SEQ ID NO 51
<211> LENGTH: 384
<212> TYPE: PRT
<213> ORGANISM: Artificial Sequence
<220> FEATURE:
<223> OTHER INFORMATION: Nanobody sequence

<400> SEQUENCE: 51

Glu Val Gln Leu Val Glu Ser Gly Gly Gly Leu Val Gln Ala Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Ala Ala
            115                 120                 125

Ala Glu Val Gln Leu Val Glu Ser Gly Gly Gly Leu Val Gln Ala Gly
        130                 135                 140

Gly Ser Leu Ser Ile Ser Cys Ala Ala Ser Gly Gly Ser Leu Ser Asn
145                 150                 155                 160

Tyr Val Leu Gly Trp Phe Arg Gln Ala Pro Gly Lys Glu Arg Glu Phe
                165                 170                 175

Val Ala Ala Ile Asn Trp Arg Gly Asp Ile Thr Ile Gly Pro Pro Asn
            180                 185                 190

Val Glu Gly Arg Phe Thr Ile Ser Arg Asp Asn Ala Lys Asn Thr Gly
            195                 200                 205

Tyr Leu Gln Met Asn Ser Leu Ala Pro Asp Thr Ala Val Tyr Tyr
        210                 215                 220

Cys Gly Ala Gly Thr Pro Leu Asn Pro Gly Ala Tyr Ile Tyr Asp Trp
225                 230                 235                 240

Ser Tyr Asp Tyr Trp Gly Arg Gly Thr Gln Val Thr Val Ser Ser Ala
                245                 250                 255

Ala Ala Glu Val Gln Leu Val Glu Ser Gly Gly Gly Leu Val Gln Ala
            260                 265                 270

Gly Gly Ser Leu Ser Ile Ser Cys Ala Ala Ser Gly Gly Ser Leu Ser
            275                 280                 285

Asn Tyr Val Leu Gly Trp Phe Arg Gln Ala Pro Gly Lys Glu Arg Glu
        290                 295                 300

Phe Val Ala Ala Ile Asn Trp Arg Gly Asp Ile Thr Ile Gly Pro Pro
305                 310                 315                 320

Asn Val Glu Gly Arg Phe Thr Ile Ser Arg Asp Asn Ala Lys Asn Thr
                325                 330                 335

Gly Tyr Leu Gln Met Asn Ser Leu Ala Pro Asp Thr Ala Val Tyr
            340                 345                 350

Tyr Cys Gly Ala Gly Thr Pro Leu Asn Pro Gly Ala Tyr Ile Tyr Asp
            355                 360                 365
```

```
Trp Ser Tyr Asp Tyr Trp Gly Arg Gly Thr Gln Val Thr Val Ser Ser
        370                 375                 380

<210> SEQ ID NO 52
<211> LENGTH: 396
<212> TYPE: PRT
<213> ORGANISM: Artificial Sequence
<220> FEATURE:
<223> OTHER INFORMATION: Nanobody sequence

<400> SEQUENCE: 52

Glu Val Gln Leu Val Glu Ser Gly Gly Gly Leu Val Gln Ala Gly Gly
  1               5                  10                  15

Ser Leu Ser Ile Ser Cys Ala Ala Ser Gly Gly Ser Leu Ser Asn Tyr
             20                  25                  30

Val Leu Gly Trp Phe Arg Gln Ala Pro Gly Lys Glu Arg Glu Phe Val
         35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
 65                  70                  75                  80

Leu Gln Met Asn Ser Leu Ala Pro Asp Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Glu Val Gln Leu Val Glu Ser Gly Gly
    130                 135                 140

Gly Leu Val Gln Ala Gly Gly Ser Leu Ser Ile Ser Cys Ala Ala Ser
145                 150                 155                 160

Gly Gly Ser Leu Ser Asn Tyr Val Leu Gly Trp Phe Arg Gln Ala Pro
                165                 170                 175

Gly Lys Glu Arg Glu Phe Val Ala Ala Ile Asn Trp Arg Gly Asp Ile
            180                 185                 190

Thr Ile Gly Pro Pro Asn Val Glu Gly Arg Phe Thr Ile Ser Arg Asp
        195                 200                 205

Asn Ala Lys Asn Thr Gly Tyr Leu Gln Met Asn Ser Leu Ala Pro Asp
    210                 215                 220

Asp Thr Ala Val Tyr Tyr Cys Gly Ala Gly Thr Pro Leu Asn Pro Gly
225                 230                 235                 240

Ala Tyr Ile Tyr Asp Trp Ser Tyr Asp Tyr Trp Gly Arg Gly Thr Gln
                245                 250                 255

Val Thr Val Ser Ser Gly Gly Gly Gly Ser Gly Gly Gly Ser Glu Val
            260                 265                 270

Gln Leu Val Glu Ser Gly Gly Gly Leu Val Gln Ala Gly Gly Ser Leu
        275                 280                 285

Ser Ile Ser Cys Ala Ala Ser Gly Gly Ser Leu Ser Asn Tyr Val Leu
    290                 295                 300

Gly Trp Phe Arg Gln Ala Pro Gly Lys Glu Arg Glu Phe Val Ala Ala
305                 310                 315                 320

Ile Asn Trp Arg Gly Asp Ile Thr Ile Gly Pro Pro Asn Val Glu Gly
                325                 330                 335

Arg Phe Thr Ile Ser Arg Asp Asn Ala Lys Asn Thr Gly Tyr Leu Gln
            340                 345                 350
```

```
Met Asn Ser Leu Ala Pro Asp Asp Thr Ala Val Tyr Tyr Cys Gly Ala
        355                 360                 365

Gly Thr Pro Leu Asn Pro Gly Ala Tyr Ile Tyr Asp Trp Ser Tyr Asp
    370                 375                 380

Tyr Trp Gly Arg Gly Thr Gln Val Thr Val Ser Ser
385                 390                 395

<210> SEQ ID NO 53
<211> LENGTH: 418
<212> TYPE: PRT
<213> ORGANISM: Artificial Sequence
<220> FEATURE:
<223> OTHER INFORMATION: Nanobody sequence

<400> SEQUENCE: 53

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Gly Gly Gly Ser Gly Gly Gly Gly Gly
    130                 135                 140

Gly Ser Glu Val Gln Leu Val Glu Ser Gly Gly Gly Leu Val Gln Ala
145                 150                 155                 160

Gly Gly Ser Leu Ser Ile Ser Cys Ala Ala Ser Gly Gly Ser Leu Ser
                165                 170                 175

Asn Tyr Val Leu Gly Trp Phe Arg Gln Ala Pro Gly Lys Glu Arg Glu
            180                 185                 190

Phe Val Ala Ala Ile Asn Trp Arg Gly Asp Ile Thr Ile Gly Pro Pro
        195                 200                 205

Asn Val Glu Gly Arg Phe Thr Ile Ser Arg Asp Asn Ala Lys Asn Thr
    210                 215                 220

Gly Tyr Leu Gln Met Asn Ser Leu Ala Pro Asp Asp Thr Ala Val Tyr
225                 230                 235                 240

Tyr Cys Gly Ala Gly Thr Pro Leu Asn Pro Gly Ala Tyr Ile Tyr Asp
                245                 250                 255

Trp Ser Tyr Asp Tyr Trp Gly Arg Gly Thr Gln Val Thr Val Ser Ser
            260                 265                 270

Gly Gly Gly Gly Ser Gly Gly Gly Ser Gly Gly Gly Gly Ser Gly
        275                 280                 285

Gly Gly Ser Glu Val Gln Leu Val Glu Ser Gly Gly Gly Leu Val
    290                 295                 300

Gln Ala Gly Gly Ser Leu Ser Ile Ser Cys Ala Ala Ser Gly Gly Ser
305                 310                 315                 320
```

Leu Ser Asn Tyr Val Leu Gly Trp Phe Arg Gln Ala Pro Gly Lys Glu
                325                 330                 335

Arg Glu Phe Val Ala Ala Ile Asn Trp Arg Gly Asp Ile Thr Ile Gly
                340                 345                 350

Pro Pro Asn Val Glu Gly Arg Phe Thr Ile Ser Arg Asp Asn Ala Lys
                355                 360                 365

Asn Thr Gly Tyr Leu Gln Met Asn Ser Leu Ala Pro Asp Asp Thr Ala
                370                 375                 380

Val Tyr Tyr Cys Gly Ala Gly Thr Pro Leu Asn Pro Gly Ala Tyr Ile
385                 390                 395                 400

Tyr Asp Trp Ser Tyr Asp Tyr Trp Gly Arg Gly Thr Gln Val Thr Val
                405                 410                 415

Ser Ser

<210> SEQ ID NO 54
<211> LENGTH: 408
<212> TYPE: PRT
<213> ORGANISM: Artificial Sequence
<220> FEATURE:
<223> OTHER INFORMATION: Nanobody sequence

<400> SEQUENCE: 54

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
                35                  40                  45

Ala Ala Ile Asn Trp Arg Gly Asp Ile Thr Ile Gly Pro Pro Asn Val
                50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Arg Gly Thr Gln Val Thr Val Ser Ser Gly Gly
                115                 120                 125

Gly Gly Ser Gly Gly Gly Ser Gly Gly Gly Ser Glu Val Gln
130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
                180                 185                 190

Asn Trp Arg Gly Asp Ile Thr Ile Gly Pro Pro Asn Val Glu Gly Arg
                195                 200                 205

Phe Thr Ile Ser Arg Asp Asn Ala Lys Asn Thr Gly Tyr Leu Gln Met
                210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

```
Trp Gly Arg Gly Thr Gln Val Thr Val Ser Ser Gly Gly Gly Ser
            260                 265                 270
Gly Gly Gly Gly Ser Gly Gly Gly Ser Glu Val Gln Leu Val Glu
            275                 280                 285
Ser Gly Gly Gly Leu Val Gln Pro Gly Gly Ser Leu Arg Leu Ser Cys
290                 295                 300
Ala Ala Ser Gly Leu Thr Leu Asp Tyr Tyr Ala Leu Gly Trp Phe Arg
305                 310                 315                 320
Gln Ala Pro Gly Lys Glu Arg Glu Gly Val Ser Cys Ile Ser Ser Ser
                325                 330                 335
Asp His Ser Thr Thr Tyr Thr Asp Ser Val Lys Gly Arg Phe Thr Ile
                340                 345                 350
Ser Trp Asp Asn Ala Lys Asn Thr Leu Tyr Leu Gln Met Asn Ser Leu
            355                 360                 365
Lys Pro Gly Asp Thr Ala Val Tyr Tyr Cys Ala Ala Asp Pro Ala Leu
            370                 375                 380
Gly Cys Tyr Ser Gly Ser Tyr Tyr Pro Arg Tyr Asp Tyr Trp Gly Gln
385                 390                 395                 400
Gly Thr Gln Val Thr Val Ser Ser
                405

<210> SEQ ID NO 55
<211> LENGTH: 408
<212> TYPE: PRT
<213> ORGANISM: Artificial Sequence
<220> FEATURE:
<223> OTHER INFORMATION: Nanobody sequence

<400> SEQUENCE: 55

Glu Val Gln Leu Val Glu Ser Gly Gly Gly Leu Val Gln Pro Gly Gly
1               5                   10                  15
Ser Leu Arg Leu Ser Cys Ala Ala Ser Gly Leu Thr Leu Asp Tyr Tyr
                20                  25                  30
Ala Leu Gly Trp Phe Arg Gln Ala Pro Gly Lys Glu Arg Glu Gly Val
            35                  40                  45
Ser Cys Ile Ser Ser Ser Asp His Ser Thr Thr Tyr Thr Asp Ser Val
    50                  55                  60
Lys Gly Arg Phe Thr Ile Ser Trp Asp Asn Ala Lys Asn Thr Leu Tyr
65                  70                  75                  80
Leu Gln Met Asn Ser Leu Lys Pro Gly Asp Thr Ala Val Tyr Tyr Cys
                85                  90                  95
Ala Ala Asp Pro Ala Leu Gly Cys Tyr Ser Gly Ser Tyr Tyr Pro Arg
            100                 105                 110
Tyr Asp Tyr Trp Gly Gln Gly Thr Gln Val Thr Val Ser Ser Gly Gly
        115                 120                 125
Gly Gly Ser Gly Gly Gly Gly Ser Gly Gly Gly Gly Ser Glu Val Gln
    130                 135                 140
Leu Val Glu Ser Gly Gly Gly Leu Val Gln Ala Gly Gly Ser Leu Ser
145                 150                 155                 160
Ile Ser Cys Ala Ala Ser Gly Gly Ser Leu Ser Asn Tyr Val Leu Gly
                165                 170                 175
Trp Phe Arg Gln Ala Pro Gly Lys Glu Arg Glu Phe Val Ala Ala Ile
            180                 185                 190
Asn Trp Arg Gly Asp Ile Thr Ile Gly Pro Pro Asn Val Glu Gly Arg
        195                 200                 205
```

```
Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
            275                 280                 285

Ser Gly Gly Gly Leu Val Gln Ala Gly Gly Ser Leu Ser Ile Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
            325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
            355                 360                 365

Ala Pro Asp Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
            405

<210> SEQ ID NO 56
<211> LENGTH: 408
<212> TYPE: PRT
<213> ORGANISM: Artificial Sequence
<220> FEATURE:
<223> OTHER INFORMATION: Nanobody sequence

<400> SEQUENCE: 56

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Gly Ser Gly Gly Gly Ser Glu Val Gln
    130                 135                 140

Leu Val Glu Ser Gly Gly Gly Leu Val Gln Pro Gly Gly Ser Leu Arg
145                 150                 155                 160
```

```
Leu Ser Cys Ala Ala Ser Gly Leu Thr Leu Asp Tyr Tyr Ala Leu Gly
            165                 170                 175
Trp Phe Arg Gln Ala Pro Gly Lys Glu Arg Glu Gly Val Ser Cys Ile
            180                 185                 190
Ser Ser Ser Asp His Ser Thr Thr Tyr Thr Asp Ser Val Lys Gly Arg
            195                 200                 205
Phe Thr Ile Ser Trp Asp Asn Ala Lys Asn Thr Leu Tyr Leu Gln Met
            210                 215                 220
Asn Ser Leu Lys Pro Gly Asp Thr Ala Val Tyr Tyr Cys Ala Ala Asp
225                 230                 235                 240
Pro Ala Leu Gly Cys Tyr Ser Gly Ser Tyr Tyr Pro Arg Tyr Asp Tyr
                    245                 250                 255
Trp Gly Gln Gly Thr Gln Val Thr Val Ser Ser Gly Gly Gly Gly Ser
                    260                 265                 270
Gly Gly Gly Gly Ser Gly Gly Gly Ser Glu Val Gln Leu Val Glu
                    275                 280                 285
Ser Gly Gly Gly Leu Val Gln Ala Gly Gly Ser Leu Ser Ile Ser Cys
            290                 295                 300
Ala Ala Ser Gly Gly Ser Leu Ser Asn Tyr Val Leu Gly Trp Phe Arg
305                 310                 315                 320
Gln Ala Pro Gly Lys Glu Arg Glu Phe Val Ala Ala Ile Asn Trp Arg
                    325                 330                 335
Gly Asp Ile Thr Ile Gly Pro Pro Asn Val Glu Gly Arg Phe Thr Ile
                    340                 345                 350
Ser Arg Asp Asn Ala Lys Asn Thr Gly Tyr Leu Gln Met Asn Ser Leu
                    355                 360                 365
Ala Pro Asp Asp Thr Ala Val Tyr Tyr Cys Gly Ala Gly Thr Pro Leu
370                 375                 380
Asn Pro Gly Ala Tyr Ile Tyr Asp Trp Ser Tyr Asp Tyr Trp Gly Arg
385                 390                 395                 400
Gly Thr Gln Val Thr Val Ser Ser
                    405

<210> SEQ ID NO 57
<211> LENGTH: 126
<212> TYPE: PRT
<213> ORGANISM: Artificial Sequence
<220> FEATURE:
<223> OTHER INFORMATION: Nanobody sequence

<400> SEQUENCE: 57

Glu Val Gln Leu Leu Glu Ser Gly Gly Gly Leu Val Gln Pro Gly Gly
1               5                   10                  15
Ser Leu Arg Leu Ser Cys Ala Ala Ser Gly Gly Ser Leu Ser Asn Tyr
            20                  25                  30
Val Leu Gly Trp Phe Arg Gln Ala Pro Gly Lys Gly Arg Glu Phe Val
            35                  40                  45
Ala Ala Ile Asn Trp Arg Gly Asp Ile Thr Ile Gly Pro Pro Asn Val
        50                  55                  60
Glu Gly Arg Phe Thr Ile Ser Arg Asp Asn Ala Lys Asn Thr Leu Tyr
65                  70                  75                  80
Leu Gln Met Asn Ser Leu Ala Pro Glu Asp Thr Ala Val Tyr Tyr Cys
                85                  90                  95
Gly Ala Gly Thr Pro Leu Asn Pro Gly Ala Tyr Ile Tyr Asp Trp Ser
            100                 105                 110
```

Tyr Asp Tyr Trp Gly Gln Gly Thr Leu Val Thr Val Ser Ser
            115                 120                 125

<210> SEQ ID NO 58
<211> LENGTH: 126
<212> TYPE: PRT
<213> ORGANISM: Artificial Sequence
<220> FEATURE:
<223> OTHER INFORMATION: Nanobody sequence

<400> SEQUENCE: 58

Glu Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 59
<211> LENGTH: 126
<212> TYPE: PRT
<213> ORGANISM: Artificial Sequence
<220> FEATURE:
<223> OTHER INFORMATION: Nanobody sequence

<400> SEQUENCE: 59

Glu Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 60
<211> LENGTH: 126
<212> TYPE: PRT
<213> ORGANISM: Artificial Sequence
<220> FEATURE:
<223> OTHER INFORMATION: Nanobody sequence

```
<400> SEQUENCE: 60

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 61
<211> LENGTH: 126
<212> TYPE: PRT
<213> ORGANISM: Artificial Sequence
<220> FEATURE:
<223> OTHER INFORMATION: Nanobody sequence

<400> SEQUENCE: 61

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 62
<211> LENGTH: 126
<212> TYPE: PRT
<213> ORGANISM: Artificial Sequence
<220> FEATURE:
<223> OTHER INFORMATION: Nanobody sequence

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45
```

```
Ala Ala Ile Asn Trp Arg Asp Ile Thr Ile Gly Pro Pro Asn Val
        50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Gln Gly Thr Leu Val Thr Val Ser Ser
                115                 120                 125

<210> SEQ ID NO 63
<211> LENGTH: 126
<212> TYPE: PRT
<213> ORGANISM: Artificial Sequence
<220> FEATURE:
<223> OTHER INFORMATION: Nanobody sequence

<400> SEQUENCE: 63

Glu Val Gln Leu Leu Glu Ser Gly Gly Gly Leu Val Gln Pro Gly Gly
1               5                   10                  15

Ser Leu Ser Ile Ser Cys Ala Ala Ser Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Leu Tyr
65                  70                  75                  80

Leu Gln Met Asn Ser Leu Ala Pro Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Gln Gly Thr Leu Val Thr Val Ser Ser
                115                 120                 125

<210> SEQ ID NO 64
<211> LENGTH: 126
<212> TYPE: PRT
<213> ORGANISM: Artificial Sequence
<220> FEATURE:
<223> OTHER INFORMATION: Nanobody sequence

<400> SEQUENCE: 64

Glu Val Gln Leu Leu Glu Ser Gly Gly Gly Leu Val Gln Pro Gly Gly
1               5                   10                  15

Ser Leu Ser Ile Ser Cys Ala Ala Ser Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110
```

Tyr Asp Tyr Trp Gly Gln Gly Thr Leu Val Thr Val Ser Ser
        115                 120                 125

<210> SEQ ID NO 65
<211> LENGTH: 126
<212> TYPE: PRT
<213> ORGANISM: Artificial Sequence
<220> FEATURE:
<223> OTHER INFORMATION: Nanobody sequence

<400> SEQUENCE: 65

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 66
<211> LENGTH: 126
<212> TYPE: PRT
<213> ORGANISM: Artificial Sequence
<220> FEATURE:
<223> OTHER INFORMATION: Nanobody sequence

<400> SEQUENCE: 66

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 67
<211> LENGTH: 126
<212> TYPE: PRT
<213> ORGANISM: Artificial Sequence
<220> FEATURE:
<223> OTHER INFORMATION: Nanobody sequence

<400> SEQUENCE: 67

Glu Val Gln Leu Leu Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 68
<211> LENGTH: 126
<212> TYPE: PRT
<213> ORGANISM: Artificial Sequence
<220> FEATURE:
<223> OTHER INFORMATION: Nanobody sequence

<400> SEQUENCE: 68

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 69
<211> LENGTH: 126
<212> TYPE: PRT
<213> ORGANISM: Artificial Sequence
<220> FEATURE:
<223> OTHER INFORMATION: Nanobody sequence

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

```
Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 70
<211> LENGTH: 126
<212> TYPE: PRT
<213> ORGANISM: Artificial Sequence
<220> FEATURE:
<223> OTHER INFORMATION: Nanobody sequence

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ser Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 71
<211> LENGTH: 126
<212> TYPE: PRT
<213> ORGANISM: Artificial Sequence
<220> FEATURE:
<223> OTHER INFORMATION: Nanobody sequence

<400> SEQUENCE: 71

Glu Val Gln Leu Leu Glu Ser Gly Gly Gly Leu Val Gln Ala Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
```

```
                    100                 105                 110

Tyr Asp Tyr Trp Gly Gln Gly Thr Leu Val Thr Val Ser Ser
        115                 120                 125

<210> SEQ ID NO 72
<211> LENGTH: 126
<212> TYPE: PRT
<213> ORGANISM: Artificial Sequence
<220> FEATURE:
<223> OTHER INFORMATION: Nanobody sequence

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 73
<211> LENGTH: 126
<212> TYPE: PRT
<213> ORGANISM: Artificial Sequence
<220> FEATURE:
<223> OTHER INFORMATION: Nanobody sequence

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 74
<211> LENGTH: 408
<212> TYPE: PRT
<213> ORGANISM: Artificial Sequence
<220> FEATURE:
```

<223> OTHER INFORMATION: Nanobody sequence

<400> SEQUENCE: 74

Glu Val Gln Leu Leu Glu Ser Gly Gly Gly Leu Val Gln Pro Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Glu Val Gln Leu Leu Glu
        275                 280                 285

Ser Gly Gly Gly Leu Val Gln Pro Gly Gly Ser Leu Arg Ile Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
        355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
            405

<210> SEQ ID NO 75
<211> LENGTH: 407
<212> TYPE: PRT
<213> ORGANISM: Artificial Sequence
<220> FEATURE:
<223> OTHER INFORMATION: Nanobody sequence

<400> SEQUENCE: 75

Glu Gln Leu Leu Glu Ser Gly Gly Leu Val Gln Pro Gly Gly Ser
1               5                   10                  15

Leu Arg Leu Ser Cys Ala Ala Ser Gly Gly Ser Leu Ser Asn Tyr Val
                20                  25                  30

Leu Gly Trp Phe Arg Gln Ala Pro Gly Lys Gly Arg Glu Phe Val Ala
            35                  40                  45

Ala Ile Asn Trp Arg Asp Asp Ile Thr Ile Gly Pro Pro Asn Val Glu
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Gly
                85                  90                  95

Ala Gly Thr Pro Leu Asn Pro Gly Ala Tyr Ile Tyr Asp Trp Ser Tyr
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Glu Val Gln Leu
130                 135                 140

Leu Glu Ser Gly Gly Gly Leu Val Gln Pro Gly Gly Ser Leu Arg Leu
145                 150                 155                 160

Ser Cys Ala Ala Ser Gly Gly Ser Leu Ser Asn Tyr Val Leu Gly Trp
                165                 170                 175

Phe Arg Gln Ala Pro Gly Lys Gly Arg Glu Phe Val Ala Ala Ile Asn
            180                 185                 190

Trp Arg Asp Asp Ile Thr Ile Gly Pro Pro Asn Val Glu Gly Arg Phe
        195                 200                 205

Thr Ile Ser Arg Asp Asn Ala Lys Asn Thr Leu Tyr Leu Gln Met Asn
210                 215                 220

Ser Leu Arg Pro Glu Asp Thr Ala Val Tyr Tyr Cys Gly Ala Gly Thr
225                 230                 235                 240

Pro Leu Asn Pro Gly Ala Tyr Ile Tyr Asp Trp Ser Tyr Asp Tyr Trp
                245                 250                 255

Gly Gln Gly Thr Leu Val Thr Val Ser Ser Gly Gly Gly Gly Ser Gly
            260                 265                 270

Gly Gly Ser Gly Gly Gly Gly Ser Glu Val Gln Leu Leu Glu Ser
        275                 280                 285

Gly Gly Gly Leu Val Gln Pro Gly Gly Ser Leu Arg Leu Ser Cys Ala
290                 295                 300

Ala Ser Gly Gly Ser Leu Ser Asn Tyr Val Leu Gly Trp Phe Arg Gln
305                 310                 315                 320

Ala Pro Gly Lys Gly Arg Glu Phe Val Ala Ala Ile Asn Trp Arg Asp
                325                 330                 335

Asp Ile Thr Ile Gly Pro Pro Asn Val Glu Gly Arg Phe Thr Ile Ser
            340                 345                 350

Arg Asp Asn Ala Lys Asn Thr Leu Tyr Leu Gln Met Asn Ser Leu Arg
        355                 360                 365

Pro Glu Asp Thr Ala Val Tyr Tyr Cys Gly Ala Gly Thr Pro Leu Asn
    370                 375                 380

Pro Gly Ala Tyr Ile Tyr Asp Trp Ser Tyr Asp Tyr Trp Gly Gln Gly
385                 390                 395                 400

Thr Leu Val Thr Val Ser Ser
                405

<210> SEQ ID NO 76
<211> LENGTH: 408
<212> TYPE: PRT
<213> ORGANISM: Artificial Sequence
<220> FEATURE:
<223> OTHER INFORMATION: Nanobody sequence

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
            130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Asp Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

```
Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Asp Asp Ile Thr Ile Gly Pro Pro Asn Val Glu Gly Arg Phe Thr Ile
                340                 345                 350

Ser Arg Asp Asn Ser Lys Asn Thr Leu Tyr Leu Gln Met Asn Ser Leu
                355                 360                 365

Arg Pro Glu Asp Thr Ala Val Tyr Tyr Cys Gly Ala Gly Thr Pro Leu
                370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 77
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 77

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser
                20                  25                  30

<210> SEQ ID NO 78
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
                20                  25                  30

<210> SEQ ID NO 79
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 79

Glu Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser
                20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 80
```

-continued

Glu Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 81

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 82

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 84

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 85

```
Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser
                20                  25                  30

<210> SEQ ID NO 86
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 86

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser
                20                  25                  30

<210> SEQ ID NO 87
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 87

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser
                20                  25                  30

<210> SEQ ID NO 88
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 88

Glu Val Gln Leu Leu Glu Ser Gly Gly Gly Leu Val Gln Ala Gly Gly
1               5                   10                  15

Ser Leu Ser Ile Ser Cys Ala Ala Ser Gly Gly Ser Leu Ser
                20                  25                  30

<210> SEQ ID NO 89
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 89

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser
                20                  25                  30

<210> SEQ ID NO 90
<211> LENGTH: 30
<212> TYPE: PRT
<213> ORGANISM: Artificial Sequence
<220> FEATURE:
<223> OTHER INFORMATION: Framework 1 sequence
```

```
<400> SEQUENCE: 90

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 91
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 92
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 92

Glu Val Gln Leu Leu Glu Ser Gly Gly Gly Leu Val Gln Ala Gly Gly
1               5                   10                  15

Ser Leu Arg Leu Ser Cys Ala Ala Ser Gly Gly Ser Leu Ser
            20                  25                  30

<210> SEQ ID NO 93
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 94
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 95
<211> LENGTH: 5
<212> TYPE: PRT
<213> ORGANISM: Artificial Sequence
<220> FEATURE:
<223> OTHER INFORMATION: CDR sequence
```

```
<400> SEQUENCE: 95

Asn Tyr Val Leu Gly
1               5

<210> SEQ ID NO 96
<211> LENGTH: 14
<212> TYPE: PRT
<213> ORGANISM: Artificial Sequence
<220> FEATURE:
<223> OTHER INFORMATION: Framework 2 sequence

<400> SEQUENCE: 96

Trp Phe Arg Gln Ala Pro Gly Lys Glu Arg Glu Phe Val Ala
1               5                  10

<210> SEQ ID NO 97
<211> LENGTH: 14
<212> TYPE: PRT
<213> ORGANISM: Artificial Sequence
<220> FEATURE:
<223> OTHER INFORMATION: Framework 2 sequence

<400> SEQUENCE: 97

Trp Phe Arg Gln Ala Pro Gly Lys Gly Arg Glu Phe Val Ala
1               5                  10

<210> SEQ ID NO 98
<211> LENGTH: 17
<212> TYPE: PRT
<213> ORGANISM: Artificial Sequence
<220> FEATURE:
<223> OTHER INFORMATION: CDR sequence

<400> SEQUENCE: 98

Ala Ile Asn Trp Arg Gly Asp Ile Thr Ile Gly Pro Pro Asn Val Glu
1               5                  10                  15

Gly

<210> SEQ ID NO 99
<211> LENGTH: 17
<212> TYPE: PRT
<213> ORGANISM: Artificial Sequence
<220> FEATURE:
<223> OTHER INFORMATION: CDR sequence

<400> SEQUENCE: 99

Ala Ile Asn Trp Arg Asp Asp Ile Thr Ile Gly Pro Pro Asn Val Glu
1               5                  10                  15

Gly

<210> SEQ ID NO 100
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 100

Arg Phe Thr Ile Ser Arg Asp Asn Ala Lys Asn Thr Gly Tyr Leu Gln
1               5                  10                  15

Met Asn Ser Leu Ala Pro Asp Asp Thr Ala Val Tyr Tyr Cys Gly Ala
            20                  25                  30
```

-continued

```
<210> SEQ ID NO 101
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 101

Arg Phe Thr Ile Ser Arg Asp Asn Ala Lys Asn Thr Leu Tyr Leu Gln
1               5                   10                  15
Met Asn Ser Leu Ala Pro Glu Asp Thr Ala Val Tyr Tyr Cys Gly Ala
            20                  25                  30

<210> SEQ ID NO 102
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 102

Arg Phe Thr Ile Ser Arg Asp Asn Ser Lys Asn Thr Leu Tyr Leu Gln
1               5                   10                  15
Met Asn Ser Leu Ala Pro Glu Asp Thr Ala Val Tyr Tyr Cys Gly Ala
            20                  25                  30

<210> SEQ ID NO 103
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 103

Arg Phe Thr Ile Ser Arg Asp Asn Ser Lys Asn Thr Leu Tyr Leu Gln
1               5                   10                  15
Met Asn Ser Leu Arg Pro Glu Asp Thr Ala Val Tyr Tyr Cys Gly Ala
            20                  25                  30

<210> SEQ ID NO 104
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 104

Arg Phe Thr Ile Ser Arg Asp Asn Ser Lys Asn Thr Leu Tyr Leu Gln
1               5                   10                  15
Met Asn Ser Leu Arg Pro Asp Asp Thr Ala Val Tyr Tyr Cys Gly Ala
            20                  25                  30

<210> SEQ ID NO 105
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 105

Arg Phe Thr Ile Ser Arg Asp Asn Ser Lys Asn Thr Leu Tyr Leu Gln
1               5                   10                  15
Met Asn Ser Leu Ala Pro Glu Asp Thr Ala Val Tyr Tyr Cys Gly Ala
            20                  25                  30
```

<210> SEQ ID NO 106
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 106

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Gly Ala
            20                  25                  30

<210> SEQ ID NO 107
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 107

Arg Phe Thr Ile Ser Arg Asp Asn Ala Lys Asn Thr Leu Tyr Leu Gln
1               5                   10                  15

Met Asn Ser Leu Ala Pro Asp Asp Thr Ala Val Tyr Tyr Cys Gly Ala
            20                  25                  30

<210> SEQ ID NO 108
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 108

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Gly Ala
            20                  25                  30

<210> SEQ ID NO 109
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 109

Arg Phe Thr Ile Ser Arg Asp Asn Ser Lys Asn Thr Leu Tyr Leu Gln
1               5                   10                  15

Met Asn Ser Leu Arg Pro Asp Asp Thr Ala Val Tyr Tyr Cys Gly Ala
            20                  25                  30

<210> SEQ ID NO 110
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 110

Arg Phe Thr Ile Ser Arg Asp Asn Ala Lys Asn Thr Gly Tyr Leu Gln
1               5                   10                  15

Met Asn Ser Leu Ala Pro Asp Asp Thr Ala Val Tyr Tyr Cys Gly Ala
            20                  25                  30

<210> SEQ ID NO 111
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 111

Arg Phe Thr Ile Ser Arg Asp Asn Ala Lys Asn Thr Gly Tyr Leu Gln
1               5                   10                  15

Met Asn Ser Leu Ala Pro Asp Asp Thr Ala Val Tyr Tyr Cys Gly Ala
            20                  25                  30

<210> SEQ ID NO 112
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 112

Arg Phe Thr Ile Ser Arg Asp Asn Ala Lys Asn Thr Gly Tyr Leu Gln
1               5                   10                  15

Met Asn Ser Leu Ala Pro Asp Asp Thr Ala Val Tyr Tyr Cys Gly Ala
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 113

Arg Phe Thr Ile Ser Arg Asp Asn Ala Lys Asn Thr Gly Tyr Leu Gln
1               5                   10                  15

Met Asn Ser Leu Ala Pro Glu Asp Thr Ala Val Tyr Tyr Cys Gly Ala
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 114

Arg Phe Thr Ile Ser Arg Asp Asn Ser Lys Asn Thr Leu Tyr Leu Gln
1               5                   10                  15

Met Asn Ser Leu Ala Pro Glu Asp Thr Ala Val Tyr Tyr Cys Gly Ala
            20                  25                  30

<210> SEQ ID NO 115
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 115

Arg Phe Thr Ile Ser Arg Asp Asn Ala Lys Asn Thr Leu Tyr Leu Gln
1               5                   10                  15

Met Asn Ser Leu Ala Pro Glu Asp Thr Ala Val Tyr Tyr Cys Gly Ala

```
                      20                  25                  30

<210> SEQ ID NO 116
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 116

Arg Phe Thr Ile Ser Arg Asp Asn Ser Lys Asn Thr Leu Tyr Leu Gln
 1               5                  10                  15

Met Asn Ser Leu Arg Pro Glu Asp Thr Ala Val Tyr Tyr Cys Gly Ala
             20                  25                  30

<210> SEQ ID NO 117
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 117

Arg Phe Thr Ile Ser Arg Asp Asn Ser Lys Asn Thr Leu Tyr Leu Gln
 1               5                  10                  15

Met Asn Ser Leu Arg Pro Glu Asp Thr Ala Val Tyr Tyr Cys Gly Ala
             20                  25                  30

<210> SEQ ID NO 118
<211> LENGTH: 17
<212> TYPE: PRT
<213> ORGANISM: Artificial Sequence
<220> FEATURE:
<223> OTHER INFORMATION: CDR sequence

<400> SEQUENCE: 118

Gly Thr Pro Leu Asn Pro Gly Ala Tyr Ile Tyr Asp Trp Ser Tyr Asp
 1               5                  10                  15

Tyr

<210> SEQ ID NO 119
<211> LENGTH: 11
<212> TYPE: PRT
<213> ORGANISM: Artificial Sequence
<220> FEATURE:
<223> OTHER INFORMATION: Framework 4 sequence

<400> SEQUENCE: 119

Trp Gly Arg Gly Thr Gln Val Thr Val Ser Ser
 1               5                  10

<210> SEQ ID NO 120
<211> LENGTH: 11
<212> TYPE: PRT
<213> ORGANISM: Artificial Sequence
<220> FEATURE:
<223> OTHER INFORMATION: Framework 4 sequence

<400> SEQUENCE: 120

Trp Gly Gln Gly Thr Leu Val Thr Val Ser Ser
 1               5                  10

<210> SEQ ID NO 121
<211> LENGTH: 5
<212> TYPE: PRT
```

```
<213> ORGANISM: Artificial Sequence
<220> FEATURE:
<223> OTHER INFORMATION: Linker sequence

<400> SEQUENCE: 121

Gly Gly Gly Gly Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Linker sequence

<400> SEQUENCE: 122

Ser Gly Gly Ser Gly Gly Ser
1               5

<210> SEQ ID NO 123
<211> LENGTH: 9
<212> TYPE: PRT
<213> ORGANISM: Artificial Sequence
<220> FEATURE:
<223> OTHER INFORMATION: Linker sequence

<400> SEQUENCE: 123

Gly Gly Gly Gly Ser Gly Gly Gly Ser
1               5

<210> SEQ ID NO 124
<211> LENGTH: 10
<212> TYPE: PRT
<213> ORGANISM: Artificial Sequence
<220> FEATURE:
<223> OTHER INFORMATION: Linker sequence

<400> SEQUENCE: 124

Gly Gly Gly Gly Ser Gly Gly Gly Gly Ser
1               5                   10

<210> SEQ ID NO 125
<211> LENGTH: 15
<212> TYPE: PRT
<213> ORGANISM: Artificial Sequence
<220> FEATURE:
<223> OTHER INFORMATION: Linker sequence

<400> SEQUENCE: 125

Gly Gly Gly Gly Ser Gly Gly Gly Gly Ser Gly Gly Gly Gly Ser
1               5                   10                  15

<210> SEQ ID NO 126
<211> LENGTH: 18
<212> TYPE: PRT
<213> ORGANISM: Artificial Sequence
<220> FEATURE:
<223> OTHER INFORMATION: Linker sequence

<400> SEQUENCE: 126

Gly Gly Gly Gly Ser Gly Gly Gly Gly Ser Gly Gly Gly Gly Gly
1               5                   10                  15

Gly Ser

<210> SEQ ID NO 127
<211> LENGTH: 20
```

<212> TYPE: PRT
<213> ORGANISM: Artificial Sequence
<220> FEATURE:
<223> OTHER INFORMATION: Linker sequence

<400> SEQUENCE: 127

Gly Gly Gly Gly Ser Gly Gly Gly Ser Gly Gly Gly Gly Ser Gly
1               5                   10                  15

Gly Gly Gly Ser
            20

<210> SEQ ID NO 128
<211> LENGTH: 25
<212> TYPE: PRT
<213> ORGANISM: Artificial Sequence
<220> FEATURE:
<223> OTHER INFORMATION: Linker sequence

<400> SEQUENCE: 128

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 129
<211> LENGTH: 30
<212> TYPE: PRT
<213> ORGANISM: Artificial Sequence
<220> FEATURE:
<223> OTHER INFORMATION: Linker sequence

<400> SEQUENCE: 129

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 130
<211> LENGTH: 35
<212> TYPE: PRT
<213> ORGANISM: Artificial Sequence
<220> FEATURE:
<223> OTHER INFORMATION: Linker sequence

<400> SEQUENCE: 130

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 131
<211> LENGTH: 15
<212> TYPE: PRT
<213> ORGANISM: Artificial Sequence
<220> FEATURE:
<223> OTHER INFORMATION: Linker sequence

<400> SEQUENCE: 131

Glu Pro Lys Ser Cys Asp Lys Thr His Thr Cys Pro Pro Cys Pro
1               5                   10                  15

<210> SEQ ID NO 132

```
<211> LENGTH: 24
<212> TYPE: PRT
<213> ORGANISM: Artificial Sequence
<220> FEATURE:
<223> OTHER INFORMATION: Linker sequence

<400> SEQUENCE: 132

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 133
<211> LENGTH: 62
<212> TYPE: PRT
<213> ORGANISM: Artificial Sequence
<220> FEATURE:
<223> OTHER INFORMATION: Linker sequence

<400> SEQUENCE: 133

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 134
<211> LENGTH: 3
<212> TYPE: PRT
<213> ORGANISM: Artificial Sequence
<220> FEATURE:
<223> OTHER INFORMATION: Linker sequence

<400> SEQUENCE: 134

Ala Ala Ala
1

<210> SEQ ID NO 135
<211> LENGTH: 126
<212> TYPE: PRT
<213> ORGANISM: Artificial Sequence
<220> FEATURE:
<223> OTHER INFORMATION: Nanobody sequence

<400> SEQUENCE: 135

Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110
```

```
Tyr Asp Tyr Trp Gly Arg Gly Thr Gln Val Thr Val Ser Ser
        115                 120                 125
```

<210> SEQ ID NO 136
<211> LENGTH: 126
<212> TYPE: PRT
<213> ORGANISM: Artificial Sequence
<220> FEATURE:
<223> OTHER INFORMATION: Nanobody sequence

<400> SEQUENCE: 136

```
Asp Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 137
<211> LENGTH: 125
<212> TYPE: PRT
<213> ORGANISM: Artificial Sequence
<220> FEATURE:
<223> OTHER INFORMATION: Nanobody sequence

<400> SEQUENCE: 137

```
Asp Gln Leu Leu Glu Ser Gly Gly Gly Leu Val Gln Pro Gly Gly Ser
1               5                   10                  15

Leu Arg Leu Ser Cys Ala Ala Ser Gly Gly Ser Leu Ser Asn Tyr Val
            20                  25                  30

Leu Gly Trp Phe Arg Gln Ala Pro Gly Lys Gly Arg Glu Phe Val Ala
        35                  40                  45

Ala Ile Asn Trp Arg Asp Asp Ile Thr Ile Gly Pro Pro Asn Val Glu
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Gly
                85                  90                  95

Ala Gly Thr Pro Leu Asn Pro Gly Ala Tyr Ile Tyr Asp Trp Ser Tyr
            100                 105                 110

Asp Tyr Trp Gly Gln Gly Thr Leu Val Thr Val Ser Ser
        115                 120                 125
```

<210> SEQ ID NO 138
<211> LENGTH: 126
<212> TYPE: PRT
<213> ORGANISM: Artificial Sequence
<220> FEATURE:
<223> OTHER INFORMATION: Nanobody sequence

<400> SEQUENCE: 138

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 139
<211> LENGTH: 408
<212> TYPE: PRT
<213> ORGANISM: Artificial Sequence
<220> FEATURE:
<223> OTHER INFORMATION: Nanobody sequence

<400> SEQUENCE: 139

Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
            165                 170                 175

Trp Phe Arg Gln Ala Pro Gly Lys Glu Arg Glu Phe Val Ala Ala Ile
        180                 185                 190

Asn Trp Arg Gly Asp Ile Thr Ile Gly Pro Pro Asn Val Glu Gly Arg
    195                 200                 205

Phe Thr Ile Ser Arg Asp Asn Ala Lys Asn Thr Gly Tyr Leu Gln Met
210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Ala Gly Gly Ser Leu Ser Ile Ser Cys
        290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365

Ala Pro Asp Asp Thr Ala Val Tyr Tyr Cys Gly Ala Gly Thr Pro Leu
        370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405

<210> SEQ ID NO 140
<211> LENGTH: 408
<212> TYPE: PRT
<213> ORGANISM: Artificial Sequence
<220> FEATURE:
<223> OTHER INFORMATION: Nanobody sequence

<400> SEQUENCE: 140

Asp Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Ile Ser Cys Ala Ala Ser Gly Gly Ser Leu Ser Asn Tyr Val Leu Gly
                165                 170                 175

```
Trp Phe Arg Gln Ala Pro Gly Lys Gly Arg Glu Phe Val Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Gln Gly Thr Leu Val Thr Val Ser Ser Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Ile Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ile Asn Trp Arg
            325                 330                 335

Gly Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
            355                 360                 365

Arg Pro Glu Asp Thr Ala Val Tyr Tyr Cys Gly Ala Gly Thr Pro Leu
            370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
            405

<210> SEQ ID NO 141
<211> LENGTH: 407
<212> TYPE: PRT
<213> ORGANISM: Artificial Sequence
<220> FEATURE:
<223> OTHER INFORMATION: Nanobody sequence

<400> SEQUENCE: 141

Asp Gln Leu Leu Glu Ser Gly Gly Gly Leu Val Gln Pro Gly Gly Ser
1               5                   10                  15

Leu Arg Leu Ser Cys Ala Ala Ser Gly Gly Ser Leu Ser Asn Tyr Val
            20                  25                  30

Leu Gly Trp Phe Arg Gln Ala Pro Gly Lys Gly Arg Glu Phe Val Ala
        35                  40                  45

Ala Ile Asn Trp Arg Asp Asp Ile Thr Ile Gly Pro Pro Asn Val Glu
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Gly
            85                  90                  95

Ala Gly Thr Pro Leu Asn Pro Gly Ala Tyr Ile Tyr Asp Trp Ser Tyr
            100                 105                 110

Asp Tyr Trp Gly Gln Gly Thr Leu Val Thr Val Ser Ser Gly Gly Gly
        115                 120                 125
```

```
Gly Ser Gly Gly Gly Gly Ser Gly Gly Gly Ser Glu Val Gln Leu
    130                 135                 140
Leu Glu Ser Gly Gly Gly Leu Val Gln Pro Gly Gly Ser Leu Arg Leu
145                 150                 155                 160
Ser Cys Ala Ala Ser Gly Gly Ser Leu Ser Asn Tyr Val Leu Gly Trp
                165                 170                 175
Phe Arg Gln Ala Pro Gly Lys Gly Arg Glu Phe Val Ala Ala Ile Asn
                180                 185                 190
Trp Arg Asp Asp Ile Thr Ile Gly Pro Pro Asn Val Glu Gly Arg Phe
                195                 200                 205
Thr Ile Ser Arg Asp Asn Ala Lys Asn Thr Leu Tyr Leu Gln Met Asn
210                 215                 220
Ser Leu Arg Pro Glu Asp Thr Ala Val Tyr Tyr Cys Gly Ala Gly Thr
225                 230                 235                 240
Pro Leu Asn Pro Gly Ala Tyr Ile Tyr Asp Trp Ser Tyr Asp Tyr Trp
                245                 250                 255
Gly Gln Gly Thr Leu Val Thr Val Ser Ser Gly Gly Gly Gly Ser Gly
                260                 265                 270
Gly Gly Ser Gly Gly Gly Gly Ser Glu Val Gln Leu Leu Glu Ser
        275                 280                 285
Gly Gly Gly Leu Val Gln Pro Gly Gly Ser Leu Arg Leu Ser Cys Ala
        290                 295                 300
Ala Ser Gly Gly Ser Leu Ser Asn Tyr Val Leu Gly Trp Phe Arg Gln
305                 310                 315                 320
Ala Pro Gly Lys Gly Arg Glu Phe Val Ala Ala Ile Asn Trp Arg Asp
                325                 330                 335
Asp Ile Thr Ile Gly Pro Pro Asn Val Glu Gly Arg Phe Thr Ile Ser
                340                 345                 350
Arg Asp Asn Ala Lys Asn Thr Leu Tyr Leu Gln Met Asn Ser Leu Arg
                355                 360                 365
Pro Glu Asp Thr Ala Val Tyr Tyr Cys Gly Ala Gly Thr Pro Leu Asn
        370                 375                 380
Pro Gly Ala Tyr Ile Tyr Asp Trp Ser Tyr Asp Tyr Trp Gly Gln Gly
385                 390                 395                 400
Thr Leu Val Thr Val Ser Ser
                405

<210> SEQ ID NO 142
<211> LENGTH: 408
<212> TYPE: PRT
<213> ORGANISM: Artificial Sequence
<220> FEATURE:
<223> OTHER INFORMATION: Nanobody sequence

<400> SEQUENCE: 142

Asp Val Gln Leu Leu Glu Ser Gly Gly Gly Leu Val Gln Pro Gly Gly
1               5                   10                  15
Ser Leu Arg Leu Ser Cys Ala Ala Ser Gly Gly Ser Leu Ser Asn Tyr
                20                  25                  30
Val Leu Gly Trp Phe Arg Gln Ala Pro Gly Lys Gly Arg Glu Phe Val
            35                  40                  45
Ala Ala Ile Asn Trp Arg Asp Asp Ile Thr Ile Gly Pro Pro Asn Val
        50                  55                  60
Glu Gly Arg Phe Thr Ile Ser Arg Asp Asn Ser Lys Asn Thr Leu Tyr
65                  70                  75                  80
```

```
Leu Gln Met Asn Ser Leu Arg Pro Glu Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130             135             140

Leu Leu Glu Ser Gly Gly Gly Leu Val Gln Pro Gly Gly Ser Leu Arg
145             150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Asp Asp Ile Thr Ile Gly Pro Pro Asn Val Glu Gly Arg
            195                 200                 205

Phe Thr Ile Ser Arg Asp Asn Ser Lys Asn Thr Leu Tyr Leu Gln Met
        210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
            325                 330                 335

Asp Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
        355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405
```

<210> SEQ ID NO 143
<211> LENGTH: 126
<212> TYPE: PRT
<213> ORGANISM: Artificial Sequence
<220> FEATURE:
<223> OTHER INFORMATION: Nanobody sequence

<400> SEQUENCE: 143

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30
```

```
Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
 65                  70                  75                  80

Leu Gln Met Asn Ser Leu Ala Pro Asp Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 144
<211> LENGTH: 126
<212> TYPE: PRT
<213> ORGANISM: Artificial Sequence
<220> FEATURE:
<223> OTHER INFORMATION: Nanobody sequence

<400> SEQUENCE: 144

Glu Val Gln Leu Val Glu Ser Gly Gly Gly Leu Val Gln Pro Gly Gly
 1               5                  10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
 65                  70                  75                  80

Leu Gln Met Asn Ser Leu Arg Pro Asp Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 145
<211> LENGTH: 126
<212> TYPE: PRT
<213> ORGANISM: Artificial Sequence
<220> FEATURE:
<223> OTHER INFORMATION: Nanobody sequence

<400> SEQUENCE: 145

Glu Val Gln Leu Val Glu Ser Gly Gly Gly Leu Val Gln Pro Gly Gly
 1               5                  10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
 65                  70                  75                  80

Leu Gln Met Asn Ser Leu Ala Pro Glu Asp Thr Ala Val Tyr Tyr Cys
                 85                  90                  95
```

Gly Ala Gly Thr Pro Leu Asn Pro Gly Ala Tyr Ile Tyr Asp Trp Ser
                100                 105                 110

Tyr Asp Tyr Trp Gly Gln Gly Thr Leu Val Thr Val Ser Ser
        115                 120                 125

<210> SEQ ID NO 146
<211> LENGTH: 126
<212> TYPE: PRT
<213> ORGANISM: Artificial Sequence
<220> FEATURE:
<223> OTHER INFORMATION: Nanobody sequence

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Gln Gly Thr Leu Val Thr Val Ser Ser
        115                 120                 125

<210> SEQ ID NO 147
<211> LENGTH: 126
<212> TYPE: PRT
<213> ORGANISM: Artificial Sequence
<220> FEATURE:
<223> OTHER INFORMATION: Nanobody sequence

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Arg Gly Thr Leu Val Thr Val Ser Ser
        115                 120                 125

<210> SEQ ID NO 148
<211> LENGTH: 126
<212> TYPE: PRT

-continued

<213> ORGANISM: Artificial Sequence
<220> FEATURE:
<223> OTHER INFORMATION: Nanobody sequence

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser
        115                 120                 125

<210> SEQ ID NO 149
<211> LENGTH: 126
<212> TYPE: PRT
<213> ORGANISM: Artificial Sequence
<220> FEATURE:
<223> OTHER INFORMATION: Nanobody sequence

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser
        115                 120                 125

<210> SEQ ID NO 150
<211> LENGTH: 126
<212> TYPE: PRT
<213> ORGANISM: Artificial Sequence
<220> FEATURE:
<223> OTHER INFORMATION: Nanobody sequence

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

```
Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
 65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
               100                 105                 110

Tyr Asp Tyr Trp Gly Arg Gly Thr Leu Val Thr Val Ser Ser
               115                 120                 125
```

<210> SEQ ID NO 151
<211> LENGTH: 126
<212> TYPE: PRT
<213> ORGANISM: Artificial Sequence
<220> FEATURE:
<223> OTHER INFORMATION: Nanobody sequence

<400> SEQUENCE: 151

```
Asp Val Gln Leu Leu Glu Ser Gly Gly Gly Leu Val Gln Pro Gly Gly
 1               5                  10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
               100                 105                 110

Tyr Asp Tyr Trp Gly Gln Gly Thr Leu Val Thr Val Ser Ser
               115                 120                 125
```

<210> SEQ ID NO 152
<211> LENGTH: 126
<212> TYPE: PRT
<213> ORGANISM: Artificial Sequence
<220> FEATURE:
<223> OTHER INFORMATION: Nanobody sequence

<400> SEQUENCE: 152

```
Asp Val Gln Leu Val Glu Ser Gly Gly Gly Leu Val Gln Pro Gly Gly
 1               5                  10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
 65                  70                  75                  80

Leu Gln Met Asn Ser Leu Ala Pro Glu Asp Thr Ala Val Tyr Tyr Cys
```

```
                    85                  90                  95
Gly Ala Gly Thr Pro Leu Asn Pro Gly Ala Tyr Ile Tyr Asp Trp Ser
                100                 105                 110
Tyr Asp Tyr Trp Gly Gln Gly Thr Leu Val Thr Val Ser Ser
            115                 120                 125

<210> SEQ ID NO 153
<211> LENGTH: 126
<212> TYPE: PRT
<213> ORGANISM: Artificial Sequence
<220> FEATURE:
<223> OTHER INFORMATION: Nanobody sequence

<400> SEQUENCE: 153

Asp Val Gln Leu Val Glu Ser Gly Gly Gly Leu Val Gln Pro Gly Gly
1               5                   10                  15
Ser Leu Arg Leu Ser Cys Ala Ala Ser Gly Gly Ser Leu Ser Asn Tyr
            20                  25                  30
Val Leu Gly Trp Phe Arg Gln Ala Pro Gly Lys Glu Arg Glu Phe Val
        35                  40                  45
Ala Ala Ile Asn Trp Arg Gly Asp Ile Thr Ile Gly Pro Pro Asn Val
    50                  55                  60
Glu Gly Arg Phe Thr Ile Ser Arg Asp Asn Ala Lys Asn Thr Gly Tyr
65                  70                  75                  80
Leu Gln Met Asn Ser Leu Arg Pro Glu Asp Thr Ala Val Tyr Tyr Cys
                85                  90                  95
Gly Ala Gly Thr Pro Leu Asn Pro Gly Ala Tyr Ile Tyr Asp Trp Ser
                100                 105                 110
Tyr Asp Tyr Trp Gly Gln Gly Thr Leu Val Thr Val Ser Ser
            115                 120                 125

<210> SEQ ID NO 154
<211> LENGTH: 126
<212> TYPE: PRT
<213> ORGANISM: Artificial Sequence
<220> FEATURE:
<223> OTHER INFORMATION: Nanobody sequence

<400> SEQUENCE: 154

Asp Val Gln Leu Val Glu Ser Gly Gly Gly Leu Val Gln Pro Gly Gly
1               5                   10                  15
Ser Leu Arg Leu Ser Cys Ala Ala Ser Gly Gly Ser Leu Ser Asn Tyr
            20                  25                  30
Val Leu Gly Trp Phe Arg Gln Ala Pro Gly Lys Glu Arg Glu Phe Val
        35                  40                  45
Ala Ala Ile Asn Trp Arg Gly Asp Ile Thr Ile Gly Pro Pro Asn Val
    50                  55                  60
Glu Gly Arg Phe Thr Ile Ser Arg Asp Asn Ala Lys Asn Thr Gly Tyr
65                  70                  75                  80
Leu Gln Met Asn Ser Leu Arg Pro Glu Asp Thr Ala Val Tyr Tyr Cys
                85                  90                  95
Gly Ala Gly Thr Pro Leu Asn Pro Gly Ala Tyr Ile Tyr Asp Trp Ser
                100                 105                 110
Tyr Asp Tyr Trp Gly Arg Gly Thr Leu Val Thr Val Ser Ser
            115                 120                 125

<210> SEQ ID NO 155
<211> LENGTH: 408
```

```
<212> TYPE: PRT
<213> ORGANISM: Artificial Sequence
<220> FEATURE:
<223> OTHER INFORMATION: Nanobody sequence

<400> SEQUENCE: 155
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 |
| Ser | Leu | Arg | Leu | Ser | Cys | Ala | Ala | Ser | Gly | Gly | Ser | Leu | Ser | Asn | Tyr |
| | | | 20 | | | | | 25 | | | | | 30 | |
| Val | Leu | Gly | Trp | Phe | Arg | Gln | Ala | Pro | Gly | Lys | Gly | Arg | Glu | Phe | Val |
| | | | 35 | | | | | 40 | | | | | 45 | |
| Ala | Ala | Ile | Asn | Trp | Arg | Gly | Asp | Ile | Thr | Ile | Gly | Pro | Pro | Asn | Val |
| | 50 | | | | | 55 | | | | | 60 | | | | |
| Glu | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Pro | Glu | Asp | Thr | Ala | Val | Tyr | Tyr | Cys |
| | | | | 85 | | | | | 90 | | | | | 95 | |
| Gly | Ala | Gly | Thr | Pro | Leu | Asn | Pro | Gly | Ala | Tyr | Ile | Tyr | Asp | Trp | Ser |
| | | | 100 | | | | | 105 | | | | | 110 | | |
| Tyr | Asp | Tyr | Trp | Gly | Gln | Gly | Thr | Leu | Val | Thr | Val | Ser | Ser | Gly | Gly |
| | | 115 | | | | | 120 | | | | | 125 | | | |
| Gly | Gly | Ser | Gly | Gly | Gly | Ser | Gly | Gly | Gly | Ser | Glu | Val | Gln |
| | 130 | | | | | 135 | | | | | 140 | | |
| Leu | Leu | Glu | Ser | Gly | Gly | Gly | Leu | Val | Gln | Pro | Gly | Gly | Ser | Leu | Arg |
| 145 | | | | | 150 | | | | | 155 | | | | | 160 |
| Leu | Ser | Cys | Ala | Ala | Ser | Gly | Gly | Ser | Leu | Ser | Asn | Tyr | Val | Leu | Gly |
| | | | | 165 | | | | | 170 | | | | | 175 | |
| Trp | Phe | Arg | Gln | Ala | Pro | Gly | Lys | Gly | Arg | Glu | Phe | Val | Ala | Ala | Ile |
| | | | 180 | | | | | 185 | | | | | 190 | | |
| Asn | Trp | Arg | Gly | Asp | Ile | Thr | Ile | Gly | Pro | Pro | Asn | Val | Glu | Gly | Arg |
| | | | 195 | | | | | 200 | | | | | 205 | | |
| Phe | Thr | Ile | Ser | Arg | Asp | Asn | Ser | Lys | Asn | Thr | Leu | Tyr | Leu | Gln | Met |
| | 210 | | | | | 215 | | | | | 220 | | | | |
| Asn | Ser | Leu | Arg | Pro | Glu | Asp | Thr | Ala | Val | Tyr | Tyr | Cys | Gly | Ala | Gly |
| 225 | | | | | 230 | | | | | 235 | | | | | 240 |
| Thr | Pro | Leu | Asn | Pro | Gly | Ala | Tyr | Ile | Tyr | Asp | Trp | Ser | Tyr | Asp | Tyr |
| | | | | 245 | | | | | 250 | | | | | 255 | |
| Trp | Gly | Gln | Gly | Thr | Leu | Val | Thr | Val | Ser | Ser | Gly | Gly | Gly | Gly | Ser |
| | | | 260 | | | | | 265 | | | | | 270 | | |
| Gly | Gly | Gly | Gly | Ser | Gly | Gly | Gly | Ser | Glu | Val | Gln | Leu | Leu | Glu |
| | | 275 | | | | | 280 | | | | | 285 | | |
| Ser | Gly | Gly | Gly | Leu | Val | Gln | Pro | Gly | Gly | Ser | Leu | Arg | Leu | Ser | Cys |
| | 290 | | | | | 295 | | | | | 300 | | | | |
| Ala | Ala | Ser | Gly | Gly | Ser | Leu | Ser | Asn | Tyr | Val | Leu | Gly | Trp | Phe | Arg |
| 305 | | | | 310 | | | | | 315 | | | | | 320 |
| Gln | Ala | Pro | Gly | Lys | Gly | Arg | Glu | Phe | Val | Ala | Ala | Ile | Asn | Trp | Arg |
| | | | | 325 | | | | | 330 | | | | | 335 | |
| Gly | Asp | Ile | Thr | Ile | Gly | Pro | Pro | Asn | Val | Glu | Gly | Arg | Phe | Thr | Ile |
| | | | 340 | | | | | 345 | | | | | 350 | | |
| Ser | Arg | Asp | Asn | Ser | Lys | Asn | Thr | Leu | Tyr | Leu | Gln | Met | Asn | Ser | Leu |
| | | 355 | | | | | 360 | | | | | 365 | | | |
| Arg | Pro | Glu | Asp | Thr | Ala | Val | Tyr | Tyr | Cys | Gly | Ala | Gly | Thr | Pro | Leu |
| | 370 | | | | | 375 | | | | | 380 | | | | |

Asn Pro Gly Ala Tyr Ile Tyr Asp Trp Ser Tyr Asp Tyr Trp Gly Gln
385                 390                 395                 400

Gly Thr Leu Val Thr Val Ser Ser
            405

<210> SEQ ID NO 156
<211> LENGTH: 408
<212> TYPE: PRT
<213> ORGANISM: Artificial Sequence
<220> FEATURE:
<223> OTHER INFORMATION: Nanobody sequence

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Arg Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
            355                 360                 365

Arg Pro Asp Asp Thr Ala Val Tyr Tyr Cys Gly Ala Gly Thr Pro Leu
        370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 157
<211> LENGTH: 408
<212> TYPE: PRT
<213> ORGANISM: Artificial Sequence
<220> FEATURE:
<223> OTHER INFORMATION: Nanobody sequence

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

```
Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
                355                 360                 365

Arg Pro Glu Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 158
<211> LENGTH: 408
<212> TYPE: PRT
<213> ORGANISM: Artificial Sequence
<220> FEATURE:
<223> OTHER INFORMATION: Nanobody sequence

<400> SEQUENCE: 158

Glu Val Gln Leu Val Glu Ser Gly Gly Leu Val Gln Pro Gly Gly
1               5                   10                  15

Ser Leu Arg Leu Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Arg Pro Glu Asp Thr Ala Val Tyr Tyr Cys Gly Ala Gly
225                 230                 235                 240
```

Thr Pro Leu Asn Pro Gly Ala Tyr Ile Tyr Asp Trp Ser Tyr Asp Tyr
                    245                 250                 255

Trp Gly Arg Gly Thr Leu Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Arg
385                 390                 395                 400

Gly Thr Leu Val Thr Val Ser Ser
                405

<210> SEQ ID NO 159
<211> LENGTH: 408
<212> TYPE: PRT
<213> ORGANISM: Artificial Sequence
<220> FEATURE:
<223> OTHER INFORMATION: Nanobody sequence

<400> SEQUENCE: 159

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

```
Asn Trp Arg Gly Asp Ile Thr Ile Gly Pro Pro Asn Val Glu Gly Arg
            195                 200                 205

Phe Thr Ile Ser Arg Asp Asn Ser Lys Asn Thr Leu Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
            275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ile Asn Trp Arg
            325                 330                 335

Gly Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
            355                 360                 365

Arg Pro Glu Asp Thr Ala Val Tyr Tyr Cys Gly Ala Gly Thr Pro Leu
            370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
            405

<210> SEQ ID NO 160
<211> LENGTH: 408
<212> TYPE: PRT
<213> ORGANISM: Artificial Sequence
<220> FEATURE:
<223> OTHER INFORMATION: Nanobody sequence

<400> SEQUENCE: 160

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
            115                 120                 125

Gly Gly Ser Gly Gly Gly Ser Gly Gly Gly Ser Glu Val Gln
            130                 135                 140
```

```
Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
            195                 200                 205

Phe Thr Ile Ser Arg Asp Asn Ala Lys Asn Thr Gly Tyr Leu Gln Met
210                 215                 220

Asn Ser Leu Arg Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Glu Val Gln Leu Val Glu
            275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
            355                 360                 365

Arg Pro Asp Asp Thr Ala Val Tyr Tyr Cys Gly Ala Gly Thr Pro Leu
            370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 161
<211> LENGTH: 408
<212> TYPE: PRT
<213> ORGANISM: Artificial Sequence
<220> FEATURE:
<223> OTHER INFORMATION: Nanobody sequence

<400> SEQUENCE: 161

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95
```

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Ser Gly Gly Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 162
<211> LENGTH: 408
<212> TYPE: PRT
<213> ORGANISM: Artificial Sequence
<220> FEATURE:
<223> OTHER INFORMATION: Nanobody sequence

<400> SEQUENCE: 162

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
 65                  70                  75                  80

Leu Gln Met Asn Ser Leu Arg Pro Glu Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser Gly Gly
        115                 120                 125

Gly Gly Ser Gly Gly Gly Ser Gly Gly Gly Ser Glu Val Gln
130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Leu Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365

Arg Pro Glu Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Arg
385                 390                 395                 400

Gly Thr Leu Val Thr Val Ser Ser
                405

<210> SEQ ID NO 163
<211> LENGTH: 30
<212> TYPE: PRT
<213> ORGANISM: Artificial Sequence
<220> FEATURE:
<223> OTHER INFORMATION: Framework 1 sequence

<400> SEQUENCE: 163

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30
```

<210> SEQ ID NO 164
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 164

```
Arg Phe Thr Ile Ser Arg Asp Asn Ala Lys Asn Thr Gly Tyr Leu Gln
1               5                   10                  15

Met Asn Ser Leu Arg Pro Asp Asp Thr Ala Val Tyr Tyr Cys Gly Ala
            20                  25                  30
```

<210> SEQ ID NO 165
<211> LENGTH: 32
<212> TYPE: PRT
<213> ORGANISM: Artificial Sequence
<220> FEATURE:
<223> OTHER INFORMATION: Framework 3 sequence

<400> SEQUENCE: 165

```
Arg Phe Thr Ile Ser Arg Asp Asn Ala Lys Asn Thr Gly Tyr Leu Gln
1               5                   10                  15

Met Asn Ser Leu Arg Pro Glu Asp Thr Ala Val Tyr Tyr Cys Gly Ala
            20                  25                  30
```

<210> SEQ ID NO 166
<211> LENGTH: 11
<212> TYPE: PRT
<213> ORGANISM: Artificial Sequence
<220> FEATURE:
<223> OTHER INFORMATION: Framework 4 sequence

<400> SEQUENCE: 166

```
Trp Gly Arg Gly Thr Leu Val Thr Val Ser Ser
1               5                   10
```

<210> SEQ ID NO 167
<211> LENGTH: 574
<212> TYPE: PRT
<213> ORGANISM: respiratory syncytial virus

<400> SEQUENCE: 167

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110
```

```
Arg Phe Met Asn Tyr Thr Leu Asn Asn Thr Lys Lys Thr Asn Val Thr
            115                 120                 125

Leu Ser Lys Lys Arg Lys Arg Arg Phe Leu Gly Phe Leu Leu Gly Val
130                 135                 140

Gly Ser Ala Ile Ala Ser Gly Thr Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Arg Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His His Val Asn Ala Gly Lys Ser Thr Thr Asn Ile Met Ile Thr
            515                 520                 525
```

```
Thr Ile Ile Ile Val Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 168
<211> LENGTH: 574
<212> TYPE: PRT
<213> ORGANISM: respiratory syncytial virus

<400> SEQUENCE: 168

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335
```

```
Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 169
<211> LENGTH: 574
<212> TYPE: PRT
<213> ORGANISM: respiratory syncytial virus

<400> SEQUENCE: 169

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
            35                  40                  45

Arg Thr Gly Trp Tyr Thr Ser Val Ile Thr Ile Glu Leu Ser Asn Ile
            50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
            130                 135                 140
```

```
Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Arg Leu Leu Pro Ile Val Asn
        195                 200                 205

Gln Gln Ser Cys Arg Ile Ser Asn Ile Glu Thr Val Ile Glu Phe Gln
    210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Leu Leu Ile Ala Ile
    530                 535                 540
```

-continued

```
Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565             570
```